United States Patent
Woodhead et al.

(10) Patent No.: US 10,052,320 B2
(45) Date of Patent: *Aug. 21, 2018

(54) SUBSTITUTED QUINOXALINES AS FGFR KINASE INHIBITORS

(71) Applicant: ASTEX THERAPEUTICS LIMITED, Cambridge (GB)

(72) Inventors: Steven John Woodhead, San Diego, CA (US); Christopher William Murray, Cambridge (GB); Valerio Berdini, Cambridge (GB); Gordon Saxty, Zagreb (HR); Gilbert Ebai Besong, Bad Duerkheim (DE); Lieven Meerpoel, Beerse (BE); Olivier Alexis Georges Querolle, Saint-Vigor (FR); Virginie Sophie Poncelet, Le Manoir (FR)

(73) Assignee: ASTEX THERAPEUTICS LTD, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/014,156

(22) Filed: Feb. 3, 2016

(65) Prior Publication Data

US 2016/0220564 A1    Aug. 4, 2016

Related U.S. Application Data

(63) Continuation of application No. 14/354,636, filed as application No. PCT/GB2012/052673 on Oct. 26, 2012, now Pat. No. 9,303,029.

(Continued)

(30) Foreign Application Priority Data

Oct. 28, 2011 (GB) .................... 1118654.1

(51) Int. Cl.
| | | |
|---|---|---|
| A61K 31/498 | (2006.01) |
| C07D 241/40 | (2006.01) |
| C07D 403/12 | (2006.01) |
| C07D 401/14 | (2006.01) |
| C07D 413/14 | (2006.01) |
| C07D 401/04 | (2006.01) |
| C07D 401/06 | (2006.01) |
| C07D 401/12 | (2006.01) |
| C07D 403/04 | (2006.01) |
| C07D 403/06 | (2006.01) |
| C07D 407/04 | (2006.01) |
| C07D 407/14 | (2006.01) |
| C07D 413/04 | (2006.01) |
| C07D 417/04 | (2006.01) |
| C07D 241/42 | (2006.01) |
| C07D 241/44 | (2006.01) |
| C07D 417/12 | (2006.01) |
| C07D 471/04 | (2006.01) |
| A61K 31/4985 | (2006.01) |
| A61K 31/506 | (2006.01) |
| A61K 45/06 | (2006.01) |

(Continued)

(52) U.S. Cl.
CPC ........ *A61K 31/498* (2013.01); *A61K 31/4985* (2013.01); *A61K 31/506* (2013.01); *A61K 31/5377* (2013.01); *A61K 45/06* (2013.01); *C07D 241/42* (2013.01); *C07D 241/44* (2013.01); *C07D 401/04* (2013.01); *C07D 401/06* (2013.01); *C07D 401/12* (2013.01); *C07D 401/14* (2013.01); *C07D 403/04* (2013.01); *C07D 403/06* (2013.01); *C07D 403/12* (2013.01); *C07D 405/04* (2013.01); *C07D 405/14* (2013.01); *C07D 407/04* (2013.01); *C07D 407/14* (2013.01); *C07D 413/04* (2013.01); *C07D 413/14* (2013.01); *C07D 417/04* (2013.01); *C07D 417/12* (2013.01); *C07D 471/04* (2013.01)

(58) Field of Classification Search
CPC ............................ A61K 31/498; C07D 241/40
USPC ............................................ 514/249; 544/350
See application file for complete search history.

(56) References Cited

U.S. PATENT DOCUMENTS 2,940,972 A    6/1960    Roch
4,666,828 A    5/1987    Gusella
(Continued)

FOREIGN PATENT DOCUMENTS

CA    2524525    12/2004
CA    2524948    12/2004
(Continued)

OTHER PUBLICATIONS

International Search Report for PCT/GB2012/052673 dated Jan. 7, 2013.

(Continued)

*Primary Examiner* — Douglas M Willis
(74) *Attorney, Agent, or Firm* — Heslin Rothenberg Farley & Mesiti P.C.

(57) ABSTRACT

The invention relates to new quinoxaline derivative compounds of formula (I),

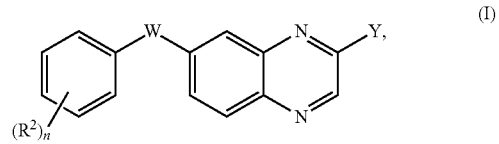

(Continued)

to pharmaceutical compositions comprising said compounds, to processes for the preparation of said compounds and to the use of said compounds in the treatment of diseases, e.g. cancer.

20 Claims, No Drawings

Related U.S. Application Data

(60) Provisional application No. 61/552,873, filed on Oct. 28, 2011.

(51) Int. Cl.
*C07D 405/04* (2006.01)
*C07D 405/14* (2006.01)
*A61K 31/5377* (2006.01)

(56) References Cited

U.S. PATENT DOCUMENTS

| | | |
|---|---|---|
| 4,683,202 A | 7/1987 | Mullis |
| 4,801,531 A | 1/1989 | Frossard |
| 5,192,659 A | 3/1993 | Simons |
| 5,272,057 A | 12/1993 | Smulson et al. |
| 5,700,823 A | 12/1997 | Hirth et al. |
| 5,882,864 A | 3/1999 | An et al. |
| 6,218,529 B1 | 4/2001 | An et al. |
| 6,271,231 B1 | 8/2001 | Bergstrand et al. |
| 6,331,555 B1 | 12/2001 | Hirth et al. |
| 7,432,279 B2 | 10/2008 | Green et al. |
| 8,895,601 B2 | 11/2014 | Saxty et al. |
| 9,145,367 B2 | 9/2015 | Tazi et al. |
| 9,221,804 B2 | 12/2015 | Leonard et al. |
| 9,290,478 B2 | 3/2016 | Saxty et al. |
| 9,303,029 B2 | 4/2016 | Woodhead et al. |
| 9,303,030 B2 | 4/2016 | Angibaud et al. |
| 9,309,241 B2 | 4/2016 | Angibaud et al. |
| 9,309,242 B2 | 4/2016 | Berdini et al. |
| 9,439,896 B2 | 9/2016 | Berdini et al. |
| 9,447,098 B2 | 9/2016 | Saxty et al. |
| 9,464,071 B2 | 10/2016 | Saxty et al. |
| 9,493,426 B2 | 11/2016 | Angibaud et al. |
| 9,527,844 B2 | 12/2016 | Angibaud et al. |
| 9,737,544 B2 | 8/2017 | Angibaud et al. |
| 9,757,364 B2 | 9/2017 | Angibaud et al. |
| 9,850,228 B2 | 12/2017 | Saxty et al. |
| 9,856,236 B2 | 1/2018 | Saxty et al. |
| 9,902,714 B2 | 2/2018 | Vermeulen |
| 2003/0207886 A1 | 11/2003 | Plucker et al. |
| 2005/0261307 A1 | 11/2005 | Cai et al. |
| 2005/0272728 A1 | 12/2005 | Altenbach et al. |
| 2005/0272736 A1 | 12/2005 | Altenbach et al. |
| 2007/0123494 A1 | 5/2007 | Seipelt et al. |
| 2007/0149484 A1 | 6/2007 | Claus et al. |
| 2008/0116789 A1 | 5/2008 | Yamaguchi et al. |
| 2009/0054304 A1 | 2/2009 | Herbert et al. |
| 2009/0118261 A1 | 5/2009 | Aquila et al. |
| 2009/0221591 A1 | 9/2009 | Hartmann et al. |
| 2010/0228026 A1 | 9/2010 | Yoshida et al. |
| 2010/0234347 A1 | 9/2010 | Dollinger et al. |
| 2011/0123545 A1 | 5/2011 | Marsh et al. |
| 2013/0072457 A1 | 3/2013 | Saxty et al. |
| 2013/0267525 A1 | 10/2013 | Saxty et al. |
| 2014/0288053 A1 | 9/2014 | Berdini et al. |
| 2014/0296236 A1 | 10/2014 | Berdini et al. |
| 2015/0031669 A1 | 1/2015 | Woodhead et al. |
| 2015/0031703 A1 | 1/2015 | Suzuki et al. |
| 2015/0057293 A1 | 2/2015 | Angibaud et al. |
| 2015/0105368 A1 | 4/2015 | Saxty et al. |
| 2015/0203589 A1 | 7/2015 | Iavarone et al. |
| 2015/0239883 A1 | 8/2015 | Angibaud et al. |
| 2015/0291589 A1 | 10/2015 | Saxty et al. |
| 2016/0031856 A1 | 2/2016 | Saxty et al. |
| 2016/0075666 A1 | 3/2016 | Angibaud et al. |
| 2016/0108034 A1 | 4/2016 | Angibaud et al. |
| 2016/0213677 A1 | 7/2016 | Angibaud et al. |
| 2016/0235744 A1 | 8/2016 | Berdini et al. |
| 2016/0287699 A1 | 10/2016 | Karkera et al. |
| 2016/0311800 A1 | 10/2016 | Saxty et al. |
| 2017/0000781 A1 | 1/2017 | Berdini et al. |
| 2017/0000796 A1 | 1/2017 | Saxty et al. |
| 2017/0100406 A1 | 4/2017 | Jovcheva et al. |
| 2017/0101396 A1 | 4/2017 | Vermeulen et al. |
| 2017/0105978 A1 | 4/2017 | Angibaud et al. |
| 2017/0119763 A1 | 5/2017 | Jovcheva et al. |
| 2018/0021332 A1 | 1/2018 | Broggini |
| 2018/0127397 A1 | 5/2018 | Saxty et al. |

FOREIGN PATENT DOCUMENTS

| | | |
|---|---|---|
| CN | 1128496A A | 8/1996 |
| CN | 102036963 A | 4/2011 |
| EP | 0544445 A2 | 6/1993 |
| EP | 1001946 | 5/2000 |
| EP | 1990342 | 11/2008 |
| EP | 2332939 | 6/2011 |
| EP | 2650293 A1 | 10/2013 |
| JP | 2003213463 A | 7/2003 |
| JP | 2006516561 A | 7/2006 |
| JP | 2008530030 A | 8/2008 |
| JP | 2008540535 A | 11/2008 |
| JP | 2010514693 A | 5/2010 |
| RU | 2377241 C2 | 12/2009 |
| WO | 94/26723 A2 | 11/1994 |
| WO | 95/19169 A2 | 7/1995 |
| WO | 98/54156 A1 | 12/1998 |
| WO | 99/17759 A2 | 4/1999 |
| WO | 00/42026 A1 | 7/2000 |
| WO | 01/19825 A1 | 2/2001 |
| WO | 01/68047 A2 | 9/2001 |
| WO | 02/076985 A1 | 10/2002 |
| WO | 03/051833 A2 | 6/2003 |
| WO | 03/055491 A1 | 7/2003 |
| WO | 03/086394 A1 | 10/2003 |
| WO | 2004/006355 A2 | 1/2004 |
| WO | 2004/030635 A2 | 4/2004 |
| WO | 2004/043950 A1 | 5/2004 |
| WO | 2004/056822 A1 | 7/2004 |
| WO | 2004065378 A1 | 8/2004 |
| WO | 2004/098494 A2 | 11/2004 |
| WO | 2004/110350 A2 | 12/2004 |
| WO | 2005/007099 A2 | 1/2005 |
| WO | 2005/009437 A1 | 2/2005 |
| WO | 2005/012288 A1 | 2/2005 |
| WO | 2005/039587 A1 | 5/2005 |
| WO | 2005/047244 A2 | 5/2005 |
| WO | 2005/054201 A1 | 6/2005 |
| WO | 2005054231 A1 | 6/2005 |
| WO | 2005/061463 A1 | 7/2005 |
| WO | 2006/040052 A1 | 4/2006 |
| WO | 2006/066361 A1 | 6/2006 |
| WO | 2006084338 A1 | 8/2006 |
| WO | 2006/092430 A1 | 9/2006 |
| WO | 2006124354 A2 | 11/2006 |
| WO | 2007/003419 A1 | 1/2007 |
| WO | 2007/023186 A1 | 3/2007 |
| WO | 2007054556 A1 | 5/2007 |
| WO | 2007/075567 A1 | 7/2007 |
| WO | 2007/125405 A2 | 11/2007 |
| WO | 2007/132227 A1 | 11/2007 |
| WO | 2008/003702 A2 | 1/2008 |
| WO | 2008/076278 A1 | 6/2008 |
| WO | 2008/078091 A1 | 7/2008 |
| WO | 2008/082198 A1 | 7/2008 |
| WO | 2008079988 A2 | 7/2008 |
| WO | 2008080015 A2 | 7/2008 |
| WO | 2008/138878 A2 | 11/2008 |
| WO | 2008/141065 A1 | 11/2008 |
| WO | 2008/148867 A2 | 12/2008 |
| WO | 2008/150827 A1 | 12/2008 |
| WO | 2008/155378 A1 | 12/2008 |
| WO | 2009/019518 A1 | 2/2009 |

(56) References Cited

FOREIGN PATENT DOCUMENTS

| | | |
|---|---|---|
| WO | 2009/021083 A1 | 2/2009 |
| WO | 2009/064835 A1 | 5/2009 |
| WO | 2009/137378 A1 | 11/2009 |
| WO | 2009/141386 A1 | 11/2009 |
| WO | 2010059771 A1 | 5/2010 |
| WO | 2010/084152 A1 | 7/2010 |
| WO | 2010088177 A1 | 8/2010 |
| WO | 2010129570 A1 | 11/2010 |
| WO | 2011/026579 A1 | 3/2011 |
| WO | 2011/028947 A2 | 3/2011 |
| WO | 2011/064250 A1 | 6/2011 |
| WO | 2011/126903 A2 | 10/2011 |
| WO | 2011/135376 A1 | 11/2011 |
| WO | 2011/146591 A1 | 11/2011 |
| WO | 2011/149937 A1 | 12/2011 |
| WO | 2012/073017 A1 | 6/2012 |
| WO | 2012/104776 A1 | 8/2012 |
| WO | 2012/118492 A1 | 9/2012 |
| WO | 2012/148540 A1 | 11/2012 |
| WO | 2013/032951 A1 | 3/2013 |
| WO | 2013/040515 A1 | 3/2013 |
| WO | 2013/043935 A1 | 3/2013 |
| WO | 2013/052699 A2 | 4/2013 |
| WO | 2013/061074 A1 | 5/2013 |
| WO | 2013/061077 A1 | 5/2013 |
| WO | 2013/061080 A1 | 5/2013 |
| WO | 2013/061081 A1 | 5/2013 |
| WO | 2013/061305 A1 | 5/2013 |
| WO | 2013/063217 A1 | 5/2013 |
| WO | 2013/179033 A1 | 12/2013 |
| WO | 2013/179034 A1 | 12/2013 |
| WO | 2014/174307 A1 | 10/2014 |
| WO | 2015144803 A1 | 10/2015 |
| WO | 2015144804 A1 | 10/2015 |
| WO | 2015144808 A1 | 10/2015 |
| WO | 2016128411 A1 | 8/2016 |
| WO | 2016/161239 A1 | 10/2016 |

OTHER PUBLICATIONS

GB Search Report for GB1118654.1 dated Feb. 27, 2012.
Yan, Lin et al. "An efficient synthesis of quinoxaline derivatives from 4-chloro-4-deoxy-α-D-galactose and their cytotoxic activities", *Bioorganic & Medicinal Chemistry Letters*, vol. 17, No. 3, 2006, pp. 609-612.
Thompson, Andrew M. et al. "Synthesis and Structure—Activity Relationships of 7-Substituted 3-(2,6-Dichlorophenyl)-1,6-napthyridin-2(1H)-ones as Selective Inhibitors of pp60$^{c-src}$", *Journal of Medicinal Chemistry*, vol. 43, No. 16, 2000, pp. 3134-3147.
Berge, Stephen M. et al. "Pharmaceutical Salts", *Journal of Pharmaceutical Sciences*, vol. 66, No. 1, 1977, pp. 1-19.
Deady, Leslie W. "Ring Nitrogen Oxidation of Amino Substituted Nitrogen Heterocycles with m-Chloroperbenzoic Acid", *Synthetic Communications*, vol. 7(8), 1977, pp. 509-514.
Knights, Victoria et al. "De-regulated FGF receptors as therapeutic targets in cancer", *Pharmacology & Therapeutics*, 2010; vol. 125(1), pp. 105-117.
Korc, M. et al. "The Role of Fibroblast Growth Factors in Tumor Growth", *Current Cancer Drug Targets*, vol. 9(5), 2009, pp. 639-651.
Angerer, Lynne M. et al. "Demonstration of Tissue-Specific Gene Expression by in Situ Hybridization", *Methods in Enzymology*, vol. 152, 1987, pp. 649-661.
Deprimo, Samuel E. et al. "Expression profiling of blood samples from an SU5416 Phase III metastatic colorectal cancer clinical trial: a novel strategy for biomarker identification", *BMC Cancer*, vol. 3, 2003; pp. 1-12.
Orre, Maxine and Rogers, Peter A.W. "VEGF, VEGFR-1, VEGFR-2, Microvessel Density and Endothelial Cell Proliferation in Tumours of the Ovary", *Int. J. Cancer (Pred. Oncol.)*, vol. 84(2), 1999, pp. 101-108.
Zhou, Wenjun et al., "A Structure-Guided Approach to Creating Covalent FGFR Inhibitors", *Chemistry & Biology*, vol. 17, pp. 285-295 (2010).
Avendaño, C., et al., "Drugs That Inhibit Signalling Pathways for Tumor Cell Growth and Proliferation", *Medicinal Chemistry of Anticancer Drugs*, pp. 251-305 (2008).
Garuti, L., et al., Irreversible Protein Kinase Inhibitors, *Current Medicinal Chemistry*, vol. 18, No. 20, Jul. 1, 2011, pp. 2981-2994.
Vippagunta, S.R. et al., Crystalline Solids, *Advanced Drug Delivery Reviews*, vol. 48, pp. 3-26 (2001).
Jordan, V.C., Tamoxifen: A Most Unlikely Pioneering Medicine, *Nature Reviews: Drug Discovery*, vol. 2, pp. 205-213 (2003).
Hackam, D.G., et al., Translation of Research Evidence From Animals to Humans, *JAMA*, vol. 14, pp. 1731-1732 (2006).
"Himicheskaja jenciklopedija" tom 4, str. 990-993, izdatel'stvo "Sovetskaja jencklopedija", Moskva, 1988 (In English: Chemical Encyclopedia, vol. 4, pp. 990-993, Publishing House "Soviet encyclopedia", Moscow, 1988).
V. Hikkinvottom, "Reakcii Organicheskih Soedinenij" Gosudarstvennoe ob#eninennoe nauchno-technicheskoe izdatel'stvo, Redakcija himicheskoj literatury, Moskva, stranicy 360-362, 1939 (In English: V. Hikkinbottom, "Reactions of Organic Compounds", State Associated Scientific-Technical Publishing House, Editor Office of Chemical Literature, pp. 360-362, Moscow, 1939).
"Himicheskaja jenciklopedija" tom. 1, stranicy 242-243, izdatel'stvo "Sovetskaja jencklopedija", Moskva, 1988 (In English: Chemical Encyclopedia (thesaurus), vol. 1, pp. 242-243, publishing house "Soviet encyclopedia", Moscow, 1988).
Dorwald, F.Z., Side Reactions in Organic Synthesis: A Guide to Successful Synthesis Design, Weinheim:Wiley-VCH Verlag GmbH & Co. KGaA, 2005, ISBN: 3-527-31021.5.
Lima, L.M., et al., "Bioisosterism: A Useful Strategy for Molecular Modification and Drug Design", *Current Medical Chemistry*, vol. 12(1), pp. 23-49 (2005).
Patani, G.A., et al., "Bioisosterism: A Rational Approach in Drug Design", *Chem. Rev.* vol. 96, pp. 3147-3176 (1996).
Dieci, M.V., et al., Fibroblast Growth Factor Receptor Inhibitors as a Cancer Treatment: From a Biologic Rationale to Medical Perspectives, Cancer Discovery, vol. 3, No. 3, pp. 264-279 (Feb. 2013).
Gallick, G.E., et al., Small-molecule protein tyrosine kinase inhibitors for the treatment of metastatic prostate cancer, Future Medicinal Chemistry, vol. 4, No. 1, pp. 107-119 (Jan. 2012).
Study to Assess the Relative Bioavailability of Orally Administered JNJ-42756493 Tablet Versus JNJ-42756493 Capsule in Healthy Participants, ClinicalTrials.gov, pp. 1-4 (2014).
Matsuda, Y., et al., Fibroblast Growth Factor Receptor-2 IIIc as a Novel Molecular Target in Colorectal Cancer, Current Colorectal Cancer Reports, vol. 10, No. 1, pp. 20-26 (2014).
Carneiro, B.A., et al., Emerging therapeutic targets in bladder cancer, Cancer Treatment Reviews, vol. 41, No. 2, pp. 170-178 (2015).
Fujita, M., et al., Generation of Formaldehyde by Pharmaceutical Excipients and Its Absorption by Meglumine, Chem. Pharm. Bull, vol. 57, No. 10, pp. 1096-1099 (2009).
Adcock, J., et al., Diversity oriented synthesis: substitution at C5 in unreactive pyrimidines by Claisen rearrangement and reactivity in nucleophilic substitution at C2 and C4 in pteridines and pyrido [2,3-d]pyrimidines, Tetrahedron, vol. 67, pp. 3226-3237 (2011).
Database Caplus, Grina, et al., Preparation of oxohydroquinazolinylaminophenylpropanesulfonamide derivatives and analogs for use as Raf inhibitors, Document No. 157:465574, Accession No. 2012:1301209 (2012).
Liang, G., et al., "Small molecule inhibition of fibroblast growth factor receptors in cancer", Cytokine & Growth Factor Reviews, vol. 24, pp. 467-475 (2013).
Golub, T.R., et al., "Molecular Classification of Cancer: Class Discovery and Class Prediction by Gene Expression Monitoring", Science, vol. 286, pp. 531-537 (1999).
Greulich, H., et al., "Targeting mutant fibroblast growth factor receptors in cancer", Trends in Molecular Medicine, vol. 17, No. 5, pp. 283-292 (2011).

(56) References Cited

OTHER PUBLICATIONS

Freshney, R.I., "Culture of Animal Cells, A Manual of Basic Technique", Published by Alan R. Liss, Inc, New York, pp. 1-6 (1983).
Cohen, P., "The development and therapeutic potential of protein kinase inhibitors", Current Opinion in Chemical Biology, vol. 3, pp. 459-465 (1999).
Cecil Textbook of Medicine, edited by Bennet, J.C., and Plum, F., 20th edition, vol. 1, pp. 1004-1010 (1996).
Hynes, N.E., et al., "Potential for Targeting the Fibroblast Growth Factor Receptors in Breast Cancer", Cancer Research, vol. 70, pp. 5199-5202 (2010).
Neidle, S., "Cancer Drug Design and Discovery", Elsevier/Academic Press, pp. 427-431 (2008).
Dermer, G.B., "Another Anniversary for the War on Cancer", Biotechnology, vol. 12, p. 320 (1994).
Katoh, Y., et al., "FGFR2-related pathogenesis and FGFR2-targeted therapeutics (Review)", International Journal of Molecular Medicine, vol. 23, pp. 307-311 (2009).
Jain, V.K., et al., "Challenges and opportunities in the targeting of fibroblast growth factor receptors in breast cancer", Breast Cancer Research, vol. 14, No. 208, pp. 1-9 (2012).
Ho, H.K., et al., "Current strategies for inhibiting FGFR activities in clinical applications: opportunities, challenges and toxicological considerations", Drug Discovery Today, vol. 19, Issue 1, pp. 51-62 (2014).
Sonpavde, G., et al., "Fibroblast growth factor receptors as therapeutic targets in clear-cell renal cell carcinoma", Expert Opinion on Investigational Drugs, vol. 23, Issue 3, pp. 305-315 (2014).
Rodriguez-Vida, A., et al., "Complexity of FGFR signaling in metastatic urothelial cancer", Journal of Hematology & Oncology, vol. 8, p. 119 et seq. (2015).

SUBSTITUTED QUINOXALINES AS FGFR KINASE INHIBITORS

CROSS REFERENCE TO RELATED APPLICATIONS

This application is a continuation application of U.S. application Ser. No. 14/354,636 filed on Apr. 28, 2014, which was a U.S. national phase entry under § 371 of International Application No. PCT/GB2012/052673 filed on Oct. 26, 2012, and published in English as WO 2013/061081 A1 on May 2, 2013, and claims priority to British Application No. 1118654.1 filed on Oct. 28, 2011 and to U.S. Provisional Application No. 61/552,873 filed on Oct. 28, 2011. The entire disclosures of each of the prior applications are hereby incorporated herein by reference.

FIELD OF THE INVENTION

The invention relates to new quinoxaline derivative compounds, to pharmaceutical compositions comprising said compounds, to processes for the preparation of said compounds and to the use of said compounds in the treatment of diseases, e.g. cancer.

SUMMARY OF THE INVENTION

According to a first aspect of the invention there is provided compounds of formula (I):

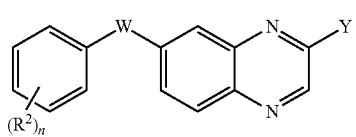

(I)

including any tautomeric or stereochemically isomeric form thereof, wherein W is —N($R^3$)— or —C($R^{3a}R^{3b}$)—;
each $R^2$ is independently selected from hydroxyl, halogen, cyano, $C_{1-4}$alkyl, $C_{2-4}$alkenyl, $C_{2-4}$alkynyl, $C_{1-4}$alkoxy, hydroxy$C_{1-4}$alkyl, hydroxy$C_{1-4}$alkoxy, halo$C_{1-4}$alkyl, halo$C_{1-4}$alkoxy, hydroxyhalo$C_{1-4}$alkyl, hydroxyhalo$C_{1-4}$alkoxy, $C_{1-4}$alkoxy$C_{1-4}$alkyl, halo$C_{1-4}$alkoxy$C_{1-4}$alkyl, $C_{1-4}$alkoxy$C_{1-4}$alkyl wherein each $C_{1-4}$alkyl may optionally be substituted with one or two hydroxyl groups, hydroxyhalo$C_{1-4}$alkoxy$C_{1-4}$alkyl, $R^{13}$, $C_{1-4}$alkyl substituted with $R^{13}$, $C_{1-4}$alkyl substituted with —C(=O)—$R^{13}$, $C_{1-4}$alkoxy substituted with $R^{13}$, $C_{1-4}$alkoxy substituted with —C(=O)—$R^{13}$, —C(=O)—$R^{13}$, $C_{1-4}$alkyl substituted with —$NR^7R^8$, $C_{1-4}$alkyl substituted with —C(=O)—$NR^7R^8$, $C_{1-4}$alkoxy substituted with —$NR^7R^8$, $C_{1-4}$alkoxy substituted with —C(=O)—$NR^7R^8$, —$NR^7R^8$ and —C(=O)—$NR^7R^8$; or when two $R^2$ groups are attached to adjacent carbon atoms they may be taken together to form a radical of formula:
—O—(C($R^{17}$)$_2$)$_p$—O—;
—X—CH=CH—; or
—X—CH=N—; wherein $R^{17}$ represents hydrogen or fluorine, p represents 1 or 2 and X represents O or S;
Y represents —C$R^{18}$=N—O$R^{19}$ or -E-D;
E represents a bond, —(C$R^{22}R^{23}$)$_n$—, $C_{2-4}$alkenediyl optionally substituted with $R^{22}$, $C_{2-4}$alkynediyl optionally substituted with $R^{22}$, —CO—(C$R^{22}R^{23}$)$_s$—, —(C$R^{22}R^{23}$)$_s$—CO—, —$NR^{22}$—(C$R^{22}R^{23}$)$_s$—, —(C$R^{22}R^{23}$)$_s$—$NR^{22}$—, —O—(C$R^{22}R^{23}$)$_s$—, —(C$R^{22}R^{23}$)$_s$—O—, —S(O)$_m$—(C$R^{22}R^{23}$)$_s$—, —(C$R^{22}R^{23}$)$_s$—S(O)$_m$—, —(C$R^{22}R^{23}$)$_s$—CO—$NR^{22}$—(C$R^{22}R^{23}$)$_s$— or —(C$R^{22}R^{23}$)$_s$—$NR^{22}$—CO—(C$R^{22}R^{23}$)$_s$—;
D represents a 3 to 12 ring membered monocyclic or bicyclic carbocyclyl or a 3 to 12 ring membered monocyclic or bicyclic heterocyclyl containing at least one heteroatom selected from N, O or S, wherein said carbocyclyl and heterocyclyl may each be optionally substituted by one or more (e.g. 1, 2 or 3) $R^1$ groups;
provided that when Y represents -E-D, and E represents a bond, then D does not represent

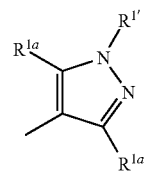

wherein $R^{1'}$ represents hydrogen, $C_{1-6}$alkyl, $C_{2-4}$alkenyl, hydroxy$C_{1-6}$alkyl, halo$C_{1-6}$alkyl, hydroxyhalo$C_{1-6}$alkyl, cyano$C_{1-4}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —C(=O)—$NR^4R^5$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^6$, $C_{1-6}$alkyl substituted with $R^6$, $C_{1-6}$alkyl substituted with —C(=O)—$R^6$, hydroxy$C_{1-6}$alkyl substituted with $R^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$; and each $R^{1a}$ is independently selected from hydrogen, $C_{1-4}$alkyl, hydroxy$C_{1-4}$alkyl, $C_{1-4}$alkyl substituted with amino or mono- or di($C_{1-4}$alkyl)amino or —NH($C_{3-8}$cycloalkyl), cyano$C_{1-4}$alkyl, $C_{1-4}$alkoxy$C_{1-4}$alkyl, and $C_{1-4}$alkyl substituted with one or more fluoro atoms;
$R^1$ represents hydrogen, halo, cyano, $C_{1-6}$alkyl, $C_{1-6}$alkoxy, —C(=O)—O—$C_{1-6}$alkyl, $C_{2-4}$alkenyl, hydroxy$C_{1-6}$alkyl, halo$C_{1-6}$alkyl, hydroxyhalo$C_{1-6}$alkyl, cyano$C_{1-4}$alkyl, $C_{1-6}$alkoxy$C_{1-6}$alkyl wherein each $C_{1-6}$alkyl may optionally be substituted with one or two hydroxyl groups, —$NR^4R^5$, $C_{1-6}$alkyl substituted with —O—C(=O)—$C_{1-6}$alkyl, $C_{1-6}$alkyl substituted with —$NR^4R^5$, —C(=O)—$NR^4R^5$, —C(=O)—$C_{1-6}$alkyl-$NR^4R^5$, $C_{1-6}$alkyl substituted with —C(=O)—$NR^4R^5$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^6$, $C_{1-6}$alkyl substituted with $R^6$, —C(=O)—$R^6$, $C_{1-6}$alkyl substituted with —C(=O)—$R^6$, hydroxy$C_{1-6}$alkyl substituted with $R^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$;
$R^{3a}$ represents —$NR^{10}R^{11}$, hydroxyl, $C_{1-6}$alkoxy, hydroxy$C_{1-6}$alkoxy, $C_{1-6}$alkoxy substituted with —NR$^{10}$R$^{11}$, C$_{1-6}$alkyl, C$_{2-6}$alkenyl, C$_{2-6}$alkynyl, haloC$_{1-6}$alkyl optionally substituted with —O—C(=O)—C$_{1-6}$alkyl, hydroxyC$_{1-6}$alkyl optionally substituted with —O—C(=O)—C$_{1-6}$alkyl, hydroxyC$_{2-6}$alkenyl, hydroxyC$_{2-6}$alkynyl, hydroxyhaloC$_{1-6}$alkyl, cyanoC$_{1-6}$alkyl, C$_{1-6}$alkyl substituted with carboxyl, C$_{1-6}$alkyl substituted with —C(=O)—C$_{1-6}$alkyl, C$_{1-6}$alkyl substituted with —C(=O)—O—C$_{1-6}$alkyl, C$_{1-6}$alkyl substituted with C$_{1-6}$alkoxyC$_{1-6}$alkyl-O—C(=O)—, C$_{1-6}$alkyl substituted with C$_{1-6}$alkoxyC$_{1-6}$alkyl-C(=O)—, C$_{1-6}$alkyl substituted with —O—C(=O)—C$_{1-6}$alkyl, C$_{1-6}$alkoxyC$_{1-6}$alkyl wherein each C$_{1-6}$alkyl may optionally be substituted with one or two hydroxyl groups or with —O—C(=O)—C$_{1-6}$alkyl, C$_{2-6}$alkenyl substituted with C$_{1-6}$alkoxy, C$_{2-6}$alkynyl substituted with C$_{1-6}$alkoxy, C$_{1-6}$alkyl substituted with R$^9$ and optionally substituted with —O—C(=O)—C$_{1-6}$alkyl, C$_{1-6}$alkyl substituted with —C(=O)—R$^9$, C$_{1-6}$alkyl substituted with hydroxyl and R$^9$, C$_{2-6}$alkenyl substituted with R$^9$, C$_{2-6}$alkynyl substituted with R$^9$, C$_{1-6}$alkyl substituted with —NR$^{10}$R$^{11}$, C$_{2-6}$alkenyl substituted with —NR$^{10}$R$^{11}$, C$_{2-6}$alkynyl substituted with —NR$^{10}$R$^{11}$, C$_{1-6}$alkyl substituted with hydroxyl and —NR$^{10}$R$^{11}$, C$_{1-6}$alkyl substituted with one or two halogens and —NR$^{10}$R$^{11}$, —C$_{1-6}$alkyl-C(R$^{12}$)=N—O—R$^{12}$, C$_{1-6}$alkyl substituted with —C(=O)—NR$^{10}$R$^{11}$, C$_{1-6}$alkyl substituted with —O—C(=O)—NR$^{10}$R$^{11}$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NR$^{12}$—S(=O)$_2$—C$_{1-6}$alkyl, C$_{1-6}$alkyl substituted with —NH—S(=O)$_2$-haloC$_{1-6}$alkyl, C$_{1-6}$alkyl substituted with —NR$^{12}$—S(=O)$_2$—NR$^{14}$R$^{15}$, R$^{13}$, C$_{1-6}$alkyl substituted with —P(=O)(OH)$_2$ or C$_{1-6}$alkyl substituted with —P(=O)(OC$_{1-6}$alkyl)$_2$;

R$^{3b}$ represents hydrogen or hydroxyl; provided that if R$^{3a}$ represents —NR$^{10}$R$^{11}$, then R$^{3b}$ represents hydrogen; or R$^{3a}$ and R$^{3b}$ are taken together to form =O, to form =NR$^{10}$, to form cyclopropyl together with the carbon atom to which they are attached, to form =CH—C$_{0-4}$alkyl substituted with R$^{3c}$, or to form

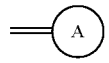

wherein ring A is a monocyclic 5 to 7 membered saturated heterocycle containing one heteroatom selected from N, O or S, said heteroatom not being positioned in alpha position of the double bond, wherein ring A is optionally being substituted with cyano, C$_{1-4}$alkyl, hydroxyC$_{1-4}$alkyl, H$_2$N—C$_{1-4}$alkyl, (C$_{1-4}$alkyl)NH—C$_{1-4}$alkyl, (C$_{1-4}$alkyl)$_2$N—C$_{1-4}$alkyl, haloC$_{1-4}$alkyl)NH—C$_{1-4}$alkyl, C$_{1-4}$alkoxyC$_{1-4}$alkyl, —C(=O)—NH$_2$, —C(=O)—NH(C$_{1-4}$alkyl), —C(=O)—N(C$_{1-4}$alkyl)$_2$;

R$^{3c}$ represents hydrogen, hydroxyl, C$_{1-6}$alkoxy, R$^9$, —NR$^{10}$R$^{11}$, cyano, —C(=O)—C$_{1-6}$alkyl or —CH(OH)—C$_{1-6}$alkyl;

R$^3$ represents hydroxyl, C$_{1-6}$alkoxy, hydroxyC$_{1-6}$alkoxy, C$_{1-6}$alkoxy substituted with —NR$^{10}$R$^{11}$, C$_{1-6}$alkyl, C$_{2-6}$alkenyl, C$_{2-6}$alkynyl, haloC$_{1-6}$alkyl optionally substituted with —O—C(=O)—C$_{1-6}$alkyl, hydroxyC$_{1-6}$alkyl optionally substituted with —O—C(=O)—C$_{1-6}$alkyl, hydroxyC$_{2-6}$alkenyl, hydroxyC$_{2-6}$alkynyl, hydroxyhaloC$_{1-6}$alkyl, cyanoC$_{1-6}$alkyl, C$_{1-6}$alkyl substituted with carboxyl, C$_{1-6}$alkyl substituted with —C(=O)—C$_{1-6}$alkyl, C$_{1-6}$alkyl substituted with —C(=O)—O—C$_{1-6}$alkyl, C$_{1-6}$alkyl substituted with C$_{1-6}$alkoxyC$_{1-6}$alkyl-O—C(=O)—, C$_{1-6}$alkyl substituted with C$_{1-6}$alkoxyC$_{1-6}$alkyl-C(=O)—, C$_{1-6}$alkyl substituted with —O—C(=O)—C$_{1-6}$alkyl, C$_{1-6}$alkoxy C$_{1-6}$alkyl wherein each C$_{1-6}$alkyl may optionally be substituted with one or two hydroxyl groups or with —O—C(=O)—C$_{1-6}$alkyl, C$_{2-6}$alkenyl substituted with C$_{1-6}$alkoxy, C$_{2-6}$alkynyl substituted with C$_{1-6}$alkoxy, C$_{1-6}$alkyl substituted with R$^9$ and optionally substituted with —O—C(=O)—C$_{1-6}$alkyl, C$_{1-6}$alkyl substituted with —C(=O)—R$^9$, C$_{1-6}$alkyl substituted with hydroxyl and R$^9$, C$_{2-6}$alkenyl substituted with R$^9$, C$_{2-6}$alkynyl substituted with R$^9$, C$_{1-6}$alkyl substituted with —NR$^{10}$R$^{11}$, C$_{2-6}$alkenyl substituted with —NR$^{10}$R$^{11}$, C$_{2-6}$alkynyl substituted with —NR$^{10}$R$^{11}$, C$_{1-6}$alkyl substituted with hydroxyl and —NR$^{10}$R$^{11}$, C$_{1-6}$alkyl substituted with one or two halogens and —NR$^{10}$R$^{11}$, —C$_{1-6}$alkyl-C(R$^{12}$)=N—O—R$^{12}$, C$_{1-6}$alkyl substituted with —C(=O)—NR$^{10}$R$^{11}$, C$_{1-6}$alkyl substituted with —O—C(=O)—NR$^{10}$R$^{11}$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NR$^{12}$—S(=O)$_2$—C$_{1-6}$alkyl, C$_{1-6}$alkyl substituted with —NH—S(=O)$_2$-haloC$_{1-6}$alkyl, C$_{1-6}$alkyl substituted with —NR$^{12}$—S(=O)$_2$—NR$^{14}$R$^{15}$, R$^{13}$, C$_{1-6}$alkyl substituted with —P(=O)(OH)$_2$ or C$_{1-6}$alkyl substituted with —P(=O)(OC$_{1-6}$alkyl)$_2$;

R$^4$ and R$^5$ each independently represent hydrogen, C$_{1-6}$alkyl, C$_{1-6}$alkyl substituted with —NR$^{14}$R$^{15}$, hydroxyC$_{1-6}$alkyl, haloC$_{1-6}$alkyl, hydroxyhaloC$_{1-6}$alkyl, C$_{1-6}$alkoxyC$_{1-6}$alkyl wherein each C$_{1-6}$alkyl may optionally be substituted with one or two hydroxyl groups, —S(=O)$_2$—C$_{1-6}$alkyl, —S(=O)$_2$-haloC$_{1-6}$alkyl, —S(=O)$_2$—NR$^{14}$R$^{15}$, —C(=O)—NR$^{14}$R$^{15}$, —C(=O)—O—C$_{1-6}$alkyl, —C(=O)—R$^{13}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl, C$_{1-6}$alkyl substituted with —NH—S(=O)$_2$—NR$^{14}$R$^{15}$, R$^{13}$ or C$_{1-6}$alkyl substituted with R$^{13}$;

R$^6$ represents C$_{3-8}$cycloalkyl, C$_{3-8}$cycloalkenyl, phenyl, 4 to 7-membered monocyclic heterocyclyl containing at least one heteroatom selected from N, O or S; said C$_{3-8}$cycloalkyl, C$_{3-8}$cycloalkenyl, phenyl, 4 to 7-membered monocyclic heterocyclyl, optionally and each independently being substituted by 1, 2, 3, 4 or 5 substituents, each substituent independently being selected from cyano, C$_{1-6}$alkyl, cyanoC$_{1-6}$alkyl, hydroxyl, carboxyl, hydroxyC$_{1-6}$alkyl, halogen, haloC$_{1-6}$alkyl, hydroxyhaloC$_{1-6}$alkyl, C$_{1-6}$alkoxy, C$_{1-6}$alkoxyC$_{1-6}$alkyl, C$_{1-6}$alkyl-O—C(=O)—, —NR$^{14}$R$^{15}$, —C(=O)—NR$^{14}$R$^{15}$, C$_{1-6}$alkyl substituted with —NR$^{14}$R$^{15}$, C$_{1-6}$alkyl substituted with —C(=O)—NR$^{14}$R$^{15}$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl or C$_{1-6}$alkyl substituted with —NH—S(=O)$_2$—NR$^{14}$R$^{15}$;

R$^7$ and R$^8$ each independently represent hydrogen, C$_{1-6}$alkyl, hydroxyC$_{1-6}$alkyl, haloC$_{1-6}$alkyl, hydroxyhaloC$_{1-6}$alkyl or C$_{1-6}$alkoxyC$_{1-6}$alkyl;

R$^9$ represents C$_{3-8}$cycloalkyl, C$_{3-8}$cycloalkenyl, phenyl, naphthyl, or 3 to 12 membered monocyclic or bicyclic heterocyclyl containing at least one heteroatom selected from N, O or S, said $C_{3-8}$cycloalkyl, $C_{3-8}$cycloalkenyl, phenyl, naphthyl, or 3 to 12 membered monocyclic or bicyclic heterocyclyl each optionally and each independently being substituted with 1, 2, 3, 4 or 5 substituents, each substituent independently being selected from =O, $C_{1-4}$alkyl, hydroxyl, carboxyl, hydroxy$C_{1-4}$alkyl, cyano, cyano$C_{1-4}$alkyl, $C_{1-4}$alkyl-O—C(=O)—, $C_{1-4}$alkyl substituted with $C_{1-4}$alkyl-O—C(=O)—, $C_{1-4}$alkyl-C(=O)—, $C_{1-4}$alkoxy$C_{1-4}$alkyl wherein each $C_{1-4}$alkyl may optionally be substituted with one or two hydroxyl groups, halogen, halo$C_{1-4}$alkyl, hydroxyhalo$C_{1-4}$alkyl, —NR$^{14}$R$^{15}$, —C(=O)—NR$^{14}$R$^{15}$, $C_{1-4}$alkyl substituted with —NR$^{14}$R$^{15}$, $C_{1-4}$alkyl substituted with —C(=O)—NR$^{14}$R$^{15}$, $C_{1-4}$alkoxy, —S(=O)$_2$—$C_{1-4}$alkyl, —S(=O)$_2$-halo$C_{1-4}$alkyl, —S(=O)$_2$—NR$^{14}$R$^{15}$, $C_{1-4}$alkyl substituted with —S(=O)$_2$—NR$^{14}$R$^{15}$, $C_{1-4}$alkyl substituted with —NH—S(=O)$_2$—$C_{1-4}$alkyl, $C_{1-4}$alkyl substituted with —NH—S(=O)$_2$-halo$C_{1-4}$alkyl, $C_{1-4}$alkyl substituted with —NH—S(=O)$_2$—NR$^{14}$R$^{15}$, R$^{13}$, —C(=O)—R$^{13}$, $C_{1-4}$alkyl substituted with R$^{13}$, phenyl optionally substituted with R$^{16}$, phenyl$C_{1-6}$alkyl wherein the phenyl is optionally substituted with R$^{16}$, a 5 or 6-membered aromatic monocyclic heterocyclyl containing at least one heteroatom selected from N, O or S wherein said heterocyclyl is optionally substituted with R$^{16}$;

or when two of the substituents of R$^9$ are attached to the same atom, they may be taken together to form a 4 to 7-membered saturated monocyclic heterocyclyl containing at least one heteroatom selected from N, O or S;

R$^{10}$ and R$^{11}$ each independently represent hydrogen, carboxyl, $C_{1-6}$alkyl, cyano$C_{1-6}$alkyl, $C_{1-6}$alkyl substituted with —NR$^{14}$R$^{15}$, $C_{1-6}$alkyl substituted with —C(=O)—NR$^{14}$R$^{15}$, halo$C_{1-6}$alkyl, hydroxy$C_{1-6}$alkyl, hydroxyhalo$C_{1-6}$alkyl, $C_{1-6}$alkoxy, $C_{1-6}$alkoxy$C_{1-6}$alkyl wherein each $C_{1-6}$alkyl may optionally be substituted with one or two hydroxyl groups, R$^6$, $C_{1-6}$alkyl substituted with R$^6$, —C(=O)—R$^6$, —C(=O)—$C_{1-6}$alkyl, —C(=O)-hydroxy$C_{1-6}$alkyl, —C(=O)-halo$C_{1-6}$alkyl, —C(=O)-hydroxyhalo$C_{1-6}$alkyl, $C_{1-6}$alkyl substituted with —Si(CH$_3$)$_3$, —S(=O)$_2$—$C_{1-6}$alkyl, —S(=O)$_2$-halo$C_{1-6}$alkyl, —S(=O)$_2$—NR$^{14}$R$^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—NR$^{14}$R$^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with carboxyl, or $C_{1-6}$alkyl substituted with —NH—S(=O)$_2$—NR$^{14}$R$^{15}$;

R$^{12}$ represents hydrogen or $C_{1-4}$alkyl optionally substituted with $C_{1-4}$alkoxy;

R$^{13}$ represents $C_{3-8}$cycloalkyl or a saturated 4 to 6-membered monocyclic heterocyclyl containing at least one heteroatom selected from N, O or S, wherein said $C_{3-8}$cycloalkyl or monocyclic heterocyclyl is optionally substituted with 1, 2 or 3 substituents each independently selected from halogen, hydroxyl, $C_{1-6}$alkyl, halo$C_{1-6}$alkyl, =O, cyano, —C(=O)—$C_{1-6}$alkyl, $C_{1-6}$alkoxy, or —NR$^{14}$R$^{15}$;

R$^{14}$ and R$^{15}$ each independently represent hydrogen, or halo$C_{1-4}$alkyl, or $C_{1-4}$alkyl optionally substituted with a substituent selected from hydroxyl, $C_{1-4}$alkoxy, amino or mono- or di($C_{1-4}$alkyl)amino;

R$^{16}$ represents hydroxyl, halogen, cyano, $C_{1-4}$alkyl, $C_{1-4}$alkoxy, —NR$^{14}$R$^{15}$ or —C(=O)NR$^{14}$R$^{15}$;

R$^{18}$ represents hydrogen, $C_{1-6}$ alkyl, $C_{3-8}$ cycloalkyl, $C_{1-4}$alkyl substituted with $C_{3-8}$ cycloalkyl;

R$^{19}$ represents hydrogen; $C_{1-6}$ alkyl; $C_{3-8}$ cycloalkyl; $C_{1-6}$alkyl substituted with —O—R$^{20}$; —(CH$_2$)$_r$—CN; —(CH$_2$)$_r$—CONR$^{20}$R$^{21}$; —(CH$_2$)$_{r1}$—NR$^{20}$R$^{21}$; —(CH$_2$)$_{r1}$—NR$^{20}$COR$^{21}$; —(CH$_2$)$_{r1}$—NR$^{20}$ (CH$_2$)$_s$—SO$_2$—R$^{21}$; —(CH$_2$)$_{r1}$—NH—SO$_2$—NR$^{20}$R$^{21}$; —(CH$_2$)$_{r1}$—NR$^{20}$CO$_2$R$^{21}$; —(CH$_2$)$_r$SO$_2$NR$^{20}$R$^{21}$; phenyl optionally substituted with 1, 2, 3, 4 or 5 substituents each independently selected from halogen, $C_{1-4}$alkyl, $C_{1-4}$alkyloxy, cyano or amino; a 5- or 6-membered aromatic monocyclic heterocycle containing at least one heteroatom selected from N, O or S, said heterocycle being optionally substituted with 1, 2, 3 or 4 substituents each independently selected from halogen, $C_{1-4}$alkyl, $C_{1-4}$alkyloxy, cyano or amino; wherein said $C_{1-6}$ alkyl and $C_{3-8}$ cycloalkyl, may be optionally substituted by one or more R$^{20}$ groups R$^{20}$ and R$^{21}$ independently represent hydrogen, $C_{1-6}$ alkyl, hydroxy$C_{1-6}$alkyl, —(CH$_2$)$_n$—O—$C_{1-6}$alkyl, or when attached to a nitrogen atom R$^{20}$ and R$^{21}$ can be taken together to form with the nitrogen atom to which they are attached a monocyclic saturated 4, 5 or 6-membered ring which optionally contains a further heteroatom selected from O, S or N;

R$^{22}$ and R$^{23}$ independently represent hydrogen, $C_{1-6}$ alkyl, or hydroxy$C_{1-6}$alkyl;

m independently represents an integer equal to 0, 1 or 2;

n independently represents an integer equal to 0, 1, 2, 3 or 4;

s independently represents an integer equal to 0, 1, 2, 3 or 4;

r independently represent an integer equal to 1, 2, 3, or 4;

r1 independently represent an integer equal to 2, 3 or 4;

provided that when R$^{3a}$ and R$^{3b}$ are taken together to form =O, n=0, Y represents -E-D, and E represents a bond, then D does not represent unsubstituted phenyl;

the N-oxides thereof, the pharmaceutically acceptable salts thereof or the solvates thereof.

WO2006/092430, WO2008/003702, WO01/68047, WO2005/007099, WO2004/098494, WO2009/141386, WO 2004/030635, WO 2008/141065, WO 2011/026579, WO 2011/028947, WO2007/003419, WO 00/42026 and WO2011/135376 which each disclose a series of heterocyclyl derivatives.

DETAILED DESCRIPTION OF THE INVENTION

Unless the context indicates otherwise, references to formula (I) in all sections of this document (including the uses, methods and other aspects of the invention) include references to all other sub-formula, sub-groups, preferences, embodiments and examples as defined herein.

The prefix "$C_{x-y}$" (where x and y are integers) as used herein refers to the number of carbon atoms in a given group. Thus, a $C_{1-6}$alkyl group contains from 1 to 6 carbon atoms, a $C_{3-6}$cycloalkyl group contains from 3 to 6 carbon atoms, a $C_{1-4}$alkoxy group contains from 1 to 4 carbon atoms, and so on.

The term 'halo' or 'halogen' as used herein refers to a fluorine, chlorine, bromine or iodine atom.

The term '$C_{1-4}$alkyl', or '$C_{1-6}$alkyl' as used herein as a group or part of a group refers to a linear or branched saturated hydrocarbon group containing from 1 to 4 or 1 to 6 carbon atoms. Examples of such groups include methyl, ethyl, n-propyl, isopropyl, n-butyl, isobutyl, sec-butyl, tert-butyl, n-pentyl, isopentyl, neopentyl or hexyl and the like.

The term '$C_{2-4}$alkenyl' or '$C_{2-6}$alkenyl' as used herein as a group or part of a group refers to a linear or branched hydrocarbon group containing from 2 to 4 or 2 to 6 carbon atoms and containing a carbon carbon double bond.

The term '$C_{2-4}$alkenediyl' as used herein as a group or part of a group refers to a linear or branched bivalent hydrocarbon group containing from 2 to 4 carbon atoms and containing a carbon carbon double bond.

The term '$C_{2-4}$alkynyl' or '$C_{2-6}$alkynyl' as used herein as a group or part of a group refers to a linear or branched hydrocarbon group having from 2 to 4 or 2 to 6 carbon atoms and containing a carbon carbon triple bond.

The term '$C_{1-4}$alkoxy' or '$C_{1-6}$alkoxy' as used herein as a group or part of a group refers to an —O—$C_{1-4}$alkyl group or an —O—$C_{1-6}$alkyl group wherein $C_{1-4}$alkyl and $C_{1-6}$alkyl are as defined herein. Examples of such groups include methoxy, ethoxy, propoxy, butoxy, and the like.

The term '$C_{1-4}$alkoxy$C_{1-4}$alkyl' or '$C_{1-6}$alkoxy$C_{1-6}$alkyl' as used herein as a group or part of a group refers to a $C_{1-4}$alkyl-O—$C_{1-4}$alkyl group or a $C_{1-6}$alkyl-O—$C_{1-6}$alkyl group wherein $C_{1-4}$alkyl and $C_{1-6}$alkyl are as defined herein. Examples of such groups include methoxyethyl, ethoxyethyl, propoxymethyl, butoxypropyl, and the like.

The term '$C_{3-8}$cycloalkyl' as used herein refers to a saturated monocyclic hydrocarbon ring of 3 to 8 carbon atoms. Examples of such groups include cyclopropyl, cyclobutyl, cyclopentyl, cyclohexyl, cycloheptyl or cyclooctyl and the like.

The term '$C_{3-8}$cycloalkenyl' as used herein refers to a monocyclic hydrocarbon ring of 3 to 8 carbon atoms having a carbon carbon double bond.

The term 'hydroxy$C_{1-4}$alkyl' or 'hydroxy$C_{1-6}$alkyl' as used herein as a group or part of a group refers to a $C_{1-4}$alkyl or $C_{1-6}$alkyl group as defined herein wherein one or more than one hydrogen atom is replaced with a hydroxyl group. The terms 'hydroxy$C_{1-4}$alkyl' or 'hydroxy$C_{1-6}$alkyl' therefore include monohydroxy$C_{1-4}$alkyl, monohydroxy $C_{1-6}$alkyl and also polyhydroxy$C_{1-4}$alkyl and polyhydroxy$C_{1-6}$alkyl. There may be one, two, three or more hydrogen atoms replaced with a hydroxyl group, so the hydroxy$C_{1-4}$alkyl or hydroxy$C_{1-6}$alkyl may have one, two, three or more hydroxyl groups. Examples of such groups include hydroxymethyl, hydroxyethyl, hydroxypropyl and the like.

The term 'halo$C_{1-4}$alkyl' or 'halo$C_{1-6}$alkyl' as used herein as a group or part of a group refers to a $C_{1-4}$alkyl or $C_{1-6}$alkyl group as defined herein wherein one or more than one hydrogen atom is replaced with a halogen. The term 'halo $C_{1-4}$alkyl' or 'halo$C_{1-6}$alkyl' therefore include monohalo $C_{1-4}$alkyl, monohalo$C_{1-6}$alkyl and also polyhalo$C_{1-4}$alkyl and polyhalo$C_{1-6}$alkyl. There may be one, two, three or more hydrogen atoms replaced with a halogen, so the halo $C_{1-4}$alkyl or halo$C_{1-6}$alkyl may have one, two, three or more halogens. Examples of such groups include fluoroethyl, fluoromethyl, trifluoromethyl or trifluoroethyl and the like.

The term 'hydroxyhalo$C_{1-4}$alkyl' or 'hydroxyhalo $C_{1-6}$alkyl' as used herein as a group or part of a group refers to a $C_{1-4}$alkyl or $C_{1-6}$alkyl group as defined herein wherein one or more than one hydrogen atom is replaced with a hydroxyl group and one or more than one hydrogen atom is replaced with a halogen. The term 'hydroxyhalo$C_{1-4}$alkyl' or 'hydroxyhalo$C_{1-6}$alkyl' therefore refers to a $C_{1-4}$alkyl or $C_{1-6}$alkyl group wherein one, two, three or more hydrogen atoms are replaced with a hydroxyl group and one, two, three or more hydrogen atoms are replaced with a halogen.

The term 'hydroxy$C_{1-4}$alkoxy' or 'hydroxy$C_{1-6}$alkoxy' as used herein as a group or part of a group refers to an —O—$C_{1-4}$alkyl group or an —O—$C_{1-6}$alkyl group wherein the $C_{1-4}$alkyl and $C_{1-6}$alkyl group is as defined above and one or more than one hydrogen atom of the $C_{1-4}$alkyl or $C_{1-6}$alkyl group is replaced with a hydroxyl group. The term 'hydroxy$C_{1-4}$alkoxy' or 'hydroxy$C_{1-6}$alkoxy' therefore include monohydroxy$C_{1-4}$alkoxy, monohydroxy$C_{1-6}$alkoxy and also polyhydroxy$C_{1-4}$alkoxy and polyhydroxy $C_{1-6}$alkoxy. There may be one, two, three or more hydrogen atoms replaced with a hydroxyl group so the hydroxy $C_{1-4}$alkoxy or hydroxy$C_{1-6}$alkoxy may have one, two, three or more hydroxyl groups. Examples of such groups include hydroxymethoxy, hydroxyethoxy, hydroxypropoxy and the like.

The term 'halo$C_{1-4}$alkoxy' or 'halo$C_{1-6}$alkoxy' as used herein as a group or part of a group refers to a —O—$C_{1-4}$alkyl group or a —O—$C_{1-6}$ alkyl group as defined herein wherein one or more than one hydrogen atom is replaced with a halogen. The terms 'halo$C_{1-4}$alkoxy' or 'halo$C_{1-6}$alkoxy' therefore include monohalo$C_{1-4}$alkoxy, monohalo$C_{1-6}$alkoxy and also polyhalo$C_{1-4}$alkoxy and polyhalo$C_{1-6}$alkoxy. There may be one, two, three or more hydrogen atoms replaced with a halogen, so the halo $C_{1-4}$alkoxy or halo$C_{1-6}$alkoxy may have one, two, three or more halogens. Examples of such groups include fluoroethyloxy, difluoromethoxy or trifluoromethoxy and the like.

The term 'hydroxyhalo$C_{1-4}$alkoxy' as used herein as a group or part of a group refers to an —O—$C_{1-4}$alkyl group wherein the $C_{1-4}$alkyl group is as defined herein and wherein one or more than one hydrogen atom is replaced with a hydroxyl group and one or more than one hydrogen atom is replaced with a halogen. The term 'hydroxyhalo$C_{1-4}$alkoxy' therefore refers to a —O—$C_{1-4}$alkyl group wherein one, two, three or more hydrogen atoms are replaced with a hydroxyl group and one, two, three or more hydrogen atoms are replaced with a halogen.

The term 'halo$C_{1-4}$alkoxy$C_{1-4}$alkyl' as used herein as a group or part of a group refers to a $C_{1-4}$alkyl-O—$C_{1-4}$alkyl group wherein $C_{1-4}$alkyl is as defined herein and wherein in one or both of the $C_{1-4}$alkyl groups one or more than one hydrogen atom is replaced with a halogen. The term 'halo$C_{1-4}$ alkoxy$C_{1-4}$alkyl' therefore refers to a $C_{1-4}$alkyl-O—$C_{1-4}$alkyl group wherein in one or both of the $C_{1-4}$alkyl groups one, two, three or more hydrogen atoms are replaced with a halogen and wherein $C_{1-4}$ alkyl is as defined herein.

Preferably, in one of the $C_{1-4}$alkyl groups one or more than one hydrogen atom is replaced with a halogen. Preferably, halo$C_{1-4}$alkoxy$C_{1-4}$alkyl means $C_{1-4}$alkyl substituted with halo$C_{1-4}$alkoxy.

The term 'hydroxyhalo$C_{1-4}$alkoxy$C_{1-4}$alkyl' as used herein refers to a $C_{1-4}$alkyl-O—$C_{1-4}$alkyl group wherein $C_{1-4}$alkyl is as defined herein and wherein in one or both of the $C_{1-4}$alkyl groups one or more than one hydrogen atom is replaced with a hydroxyl group and one or more than one hydrogen atom is replaced with a halogen. The terms 'hydroxyhalo$C_{1-4}$alkoxy$C_{1-4}$alkyl' therefore refers to a $C_{1-4}$alkyl-O—$C_{1-4}$alkyl group wherein in one or both of the $C_{1-4}$alkyl groups one, two, three or more hydrogen atoms are replaced with a hydroxyl group and one, two, three or more hydrogen atoms are replaced with a halogen and wherein $C_{1-4}$alkyl is as defined herein.

The term 'hydroxy$C_{2-6}$alkenyl' as used herein refers to a $C_{2-6}$alkenyl group wherein one or more than one hydrogen atom is replaced with a hydroxyl group and wherein $C_{2-6}$alkenyl is as defined herein.

The term 'hydroxy$C_{2-6}$alkynyl' as used herein refers to a $C_{2-6}$alkynyl group wherein one or more than one hydrogen atom is replaced with a hydroxyl group and wherein $C_{2-6}$alkynyl is as defined herein.

The term phenyl$C_{1-6}$alkyl as used herein refers to a $C_{1-6}$alkyl group as defined herein which is substituted with one phenyl group.

The term cyanoC$_{1-4}$alkyl or cyanoC$_{1-6}$alkyl as used herein refers to a C$_{1-4}$alkyl or C$_{1-6}$alkyl group as defined herein which is substituted with one cyano group.

The term "heterocyclyl" as used herein shall, unless the context indicates otherwise, include both aromatic and non-aromatic ring systems. Thus, for example, the term "heterocyclyl group" includes within its scope aromatic, non-aromatic, unsaturated, partially saturated and fully saturated heterocyclyl ring systems. In general, unless the context indicates otherwise, such groups may be monocyclic or bicyclic and may contain, for example, 3 to 12 ring members, more usually 5 to 10 ring members. Reference to 4 to 7 ring members include 4, 5, 6 or 7 atoms in the ring and reference to 4 to 6 ring members include 4, 5, or 6 atoms in the ring. Examples of monocyclic groups are groups containing 3, 4, 5, 6, 7 and 8 ring members, more usually 3 to 7, and preferably 5, 6 or 7 ring members, more preferably 5 or 6 ring members. Examples of bicyclic groups are those containing 8, 9, 10, 11 and 12 ring members, and more usually 9 or 10 ring members. Where reference is made herein to heterocyclyl groups, the heterocyclyl ring can, unless the context indicates otherwise, be optionally substituted (i.e. unsubstituted or substituted) by one or more substituents as discussed herein.

The heterocyclyl groups can be heteroaryl groups having from 5 to 12 ring members, more usually from 5 to 10 ring members. The term "heteroaryl" is used herein to denote a heterocyclyl group having aromatic character. The term "heteroaryl" embraces polycyclic (e.g. bicyclic) ring systems wherein one or more rings are non-aromatic, provided that at least one ring is aromatic. In such polycyclic systems, the group may be attached by the aromatic ring, or by a non-aromatic ring.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings, or two fused five membered rings. Each ring may contain up to about five heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, thiadiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 0, 1, 2 or 3 ring heteroatoms;
c) a pyrimidine ring fused to a 5- or 6-membered ring containing 0, 1 or 2 ring heteroatoms;
d) a pyrrole ring fused to a 5- or 6-membered ring containing 0, 1, 2 or 3 ring heteroatoms;
e) a pyrazole ring fused to a 5- or 6-membered ring containing 0, 1 or 2 ring heteroatoms;
f) an imidazole ring fused to a 5- or 6-membered ring containing 0, 1 or 2 ring heteroatoms;
g) an oxazole ring fused to a 5- or 6-membered ring containing 0, 1 or 2 ring heteroatoms;
h) an isoxazole ring fused to a 5- or 6-membered ring containing 0, 1 or 2 ring heteroatoms;
i) a thiazole ring fused to a 5- or 6-membered ring containing 0, 1 or 2 ring heteroatoms;
j) an isothiazole ring fused to a 5- or 6-membered ring containing 0, 1 or 2 ring heteroatoms;
k) a thiophene ring fused to a 5- or 6-membered ring containing 0, 1, 2 or 3 ring heteroatoms;
l) a furan ring fused to a 5- or 6-membered ring containing 0, 1, 2 or 3 ring heteroatoms;
m) a cyclohexyl ring fused to a 5- or 6-membered ring containing 1, 2 or 3 ring heteroatoms; and
n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole, imidazopyridine and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

Examples of polycyclic heteroaryl groups containing an aromatic ring and a non-aromatic ring include, tetrahydroisoquinoline, tetrahydroquinoline, dihydrobenzthiene, dihydrobenzfuran, 2,3-dihydro-benzo[1,4]dioxine, benzo[1,3]dioxole, 4,5,6,7-tetrahydrobenzofuran, tetrahydrotriazolopyrazine (e.g. 5,6,7,8-tetrahydro-[1,2,4]triazolo[4,3-a]pyrazine), indoline and indane groups.

A nitrogen-containing heteroaryl ring must contain at least one ring nitrogen atom. Each ring may, in addition, contain up to about four other heteroatoms typically selected from nitrogen, sulphur and oxygen. Typically the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), tetrazolyl, quinolinyl, isoquinolinyl, benzimidazolyl, benzoxazolyl, benzisoxazole, benzthiazolyl and benzisothiazole, indolyl, 3H-indolyl, isoindolyl, indolizinyl, isoindolinyl, purinyl (e.g., adenine [6-aminopurine], guanine [2-amino-6-hydroxypurine]), indazolyl, quinolizinyl, benzoxazinyl, benzodiazinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

The term "non-aromatic group" embraces, unless the context indicates otherwise, unsaturated ring systems without aromatic character, partially saturated and fully saturated heterocyclyl ring systems. The terms "unsaturated" and "partially saturated" refer to rings wherein the ring structure (s) contains atoms sharing more than one valence bond i.e. the ring contains at least one multiple bond e.g. a C=C, C≡C or N=C bond. The term "fully saturated" refers to rings where there are no multiple bonds between ring atoms. Saturated heterocyclyl groups include piperidine, morpholine, thiomorpholine, piperazine. Partially saturated heterocyclyl groups include pyrazolines, for example 2-pyrazoline and 3-pyrazoline.

Examples of non-aromatic heterocyclyl groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulphur. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulphones (e.g. as in sulpholane and sulpholene), cyclic sulphoxides, cyclic sulphonamides and combinations thereof (e.g. thiomorpholine).

Particular examples include morpholine, piperidine (e.g. 1-piperidinyl, 2-piperidinyl, 3-piperidinyl and 4-piperidinyl), piperidone, pyrrolidine (e.g. 1-pyrrolidinyl, 2-pyrrolidinyl and 3-pyrrolidinyl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine. In general, preferred non-aromatic heterocyclyl groups include saturated groups such as piperidine, pyrrolidine, azetidine, morpholine, piperazine and N-alkyl piperazines.

In a nitrogen-containing non-aromatic heterocyclyl ring the ring must contain at least one ring nitrogen atom. The heterocyclic groups can contain, for example cyclic amine moieties (e.g. as in pyrrolidine), cyclic amides (such as a pyrrolidinone, piperidone or caprolactam), cyclic sulphonamides (such as an isothiazolidine 1,1-dioxide, [1,2]thiazinane 1,1-dioxide or [1,2]thiazepane 1,1-dioxide) and combinations thereof. Particular examples of nitrogen-containing non-aromatic heterocyclyl groups include aziridine, morpholine, thiomorpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, dihydrothiazole, imidazoline, imidazolidinone, oxazoline, thiazoline, 6H-1,2,5-thiadiazine, 2-pyrazoline, 3-pyrazoline, pyrazolidine, piperazine, and N-alkyl piperazines such as N-methyl piperazine.

The heterocyclyl groups can be polycyclic fused ring systems or bridged ring systems such as the oxa- and aza analogues of bicycloalkanes, tricycloalkanes (e.g. adamantane and oxa-adamantane). For an explanation of the distinction between fused and bridged ring systems, see *Advanced Organic Chemistry*, by Jerry March, 4$^{th}$ Edition, Wiley Interscience, pages 131-133, 1992.

The heterocyclyl groups can each be unsubstituted or substituted by one or more substituent groups. For example, heterocyclyl groups can be unsubstituted or substituted by 1, 2, 3 or 4 substituents. Where the heterocyclyl group is monocyclic or bicyclic, typically it is unsubstituted or has 1, 2 or 3 substituents.

The term "carbocyclyl" as used herein shall, unless the context indicates otherwise, include both aromatic and non-aromatic ring systems. Thus, for example, the term "carbocyclyl group" includes within its scope aromatic, non-aromatic, unsaturated, partially saturated and fully saturated carbocyclyl ring systems. In general, unless the context indicates otherwise, such groups may be monocyclic or bicyclic and may contain, for example, 3 to 12 ring members, more usually 5 to 10 ring members. Reference to 4 to 7 ring members include 4, 5, 6 or 7 atoms in the ring and reference to 4 to 6 ring members include 4, 5, or 6 atoms in the ring. Examples of monocyclic groups are groups containing 3, 4, 5, 6, 7 and 8 ring members, more usually 3 to 7, and preferably 5, 6 or 7 ring members, more preferably 5 or 6 ring members. Examples of bicyclic groups are those containing 8, 9, 10, 11 and 12 ring members, and more usually 9 or 10 ring members. Where reference is made herein to carbocyclyl groups, the carbocyclyl ring can, unless the context indicates otherwise, be optionally substituted (i.e. unsubstituted or substituted) by one or more substituents as discussed herein.

The term carbocyclyl comprises aryl, $C_{3-8}$cycloalkyl, $C_{3-8}$cycloalkenyl.

The term aryl as used herein refers to carbocyclyl aromatic groups including phenyl, naphthyl, indenyl, and tetrahydronaphthyl groups.

Whenever used hereinbefore or hereinafter that substituents can be selected each independently out of a list of numerous definitions, all possible combinations are intended which are chemically possible. Whenever used hereinbefore or hereinafter that a particular substituent is further substituted with two or more groups, such as for example hydroxyhalo$C_{1-4}$alkyl, hydroxyhalo$C_{1-4}$alkoxy, all possible combinations are intended which are chemically possible.

In one embodiment, Y represents —CR$^{18}$=N—OR$^{19}$. In particular wherein R$^{18}$ and R$^{19}$ represent $C_{1-6}$alkyl; in particular R$^{18}$ is —CH$_3$ and R$^{19}$ is —CH$_3$ or —C(CH$_3$)$_3$.

In one embodiment, Y represents -E-D wherein E represents a bond.

In one embodiment, Y represents a 3 to 12 ring membered monocyclic or bicyclic carbocyclyl or a 3 to 12 ring membered monocyclic or bicyclic heterocyclyl containing at least one heteroatom selected from N, O or S, wherein said carbocyclyl and heterocyclyl may each be optionally substituted by one or more (e.g. 1, 2 or 3) R$^1$ groups.

In one embodiment, Y represents a 5 to 12 ring membered monocyclic or bicyclic carbocyclyl or a 5 to 12 ring membered monocyclic or bicyclic heterocyclyl containing at least one heteroatom selected from N, O or S, wherein said carbocyclyl and heterocyclyl may each be optionally substituted by one or more (e.g. 1, 2 or 3) $R^1$ groups.

In one embodiment, Y represents an aromatic 3 to 12, in particular an aromatic 5 to 12, ring membered monocyclic or bicyclic carbocyclyl or an aromatic 3 to 12, in particular an aromatic 5 to 12, ring membered monocyclic or bicyclic heterocyclyl containing at least one heteroatom selected from N, O or S, wherein said carbocyclyl and heterocyclyl may each be optionally substituted by one or more (e.g. 1, 2 or 3) $R^1$ groups.

In one embodiment, Y represents an aromatic 3 to 12 (e.g. 5 to 10) ring membered monocyclic or bicyclic carbocyclyl, wherein said carbocyclyl may be optionally substituted by one or more (e.g. 1, 2 or 3) $R^1$ groups.

In one embodiment, Y represents phenyl or naphthyl, wherein said phenyl or naphthyl may each be optionally substituted by one or more (e.g. 1, 2 or 3) $R^1$ groups.

In one embodiment, Y represents a 5 to 12 ring membered monocyclic or bicyclic heterocyclyl containing at least one heteroatom selected from N, O or S, wherein said heterocyclyl may each be optionally substituted by one or more (e.g. 1, 2 or 3) $R^1$ groups.

In one embodiment, Y represents an aromatic 5 to 12 ring membered monocyclic heterocyclyl containing at least one heteroatom selected from N, O or S, wherein said heterocyclyl group may each be optionally substituted by one or more (e.g. 1, 2 or 3) $R^1$ groups.

In one embodiment, Y represents a 5 or 6 ring membered monocyclic heterocyclyl containing at least one heteroatom selected from N, O or S, wherein said heterocyclyl may each be optionally substituted by one or more (e.g. 1, 2 or 3) $R^1$ groups.

In one embodiment, Y represents an aromatic 5 or 6 ring membered monocyclic heterocyclyl containing at least one heteroatom selected from N, O or S, wherein said heterocyclyl may each be optionally substituted by one or more (e.g. 1, 2 or 3) $R^1$ groups.

In one embodiment, Y represents a 5 ring membered monocyclic heterocyclyl containing at least one heteroatom selected from N, O or S, wherein said heterocyclyl may each be optionally substituted by one or more (e.g. 1, 2 or 3) $R^1$ groups.

In one embodiment, Y represents a 5 ring membered monocyclic aromatic heterocyclyl containing at least one heteroatom selected from N, O or S, wherein said heterocyclyl may each be optionally substituted by one or more (e.g. 1, 2 or 3) $R^1$ groups.

In one embodiment, Y represents a 6 ring membered monocyclic heterocyclyl containing at least one heteroatom selected from N, O or S, wherein said heterocyclyl may each be optionally substituted by one or more (e.g. 1, 2 or 3) $R^1$ groups.

In one embodiment, Y represents a 6 ring membered monocyclic aromatic heterocyclyl containing at least one heteroatom selected from N, O or S, wherein said heterocyclyl may each be optionally substituted by one or more (e.g. 1, 2 or 3) $R^1$ groups.

In one embodiment, Y represents a 12 ring membered bicyclic heterocyclyl containing at least one heteroatom selected from N, O or S, wherein said heterocyclyl may each be optionally substituted by one or more (e.g. 1, 2 or 3) $R^1$ groups.

In one embodiment, Y represents a 12 ring membered bicyclic aromatic heterocyclyl containing at least one heteroatom selected from N, O or S, wherein said heterocyclyl may each be optionally substituted by one or more (e.g. 1, 2 or 3) $R^1$ groups.

In one embodiment, E represents a bond, $C_{2-4}$alkenediyl optionally substituted with $R^{22}$, $-CO-(CR^{22}R^{23})_s-$, $-(CR^{22}R^{23})_s-CO-$, $-NR^{22}-(CR^{22}R^{23})_s-$, $-(CR^{22}R^{23})_s-NR^{22}-$, $-O-(CR^{22}R^{23})_s-$, $-(CR^{22}R^{23})_s-CO-NR^{22}-(CR^{22}R^{23})_s-$ or $-(CR^{22}R^{23})_s-NR^{22}-CO-(CR^{22}R^{23})_s-$.

In one embodiment, E represents a bond, $C_{2-4}$alkenediyl, $-CO-(CR^{22}R^{23})_s-$, $-(CR^{22}R^{23})_s-CO-$, $-NR^{22}-(CR^{22}R^{23})_s-$, $-(CR^{22}R^{23})_s-NR^{22}-$, $-(CR^{22}R^{23})_s-CO-NR^{22}-(CR^{22}R^{23})_s-$ or $-(CR^{22}R^{23})_s-NR^{22}-CO-(CR^{22}R^{23})_s-$.

In one embodiment, E represents $C_{2-4}$alkenediyl, $-CO-(CR^{22}R^{23})_s-$, $-(CR^{22}R^{23})_s-CO-$, $-NR^{22}-(CR^{22}R^{23})_s-$, $-(CR^{22}R^{23})_s-NR^{22}-$, $-(CR^{22}R^{23})_s-CO-NR^{22}-(CR^{22}R^{23})_s-$ or $-(CR^{22}R^{23})_s-NR^{22}-CO-(CR^{22}R^{23})_s-$.

In one embodiment, E represents a bond, $C_{2-4}$alkenediyl, $-CO-(CR^{22}R^{23})_s-$, $-NR^{22}-(CR^{22}R^{23})_s-$, $-(CR^{22}R^{23})_s-NR^{22}-$, $-(CR^{22}R^{23})_s-CO-NR^{22}-(CR^{22}R^{23})_s-$ or $-(CR^{22}R^{23})_s-NR^{22}-CO-(CR^{22}R^{23})_s-$.

In one embodiment, E represents a bond.

In one embodiment, Y represents -E-D, wherein E is other than a bond.

In one embodiment, Y represents -E-D, wherein E is other than a bond and D represents any one of the following:

- a 3 to 12 ring membered monocyclic or bicyclic carbocyclyl or a 3 to 12 ring membered monocyclic or bicyclic heterocyclyl containing at least one heteroatom selected from N, O or S, wherein said carbocyclyl and heterocyclyl may each be optionally substituted by one or more (e.g. 1, 2 or 3) $R^1$ groups;
- a 5 to 12 ring membered monocyclic or bicyclic carbocyclyl or a 5 to 12 ring membered monocyclic or bicyclic heterocyclyl containing at least one heteroatom selected from N, O or S, wherein said carbocyclyl and heterocyclyl may each be optionally substituted by one or more (e.g. 1, 2 or 3) $R^1$ groups;
- phenyl or naphthyl, wherein said phenyl or naphthyl may each be optionally substituted by one or more (e.g. 1, 2 or 3) $R^1$ groups;
- a 5 to 12 ring membered monocyclic or bicyclic heterocyclyl containing at least one heteroatom selected from N, O or S, wherein said heterocyclyl may each be optionally substituted by one or more (e.g. 1, 2 or 3) $R^1$ groups;
- a 5 or 6 ring membered monocyclic heterocyclyl containing at least one heteroatom selected from N, O or S, wherein said heterocyclyl may each be optionally substituted by one or more (e.g. 1, 2 or 3) $R^1$ groups;
- a 5 ring membered monocyclic heterocyclyl containing at least one heteroatom selected from N, O or S, wherein said heterocyclyl may each be optionally substituted by one or more (e.g. 1, 2 or 3) $R^1$ groups;
- a 5 ring membered monocyclic aromatic heterocyclyl containing at least one heteroatom selected from N, O or S, wherein said heterocyclyl group may each be optionally substituted by one or more (e.g. 1, 2 or 3) $R^1$ groups;
- a 6 ring membered monocyclic heterocyclyl containing at least one heteroatom selected from N, O or S, wherein said heterocyclyl may each be optionally substituted by one or more (e.g. 1, 2 or 3) $R^1$ groups;

a 6 ring membered monocyclic aromatic heterocyclyl containing at least one heteroatom selected from N, O or S, wherein said heterocyclyl may each be optionally substituted by one or more (e.g. 1, 2 or 3) $R^1$ groups;

a 12 ring membered bicyclic heterocyclyl containing at least one heteroatom selected from N, O or S, wherein said heterocyclyl may each be optionally substituted by one or more (e.g. 1, 2 or 3) $R^1$ groups;

a 12 ring membered bicyclic aromatic heterocyclyl containing at least one heteroatom selected from N, O or S, wherein said heterocyclyl may each be optionally substituted by one or more (e.g. 1, 2 or 3) $R^1$ groups;

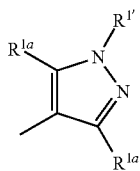

wherein $R^1$ represents hydrogen, $C_{1-6}$alkyl, $C_{2-4}$alkenyl, hydroxy$C_{1-6}$alkyl, halo$C_{1-6}$alkyl, hydroxyhalo$C_{1-6}$alkyl, cyano$C_{1-4}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —C(=O)—$NR^4R^5$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^6$, $C_{1-6}$alkyl substituted with $R^6$, $C_{1-6}$alkyl substituted with —C(=O)—$R^6$, hydroxy$C_{1-6}$alkyl substituted with $R^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$; and each $R^{1a}$ is independently selected from hydrogen, $C_{1-4}$alkyl, hydroxy$C_{1-4}$alkyl, $C_{1-4}$alkyl substituted with amino or mono- or di($C_{1-4}$alkyl)amino or —NH(C$_{3-8}$cycloalkyl), cyano$C_{1-4}$alkyl, $C_{1-4}$alkoxy$C_{1-4}$alkyl, and $C_{1-4}$alkyl substituted with one or more fluoro atoms;

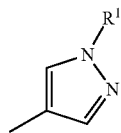

wherein $R^1$ represents hydrogen, $C_{1-6}$alkyl, $C_{2-4}$alkenyl, hydroxy$C_{1-6}$alkyl, halo$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —C(=O)—$NR^4R^5$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^6$, $C_{1-6}$alkyl substituted with $R^6$, $C_{1-6}$alkyl substituted with —C(=O)—$R^6$, hydroxy$C_{1-6}$alkyl substituted with $R^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$.

In one embodiment, D is other than phenyl. In one embodiment, D represents a 3 to 12 ring membered monocyclic or bicyclic heterocyclyl containing at least one heteroatom selected from N, O or S, said heterocyclyl being other than pyrazol-4-yl, wherein said heterocyclyl may be optionally substituted by one or more (e.g. 1, 2 or 3) $R^1$ groups.

In one embodiment, D is other than pyrazolyl, in particular D is piperidinyl, pyridinyl, phenyl, pyrrolyl, imidazolyl, triazolyl, pyrrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrrolidinyl, thiadiazolyl, oxadiazolyl, said rings being optionally substituted. Said optional substituents may represent halo, cyano, $C_{1-6}$alkyl, $C_{1-6}$alkoxy, —C(=O)—O—$C_{1-6}$alkyl, hydroxy$C_{1-6}$alkyl, —$NR^4R^5$, $C_{1-6}$alkyl substituted with —O—C(=O)—$C_{1-6}$alkyl, $C_{1-6}$alkyl substituted with —$NR^4R^5$, —C(=O)—$NR^4R^5$, —C(=O)—$C_{1-6}$alkyl-$NR^4R^5$, $R^6$, $C_{1-6}$alkyl substituted with $R^6$.

In one embodiment, D is other than pyrazolyl and phenyl, in particular D is piperidinyl, pyridinyl, pyrrolyl, imidazolyl, triazolyl, pyrrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrrolidinyl, thiadiazolyl, oxadiazolyl, said rings being optionally substituted.

In one embodiment, E is other than a bond and D is other than pyrazolyl, in particular D is piperidinyl, pyridinyl, phenyl, pyrrolyl, imidazolyl, triazolyl, pyrrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrrolidinyl, thiadiazolyl, oxadiazolyl, said rings being optionally substituted.

In one embodiment, D represents piperidinyl, pyridinyl (e.g. pyridin-3-yl or pyridine-4-yl), phenyl, pyrrolyl (e.g. pyrrol-2-yl or pyrrol-3-yl), imidazolyl (e.g. imidazol-1-yl, imidazol-2-yl or imidazol-4-yl), triazolyl (e.g. 1,2 3 triazol-4-yl or 1,2,4 triazol-1-yl), pyrrolopyridinyl (e.g. pyrrolo[2,3-b]pyridinyl), benzodioxolyl (e.g 1,3-benzodioxolyl), indolyl, thiazolyl, cyclopentyl, azetidinyl, morpholinyl, tetrazolyl, oxazolyl, piperazinyl, 1,2,3,6-tetrahydropyridinyl, 2,5-dihydropyrrolyl, pyrimidinyl (e.g. pyrimidin-5-yl), pyrrolidinyl, thiadiazolyl, oxadiazolyl (e.g. 1,3,4-oxadiazolyl), said rings being optionally substituted. Said optional substituents may represent halo, cyano, $C_{1-6}$alkyl, $C_{1-6}$alkoxy, —C(=O)—O—$C_{1-6}$alkyl, hydroxy$C_{1-6}$alkyl, —$NR^4R^5$, $C_{1-6}$alkyl substituted with —O—C(=O)—$C_{1-6}$alkyl, $C_{1-6}$alkyl substituted with —$NR^4R^5$, —C(=O)—$NR^4R^5$, —C(=O)—$C_{1-6}$alkyl-$NR^4R^5$, $R^6$, $C_{1-6}$alkyl substituted with $R^6$.

In one embodiment, said optional substituents may represent halo (e.g. fluoro or chloro), cyano, $C_{1-6}$alkyl (e.g. methyl), $C_{1-6}$alkoxy (e.g. methoxy), —C(=O)—O—$C_{1-6}$alkyl (e.g. —CO$_2$C(CH$_3$)$_3$), hydroxy$C_{1-6}$alkyl (e.g. —CH$_2$CH$_2$OH or —CH$_2$OH), —$NR^4R^5$ (e.g. —NH$_2$, —NHCH$_3$, —NHCO-morpholinyl or —NHCO$_2$C(CH$_3$)$_3$), $C_{1-6}$alkyl substituted with —O—C(=O)—$C_{1-6}$alkyl, for example —CH$_2$—O—C(=O)CH$_3$), $C_{1-6}$alkyl substituted with —$NR^4R^5$ (e.g. —CH$_2$NH$_2$), —C(=O)—$NR^4R^5$ (e.g. —C(=O)—NH—CH$_2$CH$_2$NH$_2$, —C(=O)—NH—CH$_2$CH$_2$CH$_2$NH$_2$, —C(=O)—NHCH$_3$ or —C(=O)—

NH—CH$_2$CH$_2$CH$_2$OH), —C(=O)—R$^6$ (e.g. where R$^6$ is 4 to 7-membered saturated monocyclic heterocyclyl containing at least one heteroatom selected from N or O for example R$^1$ is —C(=O)-morpholinyl), R$^6$ (e.g. 4 to 7-membered saturated monocyclic heterocyclyl containing at least one heteroatom selected from N or O such as morpholinyl, N-methylpiperazinyl or piperazinyl), or C$_{1-6}$alkyl substituted with R$^6$ (e.g. 4 to 7-membered saturated monocyclic heterocyclyl containing at least one heteroatom selected from N or O such as —CH$_2$CH$_2$-morpholinyl).

In one embodiment, E is other than a bond and D is other than pyrazolyl or phenyl, in particular D is piperidinyl, pyridinyl, phenyl, pyrolyl, imidazolyl, triazolyl, pyrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrolidinyl, said rings being optionally substituted.

In one embodiment, E is a bond and D is 1-pyrazolyl or 2-pyrazolyl or 3-pyrazolyl, all may optionally be substituted.

In one embodiment, E is a bond and D is 1-pyrazolyl or 2-pyrazolyl, both may optionally be substituted.

In one embodiment, E is other than a bond and D is 1-pyrazolyl or 2-pyrazolyl, both may optionally be substituted.

In one embodiment, E is other than a bond and D is optionally substituted pyrazolyl.

In one embodiment, E is other than a bond and D is optionally substituted pyrazol-4-yl.

In one embodiment, W is —N(R$^3$)—.

In one embodiment, W is —C(R$^{3a}$R$^{3b}$).

In one embodiment R$^1$ represents hydrogen, C$_{1-6}$alkyl, C$_{2-4}$alkenyl, hydroxyC$_{1-6}$alkyl, haloC$_{1-6}$alkyl, hydroxyhaloC$_{1-6}$alkyl, cyanoC$_{1-4}$alkyl, C$_{1-6}$alkoxyC$_{1-6}$alkyl wherein each C$_{1-6}$alkyl may optionally be substituted with one or two hydroxyl groups, C$_{1-6}$alkyl substituted with —NR$^4$R$^5$, C$_{1-6}$alkyl substituted with —C(=O)—NR$^4$R$^5$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl, C$_{1-6}$alkyl substituted with —NR$^{12}$—S(=O)$_2$—NR$^{14}$R$^{15}$, R$^6$, —C(=O)R$^6$, C$_{1-6}$alkyl substituted with R$^6$, C$_{1-6}$alkyl substituted with —C(=O)—R$^6$, hydroxyC$_{1-6}$alkyl substituted with R$^6$, C$_{1-6}$alkyl substituted with —Si(CH$_3$)$_3$, C$_{1-6}$alkyl substituted with —P(=O)(OH)$_2$ or C$_{1-6}$alkyl substituted with —P(=O)(OC$_{1-6}$alkyl)$_2$.

In one embodiment R$^1$ represents hydrogen, C$_{1-6}$alkyl, C$_{2-4}$alkenyl, hydroxyC$_{1-6}$alkyl, haloC$_{1-6}$alkyl, C$_{1-6}$alkoxyC$_{1-6}$alkyl wherein each C$_{1-6}$alkyl may optionally be substituted with one or two hydroxyl groups, C$_{1-6}$alkyl substituted with —NR$^4$R$^5$, C$_{1-6}$alkyl substituted with —C(=O)—NR$^4$R$^5$, —S(=O)$_2$—C$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —NH—S(=O)$_2$—C$_{1-6}$alkyl, R$^6$, —C(=O)R$^6$, C$_{1-6}$alkyl substituted with R$^6$, C$_{1-6}$alkyl substituted with —C(=O)—R$^6$, hydroxyC$_{1-6}$alkyl substituted with R$^6$, or C$_{1-6}$alkyl substituted with —Si(CH$_3$)$_3$.

In one embodiment R$^1$ represents halo, cyano, C$_{1-6}$alkyl, C$_{1-6}$alkoxy, —C(=O)—O—C$_{1-6}$alkyl, hydroxyC$_{1-6}$alkyl, —NR$^4$R$^5$, C$_{1-6}$alkyl substituted with —O—C(=O)—C$_{1-6}$alkyl, C$_{1-6}$alkyl substituted with —NR$^4$R$^5$, —C(=O)—NR$^4$R$^5$, —C(=O)—C$_{1-6}$alkyl-NR$^4$R$^5$, R$^6$, —C(=O)R$^6$, C$_{1-6}$alkyl substituted with R$^6$.

In one embodiment R$^1$ represents hydrogen.

In one embodiment R$^1$ represents C$_{1-6}$alkyl. In one embodiment R$^1$ represents methyl. In one embodiment each R$^2$ is independently selected from hydroxyl, halogen, cyano, C$_{1-4}$alkyl, C$_{2-4}$alkenyl, C$_{1-4}$alkoxy, hydroxyC$_{1-4}$alkyl, hydroxyC$_{1-4}$alkoxy, haloC$_{1-4}$alkyl, haloC$_{1-4}$alkoxy, C$_{1-4}$alkoxyC$_{1-4}$alkyl, R$^{13}$, C$_{1-4}$alkoxy substituted with R$^{13}$, —C(=O)—R$^{13}$, C$_{1-4}$alkyl substituted with NR$^7$R$^8$, C$_{1-4}$alkoxy substituted with NR$^7$R$^8$, —NR$^7$R$^8$ and —C(=O)—NR$^7$R$^8$; or when two R$^2$ groups are attached to adjacent carbon atoms they may be taken together to form a radical of formula —O—(C(R$^{17}$)$_2$)$_p$—O— wherein R$^{17}$ represents hydrogen or fluorine and p represents 1 or 2.

In one embodiment each R$^2$ is independently selected from hydroxyl, halogen, cyano, C$_{1-4}$alkyl, C$_{2-4}$alkenyl, C$_{1-4}$alkoxy, hydroxyC$_{1-4}$alkyl, hydroxyC$_{1-4}$alkoxy, haloC$_{1-4}$alkoxy, C$_{1-4}$alkoxyC$_{1-4}$alkyl, R$^{13}$, C$_{1-4}$alkoxy substituted with R$^{13}$, —C(=O)—R$^3$, C$_{1-4}$alkyl substituted with NR$^7$R$^8$, C$_{1-4}$alkoxy substituted with NR$^7$R$^8$, —NR$^7$R$^8$ or —C(=O)—NR$^7$R$^8$.

In one embodiment one or more R$^2$ represents C$_{1-4}$alkoxy, for example CH$_3$O—.

In one embodiment one or more R$^2$ represents C$_{1-4}$alkoxy or halogen, for example CH$_3$O— or fluoro or chloro.

In one embodiment n is equal to 0. In one embodiment n is equal to 1. In one embodiment n is equal to 2. In one embodiment n is equal to 3. In one embodiment n is equal to 4.

In one embodiment, n is equal to 2, 3 or 4.

In one embodiment n is equal to 2 and one R$^2$ is present at the 3-position and the other is present at the 5-position.

In one embodiment n is equal to 2 and one R$^2$ is present at the 3-position and the other is present at the 5-position and each R$^2$ represents C$_{1-4}$alkoxy, for example each R$^2$ represents CH$_3$O—.

In one embodiment n is equal to 3 and one R$^2$ is present at the 2-position, one R$^2$ is present at the 3-position and one R$^2$ is present at the 5-position.

In one embodiment n is equal to 3 and one R$^2$ is present at the 3-position and represents C$_{1-4}$alkoxy, for example CH$_3$O—; one R$^2$ is present at the 5-position and represents C$_{1-4}$alkoxy, for example CH$_3$O—; one R$^2$ is present at the 2-position and represents halogen, for example fluoro.

In one embodiment n is equal to 4 and one R$^2$ is present at the 2-position, one R$^2$ is present at the 3-position, one R$^2$ is present at the 5-position and one R$^2$ is present at the 6-position.

In one embodiment n is equal to 4 and one R$^2$ is present at the 3-position and represents C$_{1-4}$alkoxy, for example CH$_3$O—; one R$^2$ is present at the 5-position and represents C$_{1-4}$alkoxy, for example CH$_3$O—; one R$^2$ is present at the 2-position and represents halogen, for example fluoro, and one R$^2$ is present at the 6-position and represents halogen, for example fluoro.

In one embodiment, R$^3$ represents C$_{1-6}$alkyl, hydroxy C$_{1-6}$alkyl, hydroxyhaloC$_{1-6}$alkyl, hydroxyC$_{2-6}$alkynyl, haloC$_{1-6}$alkyl, haloC$_{1-6}$alkyl optionally substituted (e.g. substituted) with —O—C(=O)—C$_{1-6}$alkyl, C$_{1-6}$alkyl substituted with —C(=O)—C$_{1-6}$alkyl, C$_{1-6}$alkoxyC$_{1-6}$alkyl wherein each C$_{1-6}$alkyl may optionally be substituted with one or two hydroxyl groups, C$_{1-6}$alkoxyC$_{1-6}$alkyl wherein each C$_{1-6}$alkyl may optionally be substituted with one or two hydroxyl groups or with —O—C(=O)—C$_{1-6}$alkyl, C$_{1-6}$alkyl substituted with R$^9$, C$_{1-6}$alkyl substituted with —NR$^{10}$R$^{11}$, C$_{1-6}$alkyl substituted with hydroxyl and —NR$^{10}$R$^{11}$, C$_{1-6}$alkyl substituted with one or two halogens and —NR$^{10}$R$^{11}$, C$_{1-6}$alkyl substituted with —C(=O)—O—C$_{1-6}$alkyl, C$_{1-6}$alkyl substituted with —C(=O)—NR$^{10}$R$^{11}$, $C_{1-6}$alkyl substituted with carboxyl, $C_{1-6}$alkyl substituted with —O—C(=O)—NR$^{10}$R$^{11}$, $C_{1-6}$alkyl substituted with —NR$^{12}$—S(=O)$_2$—C$_{1-6}$alkyl, $C_{1-6}$alkyl substituted with —NR$^{12}$—S(=O)$_2$—NR$^{14}$R$^{15}$, $C_{1-6}$alkyl substituted with R$^9$ and optionally substituted with —O—C(=O)—C$_{1-6}$alkyl, $C_{1-6}$alkyl substituted with hydroxyl and R$^9$, —C$_{1-6}$alkyl-C(R$^{12}$)=N—O—R$^{12}$, —S(=O)$_2$—NR$^{14}$R$^{15}$, $C_{1-6}$alkyl substituted with —S(=O)$_2$—C$_{1-6}$alkyl, $C_{1-6}$alkyl substituted with —C(=O)—NR$^{10}$R$^{11}$, $C_{1-6}$alkyl substituted with —C(=O)—R$^9$, $C_{2-6}$alkenyl substituted with R$^9$, $C_{2-6}$alkynyl substituted with R$^9$, hydroxyC$_{1-6}$alkoxy, $C_{2-6}$alkenyl, $C_{2-6}$alkynyl, R$^{13}$, $C_{1-6}$alkyl substituted with $C_{1-6}$alkoxyC$_{1-6}$alkyl-C(=O)— or $C_{1-6}$alkyl substituted with —P(=O)(OC$_{1-6}$alkyl)$_2$.

In one embodiment. R$^3$ represents $C_{1-6}$alkyl, hydroxy $C_{1-6}$alkyl, hydroxyhaloC$_{1-6}$alkyl, haloC$_{1-6}$alkyl, $C_{1-6}$alkyl substituted with —C(=O)—C$_{1-6}$alkyl, $C_{1-6}$alkoxyC$_{1-6}$alkyl wherein each $C_{1-6}$alkyl may optionally be substituted with one or two hydroxyl groups, $C_{1-6}$alkyl substituted with R$^9$, $C_{1-6}$alkyl substituted with —NR$^{10}$R$^{11}$, $C_{1-6}$alkyl substituted with hydroxyl and —NR$^{10}$R$^{11}$, $C_{1-6}$alkyl substituted with one or two halogens and —NR$^{10}$R$^{11}$, $C_{1-6}$alkyl substituted with —C(=O)—O—C$_{1-6}$alkyl, $C_{1-6}$alkyl substituted with —C(=O)—NR$^{10}$R$^{11}$, $C_{1-6}$alkyl substituted with carboxyl, $C_{1-6}$alkyl substituted with —O—C(=O)—NR$^{10}$R$^{11}$, $C_{1-6}$alkyl substituted with —NR$^{12}$—S(=O)$_2$—C$_{1-6}$alkyl, $C_{1-6}$alkyl substituted with —NR$^{12}$—S(=O)$_2$—NR$^{14}$R$^{15}$, $C_{1-6}$alkyl substituted with hydroxyl and R$^9$, —C$_{1-6}$alkyl-C(R$^{12}$)=N—O—R$^{12}$, $C_{1-6}$alkyl substituted with —C(=O)—NR$^{10}$R$^{11}$, $C_{1-6}$alkyl substituted with —C(=O)—R$^9$, $C_{2-6}$alkynyl substituted with R$^9$, hydroxyC$_{1-6}$alkoxy, $C_{2-6}$alkenyl, $C_{2-6}$alkynyl, R$^{13}$ or $C_{1-6}$alkyl substituted with $C_{1-6}$alkoxyC$_{1-6}$alkyl-C(=O)—.

In one embodiment R$^3$ represents $C_{1-6}$alkyl, hydroxy $C_{1-6}$alkyl, haloC$_{1-6}$alkyl, haloC$_{1-6}$alkyl optionally substituted with —O—C(=O)—C$_{1-6}$alkyl, hydroxyhalo $C_{1-6}$alkyl, hydroxyC$_{2-6}$alkynyl, $C_{1-6}$alkyl substituted with —C(=O)—C$_{1-6}$alkyl, $C_{1-6}$alkoxyC$_{1-6}$alkyl wherein each $C_{1-6}$alkyl may optionally be substituted with one or two hydroxyl groups or with —O—C(=O)—C$_{1-6}$alkyl, $C_{1-6}$alkyl substituted with R$^9$, cyanoC$_{1-6}$alkyl, $C_{1-6}$alkyl substituted with —NR$^{10}$R$^{11}$, $C_{1-6}$alkyl substituted with hydroxyl and —NR$^{10}$R$^{11}$, $C_{1-6}$alkyl substituted with one or two halo atoms and —NR$^{10}$R$^{11}$. $C_{1-6}$alkyl substituted with —C(=O)—O—C$_{1-6}$alkyl, $C_{1-6}$alkyl substituted with $C_{1-6}$alkoxyC$_{1-6}$alkyl-C(=O)—, $C_{1-6}$alkyl substituted with —C(=O)—NR$^{10}$R$^{11}$, $C_{1-6}$alkyl substituted with —C(=O)—NR$^{14}$R$^{15}$, $C_{1-6}$alkyl substituted with carboxyl, $C_{1-6}$alkyl substituted with —O—C(=O)—NR$^{10}$R$^{11}$, $C_{1-6}$alkyl substituted with —NR$^{12}$—S(=O)$_2$—C$_{1-6}$alkyl, $C_{1-6}$alkyl substituted with —NR$^{12}$—S(=O)$_2$—NR$^{14}$R$^{15}$, $C_{1-6}$alkyl substituted with R$^9$ and substituted with —O—C(=O)—C$_{1-6}$alkyl, $C_{1-6}$alkyl substituted with hydroxyl and R$^9$, —C$_{1-6}$alkyl-C(R$^{12}$)=N—O—R$^{12}$, —S(=O)$_2$—NR$^{14}$R$^{15}$, $C_{1-6}$alkyl substituted with —S(=O)$_2$—C$_{1-6}$alkyl, $C_{1-6}$alkyl substituted with —C(=O)—R$^9$, $C_{2-6}$alkenyl substituted with R$^9$, $C_{2-6}$alkynyl substituted with R$^9$, $C_{1-6}$alkyloxyC$_{1-6}$alkyl wherein each $C_{1-6}$alkyl may optionally be substituted with one or two hydroxyl groups, $C_{2-6}$alkenyl, $C_{2-6}$alkynyl, R$^{13}$, or $C_{1-6}$alkyl substituted with —P(=O)(OC$_{1-6}$alkyl)$_2$.

In one embodiment, R$^3$ represents $C_{1-6}$alkyl, hydroxy $C_{1-6}$alkyl, hydroxyhaloC$_{1-6}$alkyl, haloC$_{1-6}$alkyl, $C_{1-6}$alkyl substituted with —C(=O)—C$_{1-6}$alkyl, $C_{1-6}$alkoxyC$_{1-6}$alkyl wherein each $C_{1-6}$alkyl may optionally be substituted with one or two hydroxyl groups, $C_{1-6}$alkyl substituted with R$^9$, $C_{1-6}$alkyl substituted with —NR$^{10}$R$^{11}$, $C_{1-6}$alkyl substituted with hydroxyl and —NR$^{10}$R$^{11}$, $C_{1-6}$alkyl substituted with one or two halogens and —NR$^{10}$R$^{11}$, $C_{1-6}$alkyl substituted with —C(=O)—O—C$_{1-6}$alkyl, $C_{1-6}$alkyl substituted with —O—C(=O)—NR$^{10}$R$^{11}$, $C_{1-6}$alkyl substituted with carboxyl, $C_{1-6}$alkyl substituted with —NR$^{12}$—S(=O)$_2$—C$_{1-6}$alkyl, $C_{1-6}$alkyl substituted with —NR$^{12}$—S(=O)$_2$—NR$^{14}$R$^{15}$, $C_{1-6}$alkyl substituted with hydroxyl and R$^9$, —C$_{1-6}$alkyl-C(R$^{12}$)=N—O—R$^{12}$, $C_{1-6}$alkyl substituted with —C(=O)—NR$^{10}$R$^{11}$, $C_{1-6}$alkyl substituted with —C(=O)—R$^9$, $C_{2-6}$alkynyl substituted with R$^9$, hydroxyC$_{1-6}$alkoxy, $C_{2-6}$alkenyl, $C_{2-6}$alkynyl or R$^{13}$.

In one embodiment R$^3$ represents $C_{2-6}$alkynyl, haloC$_{1-6}$alkyl optionally substituted with —O—C(=O)—C$_{1-6}$alkyl, hydroxyC$_{1-6}$alkyl optionally substituted with —O—C(=O)—C$_{1-6}$alkyl, hydroxyhaloC$_{1-6}$alkyl, $C_{1-6}$alkoxyC$_{1-6}$alkyl wherein each $C_{1-6}$alkyl may optionally be substituted with one or two hydroxyl groups or with —O—C(=O)—C$_{1-6}$alkyl, $C_{1-6}$alkyl substituted with R$^9$, $C_{2-6}$alkynyl substituted with R$^9$, $C_{1-6}$alkyl substituted with —NR$^{10}$R$^{11}$, or $C_{1-6}$alkyl substituted with —O—C(=O)—NR$^{10}$R$^{11}$.

In one embodiment R$^3$ represents hydroxyC$_{1-6}$alkyl, hydroxyC$_{1-6}$alkoxy, hydroxyhaloC$_{1-6}$alkyl, $C_{1-6}$alkoxy, $C_{1-6}$alkyl substituted with R$^9$, $C_{1-6}$alkyl substituted with —NR$^{10}$R$^{11}$, $C_{2-6}$alkynyl substituted with R$^9$, hydroxy $C_{1-6}$alkyl optionally substituted with —O—C(=O)—C$_{1-6}$alkyl, haloC$_{1-6}$alkyl optionally substituted with —O—C(=O)—C$_{1-6}$alkyl, $C_{2-6}$alkenyl, or $C_{2-6}$alkynyl.

In one embodiment R$^3$ represents $C_{2-6}$alkenyl. R$^3$ may represent —CH$_2$—CH=CH$_2$.

In one embodiment R$^3$ represents $C_{2-6}$alkynyl. R$^3$ may represent —CH$_2$—C≡C—H.

In one embodiment R$^3$ represents $C_{2-6}$alkynyl (e.g. —CH$_2$—C≡C—) substituted with R$^9$.

R$^9$ may represent an optionally substituted aromatic 6-membered monocyclic heterocycle containing one or two nitrogen heteroatoms, for example pyridinyl or pyrimidinyl. The heterocyclyl may be unsubstituted or substituted, for example substituted with one $C_{1-4}$alkoxyl substituent, for example —OCH$_3$. In one embodiment R$^3$ may represent-CH$_2$—C≡C— (2-pyrimidinyl) or —CH$_2$—C≡C— (3-methoxy-pyridin-2-yl).

In one embodiment R$^3$ represents hydroxyC$_{1-6}$alkyl, hydroxyhaloC$_{1-6}$alkyl, $C_{1-6}$alkyl substituted with R$^9$, $C_{1-6}$-alkyl substituted with —NR$^{10}$R$^{11}$, $C_{2-6}$alkynyl substituted with R$^9$, or $C_{2-6}$alkynyl.

In one embodiment R$^3$ represents hydroxyC$_{1-6}$alkyl, hydroxyhaloC$_{1-6}$alkyl, $C_{1-6}$alkyl substituted with R$^9$, $C_{1-6}$-alkyl substituted with —NR$^{10}$R$^{11}$, $C_{1-6}$alkoxyC$_{1-6}$alkyl wherein each $C_{1-6}$alkyl may optionally be substituted with one or two hydroxyl groups or with —O—C(=O)—C$_{1-6}$alkyl, $C_{2-6}$alkynyl substituted with R$^9$, or $C_{2-6}$alkynyl.

In one embodiment R$^3$ represents hydroxyC$_{1-6}$alkyl, haloC$_{1-6}$alkyl, $C_{1-6}$alkyl substituted with R$^9$, $C_{1-6}$-alkyl substituted with —NR$^{10}$R$^{11}$, $C_{1-6}$alkoxyC$_{1-6}$alkyl, or $C_{2-6}$alkynyl.

In one embodiment when R$^3$ represents $C_{1-6}$alkyl (e.g. $C_{1-4}$alkyl) substituted with R$^9$. R$^9$ represents an optionally substituted saturated or an aromatic 5 or 6 membered monocyclic heterocyclyl.

In one embodiment when R$^3$ represents $C_{1-6}$alkyl (e.g. $C_{1-4}$alkyl) substituted with R$^9$, wherein R$^9$ represents an optionally substituted aromatic 6 membered monocyclic heterocyclyl containing one or two nitrogen heteroatom, for example pyridinyl. The heterocyclyl may be unsubstituted or substituted, for example substituted with $C_{1-4}$alkyl substituted with —NR$^{14}$R$^{15}$ (e.g. —NH$_2$), for example —CH$_2$NH$_2$ In one embodiment when $R^3$ represents $C_{1-6}$alkyl (e.g. $C_{1-4}$alkyl) substituted with $R^9$, wherein $R^9$ represents optionally substituted 5 or 6 membered saturated monocyclic heterocyclyl containing one or two heteroatoms selected from N, or O, for example pyrrolidinyl, morpholinyl, piperidinyl and piperazinyl. In one embodiment $R^3$ represents —CH$_2$CH$_2$-morpholinyl, —CH$_2$CH$_2$-piperazinyl, —CH$_2$CH$_2$-(4-piperazin-1-yl-ethanone) or —CH$_2$CH$_2$-pyrrolidin-2-one.

In one embodiment when $R^3$ represents $C_{1-6}$alkyl (e.g. $C_{1-4}$alkyl) substituted with $R^9$, wherein $R^9$ represents $C_{3-8}$cycloalkyl, for example cyclopropyl. In one embodiment $R^3$ represents —CH$_2$-cyclopropyl.

In one embodiment $R^3$ represents $C_{1-6}$alkyl substituted with hydroxyl, halo and/or —NR$^{10}$R$^{11}$. In one embodiment $R^3$ represents $C_{1-6}$alkyl substituted with hydroxyl, halo or —NR$^{10}$R$^{11}$, wherein the $C_{1-6}$alkyl group is a straight chain alkyl group e.g. 2-ethyl, n-propyl, n-butyl. In a further embodiment $R^3$ represents $C_{1-6}$alkyl substituted with hydroxyl or —NR$^{10}$R$^{11}$.

In one embodiment $R^3$ represents hydroxy$C_{1-6}$alkyl. $R^3$ may represent —CH$_2$CHOHCH$_2$OH, —CH$_2$CH$_2$OH or —CH$_2$CH$_2$CH$_2$OH.

In one embodiment $R^3$ represents $C_{1-6}$alkoxy$C_{1-6}$alkyl wherein each $C_{1-6}$alkyl may optionally be substituted with one or two hydroxyl groups. $R^3$ may represent CH$_2$CHOHCH$_2$OCH$_3$.

In one embodiment $R^3$ represents $C_{1-6}$alkoxy$C_{1-6}$alkyl. $R^3$ may represent —CH$_2$CH$_2$OCH$_3$ or —CH$_2$CH$_2$CH$_2$OCH$_3$.

In one embodiment $R^3$ represents hydroxyhalo$C_{1-6}$alkyl, for example $R^3$ may represent —CH$_2$CHOHCF$_3$.

In one embodiment $R^3$ represents hydroxy$C_{1-6}$alkyl optionally substituted with —O—C(=O)—$C_{1-6}$alkyl such as —O—C(=O)CH$_3$, for example $R^3$ may represent —CH$_2$CH(OC(=O)CH$_3$)CH$_2$OCH$_3$.

In one embodiment $R^3$ represents halo$C_{1-6}$alkyl optionally substituted with —O—C(=O)—$C_{1-6}$alkyl such as —O—C(=O)CH$_3$, for example $R^3$ may represent —CH$_2$CH(OC(=O)CH$_3$)CF$_3$.

In a yet further embodiment $R^3$ represents $C_{1-6}$alkyl substituted with —NR$^{10}$R$^{11}$.

In one embodiment $R^3$ represents $C_{1-4}$alkyl substituted with —NR$^{10}$R$^{11}$. In one embodiment $R^3$ represents $C_{1-4}$alkyl substituted —NR$^{10}$R$^{11}$, wherein the $C_{1-4}$alkyl group is a straight chain alkyl group e.g. 2-ethyl, n-propyl. In one embodiment $R^3$ represents $C_{1-4}$alkyl substituted with —NR$^{10}$R$^{11}$, wherein the $C_{1-4}$alkyl group is an ethylene group (—CH$_2$CH$_2$—).

In one embodiment when $R^3$ represents $C_{1-6}$alkyl (e.g. 2-ethyl, n-propyl) substituted with —NR$^{10}$R$^{11}$, wherein $R^{10}$ and $R^{11}$ are independently selected from hydrogen, $C_{1-6}$alkyl and halo$C_{1-6}$alkyl (e.g. hydrogen, iso-propyl or —CH$_2$CF$_3$).

In one embodiment when $R^3$ represents $C_{1-6}$alkyl substituted with —NR$^{10}$R$^{11}$, $R^{10}$ and $R^{11}$ have the following meanings:

a) one of $R^{10}$ and $R^{11}$ represents hydrogen and the other represents $C_{1-6}$alkyl, for example CH$_3$ or —CH(CH$_3$)$_2$. $R^3$ may represent —CH$_2$CH$_2$NHCH$_3$ or —CH$_2$CH$_2$NHCH(CH$_3$)$_2$;

b) one of $R^{10}$ and $R^{11}$ represents hydrogen and the other represents halo$C_{1-6}$alkyl, for example —CH$_2$CF$_3$. $R^3$ may represent —CH$_2$CH$_2$CH$_2$NHCH$_2$CF$_3$;

c) one of $R^{10}$ and $R^{11}$ represents hydrogen and the other represents hydroxy$C_{1-6}$alkyl, for example —CH$_2$CH$_2$CH$_2$OH. $R^3$ may represent —CH$_2$CH$_2$CH$_2$NHCH$_2$CH$_2$OH;

d) both of $R^{10}$ and $R^{11}$ represents hydrogen;

In one embodiment $R^3$ represents —CH$_2$CH$_2$NHCH(CH$_3$)$_2$.

$R^{3a}$ may represent —NR$^{10}$R$^{11}$, hydroxyl, $C_{1-6}$alkyl, hydroxy$C_{1-6}$alkyl, hydroxyhalo$C_{1-6}$alkyl, halo$C_{1-6}$alkyl, $C_{1-6}$alkyl substituted with —C(=O)—$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with $R^9$, $C_{1-6}$-alkyl substituted with —NR$^{10}$R$^{11}$, $C_{1-6}$alkyl substituted with hydroxyl and —NR$^{10}$R$^{11}$, $C_{1-6}$alkyl substituted with one or two halogens and —NR$^{10}$R$^{11}$, $C_{1-6}$alkyl substituted with —C(=O)—O—$C_{1-6}$alkyl, $C_{1-6}$alkyl substituted with —O—C(=O)—NR$^{10}$R$^{11}$, $C_{1-6}$alkyl substituted with carboxyl, $C_{1-6}$alkyl substituted with —O—C(=O)—NR$^{10}$R$^{11}$, $C_{1-6}$alkyl substituted with —NR$^{12}$—S(=O)$_2$—$C_{1-6}$alkyl, $C_{1-6}$alkyl substituted with —NR$^{12}$—S(=O)$_2$—NR$^{14}$R$^{15}$, $C_{1-6}$alkyl substituted with hydroxyl and $R^9$, —$C_{1-6}$alkyl-C(R$^{12}$)=N—O—R$^{12}$, $C_{1-6}$-alkyl substituted with —C(=O)—NR$^{10}$R$^{11}$, $C_{1-6}$alkyl substituted with —C(=O)—R$^9$, $C_{2-6}$alkynyl substituted with $R^9$, hydroxy$C_{1-6}$alkoxy, $C_{2-6}$alkenyl, $C_{2-6}$alkynyl, $R^{13}$ or $C_{1-6}$alkyl substituted with $C_{1-6}$alkoxy$C_{1-6}$alkyl-C(=O)—.

In one embodiment $R^{3a}$ is —NR$^{10}$R$^{11}$, hydroxyl, hydroxy$C_{1-6}$alkyl, cyano$C_{1-6}$alkyl, $C_{1-6}$alkyl substituted with —C(=O)—$C_{1-6}$alkyl, $C_{1-6}$alkyl substituted with —C(=O)—O—$C_{1-6}$alkyl, $C_{1-6}$alkyl substituted with $R^9$, $C_{1-6}$-alkyl substituted with —NR$^{10}$R$^{11}$, $C_{1-6}$alkyl substituted with hydroxyl and —NR$^{10}$R$^{11}$, or $C_{1-6}$alkyl substituted with —C(=O)—NR$^{10}$R$^{11}$.

In one embodiment $R^{3a}$ represents hydroxyl.
In one embodiment $R^{3b}$ represents hydrogen.
In one embodiment $R^{3b}$ represents hydroxyl.
In one embodiment $R^{3a}$ represents hydroxyl and $R^{3b}$ represents hydrogen.

In one embodiment $R^{3a}$ and $R^{3b}$ are taken together to form =O, to form =NR$^{10}$, to form cyclopropyl together with the carbon atom to which they are attached, to form =CH—C$_{0-4}$alkyl substituted with $R^{3c}$, or to form

wherein ring A is a monocyclic 5 to 7 membered saturated heterocycle containing one heteroatom selected from N, O or S, said heteroatom not being positioned in alpha position of the double bond, wherein ring A is optionally being substituted with cyano, $C_{1-4}$alkyl, hydroxy$C_{1-4}$alkyl, H$_2$N—$C_{1-4}$alkyl, ($C_{1-4}$alkyl)NH—$C_{1-4}$alkyl, ($C_{1-4}$alkyl)$_2$N—$C_{1-4}$alkyl, (halo$C_{1-4}$alkyl)NH—$C_{1-4}$alkyl, $C_{1-4}$alkoxy$C_{1-4}$alkyl, —C(=O)—NH$_2$, —C(=O)—NH($C_{1-4}$alkyl), or —C(=O)—N($C_{1-4}$alkyl)$_2$.

In one embodiment $R^{3a}$ and $R^{3b}$ are taken together to form =O, to form cyclopropyl together with the carbon atom to which they are attached, to form =CH—C$_{0-4}$alkyl substituted with $R^{3c}$, or to form

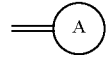

wherein ring A is a monocyclic 5 to 7 membered saturated heterocycle containing one heteroatom selected from N, O or S, said heteroatom not being positioned in alpha position of the double bond.

In one embodiment $R^{3a}$ and $R^{3b}$ are taken together to form =O.

In one embodiment $R^{3a}$ and $R^{3b}$ are taken together to form cyclopropyl together with the carbon atom to which they are attached.

In one embodiment $R^{3a}$ and $R^{3b}$ are taken together to form =CH—$C_{0-4}$alkyl substituted with $R^{3c}$.

In one embodiment $R^{3c}$ represents hydrogen.

In one embodiment $R^{3c}$ represents hydroxyl, $C_{1-6}$alkoxy, $R^9$, —$NR^{10}R^{11}$, cyano, —C(=O)—$C_{1-6}$alkyl or —CH(OH)—$C_{1-6}$alkyl.

In one embodiment $R^{3c}$ represents hydroxyl, —$NR^{10}R^{11}$, cyano, or —C(=O)—$C_{1-6}$alkyl.

In one embodiment $R^{3a}$ and $R^{3b}$ are taken together to form =CH—$C_{0-4}$alkyl in the Z configuration.

In one embodiment, $R^4$ and $R^5$ each independently represent hydrogen, $C_{1-6}$alkyl, $C_{1-6}$alkyl substituted with —$NR^{14}R^{15}$, hydroxy$C_{1-6}$alkyl, $C_{1-6}$alkoxy$C_{1-6}$alkyl wherein each $C_{1-6}$alkyl may optionally be substituted with one hydroxyl group, —C(=O)—$NR^{14}R^{15}$, —C(=O)—O—$C_{1-6}$alkyl or —C(=O)—$R^{13}$.

In one embodiment, $R^4$ represents hydrogen, $C_{1-6}$alkyl, $C_{1-6}$alkyl substituted with —$NR^{14}R^{15}$, hydroxy$C_{1-6}$alkyl, $C_{1-6}$alkoxy$C_{1-6}$alkyl wherein each $C_{1-6}$alkyl may optionally be substituted with one hydroxyl group, —C(=O)—$NR^{14}R^{15}$, —C(=O)—O—$C_{1-6}$alkyl, —C(=O)—$R^{13}$.

In one embodiment, $R^5$ represents hydrogen or $C_{1-6}$alkyl.

In one embodiment, $R^{14}$ and $R^{15}$ represent hydrogen.

In one embodiment, $R^{13}$ represents a saturated 6-membered monocyclic heterocyclyl containing at least one heteroatom selected from N or O, such as for example morpholinyl.

In one embodiment, $R^9$ is selected from:
an optionally substituted $C_{3-8}$cycloalkyl,
an optionally substituted aromatic 5 membered monocyclic heterocyclyl,
an optionally substituted saturated 6 membered monocyclic heterocyclyl,
a saturated or an aromatic 3, 4, 5 or 6 membered monocyclic heterocyclyl containing one or two oxygen heteroatoms,
an optionally substituted 4 membered heterocyclyl containing one oxygen heteroatom,
an optionally substituted aromatic 6 membered monocyclic heterocycle containing one or two nitrogen heteroatoms,
a partially saturated 6 membered monocyclic heterocyclyl containing one nitrogen heteroatom which may optionally be substituted,
an optionally substituted saturated 4 membered monocyclic heterocyclyl containing one nitrogen heteroatom,
a saturated 5 membered monocyclic heterocyclyl containing one nitrogen heteroatom,
a saturated 6 membered monocyclic heterocyclyl containing one nitrogen heteroatom,
a bicyclic heterocyclyl containing a benzene ring fused to a 5- or 6-membered ring containing 1, 2 or 3 ring heteroatoms,
a 4, 5 or 6 membered monocyclic saturated heterocycle substituted with two substituents which are attached to the same atom and which are taken together to form a 4 to 7-membered saturated monocyclic heterocyclyl containing at least one heteroatom selected from N, O or S,
an optionally substituted aromatic 5 membered monocyclic heterocyclyl containing one sulphur heteroatom,
an optionally substituted aromatic 5 membered monocyclic heterocyclyl containing one sulphur and one nitrogen heteroatom,
a saturated 6 membered monocyclic heterocyclyl containing two nitrogen heteroatoms,
an aromatic 5 membered monocyclic heterocyclyl containing four nitrogen heteroatoms,
an aromatic 5 membered monocyclic heterocyclyl containing one oxygen and two nitrogen heteroatoms,
an optionally substituted aromatic 5 membered monocyclic heterocyclyl containing two nitrogen heteroatoms,
an optionally substituted aromatic 5 membered monocyclic heterocyclyl containing three nitrogen heteroatoms,
a saturated 5 membered monocyclic heterocyclyl containing one nitrogen and one oxygen heteroatom,
a saturated 6 membered monocyclic heterocyclyl containing one nitrogen and one sulphur heteroatom,
a saturated 7 membered monocyclic heterocyclyl containing two nitrogen heteroatoms,
a saturated 7 membered monocyclic heterocyclyl containing one nitrogen and one oxygen heteroatom, and
phenyl or naphthyl, in particular phenyl.

In one embodiment, $R^9$ represents $C_{3-6}$cycloalkyl, such as for example cyclopropyl, a 3 membered saturated heterocyclyl, such as for example oxiranyl, an optionally substituted 5 membered saturated heterocycle, such as for example pyrolidinonyl, an optionally substituted 6 membered aromatic or saturated heterocycle, such as for example pyridyl, pyrimidinyl, pyrazinyl, piperazinyl, or morpholinyl, an optionally substituted bicyclic heterocycle, such as for example 1H-isoindol-1,3-dione. Optional substituents may represent =O, $C_{1-4}$alkoxy, $C_{1-4}$alkyl substituted with —$NR^{14}R^{15}$ hydroxy$C_{1-4}$alkyl, or $C_{1-4}$alkyl-C(=O)—.

In one embodiment, $R^9$ represents an optionally substituted 5 membered aromatic heterocycle, such as for example imidazolyl, or an optionally substituted 6 membered aromatic heterocycle, such as for example pyridyl, pyrimidinyl or pyrazinyl. Optional substituents may represent $C_{1-4}$alkoxy or —S(=O)$_2$—$NR^{14}R^{15}$.

In one embodiment, $R^9$ represents an optionally substituted 5 membered aromatic heterocycle, such as for example imidazolyl. Optional substituents may represent —S(=O)$_2$—$NR^{14}R^{15}$.

In one embodiment, $R^9$ represents an optionally substituted 6 membered aromatic heterocycle, such as for example pyridinyl or pyrimidinyl. Optional substituents may represent $C_{1-4}$alkoxy.

In one embodiment, $R^9$ represents an optionally substituted 5 membered aromatic or saturated heterocycle, such as for example imidazolyl, pyrrolidinyl, oxazolidinyl. Optional substituents may represent =O, a 5 or 6-membered aromatic monocyclic heterocyclyl containing at least one heteroatom selected from N, O or S wherein said heterocyclyl is optionally substituted with $R^{16}$; or —S(=O)$_2$—$NR^{14}R^{15}$.

In one embodiment $R^{10}$ represents hydrogen or $C_{1-6}$alkyl,

In one embodiment $R^{10}$ is hydrogen.

In one embodiment $R^{11}$ represents hydrogen, $C_{1-6}$alkyl, halo$C_{1-6}$alkyl, —C(=O)—$C_{1-6}$alkyl, —S(=O)$_2$—$C_{1-6}$alkyl, —S(=O)$_2$—$NR^{14}R^{15}$, hydroxy$C_{1-6}$alkyl, —C(=O)-hydroxyhalo$C_{1-6}$alkyl, —C(=O)—$R^6$, cyano $C_{1-6}$alkyl, $R^6$, —C(=O)—$R^6$, $C_{1-6}$alkyl substituted with $R^6$, —C(=O)-halo$C_{1-6}$alkyl, $C_{1-6}$alkyl substituted with —Si(CH$_3$)$_3$, $C_{1-6}$alkyl substituted with —$NR^{14}R^{15}$, $C_{1-6}$alkyl substituted with —C(=O)—$NR^{14}R^{15}$, $C_{1-6}$alkoxy, hydroxyhalo$C_{1-6}$alkyl, carboxyl, or $C_{1-6}$alkoxy$C_{1-6}$alkyl.

In one embodiment $R^{10}$ or $R^{11}$ represents hydrogen, $C_{1-6}$alkyl, halo$C_{1-6}$alkyl, hydroxy$C_{1-6}$alkyl, $C_{1-6}$alkyl substituted with —$NR^{14}R^{15}$, $C_{1-6}$alkyl substituted with carboxyl.

In one embodiment $R^{10}$ and $R^{11}$ represent hydrogen or $C_{1-6}$alkyl.

In one embodiment $R^{10}$ represents hydrogen or $C_{1-6}$alkyl.

In one embodiment $R^{10}$ is hydrogen.

In one embodiment $R^{11}$ represents hydrogen, $C_{1-6}$alkyl, halo$C_{1-6}$alkyl, —C(=O)—$C_{1-6}$alkyl, —S(=O)$_2$—$C_{1-6}$alkyl, —S(=O)$_2$—$NR^{14}R^{15}$, hydroxy$C_{1-6}$alkyl, —C(=O)-hydroxyhalo$C_{1-6}$alkyl, —C(=O)—$R^6$, cyano $C_{1-6}$alkyl, $R^6$, —C(=O)—$R^6$, $C_{1-6}$alkyl substituted with $R^6$, —C(=O)-halo$C_{1-6}$alkyl, $C_{1-6}$alkyl substituted with —Si(CH$_3$)$_3$, $C_{1-6}$alkyl substituted with —$NR^{14}R^{15}$, $C_{1-6}$alkyl substituted with —C(=O)—$NR^{14}R^{15}$, $C_{1-6}$alkoxy, hydroxyhalo$C_{1-6}$alkyl, carboxyl, or $C_{1-6}$alkoxy$C_{1-6}$alkyl.

In one embodiment, $R^6$ represents a 6-membered monocyclic saturated heterocyclyl which is optionally substituted. For example piperazinyl or morpholinyl or tetrahydropyranyl, optionally substituted with halogen, $C_{1-6}$alkyl, or $C_{1-6}$alkyl-O—C(=O)—.

In one embodiment, $R^6$ represents a 6-membered monocyclic aromatic heterocyclyl which is optionally substituted. For example pyridinyl, optionally substituted with halogen, $C_{1-6}$alkyl, or $C_{1-6}$alkyl-O—C(=O)—.

In one embodiment, $R^{12}$ represents hydrogen or $C_{1-4}$alkyl optionally substituted with $C_{1-4}$alkyloxy.

In one embodiment, $R^{13}$ represents a saturated 4 to 6-membered monocyclic heterocyclyl containing at least one heteroatom selected from N or O.

In one embodiment, $R^{14}$ and $R^{15}$ each independently represent hydrogen or $C_{1-4}$alkyl.

In one embodiment, $R^{22}$ and $R^{23}$ each independently represent hydrogen.

In one embodiment, Y represents —CR$^{18}$=N—OR$^{19}$ or -E-D; $R^{18}$ and $R^{19}$ represent $C_{1-6}$alkyl; E represents a bond, $C_{2-4}$alkenediyl, —CO—(CR$^{22}$R$^{23}$)$_s$—, —NR$^{22}$—(CR$^{22}$R$^{23}$)$_s$—, —(CR$^{22}$R$^{23}$)$_s$—NR$^{22}$—, —(CR$^{22}$R$^{23}$)$_s$—CO—NR$^{22}$—(CR$^{22}$R$^{23}$)$_s$— or —(CR$^{22}$R$^{23}$)$_s$—NR$^{22}$—CO—(CR$^{22}$R$^{23}$)$_s$—; D is piperidinyl, pyridinyl, phenyl, pyrolyl, imidazolyl, triazolyl, pyrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrolidinyl, thiadiazolyl, oxadiazolyl, pyrazolyl, said rings being optionally substituted with halo, cyano, $C_{1-6}$alkyl, $C_{1-6}$alkoxy, —C(=O)—O—$C_{1-6}$alkyl, hydroxy$C_{1-6}$alkyl, —NR$^4$R$^5$, $C_{1-6}$alkyl substituted with —O—C(=O)— $C_{1-6}$alkyl, $C_{1-6}$alkyl substituted with —NR$^4$R$^5$, —C(=O)—NR$^4$R$^5$, —C(=O)—$C_{1-6}$alkyl-NR$^4$R$^5$, $R^6$, $C_{1-6}$alkyl substituted with $R^6$; W is —N(R$^3$)—; $R^2$ represents $C_{1-4}$alkoxy; n is equal to 2; $R^3$ represents $C_{2-6}$alkynyl, halo$C_{1-6}$alkyl optionally substituted with —O—C(=O)—$C_{1-6}$alkyl, hydroxy $C_{1-6}$alkyl optionally substituted with —O—C(=O)—$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, $C_{1-6}$alkyl substituted with $R^9$, $C_{2-6}$alkynyl substituted with $R^9$, $C_{1-6}$alkyl substituted with —NR$^{10}$R$^{11}$, $C_{1-6}$alkyl substituted with —O—C(=O)—NR$^{10}$R$^{11}$; $R^9$ represents $C_{3-6}$cycloalkyl, a 3 membered saturated heterocyclyl, an optionally substituted 5 membered saturated heterocycle, an optionally substituted 6 membered aromatic or saturated heterocycle, an optionally substituted bicyclic heterocycle; $R^{10}$ and $R^{11}$ represents hydrogen, $C_{1-6}$alkyl, halo$C_{1-6}$alkyl, hydroxy$C_{1-6}$alkyl, $C_{1-6}$alkyl substituted with —NR$^{14}$R$^{15}$, $C_{1-6}$alkyl substituted with carboxyl; $R^6$ represents a 6-membered monocyclic saturated or aromatic heterocyclyl which is optionally substituted; $R^{14}$ and $R^{15}$ each independently represent hydrogen or $C_{1-4}$alkyl; $R^{22}$ and $R^{23}$ each independently represent hydrogen.

In one embodiment there is provided compounds of formula (I) including any tautomeric or stereochemically isomeric form thereof, wherein W is —N(R$^3$)—;
each $R^2$ represents $C_{1-4}$alkoxy, for example CH$_3$O—;
Y represents —CR$^{18}$=N—OR$^{19}$ or -E-D;
E represents a bond, $C_{2-4}$alkynediyl for example —C(triple bond)C—, —CO—(CR$^{22}$R$^{23}$)$_s$— for example —C(=O)—, —NR$^{22}$—(CR$^{22}$R$^{23}$)$_s$— for example —NH—, or —NH—(CH$_2$)—, —(CR$^{22}$R$^{23}$)$_s$—CO—NR$^{22}$—(CR$^{22}$R$^{23}$)$_s$— for example —C(=O)—NH—, —C(=O)—NH—(CH$_2$)$_2$—, —C(=O)—NH—(CH$_2$)—, —C(=O)—NH—(CH$_2$)$_3$—, or —(CR$^{22}$R$^{23}$)$_s$—NR$^{22}$—CO—(CR$^{22}$R$^{23}$)$_s$— for example —NH—C(=O)—;
D represents a 3 to 12 ring membered monocyclic or bicyclic carbocyclyl or a 3 to 12 ring membered monocyclic or bicyclic heterocyclyl containing at least one heteroatom selected from N, O or S, wherein said carbocyclyl and heterocyclyl may each be optionally substituted by one or more (e.g. 1, 2 or 3) $R^1$ groups; for example D represents piperidinyl, pyridinyl, phenyl, pyrolyl, imidazolyl, triazolyl, pyrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrolidinyl, thiadiazolyl, oxadiazolyl, pyrazolyl (e.g. 1-pyrazolyl, 2-pyrazolyl, or 3-pyrazolyl);
$R^1$ represents
halo, for example fluoro or chloro;
cyano;
$C_{1-6}$alkyl, for example —CH$_3$;
$C_{1-6}$alkoxy, for example —O—CH$_3$;
—C(=O)—O—$C_{1-6}$alkyl, for example —C(=O)—O—CH$_2$CH$_3$, —C(=O)—O—C(CH$_3$)$_3$, —C(=O)—O—CH$_3$;
hydroxy$C_{1-6}$alkyl, for example —CH$_2$CH$_2$OH, —CH$_2$OH;
—NR$^4$R$^5$, for example —NH$_2$, —NHCH$_3$, —NH—C(=O)—O—C(CH$_3$)$_3$, —NCH$_3$—C(=O)—O—C(CH$_3$)$_3$, —NH—C(=O)—NH—CH(CH$_3$)$_2$, —NH—C(=O)— substituted with morpholin-4-yl;
$C_{1-6}$alkyl substituted with —O—C(=O)— $C_{1-6}$alkyl, for example —CH$_2$—O—C(=O)—CH$_3$;
$C_{1-6}$alkyl substituted with —NR$^4$R$^5$, for example —CH$_2$NH$_2$, —CH$_2$NH—C(=O)—O—C(CH$_3$)$_3$;
—C(=O)—NR$^4$R$^5$, for example —C(=O)—NH(CH$_3$), —C(=O)—NH(CH$_2$)$_3$NH$_2$, —C(=O)—NH(CH$_2$)$_4$NH$_2$, —C(=O)—NH(CH$_2$)$_5$NH$_2$, —C(=O)—NH(CH$_2$)$_5$OH;
$R^6$, for example morpholinyl, tetrahydropyranyl, piperazinyl, pyridinyl substituted with chlorine, piperazinyl substituted with —CH$_3$ or —C(=O)—O—C(CH$_3$)$_3$;
$C_{1-6}$alkyl substituted with $R^6$, for example —CH$_2$CH$_2$— substituted with morpholin-4-yl; or
—C(=O)—$R^6$, for example —C(=O) substituted with morpholin-4-yl;
$R^3$ represents
$C_{2-6}$alkynyl, for example —CH$_2$—C(triple bond)CH;
halo$C_{1-6}$alkyl optionally substituted with —O—C(=O)—$C_{1-6}$alkyl, for example —CH$_2$CH(—O—C(=O)—CH$_3$)CF$_3$;
hydroxy$C_{1-6}$alkyl optionally substituted with —O—C(=O)—$C_{1-6}$alkyl, for example —CH$_2$CH$_2$OH, —CH$_2$CH$_2$CH$_2$OH, —CH$_2$CH(OH)CH$_2$(OH);
hydroxyhalo$C_{1-6}$alkyl, for example —CH$_2$CH(OH)CF$_3$;
$C_{1-6}$alkoxy$C_{1-6}$alkyl wherein each $C_{1-6}$alkyl may optionally be substituted with one or two hydroxyl groups or with —O—C(=O)—$C_{1-6}$alkyl, for example —CH$_2$CH$_2$—O—CH$_3$, —CH$_2$CH$_2$CH$_2$—O—CH$_3$, —CH$_2$CH(OH)CH$_2$—O—CH$_3$, —CH$_2$CH(—O—C(=O)—CH$_3$)CH$_2$—O—CH$_3$;

C$_{1-6}$alkyl substituted with R$^9$, for example —CH$_2$—(C$_3$H$_5$), —CH$_2$CH$_2$ substituted with 1H-isoindol-1,3-dione or with pyrrolidin-1-yl substituted in the 4 position with =O or —CH$_2$OH, —CH$_2$— substituted with oxiranyl or pyridine-5-yl substituted in the 2 position with —CH$_2$NH$_2$, —CH$_2$CH$_2$— substituted with piperazin-1-yl optionally substituted in the 4 position with —C(=O)—CH$_3$, —CH$_2$CH$_2$— substituted with morpholin-4-yl;

C$_{2-6}$alkynyl substituted with R$^9$, for example —CH$_2$—C(triple bond)C substituted with pyridin-2-yl substituted in the 3 position with —O—CH$_3$ or with pyrimidin-2-yl;

C$_{1-6}$alkyl substituted with —NR$^{10}$R$^{11}$, for example —CH$_2$CH$_2$NH$_2$, —CH$_2$CH$_2$NHCH(CH$_3$)$_2$, —CH$_2$CH$_2$CH$_2$NHCH(CH$_3$)$_2$, —CH$_2$CH$_2$NHCH$_3$, —CH$_2$CH$_2$NHCH$_2$CF$_3$, —CH$_2$CH$_2$CH$_2$NHCH$_2$CF$_3$, CH$_2$CH$_2$CH$_2$NHCH$_2$C(=O)—OH, —CH$_2$CH$_2$CH$_2$NHCH$_2$CH$_2$CH$_2$OH; or C$_{1-6}$alkyl substituted with —O—C(=O)—NR$^{10}$R$^{11}$; for example —CH$_2$CH$_2$—O—C(=O)—NHCH$_3$;

R$^{18}$ represents C$_{1-6}$ alkyl, for example —CH$_3$;

R$^{19}$ represents C$_{1-6}$ alkyl, for example —CH$_3$, C(CH$_3$)$_3$; and n represents an integer equal to 2;

the N-oxides thereof, the pharmaceutically acceptable salts thereof or the solvates thereof.

In one embodiment, the compound of formula (I) is any one of the following compounds

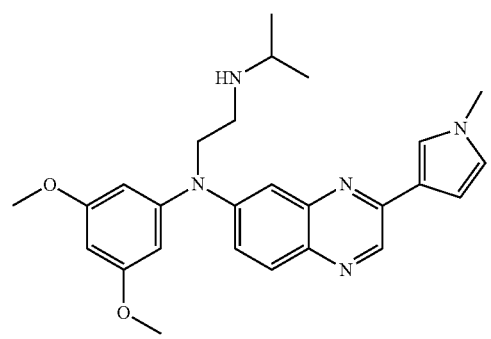

as a HCl salt

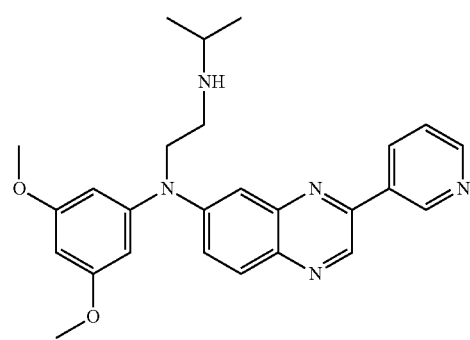

as a HCl salt

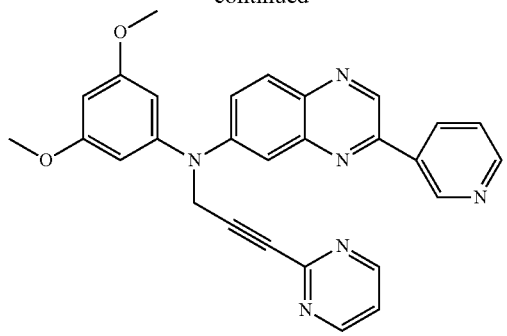

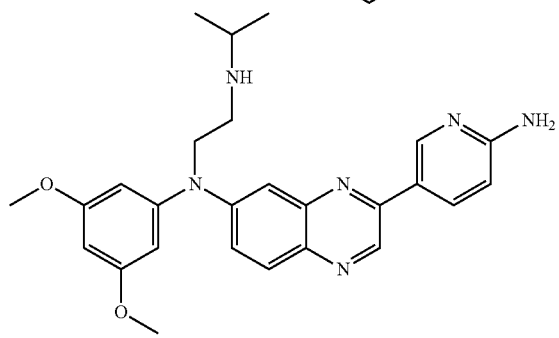

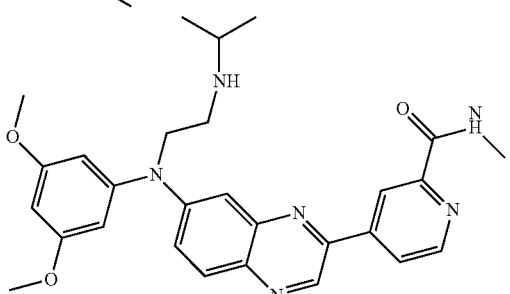

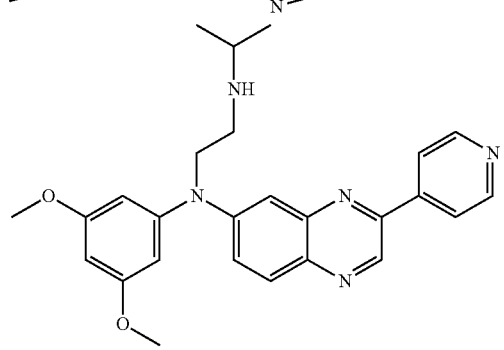

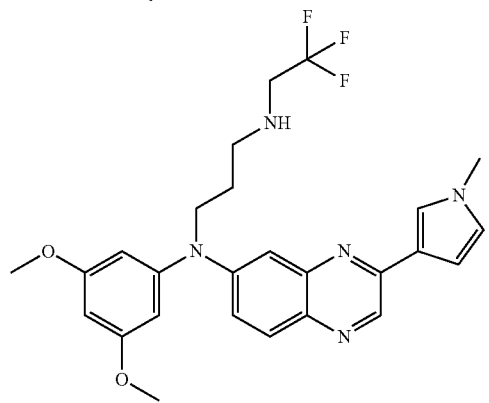

as a HCl salt

-continued

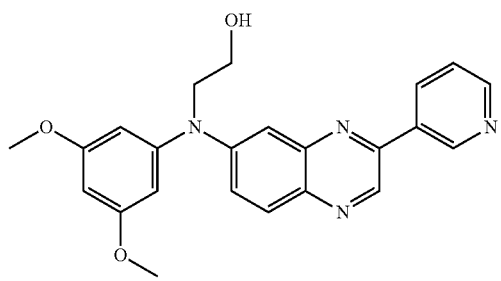

a N-oxide thereof, a pharmaceutically acceptable salt thereof or a solvate thereof.

In one embodiment, W is —N(R$^3$)— and Y is D (E is a bond).

In one embodiment, W is —N(R$^3$)— and Y is -E-D wherein E is other than a bond.

In one embodiment, W is —N(R$^3$)—, and Y is —CR$^{18}$=N—OR$^{19}$.

In one embodiment, W is —N(R$^3$)—, Y is -E-D, wherein E is a bond and D is a 5 or 6 membered monocyclic aromatic heterocyclyl, wherein said heterocyclyl may optionally be substituted by one or more (e.g. 1, 2 or 3) R$^1$ groups, and wherein one or more of the following applies:

n is 2;

R$^2$ is C$_{1-6}$alkyloxy;

R$^2$ is placed in position 3 and 5.

In one embodiment, W is —N(R$^3$)—, Y is -E-D, wherein E is a bond and D is piperidinyl, pyridinyl, phenyl, pyrolyl, imidazolyl, triazolyl, pyrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrolidinyl, thiadiazolyl, oxadiazolyl, said rings being optionally substituted, more in particular D is piperidinyl, pyridinyl, phenyl, pyrolyl, imidazolyl, triazolyl, pyrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrolidinyl, thiadiazolyl, oxadiazolyl, said rings being optionally substituted and n is 2, even more in particular D is piperidinyl, pyridinyl, phenyl, pyrolyl, imidazolyl, triazolyl, pyrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrolidinyl, thiadiazolyl, oxadiazolyl, said rings being optionally substituted; n is 2, R$^2$ is C$_{1-6}$alkyloxy, even further in particular D is piperidinyl, pyridinyl, phenyl, pyrolyl, imidazolyl, triazolyl, pyrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrolidinyl, thiadiazolyl, oxadiazolyl, said rings being optionally substituted; n is 2, R$^2$ is C$_{1-6}$alkyloxy and said R$^2$ is placed in position 3 and 5.

In one embodiment, W is —C(R$^{3a}$R$^{3b}$)— and Y is D (E is a bond).

In one embodiment, W is —C(R$^{3a}$R$^{3b}$)— and Y is -E-D wherein E is other than a bond.

In one embodiment, W is —C(R$^{3a}$R$^{3b}$)—, and Y is —CR$^{18}$=N—OR$^{19}$.

In one embodiment, W is —C(R$^{3a}$R$^{3b}$)—, Y is -E-D, wherein E is a bond and D is a 5 or 6 membered monocyclic aromatic heterocyclyl, wherein said heterocyclyl may optionally be substituted by one or more (e.g. 1, 2 or 3) R$^1$ groups, and wherein one or more of the following applies:

n is 2;

R$^2$ is C$_{1-6}$alkyloxy;

R$^2$ is placed in position 3 and 5.

In one embodiment, W is —C(R$^{3a}$R$^{3b}$)—, Y is -E-D, wherein E is a bond and D is piperidinyl, pyridinyl, phenyl, pyrolyl, imidazolyl, triazolyl, pyrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrolidinyl, thiadiazolyl, oxadiazolyl, said rings being optionally substituted, more in particular D is piperidinyl, pyridinyl, phenyl, pyrolyl, imidazolyl, triazolyl, pyrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrolidinyl, thiadiazolyl, oxadiazolyl, said rings being optionally substituted and n is 2, even more in particular D is piperidinyl, pyridinyl, phenyl, pyrolyl, imidazolyl, triazolyl, pyrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrolidinyl, thiadiazolyl, oxadiazolyl, said rings being optionally substituted; n is 2, R$^2$ is C$_{1-6}$alkyloxy, even further in particular D is piperidinyl, pyridinyl, phenyl, pyrolyl, imidazolyl, triazolyl, pyrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrolidinyl, thiadiazolyl, oxadiazolyl, said rings being optionally substituted; n is 2, R$^2$ is C$_{1-6}$alkyloxy and said R$^2$ is placed in position 3 and 5.

For the avoidance of doubt, it is to be understood that each general and specific preference, embodiment and example for one substituent may be combined, whenever possible, with each general and specific preference, embodiment and example for one or more, preferably, all other substituents as defined herein and that all such embodiments are embraced by this application.

Methods for the Preparation of Compounds of Formula (I)

In this section, as in all other sections of this application unless the context indicates otherwise, references to formula (I) also include all other sub-groups and examples thereof as defined herein.

In general, compounds of formula (I) wherein W is —N(R$^3$)— and Y is D (E is a bond), said compounds being represented by formula (Ia), can be prepared according to the following reaction Scheme 1.

Scheme 1
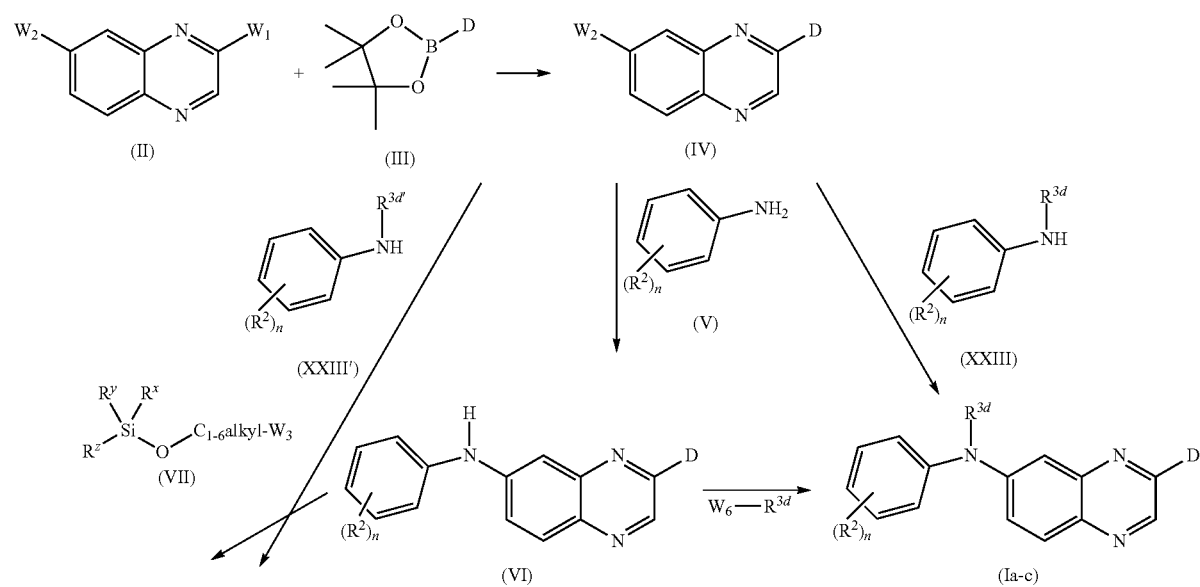
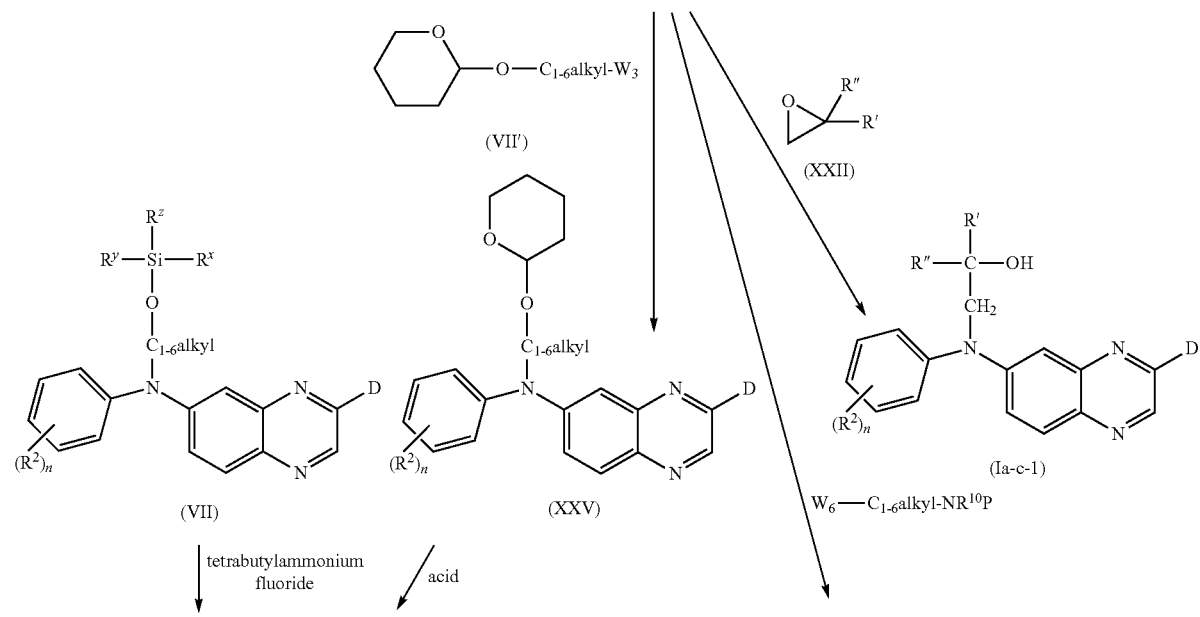

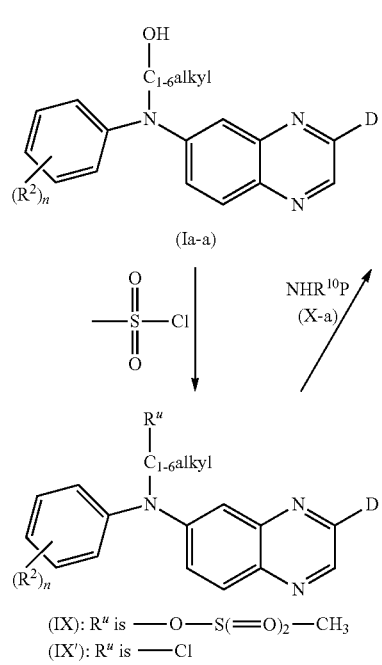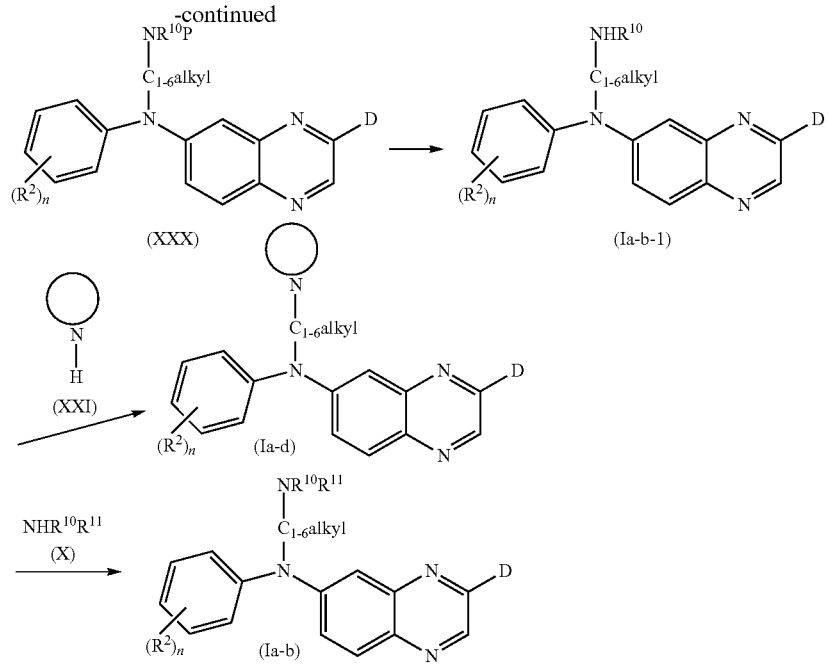

In scheme 1, an intermediate of formula (IV) is prepared by reacting an intermediate of formula (II) wherein $W_1$ and $W_2$, each independently represent a suitable leaving group, such as for example halo, e.g. chloro or bromo and the like, with an intermediate of formula (III) in the presence of a suitable catalyst, such as for example tetrakis(triphenylphosphine)palladium (0) or palladium (II) acetate, a suitable base, such as for example sodium carbonate, a suitable ligand, such as for example triphenylphosphine, and a suitable solvent or solvent mixture, such as for example ethylene glycol dimethylether and water. Instead of an intermediate of formula (III) also the boronic acid of D can be used. The intermediate of formula (IV) is then further reacted in a next step with an intermediate of formula (V) in the presence of a suitable catalyst, such as for example palladium (II) acetate, a suitable base, such as sodium tert-butoxide or $Cs_2CO_3$, a suitable ligand, such as for example 1,1'-[1,1'-binaphthalene]-2,2'-diylbis[1,1-diphenylphosphine], and a suitable solvent or solvent mixture, such as for example dioxane or ethylene glycol dimethylether and water, resulting in an intermediate of formula (VI). Said intermediate of formula (VI) can then be reacted with an intermediate of formula (VII) wherein $W_3$ represents a suitable leaving group, such as for example halo, e.g. bromo and wherein $R^x$ and $R^y$ represent $C_{1-4}$alkyl, and $R^z$ represent $C_{1-4}$alkyl or phenyl, for instance $R^x$ and $R^y$ represent $CH_3$ and $R^z$ represents $C(CH_3)_3$ or phenyl, in the presence of a suitable base, such as for example sodium hydride, and a suitable solvent, such as for example N,N-dimethylformamide or N,N-dimethylacetamide, resulting in an intermediate of formula (VIII). Intermediates of formula (VIII) or intermediates of formula (VIII) wherein the $R^1$ substituent carries a suitable protective group can also be prepared by reacting an intermediate of formula (IV) or an intermediate of formula (IV) wherein the $R^1$ substituent carries a suitable protective group with an intermediate of formula (XXIII') wherein $R^{3d'}$ represent —$C_{1-6}$alkyl-O—Si($R^x$)($R^y$)($R^z$) in the presence of a suitable catalyst, such as for example palladium (II) acetate, a suitable ligand, such as for example racemic-2,2'-bis(diphenylphosphino)-1,1'-binaphtyl, a suitable base, such as for example $Cs_2CO_3$, and a suitable solvent, such as for example 1,2-dimethoxyethane. Intermediates of formula (VIII) can be converted into a compound of formula (I) wherein $R^3$ represents —$C_{1-6}$alkyl-OH, said compounds being represented by formula (Ia-a) or compounds of formula (I-a) wherein the $R^1$ substituent carries a suitable protective group, by reaction with tetrabutylammonium fluoride in the presence of a suitable solvent, such as for example tetrahydrofuran. This type of reaction can also be performed in the presence of a suitable acid, such as for example acetic acid or HCl, and a suitable solvent, such as for example tetrahydrofurane or dioxane. Alternatively, an intermediate of formula (VI) can react with an intermediate of formula (VII') wherein $W_3$ represents a suitable leaving group, such as for example halo, e.g. bromo and the like, in the presence of a suitable base, such as for example sodium hydride, and a suitable solvent, such as for example N,N-dimethylformamide or N,N-dimethylacetamide, resulting in an intermediate of formula (XXV) which can then be deprotected in the presence of a suitable acid, such as for example HCl, and a suitable solvent, such as for example an alcohol, e.g. methanol or isopropanol, to give a compound of formula (Ia-a). The compounds of formula (Ia-a) or compounds of formula (Ia-a) wherein the $R^1$ substituent carries a suitable protective group can be reacted with methanesulfonyl chloride in the presence of a suitable base, such as for example triethylamine, diisopropylethanamine or N,N-dimethyl-4-aminopyridine, and a suitable solvent, such as for example dichloromethane or tetrahydrofuran, to result in an intermediate of formula (IX) (mesylate derivative) or an intermediate of formula (IX') (chloride derivative) or intermediates of formula (IX) or (IX') wherein the $R^1$ substituent carries a suitable protective group. Intermediates of formula (IX) or (IX') can then be reacted with an intermediate of formula (X) to obtain a compound of formula (Ia) wherein $R^3$ represents $C_{1-6}$alkyl substituted with $NR^{10}R^{11}$, said compounds being represented by formula (Ia-b) or compounds of formula (Ia-b) wherein the $R^1$ substituent carries a suitable protective group. This reaction may optionally be performed in the presence of a suitable base, such as for example triethylamine, $K_2CO_3$, $Na_2CO_3$ or sodium hydride and optionally a suitable solvent, such as for example acetonitrile, tetrahydrofuran, dioxane, N,N-dimethylformamide, 1-methyl-pyrrolidinone, a suitable alcohol, e.g. 1-butanol and the like. This type of reaction can also be performed with a suitable salt of the intermediate of formula (X), e.g. HCl salt of intermediate of formula (X), or may be performed in the presence of potassium iodide. In this way compounds wherein $R^3$ represents iodo$C_{1-6}$alkyl can be obtained. Compounds of formula (Ia-b) wherein the $R^1$ substituent carries a suitable protective group can be converted in a compound of formula (Ia-b) by reaction with a suitable acid, such as for example trifluoroacetic acid, in the presence of a suitable solvent, such as for example dichloromethane.

Intermediates of formula (IX) can also react with a suitable nitrogen containing ring within the definition of $R^9$, said ring being represented by formula (XXI) or a suitable salt of an intermediate of formula (XXI), in the presence of a suitable solvent, such as for example acetonitrile, 1-methyl-2-pyrrolidinone, or an alcohol, e.g. 1-butanol, optionally in the presence of potassium iodide or a suitable base, such as for example $Na_2CO_3$, $K_2CO_3$ or triethylamine, resulting in a compound of formula (Ia-d). Intermediates of formula (IX) can also react with an intermediate of formula (X-a) wherein P represents a suitable protective group, such as for example —C(=O)—O—C(CH$_3$)$_3$, in the presence of a suitable base, such as for example sodium hydride, and a suitable solvent, such as for example dimethylacetamide, resulting in an intermediate of formula (XXX) which can be deprotected to a compound of formula (Ia-b-1) in the presence of a suitable acid, such as for example HCl or trifluoroacetic acid, and a suitable solvent, such as for example dichloromethane or an alcohol, e.g. methanol. Intermediates of formula (XXX) can also be prepared by reacting an intermediate of formula (VI) with an intermediate of formula $W_6$—$C_{1-6}$alkyl-$NR^{10}$P wherein $W_e$ represents a suitable leaving group, such as for example halo, e.g. bromo and the like, or —O—S(=O)$_2$—CH$_3$, and P is as defined above, in the presence of a suitable base, such as for example sodium hydride, and a suitable solvent, e.g. N,N-dimethylformamide or N,N-dimethylacetamide. Alternatively compounds of formula (Ia-d) or (Ia-b-1) can also be prepared by reacting respectively an intermediate of formula (VI) with an intermediate of formula $W_6$—$C_{1-6}$alkyl-Ncycle or $W_6$—$C_{1-6}$alkyl-$NHR^{10}$ wherein $W_6$ is as defined above.

Intermediates of formula (VI) can react with $W_6$—$R^{3d}$ wherein $W_6$ represents a suitable leaving group, such as for example halo, e.g. bromo and the like, or —O—S(=O)$_2$—CH$_3$, and $R^{3d}$ represents optionally substituted $C_{1-6}$alkyl, such as for example —CH$_2$—C$_3$H$_5$, in the presence of a suitable base, such as for example sodium hydride or $Cs_2CO_3$, and a suitable solvent, such as for example N,N-dimethylformamide, N,N-dimethylacetamide or acetonitrile, resulting in a compound of formula (Ia-c). In this way, compounds of formula (Ia-c) wherein $R^3$ represents —S(=O)$_2$—N(CH$_3$)$_2$ can also be prepared by reacting an intermediate of formula (VI) with dimethylsulfamoyl chloride, in the presence of a suitable base, such as for example NaH, and a suitable solvent, such as for example N,N-dimethylformamide.

Compounds of formula (Ia-c) wherein $R^{3d}$ represents —CH$_2$—C(OH)(R')(R") wherein R' represents optionally substituted $C_{1-4}$alkyl and R" represents hydrogen or optionally substituted $C_{1-4}$alkyl, said compounds being represented by formula (Ia-c-1), can be prepared by reacting the intermediate of formula (VI) with an intermediate of formula (XXII) in the presence of a suitable base, such as for example sodium hydride, $Cs_2CO_3$, or potassium hydroxide, and a suitable solvent, such as for example N,N-dimethylformamide, N,N-dimethylacetamide, acetonitrile or water.

Intermediates of formula (IV) can also react with an intermediate of formula (XXIII) in the presence of a suitable catalyst, such as for example palladium (II) acetate or tris(dibenzylideneacetone)dipalladium (0), a suitable base, such as for example sodium tert-butoxide, a suitable ligand, such as for example 1,1'-[1,1'-binaphthalene]-2,2'-diylbis[1,1-diphenylphosphine] or 2-dicyclohexylphosphino-2'-(N,N-dimethylamino)biphenyl, and a suitable solvent, such as for example dioxane, resulting in a compound of formula (Ia-c).

Compounds of formula (Ia-b) wherein $R^{11}$ is $C_{1-6}$alkyl substituted with amino, said compounds being represented by formula (Ia-b-2), can also be prepared according to the following reaction Scheme 1A.

Scheme 1A

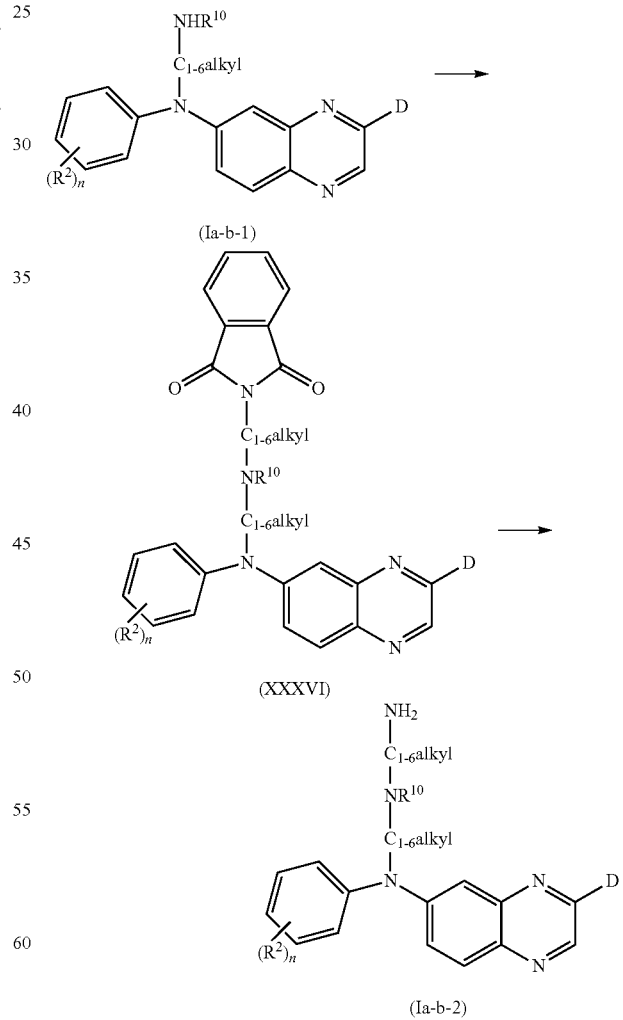

In Scheme 1A, a compound of formula (Ia-b-1) is reacted with N-(halo$C_{1-6}$alkyl)phtalimide in the presence of a suitable base, such as for example potassium carbonate, and a suitable solvent, such as for example acetonitrile, resulting in an intermediate of formula (XXXVI) which can be converted into a compound of formula (Ia-b-2) by reaction with hydrazine in the presence of a suitable solvent, such as for example an alcohol, e.g. ethanol.

Compounds of formula (Ia) wherein $R^3$ represents optionally substituted $C_{2-6}$alkynyl, said compounds being represented by formula (Ia-k), can be prepared according to reaction Scheme 1B.

$(=O)_2$—$CH_3$, can be prepared by reacting the corresponding alcohol derivative with methanesulfonyl chloride in the presence of a suitable base, such as for example triethylamine or 4-dimethylaminopyridine, and a suitable solvent, such as for example dichloromethane.

Compounds of formula (Ia-k), wherein $R^{3e}$ represents $C_{2-6}$alkynyl substituted with hydroxyl, said compounds being represented by formula (Ia-k-1), can be prepared according to the following reaction Scheme 1C.

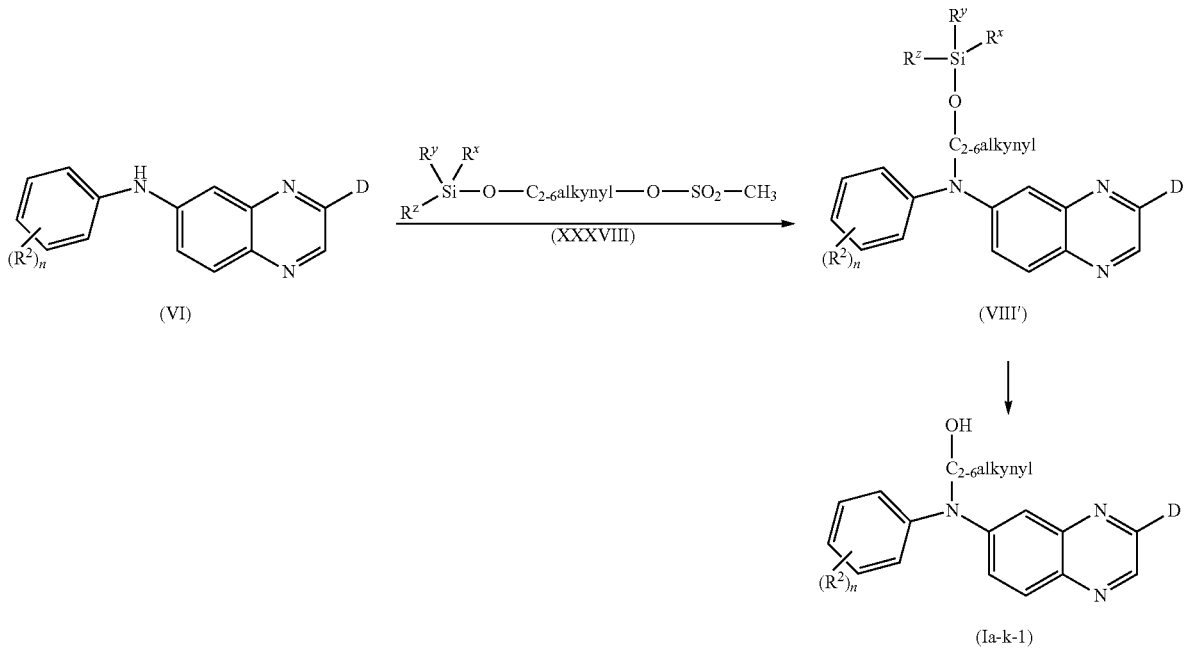

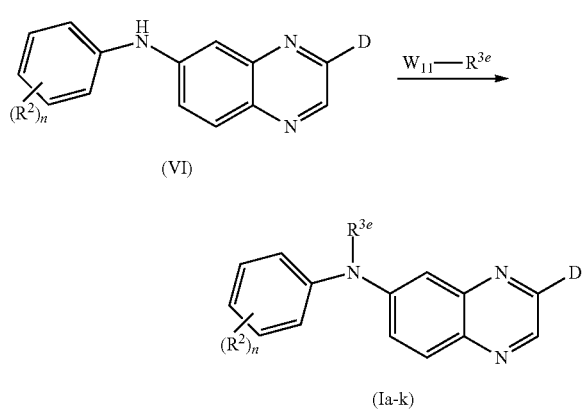

In Scheme 1B, an intermediate of formula (VI) is reacted with an intermediate of formula $W_{11}$—$R^{3e}$ wherein $R^{3e}$ represents optionally substituted $C_{2-6}$alkynyl and $W_{11}$ represents a suitable leaving group such as for example halo, e.g. chloro, or —O—S($=O)_2$—$CH_3$, in the presence of a suitable base, such as for example NaH, and a suitable solvent, such as for example N,N-dimethylformamide. The intermediate $W_{11}$—$R^{3e}$ wherein $W_{11}$ represents —O—S In Scheme 1C, an intermediate of formula (VI) is reacted with an intermediate of formula (XXXVIII) in the presence of a suitable base, such as for example NaH, and a suitable solvent, such as for example N,N-dimethylformamide, resulting in an intermediate of formula (VIII'), which is converted into a compound of formula (Ia-k-1) by reaction with a suitable acid, such as for example trifluoroacetic acid, in the presence of a suitable solvent, such as for example tetrahydrofuran. This reaction can also be performed with tetrabutyl ammonium fluoride in the presence of a suitable solvent such as for example tetrqahydrofuran.

Alternatively, instead of an intermediate of formula (XXXVIII), halo-$C_{2-6}$alkynyl-O—Si($R^x$)($R^y$)($R^z$) can also be used.

Compounds of formula (Ia-k), wherein $R^{3e}$ represents $C_{2-6}$alkynyl, said compounds being represented by formula (Ia-k-2), can be prepared according to the following reaction Scheme 1D.

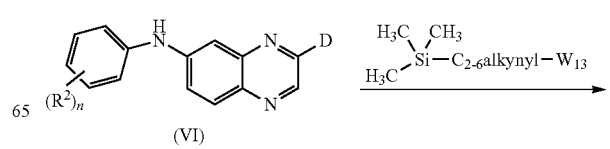

Compounds of formula (Ia), wherein $R^3$ represents ethyl substituted with —P(=O)(OC$_{1-6}$alkyl)$_2$, said compounds being represented by formula (Ia-I), can be prepared according to the following reaction Scheme 1E.

Scheme 1E

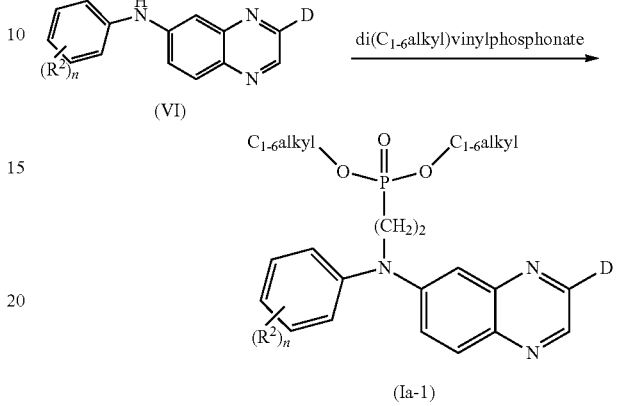

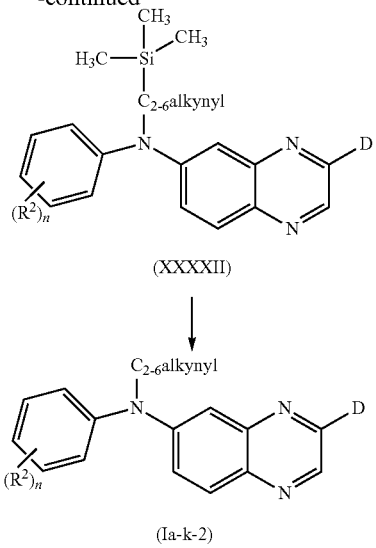

(XXXXII)

(Ia-k-2)

In Scheme 1D, a compound of formula (Ia-k-2) is prepared by deprotecting an intermediate of formula (XXXXII) in the presence of a suitable base, such as for example K$_2$CO$_3$, and a suitable solvent, such as for example an alcohol, e.g. methanol and the like. Said intermediate of formula (XXXXII) can be prepared by reacting an intermediate of formula (VI) with W$_{13}$—C$_{2-6}$alkynyl-Si(CH$_3$)$_3$ wherein W$_{13}$ is a suitable leaving group, such as for example halogen, in the presence of a suitable base, such as for example NaH, and a suitable solvent, such as for example N,N-dimethylformamide.

In scheme 1E, an intermediate of formula (VI) is reacted with di(C$_{1-6}$alkyl)vinylphosphonate in the presence of a suitable catalyst, such as for example tri-N-butylphosphine, and a suitable solvent, such as for example acetonitrile resulting in a compound of formula (Ia-I).

Intermediates of formula (VI) can also be prepared according to the following reaction Scheme 2.

Scheme 2

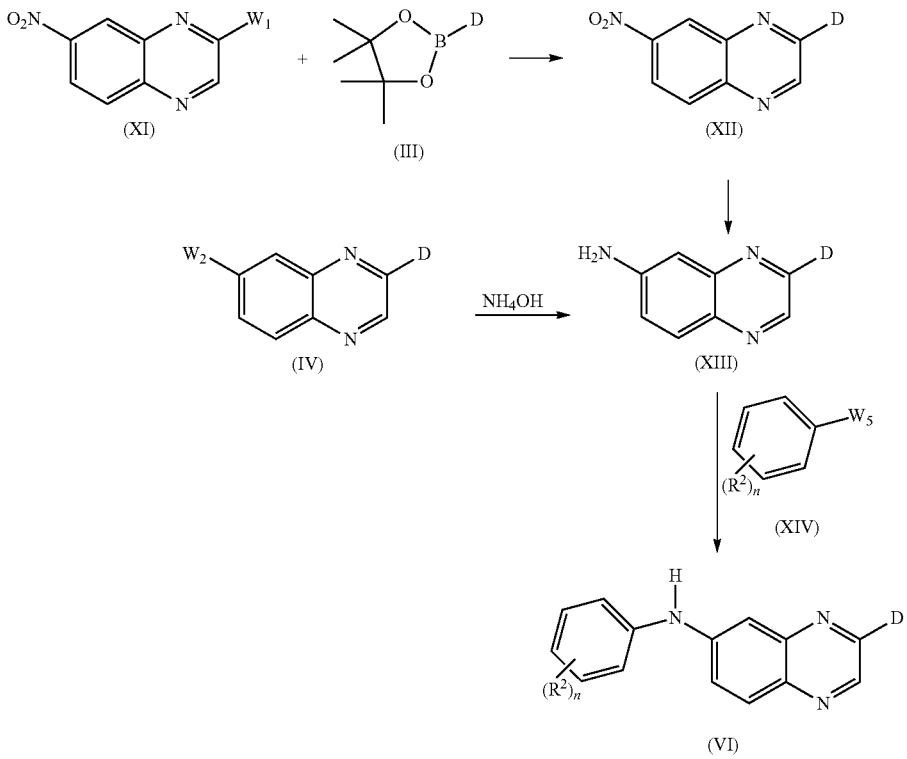

In Scheme 2, an intermediate of formula (XII) is prepared by reacting an intermediate of formula (XI) wherein $W_1$ represents a suitable leaving group, such as for example halo, e.g. chloro and the like, with an intermediate of formula (III) in the presence of a suitable catalyst, such as for example tetrakis(triphenylphosphine)palladium (0), a suitable base, such as for example $Na_2CO_3$, and a suitable solvent or solvent mixture, such as for example ethylene glycol dimethylether and water. The intermediate of formula (XII) is hydrogenated in a next step to an intermediate of formula (XIII) in the presence of a suitable catalyst, such as for example Nickel, and a suitable solvent, such as for example an alcohol, e.g. methanol, or tetrahydrofuran, or mixtures thereof. Intermediates of formula (XIII) can also be prepared by reacting an intermediate of formula (IV) with $NH_4OH$ in the presence of $Cu_2O$. In a next step, the intermediate of formula (XIII) is reacted with an intermediate of formula (XIV) wherein $W_5$ represents a suitable leaving group, such as for example halo, e.g. bromo and the like, in the presence of a suitable catalyst, such as for example palladium (II) acetate, a suitable base, such as for example sodium tert-butoxide, a suitable ligand, such as for example 1,1'-[1,1'-binaphthalene]-2,2'-diylbis[1,1-diphenylphosphine], and a suitable solvent, such as for example ethylene glycol dimethyl ether or dioxane, resulting in an intermediate of formula (VI). This reaction may also be performed in the presence of $Pd_2(dba)_3$ as catalyst, Xphos as ligand, a suitable base, such as for example $Cs_2CO_3$, and a suitable solvent, such as for example an alcohol, e.g. butanol. Intermediates of formula (IV) wherein $R^1$ is hydrogen can be converted into an intermediate of formula (IV) wherein $R^1$ is other than hydrogen, said $R^1$ being represented by $R^{1'}$, by reaction with $W_{14}$—$R^{1'}$ wherein $W_{14}$ is a suitable leaving group, such as for example halo, e.g. bromo, in the presence of a suitable base, such as for example NaH, and a suitable solvent, such as for example N,N-dimethylformamide.

Intermediates of formula (VI) can alternatively also be prepared according to the following reaction Scheme 3.

suitable catalyst, such as for example palladium (II) acetate, a suitable base, such as for example sodium tert-butoxide, a suitable ligand, such as for example 1,1'-[1,1'-binaphthalene]-2,2'-diylbis[1,1-diphenylphosphine], and a suitable solvent, such as for example ethylene glycol dimethyl ether, resulting in an intermediate of formula (XVI). In a next step, the intermediate of formula (XVI) is reacted with $P(=O)Cl_3$ or chlorosuccinimide, optionally in the presence of a solvent, such as for example acetonitrile, resulting in an intermediate of formula (XVII) which is converted into an intermediate of formula (VI) by reaction with an intermediate of formula (III) in the presence of a suitable catalyst, such as for example tetrakis(triphenylphosphine)palladium (0) or tris(dibenzylideneacetone)dipalladium (0), a suitable base, such as for example $Na_2CO_3$ or $K_3PO_4$, optionally in the presence of a suitable ligand, such as for example 2-dicyclohexylphosphino-2',6'-dimethoxybiphenyl, and a suitable solvent, such as for example ethylene glycol dimethylether.

In the above reaction, an intermediate of formula (III) can react in its protected form, such as for example

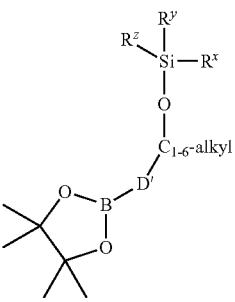

wherein D' represents the ring moiety within the D definition. The resulting protected intermediate of formula (VI) can be converted into the deprotected —$C_{1-6}$alkyl-OH inter- Scheme 3

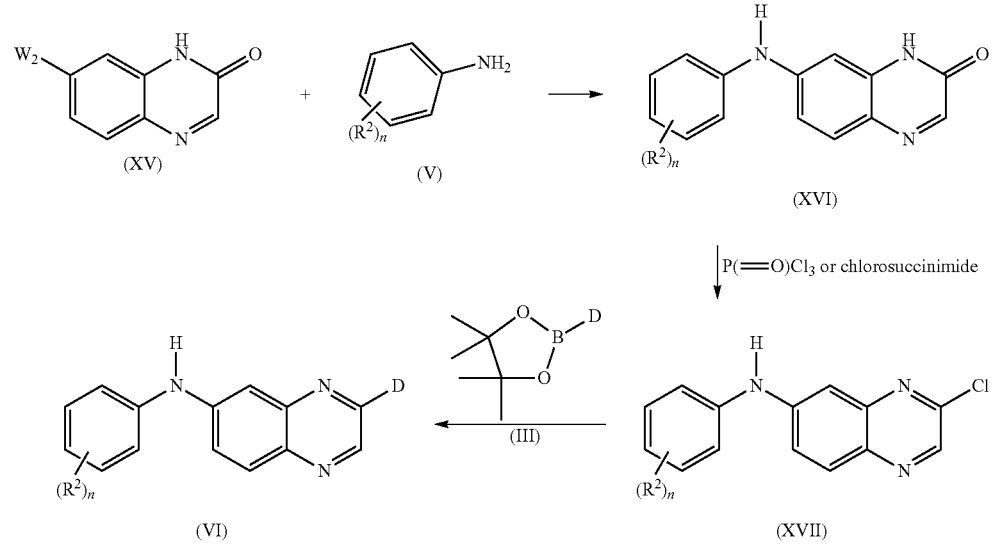

In Scheme 3, an intermediate of formula (XV) is reacted with an intermediate of formula (V) in the presence of a mediate by reaction with tetrabutylammonium fluoride, in the presence of a suitable solvent, such as for example tetrahydrofuran. Said —$C_{1-6}$alkyl-OH can be converted into —$C_{1-6}$alkyl-NH$_2$ by first reacting the —$C_{1-6}$alkyl-OH with methanesulfonyl chloride in the presence of a suitable base, such as for example triethylamine, and a suitable solvent, such as for example dichloromethane, followed by reacting the obtained intermediate with di-tert-butyl-iminocarboxylate in the presence of a suitable base, such as for example NaH, and a suitable solvent, such as for example N,N-dimethylformamide, followed by reaction with a suitable acid, such as for example trifluoroacetic acid, in a suitable solvent, such as for example dichloromethane.

Intermediates of formula (VIII) can alternatively also be prepared according to the following reaction Scheme 4.

In Scheme 4, an intermediate of formula (XVII) is reacted with an intermediate of formula (VII) in the presence of a suitable base, such as for example sodium hydride, and a suitable solvent, such as for example N,N-dimethylformamide, resulting in an intermediate of formula (XVIII). The intermediate of formula (XVIII) can then be reacted with an intermediate of formula (III) in the presence of a suitable catalyst, such as for example Pd$_2$(dba)$_3$, a suitable base, such as for example K$_3$PO$_4$, a suitable ligand, such as for example 2-dicyclohexylphosphino-2',6'-dimethoxy-biphenyl, and a suitable solvent, such as for example dioxane or water or mixtures thereof.

Intermediates of formula (VIII') can be prepared according to the following reaction Scheme 4A.

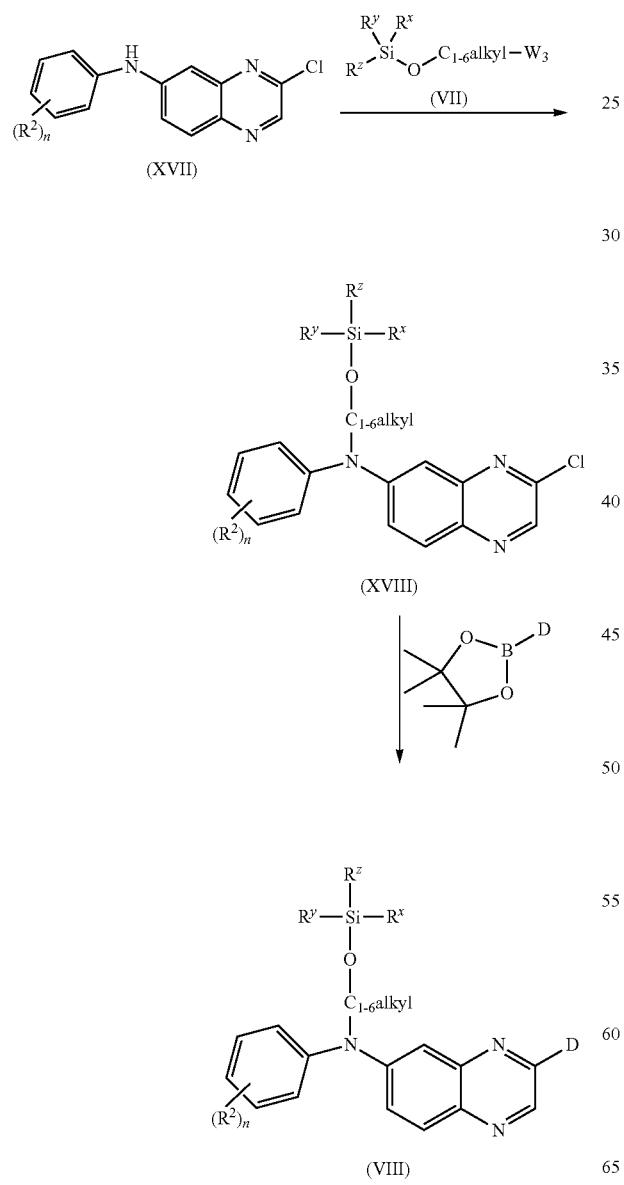

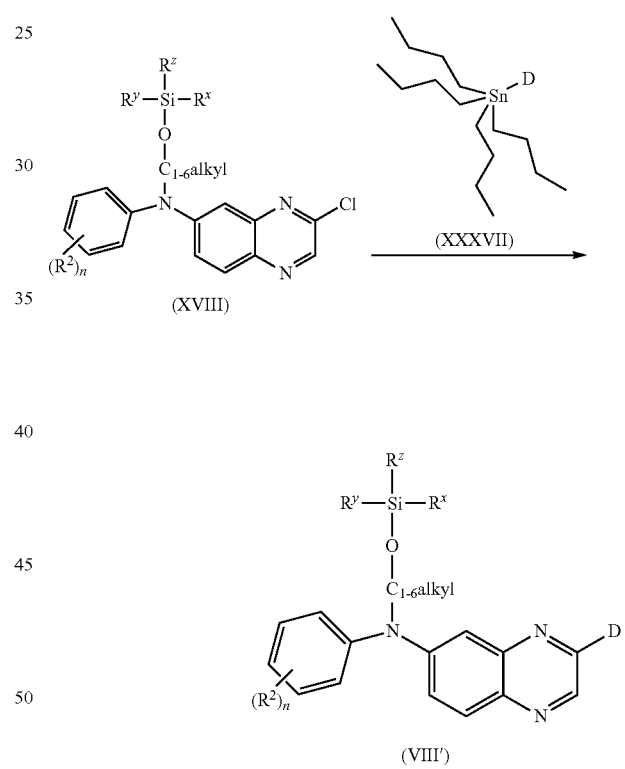

In Scheme 4A, an intermediate of formula (XVIII) is reacted with an intermediate of formula (XXXVII) in the presence of a suitable catalyst, such as for example tetrakis(triphenylphisphine)palladium (0), and a suitable solvent, such as for example toluene.

Intermediates of formula (VIII') wherein D is a ring moiety containing a nitrogen atom, as represented in Scheme 4B, can be further reacted according to the following reaction Scheme 4B.

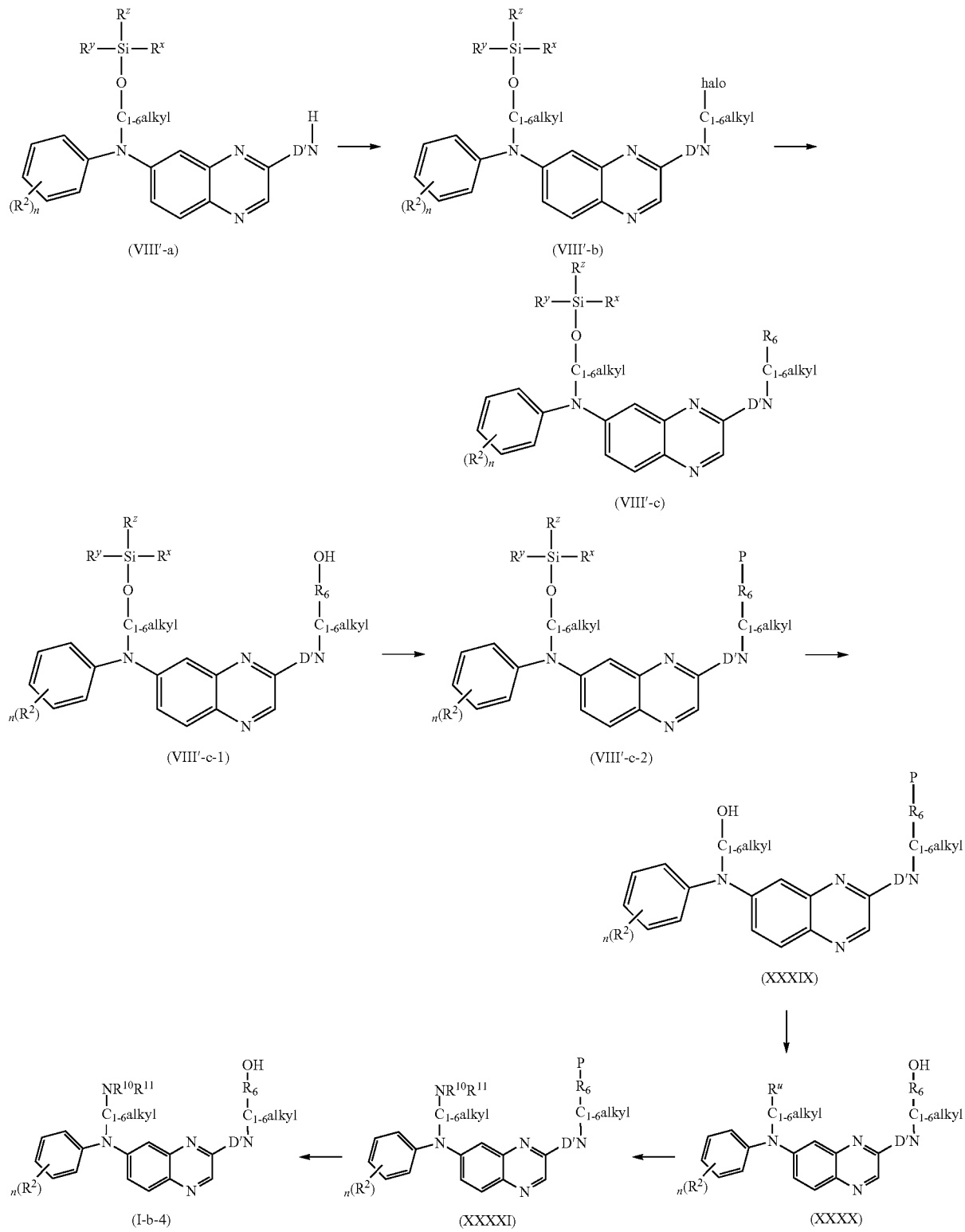

In Scheme 4B, the D'N moiety represents a -D moiety wherein the D ring moiety contains a nitrogen atom. Intermediates of formula (VIII') wherein D represents D'NH, said intermediates being represented by formula (VIII'-a), can be converted into an intermediate of formula (VIII'-b) by reaction with $W_{12}$—$C_{1-6}$alkyl-halo wherein $W_{12}$ represents a suitable leaving group, such as for example halo, e.g. chloro, in the presence of a suitable base, such as for example NaH, and a suitable solvent, such as for example N,N-dimethylformamide. Said intermediates of formula (VIII'-b) can be converted into an intermediate of formula (VIII'-c) by reaction with $R^6$ in the presence of a suitable base, such as for example $K_2CO_3$, and a suitable solvent, such as for example acetonitrile. When in an intermediate of formula (VIII'-c) the $R^6$ carries a hydroxyl group as in an intermediate of formula (VIII'-c-1), then said hydroxyl group can be protected by a suitable protective group P, such as for example —O—C(=O)—$C_{1-6}$alkyl, by reaction with $C_{1-6}$alkyl-C(=O)—$W_{12}$, in the presence of a suitable base, such as for example triethylamine, 4-dimethylaminopyridine, and a suitable solvent, such as for example dichloromethane, resulting in an intermediate of formula (VIII'-c-2) which can be converted into an intermediate of formula (XXXIX) by reaction with tetrabutylammonium fluoride in the presence of a suitable solvent, such as for example tetrahydrofuran. Said intermediate of formula (XXXIX) can be converted into an intermediate of formula (XXXX) wherein $R^u$ represents —$SO_2CH_3$, by reaction with methanesulfonyl chloride in the presence of a suitable base, such as for example triethylamine, and a suitable solvent, such as for example dichloromethane, which can be converted into an intermediate of formula (XXXXI) by reaction with an intermediate of formula (X) in a suitable solvent, such as for example acetonitrile. Said intermediate of formula (XXXXI) can then be deprotected into a compound of formula (Ia-b-4) in the presence of a suitable base, such as for example $K_2CO_3$, and a suitable solvent, such as for example an alcohol, e.g. methanol and the like. It is considered to be within the knowledge of the person skilled in the art to recognize for which other D ring moieties the described reactions also apply.

Intermediates of formula (VIII') can also be reacted to prepare compounds of the present invention according to the reaction schemes as presented in Scheme 1. It is considered to be within the knowledge of the skilled person to recognize in which condition and for which definitions of $R^1$ on the D ring moiety a protective group may be appropriate for the reactions to be carried out. For instance, a hydroxyl group within the definition of $R^1$ may be protected with a tert. butyldimethylsilyl moiety; a NH group within the definition of $R^1$ may be protected with a —C(=O)—O—C(CH$_3$)$_3$ group.

It is also considered to be within the knowledge of the skilled person to recognize appropriate deprotection reactions.

Compounds of formula (Ia) wherein $R^3$ represents optionally substituted $C_{1-6}$alkyl, said compounds being represented by formula (Ia-c), can also be prepared according to the below reaction Scheme 5.

Scheme 5

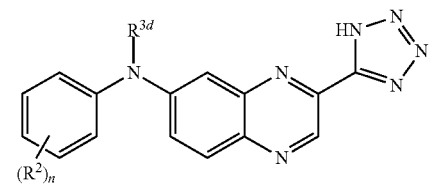

(Ia-c-3)

sodium azide

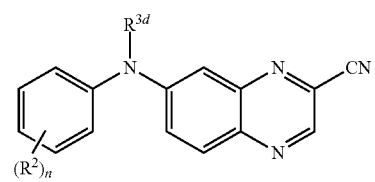

(IXL)

zinc cyanide

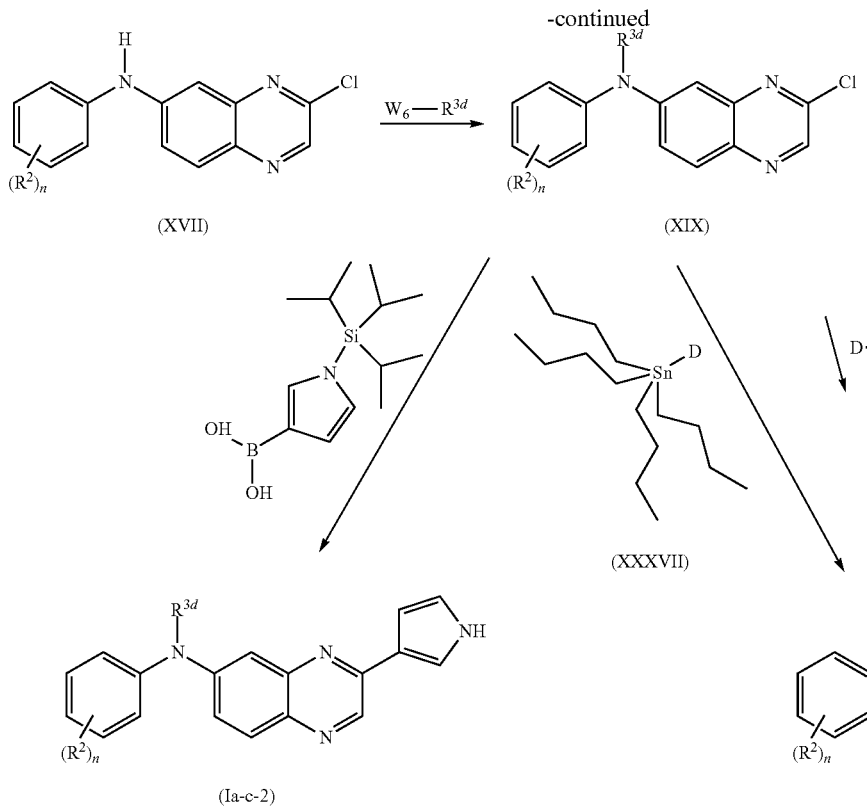

In Scheme 5, an intermediate of formula (XVII) is reacted with $W_6$—$R^{3d}$ wherein $W_6$ represents a suitable leaving group, such as for example halo, e.g. bromo and the like, and $R^{3d}$ represents optionally substituted $C_{1-6}$alkyl, such as for example —$CH_2$—$C_3H_5$, in the presence of a suitable base, such as for example sodium hydride, and a suitable solvent, such as for example N,N-dimethylformamide, resulting in an intermediate of formula (XIX). In a next step, the intermediate of formula (XIX) is reacted with an intermediate of formula (III) or (III-a) in the presence of a suitable catalyst, such as for example tetrakis(triphenyl)phosphine palladium or $Pd_2(dba)_3$ (tris(dibenzylideneacetone)dipalladium (0)), optionally a suitable ligand, such as 2-dicyclohexylphosphino-2',6'-dimethoxybiphenyl, a suitable base, such as for example $Na_2CO_3$ or $K_3PO_4$, and a suitable solvent, such as for example ethylene glycol dimethylether or dioxane or water. Or the intermediate of formula (XIX) is reacted with an intermediate of formula (XXXVII) in the presence of a suitable catalyst, such as for example tetrakis (triphenyl)phosphine palladium, and a suitable solvent, such as for example N,N-dimethylformamide or toluene. Or the intermediate of formula (XIX) is reacted with D-W, wherein W represents a suitable leaving group, such as for example halo, e.g. bromo, iodod and the like, in the presence of a suitable catalyst, such as for example tetrakis(triphenyl) phosphine palladium, ethylmagnesium chloride, zinc chloride to generated in situ a reactive organometallic species, and a suitable solvent, such as for example tetrahydrofuran. An intermediate of formula (XIX) can also react with a suitable ring moiety represented by D, e.g. imidazole or 4-methylimidazole or 3-methylpyrazole or 2-methylimidazole, in the presence of a suitable catalyst, such as for example tris(dibenzylideneacetone)dipalladium (0), a suitable ligand, such as for example Rac-bis(diphenylphosphino)-1,1'-binaphthyl, in the presence of a suitable base, such as for example sodium tert-butoxide, and a suitable solvent, such as for example toluene to obtain the corresponding final compound. Or an intermediate of formula (XIX) can react with e.g. 4-(aminomethyl)piperidine, morpholine, 1,2,4-triazole, ethyl 4-methyl-5-imidazolecarboxylate, piperazine or a derivative thereof, e.g. 1-(2-hydroxyethyl)piperazine or 1-methyl-piperazine, in the presence of a suitable base, such as for example triethylamine or sodium hydride or cesium carbonate, and a suitable solvent, such as for example, tetrahydrofuran, N,N-dimethylformamide, or an alcohol, e.g. 1-butanol, to obtain the corresponding final compound.

An intermediate of formula (XIX) can also react with 1-(triisopropylsilyl)pyrrole-3-boronic acid, in the presence of a suitable catalyst, such as for example tetrakis(triphenyl) phosphine palladium, a suitable base, such as for example sodium carbonate, tetrabutylammonium fluoride to cleave the C-silicon bond, and a suitable solvent, such as for example ethylene glycol dimethylether, to obtain a compound of formula (Ia-c-2). An intermediate of formula (XIX) can react with zinc cyanide in the presence of a suitable catalyst, such as for example tetrakis(triphenyl)phosphine palladium, a suitable ligand, such as for example triphenylphosphine, and a suitable solvent, such as for example acetonitrile. The resulting intermediate of formula (IXL) can react with sodium azide and ammonium chloride in the presence of a suitable solvent, such as for example N,N-dimethylformamide, to obtain a compound of formula (Ia-c-3). It is considered to be within the knowledge of the skilled person to recognize that instead of $R^{3d}$, also a suitable protected form of $R^{3d}$ can be used.

Compounds of formula (Ia-c) can alternatively also be prepared according to the below reaction Scheme 6.

Scheme 6

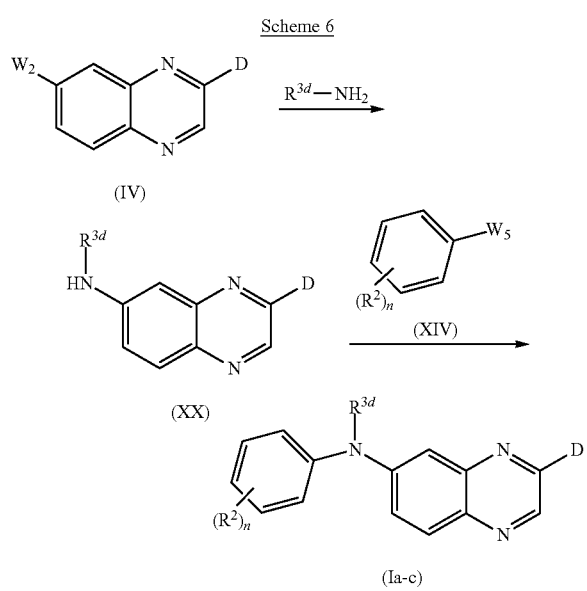

In Scheme 6, an intermediate of formula (IV) is reacted with $R^{3d}$—$NH_2$ in the presence of a suitable catalyst, such as for example palladium (II) acetate, a suitable base, such as for example sodium tert-butoxide, and a suitable ligand, such as for example 1,1'-[1,1'-binaphthalene]-2,2'-diylbis[1,1-diphenylphosphine], resulting in an intermediate of formula (XX) which is reacted in a next step with an intermediate of formula (XIV) in the presence of a suitable catalyst, such as for example palladium (II) acetate or $Pd_2(dba)_3$ (tris(dibenzylidene acetone)dipalladium (0)), a suitable ligand such as for example 2-dicyclohexylphosphino-tris-isopropyl-biphenyl or 1,1'-[1,1'-binaphthalene]-2,2'-diylbis[1,1-diphenylphosphine], a suitable base, such as for example sodium tert-butoxide, and a suitable solvent, such as for example ethylene glycol dimethylether.

Compounds of formula (I) wherein $R^3$ represents optionally substituted $C_{1-6}$alkyl, and wherein Y is E-D and E is other than a bond, said compounds being represented by formula (Ib) can be prepared according to the below reaction Scheme 7.

Scheme 7

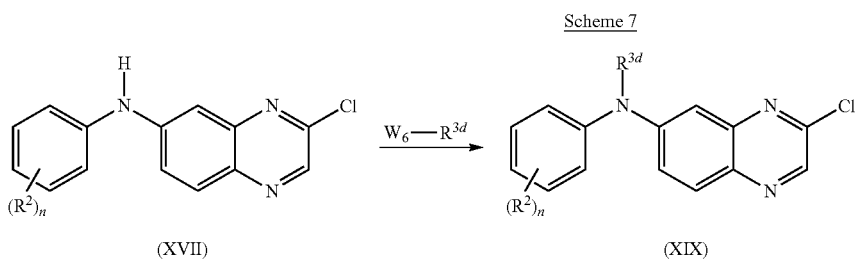

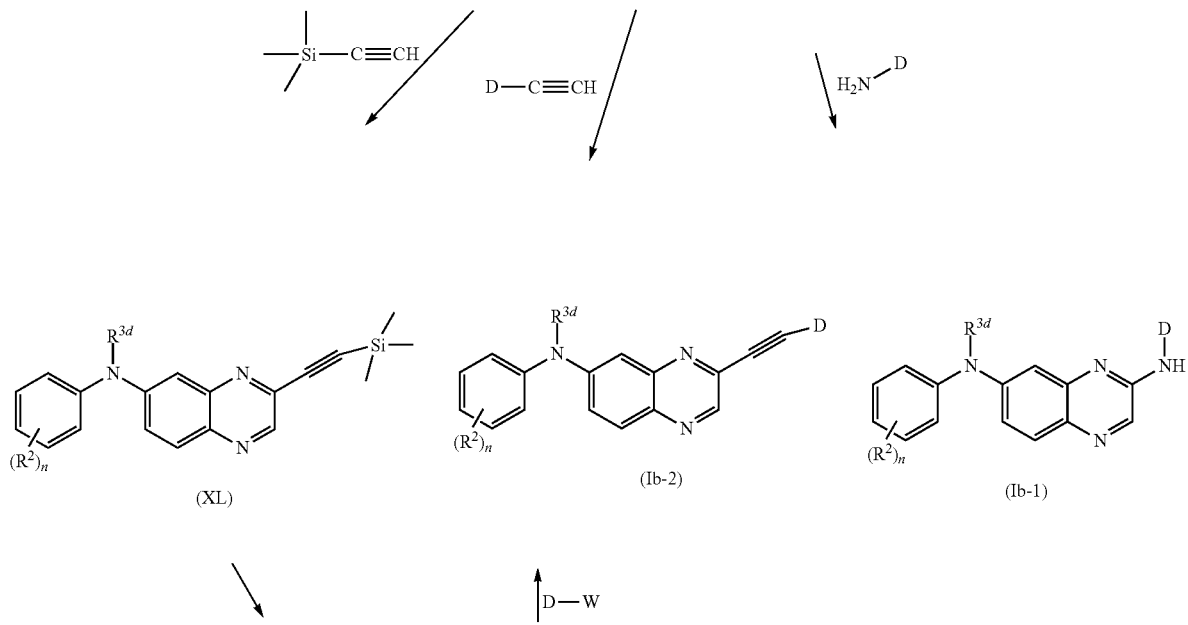

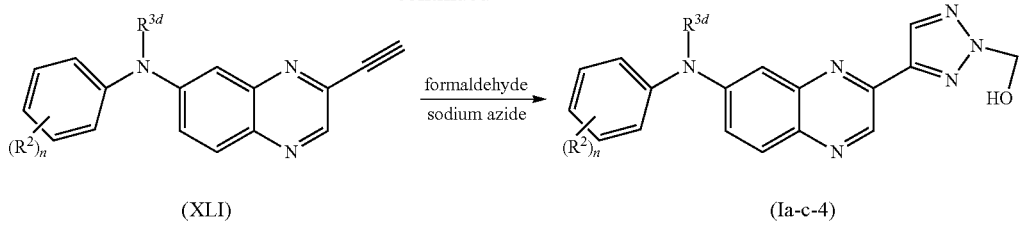

(XLI) → (Ia-c-4)

In Scheme 7, an intermediate of formula (XIX) is reacted with D-NH$_2$ in the presence of a suitable catalyst, such as for example (tris(dibenzylideneacetone)dipalladium (0)), a suitable ligand, such as for example 9,9-dimethyl-4,5-bis(diphenylphosphino)xanthene, a suitable base, such as for example cesium carbonate, and a suitable solvent, such as for example dioxane, resulting in a compound of formula (Ib-1). Or an intermediate of formula (XIX) is reacted with

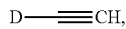
D≡≡≡CH, in the presence of a suitable catalyst, such as for example dichlorobis(triphenylphosphine) palladium (II) and copperiodide, a suitable ligand, such as for example triphenylphosphine, a suitable base, such as for example triethylamine, and a suitable solvent, such as for example N,N-dimethylformamide to obtain a compound of formula (Ib-2). A compound of formula (Ib-2) can also be prepared by reacting an intermediate of formula (XLI) with D-W as defined above, in the presence of a suitable catalyst, such as for example dichlorobis(triphenylphosphine) palladium (II) and copperiodide, a suitable base, such as for example triethylamine, and a suitable solvent, such as for example N,N-dimethylformamide and acetonitrile. The intermediate of formula (XLI) can be prepared by reacting an intermediate of (XIX) with (trimethylsilyl)acetylene in the presence of a suitable catalyst, such as for example dichlorobis(triphenylphosphine) palladium (II) and copperiodide, a suitable ligand, such as for example triphenylphosphine, a suitable base, such as for example triethylamine, and a suitable solvent, such as for example dimethylsulfoxide, followed by reacting the resulting intermediate of formula (XL) with potassium carbonate in a suitable solvent, such as for example an alcohol, e.g. methanol. The intermediate of formula (XLI) can also react with 2-(4-morpholino)ethylazide, in the presence of a suitable catalyst, such as for example copper iodide, a suitable base, such as for example N,N-diisopropylethylamine, and a suitable solvent, such as for example tetrahydrofuran, to obtain a compound wherein E is a bond and D is 2-(4-morpholino)ethyl-1-triazolyl. An intermediate of formula (XLI) can also react with sodium azide and formaldehyde in the presence of a suitable catalyst, such as for example copper sulfate and sodium L ascorbate, and a suitable solvent, such as for example dioxane and acetic acid, to obtain a compound of formula (IA-c-4).

Compounds of formula (Ib) can also be prepared according to the below reaction Scheme 7B.

Scheme 7B

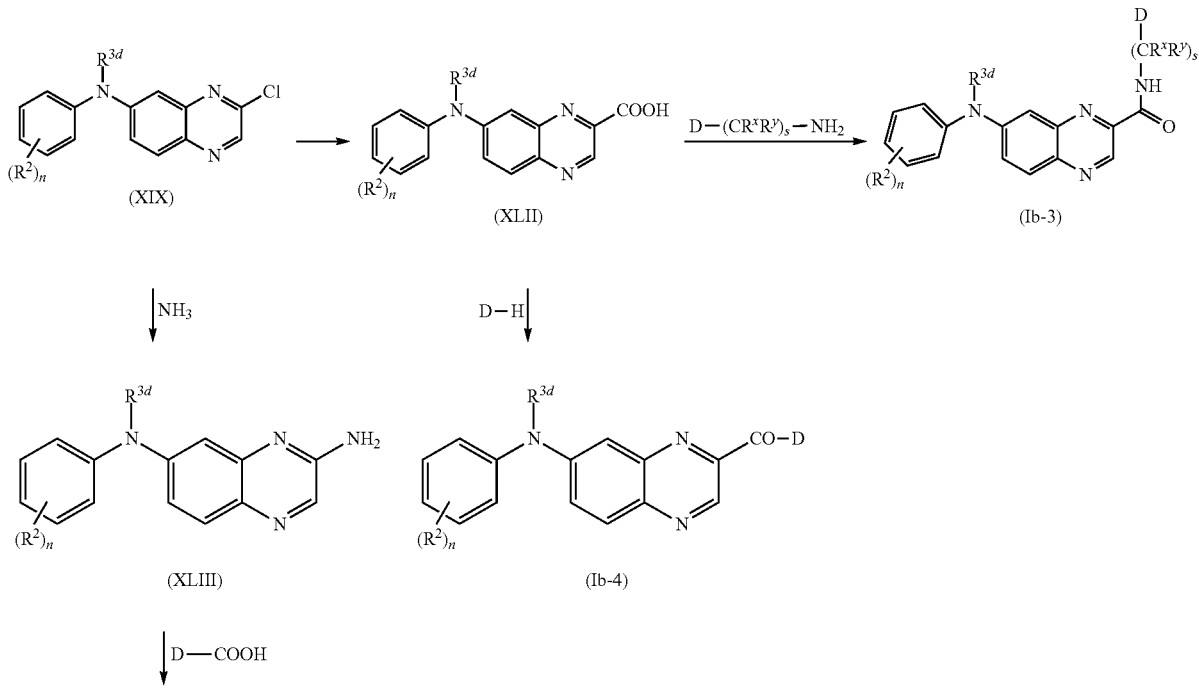

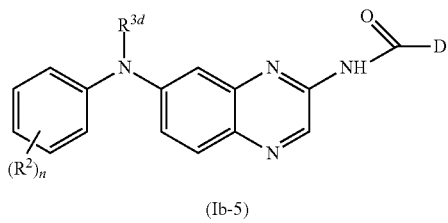

(Ib-5)

In Scheme 7B, an intermediate of formula (XIX) is reacted with CO gas, potassium acetate, in the presence of a suitable catalyst, such as for example tetrakis(triphenyl) phosphine palladium, and a suitable solvent, such as for example dioxane. The resulting intermediate of formula (XLII) is reacted with D-(CR$^x$R$^y$)$_s$—NH$_2$ in the presence of suitable peptide coupling reagents such as for example 1-(3-dimethylaminopropyl)-3-ethylcarbodiimide hydrochloride and 1-hydroxybenzotriazole, a suitable base, such as for example triethylamine, and a suitable solvent, such as for example methylene chloride, to obtain a compound of formula (Ib-3). The intermediate of formula (XLII) can also react with D-H in the presence of suitable peptide coupling reagents such as for example 1-(3-dimethylaminopropyl)-3-ethylcarbodiimide hydrochloride and 1-hydroxybenzotriazole, a suitable base, such as for example triethylamine, and a suitable solvent, such as for example methylene chloride to obtain a compound of formula (Ib-4). An intermediate of formula (XIX) can also react with NH$_3$ in the presence of a suitable solvent, such as for example ethylene glycol dimethylether to obtain intermediate (XLIII), which can react with D-COOH, in the presence of suitable peptide coupling reagents such as for example 1-(3-dimethylaminopropyl)-3-ethylcarbodiimide hydrochloride and 1-hydroxybenzotriazole, a suitable base, such as for example triethylamine, and a suitable solvent, such as for example methylene chloride to obtain a compound of formula (Ib-5).

Compounds of formula (I) wherein W is —NR$^3$—, said compound being represented by formula (Ic), and said R$^3$ is C$_{1-6}$alkyl substituted with 5-amino-1,3,4-oxadiazolyl can be prepared according to the below reaction Scheme 8.

Scheme 8

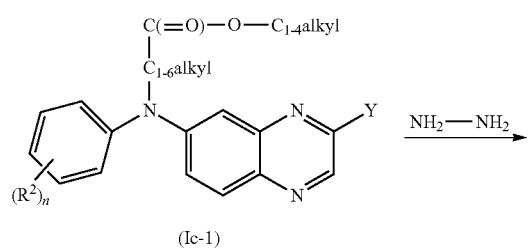

In Scheme 8, a compound of formula (Ic-1) is reacted with NH$_2$—NH$_2$ in the presence of a suitable solvent, such as for example an alcohol, e.g. ethanol resulting in an intermediate of formula (XXXI) which is then reacted in a next step with W$_8$—CN, wherein W$_8$ represents a suitable leaving group, such as for example halo, e.g. bromo, in the presence of a suitable base, such as for example NaHCO$_3$, and a suitable solvent, such as for example water or dioxane.

Compounds of formula (Ic) wherein R$^3$ is C$_{1-6}$alkyl substituted with 3,3-dimethyl-morpholine can be prepared according to the below reaction Scheme 8.A

Scheme 8A

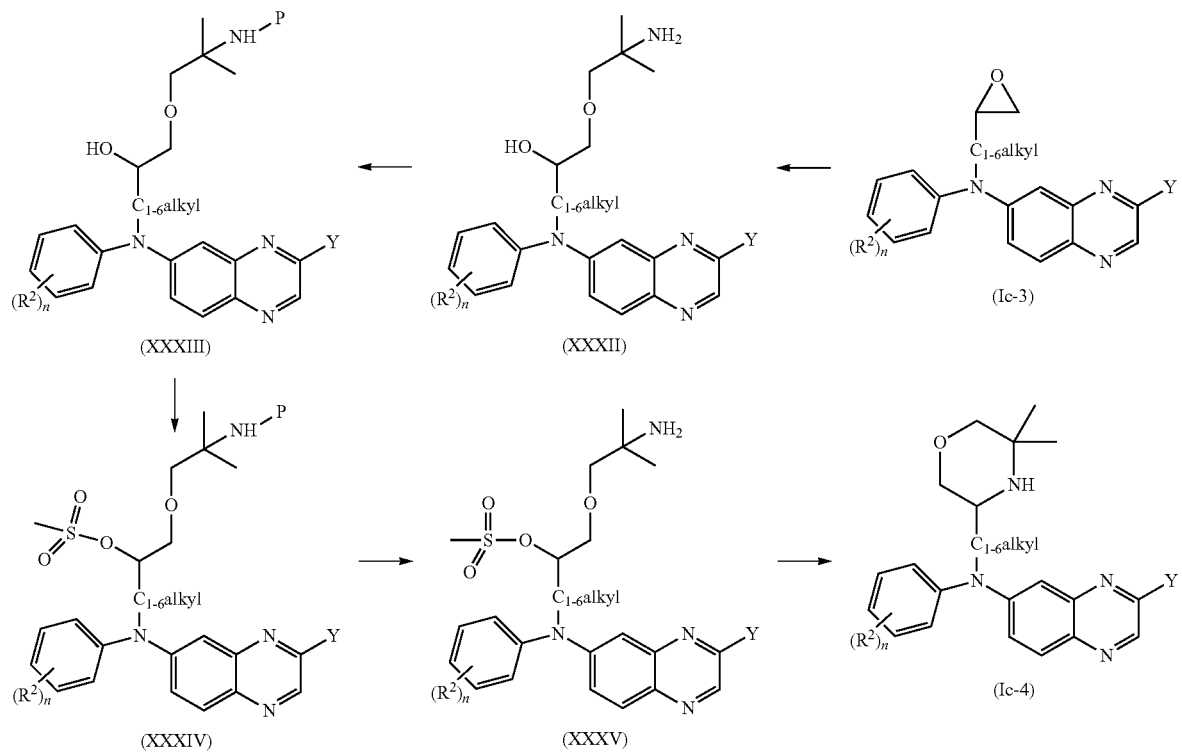

In Scheme 8A, a compound of formula (Ic-3) is reacted with 2-amino-2-methyl-1-propanol in the presence of a suitable base, such as for example NaH and in the presence of a suitable solvent, such as for example N,N-dimethylformamide resulting in an intermediate of formula (XXXII) of which the NH$_2$ moiety is protected by a suitable protecting group P, such as for example —C(=O)—O—C(CH$_3$)$_3$, by reaction with for instance di-tert-butyl dicarbonate in the presence of a suitable solvent, such as for example dioxane, and a suitable base, such as for example NaHCO$_3$, resulting in an intermediate of formula (XXXIII). In a next step, said intermediate is reacted with methanesulfonyl chloride in the presence of a suitable solvent, such as for example dichloromethane, and a suitable base, such as for example triethylamine resulting in an intermediate of formula (XXXIV) which is converted into an intermediate of formula (XXXV) by reaction with a suitable acid, such as for example trifluoroacetic acid, in the presence of a suitable solvent, such as for example dichloromethane. The intermediate of formula (XXXV) is converted into a compound of formula (Ic-4) by reaction with a suitable base, such as for example N,N-diisopropylethylamine and triethylamine in the presence of a suitable solvent, such as for example an alcohol, e.g. methanol.

In general, compounds of formula (I) wherein Y represents —CR$^{18}$=N—OR$^{19}$, said compounds being represented by formula (Id), can be prepared as in Scheme 9.

Scheme 9

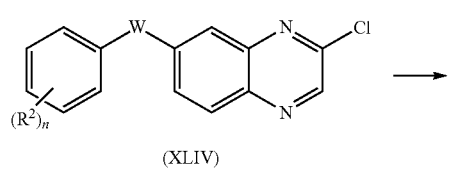

(XLIV)

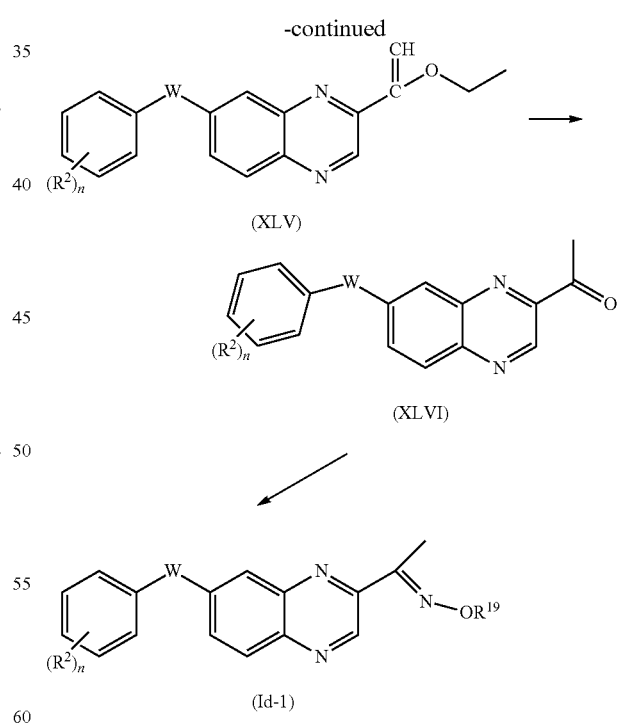

In Scheme 9, an intermediate of formula (XLIV) is reacted with tributyl(1-ethoxyvinyl)tin, in the presence of a suitable catalyst, such as for example dichlorobis(triphenylphosphine) palladium (II) optionally in the presence of copperiodide and a suitable ligand, such as for example triphenylphosphine, and in the presence of a suitable solvent, such as for example N,N-dimethylformamide, followed by reacting the resulting intermediate of formula (XLV) with a suitable acid, such as for example hydrochloric acid, and a suitable solvent, such as for example acetone. The obtained intermediate of formula (XLVI) is then reacted with $R^{19}$—O—$NH_2$ in the presence of a suitable base such as for example pyridine, and a suitable solvent, such as for example an alcohol, e.g. ethanol, resulting in a compound of formula (Id-1). A preferred intermediate of formula (XLIV) is the intermediate of formula (XIX).

An intermediate of formula (XLVI) can also be converted into a compound of formula (I) wherein E is a direct bond and D is 3-methyl-oxazole or oxazole, by reaction with 1-methyl-1-tosylmethyl isocyanide or tosylmethyl isocyanide, in the presence of a suitable base, such as for example dipotassium carbonate, and a suitable solvent, such as for example an alcohol, e.g. methanol.

In general, compounds of formula (I) wherein W is —C($R^{3a}R^{3b}$)—, said compounds being represented by formula (Ie) can be prepared according to the following reaction Scheme 1.

example tetrahydrofuran. A compound of formula (Ie-1) can also be prepared by reacting an intermediate of formula (XLVII) with an intermediate of formula (XLVIII) in the presence of CO as a reactant, a suitable catalyst, such as for example palladium(II)acetate, a suitable ligand, such as for example tricyclohexylphosphine, a suitable base, such as for example triethylamine, and a suitable solvent, such as for example toluene.

Compounds of formula (Ie) can also be prepared according to the following reaction Scheme 10A.

Scheme 10A

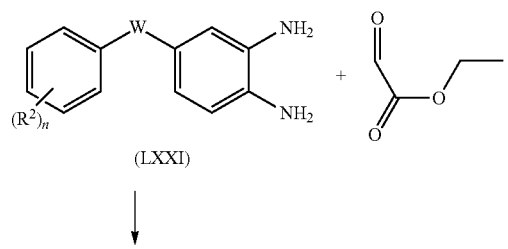

(LXXI)

Scheme 10

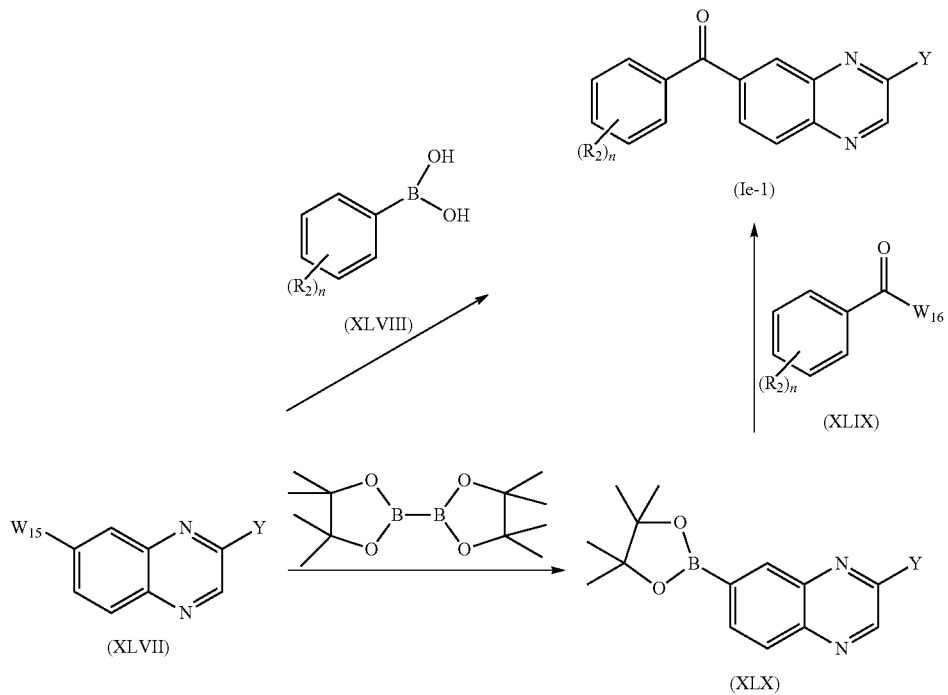

In scheme 10, a compound of formula (Ie-1) is prepared by reacting an intermediate of formula (XLVII) wherein $W_{15}$ represents a suitable group, such as for example halo, e.g. bromo and the like, with bis(pinacolato)diboron in the presence of a suitable catalyst, such as for example $PdCl_2dppf$, in the presence of a base, such as for example potassium acetate, and a suitable solvent, such as for example dioxane, followed by reacting the resulting intermediate of formula (XLX) with an intermediate of formula (XLIX) wherein $W_{16}$ represents a suitable leaving group, such as for example halo, e.g. chloro and the like, in the presence of a catalyst, such as for example dichlorobis(triphenylphosphine)palladium, a suitable base, such as for example $Na_2CO_3$, and a suitable solvent, such as for -continued

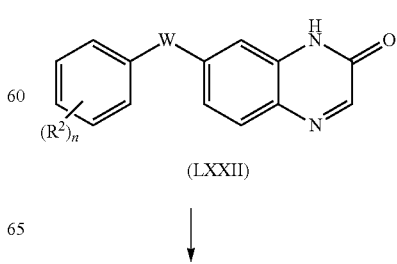

(LXXII)

-continued

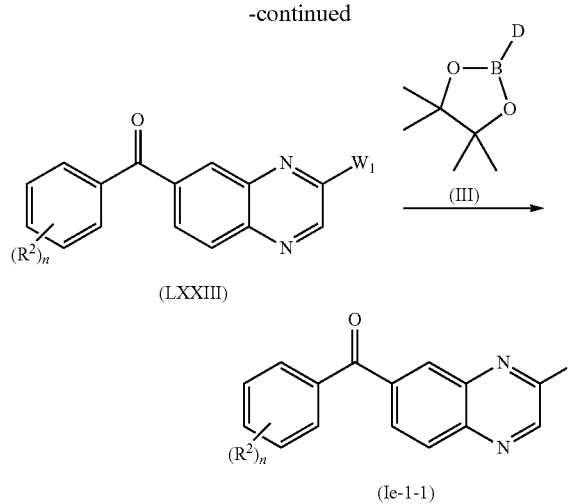

example ethylene glycol dimethylether and water, to give a compound of formula (Ie-1-1).

Compounds of formula (Ie) can also be prepared according to the following reaction Scheme 11.

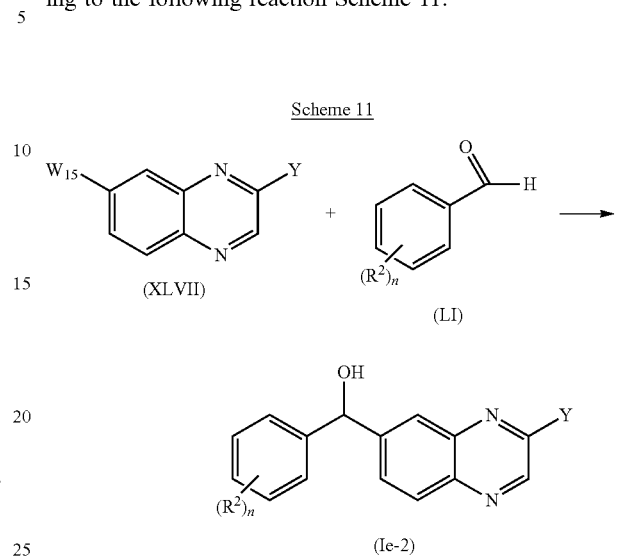

In scheme 10A, an intermediate of formula (LXXI) is reacted with an ethylglyoxalate solution, in the presence of a suitable solvent, such as for example an alcohol, e.g. ethanol and the like, resulting in an intermediate of formula (LXXII). The intermediate of formula (LXXII) is further reacted with a leaving group introducing agent, such as for example phosphorus oxychloride, resulting in an intermediate of formula (LXXIII), which is further reacted with an intermediate of formula (III) in the presence of a suitable catalyst, such as for example tetrakis(triphenylphosphine) palladium (0), a suitable base, such as for example Na$_2$CO$_3$, and a suitable solvent or solvent mixture, such as for In Scheme 11, an intermediate of formula (XLVII) is reacted with an intermediate of formula (LI) in the presence of isopropylmagnesium chloride to prepare the magnesium chloride derivative of XLVII and a suitable solvent, such as for example tetrahydrofuran.

Compounds of formula (Ie) can also be prepared according to the following reaction Scheme 12.

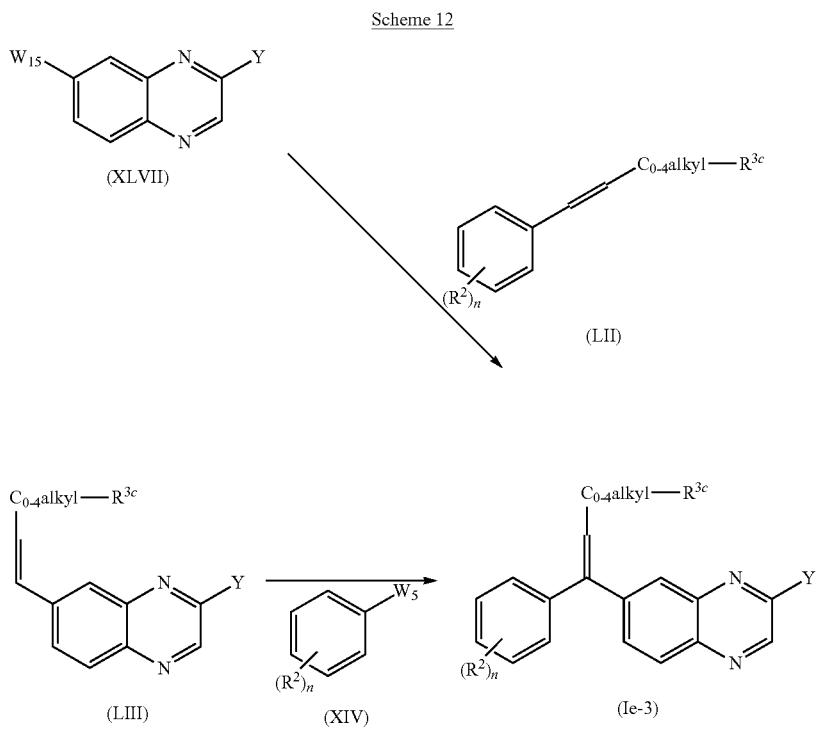

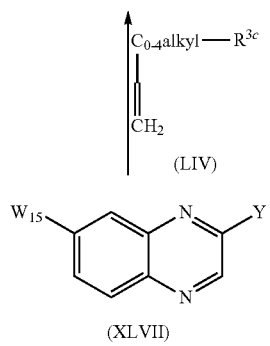

In Scheme 12, intermediates of formula (XLVII) are reacted with an intermediate of formula (LII) in the presence of a suitable catalyst, such as for example palladium(II) acetate, a suitable base, such as for example potassium acetate, and tetrabutylammonium bromide as solid base, and a suitable solvent, such as for example N,N-dimethylformamide, to give a compound of formula (Ie-3). Compounds of formula (Ie-3) can also be prepared by reacting an intermediate of formula (XLVII) with an intermediate of formula (LIV) in the presence of a suitable catalyst, such as for example palladium(II)acetate, a suitable ligand, such as for example tri-o-tolylphosphine, a suitable base, such as for example triethylamine, and a suitable solvent, such as for example acetonitrile, resulting in an intermediate of formula (LIII), which can then be reacted with an intermediate of formula (XIV) wherein $W_5$ represents a suitable leaving group, such as for example halo, e.g. bromo, in the presence of a suitable catalyst, such as for example palladium(II) acetate, a suitable base, such as for example potassium acetate, and tetrabutylammonium bromide as solid base, and a suitable solvent, such as for example N,N-dimethylformamide.

Compounds of formula (Ie) can also be prepared according to the following reaction Scheme 13.

Scheme 13

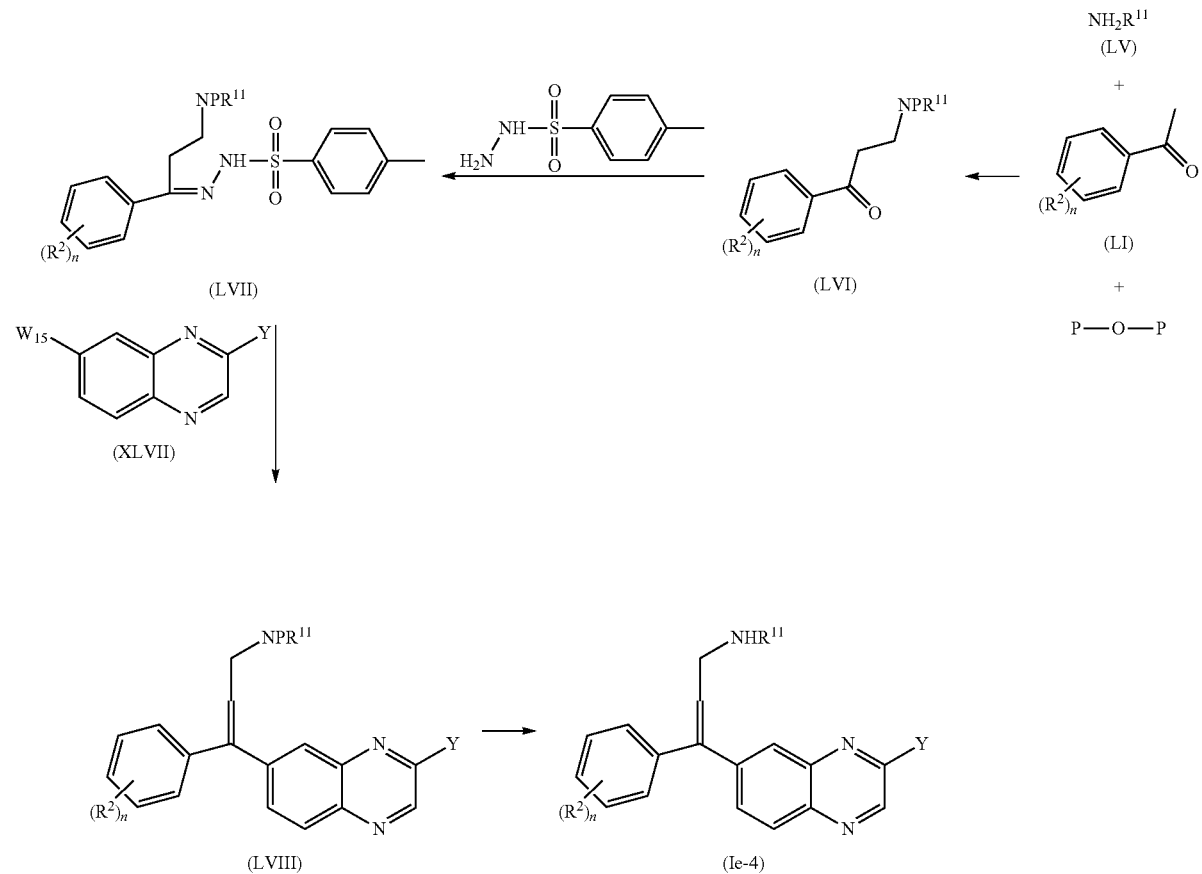

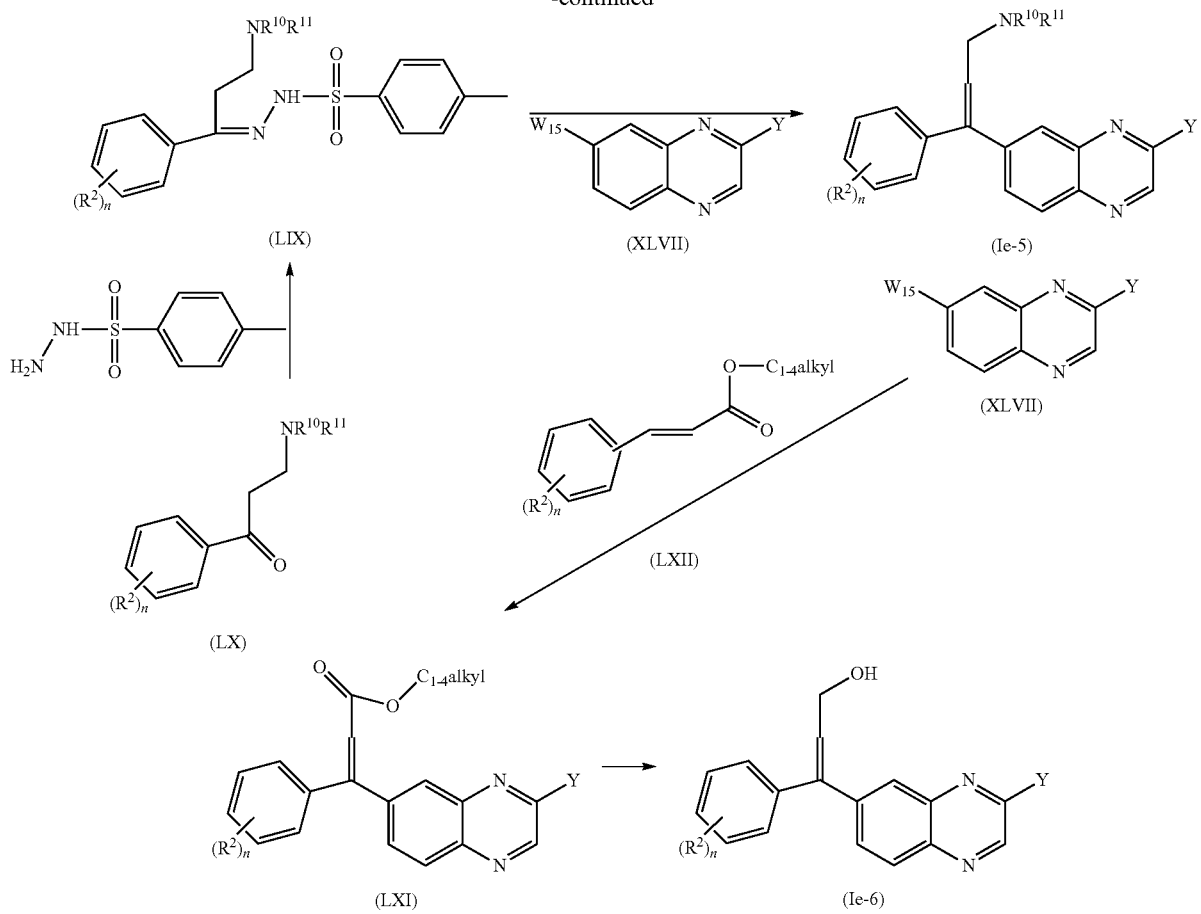

In Scheme 13, an intermediate of formula (LV) preferably in its salt form, e.g. HCl salt form, and (LI) are reacted with paraformaldehyde in the presence of a suitable solvent, such as for example an alcohol, e.g. ethanol, then a suitable agent P—O—P to introduce a suitable protective group P, such as for example C(=O)—O—C(CH$_3$)$_3$ wherein P—O—P is (CH$_3$)$_3$C—O—C(=O)—OC(=O)—O—C(CH$_3$)$_3$), is added in the presence of a suitable base, such as for example triethylamine, and a suitable solvent, such as for example dichloromethane, resulting in an intermediate of formula (LVI), which is further reacted with p-toluenesulfonhydrazide in the presence of a suitable solvent, such as for example an alcohol, e.g. ethanol, to give an intermediate of formula (LVII). The intermediate of formula (LVII) is then further reacted with an intermediate of formula (XLVII) in the presence of a suitable catalyst, such as for example tris (dibenzylideneacetone)dipalladium (0), a suitable ligand, such as for example 2-dicyclohexylphosphino-2',4',6'-triisopropyl-1,1'-biphenyl a suitable base, such as for example lithium tert-butoxide, and a suitable solvent, such as for example dioxane, resulting in an intermediate of formula (LVIII), the E and Z isomers of which can be separated by appropriate separation techniques such as column chromatography. The intermediate of formula (LVIII) can then be converted into a compound of formula (Ie-4) by deprotection in the presence of a suitable acid, such as for example HCl, and a suitable solvent, such as for example an alcohol, e.g. methanol. A compound of formula (Ie-5) is prepared by reacting an intermediate of formula (LX) with p-toluenesulfonhydrazide in the presence of a suitable acid, such as for example hydrochloric acid, and a suitable solvent, such as for example diethylether and water, resulting in an intermediate of formula (LIX), the E and Z isomers of which can be separated by appropriate separation techniques such as column chromatography. The intermediate of formula (LIX) can then be reacted with an intermediate of formula (XLVII) in the presence of a suitable catalyst, such as for example tris(dibenzylideneacetone)dipalladium (0), a suitable ligand, such as for example 2-dicyclohexylphosphino-2',4',6'-triisopropyl-1,1'-biphenyl a suitable base, such as for example lithium tert-butoxide, and a suitable solvent, such as for example dioxane, resulting in a compound of formula (Ie-5). A compound of formula (Ie-6) is prepared by reacting an intermediate of formula (LXI) with a suitable reducing agent, such as for example diisobutylaluminium hydride, and a suitable solvent, such as for example tetrahydrofuran. The intermediate of formula (LXI) is prepared by reacting an intermediate of formula (XLVII) with an intermediate of formula (LXII) in the presence of a suitable catalyst, such as for example palladium(II)acetate, a suitable ligand, such as for example tri-o-tolylphosphine, a suitable base, such as for example triethylamine, and a suitable solvent, such as for example acetonitrile.

Compounds of formula (Ie) can also be prepared according to the following reaction Scheme 14.

Scheme 14

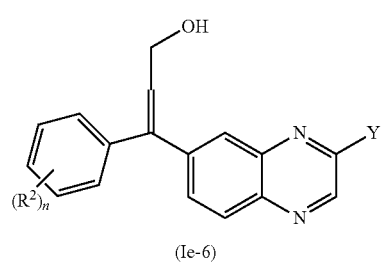
(Ie-6)

↓

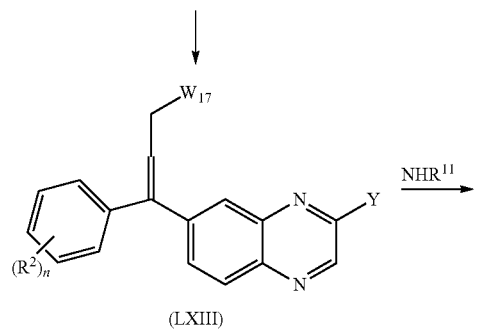
(LXIII)

NHR[11] →

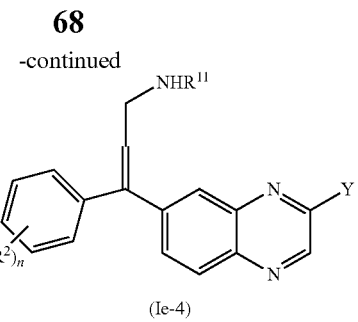
(Ie-4)

In Scheme 14, a compound of formula (Ie-6) is reacted with a leaving group introducing agent, such as for example methanesulfonyl chloride, in the presence of a suitable base, such as for example triethylamine, and a suitable solvent, such as for example dichloromethane, resulting in an intermediate of formula (LXIII) wherein $W_{17}$ represents a suitable leaving group, such as for example halo, e.g. chloro, which is then further reacted with NHR[11] in the presence of a suitable solvent, such as for example acetonitrile, to give a compound of formula (Ie-4).

Compounds of formula (Ie) can also be prepared according to the following reaction Scheme 15.

Scheme 15

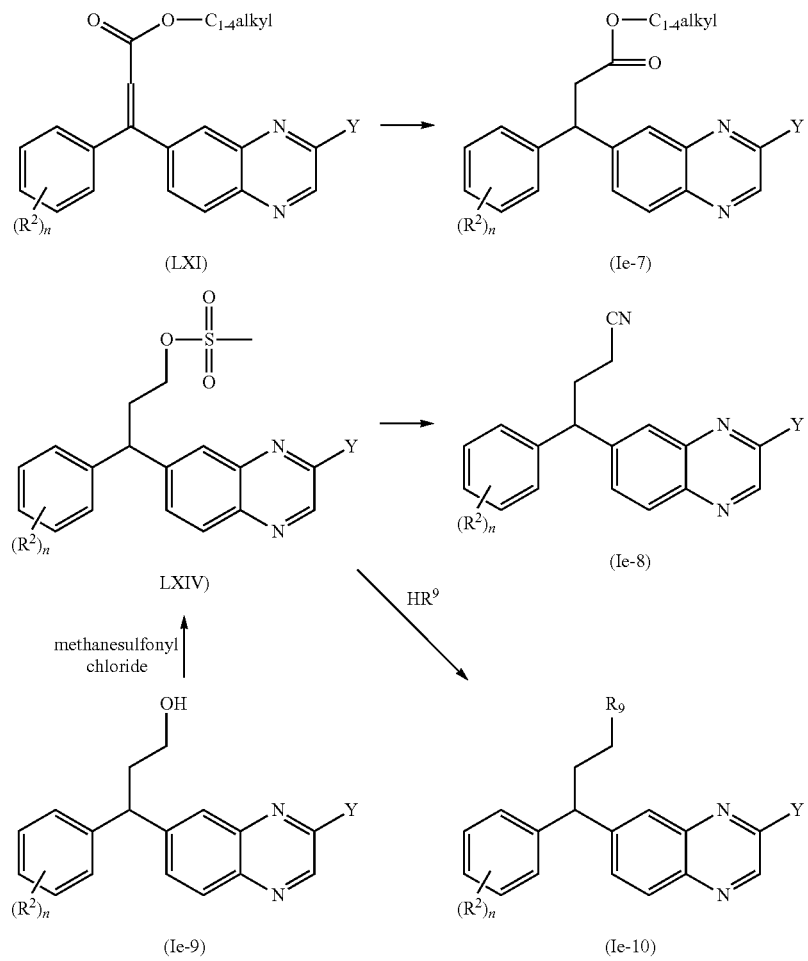

In Scheme 15, a compound of formula (Ie-7) is prepared by reacting an intermediate of formula (LXI) with magnesium in the presence of a suitable solvent, such as for example tetrahydrofuran and an alcohol, e.g. methanol and the like. A compound of formula (Ie-8) is prepared by reacting an intermediate of formula (LXIV) with potassium cyanide in the presence of a suitable solvent, such as for example N,N-dimethylformamide. The intermediate of formula (LXIV) is prepared by reacting a compound of formula (Ie-9) with methanesulfonyl chloride in the presence of a suitable base, such as for example triethylamine, and a suitable solvent, such as for example acetonitrile. (Ie-9) can be prepared by reduction of (Ie-6) for example using LiAlH$_4$, in an aprotic solvent such as THF. The intermediate of formula (LXIV) is converted into a compound of formula (Ie-10) by reaction with HR$^9$ in the presence of a suitable base, such as for example sodium hydride, and a suitable solvent, such as for example N,N-dimethylformamide.

Compounds of formula (Ie) can also be prepared according to the following reaction Scheme 16.

Scheme 16

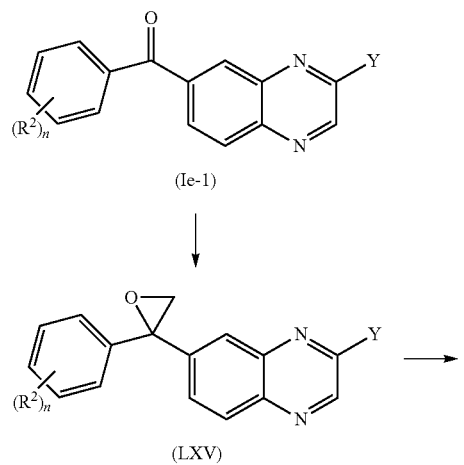

(Ie-1)

↓

(LXV) →

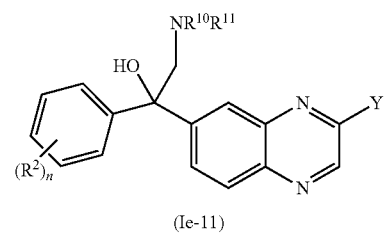

(Ie-11)

In Scheme 16, a compound of formula (Ie-1) is reacted with trimethylsulphoxonium iodide in the presence of a suitable base, such as for example potassium tert butoxide, and a suitable solvent, such as for example dimethoxymethane and dimethylsulfoxide resulting in an intermediate of formula (LXV), which can be converted into a compound of formula (Ie-11) by reaction with NHR$^{10}$R$^{11}$ in the presence of a suitable solvent, such as for example an alcohol, e.g. ethanol and the like.

Compounds of formula (Ie) can also be prepared according to the following reaction Scheme 17.

Scheme 17

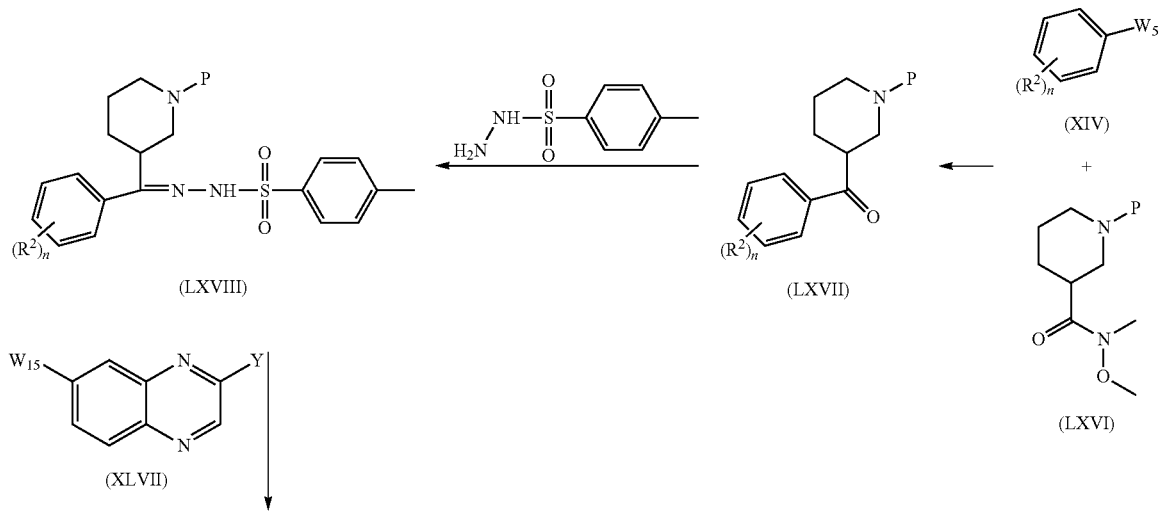

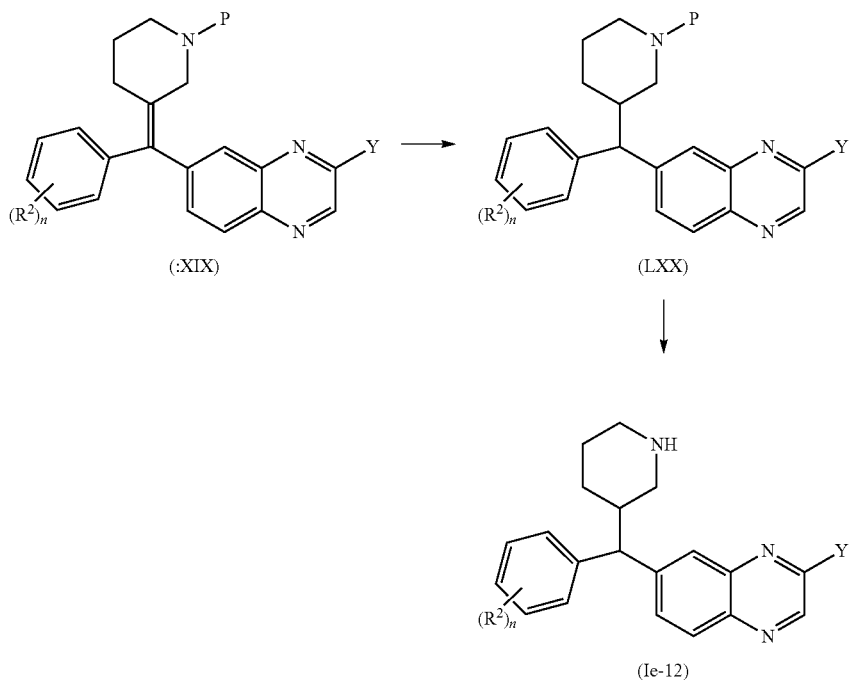

In Scheme 17, an intermediate of formula (XIV) as defined above, and (LXVI) wherein P represents a suitable protective group as defined above, is reacted with butyl-lithium in hexane in the presence of a suitable solvent, such as for example tetrahydrofuran, diethylether or mixtures thereof resulting in an intermediate of formula (LXVII), which is further reacted with p-toluenesulfonhydrazide in the presence of a suitable solvent, such as for example an alcohol, e.g. ethanol, to give an intermediate of formula (LXVIII). The intermediate of formula (LXVIII) is then further reacted with an intermediate of formula (XLVII) in the presence of a suitable catalyst, such as for example tris(dibenzylideneacetone)dipalladium (0), a suitable ligand, such as for example 2-dicyclohexylphosphino-2',4',6'-tri-isopropyl-1,1'-biphenyl, a suitable base, such as for example lithium tert-butoxide, and a suitable solvent, such as for example dioxane, resulting in an intermediate of formula (LXIX). The intermediate of formula (LXIX) is then converted into an intermediate of formula (LXX) by hydrogenation in the presence of a suitable catalyst, such as for example palladium on charcoal, and a suitable solvent, such as for example an alcohol, e.g. methanol. The intermediate of formula (LXX) can then be converted into a compound of formula (Ie-12) by reaction with a suitable acid, such as for example hydrochloric acid, in the presence of a suitable solvent, such as for example an alcohol, e.g. methanol.

As already shown above, compounds of formula (I) or some of the above-described intermediates can be prepared by deprotecting the corresponding protected compounds. Other protection-deprotection reactions are shown in the following reaction Scheme 18.

Scheme 18

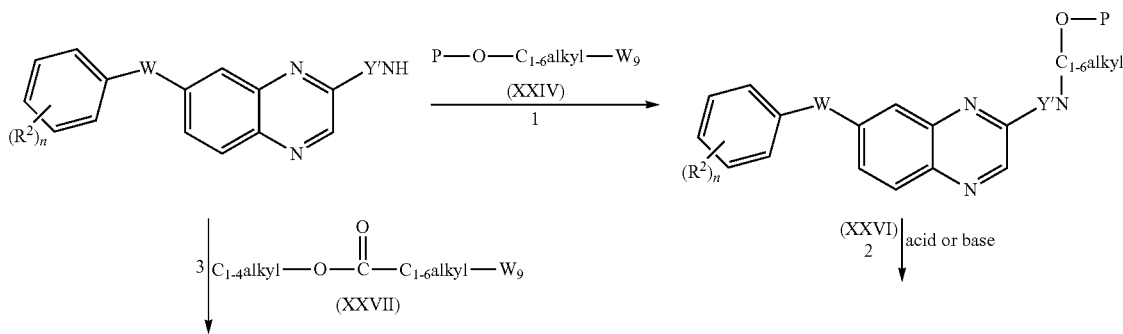

-continued

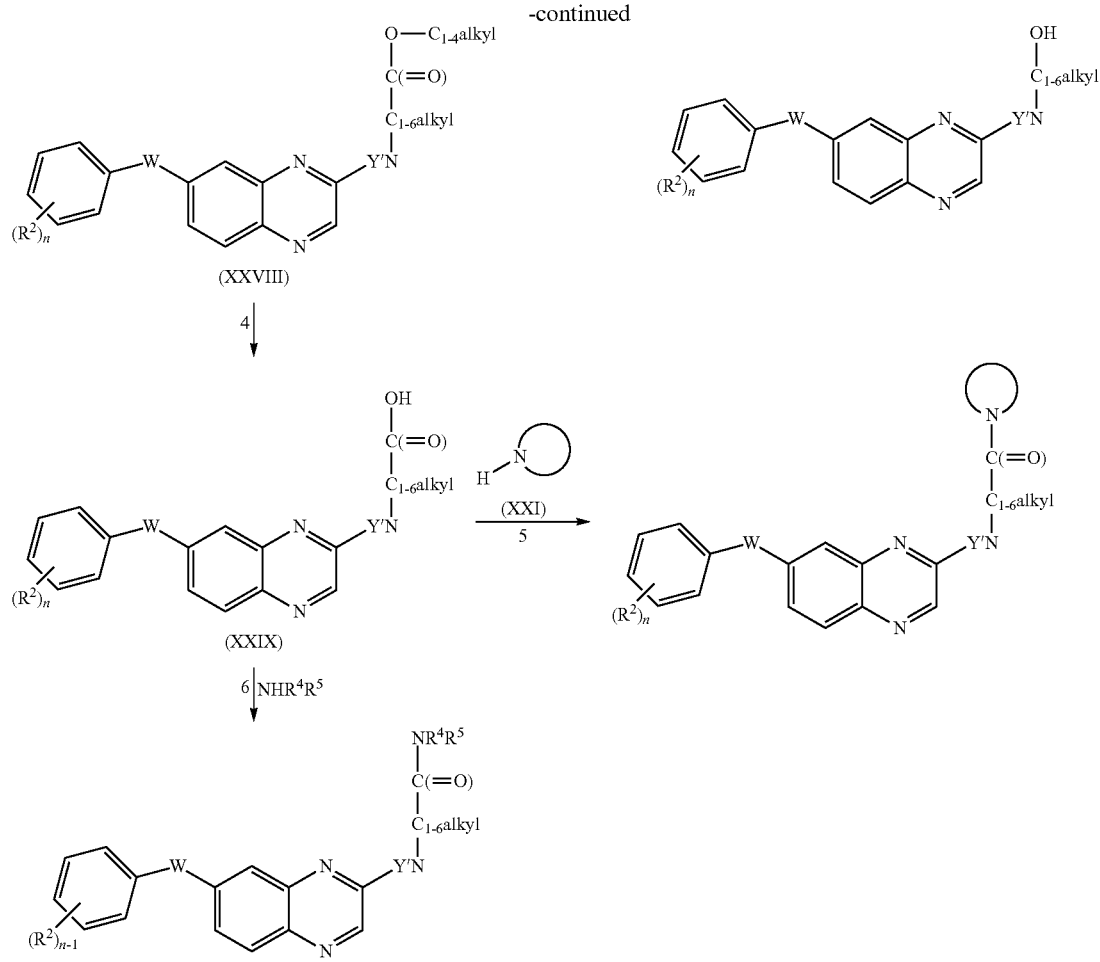

In Scheme 18, the Y'N moiety represents an E-D moiety wherein the D ring moiety contains a nitrogen atom. Compounds of formula (I) wherein $R^1$ represents hydroxy $C_{1-6}$alkyl can be prepared by deprotecting an intermediate of formula (XXVI) in the presence of a suitable acid, such as for example HCl or trifluoroacetic acid, or a suitable de-silylating agent, such as for example tetrabutyl ammonium fluoride, and a suitable solvent, such as an alcohol, e.g. methanol, or tetrahydrofuran (step 2). Intermediates of formula (XXVI) can be prepared by reacting a compound of formula (I) wherein $R^1$ is hydrogen with an intermediate of formula (XXIV) wherein $W_9$ represents a suitable leaving group, such as for example halo, e.g. bromo and the like, and P represents a suitable protective group, such as for example $Si(CH_3)_2(C(CH_3)_3)$ or

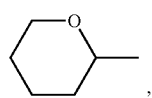, in the presence of a suitable base, such as for example sodium hydride or $K_2CO_3$, and a suitable solvent, such as for example N,N-dimethylformamide or acetonitrile (step 1). Compounds of formula (I) wherein $R^1$ represents $C_{1-6}$ alkyl substituted with $C(=O)$—$R^6$ wherein $R^6$ is an appropriate nitrogen containing ring linked to the $C(=O)$ moiety via the nitrogen atom can be prepared by reacting an intermediate of formula (XXIX) with an intermediate of formula (XXI) in the presence of suitable peptide coupling reagents such as, 1-hydroxy-benzotriazole and 1-(3-dimethylaminopropyl)-3-ethyl carbodiimide HCl (step 5). Intermediates of formula (XXIX) can be prepared by reacting an intermediate of formula (XXVIII) with LiOH in the presence of a suitable solvent, such as for example tetrahydrofuran or water (step 4). Intermediates of formula (XXVIII) can be prepared by as depicted in step 3 with an intermediate of formula (XXVII) wherein $W_9$ is as defined above, in the presence of a suitable base, such as for example sodium hydride, and a suitable solvent, such as for example N,N-dimethylformamide.

Step 6 depicts the preparation of compounds of formula (I) starting from an intermediate of formula (XXIX) by reaction with $NHR^4R^5$ in the presence of suitable peptide coupling reagents such as 1-hydroxy-benzotriazole and 1-(3-dimethylaminopropyl)-3-ethyl carbodiimide HCl and a suitable base, such as triethylamine, and a suitable solvent, such as for example dichloromethane.

Further protection-deprotection reactions can also be used as outlined in the following reaction Scheme 19.

Scheme 19

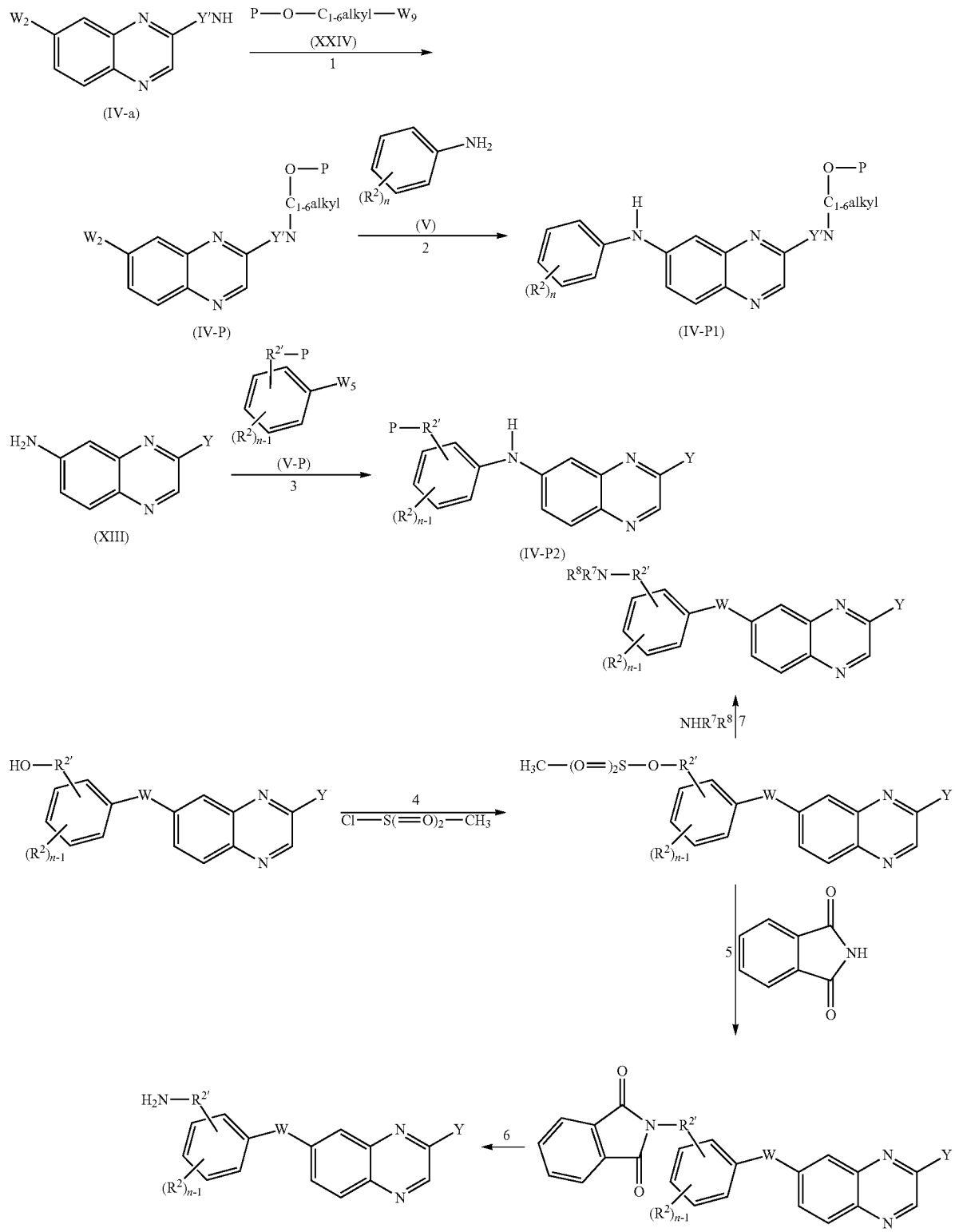

In Scheme 19, the following reaction conditions apply:
1; in the presence of a suitable base, such as for example sodium hydride, and a suitable solvent, such as for example N,N-dimethylformamide.

2: in the presence of a suitable catalyst, such as for example palladium (II)acetate, a suitable base, such as for example sodium tert-butoxide, a suitable ligand, such as for example 1,1'-[1,1'-binaphthalene]-2,2'-diylbis[1,1-diphenylphosphine], and a suitable solvent, such as for example dioxane or ethylene glycol dimethylether.

3: in the presence of a suitable catalyst, such as for example palladium (II)acetate, a suitable base, such as for example sodium tert-butoxide, a suitable ligand, such as for example 1,1'-[1,1'-binaphthalene]-2,2'-diylbis[1,1-diphenylphosphine], and a suitable solvent, such as for example dioxane or ethylene glycol dimethylether.

4: in the presence of a suitable base, such as for example triethylamine, and a suitable solvent, such as for example dichloromethane.

5: in the presence of a suitable base, such as for example $K_2CO_3$, and a suitable solvent, such as for example 1-methyl-2-pyrrolidinone.

6: in the presence of hydrazine monohydrate, and a suitable solvent, such as for example an alcohol, e.g. ethanol.

7: in the presence of a suitable base, such as for example $K_2CO_3$, and a suitable solvent, such as for example tetrahydrofuran.

It is considered to be within the knowledge of the person skilled in the art to recognize in which condition and on which part of the molecule a protective group may be appropriate. For instance, protective group on the $R^1$ substituent or on the D moiety, or protective group on the $R^3$ substituent or on the $R^2$ substituent or combinations thereof. The skilled person is also considered to be able to recognize the most feasible protective group, such as for example $C(=O)-O-C_{1-6}$alkyl or

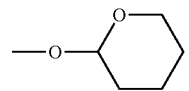

or $O-Si(CH_3)_2(C(CH_3)_3)$ or $-CH_2-O-CH_2CH_2-O-CH_3$ or $-CH_2-O-CH_2-CH_2-Si(CH_3)_3$. The skilled person is also considered to be able to recognize the most feasible deprotection reaction conditions, such as for example suitable acids, e.g. trifluoroacetic acid, hydrochloric acid, or suitable salts, such as for example tetrabutylammonium fluoride. Reference herefore is also made to the examples described in the Experimental Part hereinafter.

The skilled person is also considered to be able to recognize that when $R^1$ represents $C(=O)$-morpholinyl, said $R^1$ can be prepared from $C(=O)-NH-CH_2-CH_2-O-CH_2-CH_2-O-SO_2$-4-methylphenyl, in the presence of sodium hydride, and a suitable solvent, such as for example N,N-dimethylformamide. Or that when $R^1$ represents $NH-C(=O)$-morpholinyl, said $R^1$ can be prepared from $NH-C(=O)-O-C(CH_3)_3$ in the presence of morpholine, and a suitable solvent, such as for example 1-methyl-2-pyrrolidinone. Or that when $R^1$ represents hydroxyl$C_{1-6}$ alkyl, e.g. $CH_2-CH_2-OH$, said $R^1$ can be prepared from the corresponding alkoxycarbonyl intermediate, e.g. $CH_2-C(=O)-O-CH_2-CH_3$, in the presence of Dibal-H 1M in hexane, and a suitable solvent, such as for example tetrahydrofuran.

The present invention also comprises deuterated compounds. These deuterated compounds may be prepared by using the appropriate deuterated intermediates during the synthesis process. For instance an intermediate of formula (IV-a)

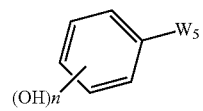

can be converted into an intermediate of formula (IV-b)

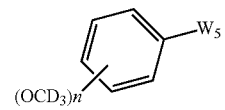

by reaction with iodomethane-D3 in the presence of a suitable base, such as for example cesium carbonate, and a suitable solvent, such as for example acetonitrile.

The compounds of formula (I) may also be converted into each other via art-known reactions or functional group transformations.

For instance, compounds of formula (I) wherein $R^1$ represents tetrahydropyranyl can be converted into a compound of formula (I) wherein $R^1$ represents hydrogen, by reaction with a suitable acid, such as for example HCl or trifluoroacetic acid, in the presence of a suitable solvent, such as for example dichloromethane, dioxane, or an alcohol, e.g. methanol, isopropanol and the like.

Compounds of formula (I) wherein $R^1$ or $R^3$ represent monohaloalkyl, can be converted into a compound of formula (I) wherein $R^1$ or $R^3$ represent $C_{1-6}$ alkyl substituted with a ring moiety as defined hereinabove by the intermediate of formula (XXI) and linked to the $C_{1-6}$ alkyl moiety by the nitrogen atom, by reaction with an intermediate of formula (XXI) optionally in the presence of a suitable base, such as for example triethylamine or $K_2CO_3$ or sodium hydride, and optionally in the presence of a suitable solvent, such as for example acetonitrile, N,N-dimethylformamide or 1-methyl-2-pyrrolidinone. Compounds of formula (I) wherein $R^1$ or $R^3$ represents $C_{1-6}$ alkyl-OH, can be converted into a compound of formula (I) wherein $R^1$ or $R^3$ represent $C_{1-6}$ alkyl-F by reaction with diethylaminosulfur trifluoride in the presence of a suitable solvent, such as for example dichloromethane and in the presence of catalytic amounts of an alcohol, such as for example ethanol. Likewise, a compound of formula (I) wherein $R^1$ or $R^3$ represent $C_{1-6}$alkyl substituted with $R^6$ or $R^9$ wherein said $R^6$ or $R^9$ is substituted with OH, can be converted into a compound of formula (I) wherein $R^1$ or $R^3$ represent $C_{1-6}$ alkyl substituted with $R^6$ or $R^9$ wherein said $R^6$ or $R^9$ is substituted with F, by reaction with diethylaminosulfur trifluoride in the presence of a suitable solvent, such as for example dichloromethane.

Compounds of formula (I) wherein $R^1$ or $R^3$ represent $C_{1-6}$ alkyl substituted with $R^6$ or $R^9$ wherein said $R^6$ or $R^9$ is substituted with $C(=O)-O-C_{1-6}$ alkyl, can be converted into a compound of formula (I) wherein $R^1$ or $R^3$ represent $C_{1-6}$ alkyl substituted with $R^6$ or $R^9$ wherein said $R^6$ or $R^9$ is substituted with $CH_2-OH$, by reaction with $LiAlH_4$ in the presence of a suitable solvent, such as for example tetrahydrofuran.

Compounds of formula (I) wherein $R^3$ represents $C_{1-6}$ alkyl substituted with 1,3-dioxo-2H-isoindol-2-yl, can be converted into a compound of formula (I) wherein $R^3$ represents $C_{1-6}$alkyl substituted with amino, by reaction with hydrazine monohydrate in the presence of a suitable solvent, such as for example an alcohol, e.g. ethanol.

Compounds of formula (I) wherein $R^1$ or $R^3$ represent $C_{1-6}$ alkyl substituted with amino, can be converted into a compound of formula (I) wherein $R^1$ or $R^3$ represents $C_{1-6}$ alkyl substituted with NH—S(=O)$_2$—$C_{1-6}$ alkyl, by reaction with Cl—S(=O)$_2$—$C_{1-6}$ alkyl in the presence of a suitable base, such as for example triethylamine, and a suitable solvent, such as for example dichloromethane.

Compounds of formula (I) wherein $R^1$ or $R^3$ represents $C_{1-6}$ alkyl substituted with halo, can be converted into a compound of formula (I) wherein $R^1$ or $R^3$ represent $C_{1-6}$ alkyl substituted with $NR^4R^5$ or $NR^{10}R^{11}$, by reaction with $NHR^4R^5$ or $NHR^{10}R^{11}$, either using such amino in large excess or in the presence of a suitable base, such as for example $K_2CO_3$, and a suitable solvent, such as for example acetonitrile, N,N-dimethylacetamide or 1-methyl-pyrrolidinone.

Compounds of formula (I) wherein $R^1$ represents hydrogen, can be converted into a compound of formula (I) wherein $R^1$ represents polyhalo$C_{1-6}$ alkyl or polyhydroxy$C_{1-6}$ alkyl or $C_{1-6}$ alkyl or S(=O)$_2$—$NR^{14}R^{15}$ or S(=O)$_2$—$C_{1-6}$ alkyl, by reaction with polyhalo$C_{1-6}$ alkyl-W or polyhydroxy$C_{1-6}$ alkyl-W or $C_{1-6}$ alkyl-W or W—S(=O)$_2$—$NR^{14}R^{15}$ or W—S(=O)$_2$—$C_{1-6}$alkyl, wherein W represents a suitable leaving group, such as for example halo, e.g. bromo and the like, in the presence of a suitable base, such as for example sodium hydride or $K_2CO_3$ or triethylamine or 4-dimethylamino-pyridine or diisopropylamine, and a suitable solvent, such as for example N,N-dimethylformamide or acetonitrile or dichloromethane. Compounds of formula (I) wherein $R^1$ represents hydrogen can also be converted into a compound of formula (I) wherein $R^1$ represents $C_{1-6}$ alkyl-OH, by reaction with W—$C_{1-6}$alkyl-O—Si(CH$_3$)$_2$(C(CH$_3$)$_3$) in the presence of a suitable base, such as for example sodium hydride, and a suitable solvent, such as for example N,N-dimethylformamide and, then followed by a reaction with a suitable desilylating agent such as tetrabutyl ammonium fluoride.

Compounds of formula (I) wherein $R^1$ represents hydrogen, can also be converted into compound of formula (I) wherein $R^1$ represents ethyl substituted with —S(=O)$_2$—$C_{1-6}$ alkyl, by reaction with $C_{1-6}$ alkyl-vinylsulfone, in the presence of a suitable base, such as for example triethylamine, and a suitable solvent, such as for example an alcohol, e.g. methanol or by reaction with $C_{1-6}$ alkyl-2-bromoethylsulfone in the presence of a suitable deprotonating agent, such as for example NaH, and a suitable solvent, such as for example dimethyformamide.

Compounds of formula (I) wherein $R^1$ represents hydrogen can also be converted into a compound of formula (I) wherein $R^1$ represents CH$_2$—CHOH—CH$_2$

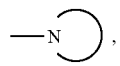, by reaction with

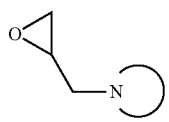

in the presence of a suitable base, such as for example sodium hydride, and a suitable solvent, such as for example N,N-dimethylformamide, wherein

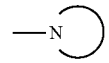

represents a suitable nitrogen containing ring within the definition of $R^6$. Compounds of formula (I) wherein $R^1$ represents $C_{1-6}$ alkyl substituted with $R^6$ wherein said $R^6$ is substituted with C(=O)—O—$C_{1-6}$ alkyl or S(=O)$_2$—$NR^{14}R^{15}$ or wherein $R^3$ represents $C_{1-6}$ alkyl substituted with $R^9$ wherein said $R^9$ is substituted with C(=O)—O—$C_{1-6}$alkyl or S(=O)$_2$—$NR^{14}R^{15}$, can be converted into a compound of formula (I) wherein the $R^6$ or $R^9$ is unsubstituted, by reaction with a suitable acid, such as for example HCl and a suitable solvent, such as for example dioxane, acetonitrile or an alcohol, e.g. isopropylalcohol. Compounds of formula (I) wherein $R^1$ represents $C_{1-6}$ alkyl substituted with $R^6$ wherein said $R^6$ is a ring moiety comprising a nitrogen atom which is substituted with CH$_2$—OH or wherein $R^3$ represents $C_{1-6}$ alkyl substituted with $R^9$ wherein said $R^9$ is a ring moiety comprising a nitrogen atom which is substituted with CH$_2$—OH, can be converted into a compound of formula (I) wherein the $R^6$ or $R^9$ is unsubstituted, by reaction with sodium hydroxide, in the presence of a suitable solvent, such as for example tetrahydrofuran.

Compounds of formula (I) wherein $R^1$ represents $C_{1-6}$ alkyl substituted with $R^6$ or $R^3$ represents $C_{1-6}$ alkyl substituted with $R^9$, wherein said $R^6$ or said $R^9$ is unsubstituted, can be converted into a compound of formula (I) wherein said $R^6$ or said $R^9$ is substituted with $C_{1-6}$ alkyl, by reaction with W—$C_{1-6}$ alkyl wherein W is as defined above, in the presence of a suitable base. Such as for example sodium hydride, and a suitable solvent, such as for example N,N-dimethylformamide.

Compounds of formula (I) wherein $R^1$ or $R^3$ represent hydroxy$C_{1-6}$ alkyl, can be converted into the corresponding carbonyl compound, by reaction with dess-Martin-periodinane, in the presence of a suitable solvent, such as for example dichloromethane.

Compounds of formula (I) wherein $R^1$ represents $C_{1-6}$ alkyl substituted with $R^6$ or $R^3$ represents $C_{1-6}$ alkyl substituted with $R^9$, wherein said $R^6$ or said $R^9$ is substituted with $C_{1-6}$alkyl-halo, can be converted into a compound of formula (I) wherein said $R^6$ or said $R^9$ is substituted with $C_{1-6}$ alkyl-CN, by reaction with sodium cyanide, in the presence of a suitable solvent, such as for example water or an alcohol, e.g. ethanol.

Compounds of formula (I) wherein $R^1$ represents $C_{1-6}$ alkyl substituted with $R^6$ wherein said $R^6$ is unsubstituted or wherein $R^3$ represents $C_{1-6}$ alkyl substituted with $R^9$ wherein said $R^9$ is unsubstituted, can be converted into a compound of formula (I) wherein $R^6$ or $R^9$ is substituted with CH$_3$ or CH(CH$_3$)$_2$, by reaction with formaldehyde or acetone and NaBH3CN, in the presence of a suitable solvent, such as for example tetrahydrofuran or an alcohol, e.g. methanol. Compounds of formula (I) wherein $R^1$ contains a $R^6$ substituent substituted with OH or wherein $R^3$ contains a $R^9$ substituent substituted with OH, can be converted into a compound of formula (I) wherein the $R^6$ or $R^9$ substituent is substituted with $C_{1-6}$ alkyloxy, by reaction with W—$C_{1-6}$ alkyl, in the presence of a suitable base, such as for example sodium hydride, and a suitable solvent, such as for example N,N-dimethylformamide. Compounds of formula (I) wherein $R^1$ contains a $R^6$ substituent substituted with $C_{1-6}$alkyloxy or wherein $R^3$ contains a $R^9$ substituent substituted with $C_{1-6}$ alkyloxy, can be converted into a compound of formula (I) wherein the $R^6$ or $R^9$ substituent is substituted with OH by reaction with a suitable acid, such as for example hydrochloric acid. Compounds of formula (I) wherein $R^1$ contains a $R^6$ substituent substituted with halo or wherein $R^3$ contains a $R^9$ substituent substituted with halo can be converted into a compound of formula (I) wherein the $R^6$ or $R^9$ substituent is substituted with $NR^{14}R^{15}$ by reaction with $NHR^{14}R^{15}$ in a suitable solvent, such as for example 1-methyl-pyrrolidinone. Compounds of formula (I) wherein $R^3$ represents $C_{1-6}$ alkyl substituted with $C(=O)-O-C_{1-6}$alkyl, can be converted into a compound of formula (I) wherein $R^3$ represents $C_{1-6}$ alkyl substituted with COOH, by reaction with LiOH in the presence of a suitable solvent, such as for example tetrahydrofuran. Said compounds of formula (I) wherein $R^3$ represents $C_{1-6}$ alkyl substituted with COOH, can be converted into a compound of formula (I) wherein $R^3$ represents $C_{1-6}$ alkyl substituted with $C(=O)-NH_2$ or $-C(=O)-NHCH_3$ or $-C(=O)NR^{10}R^{11}$, by reaction with $NH(Si(CH_3)_3)_2$ or $MeNH_3{}^+Cl^-$ or $NHR^{10}R^{11}$ in the presence of suitable peptide coupling reagents such as for example 1-(3-dimethylaminopropyl)-3-ethylcarbodiimide HCl and 1-hydroxybenzotriazole, a suitable base, such as for example triethylamine and a suitable solvent such as for example dichloromethane or N,N-dimethylformamide. Compounds of formula (I) wherein $R^3$ represents $C_{1-6}$ alkyl substituted with COOH, can also be converted into a compound of formula (I) wherein $R^3$ represents $C_{1-6}$ alkyl substituted with $C(=O)-N(CH_3)(OCH_3)$ by reaction with methylmethoxyamine, in the presence of carbonyldiimidazole and a suitable solvent, such as for example dichloromethane.

Compounds of formula (I) wherein $R^3$ represents $C_{1-6}$ alkyl substituted with

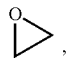

can be converted into a compound of formula (I) wherein $R^3$ represents $C_{1-6}$ alkyl substituted with 2 OH's, by reaction with a suitable acid, such as for example trifluoroacetic acid, and a suitable solvent, such as for example dioxane or water. These compounds of formula (I) wherein $R^3$ represents $C_{1-6}$ alkyl substituted with

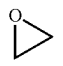

can also be converted into a compound of formula (I) wherein $R^3$ represents $C_{1-6}$ alkyl substituted with OH and $NR^{10}R^{11}$, by reaction with $NH_2R^{10}R^{11}$ optionally in salt form, such as for example $NHR^{10}R^{11+}Cl^-$, optionally in the presence of a suitable base, such as for example sodium hydride or $Na_2CO_3$ or triethylamine, a suitable additive such as for example KI, and in the presence of a suitable solvent, such as for example N,N-dimethylformamide or an alcohol, e.g. 1-butanol or ethanol.

Compounds of formula (I) wherein $R^3$ represents $C_{1-3}$ alkyl substituted with $C(=O)-O-C_{1-6}$alkyl, can be converted into a compound of formula (I) wherein $R^3$ represents $C_{1-3}$ alkyl substituted with $C(CH_3)_2-OH$, by reaction with iodomethane and Mg powder, in the presence of a suitable solvent, such as for example diethylether or tetrahydrofuran. Compounds of formula (I) wherein $R^3$ represents $C_{1-5}$alkyl substituted with $C(=O)-O-C_{1-6}$alkyl, can be converted into a compound of formula (I) wherein $R^3$ represents $C_{1-6}$ alkyl substituted with OH, by reaction with $LiAlH_4$ in a suitable solvent, such as for example tetrahydrofuran.

Compounds of formula (I) wherein $R^3$ represents $C_{1-5}$alkyl substituted with OH, can be converted into a compound of formula (I) wherein $R^3$ represents $C_{1-5}$alkyl substituted with $-O-C(=O)-C_{1-6}$ alkyl by reaction with $Cl-C(=O)-C_{1-6}$alkyl in the presence of a suitable base, such as for example NaH, and a suitable solvent, such as for example tetrahydrofuran.

Compounds of formula (I) wherein $R^3$ represents $CH_2-CH=CH_2$, can be converted into a compound of formula (I) wherein $R^3$ represents $CH_2-CHOH-CH_2-OH$, by reaction with potassium permanganate, and a suitable solvent, such as for example acetone or water. Compounds of formula (I) wherein $R^3$ represents $C_{1-6}$ alkyl substituted with $C(=O)-C_{1-4}$alkyl, can be converted into a compound of formula (I) wherein $R^3$ represents $C_{1-6}$ alkyl substituted with $C(C_{1-6}alkyl)=N-OH$, by reaction with hydroxylamine, in the presence of a suitable base, such as for example pyridine, and a suitable solvent, such as for example an alcohol, e.g. ethanol.

Compounds of formula (I) wherein $R^3$ represents $C_{1-6}$ alkyl substituted with $NH_2$, can be converted into a compound of formula (I) wherein $R^3$ represents $C_{1-6}$ alkyl substituted with $-NH-C(=O)-R^6$ or with $-NH-C(=O)-C_{1-6}$ alkyl or with $-NH-C(=O)$-polyhydroxy$C_{1-6}$ alkyl or with $-NH-C(=O)$-polyhalo$C_{1-6}$ alkyl or with $-NH-C(=O)$-polyhydroxypolyhalo$C_{1-6}$ alkyl, by reaction with the corresponding COOH analogue, e.g. $R^6-COOH$ or $CF_3-C(CH_3)(OH)-COOH$ and the like, in the presence of suitable peptide coupling reagents such as 1-hydroxy-benzotriazole and 1-(3-dimethylamino)propyl) carbodiimide optionally in the presence of a suitable base, such as for example triethylamine. Said compounds of formula (I) wherein $R^3$ represents $C_{1-6}$ alkyl substituted with $NH_2$, can also be converted into a compound of formula (I) wherein $R^3$ represents $C_{1-6}$ alkyl substituted with $NH-C(=O)-CF_3$, by reaction with trifluoroacetic anhydride, in the presence of a suitable base, such as for example triethylamine, and a suitable solvent, such as for example tetrahydrofuran. Said compounds of formula (I) wherein $R^3$ represents $C_{1-6}$ alkyl substituted with $NH_2$, can also be converted into a compound of formula (I) wherein $R^3$ represents $C_{1-6}$ alkyl substituted with NH-polyhalo$C_{1-6}$ alkyl, e.g. $NH-CH_2-CH_2-F$, by reaction with polyhalo$C_{1-6}$ alkyl-W, with W as defined above, e.g. iodo-2-fluoroethane, in the presence of a suitable base, such as for example $K_2CO_3$, and a suitable solvent, such as for example N,N-dimethylformamide or dioxane.

Said compounds of formula (I) wherein $R^3$ represents $C_{1-6}$ alkyl substituted with $NH_2$ can also be converted into a compound of formula (I) wherein $R^3$ represents $C_{1-6}$ alkyl substituted with $NH-R^6$ or $N(R^6)_2$ wherein $R^6$ represents for example oxetane, by reaction with the appropriate $R^6$ in the presence of a suitable reducing agent, such as for example sodium triacetoxyborohydride, a suitable acid, such as for example acetic acid, and a suitable solvent, such as for example 1,2-dichloroethane.

Compounds of formula (I) wherein $R^3$ represents $C_{1-6}$ alkyl substituted with cyano, can be converted into a compound of formula (I) wherein $R^3$ represents $C_{1-6}$ alkyl substituted with tetrazolyl by reaction with sodium azide, and NH$_4^+$Cl$^-$ in the presence of a suitable solvent, such as for example N,N-dimethylformamide.

Compounds of formula (I) wherein R$^3$ represents —CH2-C≡CH, can be converted into a compound of formula (I) wherein R$^3$ represents

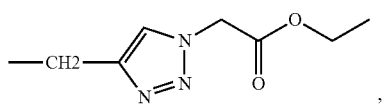

by reaction with ethyl azidoacetate in the presence of CuI and a suitable base, such as for example diisopropylamine, and a suitable solvent, such as for example tetrahydrofuran. Compounds of formula (I) wherein R$^3$ represents —CH2-C≡CH, can be converted into a compound of formula (I) wherein R$^3$ represents

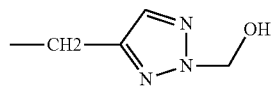

by reaction with sodium azide and formaldehyde, in the presence of a suitable catalyst, such as for example CuSO$_4$ and sodium L ascorbate, a suitable acid, such as for example acetic acid, and a suitable solvent, such as for example dioxane.

Compounds of formula (I) wherein R$^3$ represent C$_{2-6}$ alkynyl, can be converted into a compound of formula (I) wherein R$^3$ represents C$_{2-6}$ alkynyl substituted with R$^9$, by reaction with W—R$^9$ wherein W is as defined above, in the presence of a suitable catalyst, such as for example dichlorobis(triphenylphosphine)palladium, a suitable co-catalyst such as CuI, a suitable base, such as for example triethylamine, and a suitable solvent, such as for example dimethylsulfoxide.

Compounds of formula (I) wherein R$^3$ comprises R$^9$ substituted with halo, can be converted into a compound of formula (I) wherein R$^3$ comprises R$^9$ substituted with —NR$^{14}$R$^{15}$ by reaction with NHR$^{14}$R$^{15}$ in the presence of a suitable solvent, such as for example 1-methyl-2-pyrrolidinone.

Compounds of formula (I) wherein R$^3$ comprises C$_{2-6}$ alkynyl, can be hydrogenated into a compound of formula (I) wherein R$^3$ comprises C$_{2-6}$alkyl in the presence of a suitable catalyst, such as for example palladium on charcoal, and a suitable solvent, such as for example ethylacetate.

Compounds of formula (I) wherein R$^3$ comprises C$_{2-6}$ alkynyl, can be hydrogenated into a compound of formula (I) wherein R$^3$ comprises C$_{2-6}$ alkenyl in the presence of a suitable catalyst, such as for example Lindlar catalyst, and a suitable solvent, such as for example ethylacetate.

Compounds of formula (I) wherein R$^3$ represents C$_{1-6}$ alkyl substituted with —P(=O)(OC$_{1-6}$alkyl)$_2$ can be converted into a compound of formula (I) wherein R$^3$ represents C$_{1-6}$ alkyl substituted with —P(=O)(OH)$_2$ by reaction with bromotrimethylsilane in the presence of a suitable solvent, such as for example dichloromethane.

Compounds of formula (I) wherein the R$^9$ substituent is substituted with =O, can be converted into the corresponding reduced R$^9$ substituent by reaction with a suitable reducing agent, such as for example LiAlH$_4$ in a suitable solvent, such as for example tetrahydrofuran.

Compounds of formula (I) wherein R$^3$ comprises —NHR$^{10}$ can be converted into a compound of formula (I) wherein R$^3$ comprises —NR$^{19}$—(C=O)— optionally substituted C$_{1-6}$alkyl, by reaction with the corresponding W—(C=O)-optionally substituted C$_{1-6}$ alkyl wherein W represents a suitable leaving group, such as for example halo, e.g. chloro and the like, in the presence of a suitable base, such as for example triethylamine, and a suitable solvent, such as for example acetonitrile.

Compounds of formula (I) wherein R$^3$ represents C$_{1-6}$ alkyl substituted with NR$^{10}$(benzyl) can be converted into a compound of formula (I) wherein R$^3$ represents C$_{1-6}$ alkyl substituted with NHR$^{10}$, by reaction with 1-chloroethylchloroformate in the presence of a suitable solvent, such as for example dichloromethane Compounds of formula (I) wherein R$^1$ represents unsubstituted piperidine, can be converted into a compound of formula (I) wherein R$^1$ represents 1-methyl-piperidine, by reaction with iodomethane in the presence of a suitable base, such as for example potassium carbonate, and a suitable solvent, such as for example acetonitrile.

Compounds of formula (I) wherein R$^1$ represents hydrogen can be converted into a compound of formula (I) wherein R$^1$ represents optionally substituted C$_{1-6}$ alkyl, by reaction with optionally substituted C$_{1-6}$ alkyl-W wherein W represents a suitable leaving group, such as for example halo, e.g. bromo and the like, in the presence of a suitable base, such as for example potassium carbonate, and a suitable solvent, such as for example acetonitrile.

Compounds of formula (I) wherein R$^2$ represents halo, e.g. bromo, can be converted into a compound of formula (I) wherein R$^2$ represents cyano, by reaction with zinc cyanide, in the presence of a suitable catalyst, such as for example Pd$_2$(dba)$_3$ and a suitable ligand, such as for example 1,1-bis(diphenylphosphino)ferrocene, in the presence of a suitable solvent, such as for example N,N-dimethylformamide.

Said R$^2$ substituent being cyano can be converted into CH$_2$—NH$_2$ by hydrogenation in the presence of NH$_3$ and Nickel.

Compounds of formula (I) wherein R$^2$ represents OCH$_3$ can be converted into a compounds of formula (I) wherein R$^2$ represents OH by reaction with boron tribromide in the presence of a suitable solvent, such as for example dichloromethane. Compounds of formula (I) wherein R$^2$ represents OH can be converted into a compounds of formula (I) wherein R$^2$ represents OCH$_3$ by reaction with methyl iodine in the presence of a suitable base, such as for example potassium carbonate, and a suitable solvent, such as for example N,N-dimethylformamide.

Compounds of formula (I) wherein R$^2$ represents hydrogen, can be converted into a compound of formula (I) wherein R$^2$ represents CHOH—CF$_3$ by reaction with trifluoroacetaldehyde methyl hemiketal.

For the conversion reactions, reference is also made to the examples described in the Experimental Part hereinafter.

A further aspect of the invention is a process for the preparation of a compound of formula (I) as defined herein, which process comprises:

(i) deprotecting a compound of formula (XXX) wherein P represents a suitable protective group, such as for example a butyloxycarbonyl-group (—CO$_2$C(CH$_3$)$_3$) in the presence of a suitable acid, such as for example HCl or trifluoroacetic acid;

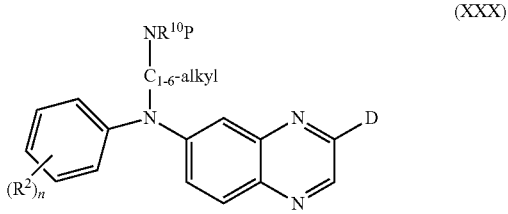

(XXX)

or
(ii) the reaction of a compound of the formula (IX) or (IX'):

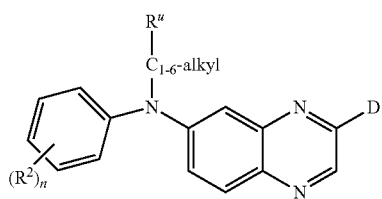

(IX): $R^u$ is —O—(S=O)$_2$—CH$_3$
(IX'): $R^u$ is Cl or a protected form thereof, with an appropriately substituted amine or a reactive derivative thereof, such as for example NHR$^{10}$R$^{11}$ (X), NHR$^{10}$P (X-a) or

(XXI)

for example in a sealed vessel, in the presence of a suitable base, such as for example sodium hydride and/or in the presence or absence of a solvent such as acetonitrile, N,N-dimethylformamide or N,N-dimethylacetamide; or
(iii) the reaction of a compound of the formula (VI):

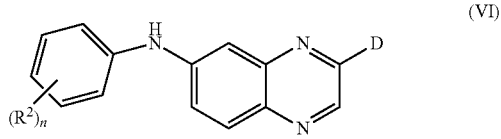

(VI)

or a protected form thereof, with a compound of formula W$_6$—C$_{1-6}$ alkyl-NR$^{10}$P wherein P represents a suitable protective group and W$_6$ represents a suitable leaving group, such as for example halo, e.g. bromo and the like, or O—S(=O)$_2$—CH$_3$, in the presence of a suitable base, such as for example sodium hydride, and a suitable solvent, e.g. N,N-dimethylformamide or N,N-dimethylacetamide, followed by removing P and optionally removing any further protecting group present; or
(iv) the reaction of a compound of the formula (VI):

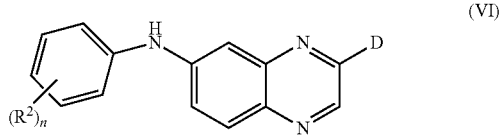

(VI)

or a protected thereof, with a compound of formula W$_6$—C$_{1-6}$ alkyl-NHR$^{10}$ wherein W$_6$ represents a suitable leaving group, such as for example halo, e.g. bromo and the like, or O—S(=O)$_2$—CH$_3$, in the presence of a suitable base, such as for example sodium hydride, and a suitable solvent, e.g. N,N-dimethylformamide or N,N-dimethylacetamide;
(v) the reaction of a compound of formula (XXXVI)

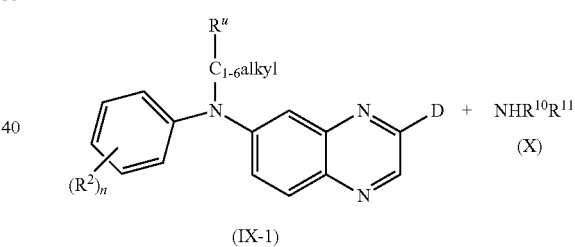

(XXXVI)

with hydrazine in the presence of a suitable solvent, such as for example an alcohol, e.g. ethanol;
(vi) the reaction of a compound of formula (IX-1) wherein $R^u$ represents O—S(=O)$_2$—CH$_3$,

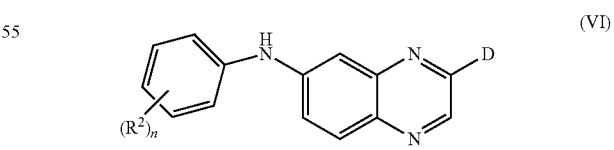

(IX-1)

with an intermediate of formula (X) in the presence of a suitable solvent, such as for example acetonitrile;
(vii) the reaction of a compound of formula (VI)

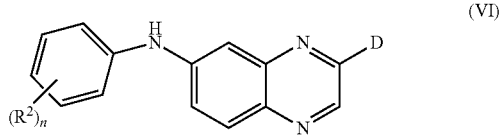

(VI)

with an intermediate of formula W$_{11}$—R$^{3b}$ wherein R$^{3b}$ represents optionally substituted C$_{2-6}$alkynyl and represents a suitable leaving group such as for example halo, e.g. chloro, or O—S(=O)$_2$—CH$_3$, in the presence of a suitable base, such as for example NaH, and a suitable solvent, such as for example N,N-dimethylformamide;

(viii) the reaction of a compound of formula (VIII') wherein $R^x$ and $R^y$ represent $C_{1-4}$alkyl, and $R^z$ represent $C_{1-4}$alkyl or phenyl,

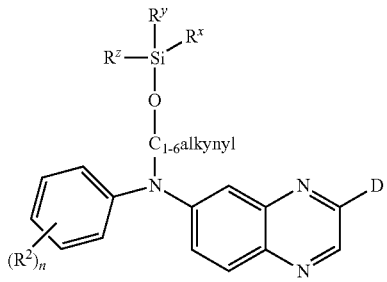

(VIII')

with a suitable acid, such as for example trifluoroacetic acid, in the presence of a suitable solvent, such as for example tetrahydrofuran;

(viii) deprotecting a compound of formula (XXXXII)

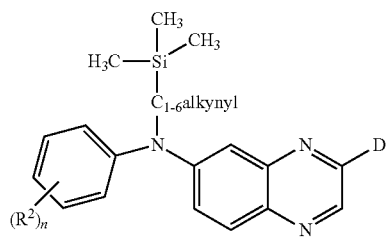

(XXXXII)

in the presence of a suitable base, such as for example $K_2CO_3$, and a suitable solvent, such as for example an alcohol, e.g. methanol and the like;

(ix) the reaction of a compound of formula (VI)

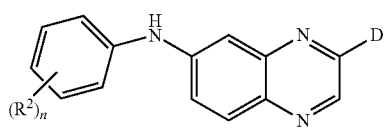

(VI)

with di($C_{1-6}$ alkyl)vinylphosphonate in the presence of a suitable catalyst, such as for example tri-N-butylphosphine, and a suitable solvent, such as for example acetonitrile;

(x) deprotecting a compound of formula (XXXXI) wherein the D'N moiety represents a D moiety wherein the D moiety contains a nitrogen atom

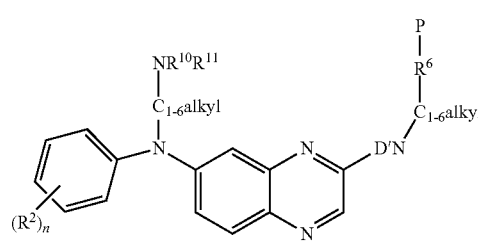

(XXXXI)

in the presence of a suitable base, such as for example $K_2CO_3$, and a suitable solvent, such as for example an alcohol, e.g. methanol and the like;

(xi) the reaction of a compound of formula (XIX) with a compound of formula (III) or (III-a)

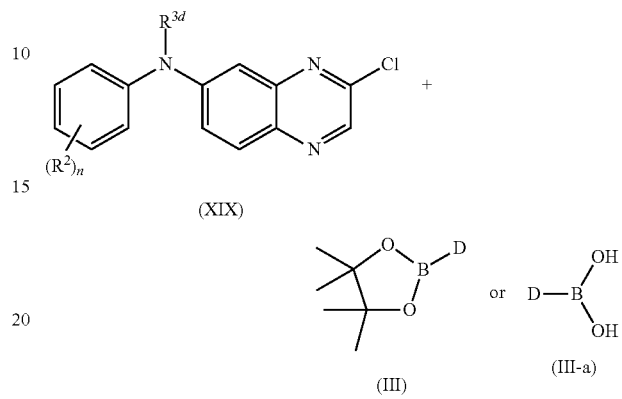

(XIX)

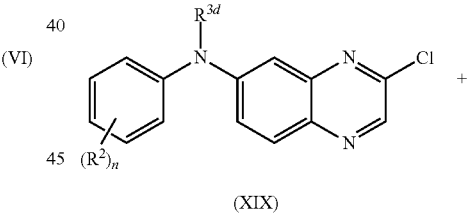

(III)          (III-a)

in the presence of a suitable catalyst, such as for example tetrakis(triphenyl)phosphine palladium or $Pd_2(dba)_3$ (tris(dibenzylideneacetone)dipalladium (0)), a suitable ligand, such as 2-dicyclohexylphosphino-2',6'-dimethoxybiphenyl, a suitable base, such as for example $Na_2CO_3$ or $K_3PO_4$, and a suitable solvent, such as for example ethylene glycol dimethylether or dioxane or water;

(xi-1) the reaction of a compound of formula (XIX) with a compound of formula (XXXVII)

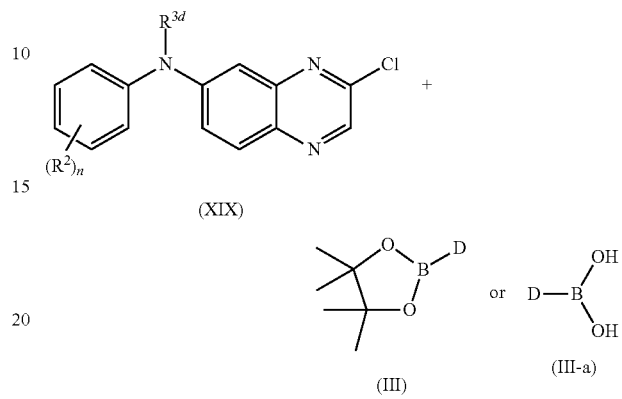

(XIX)

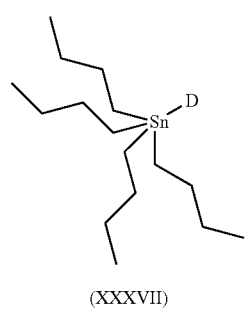

(XXXVII)

in the presence of a suitable catalyst, such as for example tetrakis(triphenyl)phosphine palladium, and a suitable solvent, such as for example N,N-dimethylformamide or toluene.

(xi-2) the reaction of a compound of formula (XIX) with D-W, wherein W represents a suitable leaving group, such as for example halo, e.g. bromo, iodod and the like,

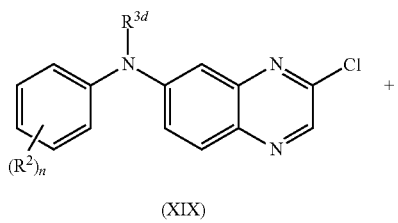

(XIX)     + D—W in the presence of a suitable catalyst, such as for example tetrakis(triphenyl)phosphine palladium, ethylmagnesium chloride, zinc chloride to generated in situ a reactive organometallic species, and a suitable solvent, such as for example tetrahydrofuran.

(xii) the reaction of a compound of formula (XX) wherein $R^{3a}$ represents optionally substituted $C_{1-6}$ alkyl, with a compound of formula (XIV)

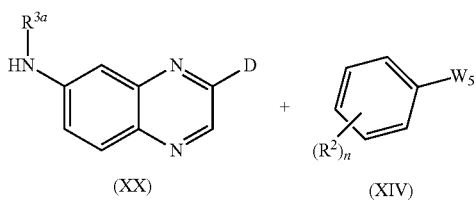 + 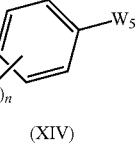

(XX)     (XIV)

in the presence of a suitable catalyst, such as for example palladium (II) acetate or $Pd_2(dba)_3$ (tris(dibenzylidene acetone)dipalladium (0)), a suitable ligand such as for example 2-dicyclohexylphosphino-tris-isopropyl-biphenyl or 1,1'-[1,1'-binaphthalene]-2,2'-diylbis[1,1-diphenylphosphine], a suitable base, such as for example sodium tert-butoxide, and a suitable solvent, such as for example ethylene glycol dimethylether;

(xiii) the reaction of a compound of formula (XXXI)

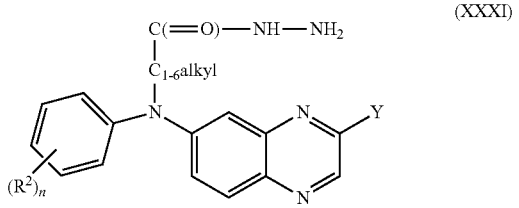

(XXXI)

with $W_8$—CN, wherein $W_8$ represents a suitable leaving group, such as for example halo, e.g. bromo, in the presence of a suitable base, such as for example $NaHCO_3$, and a suitable solvent, such as for example water or dioxane;

(xiv) the reaction of a compound of formula (XXXV)

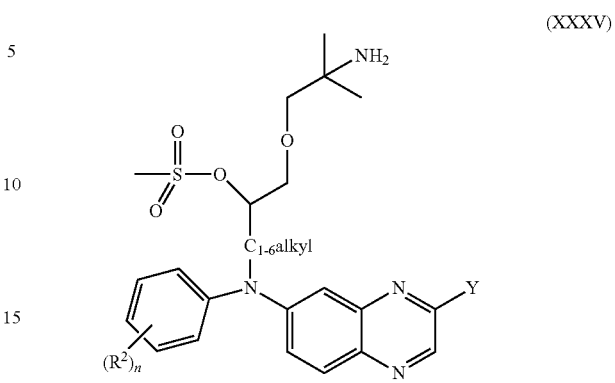

(XXXV)

with a suitable base, such as for example N,N-diisopropylethylamine and triethylamine, in the presence of a suitable solvent, such as for example an alcohol, e.g. methanol;

(xv) deprotecting a compound of formula (XXVI) wherein P represents a suitable protective group such as for example —O—Si(CH$_3$)$_2$(C(CH$_3$)$_3$) or

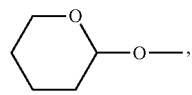

and wherein Y'N represents an -E-D moiety wherein the D ring moiety contains a nitrogen atom

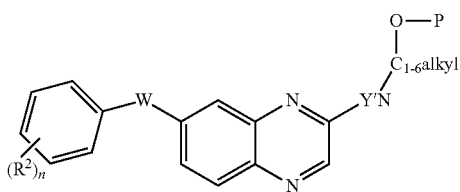

(XXVI)

in the presence of a suitable acid, such as for example HCl or trifluoroacetic acid, or a suitable de-silylating agent, such as for example tetrabutyl ammonium fluoride, and a suitable solvent, such as an alcohol, e.g. methanol, or tetrahydrofuran;

(xvi) the reaction of a compound of formula (XXIX) wherein Y'N represents an E-D moiety wherein the D ring moiety contains a nitrogen atom, with a compound of formula (XXI)

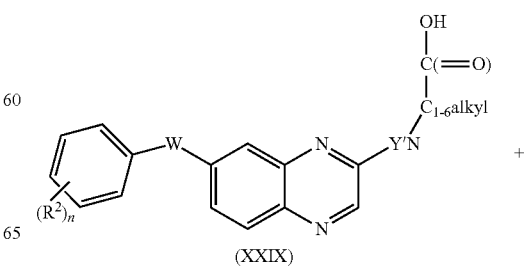 +

(XXIX)

-continued

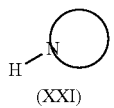
(XXI)

in the presence of suitable peptide coupling reagents such as, 1-hydroxy-benzotriazole and 1-(3-dimethylaminopropyl)-3-ethyl carbodiimide HCl;

(xvii) the reaction of a compound of formula (XXIX) wherein Y'N represents an E-D moiety wherein the D ring moiety contains a nitrogen atom

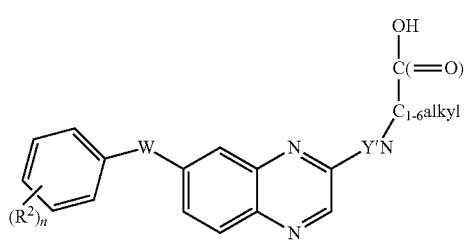
(XXIX)

with $NHR^4R^5$ in the presence of suitable peptide coupling reagents such as 1-hydroxy-benzotriazole and 1-(3-dimethylaminopropyl)-3-ethyl carbodiimide HCl and a suitable base, such as triethylamine, and a suitable solvent, such as for example dichloromethane;

(xviii) reacting the below compound

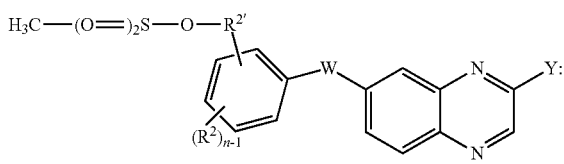

with $NHR^7R^8$ in the presence of a suitable base, such as for example $K_2CO_3$, and a suitable solvent, such as for example tetrahydrofuran;

(xviii) deprotecting the below compound

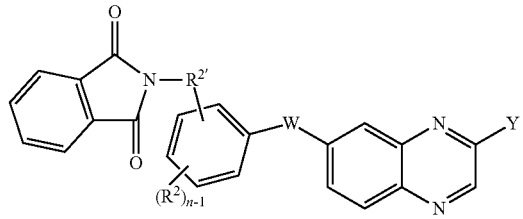

in the presence of hydrazine monohydrate, and a suitable solvent, such as for example an alcohol, e.g. ethanol;

(xix) the reaction of a compound of formula (XLI) with D-W

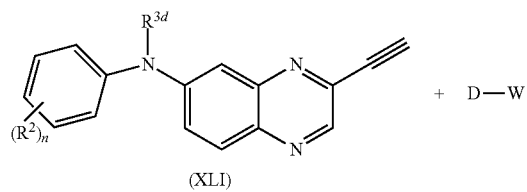
(XLI)

in the presence of a suitable catalyst, such as for example dichlorobis(triphenylphosphine) palladium (II) and copperiodide, a suitable base, such as for example triethylamine, and a suitable solvent, such as for example N,N-dimethylformamide and acetonitrile;

(xx) the reaction of a compound of formula (XIX) with $D-NH_2$

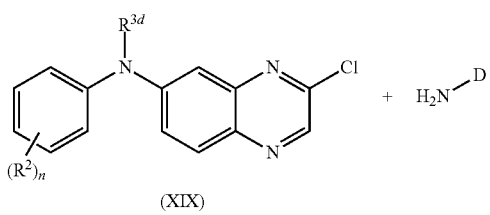
(XIX)

in the presence of a suitable catalyst, such as for example (tris(dibenzylideneacetone)dipalladium (0)), a suitable ligand, such as for example 9,9-dimethyl-4,5-bis(diphenylphosphino)xanthene, a suitable base, such as for example cesium carbonate, and a suitable solvent, such as for example dioxane;

(xxi) the reaction of a compound of formula (XIX) with

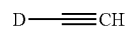

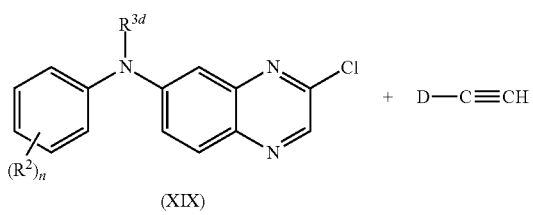
(XIX)

in the presence of a suitable catalyst, such as for example dichlorobis(triphenylphosphine) palladium (II) and copperiodide, a suitable ligand, such as for example triphenylphosphine, a suitable base, such as for example triethylamine, and a suitable solvent, such as for example N,N-dimethylformamide (xxii) the reaction of a compound of formula (XLII) with D-H

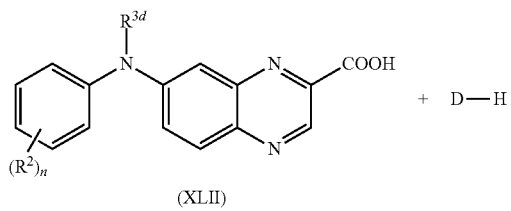

(XLII)

in the presence of suitable peptide coupling reagents such as for example 1-(3-dimethylaminopropyl)-3-ethylcarbodiimide hydrochloride and 1-hydroxybenzotriazole, a suitable base, such as for example triethylamine, and a suitable solvent, such as for example methylene chloride (xxiii) the reaction of a compound of formula (XLII) with D-(CR$^x$R$^y$)$_s$—NH$_2$

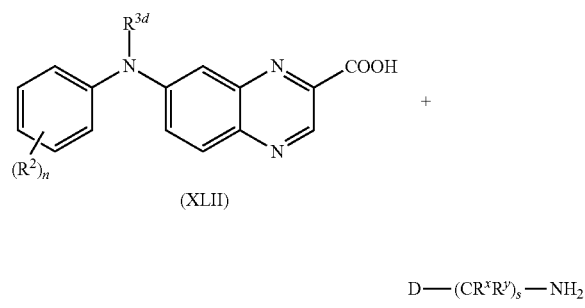

in the presence of suitable peptide coupling reagents such as for example 1-(3-dimethylaminopropyl)-3-ethylcarbodiimide hydrochloride and 1-hydroxybenzotriazole, a suitable base, such as for example triethylamine, and a suitable solvent, such as for example methylene chloride, (xxiv) the reaction of a compound of formula (XLIII) with D-COOH

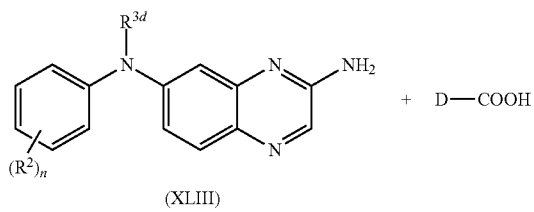

(XLIII)

in the presence of suitable peptide coupling reagents such as for example 1-(3-dimethylaminopropyl)-3-ethylcarbodiimide hydrochloride and 1-hydroxybenzotriazole, a suitable base, such as for example triethylamine, and a suitable solvent, such as for example methylene chloride (x) the reaction of a compound of formula (XLVI) with R$^{19}$—O—NH$_2$

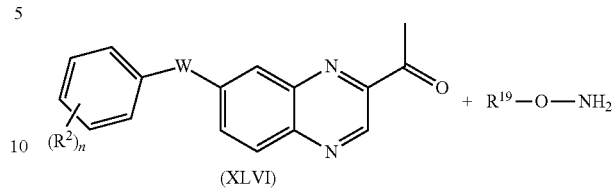

(XLVI)

in the presence of a suitable base such as for example pyridine, and a suitable solvent, such as for example an alcohol, e.g. ethanol, (xxvi) the reaction of a compound of formula (XLVII) with a compound of formula (XLVIII)

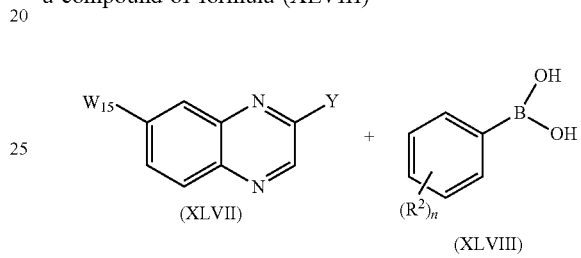

(XLVII)          (XLVIII)

in the presence of CO as a reactant, a suitable catalyst, such as for example palladium(II)acetate, a suitable ligand, such as for example tricyclohexylphosphine, a suitable base, such as for example triethylamine, and a suitable solvent, such as for example toluene (xxvii) the reaction of a compound of formula (XLX) with a compound of formula (XLIX) wherein W$_{16}$ represents a suitable leaving group such as for example halo, e.g. bromo and the like,

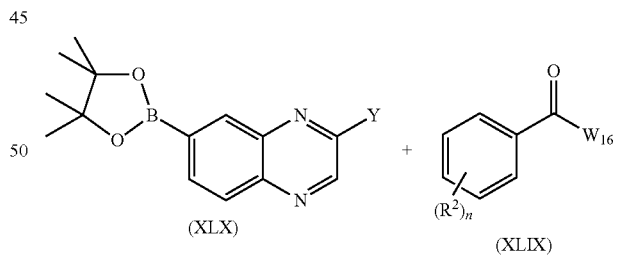

(XLX)          (XLIX)

in the presence of a catalyst, such as for example dichlorobis(triphenylphosphine)palladium, a suitable base, such as for example Na$_2$CO$_3$, and a suitable solvent, such as for example tetrahydrofuran wherein the variables are as defined herein; and optionally thereafter converting one compound of the formula (I) into another compound of the formula (I).

A further embodiment is a process for synthesis of a compound of formula (VI) wherein:

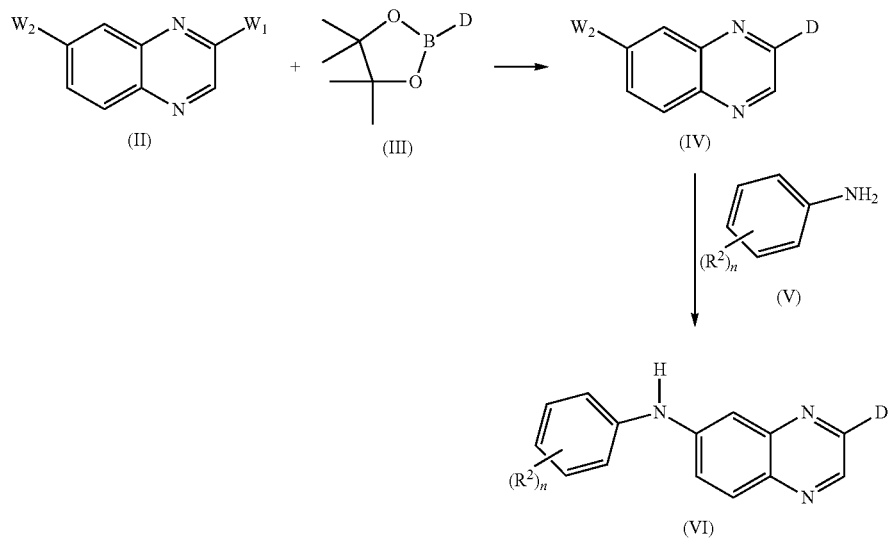

1) a compound of formula (II) is reacted with an intermediate of formula (III) in the presence of a suitable catalyst, such as for example tetrakis(triphenylphosphine)palladium (0) or palladium (II) acetate, a suitable base, such as for example sodium carbonate, a suitable ligand, such as for example triphenylphosphine, and a suitable solvent or solvent mixture, such as for example ethylene glycol dimethylether and water; wherein $W_1$ and $W_2$, each independently represent a suitable leaving group, such as for example halo, e.g. chloro or bromo;
and then
2) a compound of formula (IV) is reacted with an intermediate of formula (V) in the presence of a suitable catalyst, such as for example palladium (II) acetate, a suitable base, such as sodium tert-butoxide or 052003, a suitable ligand, such as for example 1,1'-[1,1'-binaphthalene]-2,2'-diylbis[1,1-diphenylphosphine], and a suitable solvent or solvent mixture, such as for example dioxane or ethylene glycol dimethylether and water;
wherein optionally the intermediate of formula (II) wherein $W_1$ is chloro and $W_2$ is bromo is prepared by reacting 7-bromo-2(1H)-quinoxalinone with phosphorus oxychloride, or alternatively with thionyl chloride and N,N-dimethylformamide in a suitable solvent, such as, for example toluene;
or vice versa, wherein a compound of formula (II) is reacted with an intermediate of formula (V) first and then reacted with an intermediate of formula (III) using the methods described above.

In a further embodiment the invention provides a novel intermediate. In one embodiment the invention provides a novel intermediate of formula described above. In another embodiment the invention provides a novel intermediate of formula (VI) or formula (IX).

In one embodiment, the present invention also relates to a compound having the following formula:

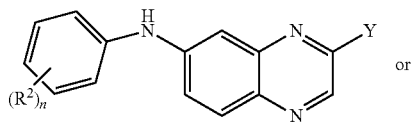

or

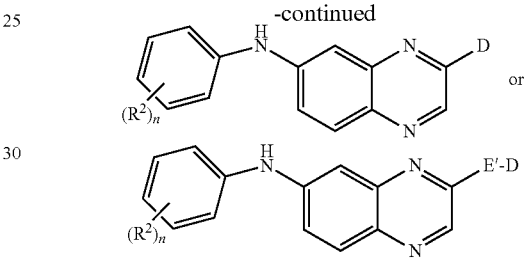

wherein E' represents $-(CR^{22}R^{23})_n-$, $C_{2-4}$ alkenediyl optionally substituted with $R^{22}$, $C_{2-4}$ alkynediyl optionally substituted with $R^{22}$, $-CO-(CR^{22}R^{23})_s-$, $-(CR^{22}R^{23})_s-CO-$, $-NR^{22}-(CR^{22}R^{23})_s-$, $-(CR^{22}R^{23})_s-NR^{22}-$, $-O-(CR^{22}R^{23})_s-$, $-(CR^{22}R^{23})_s-O-$, $-S(O)_m-(CR^{22}R^{23})_s-$, $-(CR^{22}R^{23})_s-S(O)_m-$, $(CR^{22}R^{23})_s-CO-NR^{22}-(CR^{22}R^{23})_s-$ or $-(CR^{22}R^{23})_s-NR^{22}-CO-(CR^{22}R^{23})_s-$;
wherein Y, D, $R^2$ and n are as defined for a compound of formula (I) above.

Pharmaceutically Acceptable Salts, Solvates or Derivatives Thereof

In this section, as in all other sections of this application, unless the context indicates otherwise, references to formula (I) include references to all other sub-groups, preferences, embodiments and examples thereof as defined herein.

Unless otherwise specified, a reference to a particular compound also includes ionic forms, salts, solvates, isomers, tautomers, N-oxides, esters, prodrugs, isotopes and protected forms thereof, for example, as discussed below; preferably, the ionic forms, or salts or tautomers or isomers or N-oxides or solvates thereof; and more preferably, the ionic forms, or salts or tautomers or solvates or protected forms thereof, even more preferably the salts or tautomers or solvates thereof. Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds. It will be appreciated that references to "derivatives" include references to ionic forms, salts, solvates, isomers, tautomers, N-oxides, esters, prodrugs, isotopes and protected forms thereof.

According to one aspect of the invention there is provided a compound as defined herein or a salt, tautomer, N-oxide or solvate thereof. According to a further aspect of the invention there is provided a compound as defined herein or a salt or solvate thereof. References to compounds of the formula (I) and sub-groups thereof as defined herein include within their scope the salts or solvates or tautomers or N-oxides of the compounds.

The salt forms of the compounds of the invention are typically pharmaceutically acceptable salts, and examples of pharmaceutically acceptable salts are discussed in Berge et al. (1977) "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used. The compounds of the invention may exist as mono- or di-salts depending upon the pKa of the acid from which the salt is formed.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethane-sulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic, (±)-DL-lactic), lactobionic, maleic, malic, (−)-L-malic, malonic, (±)-DL-mandelic, methanesulphonic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, pyruvic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of salts consists of salts formed from acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids. Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

If the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth metal cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$).

Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I). Compounds of the formula (I) containing an amine function may also form N-oxides. A reference herein to a compound of the formula (I) that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* (1977), 7, 509-514) in which the amine compound is reacted with m-chloroperoxybenzoic acid (MCPBA), for example, in an inert solvent such as dichloromethane.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS. Alternatively the skilled person can deliberately form a solvate using crystallisation conditions that include an amount of the solvent required for the particular solvate. Thereafter the standard methods described above, can be used to establish whether solvates had formed. Also encompassed by formula (I) are any complexes (e.g. inclusion complexes or clathrates with compounds such as cyclodextrins, or complexes with metals) of the compounds.

Furthermore, the compounds of the present invention may have one or more polymorph (crystalline) or amorphous forms and as such are intended to be included in the scope of the invention.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I). Other examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

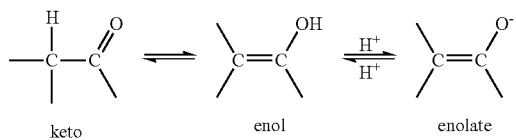
keto    enol    enolate

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) of two or more optical isomers, unless the context requires otherwise. The optical isomers may be characterised and identified by their optical activity (i.e. as + and isomers, or d and l isomers) or they may be characterised in terms of their absolute stereochemistry using the "R and S" nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog (1966) *Angew. Chem. Int. Ed. Engl.*, 5, 385-415. Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

The invention includes all isomeric forms of the compounds of the invention, either pure isomeric forms or as a mixture of two or more isomeric forms.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer). When a specific isomeric form is identified (e.g. S configuration, or E isomer), this means that said isomeric form is substantially free of the other isomer(s), i.e. said isomeric form is present in at least 55%, 60%, 65%, 70%, 75%, 80%, 85%, 90%, 95%, 99% or more (e.g. substantially all) of the total amount of the compound of the invention.

The compounds of the invention include compounds with one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters of the compounds of formula (I) bearing a carboxylic acid group or a hydroxyl group are also embraced by formula (I). In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group. Examples of esters are compounds containing the group —C(=O)OR, wherein R is an ester substituent, for example, a $C_{1-6}$ alkyl group, a heterocyclyl group, or a $C_{5-20}$ aryl group, preferably a $C_{1-6}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

For example, some prodrugs are esters of the active compound (e.g., a physiologically acceptable metabolically labile ester). By "prodrugs" is meant for example any compound that is converted in vivo into a biologically active compound of the formula (I). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is: $C_{1-6}$ alkyl (e.g., -Me, -Et, -nPr, -iPr, -nBu, -sBu, -iBu, -tBu); $C_{1-6}$ aminoalkyl [e.g., aminoethyl; 2-(N,N-diethylamino)ethyl; 2-(4-morpholino)ethyl); and acyloxy-$C_{1-7}$ alkyl [e.g., acyloxymethyl; acyloxyethyl; pivaloyloxymethyl; acetoxymethyl; 1-acetoxyethyl; 1-(1-methoxy-1-methyl)ethyl-carbonyloxy-ethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyl]. Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT) and ligand-directed enzyme pro-drug therapy (LIDEPT) etc.). For example, the prodrug may be a sugar derivative or other glycoside conjugate, or may be an amino acid ester derivative.

Protein Tyrosine Kinases (PTK)

The compounds of the invention described herein inhibit or modulate the activity of certain tyrosine kinases, and thus the compounds will be useful in the treatment or prophylaxis, in particular the treatment, of disease states or conditions mediated by those tyrosine kinases, in particular FGFR.

FGFR

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of FGFs, extracellular signalling molecules which act as autocrine as well as paracrine factors. Autocrine FGF signalling may be particularly important in the progression of steroid hormone-dependent cancers to a hormone independent state. FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signalling in human pancreatic cancer (Knights et al., Pharmacology and Therapeutics 2010 125:1 (105-117); Korc M. et al Current Cancer Drug Targets 2009 9:5 (639-651)).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors (FGFR) numbered 1 to 4 (FGFR1 to FGFR4).

Disruption of the FGFR1 pathway should affect tumor cell proliferation since this kinase is activated in many tumor types in addition to proliferating endothelial cells. The over-expression and activation of FGFR1 in tumor-associated vasculature has suggested a role for these molecules in tumor angiogenesis.

A recent study has shown a link between FGFR1 expression and tumorigenicity in Classic Lobular Carcinomas (CLC). CLCs account for 10-15% of all breast cancers and, in general, lack p53 and Her2 expression whilst retaining expression of the oestrogen receptor. A gene amplification of 8p12-p11.2 was demonstrated in ~50% of CLC cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway. Rhabdomyosarcoma (RMS) is the most common pediatric soft tissue sarcoma likely results from abnormal proliferation and differentiation during skeletal myogenesis. FGFR1 is over-expressed in primary rhabdomyosarcoma tumors and is associated with hypomethylation of a 5' CpG island and abnormal expression of the AKT1, NOG, and BMP4 genes. FGFR1 has also been linked to squamous lung cancer, colorectal cancer, glioblastoma, astrocytomas, prostate cancer, small cell lung cancer, melanoma, head and neck cancer, thyroid cancer, uterine cancer.

Fibroblast growth factor receptor 2 has high affinity for the acidic and/or basic fibroblast growth factors, as well as the keratinocyte growth factor ligands. Fibroblast growth factor receptor 2 also propagates the potent osteogenic effects of FGFs during osteoblast growth and differentiation. Mutations in fibroblast growth factor receptor 2, leading to complex functional alterations, were shown to induce abnormal ossification of cranial sutures (craniosynostosis), implying a major role of FGFR signalling in intramembranous bone formation. For example, in Apert (AP) syndrome, characterized by premature cranial suture ossification, most cases are associated with point mutations engendering gain-of-function in fibroblast growth factor receptor 2. In addition, mutation screening in patients with syndromic craniosynostoses indicates that a number of recurrent FGFR2 mutations accounts for severe forms of Pfeiffer syndrome. Particular mutations of FGFR2 include W290C, D321A, Y340C, C342R, C342S, C342W, N549H, K641R in FGFR2.

Several severe abnormalities in human skeletal development, including Apert, Crouzon, Jackson-Weiss, Beare-Stevenson cutis gyrata, and Pfeiffer syndromes are associated with the occurrence of mutations in fibroblast growth factor receptor 2. Most, if not all, cases of Pfeiffer Syndrome (PS) are also caused by de novo mutation of the fibroblast growth factor receptor 2 gene, and it was recently shown that mutations in fibroblast growth factor receptor 2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signalling and suggests that the severe phenotypes of these disease syndromes result from ectopic ligand-dependent activation of fibroblast growth factor receptor 2.

Genetic aberrations of the FGFR3 receptor tyrosine kinase such as chromosomal translocations or point mutations result in ectopically expressed or deregulated, constitutively active, FGFR3 receptors. Such abnormalities are linked to a subset of multiple myelomas and in bladder, hepatocellular, oral squamous cell carcinoma and cervical carcinomas. Accordingly, FGFR3 inhibitors would be useful in the treatment of multiple myeloma, bladder and cervical carcinomas. FGFR3 is also over-expressed in bladder cancer, in particular invasive bladder cancer. FGFR3 is frequently activated by mutation in urothelial carcinoma (UC). Increased expression was associated with mutation (85% of mutant tumors showed high-level expression) but also 42% of tumors with no detectable mutation showed over-expression, including many muscle-invasive tumors. FGFR3 is also linked to endometrial and thyroid cancer.

Over expression of FGFR4 has been linked to poor prognosis in both prostate and thyroid carcinomas. In addition a germline polymorphism (Gly388Arg) is associated with increased incidence of lung, breast, colon, liver (HCC) and prostate cancers. In addition, a truncated form of FGFR4 (including the kinase domain) has also been found to be present in 40% of pituitary tumours but not present in normal tissue. FGFR4 overexpression has been observed in liver, colon and lung tumours. FGFR4 has been implicated in colorectal and liver cancer where expression of its ligand FGF19 is frequently elevated. FGFR4 is also linked to astrocytomas, rhabdomyosarcoma.

Fibrotic conditions are a major medical problem resulting from abnormal or excessive deposition of fibrous tissue. This occurs in many diseases, including liver cirrhosis, glomerulonephritis, pulmonary fibrosis, systemic fibrosis, rheumatoid arthritis, as well as the natural process of wound healing. The mechanisms of pathological fibrosis are not fully understood but are thought to result from the actions of various cytokines (including tumor necrosis factor (TNF), fibroblast growth factors (FGF's), platelet derived growth factor (PDGF) and transforming growth factor beta. (TGFβ) involved in the proliferation of fibroblasts and the deposition of extracellular matrix proteins (including collagen and fibronectin). This results in alteration of tissue structure and function and subsequent pathology.

A number of preclinical studies have demonstrated the up-regulation of fibroblast growth factors in preclinical models of lung fibrosis. TGFβ1 and PDGF have been reported to be involved in the fibrogenic process and further published work suggests the elevation of FGF's and consequent increase in fibroblast proliferation, may be in response to elevated TGFβ1. The potential therapeutic benefit of targeting the fibrotic mechanism in conditions such as idiopathic pulmonary fibrosis (IPF) is suggested by the reported clinical effect of the anti-fibrotic agent pirfenidone. Idiopathic pulmonary fibrosis (also referred to as Cryptogenic fibrosing alveolitis) is a progressive condition involving scarring of the lung. Gradually, the air sacs of the lungs become replaced by fibrotic tissue, which becomes thicker, causing an irreversible loss of the tissue's ability to transfer oxygen into the bloodstream. The symptoms of the condition include shortness of breath, chronic dry coughing, fatigue, chest pain and loss of appetite resulting in rapid weight loss. The condition is extremely serious with approximately 50% mortality after 5 years.

As such, the compounds which inhibit FGFR will be useful in providing a means of preventing the growth or inducing apoptosis in tumours, particularly by inhibiting angiogenesis. It is therefore anticipated that the compounds will prove useful in treating or preventing proliferative disorders such as cancers. In particular tumours with activating mutants of receptor tyrosine kinases or upregulation of receptor tyrosine kinases may be particularly sensitive to the inhibitors. Patients with activating mutants of any of the isoforms of the specific RTKs discussed herein may also find treatment with RTK inhibitors particularly beneficial.

Vascular Endothelial Growth Factor (VEGFR)

Chronic proliferative diseases are often accompanied by profound angiogenesis, which can contribute to or maintain an inflammatory and/or proliferative state, or which leads to tissue destruction through the invasive proliferation of blood vessels.

Angiogenesis is generally used to describe the development of new or replacement blood vessels, or neovascularisation. It is a necessary and physiological normal process by which vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage. In diabetes (and in many different eye diseases), new vessels invade the macula or retina or other ocular structures, and may cause blindness. The process of atherosclerosis has been linked to angiogenesis. Tumor growth and metastasis have been found to be angiogenesis-dependent.

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis, ocular diseases, arthritis and hemangioma.

Vascular endothelial growth factor (VEGF), a polypeptide, is mitogenic for endothelial cells in vitro and stimulates angiogenic responses in vivo. VEGF has also been linked to inappropriate angiogenesis. VEGFR(s) are protein tyrosine kinases (PTKs). PTKs catalyze the phosphorylation of specific tyrosine residues in proteins involved in cell function thus regulating cell growth, survival and differentiation.

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction. Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis.

Inhibition at the kinase domain binding site of VEGFR-2 would block phosphorylation of tyrosine residues and serve to disrupt initiation of angiogenesis.

Angiogenesis is a physiologic process of new blood vessel formation mediated by various cytokines called angiogenic factors. Although its potential pathophysiologic role in solid tumors has been extensively studied for more than 3 decades, enhancement of angiogenesis in chronic lymphocytic leukemia (CLL) and other malignant hematological disorders has been recognized more recently. An increased level of angiogenesis has been documented by various experimental methods both in bone marrow and lymph nodes of patients with CLL. Although the role of angiogenesis in the pathophysiology of this disease remains to be fully elucidated, experimental data suggest that several angiogenic factors play a role in the disease progression. Biologic markers of angiogenesis were also shown to be of prognostic relevance in CLL. This indicates that VEGFR inhibitors may also be of benefit for patients with leukemia's such as CLL.

In order for a tumour mass to get beyond a critical size, it must develop an associated vasculature. It has been proposed that targeting a tumor vasculature would limit tumor expansion and could be a useful cancer therapy. Observations of tumor growth have indicated that small tumour masses can persist in a tissue without any tumour-specific vasculature. The growth arrest of nonvascularized tumors has been attributed to the effects of hypoxia at the center of the tumor. More recently, a variety of proangiogenic and antiangiogenic factors have been identified and have led to the concept of the "angiogenic switch," a process in which disruption of the normal ratio of angiogenic stimuli and inhibitors in a tumor mass allows for autonomous vascularization. The angiogenic switch appears to be governed by the same genetic alterations that drive malignant conversion: the activation of oncogenes and the loss of tumour suppressor genes. Several growth factors act as positive regulators of angiogenesis. Foremost among these are vascular endothelial growth factor (VEGF), basic fibroblast growth factor (bFGF), and angiogenin. Proteins such as thrombospondin (Tsp-1), angiostatin, and endostatin function as negative regulators of angiogenesis.

Inhibition of VEGFR2 but not VEGFR1 markedly disrupts angiogenic switching, persistent angiogenesis, and initial tumor growth in a mouse model. In late-stage tumors, phenotypic resistance to VEGFR2 blockade emerged, as tumors regrew during treatment after an initial period of growth suppression. This resistance to VEGF blockade involves reactivation of tumour angiogenesis, independent of VEGF and associated with hypoxia-mediated induction of other proangiogenic factors, including members of the FGF family. These other proangiogenic signals are functionally implicated in the revascularization and regrowth of tumours in the evasion phase, as FGF blockade impairs progression in the face of VEGF inhibition.

There is evidence for normalization of glioblastoma blood vessels in patients treated with a pan-VEGF receptor tyrosine kinase inhibitor, AZD2171, in a phase 2 study. MRI determination of vessel normalization in combination with circulating biomarkers provides for an effective means to assess response to antiangiogenic agents.

PDGFR

A malignant tumour is the product of uncontrolled cell proliferation. Cell growth is controlled by a delicate balance between growth-promoting and growth-inhibiting factors. In normal tissue the production and activity of these factors results in differentiated cells growing in a controlled and regulated manner that maintains the normal integrity and functioning of the organ. The malignant cell has evaded this control; the natural balance is disturbed (via a variety of mechanisms) and unregulated, aberrant cell growth occurs. A growth factor of importance in tumour development is the platelet-derived growth factor (PDGF) that comprises a family of peptide growth factors that signal through cell surface tyrosine kinase receptors (PDGFR) and stimulate various cellular functions including growth, proliferation, and differentiation.

Advantages of a Selective Inhibitor

Development of FGFR kinase inhibitors with a differentiated selectivity profile provides a new opportunity to use these targeted agents in patient sub-groups whose disease is driven by FGFR deregulation. Compounds that exhibit reduced inhibitory action on additional kinases, particularly VEGFR2 and PDGFR-beta, offer the opportunity to have a differentiated side-effect or toxicity profile and as such allow for a more effective treatment of these indications. Inhibitors of VEGFR2 and PDGFR-beta are associated with toxicities such as hypertension or oedema respectively. In the case of VEGFR2 inhibitors this hypertensive effect is often dose limiting, may be contraindicated in certain patient populations and requires clinical management.

Biological Activity and Therapeutic Uses

The compounds of the invention, and subgroups thereof, have fibroblast growth factor receptor (FGFR) inhibiting or modulating activity and/or vascular endothelial growth factor receptor (VEGFR) inhibiting or modulating activity, and/or platelet derived growth factor receptor (PDGFR) inhibiting or modulating activity, and which will be useful in preventing or treating disease states or conditions described herein. In addition the compounds of the invention, and subgroups thereof, will be useful in preventing or treating diseases or condition mediated by the kinases. References to the preventing or prophylaxis or treatment of a disease state or condition such as cancer include within their scope alleviating or reducing the incidence of cancer.

As used herein, the term "modulation", as applied to the activity of a kinase, is intended to define a change in the level of biological activity of the protein kinase. Thus, modulation encompasses physiological changes which effect an increase or decrease in the relevant protein kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity. Thus, modulation may imply elevated/suppressed expression or over- or under-expression of a kinase, including gene amplification (i.e. multiple gene copies) and/or increased or decreased expression by a transcriptional effect, as well as hyper- (or hypo-)activity and (de)activation of the protein kinase(s) (including (de)activation) by mutation(s). The terms "modulated", "modulating" and "modulate" are to be interpreted accordingly.

As used herein, the term "mediated", as used e.g. in conjunction with a kinase as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease, state or condition, the biological role played by a kinase may be direct or indirect and may be necessary and/or sufficient for the manifestation of the symptoms of the disease, state or condition (or its aetiology or progression). Thus, kinase activity (and in particular aberrant levels of kinase activity, e.g. kinase over-expression) need not necessarily be the proximal cause of the disease, state or condition: rather, it is contemplated that the kinase mediated diseases, states or conditions include those having multifactorial aetiologies and complex progressions in which the kinase in question is only partially involved. In cases where the term is applied to treatment, prophylaxis or intervention, the role played by the kinase may be direct or indirect and may be necessary and/or sufficient for the operation of the treatment, prophylaxis or outcome of the intervention. Thus, a disease state or condition mediated by a kinase includes the development of resistance to any particular cancer drug or treatment.

Thus, for example, the compounds of the invention may be useful in alleviating or reducing the incidence of cancer.

More particularly, the compounds of the formulae (I) and sub-groups thereof are inhibitors of FGFRs. For example, compounds of the invention have activity against FGFR1, FGFR2, FGFR3, and/or FGFR4, and in particular FGFRs selected from FGFR1, FGFR2 and FGFR3; or in particular the compounds of formula (I) and sub-groups thereof are inhibitors of FGFR4.

Preferred compounds are compounds that inhibit one or more FGFR selected from FGFR1, FGFR2, FGFR3, and FGFR4. Preferred compounds of the invention are those having $IC_{50}$ values of less than 0.1 µM.

Compounds of the invention also have activity against VEGFR.

In addition many of the compounds of the invention exhibit selectivity for the FGFR 1, 2, and/or 3, and/or 4 compared to VEGFR (in particular VEGFR2) and/or PDGFR and such compounds represent one preferred embodiment of the invention. In particular, the compounds exhibit selectivity over VEGFR2. For example, many compounds of the invention have $IC_{50}$ values against FGFR1, 2 and/or 3 and/or 4 that are between a tenth and a hundredth of the $IC_{50}$ against VEGFR (in particular VEGFR2) and/or PDGFR B. In particular preferred compounds of the invention have at least 10 times greater activity against or inhibition of FGFR in particular FGFR1, FGFR2, FGFR3 and/or FGFR4 than VEGFR2. More preferably the compounds of the invention have at least 100 times greater activity against or inhibition of FGFR in particular FGFR1, FGFR2, FGFR3 and/or FGFR4 than VEGFR2. This can be determined using the methods described herein.

As a consequence of their activity in modulating or inhibiting FGFR, and/or VEGFR kinases, the compounds will be useful in providing a means of preventing the growth or inducing apoptosis of neoplasias, particularly by inhibiting angiogenesis. It is therefore anticipated that the compounds will prove useful in treating or preventing proliferative disorders such as cancers. In addition, the compounds of the invention could be useful in the treatment of diseases in which there is a disorder of proliferation, apoptosis or differentiation.

In particular tumours with activating mutants of VEGFR or upregulation of VEGFR and patients with elevated levels of serum lactate dehydrogenase may be particularly sensitive to the compounds of the invention. Patients with activating mutants of any of the isoforms of the specific RTKs discussed herein may also find treatment with the compounds of the invention particularly beneficial. For example, VEGFR overexpression in acute leukemia cells where the clonal progenitor may express VEGFR. Also, particular tumours with activating mutants or upregulation or overexpression of any of the isoforms of FGFR such as FGFR1, FGFR2 or FGFR3 or FGFR4 may be particularly sensitive to the compounds of the invention and thus patients as discussed herein with such particular tumours may also find treatment with the compounds of the invention particularly beneficial. It may be preferred that the treatment is related to or directed at a mutated form of one of the receptor tyrosine kinases, such as discussed herein. Diagnosis of tumours with such mutations could be performed using techniques known to a person skilled in the art and as described herein such as RTPCR and FISH.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example adenocarcinoma, small cell lung cancer and non-small cell lung carcinomas, squamous lung cancer), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma), T-cell lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; hepatocellular cancer, a tumour of mesenchymal origin (e.g. Ewing's sarcoma), for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma; teratocarcinoma; osteosarcoma; xeroderma pigmentosum; keratoctanthoma; thyroid follicular cancer; or Kaposi's sarcoma. In particular, squamous lung cancer, breast cancer, colorectal cancer, glioblastoma, astrocytomas, prostate cancer, small cell lung cancer, melanoma, head and neck cancer, thyroid cancer, uterine cancer, gastric cancer, hepatocellular cancer, cervix cancer, multiple myeloma, bladder cancer, endometrial cancer, urothelial cancer, colon cancer, rhabdomyosarcoma, pituitary gland cancer.

Certain cancers are resistant to treatment with particular drugs. This can be due to the type of the tumour or can arise due to treatment with the compound. In this regard, references to multiple myeloma includes bortezomib sensitive multiple myeloma or refractory multiple myeloma. Similarly, references to chronic myelogenous leukemia includes imitanib sensitive chronic myelogenous leukemia and refractory chronic myelogenous leukemia. Chronic myelogenous leukemia is also known as chronic myeloid leukemia, chronic granulocytic leukemia or CML. Likewise, acute myelogenous leukemia, is also called acute myeloblastic leukemia, acute granulocytic leukemia, acute nonlymphocytic leukaemia or AML.

The compounds of the invention can also be used in the treatment of hematopoetic diseases of abnormal cell proliferation whether pre-malignant or stable such as myeloproliferative diseases. Myeloproliferative diseases ("MPD"s) are a group of diseases of the bone marrow in which excess cells are produced. They are related to, and may evolve into, myelodysplastic syndrome. Myeloproliferative diseases include polycythemia vera, essential thrombocythemia and primary myelofibrosis. A further haematological disorder is hypereosinophilic syndrome. T-cell lymphoproliferative diseases include those derived from natural Killer cells.

In addition the compounds of the invention can be used to gastrointestinal (also known as gastric) cancer e.g. gastrointestinal stromal tumours. Gastrointestinal cancer refers to malignant conditions of the gastrointestinal tract, including the esophagus, stomach, liver, biliary system, pancreas, bowels, and anus.

Thus, in the pharmaceutical compositions, uses or methods of this invention for treating a disease or condition comprising abnormal cell growth, the disease or condition comprising abnormal cell growth in one embodiment is a cancer.

Particular subsets of cancers include multiple myeloma, bladder, cervical, prostate and thyroid carcinomas, lung, breast, and colon cancers.

A further subset of cancers includes multiple myeloma, bladder, hepatocellular, oral squamous cell carcinoma and cervical carcinomas.

The compound of the invention, having FGFR such as FGFR1 inhibitory activity, may be particularly useful in the treatment or prevention of breast cancer in particular Classic Lobular Carcinomas (CLC).

As the compounds of the invention have FGFR4 activity they will also be useful in the treatment of prostate or pituitary cancers, or they will be useful in the treatment of breast cancer, lung cancer, prostate cancer, liver cancer (HCC) or lung cancer.

In particular the compounds of the invention as FGFR inhibitors, are useful in the treatment of multiple myeloma, myeloproliferatoive disorders, endometrial cancer, prostate cancer, bladder cancer, lung cancer, ovarian cancer, breast cancer, gastric cancer, colorectal cancer, and oral squamous cell carcinoma.

Further subsets of cancer are multiple myeloma, endometrial cancer, bladder cancer, cervical cancer, prostate cancer, lung cancer, breast cancer, colorectal cancer and thyroid carcinomas.

In particular the compounds of the invention are useful in the treatment of multiple myeloma (in particular multiple myeloma with t(4; 14) translocation or overexpressing FGFR3), prostate cancer (hormone refractory prostrate carcinomas), endometrial cancer (in particular endometrial tumours with activating mutations in FGFR2) and breast cancer (in particular lobular breast cancer).

In particular the compounds are useful in the treatment of lobular carcinomas such as CLC (Classic lobular carcinoma).

As the compounds have activity against FGFR3 they will be useful in the treatment of multiple myeloma and bladder cancer.

In particular the compounds are useful for the treatment of t(4; 14) translocation positive multiple myeloma.

In one embodiment the compounds may be useful for the treatment of sarcoma. In one embodiment the compounds may be useful for the treatment of lung cancer, e.g. squamous cell carcinoma.

As the compounds have activity against FGFR2 they will be useful in the treatment of endometrial, ovarian, gastric, hepatocellular, uterine, cervix and colorectal cancers. FGFR2 is also overexpressed in epithelial ovarian cancer, therefore the compounds of the invention may be specifically useful in treating ovarian cancer such as epithelial ovarian cancer.

In one embodiment, the compounds may be useful for the treatment of lung cancer, in particular NSCLC, squamous cell carcinoma, liver cancer, kidney cancer, breast cancer, colon cancer, colorectal cancer, prostate cancer.

In one embodiment, the compounds may be useful for the treatment of prostate cancer, bladder cancer, lung cancer such as NSCLC, breast cancer, gastric cancer, and liver cancer (HCC (hepatocellular cancer)).

Compounds of the invention may also be useful in the treatment of tumours pre-treated with VEGFR2 inhibitor or VEGFR2 antibody (e.g. Avastin).

In particular the compounds of the invention may be useful in the treatment of VEGFR2-resistant tumours. VEGFR2 inhibitors and antibodies are used in the treatment of thyroid and renal cell carcinomas, therefore the compounds of the invention may be useful in the treatment of VEGFR2-resistant thyroid and renal cell carcinomas.

The cancers may be cancers which are sensitive to inhibition of any one or more FGFRs selected from FGFR1, FGFR2, FGFR3, FGFR4, for example, one or more FGFRs selected from FGFR1, FGFR2 or FGFR3.

Whether or not a particular cancer is one which is sensitive to inhibition of FGFR or VEGFR signalling may be determined by means of a cell growth assay as set out below or by a method as set out in the section headed "Methods of Diagnosis".

The compounds of the invention, and in particular those compounds having FGFR, or VEGFR inhibitory activity, may be particularly useful in the treatment or prevention of cancers of a type associated with or characterised by the presence of elevated levels of FGFR, or VEGFR, for example the cancers referred to in this context in the introductory section of this application.

The compounds of the present invention may be useful for the treatment of the adult population. The compounds of the present invention may be useful for the treatment of the pediatric population.

It has been discovered that some FGFR inhibitors can be used in combination with other anticancer agents. For example, it may be beneficial to combine an inhibitor that induces apoptosis with another agent which acts via a different mechanism to regulate cell growth thus treating two of the characteristic features of cancer development. Examples of such combinations are set out below.

The compounds of the invention may be useful in treating other conditions which result from disorders in proliferation such as type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

One sub-group of disease states and conditions that the compounds of the invention may be useful consists of inflammatory diseases, cardiovascular diseases and wound healing.

FGFR, and VEGFR are also known to play a role in apoptosis, angiogenesis, proliferation, differentiation and transcription and therefore the compounds of the invention could also be useful in the treatment of the following diseases other than cancer; chronic inflammatory diseases, for example systemic lupus erythematosus, autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

In addition, mutations of FGFR2 are associated with several severe abnormalities in human skeletal development and thus the compounds of invention could be useful in the treatment of abnormalities in human skeletal development, including abnormal ossification of cranial sutures (craniosynostosis), Apert (AP) syndrome, Crouzon syndrome, Jackson-Weiss syndrome, Beare-Stevenson cutis gyrate syndrome, and Pfeiffer syndrome.

The compound of the invention, having FGFR such as FGFR2 or FGFR3 inhibitory activity, may be particularly useful in the treatment or prevention of the skeletal diseases. Particular skeletal diseases are achondroplasia or thanatophoric dwarfism (also known as thanatophoric dysplasia).

The compound of the invention, having FGFR such as FGFR1, FGFR2 or FGFR3 inhibitory activity, may be particularly useful in the treatment or prevention in pathologies in which progressive fibrosis is a symptom. Fibrotic conditions in which the compounds of the inventions may be useful in the treatment of include diseases exhibiting abnormal or excessive deposition of fibrous tissue for example in liver cirrhosis, glomerulonephritis, pulmonary fibrosis, systemic fibrosis, rheumatoid arthritis, as well as the natural process of wound healing. In particular the compounds of the inventions may also be useful in the treatment of lung fibrosis in particular in idiopathic pulmonary fibrosis.

The over-expression and activation of FGFR and VEGFR in tumor-associated vasculature has also suggested a role for compounds of the invention in preventing and disrupting initiation of tumor angiogenesis. In particular the compounds of the invention may be useful in the treatment of cancer, metastasis, leukemia's such as CLL, ocular diseases such as age-related macular degeneration in particular wet form of age-related macular degeneration, ischemic proliferative retinopathies such as retinopathy of prematurity (ROP) and diabetic retinopathy, rheumatoid arthritis and hemangioma.

The activity of the compounds of the invention as inhibitors of FGFR1-4, VEGFR and/or PDGFR A/B can be measured using the assays set forth in the examples below and the level of activity exhibited by a given compound can be defined in terms of the $IC_{50}$ value.

Preferred compounds of the present invention are compounds having an $IC_{50}$ value of less than 1 µM, more preferably less than 0.1 µM.

The invention provides compounds that have FGFR inhibiting or modulating activity, and which may be useful in preventing or treating disease states or conditions mediated by FGFR kinases.

In one embodiment, there is provided a compound as defined herein for use in therapy, for use as a medicine. In a further embodiment, there is provided a compound as defined herein for use in the prophylaxis or treatment, in particular in the treatment, of a disease state or condition mediated by a FGFR kinase.

Thus, for example, the compounds of the invention may be useful in alleviating or reducing the incidence of cancer. Therefore, in a further embodiment, there is provided a compound as defined herein for use in the prophylaxis or treatment, in particular the treatment, of cancer. In one embodiment, the compound as defined herein is for use in the prophylaxis or treatment of FGFR-dependent cancer. In one embodiment, the compound as defined herein is for use in the prophylaxis or treatment of cancer mediated by FGFR kinases.

Accordingly, the invention provides inter alia:

A method for the prophylaxis or treatment of a disease state or condition mediated by a FGFR kinase, which method comprises administering to a subject in need thereof a compound of the formula (I) as defined herein.

A method for the prophylaxis or treatment of a disease state or condition as described herein, which method comprises administering to a subject in need thereof a compound of the formula (I) as defined herein.

A method for the prophylaxis or treatment of cancer, which method comprises administering to a subject in need thereof a compound of the formula (I) as defined herein.

A method for alleviating or reducing the incidence of a disease state or condition mediated by a FGFR kinase, which method comprises administering to a subject in need thereof a compound of the formula (I) as defined herein.

A method of inhibiting a FGFR kinase, which method comprises contacting the kinase with a kinase-inhibiting compound of the formula (I) as defined herein.

A method of modulating a cellular process (for example cell division) by inhibiting the activity of a FGFR kinase using a compound of the formula (I) as defined herein.

A compound of formula (I) as defined herein for use as a modulator of a cellular process (for example cell division) by inhibiting the activity of a FGFR kinase.

A compound of formula (I) as defined herein for use in the prophylaxis or treatment of cancer, in particular the treatment of cancer.

A compound of formula (I) as defined herein for use as a modulator (e.g. inhibitor) of FGFR.

The use of a compound of formula (I) as defined herein for the manufacture of a medicament for the prophylaxis or treatment of a disease state or condition mediated by a FGFR kinase, the compound having the formula (I) as defined herein.

The use of a compound of formula (I) as defined herein for the manufacture of a medicament for the prophylaxis or treatment of a disease state or condition as described herein.

The use of a compound of formula (I) as defined herein for the manufacture of a medicament for the prophylaxis or treatment, in particular the treatment, of cancer.

The use of a compound of formula (I) as defined herein for the manufacture of a medicament for modulating (e.g. inhibiting) the activity of FGFR.

Use of a compound of formula (I) as defined herein in the manufacture of a medicament for modulating a cellular process (for example cell division) by inhibiting the activity of a FGFR kinase.

The use of a compound of the formula (I) as defined herein for the manufacture of a medicament for prophylaxis or treatment of a disease or condition characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of a cancer, the cancer being one which is characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of cancer in a patient selected from a sub-population possessing a genetic aberrations of FGFR3 kinase.

The use of a compound of the formula (I) as defined herein for the manufacture of a medicament for the prophylaxis or treatment of cancer in a patient who has been diagnosed as forming part of a sub-population possessing a genetic aberrations of FGFR3 kinase.

A method for the prophylaxis or treatment of a disease or condition characterised by up-regulation of a FGFR kinase (e.g. FGFR1 or FGFR2 or FGFR3 or FGFR4), the method comprising administering a compound of the formula (I) as defined herein.

A method for alleviating or reducing the incidence of a disease or condition characterised by up-regulation of a FGFR kinase (e.g. FGFR1 or FGFR2 or FGFR3 or FGFR4), the method comprising administering a compound of the formula (I) as defined herein.

A method for the prophylaxis or treatment of (or alleviating or reducing the incidence of) cancer in a patient suffering from or suspected of suffering from cancer; which method comprises (i) subjecting a patient to a diagnostic test to determine whether the patient possesses a genetic aberrations of FGFR3 gene; and (ii) where the patient does possess the said variant, thereafter administering to the patient a compound of the formula (I) as defined herein having FGFR3 kinase inhibiting activity.

A method for the prophylaxis or treatment of (or alleviating or reducing the incidence of) a disease state or condition characterised by up-regulation of an FGFR kinase (e.g. FGFR1 or FGFR2 or FGFR3 or FGFR4); which method comprises (i) subjecting a patient to a diagnostic test to detect a marker characteristic of up-regulation of a FGFR kinase (e.g. FGFR1 or FGFR2 or FGFR3 or FGFR4) and (ii) where the diagnostic test is indicative of up-regulation of a FGFR kinase, thereafter administering to the patient a compound of the formula (I) as defined herein having FGFR kinase inhibiting activity.

In one embodiment, the disease mediated by FGFR kinases is a oncology related disease (e.g. cancer). In one embodiment, the disease mediated by FGFR kinases is a non-oncology related disease (e.g. any disease disclosed herein excluding cancer). In one embodiment the disease mediated by FGFR kinases is a condition described herein. In one embodiment the disease mediated by FGFR kinases is a skeletal condition described herein. Particular abnormalities in human skeletal development, include abnormal ossification of cranial sutures (craniosynostosis), Apert (AP) syndrome, Crouzon syndrome, Jackson-Weiss syndrome, Beare-Stevenson cutis gyrate syndrome, Pfeiffer syndrome, achondroplasia and thanatophoric dwarfism (also known as thanatophoric dysplasia).

Mutated Kinases

Drug resistant kinase mutations can arise in patient populations treated with kinase inhibitors. These occur, in part, in the regions of the protein that bind to or interact with the particular inhibitor used in therapy. Such mutations reduce or increase the capacity of the inhibitor to bind to and inhibit the kinase in question. This can occur at any of the amino acid residues which interact with the inhibitor or are important for supporting the binding of said inhibitor to the target. An inhibitor that binds to a target kinase without requiring the interaction with the mutated amino acid residue will likely be unaffected by the mutation and will remain an effective inhibitor of the enzyme.

A study in gastric cancer patient samples showed the presence of two mutations in FGFR2, Ser167Pro in exon IIIa and a splice site mutation 940-2A-G in exon IIIc. These mutations are identical to the germline activating mutations that cause craniosynotosis syndromes and were observed in 13% of primary gastric cancer tissues studied. In addition activating mutations in FGFR3 were observed in 5% of the patient samples tested and overexpression of FGFRs has been correlated with a poor prognosis in this patient group.

In addition there are chromosomal translocations or point mutations that have been observed in FGFR which give rise to gain-of-function, over-expressed, or constitutively active biological states.

The compounds of the invention would therefore find particular application in relation to cancers which express a mutated molecular target such as FGFR. Diagnosis of tumours with such mutations could be performed using techniques known to a person skilled in the art and as described herein such as RTPCR and FISH.

It has been suggested that mutations of a conserved threonine residue at the ATP binding site of FGFR would result in inhibitor resistance. The amino acid valine 561 has been mutated to a methionine in FGFR1 which corresponds to previously reported mutations found in Abl (T315) and EGFR (T766) that have been shown to confer resistance to selective inhibitors. Assay data for FGFR1 V561M showed that this mutation conferred resistance to a tyrosine kinase inhibitor compared to that of the wild type.

Methods of Diagnosis

Prior to administration of a compound of the formula (I), a patient may be screened to determine whether a disease or condition from which the patient is or may be suffering is one which would be susceptible to treatment with a compound having activity against FGFR, and/or VEGFR.

For example, a biological sample taken from a patient may be analysed to determine whether a condition or disease, such as cancer, that the patient is or may be suffering from is one which is characterised by a genetic abnormality or abnormal protein expression which leads to up-regulation of the levels or activity of FGFR, and/or VEGFR or to sensitisation of a pathway to normal FGFR, and/or VEGFR activity, or to upregulation of these growth factor signalling pathways such as growth factor ligand levels or growth factor ligand activity or to upregulation of a biochemical pathway downstream of FGFR, and/or VEGFR activation.

Examples of such abnormalities that result in activation or sensitisation of the FGFR, and/or VEGFR signal include loss of, or inhibition of apoptotic pathways, up-regulation of the receptors or ligands, or presence of mutant variants of the receptors or ligands e.g PTK variants. Tumours with mutants of FGFR1, FGFR2 or FGFR3 or FGFR4 or up-regulation, in particular over-expression of FGFR1, or gain-of-function mutants of FGFR2 or FGFR3 may be particularly sensitive to FGFR inhibitors.

For example, point mutations engendering gain-of-function in FGFR2 have been identified in a number of conditions. In particular activating mutations in FGFR2 have been identified in 10% of endometrial tumours.

In addition, genetic aberrations of the FGFR3 receptor tyrosine kinase such as chromosomal translocations or point mutations resulting in ectopically expressed or deregulated, constitutively active, FGFR3 receptors have been identified and are linked to a subset of multiple myelomas, bladder and cervical carcinomas. A particular mutation T6741 of the PDGF receptor has been identified in imatinib-treated patients. In addition, a gene amplification of 8p12-p11.2 was demonstrated in ~50% of lobular breast cancer (CLC) cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway.

Alternatively, a biological sample taken from a patient may be analysed for loss of a negative regulator or suppressor of FGFR or VEGFR. In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of FGFR, and/or VEGFR. The term diagnosis includes screening. By marker we include genetic markers including, for example, the measurement of DNA composition to identify mutations of FGFR, and/or VEGFR. The term marker also includes markers which are characteristic of up regulation of FGFR and/or VEGFR, including enzyme activity, enzyme levels, enzyme state (e.g. phosphorylated or not) and mRNA levels of the aforementioned proteins.

The diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, buccal spears, biopsy or urine.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH).

Identification of an individual carrying a mutation in FGFR, and/or VEGFR may mean that the patient would be particularly suitable for treatment with a FGFR, and/or VEGFR inhibitor. Tumours may preferentially be screened for presence of a FGFR, and/or VEGFR variant prior to treatment. The screening process will typically involve direct sequencing, oligonucleotide microarray analysis, or a mutant specific antibody. In addition, diagnosis of tumours with such mutations could be performed using techniques known to a person skilled in the art and as described herein such as RT-PCR and FISH.

In addition, mutant forms of, for example FGFR or VEGFR2, can be identified by direct sequencing of, for example, tumour biopsies using PCR and methods to sequence PCR products directly as hereinbefore described. The skilled artisan will recognize that all such well-known techniques for detection of the over expression, activation or mutations of the aforementioned proteins could be applicable in the present case.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radio-isotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer*, 3:3). Briefly, the protocol is as follows: double-stranded cDNA is synthesized from total RNA Using a $(dT)_{24}$ oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of FGFR, and/or VEGFR, or detection of FGFR, and/or VEGFR variants or mutants could be applicable in the present case.

Abnormal levels of proteins such as FGFR or VEGFR can be measured using standard enzyme assays, for example, those assays described herein. Activation or overexpression could also be detected in a tissue sample, for example, a tumour tissue. By measuring the tyrosine kinase activity with an assay such as that from Chemicon International. The tyrosine kinase of interest would be immunoprecipitated from the sample lysate and its activity measured.

Alternative methods for the measurement of the over expression or activation of FGFR or VEGFR including the isoforms thereof, include the measurement of microvessel density. This can for example be measured using methods described by Orre and Rogers (Int J Cancer (1999), 84(2) 101-8). Assay methods also include the use of markers, for example, in the case of VEGFR these include CD31, CD34 and CD105.

Therefore all of these techniques could also be used to identify tumours particularly suitable for treatment with the compounds of the invention.

The compounds of the invention are particular useful in treatment of a patient having a mutated FGFR. The G697C mutation in FGFR3 is observed in 62% of oral squamous cell carcinomas and causes constitutive activation of the kinase activity. Activating mutations of FGFR3 have also been identified in bladder carcinoma cases. These mutations were of 6 kinds with varying degrees of prevelence: R248C, S249C, G372C, S373C, Y375C, K652Q. In addition, a Gly388Arg polymorphism in FGFR4 has been found to be associated with increased incidence and aggressiveness of prostate, colon, lung, liver (HCC) and breast cancer.

Therefore in a further aspect the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with a compound having activity against FGFR.

Particular mutations a patient is screened for include G697C, R248C, S249C, G372C, S373C, Y375C, K652Q mutations in FGFR3 and Gly388Arg polymorphism in FGFR4.

In another aspect the invention includes a compound of the invention for use in the prophylaxis or treatment of cancer in a patient selected from a sub-population possessing a variant of the FGFR gene (for example G697C mutation in FGFR3 and Gly388Arg polymorphism in FGFR4).

MRI determination of vessel normalization (e.g. using MRI gradient echo, spin echo, and contrast enhancement to measure blood volume, relative vessel size, and vascular permeability) in combination with circulating biomarkers (circulating progenitor cells (CPCs), CECs, SDF1, and FGF2) may also be used to identify VEGFR2-resistant tumours for treatment with a compound of the invention.

Pharmaceutical Compositions and Combinations

In view of their useful pharmacological properties, the subject compounds may be formulated into various pharmaceutical forms for administration purposes.

In one embodiment the pharmaceutical composition (e.g. formulation) comprises at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

To prepare the pharmaceutical compositions of this invention, an effective amount of a compound of the present invention, as the active ingredient is combined in intimate admixture with a pharmaceutically acceptable carrier, which carrier may take a wide variety of forms depending on the form of preparation desired for administration. The pharmaceutical compositions can be in any form suitable for oral, parenteral, topical, intranasal, ophthalmic, otic, rectal, intravaginal, or transdermal administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compound of the invention is administered in an amount sufficient to exert its anti-tumour activity.

Those skilled in the art could easily determine the effective amount from the test results presented hereinafter. In general it is contemplated that a therapeutically effective amount would be from 0.005 mg/kg to 100 mg/kg body weight, and in particular from 0.005 mg/kg to 10 mg/kg body weight. It may be appropriate to administer the required dose as single, two, three, four or more sub-doses at appropriate intervals throughout the day. Said sub-doses may be formulated as unit dosage forms, for example, containing 0.5 to 500 mg, in particular 1 mg to 500 mg, more in particular 10 mg to 500 mg of active ingredient per unit dosage form.

Depending on the mode of administration, the pharmaceutical composition will preferably comprise from 0.05 to 99% by weight, more preferably from 0.1 to 70% by weight, even more preferably from 0.1 to 50% by weight of the compound of the present invention, and, from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anti-cancer agent is envisaged, especially for use as a medicine, more specifically for use in the treatment of cancer or related diseases.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

platinum coordination compounds for example cisplatin optionally combined with amifostine, carboplatin or oxaliplatin;

taxane compounds for example paclitaxel, paclitaxel protein bound particles (Abraxane™) or docetaxel;

topoisomerase I inhibitors such as camptothecin compounds for example irinotecan, SN-38, topotecan, topotecan hcl;

topoisomerase II inhibitors such as anti-tumour epipodophyllotoxins or podophyllotoxin derivatives for example etoposide, etoposide phosphate or teniposide;

anti-tumour vinca alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, telozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetrocarcin A;

glucocorticolden for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, ONTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrazole, testolactone and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example premetrexed disodium;

antibiotics for example antinomycin D, bleomycin, mitomycin C, dactinomycin, carminomycin, daunomycin, levamisole, plicamycin, mithramycin;

antimetabolites for example clofarabine, aminopterin, cytosine arabinoside or methotrexate, azacitidine, cytarabine, floxuridine, pentostatin, thioguanine;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;

farnesyltransferase inhibitors for example tipifarnib;

histone deacetylase (HDAC) inhibitors for example sodium butyrate, suberoylanilide hydroxamide acid (SAHA), depsipeptide (FR 901228), NVP-LAQ824, R306465, JNJ-26481585, trichostatin A, vorinostat;

Inhibitors of the ubiquitin-proteasome pathway for example PS-341, MLN 0.41 or bortezomib;

Yondelis;

Telomerase inhibitors for example telomestatin;

Matrix metalloproteinase inhibitors for example batimastat, marimastat, prinostat or metastat.

Recombinant interleukins for example aldesleukin, denileukin diftitox, interferon alfa 2a, interferon alfa 2b, peginterferon alfa 2b MAPK inhibitors Retinoids for example alitretinoin, bexarotene, tretinoin Arsenic trioxide Asparaginase Steroids for example dromostanolone propionate, megestrol acetate, nandrolone (decanoate, phenpropionate), dexamethasone Gonadotropin releasing hormone agonists or antagonists for example abarelix, goserelin acetate, histrelin acetate, leuprolide acetate Thalidomide, lenalidomide Mercaptopurine, mitotane, pamidronate, pegademase, pegaspargase, rasburicase BH3 mimetics for example ABT-737

MEK inhibitors for example PD98059, AZD6244, CI-1040 colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin.

a steroidal cytochrome P450 17alpha-hydroxylase-17,20-lyase inhibitor (CYP17), e.g. abiraterone, abiraterone acetate.

The compounds of the present invention also have therapeutic applications in sensitising tumour cells for radiotherapy and chemotherapy.

Hence the compounds of the present invention can be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogoues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

In view of their useful pharmacological properties, the components of the combinations according to the invention, i.e. the one or more other medicinal agent and the compound according to the present invention may be formulated into various pharmaceutical forms for administration purposes. The components may be formulated separately in individual pharmaceutical compositions or in a unitary pharmaceutical composition containing all components.

The present invention therefore also relates to a pharmaceutical composition comprising the one or more other medicinal agent and the compound according to the present invention together with a pharmaceutical carrier.

The present invention further relates to the use of a combination according to the invention in the manufacture of a pharmaceutical composition for inhibiting the growth of tumour cells.

The present invention further relates to a product containing as first active ingredient a compound according to the invention and as further active ingredient one or more anticancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg, for carmustine in a dosage of about 150 to 200 mg/m$^2$, and for lomustine in a dosage of about 100 to 150 mg/m$^2$ per course of treatment.

The anti-tumour anthracycline derivative is advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m$^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m$^2$) of body surface area, or as known in the art, if different. Trastuzumab is advantageously administered in a dosage of 1 to 5 mg per square meter (mg/m$^2$) of body surface area, particularly 2 to 4 mg/m$^2$ per course of treatment. These dosages may be administered for example once, twice or more per course of treatment, which may be repeated for example every 7, 14, 21 or 28 days.

The compounds of formula (I), the pharmaceutically acceptable addition salts, in particular pharmaceutically acceptable acid addition salts, and stereoisomeric forms thereof can have valuable diagnostic properties in that they can be used for detecting or identifying the formation of a complex between a labelled compound and other molecules, peptides, proteins, enzymes or receptors.

The detecting or identifying methods can use compounds that are labelled with labelling agents such as radioisotopes, enzymes, fluorescent substances, luminous substances, etc. Examples of the radioisotopes include $^{125}$I, $^{131}$I, $^3$H and $^{14}$O. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase.

Biological samples can be defined as body tissue or body fluids. Examples of body fluids are cerebrospinal fluid, blood, plasma, serum, urine, sputum, saliva and the like.

General Synthetic Routes

The following examples illustrate the present invention but are examples only and are not intended to limit the scope of the claims in any way.

Experimental Part

Hereinafter, the term 'rm.' means reaction mixture(s), 'min' means minute(s), 'h' means hours, 'rt.' means room temperature, 'aq.' means aqueous, 'ACN' means acetonitrile, 'DCM' means dichloromethane, 'TBAF' means tetrabutylammonium fluoride, 'K$_2$CO$_3$' means potassium carbonate, 'MgSO$_4$' means magnesium sulphate, 'CuI' means copper (I) iodide, 'MeOH' means methanol, 'EtOH' means ethanol, 'EtOAc' means ethyl acetate, 'Et$_3$N' means triethylamine, 'Et$_2$O' means diethyl ether, 'DIPE' means diisopropyl ether, 'THF' means tetrahydrofuran, 'NH$_4$Cl' means ammonium chloride, 'Pd(PPh$_3$)$_4$' means tetrakis(triphenylphosphine)palladium, 'NMP' means 1-methyl-2-pyrrolidinone, DIPEA' means N-ethyl-N-(1-methylethyl)-2-propylamine, DMA' means N,N-dimethylacetamide, DMF' means N,N-dimethylformamide, 'NaH' means sodium hydride, 'Pd$_2$(dba)$_3$' means tris(dibenzylideneacetone)dipalladium (0), 'HOAc' means acetic acid, 'PPh$_3$' means triphenylphosphine, 'NH$_4$OH' means ammonium hydroxide, 'TBDMSCl' means tert-butyldimethylsilyl chloride, 'S-Phos' means dicyclohexyl(2',6'-dimethoxy[1,1'-biphenyl]-2-yl)phosphine, 'Na$_2$SO$_4$' means sodium sulfate, 'iPrOH' means 2-propanol, 't-BuOH' means 2-methyl-2-propanol, 'K$_3$PO$_4$' means potassium phosphate, 'MP' means melting point, 'PdCl$_2$(PPh$_3$)$_2$' means dichlorobis(triphenylphosphine)palladium, '18-crown-6' means 1,4,7,10,13,16-Hexaoxacyclooctadecane, 'DMSO' means dimethylsulfoxyde, 'Na$_2$CO$_3$' means sodium carbonate, 'NaHCO$_3$' means sodium bicarbonate, 'Cs$_2$CO$_3$' means cesium carbonate, 'DMAP' means 4-dimethylaminopyridine, 'NaOtBu' means sodium tert-butoxide, 'HCl' means hydrochloric acid, 'TFA' means trifluoroacetic acid, 'H$_2$SO$_4$' means sulfuric acid, 'EDCl' means 1-ethyl-3-(3-dimethylaminopropyl)carbodiimide monohydrochloride, 'CO$_2$' means carbon dioxide, 'CO' means carbon monoxide, 'DPPP' means 1,3-propanediylbis[diphenylphosphine], 'Pd(OAc)$_2$' means Palladium (II) acetate, 'PdCl$_2$dppf means dichloro[1,1'-bis (diphenylphosphino) ferrocene] palladium(II), '(±)-BINAP' means Rac-bis(diphenylphosphino)-1,1'-binaphthyl, 'SiOH' means bare silica, 'DSC' means differential scanning calorimetry.

Celite® is diatomaceous earth.

NaH was used as 60% in mineral oil.

For a number of compounds, melting points were obtained with a Kofler hot bench, consisting of a heated plate with linear temperature gradient, a sliding pointer and a temperature scale in degrees Celsius.

For a number of compounds, melting points (m.p.) were determined with a DSC1 (Mettler-Toledo). Melting points were measured with a temperature gradient of 10° C./minute. Maximum temperature was 350° C. Values are peak values.

Some compounds of the present invention were obtained as salt forms or hydrates or contain some amounts of solvent. Hereinafter, these compounds are reported as determined based on elemental analysis.

A. Preparation of the Intermediates

Example A1 a) Preparation of Intermediate 1

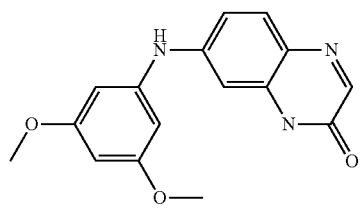 [SMILES: COc1cc(Nc2ccc3ncc(=O)[nH]c3c2)cc(OC)c1]

A mixture of 7-Bromo-2(1H)-quinoxalinone (25 g; 0.11 mol), 3,5-dimethoxyaniline (20.42 g; 0.13 mol), sodium tert-butoxide (32 g; 0.333 mol), and (±)-BINAP (6.9 g; 0.01 mol) in ethylene glycol dimethyl ether (400 mL) was degassed with N2 for 10 min. Pd(OAc)$_2$ (2.5 g; 0.01 mol) was added and the mixture was refluxed for 5 h. The r.m. was cooled to r.t. and the solvent was concentrated under vacuum to 150 mL. The residue was poured onto ice water (1.5 L) under stirring and EtOAc was added (100 mL). The suspension was stirred at r.t. overnight and the precipitate was filtered off, washed with water, then ACN and dried, yielding 33 g of intermediate 1.

b-1) Preparation of Intermediate 2

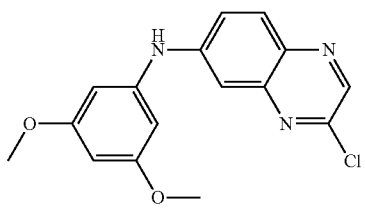 [SMILES: COc1cc(Nc2ccc3ncc(Cl)nc3c2)cc(OC)c1]

Intermediate 1 (30 g; 0.1 mol) was added portionwise at r.t. to phosphorus oxychloride (415 mL). Then, the r.m. was heated at 80° C. and stirred at this temperature for 40 min. The mixture was cooled to r.t. and phosphorous oxychloride was removed under vacuum. The residue was carefully poured onto an aq. solution of K$_2$CO$_3$. The aq. layer was extracted with DCM. The organic layer was dried (MgSO$_4$), filtered and evaporated to dryness. The residue was purified by chromatography over silica gel (Irregular SiOH, 15-40 µm, 450 g; mobile phase, gradient from 100% DCM to 98% DCM, 2% MeOH). The product fractions were collected and the solvent was evaporated, to give 22.6 g (70%) of intermediate 2 (m.p.=137° C., Kofler).

b-2) Intermediate 2 was Alternatively Also Prepared Using the Following Procedure N-Chlorosuccinimide (11.23 g; 84.08 mmol) was added portionwise at r.t. to a suspension of PPh$_3$ (22.05 g, 84.08 mmol) in dioxane (500 mL). The r.m. was stirred for 30 min. Intermediate 1 (5 g; 16.8 mmol) was added and the r.m. was refluxed for 5 h, then cooled to r.t. and basified with Et$_3$N (10 mL) under stirring. The suspension was stirred overnight and the insoluble material was removed by filtration. The filtrate was concentrated and the residue (35 g) was purified by chromatography over silica gel (Irregular SiOH, 15-40 µm, 400 g; mobile phase 100% DCM). The pure fractions were collected and evaporated to dryness, yielding 2 g (37%) of intermediate 2.

c) Preparation of Intermediate 3

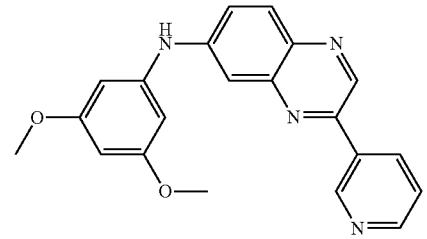 [SMILES: COc1cc(Nc2ccc3ncc(-c4cccnc4)nc3c2)cc(OC)c1]

The following operating procedure was repeated twice on 5 g of intermediate 2. Then, the r.m. were combined for the work-up and the purification A mixture of intermediate 2 (5 g; 15.8 mmol), 3-(4,4,5,5-tetramethyl-1,3,2-dioxaborolan-2-yl)-pyridine (3.9 g; 19 mmol), K$_3$PO$_4$ (8.4 g; 39.6 mmol) and S-Phos (0.65 g; 1.6 mmol) in 1,4-dioxane (180 mL) and H$_2$O (13 mL) was stirred at r.t. under N2 flow for 10 min. Pd$_2$(dba)$_3$ (1.45 g; 1.6 mmol) was added portionwise and the r.m. was heated overnight at 80° C.

The r.m were cooled to r.t. and combined. The resulting mixture was poured onto ice water and extracted with EtOAc. The mixture was filtered through a pad of Celite®. The organic layer was washed (brine), dried (MgSO$_4$), filtered and evaporated to dryness. The residue was purified by chromatography over silica gel (Irregular SiOH 20-45 µm 450 g; mobile phase: 0.1% NH$_4$OH, 96% DCM, 4% MeOH). The pure fractions were collected and evaporated to dryness yielding 9.8 g (85%) of intermediate 3.

d) Preparation of Intermediate 4

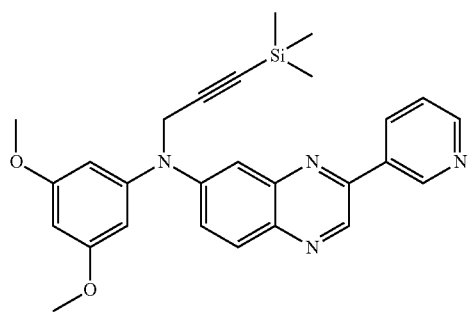 [SMILES: COc1cc(OC)cc(N(CC#C[Si](C)(C)C)c2ccc3ncc(-c4cccnc4)nc3c2)c1]

NaH 60% in oil (0.9 g; 22.3 mmol) was added portion wise to intermediate 3 (4 g; 11.2 mmol) in DMF (130 mL). The r.m. was stirred at 5° C. for 30 min. Then, 3-bromo-(1-trimethylsilyl)-1-propyne (4.9 mL; 30.9 mmol) was added drop wise at 5° C. under N2 flow. The r.m. was stirred at 5° C. for 1 h, poured onto ice water and extracted with EtOAc. The organic layer was separated and washed with brine, dried over MgSO$_4$, filtered and evaporated to dryness. The residue was purified by chromatography over silica gel (Irregular SiOH 20-45 μm 450 g; mobile phase: 98% DCM, 2% MeOH, 0.1% NH$_4$OH). The pure fractions were collected and evaporated to dryness yielding 1.45 g of a crude mixture containing intermediate 4 (used as such in next reaction step).

Example A2 a) Preparation of Intermediate 5a

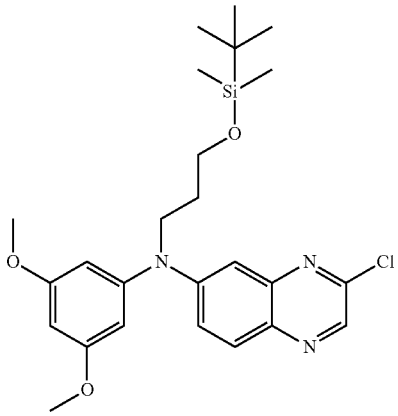 [SMILES: COc1cc(OC)cc(N(CCCO[Si](C)(C)C(C)(C)C)c2ccc3ncc(Cl)nc3c2)c1]

NaH (1.48 g; 37.1 mmol) was added portionwise to a solution of intermediate 2 (9 g; 28.50 mmol) in DMF (100 mL) at 5° C. under N2 flow. The r.m. was stirred at 5° C. for 1 h, then, (3-bromopropoxy)(1,1-dimethylethyl)dimethylsilane (8.58 mL; 37.1 mmol) was added dropwise at 5° C. under N2 flow. The r.m. was stirred for 1 h at 5° C., then allowed to warm to r.t. and stirred for 4 h. The reaction was poured onto ice water and EtOAc was added. The organic layer was separated, washed with brine, dried (MgSO$_4$), filtered and the solvent was evaporated. The residue (17.5 g) was purified by chromatography over silica gel (Irregular SiOH, 20-45 μm, 1000 g; mobile phase 98% DCM, 2% Cyclohexane). The pure fractions were collected and the solvent was evaporated, yielding 13.3 g (95%) of intermediate 5a.

Intermediate 5b

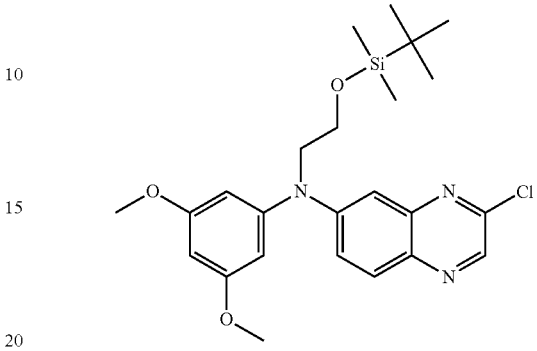

was obtained by following an analogous reaction protocol as described for the preparation of intermediate 5a. (2-Bromoethoxy)-tert-butyldimethylsilane was used instead of (3-bromopropoxy)-tert-butyldimethylsilane as starting material.

b) Preparation of Intermediate 6

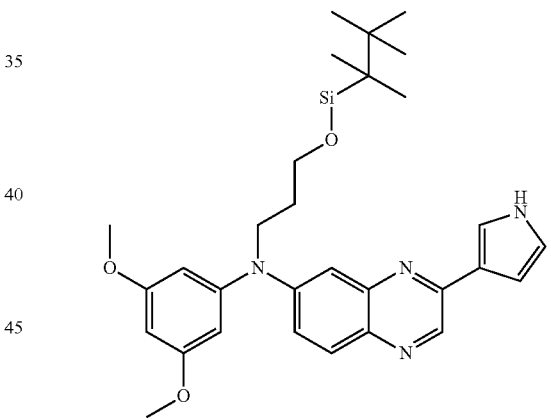

A mixture of intermediate 5a (1.9 g; 4 mmol), 1-(triisopropylsilyl)pyrrole-3-boronic acid (1.4 g; 5.2 mmol), a 2M aq. solution of Na$_2$CO$_3$ (8 mL; 16 mmol) in ethylene glycol dimethyl ether (60 mL) was stirred at r.t. under N2 flow for 10 min. Pd(PPh$_3$)$_4$ (0.5 g; 0.4 mmol) was added portion wise and the r.m. was heated at 100° C. for 12 h. The r.m. was cooled to r.t., poured onto ice water and extracted with EtOAc. The organic layer was washed with brine, dried over MgSO$_4$, filtered and evaporated to dryness. The residue was purified by chromatography over silica gel (Irregular SiOH 20-45 μm; mobile phase: 65% heptane, 35% EtOAc). The pure fractions were collected and evaporated to dryness yielding 1 g (49%) of intermediate 6.

The following intermediates were synthesized according to an analogous reaction protocol, starting from intermediate 5b instead of intermediate 5a:

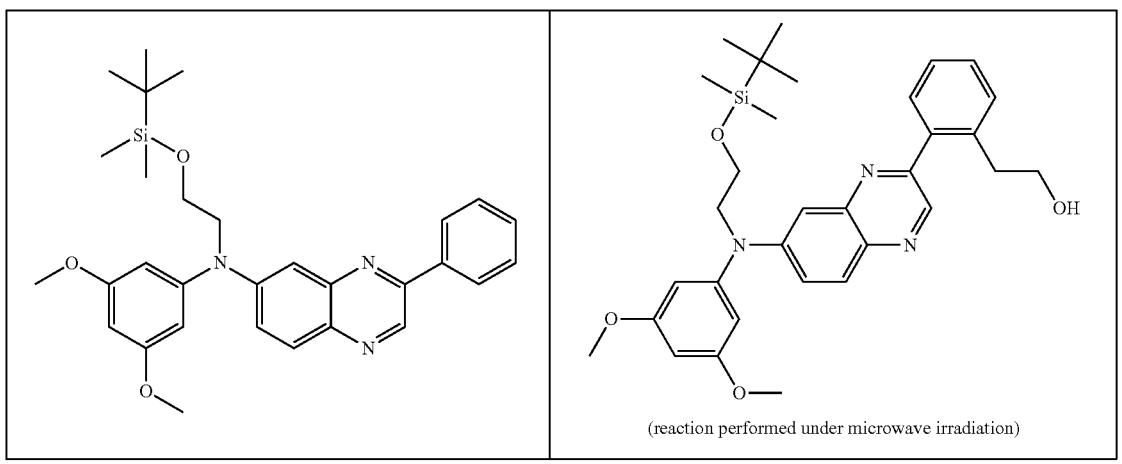 [SMILES: COc1cc(OC)cc(N(CCO[Si](C)(C)C(C)(C)C)c2ccc3ncc(-c4ccccc4)nc3c2)c1 ; COc1cc(OC)cc(N(CCO[Si](C)(C)C(C)(C)C)c2ccc3ncc(-c4ccccc4CCO)nc3c2)c1]

(reaction performed under microwave irradiation)

c) Preparation of Intermediate 7

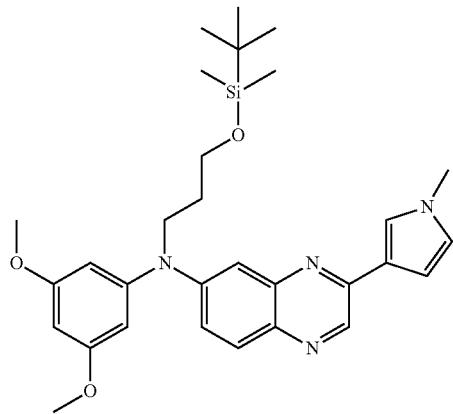 [SMILES: COc1cc(OC)cc(N(CCCO[Si](C)(C)C(C)(C)C)c2ccc3ncc(-c4ccn(C)c4)nc3c2)c1]

Potassium tert-butoxide (0.3 g; 2.5 mmol) and 18-crown-6 (0.06 g; 0.23 mmol) were added to a solution of intermediate 6 (1 g; 1.9 mmol) in DMSO (20 mL) at r.t. The r.m. was stirred at r.t. for 30 min and iodomethane (0.4 mL, 5.7 mmol) was added. The r.m. was stirred at r.t. for 1 h, poured onto ice and extracted with EtOAc. The organic layer was dried (MgSO$_4$), filtered and evaporated, yielding 1.9 g of a crude mixture containing intermediate 7 (brown oil).

Example A3

Preparation of Intermediate 8

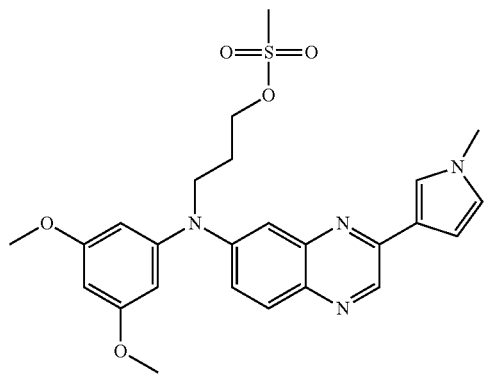 [SMILES: COc1cc(OC)cc(N(CCCOS(C)(=O)=O)c2ccc3ncc(-c4ccn(C)c4)nc3c2)c1]

Methanesulfonyl chloride (0.22 mL; 2.3 mmol) was added drop wise at 5° C. under N2 flow to a solution of compound 4 (0.6 g; 1.4 mmol) and Et$_3$N (0.5 mL; 3.5 mmol) in DCM (12 mL). The r.m. was stirred at 5° C. for 30 min then 1 h at r.t. The r.m. was poured onto ice water and extracted with DCM. The organic layer was separated, dried over MgSO$_4$, filtered and evaporated to dryness to afford 0.78 g (100%) of intermediate 8.

The following intermediates were synthesized according to an analogous reaction protocol:

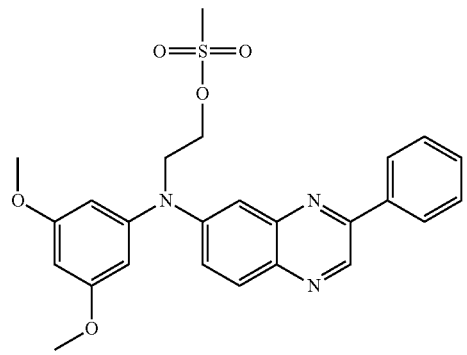

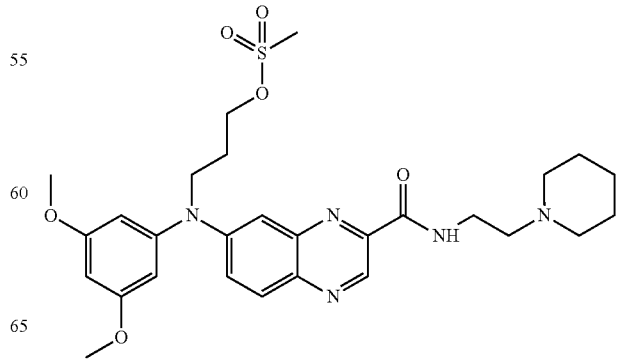

131
-continued
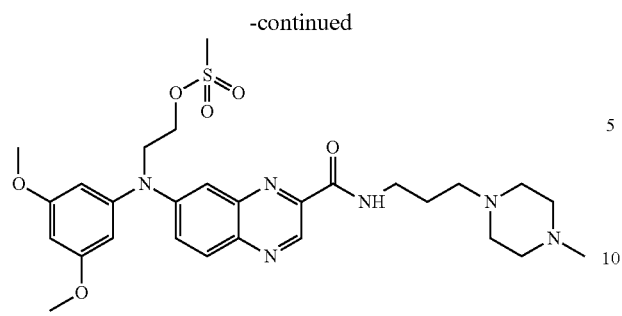
132
-continued
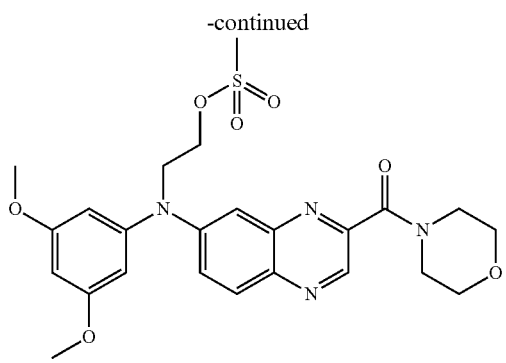
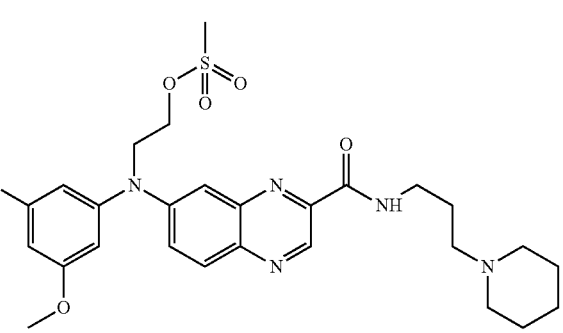
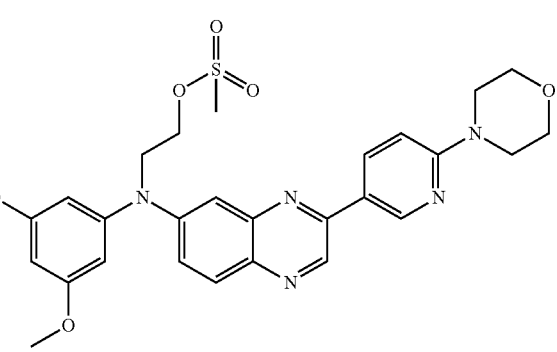
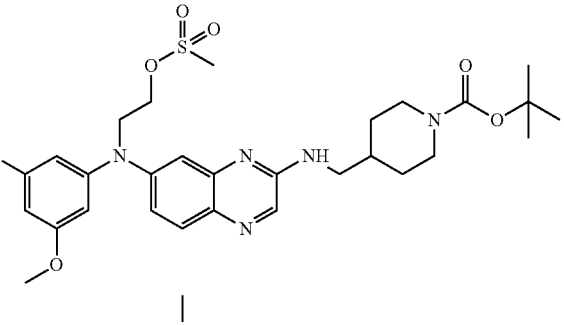
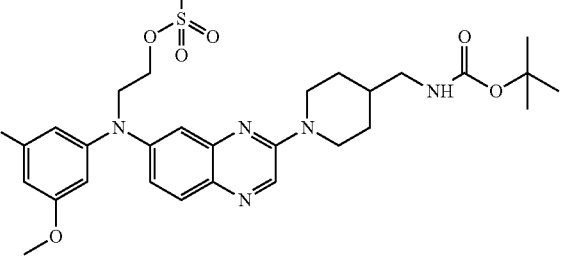

-continued

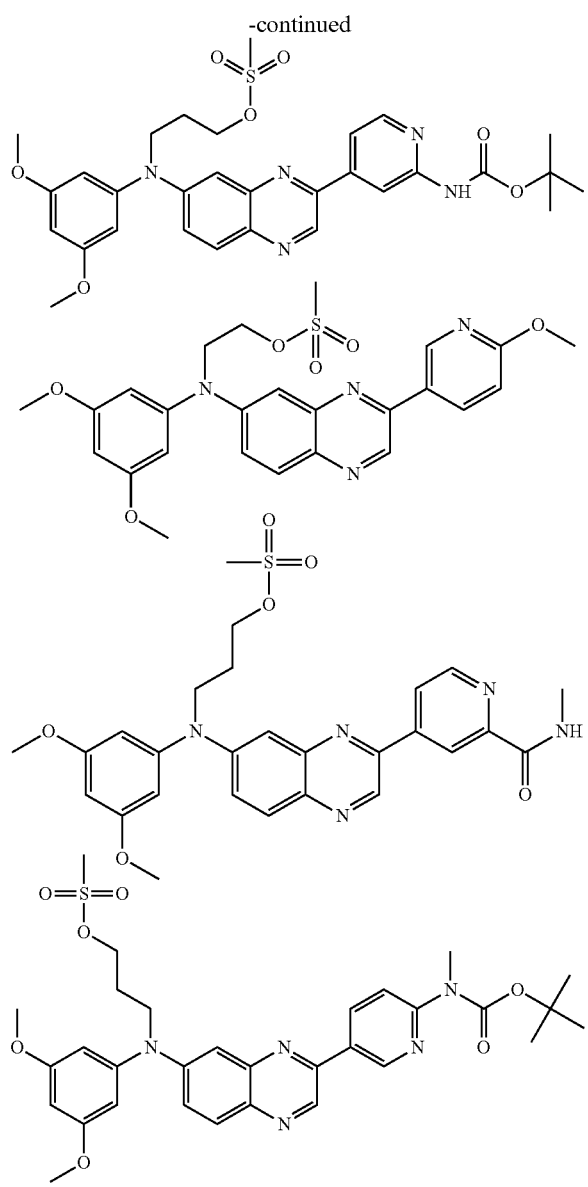

Example A4 a) Preparation of Intermediate 9

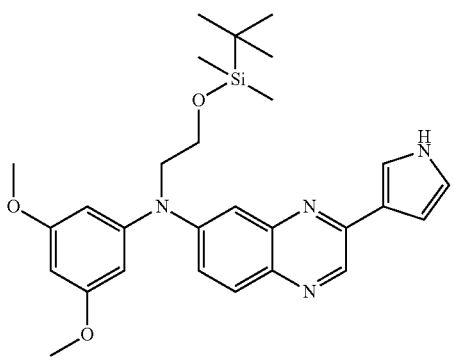 [SMILES: COc1cc(OC)cc(N(CCO[Si](C)(C)C(C)(C)C)c2ccc3ncc(-c4cc[nH]c4)nc3c2)c1]

A mixture of intermediate 5b (3.7 g; 7.8 mmol), 1-(Triisopropylsilyl)pyrrole-3-boronic acid (2.7 g; 10.1 mmol), a 2M aq. solution of Na$_2$CO$_3$ (15.5 mL; 31 mmol) in ethylene glycol dimethyl ether (110 mL) was stirred at r.t. under N2 flow. After 10 min, Pd(PPh$_3$)$_4$ (1.45 g; 1.6 mmol) was added portionwise. The r.m. was heated at 100° C. for 12 h, cooled to r.t., poured onto ice water and extracted with EtOAc. The organic layer was washed with brine, dried over MgSO$_4$, filtered and evaporated to dryness. The residue was purified by chromatography over silica gel (SiOH 20-45 µm; mobile phase: 60% heptane, 40% EtOAc). The pure fractions were collected and evaporated to dryness yielding 1.6 g (41%) of intermediate 9.

b) Preparation of Intermediate 10

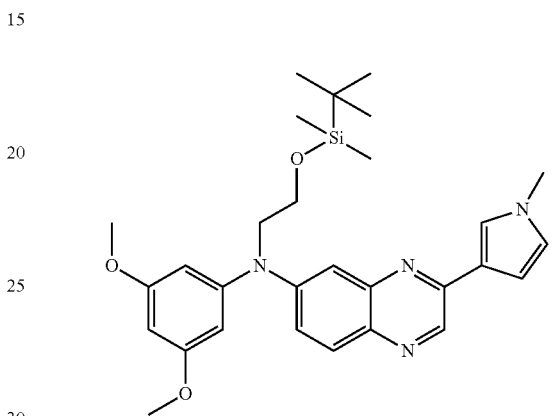

Potassium tert-butoxide (0.4 g; 3.9 mmol) and 18-crown-6 (0.1 g; 0.4 mmol) were added to a solution of intermediate 9 (1.6 g; 3.1 mmol) in DMSO (30 mL) at r.t. The mixture was stirred for 30 min and iodomethane (0.6 mL; 9.1 mmol) was added. The mixture was stirred at r.t. for 1 h, poured onto ice and extracted (EtOAc). The organic layer was dried (MgSO$_4$), filtered and evaporated to dryness yielding 2.85 g of a crude mixture containing intermediate 10 (brown oil).

Example A5

Preparation of Intermediate 11

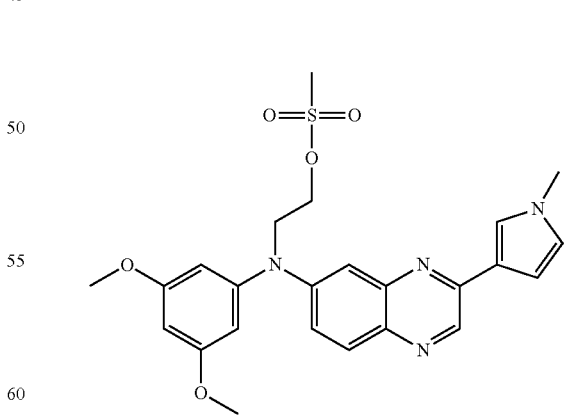

Methanesulfonyl chloride (0.37 mL; 4.7 mmol) was added dropwise at 5° C. under N2 flow to a solution of compound 7 (0.95 g; 2.4 mmol) and Et$_3$N (0.8 mL; 5.9 mmol) in DCM (20 mL). The r.m. was stirred at 5° C. for 30 min then, 1 h at r.t., poured onto ice water and extracted with DCM. The organic layer was separated, dried over MgSO₄, filtered and evaporated to dryness yielding 1 g (96%) of intermediate 11.

Example A6

Preparation of Intermediate 12

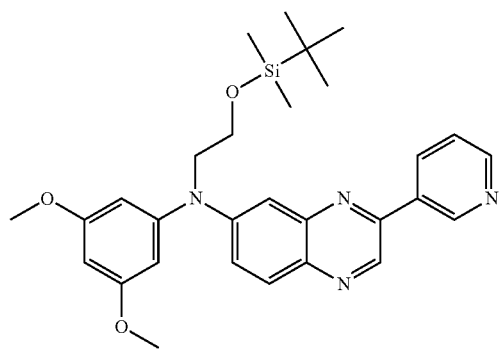 [SMILES: COc1cc(OC)cc(N(CCO[Si](C)(C)C(C)(C)C)c2ccc3ncc(-c4cccnc4)nc3c2)c1]

A mixture of intermediate 5b (1.5 g; 3.2 mmol), 3-(4,4,5,5-tetramethyl-1,3,2-dioxaborolan-2-yl)-pyridine (0.7 g; 3.5 mmol), K₃PO₄ (1.4 g; 6.4 mmol) and S-Phos (0.13 g; 0.32 mmol) in 1,4-dioxane (45 mL) and H₂O (15 mL) was stirred at r.t. under N2 flow for 10 min. Pd₂(dba)₃ (0.3 g; 0.32 mmol) was added portion wise and the r.m. was heated at 80° C. for 4 h, cooled to r.t., poured onto ice water and extracted with EtOAc. The mixture was filtered through a pad of Celite®. The organic layer was washed with brine, dried over MgSO₄, filtered and evaporated to dryness yielding 2 g (quantitative) of intermediate 12 which was used as such in the next reaction step.

The following intermediates were synthesized according to an analogous reaction protocol:

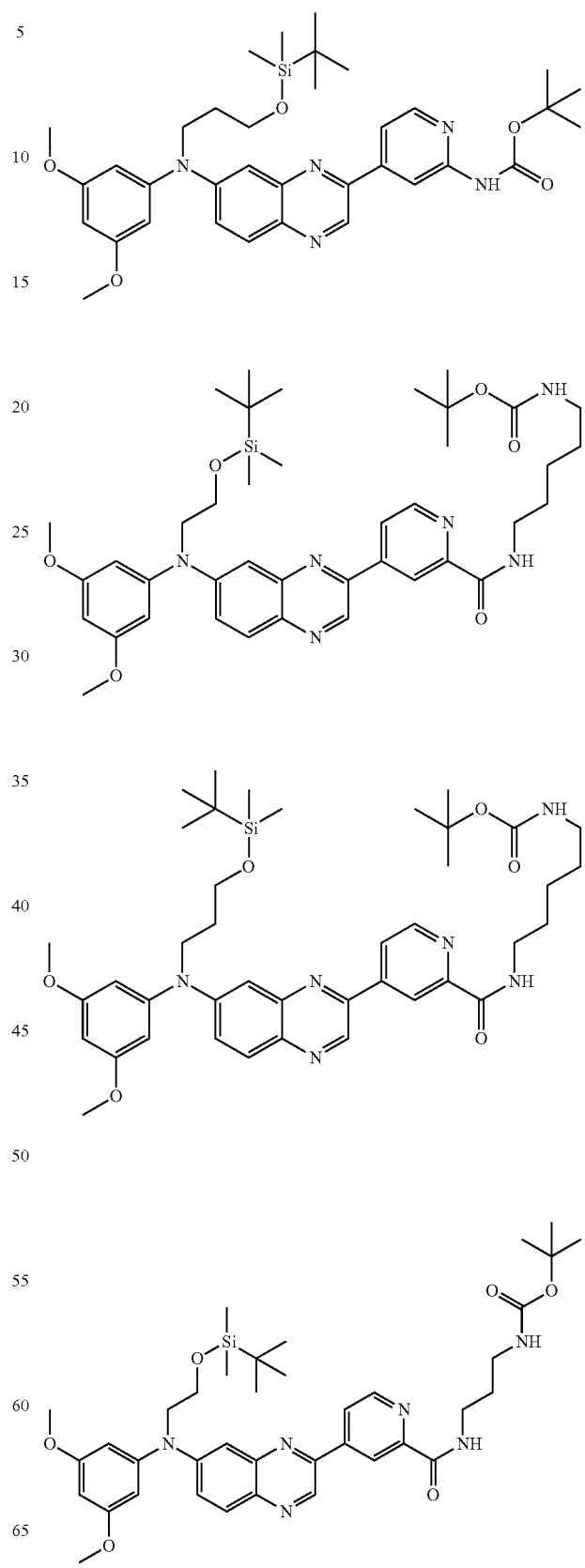

-continued

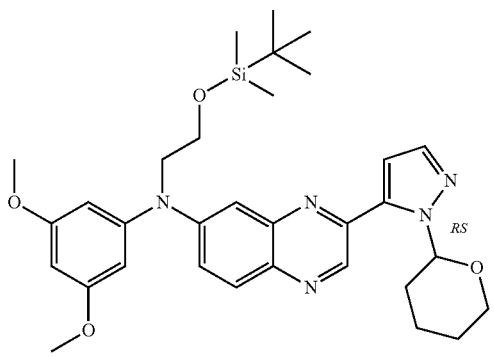

Intermediate 76

Example A7

Preparation of Intermediate 13

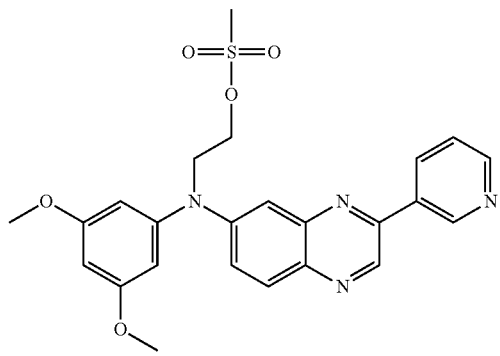 [SMILES: COc1cc(OC)cc(N(CCOS(C)(=O)=O)c2ccc3ncc(-c4cccnc4)nc3c2)c1]

Methanesulfonyl chloride (0.25 mL; 3.2 mmol) was added drop wise at 5° C. under N2 flow to a solution of compound 9 (0.65 g; 1.6 mmol), Et₃N (0.5 mL; 3.7 mmol) and DMAP (0.02 g, 0.16 mmol) in DCM (15 mL). The r.m. was stirred 1 h at r.t., poured onto ice water and extracted with DCM. The organic layer was separated, dried (MgSO₄), filtered and evaporated to dryness. The solid residue was taken up with Et₂O and the precipitate was filtered and dried yielding 0.8 g (99%) of intermediate 13.

Example A8

Preparation of Intermediate 15

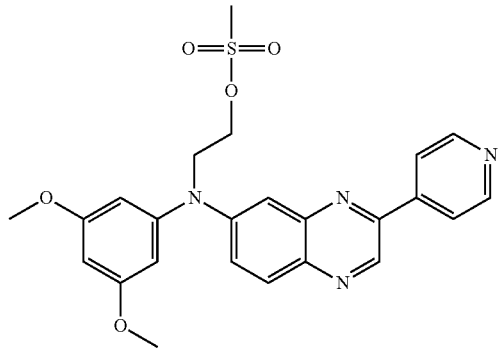 [SMILES: COc1cc(OC)cc(N(CCOS(C)(=O)=O)c2ccc3ncc(-c4ccncc4)nc3c2)c1]

Methanesulfonyl chloride (0.17 mL; 2.1 mmol) was added drop wise at 5° C. under N2 flow to a solution of compound 11 (0.43 g; 1 mmol), Et₃N (0.34 mL; 2.5 mmol) and DMAP (0.013 g, 0.11 mmol) in DCM (10 mL). The r.m. was stirred 1 h at r.t., poured onto ice water and extracted (DCM). The organic layer was separated, dried (MgSO₄), filtered and evaporated to dryness to give 0.51 g (100%) of intermediate 15.

Example A9 a) Preparation of Intermediate 16a

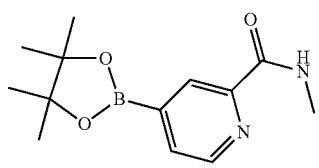

4-Chloro-N-methylpyridine-2-carboxamide (1 g; 5.8 mmol), bis(pinacolato)diboron (1.8 g; 7 mmol), potassium acetate (0.9 g; 8.7 mmol) and S-Phos (0.14 g; 0.3 mmol) in 1,4-dioxane (16 mL) was stirred at r.t. under N2 flow for 10 min. Pd(OAc)₂ (0.04 g; 0.2 mmol) was added portion wise and the r.m. was heated at 100° C. for 18 h. The r.m. was cooled to r.t. and poured onto ice water and EtOAc was added. The mixture was filtered through a pad of Celite®. The organic layer was washed with brine, dried over MgSO₄, filtered and evaporated to dryness to afford 1.9 g (99%) of intermediate 16a.

b) Preparation of Intermediate 16

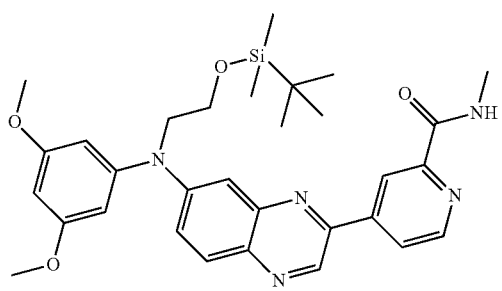

A mixture of intermediate 5b (1.5 g; 3.2 mmol), intermediate 16a (1.7 g; 6.4 mmol), K₃PO₄ (1.4 g; 6.4 mmol) and S-Phos (0.13 g; 0.3 mmol) in 1,4-dioxane (45 mL) and H₂O (15 mL) was stirred at r.t. under N2 flow for 10 min. Pd₂(dba)₃ (0.3 g; 3.2 mmol) was added portionwise and the r.m. was heated at 80° C. for 18 h. The r.m. was cooled to r.t. and poured onto ice water and EtOAc was added. The mixture was filtered through a pad of Celite®. The organic layer was washed with brine, dried over MgSO₄, filtered and evaporated to dryness. The residue was purified by chromatography over silica gel (Irregular SiOH 15-40 μm 300 g; mobile phase: 0.1% NH₄OH, 97% DCM, 3% MeOH). The pure fractions were collected and evaporated to dryness to give 0.8 g (44%) of intermediate 16.

Example A10

Preparation of Intermediate 17

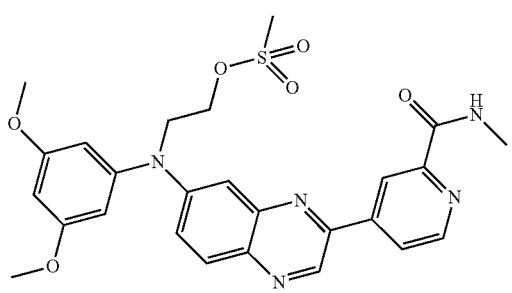

Methanesulfonyl chloride (0.2 mL; 2.6 mmol) was added drop wise at 5° C. under N2 flow to a solution of compound 13 (0.6 g; 1.3 mmol), Et$_3$N (0.45 mL; 3.3 mmol) in DCM (30 mL). The r.m. was stirred 1 h at r.t., poured onto ice water and extracted with DCM. The organic layer was separated, dried over MgSO$_4$, filtered and the solvent was evaporated to dryness to afford 0.7 g of intermediate 17 which was used without further purification for the next step.

Example A11 a) Preparation of Intermediate 18

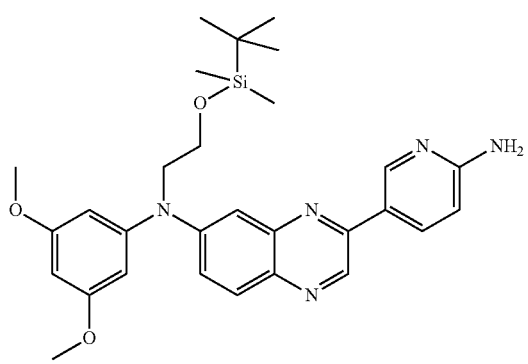 [SMILES: COc1cc(OC)cc(N(CCO[Si](C)(C)C(C)(C)C)c2ccc3ncc(-c4ccc(N)nc4)nc3c2)c1]

A mixture of intermediate 5b (10 g; 21 mmol), 2-aminopyridine-5-boronic acid pinacol ester (4.6 g; 21 mmol), K$_3$PO$_4$ (11.2 g; 52.7 mmol) and S-Phos (0.87 g; 2.1 mmol) in 1,4-dioxane (250 mL) and H$_2$O (50 mL) was stirred at r.t. under N2 flow for 10 min. Pd$_2$(dba)$_3$ (1.9 g; 2.1 mmol) was added portionwise and the r.m. was heated at 80° C. for 18 h, cooled to r.t., poured onto ice water and EtOAc was added. The mixture was filtered through a pad of Celite®. The organic layer was washed with brine, dried over MgSO$_4$, filtered and the solvent was evaporated. The residue was purified by chromatography over silica gel (Irregular SiOH 20-45 μm, 1 kg; mobile phase: 0.5% NH$_4$OH, 95% DCM, 5% MeOH). The pure fractions were collected and evaporated to dryness to give 6.8 g (60%) of intermediate 18.

The following intermediates were synthesized according to an analogous reaction protocol:

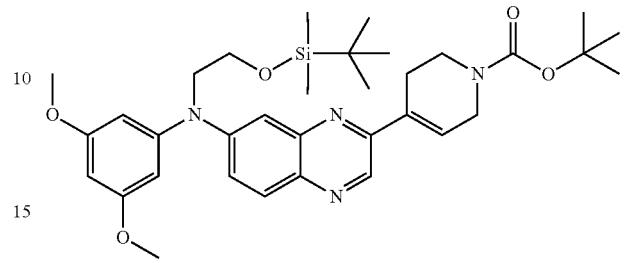

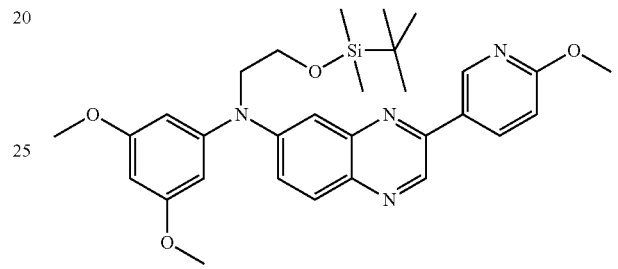

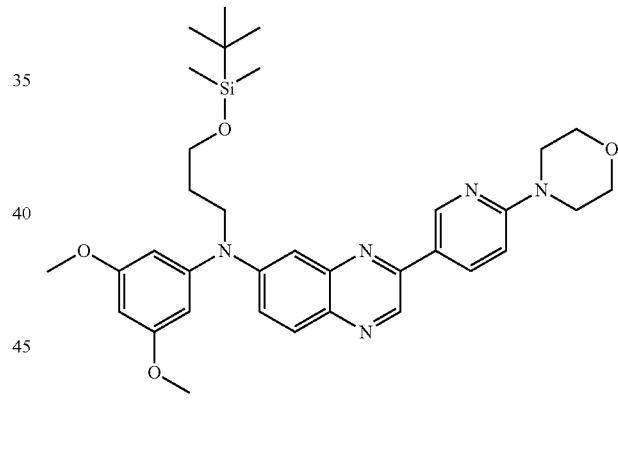

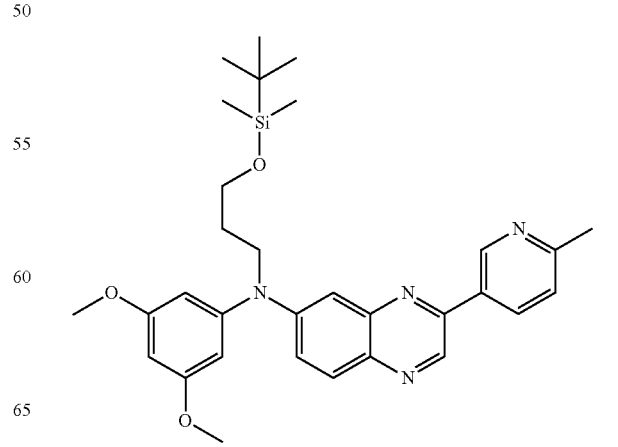

141
-continued
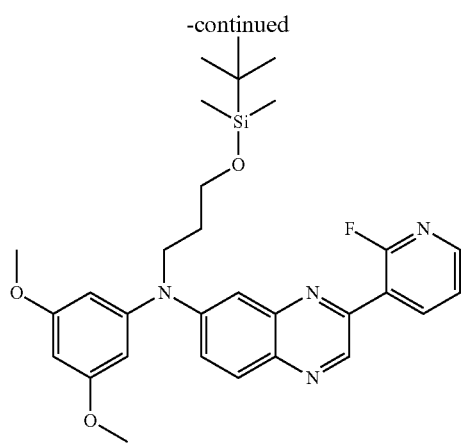
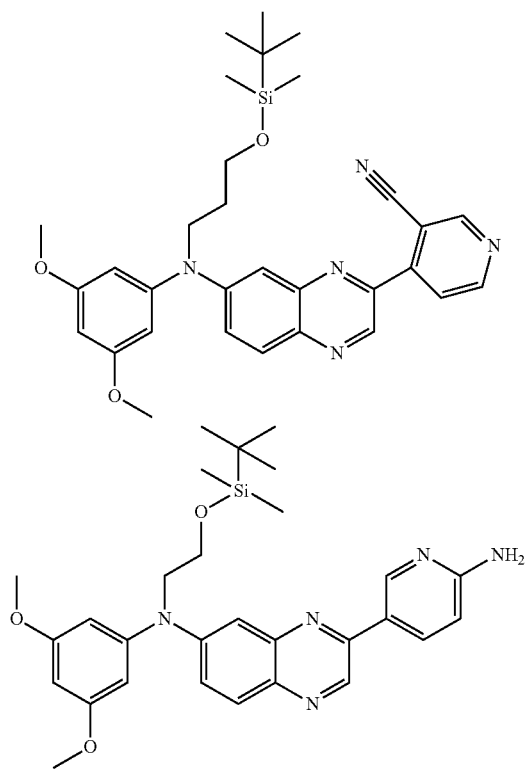
142
-continued
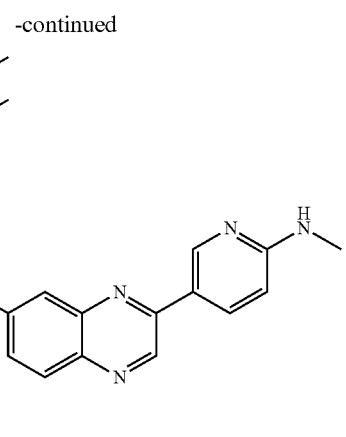
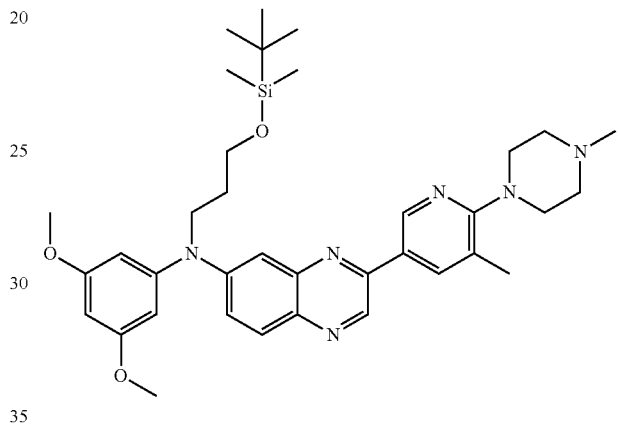
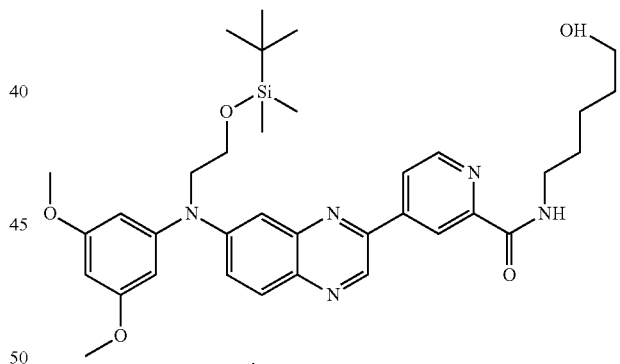
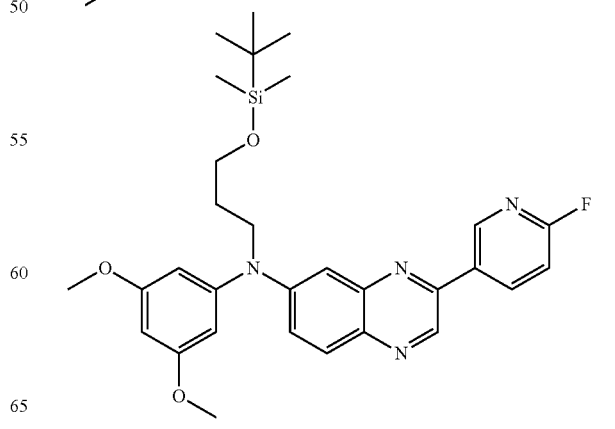

b-1) Preparation of Intermediate 19

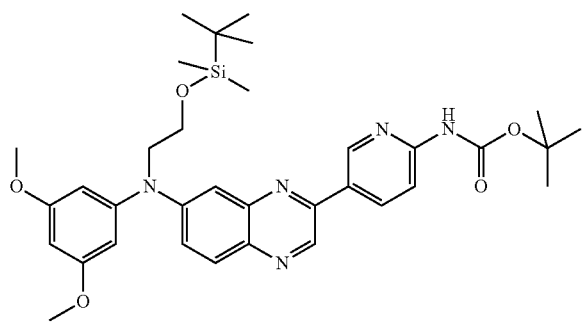 [SMILES: COc1cc(OC)cc(N(CCO[Si](C)(C)C(C)(C)C)c2ccc3ncc(-c4ccc(NC(=O)OC(C)(C)C)nc4)nc3c2)c1]

Sulfamic acid (0.062 g; 0.64 mmol) then di-tert-butyl-dicarbonate (8.4 g; 38.4 mmol) were added to a solution of intermediate 18 (6.8 g; 12.8 mmol) in 2-methyl-propanol (30 mL). The r.m. was stirred 45° C. for 16 h. The mixture was poured onto ice water and DCM was added. The mixture was basified with $K_2CO_3$ 10% and the organic layer was separated, washed with brine, dried over $MgSO_4$, filtered and evaporated to dryness. The residue was purified by chromatography over silica gel (Irregular SiOH 35-45 μm; mobile phase: gradient form 100% DCM, 0% MeOH to 99% DCM, 1% MeOH). The pure fractions were collected and evaporated to dryness to give 6.5 g (80%) of intermediate 19.

b-2) Preparation of Intermediate 69

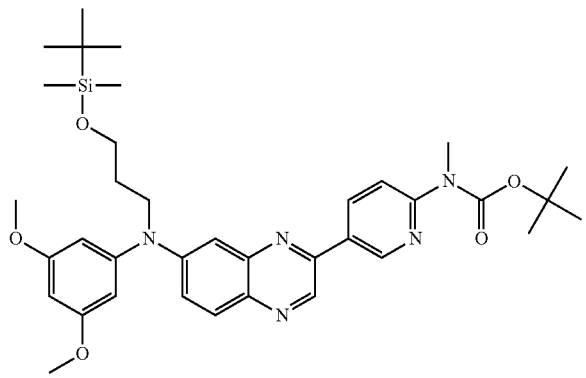 [SMILES: COc1cc(OC)cc(N(CCCO[Si](C)(C)C(C)(C)C)c2ccc3ncc(-c4ccc(N(C)C(=O)OC(C)(C)C)nc4)nc3c2)c1]

A mixture of

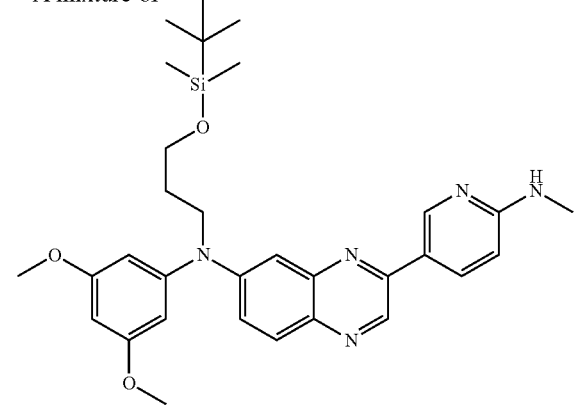

(1.3 g; 2.32 mmol), di-tert-butyl dicarbonate (2.5 g; 11.61 mmol) and DMAP (28 mg; 0.23 mmol) in DCM (25 mL) was stirred at r.t. for 4 h, poured onto water and extracted with DCM. The organic layer was dried over $MgSO_4$, filtered and evaporated to dryness yielding intermediate 69 which was used as such for the next reaction step.

Example A12

Preparation of Intermediate 20

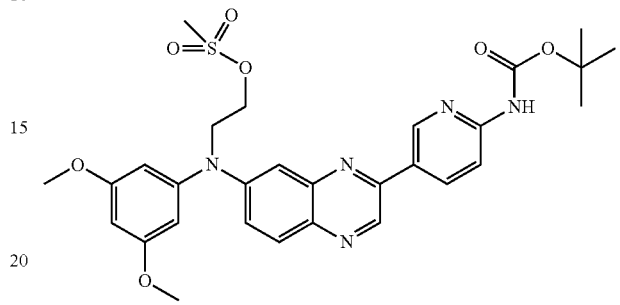

Methanesulfonyl chloride (0.81 mL; 10.4 mmol) was added drop wise at 5° C. under N2 flow to a solution of compound 15 (2 g; 3.9 mmol), $Et_3N$ (1.6 mL; 11.6 mmol) and DMAP (0.047 g, 0.4 mmol) in DCM (80 mL). The r.m. was stirred 1 h at r.t., poured onto ice water and DCM was added. The organic layer was separated, dried over $MgSO_4$, filtered and evaporated to dryness. The solid residue was taken up with DIPE and the precipitate was filtered and dried yielding 2.3 g (100%) of intermediate 20.

Example A13

Preparation of Intermediate 14

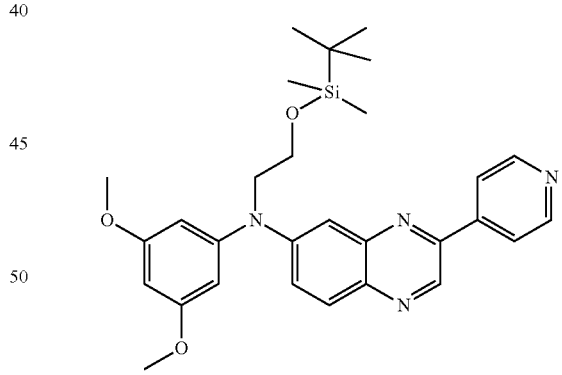

A mixture of intermediate 5b (1.5 g; 3.2 mmol), 4-(4,4,5,5-tetramethyl-1,3,2-dioxaborolan-2-yl)-pyridine (0.7 g; 3.5 mmol), potassium phosphate (1.4 g; 6.4 mmol) and S-Phos (0.13 g; 0.32 mmol) in 1,4-dioxane (45 mL) and $H_2O$ (15 mL) was stirred at r.t. under N2 flow for 10 min. $Pd_2(dba)_3$ (0.3 g; 0.32 mmol) was added portion wise and the r.m. was heated at 80° C. for 4 h. The r.m. was cooled to r.t. and poured onto ice water and EtOAc was added. The mixture was filtered through a pad of Celite®. The organic layer was washed with brine, dried ($MgSO_4$), filtered and evaporated to dryness yielding 2 g (quantitative) of intermediate 14 which was used as such in the next reaction step.

Example A14 a) Preparation of Intermediate 21

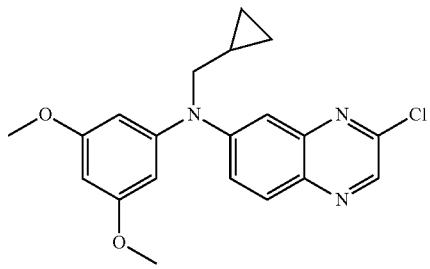 [SMILES: COc1cc(OC)cc(N(CC2CC2)c2ccc3ncc(Cl)nc3c2)c1]

NaH (882 mg; 22.04 mmol) was added portionwise to a solution of intermediate 2 (5.8 g; 18.4 mmol) in DMF (100 mL) under N2 at 5° C. The r.m. was stirred for 20 min and (bromomethyl)cyclopropane (2.2 mL; 22.04 mmol) was added dropwise. The mixture was stirred for another 20 min at 5° C., then at r.t. for 1.5 h. The r.m. was poured into $H_2O$ and extracted with EtOAc. The organic layer was dried ($MgSO_4$), filtered and evaporated to dryness, yielding 6.7 g (98%) of intermediate 21.

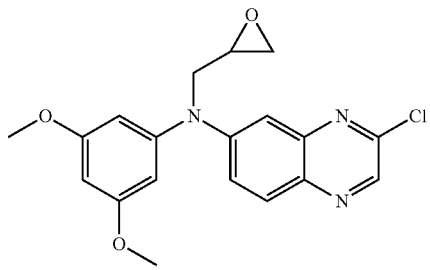 [SMILES: COc1cc(OC)cc(N(CC2CO2)c2ccc3ncc(Cl)nc3c2)c1]

was prepared according to an analogous reaction protocol.

b) Preparation of Intermediate 22

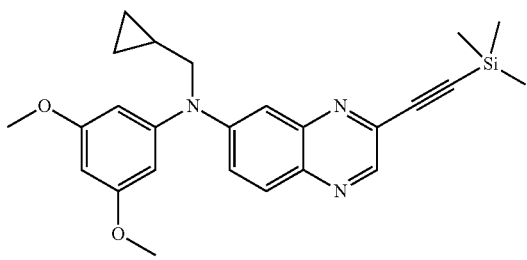

A mixture of intermediate 21 (3 g, 8.11 mmol), trimethylsilylacetylene (5.77 mL; 40.55 mmol), $Et_3N$ (3.38 mL; 24.33 mmol) and $PPh_3$ polymer bound (54 mg; 0.16 mmol) in DMSO (100 mL) was degassed for 10 min with N2. CuI (15.5 mg; 0.08 mmol) and $PdCl_2(PPh_3)_2$ (114 mg; 0.16 mmol) were added and the r.m. was heated at 65° C. for 5 h, cooled to r.t., poured onto iced water and extracted (EtOAc). The organic layer was separated, washed (brine), dried ($MgSO_4$), filtered and evaporated to dryness. The residue was purified by chromatography over silica gel (SiOH 15/40 μm 30 g; mobile phase: gradient from DCM 100% MeOH 0% to DCM 99% MeOH 1° C.). The pure fractions were collected and evaporated to dryness yielding 2.66 g (76%) of intermediate 22.

c) Preparation of Intermediate 23

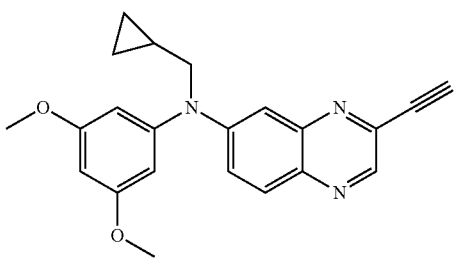 [SMILES: C#Cc1cnc2ccc(N(CC3CC3)c3cc(OC)cc(OC)c3)cc2n1]

A mixture of intermediate 22 (2.6 g; 6.02 mmol) and $K_2CO_3$ (1.25 g; 9.0 mmol) in MeOH (150 mL) was stirred at r.t. for 2 h. The r.m. was diluted with DCM and poured onto water. The organic layer was decanted, dried ($MgSO_4$), filtered and evaporated to dryness. The residue was purified by chromatography over silica gel (Irregular SiOH 15-40 μm 50 g; mobile phase: gradient from DCM 100% MeOH 0% to DCM 98% MeOH 2%). The pure fractions were collected and evaporated to dryness yielding 1.85 g (85%) of intermediate 23.

Example A15

Preparation of Intermediate 24

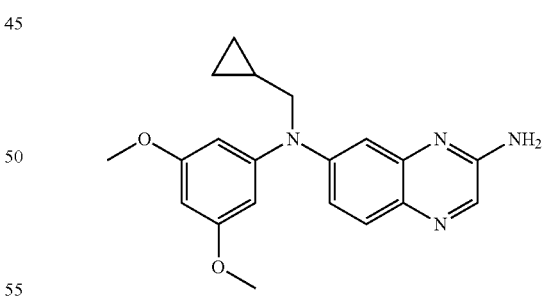

In a pressure vessel, liquid $NH_3$ (50 mL) was added to a solution of intermediate 21 (5 g; 13.5 mmol) in DME (25 mL). The r.m. was heated for 15 h at 110° C. (pressure raised 60 bars), cooled to r.t. and evaporated to dryness. The residue was purified by chromatography over silica gel (Irregular SiOH 15-40 μm 30 g; mobile phase: 95% DCM, 5% MeOH, 0.1% $NH_4OH$). The pure fractions were concentrated to give 3.15 g (66%) of intermediate 24 (MP: 146° C. (DSC)).

Example A16 a) Preparation of Intermediate 25

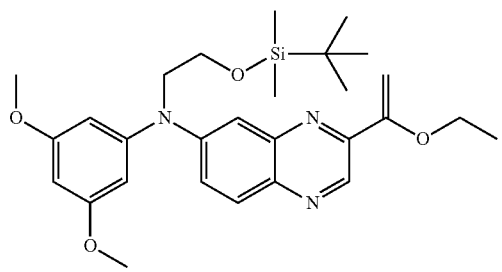 [SMILES: C=C(OCC)c1cnc2ccc(N(CCO[Si](C)(C)C(C)(C)C)c3cc(OC)cc(OC)c3)cc2n1]

PdCl$_2$(PPh$_3$)$_2$ (31 mg; 0.044 mmol) was added to a degassed solution of intermediate 5b (1.09 g; 2.30 mmol) and tributyl-(1-ethoxyvinyl)tin (0.854 mL; 2.53 mmol) in DMF (10 mL). The r.m. was heated at 70° C. overnight, cooled to r.t., poured into ice and extracted with EtOAc. The organic layer was decanted, washed with water, dried over MgSO$_4$, filtered and evaporated to dryness. The residue was purified by chromatography over silica gel (irregular SiOH 15-40 μm 30 g; mobile phase: 85% cyclohexane, 15% EtOAc).

The pure fractions were evaporated to dryness yielding 600 mg (51%) of intermediate 25.

b) Preparation of Intermediate 26

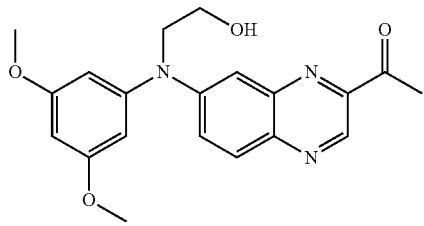 [SMILES: COc1cc(OC)cc(N(CCO)c2ccc3ncc(C(C)=O)nc3c2)c1]

A solution of intermediate 25 (600 mg; 1.18 mmol) in aq. HCl 3M (2 mL) and acetone (10 mL) was stirred at r.t. for 18 h. The r.m. was diluted with Et$_2$O and basified with a 10% solution of K$_2$CO$_3$. The organic layer was decanted, dried over MgSO$_4$, filtered and evaporated to dryness. The residue was purified by chromatography over silica gel (irregular 15-40 μm 30 g; mobile phase: gradient from 100% DCM, 0% MeOH to 95% DCM, 5% MeOH). The pure fractions were evaporated to dryness yielding 410 mg (95%) intermediate 26.

Example A17 a) Preparation of Intermediate 27

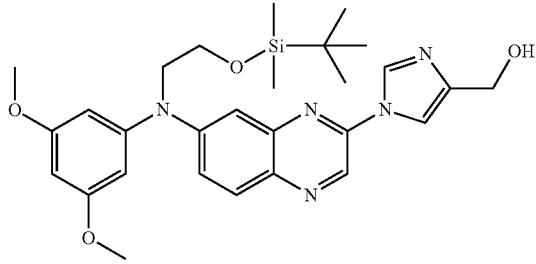 [SMILES: COc1cc(OC)cc(N(CCO[Si](C)(C)C(C)(C)C)c2ccc3ncc(-n4cnc(CO)c4)nc3c2)c1]

NaH 60% in oil (337 mg; 8.44 mmol) was added at 0° C. to a solution of 4(5)-(hydroxymethyl)-imidazole (853 mg; 8.44 mmol) in 1-methyl-2-pyrrolidinone (10 mL). The mixture was stirred for 30 min at 0° C. and then a solution of intermediate 5b (2 g; 4.22 mmol) in 1-methyl-2-pyrrolidinone (10 mL) was added. The r.m. was heated at 65° C. overnight, cooled to r.t., poured onto water and extracted with EtOAc. The organic layer was washed twice with brine, dried over MgSO$_4$, filtered and evaporated to dryness. The residue was purified by chromatography over silica gel (Irregular SiOH 15-40 μm 300 g; mobile phase: 0.1% NH$_4$OH, 95% DCM, 5% MeOH). The pure fractions were evaporated to dryness yielding 925 mg (41%) of intermediate 27.

b) Preparation of Intermediate 28

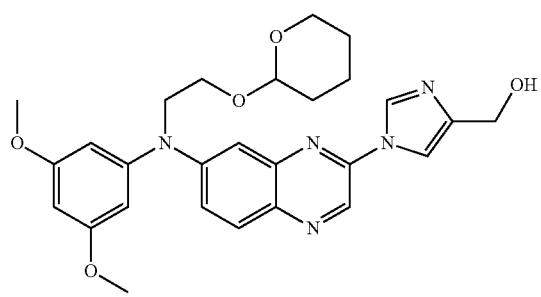 [SMILES: COc1cc(OC)cc(N(CCOC2CCCCO2)c2ccc3ncc(-n4cnc(CO)c4)nc3c2)c1]

A mixture of intermediate 27 (1 g; 1.87 mmol), 3,4-dihydro-2H-pyran (0.183 mL; 2.00 mmol) and p-toluenesulfonic acid (314 mg; 1.82 mmol) in DCM (10 mL) was stirred at r.t. for 5 h then refluxed overnight. THF (10 mL) was added, and the r.m. was refluxed for 5 h. The mixture was poured onto ice and extracted with EtOAc. The organic layer was dried over MgSO$_4$, filtered and evaporated till dryness. The residue was purified by chromatography over silica gel (Irregular SiOH 15-40 μm 300 g; mobile phase: gradient from 0.5% NH$_4$OH, 95% DCM, 5% MeOH to 0.5% NH$_4$OH, 90% DCM, 10% MeOH), The pure fractions were collected and evaporated to dryness yielding 160 mg (16%) of intermediate 28.

Example A18

Preparation of Intermediate 29

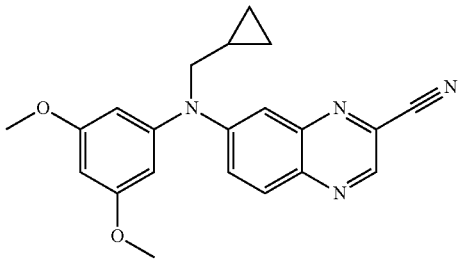 [SMILES: COc1cc(OC)cc(N(CC2CC2)c2ccc3ncc(C#N)nc3c2)c1]

In a pressure vessel, a suspension of intermediate 21 (2.4 g; 6.5 mmol), PPh$_3$ (170 mg; 0.65 mmol) and zinc cyanide (762 mg; 6.5 mmol) in ACN (24 mL) was degassed with N2 for 5 min. Pd(PPh$_3$)$_4$ was added and the mixture was further degassed for 5 min. The r.m. was stirred at 140° C. for 2 h, evaporated to dryness and taken up with a mixture of water/DCM. The organic layer was separated, dried on MgSO$_4$, filtered and evaporated to dryness. The residue was purified by chromatography over silica gel (SiOH 15-40 μm 90 g; mobile phase: 80% cyclohexane, 20% EtOAc). The pure fractions were evaporated until dryness and the residue was crystallized from Et₂O. Filtration of the precipitate afforded 1.73 g (74%) of intermediate 29.

Example A19

Preparation of Intermediate 30

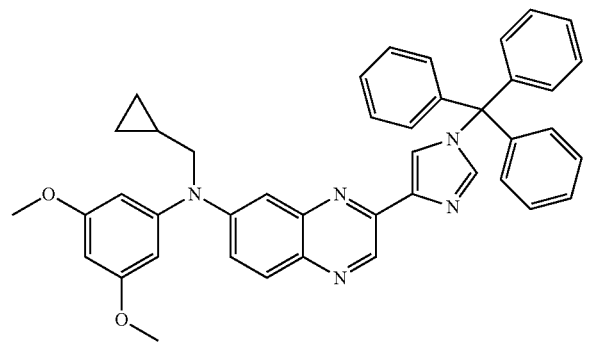 [SMILES: COc1cc(OC)cc(N(CC2CC2)c2ccc3ncc(-c4cn(C(c5ccccc5)(c5ccccc5)c5ccccc5)cn4)nc3c2)c1]

At r.t., ethyl magnesium bromide (3M in Et₂O) (460 μL; 1.38 mmol) was added dropwise to a solution of 4-iodo-1-trityl-1H-imidazole (0.5 g; 1.15 mmol) in THF (3 mL) under a N2 flow. The mixture was stirred at r.t. for 30 min. Then, ZnCl (313 mg; 2.29 mmol) was added and the mixture was stirred at r.t. for 1 h. A solution of intermediate 21 (424 mg; 1.15 mmol) in THF (2 mL) and Pd(PPh₃)₄ (66 mg; 0.057 mmol) were added and the mixture was refluxed overnight. The r.m. was poured onto water and filtered through a pad of Celite®. The aq. layer was extracted with DCM and the organic layer was separated, dried over MgSO₄, filtered and evaporated to dryness. The residue was purified by chromatography over silica gel (Irregular SiOH 15-40 μm; mobile phase: gradient from 100% DCM, 0% MeOH to 98% DCM, 2% MeOH). The pure fractions were collected and the solvent was evaporated to give 2 fractions containing intermediate 30: 128 mg (purity: 83% based on LC/MS) of intermediate 30 and 110 mg (purity: 81% based on LC/MS) of intermediate 30.

Example A20 a) Preparation of Intermediate 31

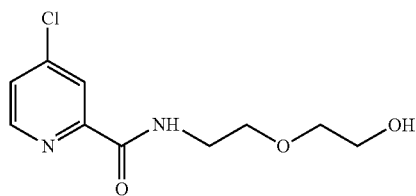 [SMILES: O=C(NCCOCCO)c1cc(Cl)ccn1]

4-chloro-2-Pyridinecarboxylic acid methyl ester (2 g; 11.6 mmol) was added at 70° C. to a solution of 2-(2-aminoethoxy)-ethanol (11.7 mL; 116.5 mmol) in THF (120 mL). The r.m. was refluxed for 2 h, cooled to r.t. and evaporated to dryness. The residue was purified by chromatography over silica gel (Irregular SiOH 20-45 μm 450 g; mobile phase: 95% DCM, 5% MeOH, 0.5% NH₄OH). The pure fractions were collected and evaporated to dryness yielding 2.4 g (84%) of intermediate 31.

b) Preparation of Intermediate 32

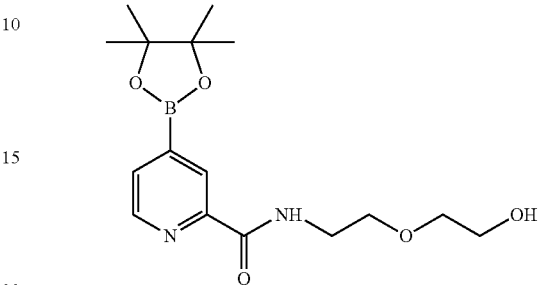

A mixture of intermediate 31 (2.3 g; 9.4 mmol), bis(pinacolato)diboron (2.86 g; 11.3 mmol), potassium acetate (1.38 g; 14.1 mmol), S-Phos (231 mg; 0.56 mmol) in 1,4-dioxane (45 mL) was degassed with N2. After 10 min, Pd(OAc)₂ (63 mg; 0.29 mmol) was added. The r.m. was heated at 100° C. for 1 h, cooled to r.t., poured into water and extracted with EtOAc. The organic layer was dried over MgSO₄, filtered and evaporated to dryness yielding 2.1 g (66%) of intermediate 32.

c) Preparation of Intermediate 33

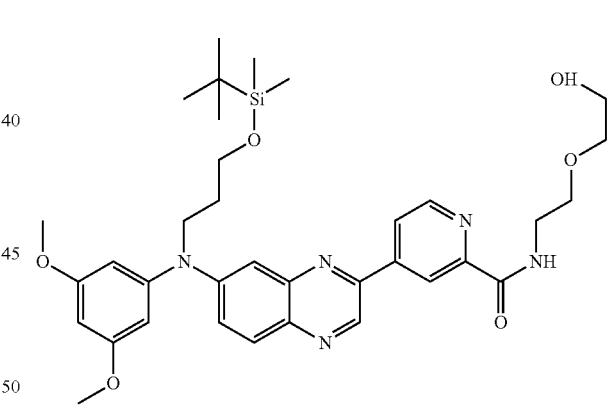

A mixture of intermediate 5a (968 mg; 1.98 mmol), intermediate 32 (1 g; 2.97 mmol), K₃PO₄ (842 mg; 3.97 mmol), S-Phos (81.4 mg; 0.198 mmol) in 1,4-dioxane (20 mL) and H₂O (7 mL) was stirred at r.t. under N2 flow. After 10 min, Pd₂(dba)₃ (182 mg; 0.198 mmol) was added portionwise. The r.m. was heated at 100° C. for 18 h, cooled to r.t., poured onto ice water and extracted with DCM. The organic layer was dried over MgSO₄, filtered and evaporated to dryness. The residue was purified by chromatography over silica gel (Irregular SiOH 20-45 μm 450; mobile phase: 96% DCM, 4% MeOH, 0.1% NH₄OH). The pure fractions were collected and evaporated to dryness yielding 624 mg (47%) of intermediate 33.

d) Preparation of Intermediate 34

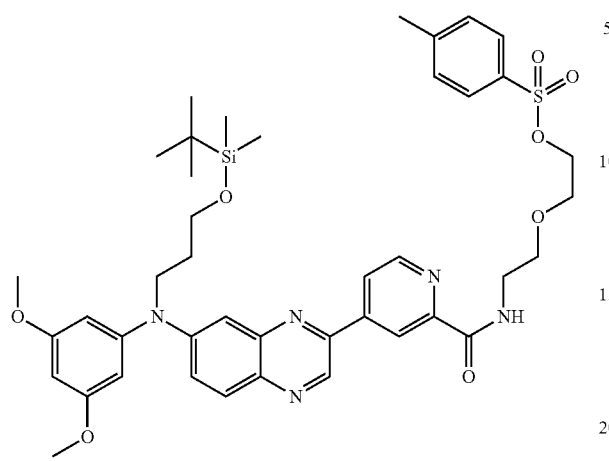

p-Toluenesulfonyl chloride (317 mg; 1.66 mmol) was added portion wise at 5° C. under N2 flow to a solution of intermediate 33 (550 mg; 0.83 mmol), DMAP (10 mg; 0.08 mmol) and Et$_3$N (266 µL; 1.91 mmol) in DCM (12 mL). The r.m. was allowed to warm to r.t. and stirred for 18 h. The r.m. was diluted with DCM and water was added. The organic layer was decanted, dried over MgSO$_4$, filtered and evaporated to dryness. The residue was purified by chromatography over silica gel (Irregular SiOH 15-40 µm 30 g; mobile phase: gradient from 100% DCM, 0% MeOH to 96% DCM, 4% MeOH). The pure fractions were collected and evaporated to dryness yielding 400 mg (59%) of intermediate 34.

e) Preparation of Intermediate 35

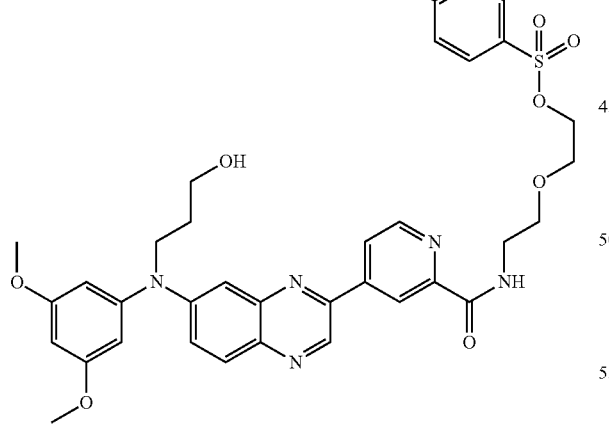

A solution of TBAF 1M in THF (637 µL; 0.64 mmol) was added to a solution of intermediate 34 (400 mg; 0.49 mmol) in THF (6 mL). The r.m. was stirred for 2 h, poured onto water and extracted with DCM. The organic layer was decanted, dried over MgSO$_4$, filtered and evaporated to dryness. The residue was purified by chromatography over silica gel (Spherical SiOH, 5 µm 150×30.0 mm; mobile phase: gradient from 99% DCM, 1% MeOH, 0.1% NH$_4$OH to 92% DCM, 8% MeOH, 0.8% NH$_4$OH). The pure fractions were collected and evaporated to dryness yielding 118 mg (34%) of intermediate 35, and 50 mg (19%) of compound 43 (which can also be prepared according to the synthesis protocol described in B40).

Example A21 a) Preparation of Intermediate 36

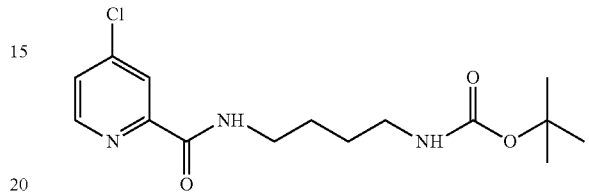

Magnesium chloride (190 mg; 1.99 mmol) then N-Boc-1,4-diaminobutane (1.5 g; 7.97 mmol) were added at r.t. to a solution of 4-chloro-2-pyridinecarboxylic acid methyl ester (883 mg; 3.98 mmol) in THF (7 mL). The r.m. was stirred at r.t. for 2 h then 5 mL of water were added followed by 2.5 mL of HCl 1 N. The r.m. was extracted with EtOAc. The organic layer was washed with brine, dried over MgSO$_4$, filtered and evaporated to dryness. The residue was purified by chromatography over silica gel (Irregular SiOH 15-40 µm, 40 g; mobile phase: 0% MeOH, 100% DCM to 2% MeOH, 98% DCM). The pure fractions were collected and evaporated to dryness yielding 1 g (76%) of intermediate 36.

b) Preparation of Intermediate 37

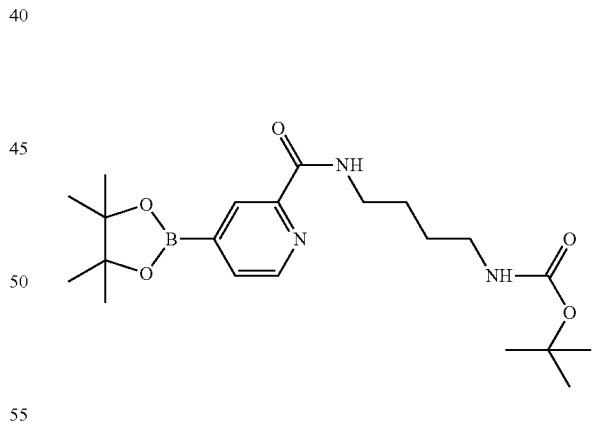

A mixture of intermediate 36 (1 g; 3.05 mmol), bis(pinacolato)diboron (0.93 g; 3.66 mmol), potassium acetate (449 mg; 4.57 mmol), S-Phos (75 mg; 0.18 mmol) in 1,4-dioxane (15 mL) was degassed with N2. After 10 min, Pd(OAc)$_2$ (20.5 mg; 0.09 mmol) was added. The r.m. was heated at 100° C. for 1 h, cooled to r.t. and poured into water. EtOAc was added and the mixture was filtered through of layer of Celite®. The organic layer was washed with brine, dried over MgSO$_4$, filtered and evaporated to dryness yielding intermediate 37 which was used as such for the next reaction step.

c) Preparation of Intermediate 38

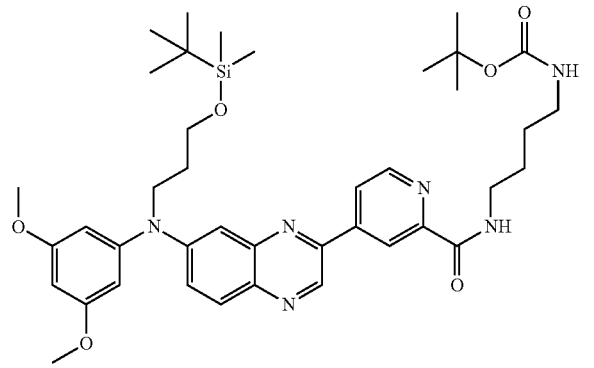 [SMILES: COc1cc(OC)cc(N(CCCO[Si](C)(C)C(C)(C)C)c2ccc3ncc(-c4ccnc(C(=O)NCCCCNC(=O)OC(C)(C)C)c4)nc3c2)c1]

A mixture of intermediate 5a (1 g; 2.05 mmol), intermediate 37 (1.28 g; 3.05 mmol), potassium phosphate (869 mg; 4.1 mmol), S-Phos (84 mg; 0.20 mmol) in 1,4-dioxane (25 mL) and $H_2O$ (8 mL) was stirred at r.t. under N2 flow. After 10 min, $Pd_2(dba)_3$ (187 mg; 0.20 mmol) was added portionwise. The r.m. was heated at 100° C. for 4 h, cooled to r.t., poured onto ice water and extracted with EtOAc. The organic layer was dried over $MgSO_4$, filtered and evaporated to dryness. The residue was purified by chromatography over silica gel (Irregular SiOH, 15-40 μm, 40 g; mobile phase: 97% DCM, 3% MeOH, 0.1% $NH_4OH$). The pure fractions were collected and evaporated to dryness yielding 1.27 g (83%) of intermediate 38.

d) Preparation of Intermediate 39

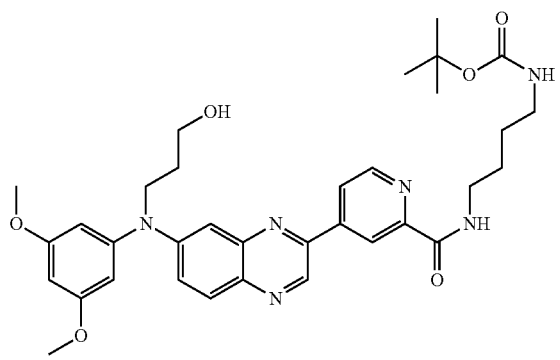 [SMILES: COc1cc(OC)cc(N(CCCO)c2ccc3ncc(-c4ccnc(C(=O)NCCCCNC(=O)OC(C)(C)C)c4)nc3c2)c1]

A solution of TBAF 1M in THF (443 μL; 0.44 mmol) was added at 0° C. under N2 flow to a solution of intermediate 78.4 (300 mg; 0.40 mmol) in THF (4 mL). The r.m. was allowed to warm to r.t. and stirred for 2 h, poured onto water and extracted with EtOAc. The organic layer was decanted, dried over $MgSO_4$, filtered and evaporated to dryness. The residue was purified by chromatography over silica gel (Spherical silica, 5 μm 150×30.0 mm; mobile phase: gradient from 98% DCM, 2% MeOH to 95% DCM, 5% MeOH). The pure fractions were collected and evaporated to dryness yielding 251 mg (99%) of intermediate 39.

e) Preparation of Intermediate 40

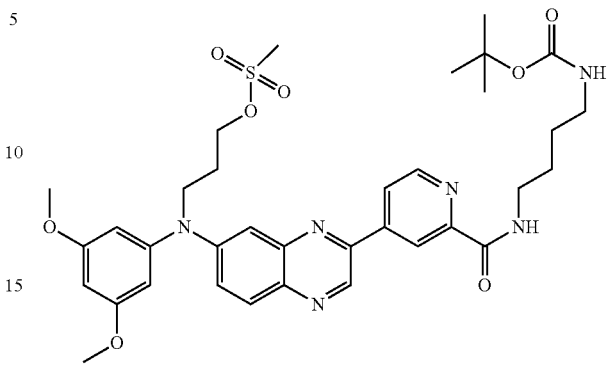

Methanesulfonyl chloride (36.8 μL; 0.47 mmol) was added drop wise at 5° C. under N2 flow to a solution of intermediate 39 (250 mg; 0.39 mmol), and $Et_3N$ (85.1 μL; 0.59 mmol) in DCM (20 mL). The r.m. was allowed to warm to r.t. and stirred for 2 h. The r.m. was diluted with DCM and water was added. The organic layer was decanted, dried over $MgSO_4$, filtered and evaporated to dryness yielding 267 mg (95%) of intermediate 40.

f) Preparation of Intermediate 41

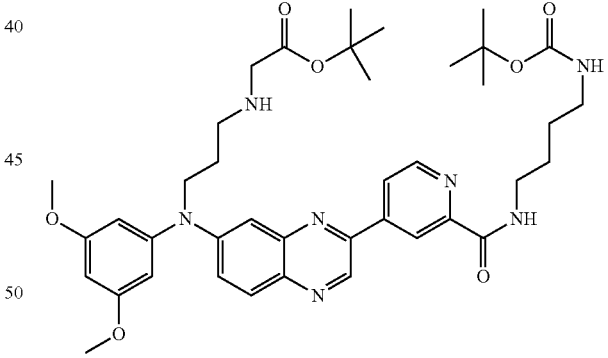

A mixture of intermediate 40 (100 mg; 1.08 mmol) and glycine tert-butyl ester (96 μL; 0.705 mmol) in DMF (0.7 mL) was heated at 70° C. for 4 h. The r.m. was cooled to r.t., diluted with EtOAc and poured onto water. The organic layer was washed with brine, dried over $MgSO_4$, filtered and evaporated to dryness. The residue was purified by chromatography over silica gel (mobile phase: gradient from 0.4% $NH_4OH$, 96% DCM, 4% MeOH to 0.5% $NH_4OH$, 95% DCM, 5% MeOH). The pure fractions were collected and evaporated to dryness yielding 90 mg (86%) of intermediate 41.

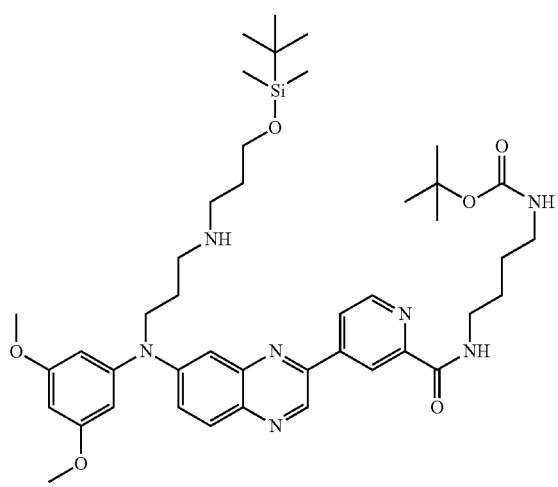 [SMILES: COc1cc(OC)cc(N(CCCNCCCO[Si](C)(C)C(C)(C)C)c2ccc3ncc(-c4ccnc(C(=O)NCCCCNC(=O)OC(C)(C)C)c4)nc3c2)c1]

was prepared according to an analogous reaction protocol as described for intermediate 41.

Example A22

Preparation of Intermediate 42

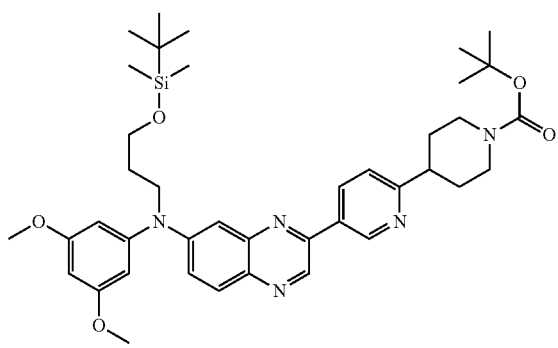 [SMILES: COc1cc(OC)cc(N(CCCO[Si](C)(C)C(C)(C)C)c2ccc3ncc(-c4ccc(C5CCN(C(=O)OC(C)(C)C)CC5)nc4)nc3c2)c1]

Intermediate 5a (3.75 g; 7.68 mmol), 2-(4-boc-piperazine)pyridine-5-boronic acid pinacol (2.99 g; 7.68 mmol) and potassium phosphate (4.08 g; 19.2 mmol) in a mixture of 1,4-dioxane (100 mL) and water (20 mL) was stirred and degassed at r.t. under a N2 flow (bubbling). After 10 min, Pd$_2$(dba)$_3$ (705 mg; 0.77 mmol) and S-Phos (315 mg; 0.768 mmol) were added. The r.m. was heated at 80° C. for 2 h, cooled down to r.t. and evaporated to dryness. The oil was diluted with EtOAc and washed with water. The organic layer was dried over Na$_2$SO$_4$, filtered and evaporated under reduced pressure.

The residue was purified by chromatography over silica gel (mobile phase: gradient from 60% heptane, 40% EtOAc to 40% heptane, 60% EtOAc). The pure fractions were collected and concentrated to afford 2.14 g (37%) of intermediate 42.

Example A23 a) Preparation of Intermediate 43

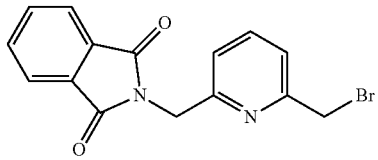 [SMILES: O=C1c2ccccc2C(=O)N1Cc1cccc(CBr)n1]

Potassium phthalimide (2.64 g; 14.3 mmol) was added portion wise at r.t. to 2,6-bis(bromomethyl)pyridine (3.78 g; 14.3 mmol) in DMF (40 mL). The mixture was stirred at r.t. over the weekend. The mixture was poured onto ice. The obtained precipitate was filtered, dried and purified by chromatography over silica gel (SiOH 35/45 µm 80 g; mobile phase: DCM 100%). The pure fractions were evaporated to dryness to give 2.23 g (47%) of intermediate 43.

b) Preparation of Intermediate 44

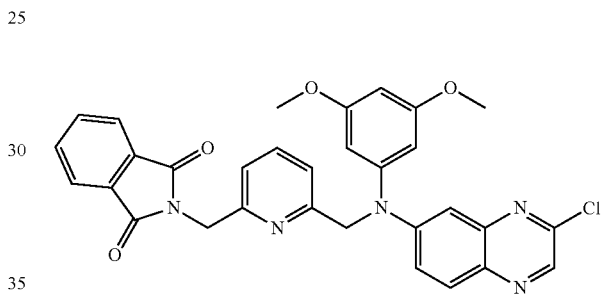

Sodium hydride 60% in oil (294 mg; 7.35 mmol) was added portionwise at 5° C. under N2 to a solution of intermediate 2 (1.93 g; 6.12 mmol) in DMF (20 mL). The r.m. was stirred for 20 min and intermediate 43 (2.23 g; 6.73 mmol) was added dropwise. The r.m. was stirred for 20 min at 5° C. then, at r.t. for 3 h. The r.m. was poured onto ice and the aq. layer was extracted with EtOAc. The organic layer was dried over MgSO$_4$, filtered and evaporated to dryness. The residue was crystallized from Et$_2$O and dried to give 3 g (87%) of intermediate 44.

c) Preparation of Intermediate 45

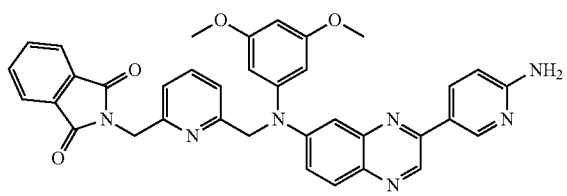 [SMILES: COc1cc(OC)cc(N(Cc2cccc(CN3C(=O)c4ccccc4C3=O)n2)c2ccc3ncc(-c4ccc(N)nc4)nc3c2)c1]

A mixture of intermediate 44 (1.2 g; 2.12 mmol), 2-aminopyridine-5-boronic acid pinacol ester (0.56 g; 2.54 mmol), S-Phos (87 mg; 0.21 mmol) and potassium phosphate (900 mg; 4.24 mmol) in 1,4-dioxane (58 mL) and water (17 mL) was stirred at r.t. under a N2 flow (bubbling). After 10 min, Pd$_2$(dba)$_3$ was added portionwise and the mixture was heated at 80° C. for 20 h. The r.m. was cooled down to r.t.

and poured onto ice water. EtOAc was added and the mixture was filtered through a pad of Celite® which was washed with EtOAc. The organic and aq. layers were separated. Then, the aq. layer was extracted with EtOAc. The organic layers were mixed, washed with brine, dried over MgSO$_4$, filtered and the solvent was evaporated to dryness. The residue was purified by chromatography over silica gel (Spherical Silica 5 μm 150×30.0 mm; mobile phase: gradient from 0% NH$_4$OH, 100% DCM, 0% MeOH to 0.7% NH$_4$OH, 93% DCM, 7% MeOH). The pure fractions were evaporated to dryness to give 0.22 g (16%) of intermediate 45.

Example A24 a) Preparation of Intermediate 46 and Intermediate 46a intermediate 46

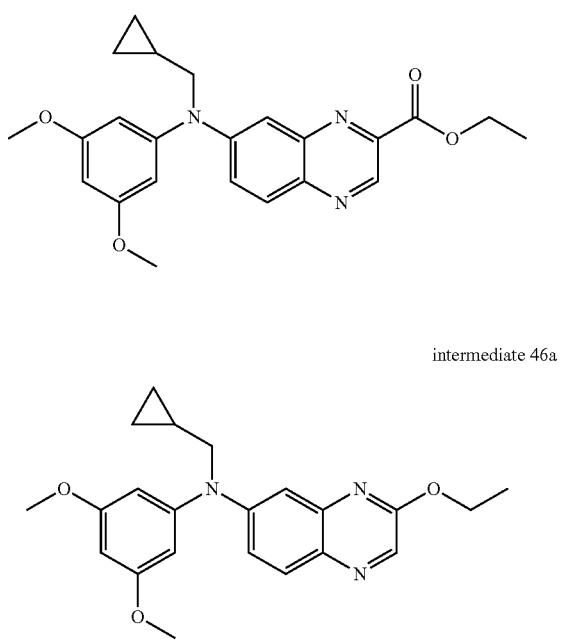

intermediate 46a

A mixture of intermediate 21 (3.2 g; 8.65 mmol), Pd(OAc)$_2$ (194 mg; 0.86 mmol), PPh$_3$ (3.4 g; 12.98 mmol), K$_2$CO$_3$ (2.39 g; 17.30 mmol) in DMF (32 mL) and EtOH (32 mL) was heated at 90° C. overnight under 10 Bars of CO$_2$ in a pressure vessel. The r.m. was cooled to r.t. and poured onto ice water. EtOAc was added and the mixture was filtered through a pad of Celite® which was washed with EtOAc. Then, the filtrate was extracted with EtOAc. The organic layer washed with brine, dried over MgSO$_4$, filtered and evaporated to dryness. The residue was purified by chromatography over silica gel (Irregular SiOH 15-40 μm 90 g; mobile phase: 80% cyclohexane, 20% EtOAc). Two product fractions were collected and evaporated to dryness: 500 mg (14%) of intermediate 46; and 340 mg of an intermediate residue which was crystallized from DI PE/pentane, filtered and dried in vacuum yielding 108 mg (3%) of intermediate 46a (MP: 85° C. Kofler).

b) Preparation of Intermediate 47

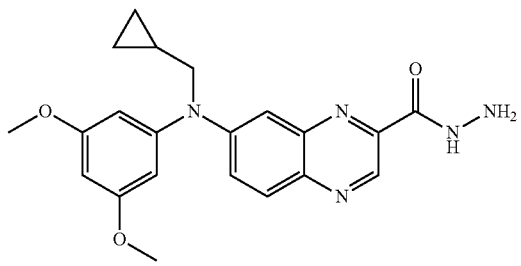 [SMILES: COc1cc(OC)cc(N(CC2CC2)c2ccc3ncc(C(=O)NN)nc3c2)c1]

Hydrazine monohydrate (381 μL; 12.27 mmol) was added dropwise at r.t. to a suspension of intermediate 46 (500 mg; 1.23 mmol) in EtOH (15 mL). The r.m. was heated at 80° C. for 6 h, cooled down to r.t. and evaporated to dryness. The residue was triturated with Et$_2$O. The precipitate was filtered and dried under vacuum to give 420 mg (87%) of intermediate 47.

Example A25

Preparation of Intermediate 48

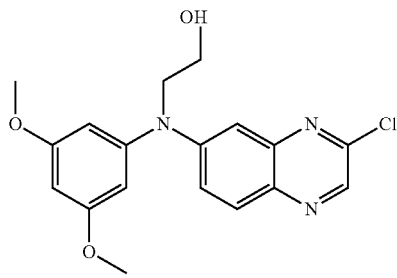 [SMILES: COc1cc(OC)cc(N(CCO)c2ccc3ncc(Cl)nc3c2)c1]

A solution of TBAF 1M in THF (1.7 mL; 1.671 mmol) was added dropwise to a solution of intermediate 5b (720 mg; 1.519 mmol) in THF (14 mL) at r.t. The r.m. was stirred at r.t. for 2 h, poured onto water and extracted with DCM. The organic layer was decanted, dried over MgSO$_4$, filtered and evaporated to dryness. The residue was purified by chromatography over silica gel (Irregular SiOH 15-40 μm 30 g; mobile phase: gradient from 100% DCM, 0% MeOH to 97% DCM, 3% MeOH). The pure fractions were collected and evaporated to dryness yielding 491 mg (90%) of intermediate 48.

Example A26-A

Preparation of Intermediate 49

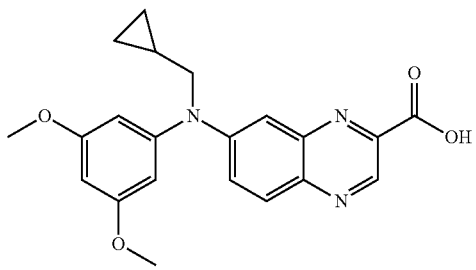 [SMILES: COc1cc(OC)cc(N(CC2CC2)c2ccc3ncc(C(=O)O)nc3c2)c1]

A mixture of intermediate 21 (2.4 g, 6.49 mmol) and potassium acetate (1.4 g; 14.27 mmol) in 1,4-dioxane (50 mL) was degassed for 10 min. Pd(PPh$_3$)$_4$ (0.75 g; 0.65 mmol) was added and the r.m. was heated at 100° C. under 10 Bars of CO$_2$ for 15 h. The reaction was cooled to r.t., poured onto water and extracted with EtOAc. The r.m. was decanted and the aq. layer was extracted twice with EtOAc. The combined organic layers were washed with brine, dried over MgSO$_4$, filtered and evaporated to dryness. The solid residue was taken up with ACN and the precipitate was filtered off, washed with Et$_2$O and dried yielding 1.6 g (65%) of intermediate 49. The filtrate was evaporated to dryness. The residue was purified by chromatography over silica gel (Irregular SiOH, 15-40 µm 50 g; mobile phase: gradient from 0% aq. formic acid, 95% DCM, 5% MeOH to 0.2% aq. formic acid, 93% DCM, 7% MeOH). The pure fractions were collected and evaporated to dryness. The resulting residue was taken up with ACN/Et$_2$O. The precipitate was filtered and dried yielding an additional amount (143 mg; 6%) of intermediate 49 (MP: 196° C. (DSC)).

Example A26-B a) Preparation of Intermediate 50

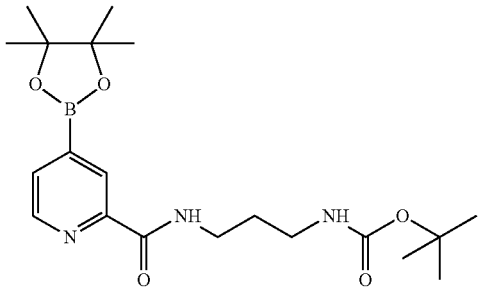 [SMILES: CC(C)(C)OC(=O)NCCCNC(=O)c1cc(B2OC(C)(C)C(C)(C)O2)ccn1]

A mixture of [3-[[(4-chloro-2-pyridinyl)carbonyl]amino]propyl]carbamic acid, 1,1-dimethylethyl ester (1.32 g; 4.21 mmol), bis(pinacolato)diboron (1.28 g; 5.05 mmol), potassium acetate (619 mg; 6.31 mmol), S-Phos (104 mg; 0.25 mmol) in 1,4-dioxane (20 mL) was degassed with N2. After 10 min, Pd(OAc)$_2$ (28 mg; 0.13 mmol) was added. The r.m. was heated at 100° C. for 1 h. The r.m. was cooled to r.t. and poured into water. EtOAc was added and the mixture was filtered through of layer of Celite®. The organic layer was washed with brine, dried over MgSO$_4$, filtered and evaporated to dryness yielding intermediate 50 which was used as such for the next reaction step.

b) Preparation of Intermediate 51

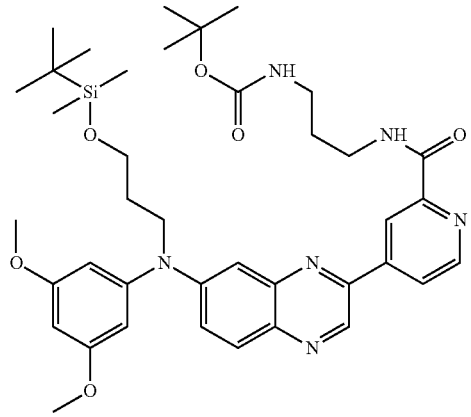 [SMILES: COc1cc(OC)cc(N(CCCO[Si](C)(C)C(C)(C)C)c2ccc3ncc(-c4ccnc(C(=O)NCCCNC(=O)OC(C)(C)C)c4)nc3c2)c1]

A mixture of intermediate 5a (1 g; 2.05 mmol), intermediate 50 (1.16 g; 2.87 mmol), K$_3$PO$_4$ (869 mg; 4.1 mmol), S-Phos (84 mg; 0.21 mmol) in 1,4-dioxane (25 mL) and H$_2$O (8 mL) was stirred at r.t. under N2 flow. After 10 min, Pd$_2$(dba)$_3$ (187 mg; 0.21 mmol) was added portionwise. The r.m. was heated at 100° C. for 4 h, cooled to r.t., poured onto ice water and extracted with EtOAc. The organic layer was dried over MgSO$_4$, filtered and evaporated to dryness. The residue was purified by chromatography over silica gel (Irregular SiOH 15-40 µm 40 g; mobile phase: gradient from 100% DCM, 0% MeOH, 0% NH$_4$OH to 95% DCM, 5% MeOH, 0.5% NH$_4$OH). The pure fractions were collected and evaporated to dryness yielding 1.35 g (90%) of intermediate 51.

Example A27 a) Preparation of Intermediate 52

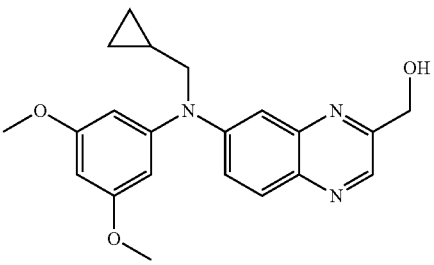 [SMILES: COc1cc(OC)cc(N(CC2CC2)c2ccc3ncc(CO)nc3c2)c1]

Isobutyl chloroformate (2 mL; 15.4 mmol) was added drop wise at 5° C. to a solution of intermediate 49 (4.5 g; 11.86 mmol) and Et$_3$N (3.3 mL; 23.72 mmol) in THF (40 mL). The r.m. was stirred at this temperature for 1 h, and was then added dropwise to a solution of sodium borohydride (897 mg; 23.721 mmol) in a mixture of THF (40 mL) and water (80 mL) keeping the temperature at 5° C. The r.m. was stirred at this temperature for 1 more h, and was then quenched with water and extracted with EtOAc. The organic layer was separated, washed with brine, dried over MgSO$_4$, filtered and evaporated to dryness. The residue was purified by chromatography over silica gel (Irregular SiOH 15-40 µm 300 g; mobile phase: 0.5% NH$_4$OH, 97% DCM, 3% MeOH). The pure fractions were collected and evaporated to dryness yielding 1.5 g (35%) of intermediate 52.

b) Preparation of Intermediate 53

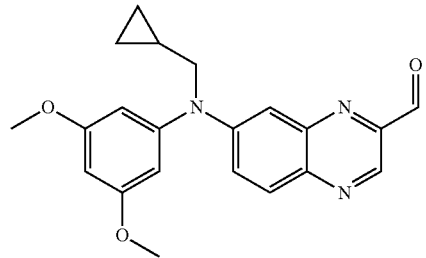 [SMILES: COc1cc(OC)cc(N(CC2CC2)c2ccc3ncc(C=O)nc3c2)c1]

Manganese (IV) oxide (1.49 g; 17.1 mmol) was added to a solution of intermediate 52 (1.25 g; 3.42 mmol) in DCM (50 mL). The r.m. was refluxed for 18 h, then, cooled down to r.t. and the catalyst was removed by filtration. The filtrate was evaporated to dryness yielding 1.2 g (96%) of intermediate 53 which was directly used in the next reaction step without any further purification.

Example A28

Preparation of Intermediate 54

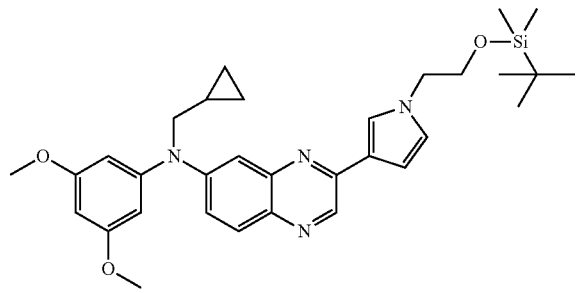 [SMILES: COc1cc(OC)cc(N(CC2CC2)c2ccc3ncc(-c4ccn(CCO[Si](C)(C)C(C)(C)C)c4)nc3c2)c1]

NaH 60% in oil (104 mg; 2.6 mmol) was added portion wise at 0° C. to compound 36 (650 mg; 1.62 mmol) and (2-bromoethoxy)-tert-butyldimethylsilane (621 mg; 2.6 mmol) in THF (5 mL). The mixture was refluxed overnight in a sealed tube, poured into ice and extracted with EtOAc. The organic layer was dried over $MgSO_4$, filtered and evaporated until dryness. The residue was purified by chromatography over silica gel (SiOH 15-40 μm 30 g; mobile phase: 98% DCM, 2% MeOH). The pure fractions were evaporated until dryness to give 570 mg (63%) of intermediate 54.

Example A29

Preparation of Intermediate 55

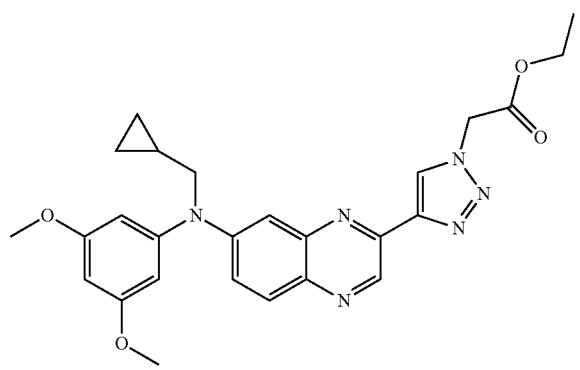 [SMILES: CCOC(=O)Cn1cc(-c2cnc3ccc(N(CC4CC4)c4cc(OC)cc(OC)c4)cc3n2)nn1]

CuI (19 mg; 0.10 mmol) then DIPEA (302 μL; 1.73 mmol) were added at 5° C. to a solution of intermediate 23 (362 mg; 1.01 mmol) and ethyl azidoacetate (0.5 mL; 2.01 mmol) in THF (10 mL). The r.m. was stirred at r.t. for 3 h poured onto water and extracted with EtOAc. The organic layer was decanted, dried over $MgSO_4$, filtered and evaporated to dryness. The residue was purified by chromatography over silica gel (Spherical Silica 5 μm 150×30.0 mm; mobile phase: gradient from 0% $NH_4OH$, 100% DCM, 0% MeOH to 0.3% $NH_4OH$, 97% DCM, 3% MeOH). The pure fractions were collected and evaporated to dryness yielding 370 mg (75%) of intermediate 55.

Example A30 a) Preparation of Intermediate 56

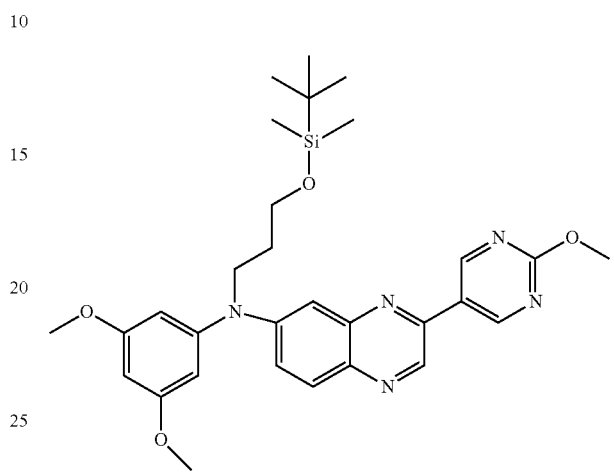

A mixture of intermediate 5a (500 mg; 1.02 mmol), 2-methoxypyrimidine-5-boronic acid (237 mg; 1.54 mmol), $K_3PO_4$ (435 mg; 2.05 mmol) and S-Phos (84 mg; 0.21 mmol) in 1,4-dioxane (12.25 mL) and $H_2O$ (5 mL) was degassed with N2. After 10 min, $Pd_2(dba)_3$ (94 mg; 0.10 mmol) was added portionwise. The r.m. was heated at 90° C. for 5 h, cooled to r.t., poured onto ice water and extracted with EtOAc. The organic layer was washed with brine, dried over $MgSO_4$, filtered and evaporated to dryness. The residue was purified by chromatography over silica gel (Irregular SiOH 15-40 μm 300 g; mobile phase: 98% DCM, 2% MeOH). The pure fractions were collected and evaporated to dryness yielding 420 mg (73%) of intermediate 56.

Intermediate 56 is used in the synthesis of compound 141.

The following intermediates were synthesized according to an analogous reaction protocol:

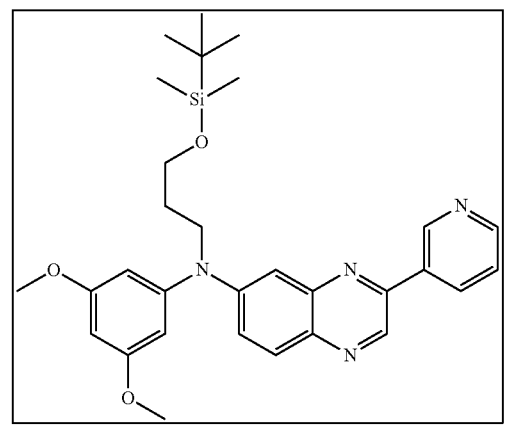 [SMILES: COc1cc(OC)cc(N(CCCO[Si](C)(C)C(C)(C)C)c2ccc3ncc(-c4cccnc4)nc3c2)c1]

b-1) Preparation of Intermediate 57

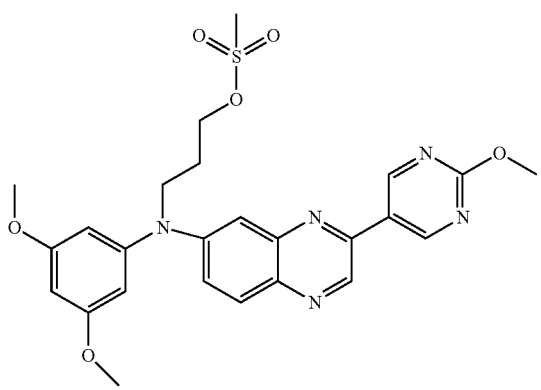 [SMILES: COc1cc(OC)cc(N(CCCOS(C)(=O)=O)c2ccc3ncc(-c4cnc(OC)nc4)nc3c2)c1]

Methanesulfonyl chloride (64 µL; 0.83 mmol) was added dropwise at 5° C. under N2 flow to a solution of compound 141 (275 mg; 0.61 mmol), and Et₃N (132 µL; 0.92 mmol) in DCM (10 mL). The r.m. was allowed to warm to r.t. and stirred for 2 h. The r.m. was diluted with DCM and water was added. The organic layer was decanted, dried over MgSO₄, filtered and evaporated to dryness yielding 302 mg (93%) of intermediate 57.

b-2) Preparation of Intermediate 58

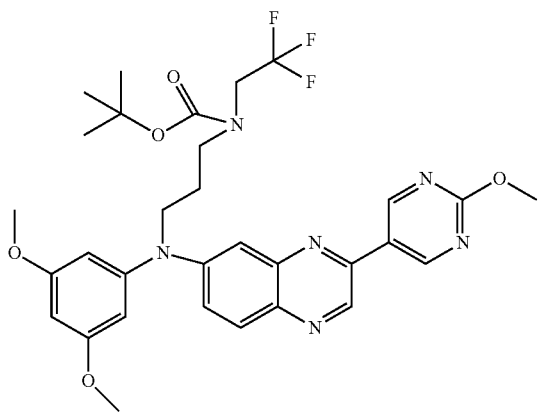 [SMILES: COc1cc(OC)cc(N(CCCN(CC(F)(F)F)C(=O)OC(C)(C)C)c2ccc3ncc(-c4cnc(OC)nc4)nc3c2)c1]

NaH 60% in oil (45.7 mg; 1.14 mmol) was added portionwise to a solution of intermediate 57 (300 mg; 0.57 mmol) in DMA (10 mL) at 5° C. under N2 flow. The r.m. was stirred at 5° C. for 15 min, and then tert-butyl N-(2,2,2-trifluoroethyl) carbamate (227 mg; 1.14 mmol) was added. The r.m. was allowed to warm to r.t., quenched with water and extracted with EtOAc. The organic layer was decanted, washed with brine, dried over MgSO₄, filtered and evaporated to dryness yielding intermediate 58 which was used as such for the next reaction step.

Example A31 a) Preparation of Intermediate 59

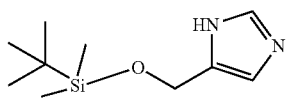

Et₃N (1.7 mL; 12.3 mmol) followed by tert-butyldimethylsilylchloride (0.82 g; 5.44 mmol) were added to a solution of 4(5)-(hydroxymethyl)-imidazole (0.5 g; 4.94 mmol) in DMF (7 mL). The r.m. was stirred for 3 h at r.t. and partitioned between water and EtOAc. The organic layer was dried over MgSO₄, filtered and concentrated. The residue was purified by chromatography over silica gel (mobile phase: 100% DCM) to afford 920 mg (87%; colourless oil) of intermediate 59.

b) Preparation of Intermediate 60

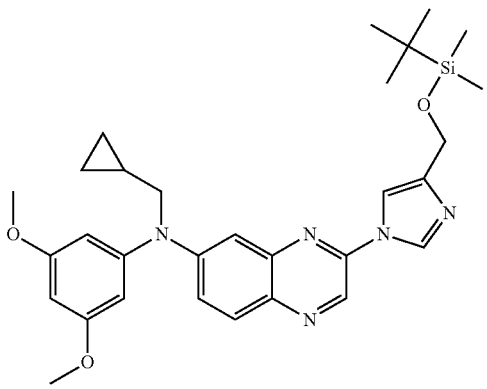 [SMILES: COc1cc(OC)cc(N(CC2CC2)c2ccc3ncc(-n4cnc(CO[Si](C)(C)C(C)(C)C)c4)nc3c2)c1]

NaH (26 mg; 0.649 mmol) was added at 0° C. to intermediate 59 (122 mg; 0.54 mmol) in solution in DMF (2 mL). The mixture was stirred for 30 min at 0° C. then intermediate 21 (200 mg; 0.54 mmol) in solution in DMF (1 mL) was added. The r.m. was heated at 65° C. overnight, cooled down to r.t. and partitioned between water and EtOAc. The organic layer was dried over MgSO₄, filtered and concentrated. The residue (302 mg, orange oil) was purified by chromatography over silica gel (Spherical SiOH 10 µm 60 g; mobile phase: 0.1% NH₄OH, 97% DCM, 3% MeOH). The pure fractions were mixed and concentrated to give 2 fractions of respectively 85 mg (29%) and 61 mg (21%) of intermediate 60.

Intermediate 60 was used for the synthesis of compound 105.

Example A32

Preparation of Intermediate 61

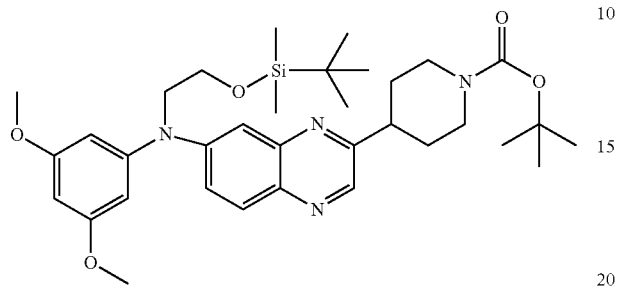

4-Piperidinylzinc iodide (610 mg; 1.62 mmol) was added dropwise under N2 flow to a mixture of intermediate 5b (554 mg; 1.16 mmol), PdCl$_2$dppf.DCM complex (28 mg; 0.035 mmol) and CuI (13 mg; 0.069 mmol) in DMA (3 mL). The mixture was stirred at 115° C. for 3 h. The r.m. was poured ice water and extracted with EtOAc. The organic layer was washed with water, dried over MgSO$_4$, filtered and evaporated to dryness. The residue was purified by chromatography over silica gel (Spherical Silica 5 μm 150×30.0 mm; mobile phase: gradient from 100% DCM, 0% MeOH, 0% NH$_4$OH to 97% DCM, 3% MeOH, 0.3% NH$_4$OH). The pure fractions were evaporated to dryness yielding 65 mg (9%) of intermediate 61.

Example A33

Preparation of Intermediate 62 and Intermediate 63 intermediate 62

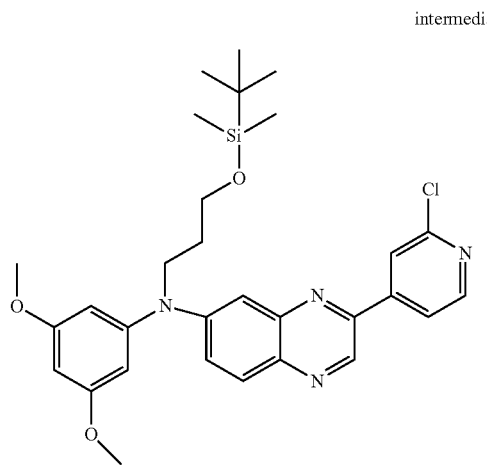

intermediate 63

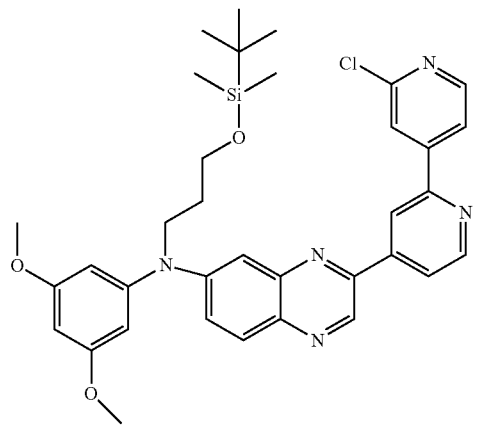

A mixture of intermediate 5a (500 mg; 1.024 mmol), 2-chloropyridine-4-boronic acid (242 mg; 1.537 mmol), K$_3$PO$_4$ (435 mg; 2.05 mmol) and S-Phos (84 mg; 0.21 mmol) in 1,4-dioxane (12 mL) and H$_2$O (5 mL) was degassed with N2. After 10 min, Pd$_2$(dba)$_3$ (94 mg; 0.10 mmol) was added portionwise. The r.m. was heated at 80° C. for 3 h, cooled to r.t., poured onto ice water and extracted with EtOAc. The organic layer was washed with brine, dried over MgSO$_4$, filtered and evaporated to dryness. The residue was purified by chromatography over silica gel (Irregular SiOH 15-40 μm 300 g; mobile phase: 60% heptane, 40% EtOAc). The pure fractions were collected and evaporated to dryness yielding 325 mg (56%) of intermediate 62 and 207 mg (31% of intermediate 63.

Intermediate 62 was used for the synthesis of compound 136.

Intermediate 63 was used for the synthesis of compound 133.

Example A34 a) Preparation of Intermediate 64

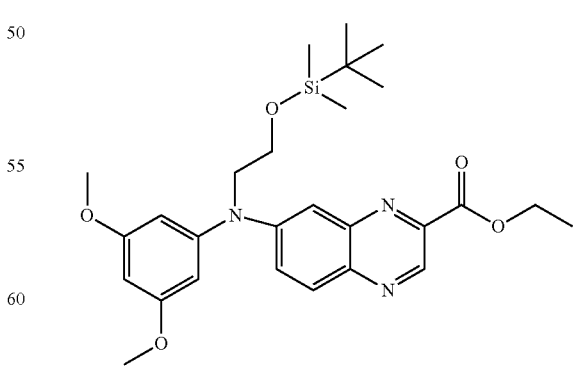

A mixture of intermediate 5b (3 g; 6.33 mmol), palladium (II) acetate (710 mg; 3.16 mmol), 1,3-bis(diphenylphosphino) propane (1.3 g; 3.16 mmol) and potassium acetate (1.2 g; 12.66 mmol) in EtOH (120 mL) was heated under 5 bars of CO in a pressure vessel at 90° C. for 18 h. The r.m. was filtered over a pad of Celite® and the filtrate was evaporated to dryness. The residue was filtered over a pad of silica gel (Irregular SiOH 60 µM; mobile phase: 99% DCM, 1% MeOH). The filtrate was evaporated to dryness yielding 3.4 g (100%) of intermediate 64.

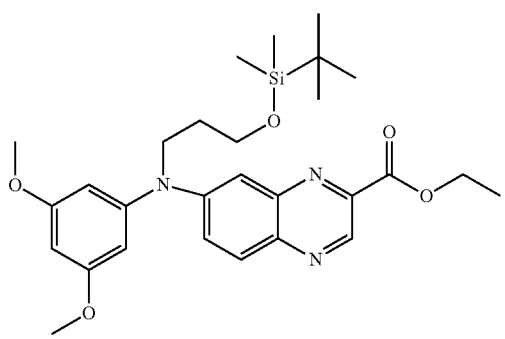 [SMILES: CCOC(=O)c1cnc2ccc(N(CCCO[Si](C)(C)C(C)(C)C)c3cc(OC)cc(OC)c3)cc2n1]

(intermediate 64b) was prepared according to an analogous protocol, but intermediate 5a was used instead of intermediate 5b.

b) Preparation of Intermediate 65

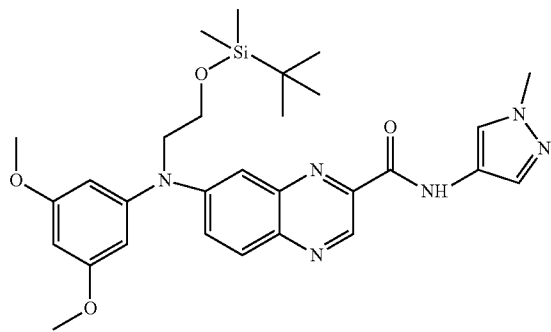 [SMILES: COc1cc(OC)cc(N(CCO[Si](C)(C)C(C)(C)C)c2ccc3ncc(C(=O)Nc4cnn(C)c4)nc3c2)c1]

A mixture of intermediate 64 (500 mg; 0.98 mmol) and 1-methyl-1-H-pyrazol-4-ylamine (285 mg; 2.93 mmol) in N,N-diisopropylethylamine (5 mL) was heated at 90° C. for 18 h in a sealed tube. The r.m. was poured onto water and extracted with DCM. The organic layer was decanted, dried over MgSO₄, filtered and evaporated to dryness. The residue was purified by chromatography over silica gel (Irregular SiOH 15-40 µm, 40 g; mobile phase: 98% DCM, 2% MeOH). The pure fractions were collected and evaporated to dryness yielding 65 mg (12%) of intermediate 65.

Intermediate 65 was used for the synthesis of compound 184.

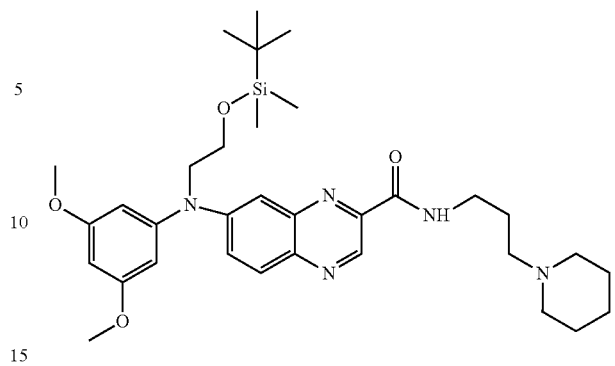

was prepared from intermediate 64 according to an analogous protocol, but 1-(3-aminopropyl)-piperidine was used instead of 1-methyl-1-H-pyrazol-4-ylamine, and no N,N-diisopropylethylamine was added to the r.m. Used for the synthesis of compound 177.

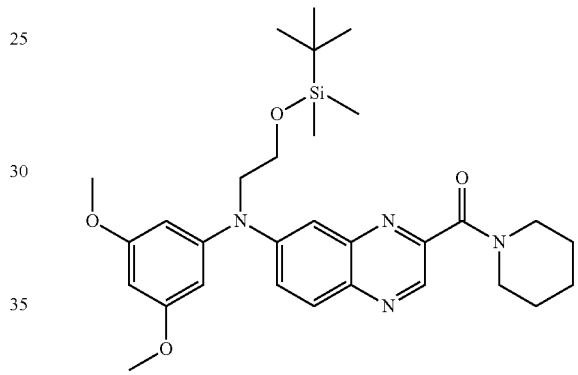

was prepared from intermediate 64 according to an analogous protocol, but piperidine was used instead of 1-methyl-1-H-pyrazol-4-ylamine, and no N,N-diisopropylethylamine was added to the r.m. Used for the synthesis of compound 175.

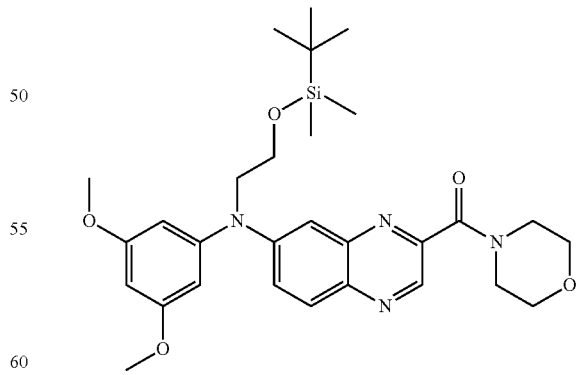

was prepared from intermediate 64 according to an analogous protocol, but morpholine was used instead of 1-methyl-1-H-pyrazol-4-ylamine, and no N,N-diisopropylethylamine was added to the r.m. Used for the synthesis of compound 176.

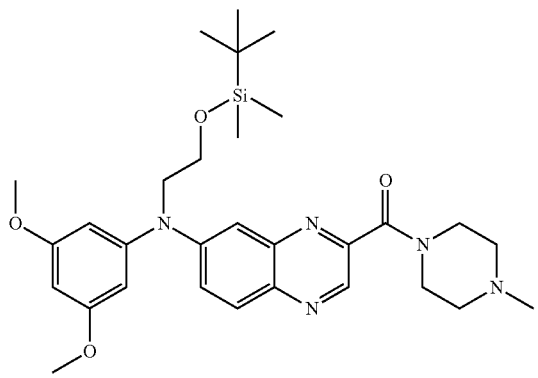 [SMILES: COc1cc(OC)cc(N(CCO[Si](C)(C)C(C)(C)C)c2ccc3ncc(C(=O)N4CCN(C)CC4)nc3c2)c1]

was prepared from intermediate 64 according to an analogous protocol, but 1-methylpiperazine was used instead of 1-methyl-1-H-pyrazol-4-ylamine, and no N,N-diisopropylethylamine was added to the r.m. Used for the synthesis of compound 174.

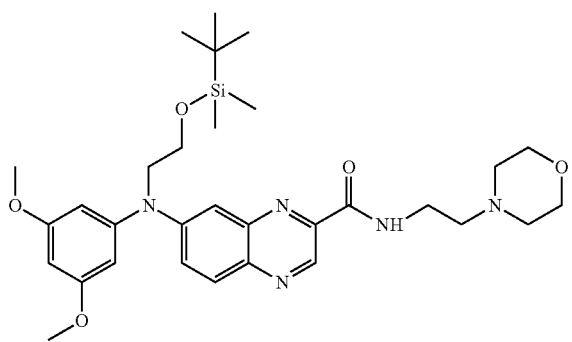 [SMILES: COc1cc(OC)cc(N(CCO[Si](C)(C)C(C)(C)C)c2ccc3ncc(C(=O)NCCN4CCOCC4)nc3c2)c1]

was prepared from intermediate 64 according to an analogous protocol, but 4-(2-aminoethyl)-morpholine was used instead of 1-methyl-1-H-pyrazol-4-ylamine, and no N,N-diisopropylethylamine was added to the r.m. Used for the synthesis of compound 153.

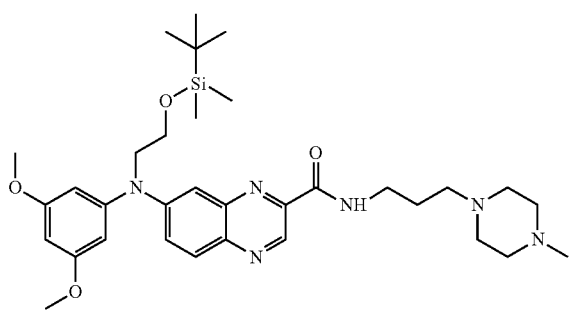 [SMILES: COc1cc(OC)cc(N(CCO[Si](C)(C)C(C)(C)C)c2ccc3ncc(C(=O)NCCCN4CCN(C)CC4)nc3c2)c1]

was prepared from intermediate 64 according to an analogous protocol, but 1-(3-aminopropyl)-4-methyl piperazine was used instead of 1-methyl-1-H-pyrazol-4-ylamine, and no N,N-diisopropylethylamine was added to the r.m. Used for the synthesis of compound 154.

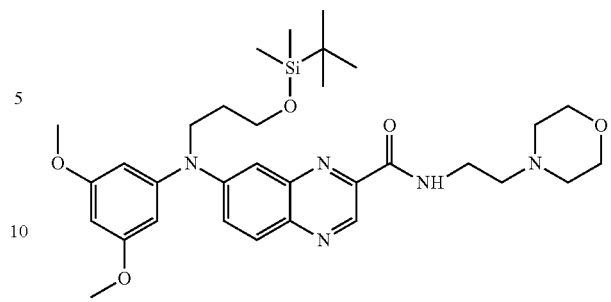

was prepared from intermediate 64b according to an analogous protocol, but 2-morpholinoethanamine was used instead of 1-methyl-1-H-pyrazol-4-ylamine, and no N,N-diisopropylethylamine was added to the r.m. Used for the synthesis of compound 152.

Example A35 a) Preparation of Intermediate 66

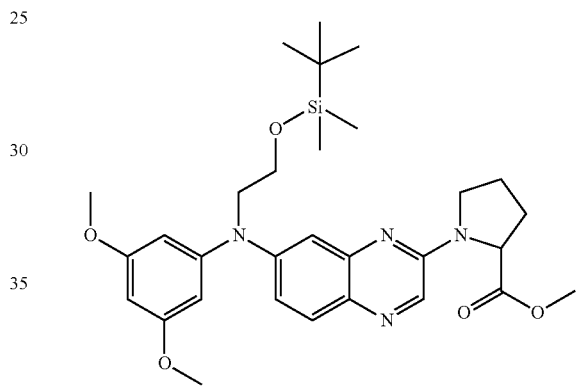

A mixture of intermediate 5b (500 mg; 1.055 mmol), L-proline methyl ester hydrochloride (349 mg; 2.11 mmol) and Et₃N (0.44 mL; 3.16 mmol) in ACN was heated at 90° C. for 18 h. The r.m. was poured onto water and extracted with DCM. The organic layer was decanted, dried over MgSO₄, filtered and evaporated to dryness. The residue was purified by chromatography over silica gel (irregular 15-40 μm 30 g; mobile phase: gradient from 100% DCM, 0% MeOH to 97% DCM, 3% MeOH). The pure fractions were collected and evaporated to dryness yielding 125 mg (21%) of intermediate 66. Intermediate 66 was used for the synthesis of compound 172.

Example A36 a) Preparation of Intermediate 67

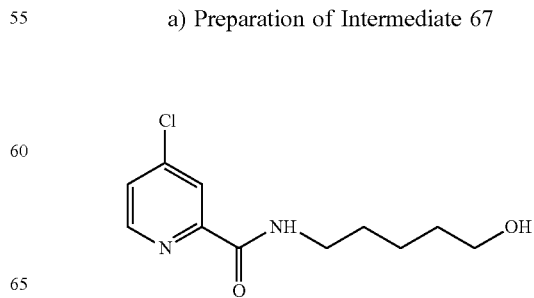

Methyl 4-chloropicolinate (2 g; 11.66 mmol) was added portionwise at 70° C. to a solution of 5-amino-1-pentanol (6 g; 58.28 mmol) in THF (120 mL). The r.m. was refluxed for 2 hours, cooled to r.t. and evaporated to dryness. The residue was purified by chromatography over silica gel (Irregular SiOH 20-45 µm 450 g; mobile phase: 0.5% NH₄OH, 95% DCM, 5% MeOH). The pure fractions were collected and evaporated to dryness yielding 2.3 g (81%) of intermediate 67.

b) Preparation of Intermediate 68

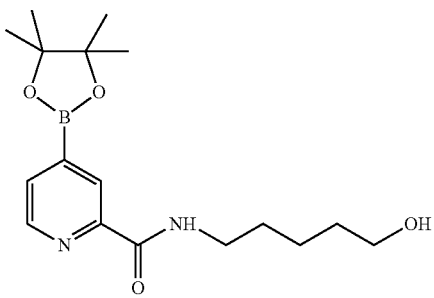 [SMILES: CC1(C)OB(c2ccnc(C(=O)NCCCCCO)c2)OC1(C)C]

A mixture of intermediate 67 (2.3 g; 9.48 mmol), bis (pinacolato)diboron (2.9 g; 11.37 mmol), potassium acetate (1.4 g; 14.22 mmol), S-Phos (233 mg; 0.57 mmol) in 1,4-dioxane (40 mL) was degassed with N2. After 10 min, Palladium(II) acetate (281 mg; 0.31 mmol) was added. The r.m. was heated at 100° C. for 6 h, cooled to r.t., poured onto ice water and extracted with DCM. The organic layer was washed with brine, dried over MgSO₄, filtered and evaporated to dryness yielding intermediate 68 which was used as it is for the next step.

Example A37 a) Preparation of Intermediate 70

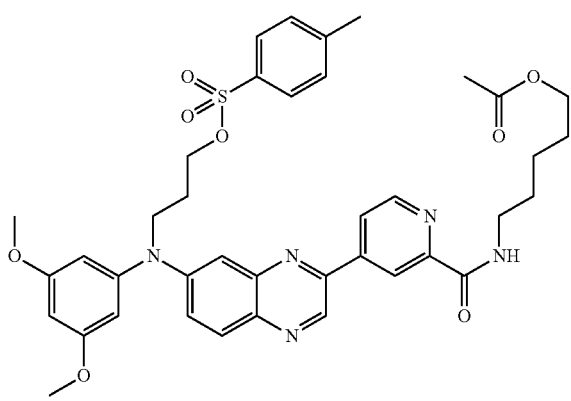 [SMILES: COc1cc(OC)cc(N(CCCOS(=O)(=O)c2ccc(C)cc2)c2ccc3ncc(-c4ccnc(C(=O)NCCCCCOC(C)=O)c4)nc3c2)c1]

Intermediate 70 was prepared according to an analogous reaction protocol as described in Example A3.

b) Preparation of Intermediate 71

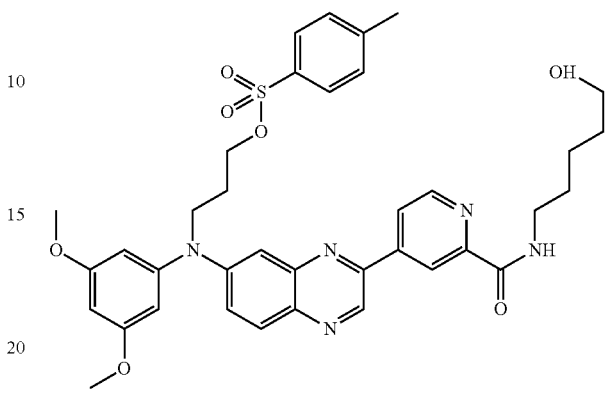

K₂CO₃ (782 mg; 5.66 mmol) was added to a solution of intermediate 70 (1.4 g; 1.89 mmol) in MeOH (100 mL). The r.m. was stirred at r.t. overnight, poured onto water and extracted with DCM. The organic layer was decanted, dried over MgSO₄, filtered and evaporated to dryness. The residue was purified by chromatography over silica gel (Irregular SiOH 15-40 µm 50 g; mobile phase: 95% DCM, 5% MeOH, 0.5% NH₄OH). The pure fractions were collected and evaporated to dryness yielding 1.11 g (84%) of intermediate 71.

Example A38 a) Preparation of Intermediate 72

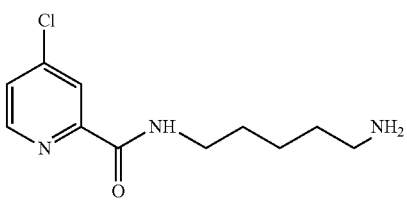 [SMILES: NCCCCCNC(=O)c1cc(Cl)ccn1]

4-chloro-2-Pyridinecarboxylic acid methyl ester (1.5 g; 8.72 mmol) was added portionwise at 70° C. to a solution of 1,5-diaminopentane (5 g; 48.93 mmol) in THF (90 mL). The r.m. was refluxed for 5 h, cooled to r.t. and the solvent was evaporated. The residue was taken up with DCM and the organic layer was washed with water several times, dried over MgSO₄, filtered and evaporated to dryness. The residue was purified by chromatography over silica gel (Irregular SiOH 20-45 µm 450 g; mobile phase: 1% NH₄OH, 90% DCM, 10% MeOH). The pure fractions were collected and evaporated to dryness yielding 1.55 g (73%) of intermediate 72.

b) Preparation of Intermediate 73

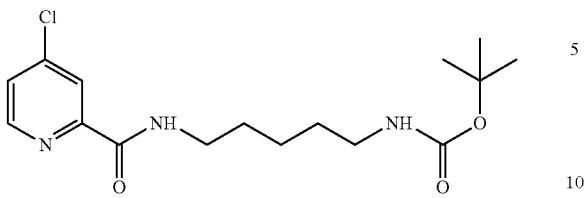

di-tert-butyl dicarbonate (1.8 g; 8.34 mmol) was added portionwise to a solution of intermediate 72 (1.55 g; 6.41 mmol), DMAP (78 mg; 0.64 mmol) and Et$_3$N (1.34 mL; 9.62 mmol) in THF (30 mL). The r.m. was allowed to warm to r.t. and stirred for 1 h. The r.m. was diluted with DCM and water was added. The organic layer was decanted, dried over MgSO$_4$, filtered and evaporated to dryness. The residue was purified by chromatography over silica gel (Irregular SiOH 15-40 µm 40 g; mobile phase: 98% DCM, 2% MeOH). The pure fractions were collected and evaporated to dryness yielding 2 g (91%) of intermediate 73.

c) Preparation of Intermediate 74

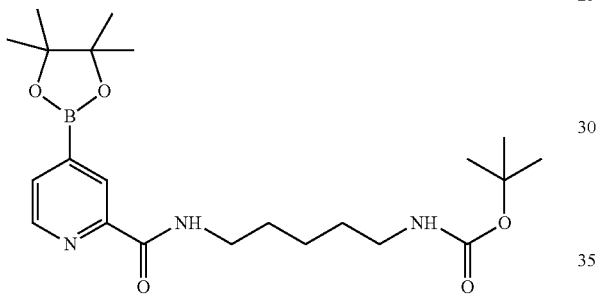

A mixture of intermediate 73 (1.92 g; 5.62 mmol), bis(pinacolato)diboron (1.71 g; 6.74 mmol), potassium acetate (827 mg; 8.42 mmol), S-Phos (138 mg; 0.34 mmol) in 1,4-dioxane (40 mL) was degassed with N2. After 10 min, Pd(OAc)$_2$ (38 mg; 0.17 mmol) was added. The r.m. was heated at 100° C. for 1 hour, cooled to r.t., poured onto ice water and extracted with EtOAc. The organic layer was washed with brine, dried over MgSO$_4$, filtered and evaporated to dryness yielding intermediate 74 which was used as such for the next reaction step.

Example A39

Preparation of a Mixture of Intermediates 77 and 78 intermediate 77

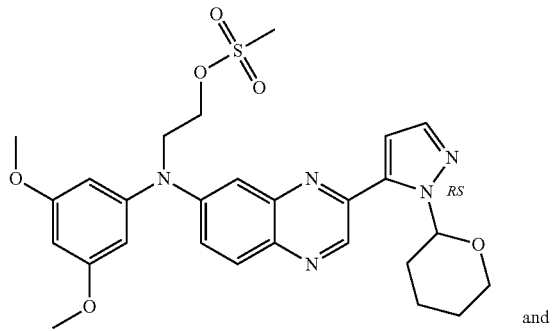

and intermediate 78

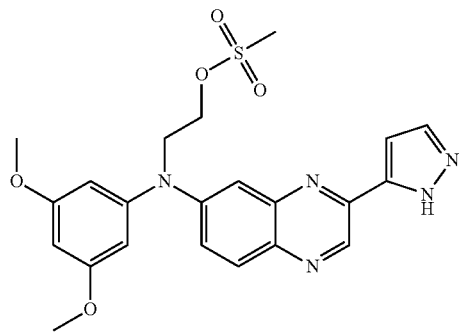

Methanesulfonyl chloride (0.249 mL; 3.22 mmol) was added drop wise to a solution of compound 187 (0.51 g; 1.07 mmol) and triethylamine (0.448 ml; 3.22 mmol) in DCM (10 mL) at −10° C. under N2 flow. The reaction mixture was stirred below 0° C. for 1 hour then, at room temperature overnight. The reaction mixture was poured onto ice and DCM was added. The organic layer was separated, dried over MgSO$_4$, filtered and the solvent was evaporated to dryness (rotovapor bath temperature: 25 to 30° C.) to give 0.59 g of a mixture of intermediate 77 and intermediate 78 which was used in the next step without further purification.

B. Preparation of the Compounds

Example B1

Preparation of Compound 1

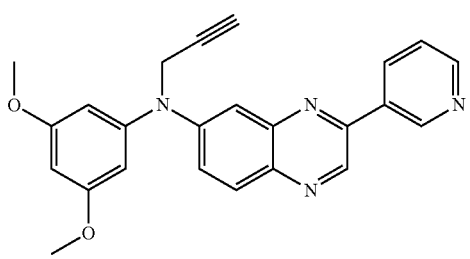 [SMILES: C#CCN(c1cc(OC)cc(OC)c1)c1ccc2ncc(-c3cccnc3)nc2c1]

K$_2$CO$_3$ (0.43 g; 3.1 mmol) was added to intermediate 4 as obtained in Example A1.d (1.45 g; 3.1 mmol) in MeOH (40 mL). The solution was stirred at r.t. for 3 h, poured onto water and extracted with EtOAc. The organic layer was dried over MgSO$_4$, filtered and evaporated to dryness yielding 1.1 g (89%) of compound 1.

Example B2

Preparation of Compounds 3a, 3 and 4

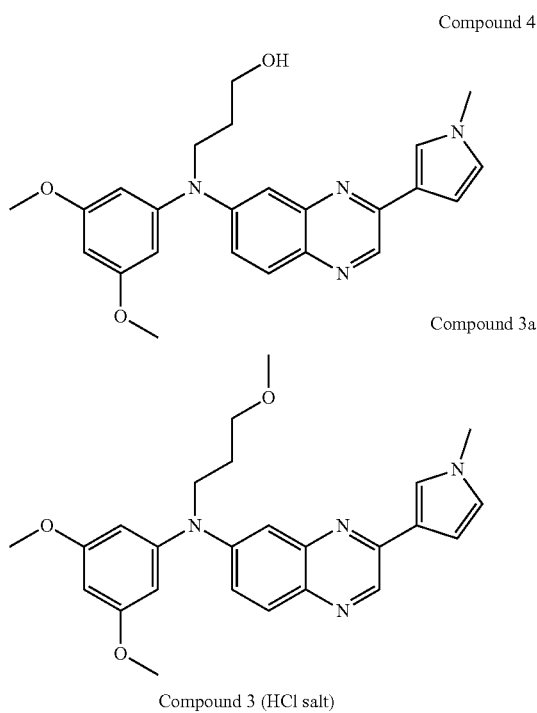

Compound 4

Compound 3a

Compound 3 (HCl salt)

A solution of TBAF (3.1 mL; 3.14 mmol) was added drop wise to a solution of the crude residue (1.9 g) obtained in Example A2.c (containing intermediate 7) in THF (30 mL) at r.t. The r.m. was stirred for 3 h, then water was added and the solvent was evaporated under vacuum. The residue was extracted with EtOAc. The organic layer was dried over MgSO$_4$, filtered and evaporated to dryness. The residue was purified by chromatography over silica gel (Irregular SiOH 15-40 μm 300 g; mobile phase: gradient from 99% DCM, 1% MeOH to 98% DCM, 2% MeOH). The pure fractions were collected and evaporated to dryness yielding 585 mg (72%) of compound 4 and 55 mg of compound 3a which was converted into its hydrochloride salt in MeOH/Et$_2$O. The precipitate was filtered and dried yielding 49 mg (15%) of compound 3 (1.06 HCl) (MP: 180° C. DSC).

Example B3

Preparation of Compounds 5 and 5a

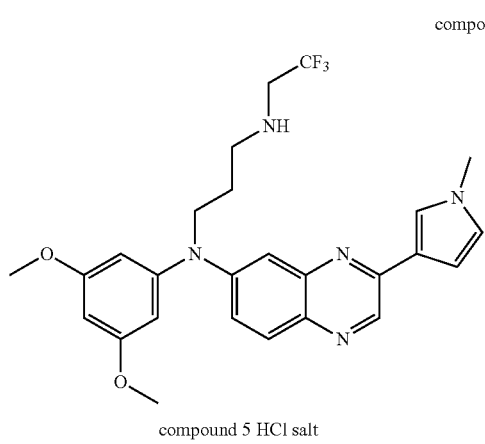

compound 5a compound 5 HCl salt

A mixture of intermediate 8 (0.8 g; 1.6 mmol) and 2,2,2-trifluoroethylamine (2.5 mL; 31.2 mmol) in ACN (3 mL) was heated at 90° C. in a sealed vessel for 18 h. The r.m. was cooled to r.t., was poured onto ice water and extracted with EtOAc. The organic layer was washed with brine, dried over MgSO$_4$, filtered and evaporated till dryness, yielding 0.670 g of a brown oil. The brown oil was purified by chromatography over silica gel (Irregular SiOH 15-40 μm; mobile phase: gradient from 100% DCM, 0% MeOH to 99% DCM, 1% MeOH). The pure fractions were collected and evaporated to dryness. The oil (compound 5a) (0.3 g; 39%) was converted into its hydrochloride salt (5 eq.) in MeOH. Diethyl ether was added and the precipitate was filtered and dried to give 0.33 g (38%) of compound 5 (1.81 HCl; MP: 186° C. DSC).

Example B4

Preparation of Compounds 6 and 7

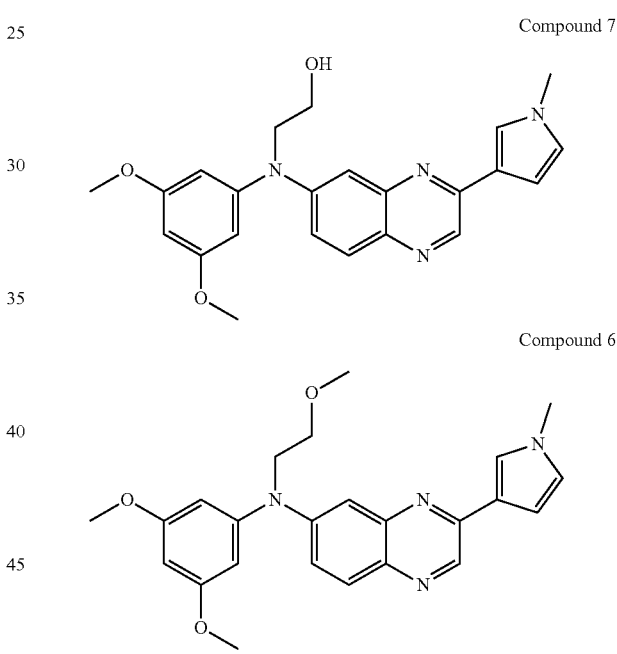

Compound 7

Compound 6

A 1M solution of TBAF in THF (4.8 mL; 4.8 mmol) was added drop wise to a solution of intermediate 10 as obtained in A4.b (2.85 g; 4.4 mmol) in THF (45 mL) at r.t. The r.m. was stirred for 18 h, poured onto ice water and extracted with EtOAc. The mixture was basified with 10% aq. K$_2$CO$_3$ and the organic layer was separated, washed with brine, dried over MgSO$_4$, filtered and evaporated to dryness. The residue was purified by chromatography over silica gel (Irregular SiOH 15-40 μm; mobile phase: gradient from 99% DCM, 1% MeOH to 98% DCM, 2% MeOH).

Two different product fractions were collected and the solvent of each fraction was evaporated, yielding 0.170 g of crude compound 6 as a yellow oil and 0.96 g of compound 7 as a yellow oil (54%). Crude compound 6 was solubilized in MeOH (1 mL). Then, Et$_2$O was added and the resulting precipitate was filtered, dried to give 0.135 g (7%) of compound 6 (MP: 135° C. DSC).

Example B5

Preparation of Compounds 8a and 8

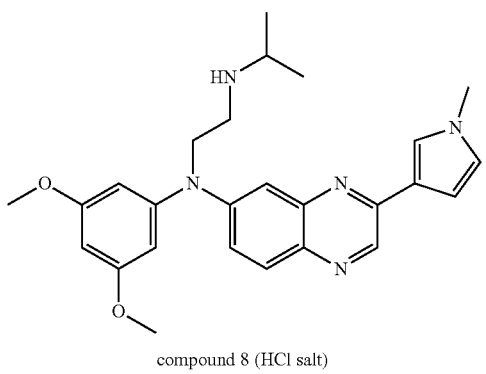

compound 8a compound 8 (HCl salt)

A mixture of intermediate 11 (0.3 g; 0.62 mmol) and 2-propanamine (2.7 mL; 31.1 mmol) in ACN (3 mL) was heated at 90° C. in a sealed vessel for 7 h. The r.m. was cooled to r.t., poured onto a mixture of ice water and EtOAc. The layers were separated; the organic layer was washed with brine, dried over MgSO$_4$, filtered and evaporated to dryness. The residue was purified by chromatography over silica gel (SiOH, 10 µm; mobile phase 0.5% NH$_4$OH, 97% DCM, 3% MeOH). The pure fractions were collected and evaporated to dryness. The oil (compound 8a; 140 mg; 51%) was converted into its hydrochloride salt by addition of 5 eq. of HCl in MeOH. Et$_2$O was added. The precipitate was filtered and dried yielding 160 mg (51%) of compound 8 (1.79 HCl) (MP: 200° C. Kofler).

Example B6

Preparation of Compound 9

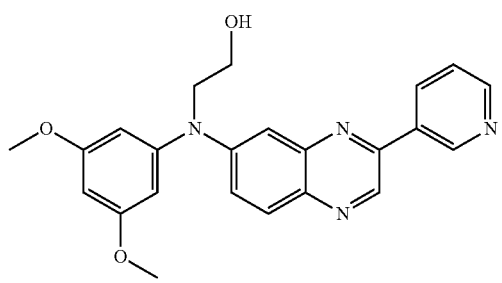 [SMILES: COc1cc(OC)cc(N(CCO)c2ccc3ncc(-c4cccnc4)nc3c2)c1]

A 1M solution of TBAF in THF (4.1 mL, 4.1 mmol) was added dropwise to a solution of intermediate 12 (1.6 g; 3.2 mmol) in THF (30 mL) at r.t. The r.m. was stirred for 3 h, poured onto ice water and extracted with EtOAc. The mixture was basified with a 10% solution of K$_2$CO$_3$ and the organic layer was separated, washed with brine, dried over MgSO$_4$, filtered and evaporated to dryness. The residue was purified by chromatography over silica gel (Irregular SiOH 20-45 µm; mobile phase: 95% DCM, 5% MeOH, 5% NH$_4$OH). The pure fractions were collected and evaporated to dryness. The oily residue (0.86 g, 67%) was crystallized from ACN, the precipitate was filtered and dried yielding 0.78 g (61%) of compound 9 (MP: 151° C. DSC).

Example B7

Preparation of Compounds 10a and 10

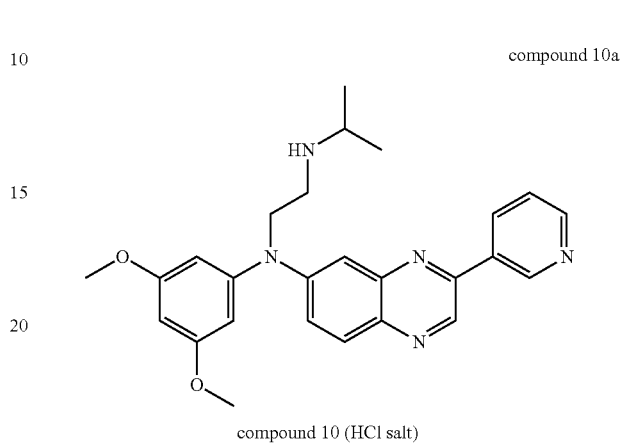

compound 10a compound 10 (HCl salt)

A mixture of intermediate 13 (0.76 g; 1.6 mmol) and 2-propanamine (5.4 mL; 63.6 mmol) was heated at 90° C. in a sealed vessel for 3 h. The r.m. was cooled to r.t. and poured onto a mixture of ice water and DCM. The layers were separated and the organic layer was washed with brine, dried over MgSO$_4$, filtered and evaporated to dryness. The residue was purified by chromatography over silica gel (SiOH 15-40 µm; mobile phase: 0.1% NH$_4$OH, 98% DCM, 2% MeOH). The pure fractions were collected and evaporated to dryness. The residue (compound 10a) (0.5 g; 70%) was dissolved in Et$_2$O. The solution was cooled in an ice bath and a solution of HCl 4N in 1,4-dioxane was added drop wise. The precipitate was filtered and dried yielding 0.45 g (52%) of compound 10 (0.2.14 HCl.H$_2$O) (MP: 174° C. Kofler).

Example B8

Preparation of Compound 11

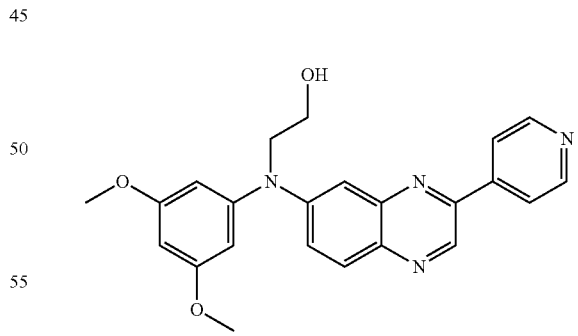

A 1M solution of TBAF in THF (4.1 mL; 4.1 mmol) was added dropwise to a solution of intermediate 14 (1.6 g; 3.2 mmol) in THF (30 mL) at r.t. The r.m. was stirred for 3 h, poured onto ice water and EtOAc was added. The mixture was basified with K$_2$CO$_3$ 10% and the organic layer was separated, washed with brine, dried over MgSO$_4$, filtered and evaporated to dryness. The residue (3 g) was purified by chromatography over silica gel (Irregular SiOH 15-40 µm; mobile phase: 97% DCM, 3% MeOH 0.1% NH$_4$OH). The pure fractions were collected and evaporated to dryness. The oily residue was crystallized from ACN. The precipitate was filtered off and dried to afford 0.7 g (54%) of compound 11

Example B9

Preparation of Compound 12

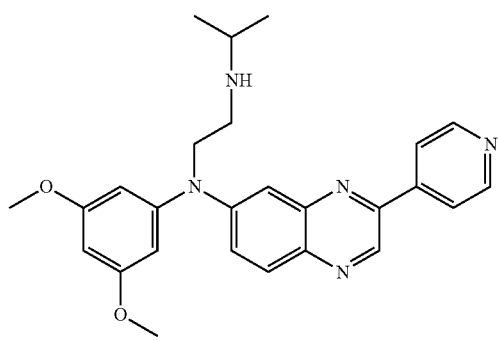 [SMILES: COc1cc(OC)cc(N(CCNC(C)C)c2ccc3ncc(-c4ccncc4)nc3c2)c1]

A mixture of intermediate 15 (0.51 g; 1 mmol) and 2-propanamine (3.6 mL; 42 mmol) was heated at 90° C. in a sealed vessel for 3 h. The r.m. was cooled to r.t., poured onto ice water and extracted with DCM. The organic layer was washed with water, dried over MgSO$_4$, filtered and evaporated till dryness. The residue was purified by chromatography over silica gel (Irregular SiOH 5 µm; mobile phase: gradient from 0.2% NH$_4$OH, 98% DCM, 2% MeOH to 0.9% NH$_4$OH, 91% DCM, 9% MeOH). The pure fractions were collected and evaporated to dryness. The oily residue (0.33 g; 70%) was crystallized from ACN/Et$_2$O. The precipitate was filtered and dried to give 0.28 g (60%) of compound 12 (MP: 118° C. DSC).

Compound 150

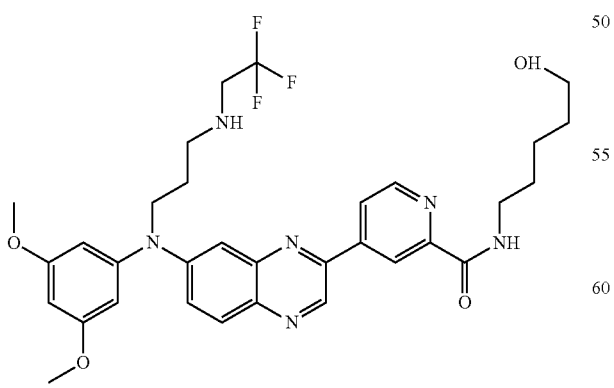

was prepared according to an analogous reaction protocol, starting from intermediate 71.

Example B10

Preparation of Compound 13

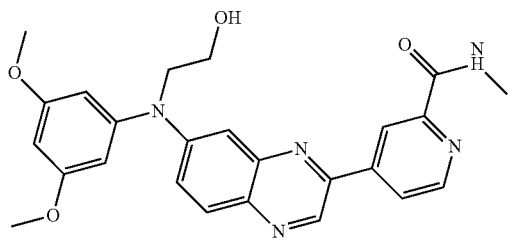

A 1M solution of TBAF in THF (5.35 mL, 5.35 mmol) was added dropwise to a solution of intermediate 16 (3.07 g, 5.35 mmol) in THF (30 mL) at r.t. The r.m. was stirred for 18 h, poured onto ice water and extracted with EtOAc. The mixture was basified with a 10% solution of aq. K$_2$CO$_3$ and the organic layer was separated, washed with brine, dried over MgSO$_4$, filtered and evaporated to dryness. The residue was taken up with pentane. The precipitate was filtered and dried to give 2.61 g (quantitive) of compound 13.

Analogous preparation of compound 187

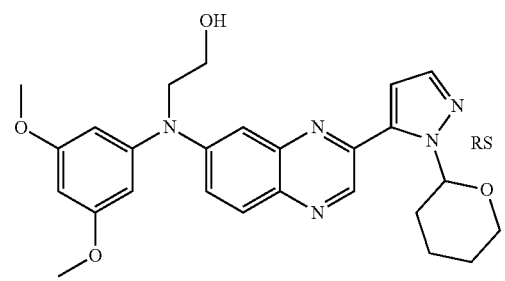 [SMILES: COc1cc(OC)cc(N(CCO)c2ccc3ncc(-c4ccnn4C4CCCCO4)nc3c2)c1]

starting from intermediate 76

Example B11

Preparation of Compound 14

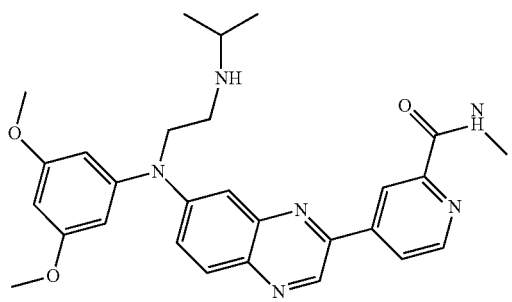

A mixture of intermediate 17 (0.7 g; 1.3 mmol) and 2-propanamine (11.4 mL; 133.1 mmol) in ACN (5 mL) was heated at 100° C. in a sealed vessel for 16 h. The r.m. was cooled to r.t., was poured onto ice water and extracted with EtOAc. The organic layer was separated, washed with brine, dried over MgSO$_4$, filtered and evaporated till dryness. The residue was purified by chromatography over silica gel (Irregular SiOH 15-40 μm 300 g; mobile phase: 0.5% NH₄OH, 95% DCM, 5% MeOH). The pure fractions were collected and evaporated to dryness. The residue was precipitated from Et₂O and a small amount of acetone to give 0.38 g (58%) of compound 14 (MP: 68° C. Kofler).

Analogous preparation of compound 188

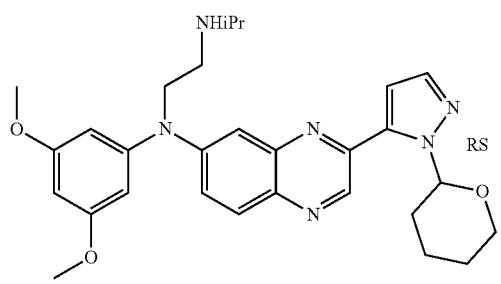

starting from a mixture of intermediates 77 and 78

Example B12

Preparation of Compound 15

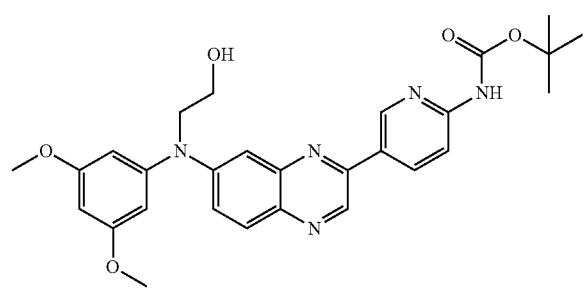 [SMILES: COc1cc(OC)cc(N(CCO)c2ccc3ncc(-c4ccc(NC(=O)OC(C)(C)C)nc4)nc3c2)c1]

A 1M solution of TBAF in THF (12.4 mL; 12.4 mmol) was added drop wise to a solution of intermediate 19 (6.5 g; 10.3 mmol) in THF (200 mL) at r.t. The r.m. was stirred at r.t. for 2 h, poured onto ice water and EtOAc was added. The mixture was basified with a 10% solution of K₂CO₃ and the organic layer was separated, washed with brine, dried over MgSO₄, filtered and evaporated to dryness. The solid residue was taken up with DIPE and the precipitate was filtered off and dried to give 5 g (93%) of compound 15.

Example B13

Preparation of Compound 16

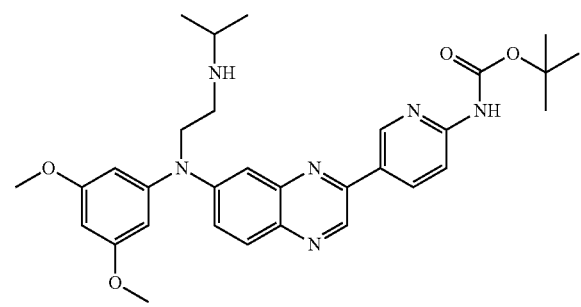 [SMILES: COc1cc(OC)cc(N(CCNC(C)C)c2ccc3ncc(-c4ccc(NC(=O)OC(C)(C)C)nc4)nc3c2)c1]

A mixture of intermediate 20 (2.3 g; 3.8 mmol) and 2-propanamine (60 mL; 705 mmol) in DMF (20 ml) was heated at 75° C. in a sealed vessel for 4 days. The r.m. was cooled to r.t., was poured onto ice water and extracted with EtOAc. The organic layer was separated and evaporated till dryness. The residue was taken up with ACN and H₂O and the precipitate was filtered off, washed with ACN then diethyl ether and dried yielding 1.6 g (75%) of compound 16.

Example B14

Preparation of Compound 18

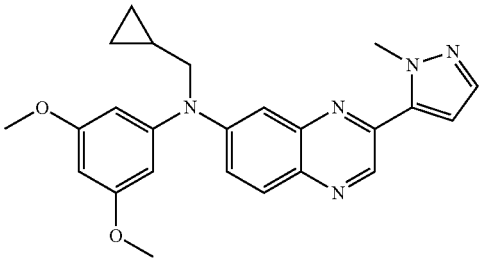 [SMILES: COc1cc(OC)cc(N(CC2CC2)c2ccc3ncc(-c4ccnn4C)nc3c2)c1]

A mixture of intermediate 21 (238 mg; 0.64 mmol), 2-Methyl-2H-pyrazole-3-boronic acid (161 mg; 0.77 mmol), Pd(PPh₃)₄ (74 mg; 0.064 mmol) and a 2M aq. solution of Na₂CO₃ (0.64 mL; 1.28 mmol) in DME (3.5 mL) were heated for 6 h at 100° C. The r.m. was cooled down to r.t., poured onto aq. K₂CO₃ and extracted with EtOAc. The organic layer was dried over MgSO₄, filtered and concentrated. The residue was purified by chromatography over silica gel (Irregular SiOH 15-40 μm 30 g; mobile phase: gradient 100% DCM, 0% MeOH to 98% DCM, 2% MeOH). The fractions containing the product were mixed and concentrated to give 300 mg of fraction A (impure).

Fraction A was purified by column chromatography over silica gel (Irregular SiOH 15-40 μm 30 g; mobile phase: gradient 100% DCM, 0% MeOH to 98% DCM, 2% MeOH).

The pure fractions were mixed and concentrated to give 225 mg (84%) of an intermediate fraction which was crystallized from a mixture of DIPE/Et₂O. The precipitate was filtered to afford 179 mg (67%) of compound 18 (MP: 132° C. DSC).

Example B15

Preparation of Compound 19

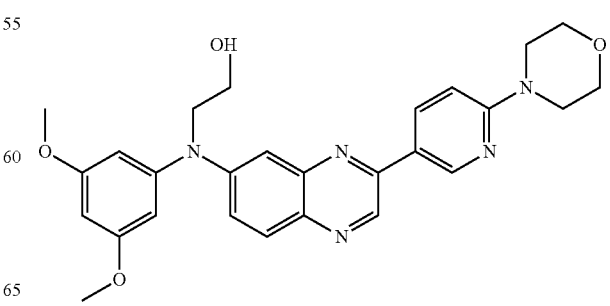

A mixture of intermediate 48 (400 mg; 1.11 mmol), 4-[5-(4,4,5,5-tetramethyl-1,3,2-dioxaborolan-2-yl)pyridin-2-yl]morpholine (387 mg; 1.33 mmol), K₃PO₄ (472 mg; 2.22 mmol), S-Phos (91 mg; 0.22 mmol) in 1,4-dioxane (13 mL) and H₂O (5.4 mL) was stirred at r.t. under N2 flow. After 10 min, Pd₂(dba)₃ (102 mg; 0.11 mmol) was added portionwise. The r.m. was heated at 100° C. for 3 h. The r.m. was cooled to r.t., poured onto ice water and extracted with DCM. The organic layer was washed with brine, dried over MgSO₄, filtered and evaporated to dryness. The residue was purified by chromatography over silica gel (Stability Silica 5 μm 150×30.0 mm; mobile phase: gradient from 0% NH₄OH, 100% DCM, 0% MeOH to 0.5% NH₄OH, 95% DCM, 5% MeOH). The pure fractions were collected and evaporated to dryness. The oily residue (325 mg; 60%) was crystallized from ACN. The precipitate was filtered and dried yielding 272 mg (50%) of compound 19 (MP: 193° C. (Kofler)).

Example B16

Preparation of Compound 20a and Compound 20

Compound 20a

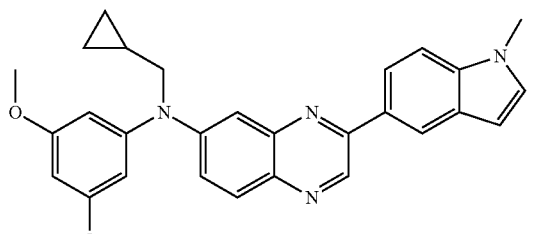

Comound 20 (HCl salt)

A mixture of intermediate 21 (305 mg; 0.82 mmol), 1-methyl-5-(4,4,5,5-tetramethyl-1,3,2-dioxaborolan-2-yl)indole (254 mg; 0.99 mmol), K₃PO₄ (438 mg; 2.06 mmol), S-Phos (34 mg; 0.082 mmol) in 1,4-dioxane (9 mL) and water (3 mL) was stirred at r.t. under N2 flow. After 10 min, Pd₂(dba)₃ (75.5 mg; 0.082 mmol) was added portionwise. The r.m. was heated at 80° C. for 4 h, cooled to r.t. and poured onto ice water. EtOAc was added and the mixture was filtered through a layer of Celite®. The organic layer was washed with brine, dried (MgSO₄), filtered and evaporated to dryness. The residue was purified by chromatography over silica gel (Irregular SiOH 30 g 15-40 μm; mobile phase: gradient from 80% cyclohexane, 20% EtOAc to 50% cyclohexane, 50% EtOAc). The pure fractions were collected and evaporated to dryness. The residue (compound 20a; free base) (176 mg; 46%) was dissolved in MeOH and 0.15 mL of HCl (5 to 6N in isopropanol) was added. The solution was stirred at r.t. for 30 min and evaporated to dryness. The residue was crystallized from Et₂O. The precipitate was filtered and dried yielding 145 mg (34%) of compound 20 (1.19 HCl 0.68 H₂O; MP: 105° C. (Kofler)).

Example B17

Preparation of Compound 60

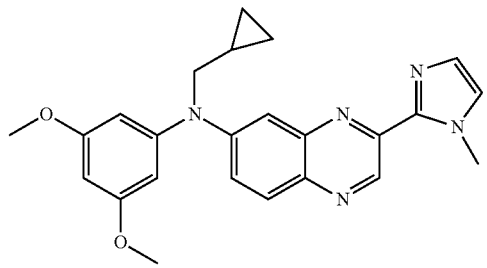 [SMILES: COc1cc(OC)cc(N(CC2CC2)c2ccc3ncc(-c4nccn4C)nc3c2)c1]

A solution of intermediate 21 (900 mg; 2.45 mmol) and 1-Methyl-2-tributylstannanyl-1H-imidazole (1 g; 2.42 mmol) in DMF (9 mL) was degassed with N2 for 15 mn. Pd(PPh₃)₄ (0.28 g; 0.24 mmol) was added and the mixture was heated at 100° C. overnight. The r.m. was partitioned between water and EtOAc. The organic layer was dried over MgSO₄, filtered and concentrated. The residue was purified by chromatography over silica gel (Irregular SiOH 15-40 μm 300 g; mobile phase: 0.1% NH₄OH, 97% DCM, 3% MeOH). The pure fractions were mixed together and concentrated to give 270 mg (26%; yellow powder) of compound 60 (MP=178° C. (Kofler)).

Example B18

Preparation of Compound 61

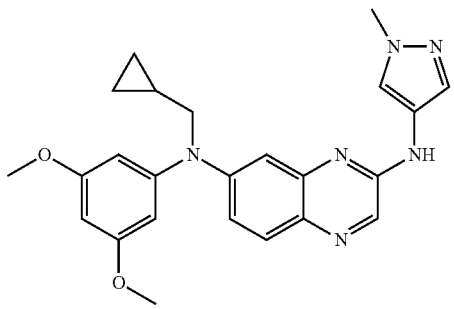 [SMILES: COc1cc(OC)cc(N(CC2CC2)c2ccc3ncc(Nc4cnn(C)c4)nc3c2)c1]

A mixture of intermediate 21 (0.3 g, 0.81 mmol), 1-Methyl-1H-pyrazol-4-amine (94 mg, 0.97 mmol), 9,9-dimethyl-4-,5-bis(diphenylphosphino)xanthene (37 mg, 0.065 mmol) and Cs₂CO₃ (317 mg; 0.97 mmol) in 1,4-dioxane (4 mL) was degassed with a stream of N2 for 30 min. Pd₂(dba)₃ (37 mg, 0.041 mmol) was added and the mixture was heated at 85° C. overnight in a sealed tube. The mixture was poured onto water and filtered through a pad of Celite®. The aq. layer was extracted with DCM. The organic layer was separated, dried over MgSO₄, filtered and concentrated to dryness. The residue was purified by chromatography over silica gel (Stability Silica 5 μm 150×30.0 mm; mobile phase: gradient from 0% NH₄OH, 100% DCM, 0% MeOH to 0.9% NH₄OH, 91% DCM, 9% MeOH). The pure fractions were collected and the solvent was evaporated. The residue (50 mg, 14%) was crystallized from DIPE/ACN (90/10). The precipitate was filtered, dried under vacuum to give 30 mg (8%) of compound 61 (MP: 160° C. (Kofler)).

Example B19

Preparation of Compound 21

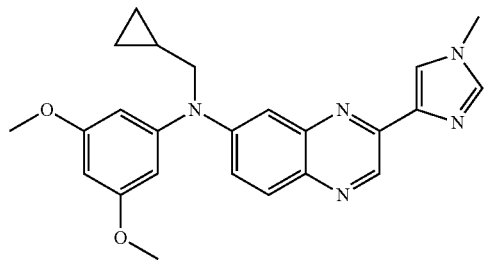 [SMILES: COc1cc(OC)cc(N(CC2CC2)c2ccc3ncc(-c4cn(C)cn4)nc3c2)c1]

Ethylmagnesium chloride 2.8 M in THF (0.266 mL; 0.74 mmol) was added drop wise at r.t. under N2 flow to a solution of 5-bromo-1-methyl-1H-imidazole (0.1 g; 0.62 mmol) in THF (1.3 mL). The r.m. was stirred at r.t. for 30 min and ZnCl (0.170 g; 1.24 mmol) was added. The r.m. was stirred at r.t. for 1 h. Then a solution of intermediate 21 (0.230 g; 0.62 mmol) in THF (1 mL) and Pd(PPh$_3$)$_4$ (36 mg, 0.03 mmol) were added. The mixture was refluxed overnight, cooled to r.t. and partitioned between EtOAc and water. The aq. layer was extracted once with EtOAc. The organic layers were combined, dried, filtered and concentrated. The residue was purified by chromatography over silica gel (Spherical Silica 5 μm 150×30.0 mm; mobile phase: gradient from 0% NH$_4$OH, 100% DCM, 0% MeOH to 0.6% NH$_4$OH, 94% DCM, 6% MeOH). The pure fractions were combined and concentrated to afford an intermediate residue (0.135 g, yellow oil, 52%) which was precipitated with a 1/1/1 mixture of Et$_2$O/ACN/pentane to afford 87 mg (33%, yellow solid) of compound 21 (MP: 140° C. (Kofler)).

Example B20

Preparation of Compound 22

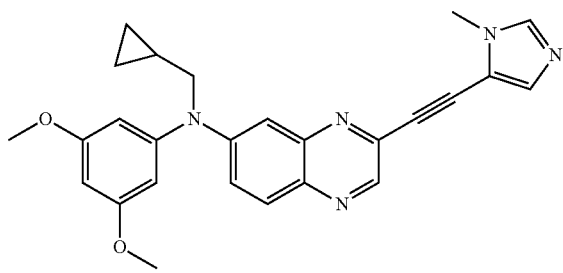 [SMILES: COc1cc(OC)cc(N(CC2CC2)c2ccc3ncc(C#Cc4cncn4C)nc3c2)c1]

A mixture of intermediate 21 (300 mg; 0.81 mmol), 5-ethynyl-1-methyl-1H-imidazole (412 μL; 4.05 mmol), Et$_3$N (338 μL; 2.43 mmol) and PPh$_3$ (4 mg; 0.016 mmol) in DMF (3 mL) was degassed for 10 min with N2 in a sealed tube. CuI (1.5 mg; 0.008 mmol) and PdCl$_2$(PPh$_3$)$_2$ (11 mg; 0.016 mmol) were added and the mixture was heated at 70° C. for 8 h. The r.m. was cooled to r.t. and poured onto ice water. DCM was added and the mixture was filtered through a layer of Celite®. The organic layer was washed with brine, dried (MgSO$_4$), filtered and evaporated to dryness. The residue was purified by column chromatography over silica gel (Irregular SiOH 15-40 μm; mobile phase 95% DCM, 5% MeOH). The pure fractions were collected and evaporated to dryness. The residue was crystallized from DIPE. The precipitate was filtered and dried under vacuum yielding 128 mg (38%) of compound 22 (MP: 166° C. (Kofler)).

Example B21

Preparation of Compound 23

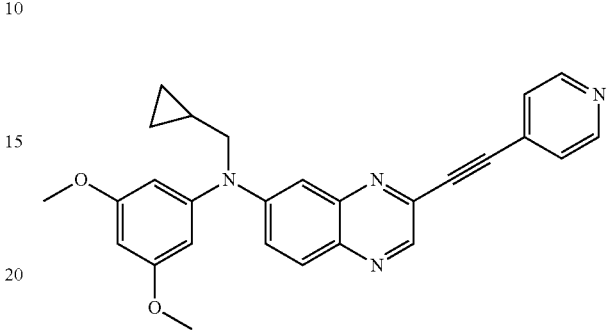

A suspension of intermediate 23 (140 mg; 0.39 mmol), PdCl$_2$(PPh$_3$)$_2$ (54.7 mg; 0.078 mmol), Et$_3$N (1 mL; 7.19 mmol) in a mixture of ACN (5 mL) and DMF (2.5 mL) was degassed under N$_2$. 4-iodopyridine (399 mg; 1.95 mmol) and CuI (7.5 mg; 0.04 mmol) were added and the r.m. was stirred at r.t. for 18 h. Water was added and the aq. layer was extracted with EtOAc. The organic layer was decanted, washed with brine, dried over MgSO$_4$, filtered and evaporated to dryness. The residue was purified by chromatography over silica gel (Spherical Silica 5 μm 150×30.0 mm; mobile phase: gradient from 0% NH$_4$OH, 100% DCM, 0% MeOH to 0.6% NH$_4$OH, 94% DCM, 6% MeOH). The pure fractions were collected and evaporated to dryness yielding 19 mg (11%) of compound 23 (gum below 60° C. Kofler).

Example B22

Preparation of Compound 24

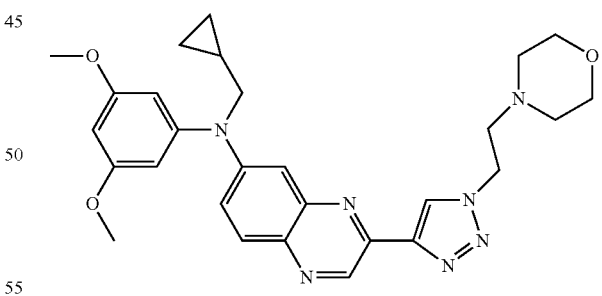

CuI (11.1 mg; 0.06 mmol) and DIPEA (175 μL; 1 mmol) were added at 5° C. to a solution of intermediate 23 (210 mg; 0.58 mmol) and 2-(4-morpholino)-ethylazide (292 μL; 1.17 mmol) in THF (6 mL). The r.m. was stirred at r.t. for 3 h, poured onto water and extracted with EtOAc. The organic layer was decanted, dried over MgSO$_4$, filtered and evaporated to dryness. The residue was purified by chromatography over silica gel (Spherical SiOH 10 μm 60 g; mobile phase: 0.1% NH$_4$OH, 98% DCM, 2% MeOH). The pure fractions were collected and evaporated to dryness. The oily residue was crystallized from DIPE/pentane/ACN. The precipitate was filtered and dried yielding 222 mg (73%) of compound 24 (MP: 128° C. (DSC)).

Example B23

Preparation of Compound 25

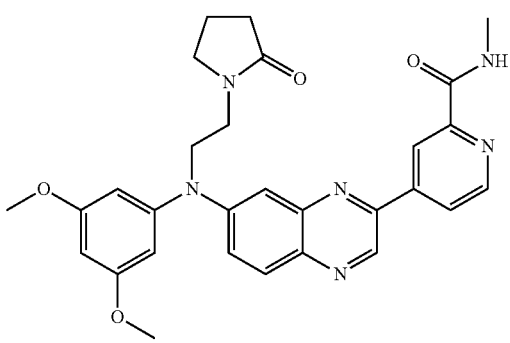

NaH in oil (179 mg; 4.46 mmol) was added portionwise at 5° C. under N2 flow to a solution of 2-pyrrolidinone (0.35 mL; 4.46 mmol) in DMF (73 mL). The r.m. was stirred at 5° C. for 1 h. Subsequently, intermediate 17 (800 mg; 1.49 mmol) was added at 5° C. The r.m. was stirred at 5° C. for 1 h, then overnight at r.t. The r.m. was poured onto ice water and EtOAc was added. The organic layer was separated, washed with brine, dried (MgSO$_4$), filtered and the solvent was evaporated. The residue was purified by chromatography over silica gel (Irregular SiOH 15-40 µm 300 g; mobile phase: 0.5% NH$_4$OH, 97% DCM, 3% MeOH). The pure fractions were evaporated till dryness to give 800 mg of fraction A (not pure enough). Fraction A was purified by achiral Super critical fluid chromatography (AMINO 6 µm 150×21.2 mm; mobile phase: 0.3% isopropylamine, 13% MeOH, 87% CO$_2$). The pure fractions were evaporated till dryness. The residue was crystallized from acetone to give after filtration and drying 166 mg (21%) of compound 25 (MP: 176° C. (DSC)).

Example B24

Preparation of Compound 26

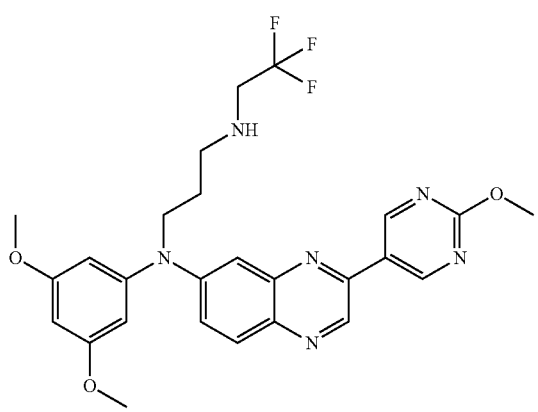 [SMILES: COc1cc(OC)cc(N(CCCNCC(F)(F)F)c2ccc3ncc(-c4cnc(OC)nc4)nc3c2)c1]

TFA (919 µL) was added to solution of intermediate 58 (517 mg; 0.82 mmol) in DCM (9 mL). The r.m. was stirred for 18 h, basified with a saturated solution of NaHCO$_3$ aq. and extracted with a solution of DCM/MeOH 90/10. The organic layer was decanted, dried over MgSO$_4$, filtered and evaporated to dryness. The residue was purified by chromatography over silica gel (Irregular SiOH 15-40 µm 30 g; mobile phase: gradient from 0.1% NH$_4$OH, 99% DCM, 1% MeOH to 1% NH$_4$OH, 90% DCM, 10% MeOH). The pure fractions were collected and evaporated to dryness. The residue (75 mg; 17%) was crystallized from ACN. The precipitate was filtered and dried yielding 55 mg (13%) of compound 26 (MP: 96° C. Kofler).

Example B25

Preparation of Compound 27

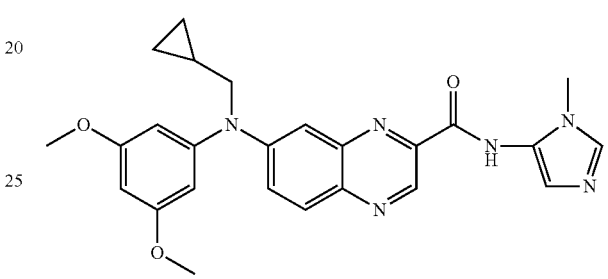

A mixture of intermediate 49 (250 mg; 0.66 mmol), EDCl (153 mg; 0.99 mmol), HOBT (133 mg; 0.99 mmol), Et$_3$N (138 µL; 0.99 mmol) in DCM (10 mL) was stirred at r.t. then, a solution of 1-methyl-1H-Imidazol-5-amine (320 mg; 3.3 mmol) in 1,4-dioxane (10 mL) was added dropwise at r.t. The r.m. was stirred for 5 h, poured onto ice water and extracted with DCM. The organic layer was separated, washed with brine, dried over MgSO$_4$, filtered and the solvent was evaporated. The residue was purified by chromatography over silica gel (Irregular SiOH 15-40 µm 30 g; mobile phase: gradient 100% DCM, 0% MeOH to 95% DCM, 5% MeOH). The pure fractions were mixed and concentrated to give 60 mg (20%) of an intermediate fraction which was triturated with a mixture of Et$_2$O/ACN. The precipitate was filtered and dried under vacuum at 60° C. to afford 35 mg (11%) of compound 27 (MP: 180° C. (Kofler)).

Example B26

Preparation of Compound 28

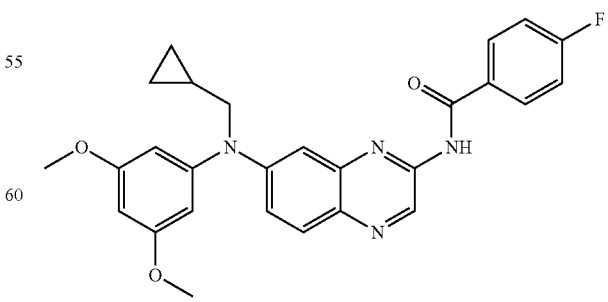

At r.t., EDCl (136 mg; 0.87 mmol) was added portionwise to a solution of intermediate 24 (204 mg; 0.58 mmol), 4-fluorobenzoic acid (122 mg; 0.87 mmol), HOBT (118 mg; 0.87 mmol) and Et₃N (121 µL; 0.87 mmol) in DCM (4 mL). The r.m. was stirred 15 h, poured into H₂O and extracted with DCM. The organic layer was dried over MgSO₄, filtered and evaporated to dryness. The residue was purified by chromatography over silica gel (Irregular SiOH 15-40 µm 30 g; mobile phase: gradient 100% DCM, 0% MeOH to 98% DCM, 2% MeOH). The pure fractions were mixed and concentrated to give 116 mg (42%) of an intermediate fraction which was crystallized in DIPE. The precipitate was filtered to afford 104 mg (38%) of compound 28 (MP: 135° C. (DSC)).

Example B27

Preparation of Compound 29

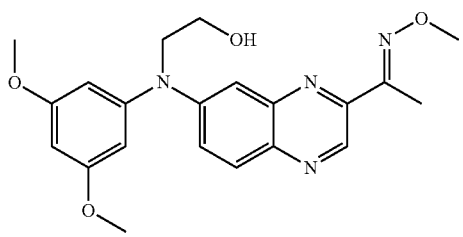 [SMILES: CO/N=C(\C)c1cnc2ccc(N(CCO)c3cc(OC)cc(OC)c3)cc2n1]

Methoxylamine.HCl (51.2 mg; 1.09 mmol) was added to a suspension of intermediate 26 (200 mg; 0.54 mmol) and pyridine (88.1 µL; 1.09 mmol) in EtOH (5 mL). The r.m. was stirred overnight at r.t. The solution was poured into 50 mL of water and extracted with EtOAc. The organic layer was dried (MgSO₄), filtered and evaporated to dryness. The residue was purified by chromatography over silica gel (Irregular Silica 5 µm 150×30.0 mm. mobile phase: gradient from 0% NH₄OH, 100% DCM, 0% MeOH to 0.5% NH₄OH, 95% DCM, 5% MeOH). The pure fractions were evaporated to dryness. The residue was purified by achiral super critical fluid chromatography (diphenyl 5 µm 150×21.2 mm; mobile phase: 95% CO₂, 5% MeOH). The pure fractions were evaporated to dryness. The residue was taken up by pentane. The precipitate was filtered off and dried. Yield: 62 mg (28%) of compound 29 (MP: 149° C. (Kofler)).

Example B28

Preparation of Compound 30

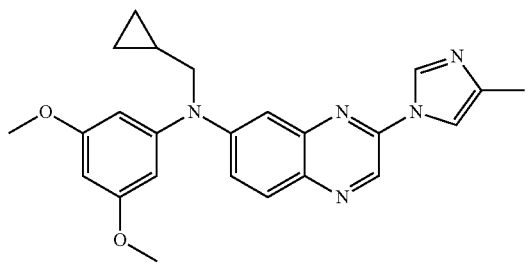

A mixture of intermediate 21 (283 mg; 0.76 mmo), 4-methylimidazole (85 mg; 1.03 mmol), Pd₂(dba)₃ (24.5 mg; 0.027 mmol), NaOtBu (169 mg; 1.76 mmol), (±)-BINAP (28.6 mg; 0.046 mmol) in toluene (6 mL) was heated at 90° C. for 20 h under N2. The r.m. was cooled to r.t., poured onto aq. K₂CO₃ and extracted with EtOAc. The organic layer was dried over MgSO₄, filtered and evaporated to dryness. The residue was purified by chromatography over silica gel (SiOH 15-40 µm 30 g; mobile phase: gradient from 100% DCM, 0% MeOH, 0% NH₄OH to 95% DCM, 5% MeOH, 0.1% NH₄OH). The fractions containing the product were mixed and concentrated to give 104 mg of a fraction A (impure).

Fraction A was purified by chromatography over silica gel (Spherical Silica 5 µm 150×30.0 mm; mobile phase: gradient from 0% NH₄OH, 100% DCM, 0% MeOH to 0.6% NH₄OH, 94% DCM, 6% MeOH). The fractions containing the product were mixed and concentrated to give 73 mg (23%) of a fraction B (impure). Crystallization of fraction B failed, so this fraction was purified again by achiral super critical fluid chromatography (CYANO 6 µm 150×21.2 mm; mobile phase 0.3% isopropylamine, 90% CO₂, 10% MeOH). The pure fractions were mixed and concentrated to give 45 mg (14%) of a fraction C which was crystallized in pentane to give 26 mg (8%) of compound 30 (MP: 113° C. (Kofler)).

Example B29

Preparation of Compound 31 and Compound 62

Compound 31

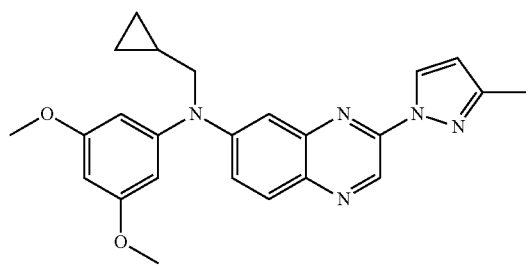

Compound 62

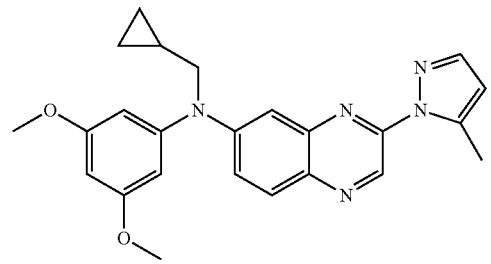

A mixture of intermediate 21 (236 mg; 0.64 mmol), 3-methylpyrazole (62 µL; 0.77 mmol), Pd₂(dba)₃ (20.5 mg; 0.022 mmol), (±)-Binap (23.8 mg; 0.038 mmol) and NaOtBu (141 mg; 1.47 mmol) in toluene (5.8 mL) was heated at 90° C. under N2 for 20 h. The r.m. was cooled down to r.t., poured onto aq. K₂CO₃ and extracted with EtOAc. The organic layer was dried over MgSO₄, filtered and concentrated. The residue was purified by chromatography over silica gel (SiOH 15-40 µm 30 g; mobile phase: gradient from 100% DCM, 0% MeOH, 0% NH₄OH to 98% DCM, 2% MeOH, 0.2% NH₄OH). The pure fractions were mixed and concentrated to afford 37 mg of fraction A and 68 mg of fraction B.

Fraction B was purified by chromatography over silica gel (Spherical Silica 5 µm 150×30.0 mm; mobile phase: gradient from 0% NH₄OH, 100% DCM, 0% MeOH to 0.2% NH₄OH, 98% DCM, 2% MeOH). The pure fractions were mixed and concentrated to afford 14 mg of fraction C and 27 mg of fraction D.

Fractions A and C were gathered to afford a residue (51 mg) which was dissolved in iPrOH. This solution was poured onto aq. K₂CO₃ and extracted with EtOAc. The organic layer was dried over MgSO₄, filtered and concentrated to dryness. The residue was crystallized from pentane and the precipitate was filtered and dried to give 31 mg (12%) of compound 31 (MP: 107° C., DSC).

Fraction D was crystallized from pentane to afford after filtration and drying 13 mg (5%) of compound 62 (MP=139° C., kofler).

Example B30

Preparation of Compound 32a and Compound 32

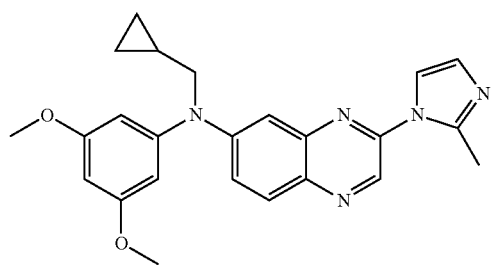

Compound 32a
Compound 32 (HCl salt)

Intermediate 21 (226 mg; 0.61 mmol), 2-methylimidazole (60 mg; 0.73 mmol); Pd₂(dba)₃ (19.6 mg; 0.021 mmol); (±)-BINAP (22.8 mg; 0.037 mmol) and NaOtBu (135 mg; 1.4 mmol) in toluene (5.8 mL) were heated at 90° C. for 20 h under N2. The r.m. was cooled to r.t., poured onto aq. K₂CO₃. The aq. layer was extracted with EtOAc. The organic layer was dried over MgSO₄, filtered and concentrated. The residue was purified by chromatography over silica gel (irregular SiOH 15-40 μm 30 g; mobile phase: gradient from 100% DCM, 0% MeOH, 0% NH₄OH to 95% DCM, 5% MeOH, 0.1% NH₄OH). The pure fractions were mixed and concentrated to give 154 mg of fraction A not pure enough. Fraction A was purified by chromatography over silica gel (Irregular SiOH 15-40 μm 30 g; mobile phase: 60% DCM, 40% EtOAc). The pure fractions were mixed and concentrated to give 80 mg (32%) of fraction B (compound 32a; free base) which was dissolved in isopropanol. HCl (5 to 6N in IprOH) was added and the mixture was stirred for 30 min at r.t. The solvent was evaporated to dryness and the resulting residue was crystallized with Et₂O. The precipitate was filtered and dried to give 55 mg (20%) of compound 32 (0.99 HCl) (MP: 223° C. (DSC)).

Example B31

Preparation of Compound 33

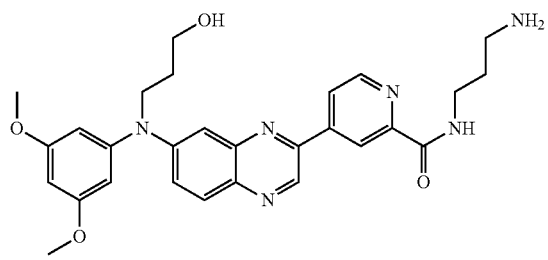 [SMILES: COc1cc(OC)cc(N(CCCO)c2ccc3ncc(-c4ccnc(C(=O)NCCCN)c4)nc3c2)c1]

A solution of intermediate 51 (100 mg; 0.137 mmol) in HCl 3N (1 mL) and MeOH (2 mL) was heated at 70° C. for 2 h. The r.m. was cooled to r.t., diluted with DCM and basified by a saturated solution of Na₂CO₃ (aq.). The organic layer was decanted, dried over MgSO₄, filtered and evaporated to dryness. The residue was purified by chromatography over silica gel (Irregular SiOH 15-40 μm 300 g; mobile phase: gradient from 0.5% NH₄OH, 93% DCM, 7% MeOH to 0.5% NH₄OH, 92% DCM, 8% MeOH). The pure fractions were collected and evaporated to dryness. The oily residue (43 mg; 61%) was crystallized from ACN. The precipitate was filtered off and dried yielding 27 mg (38%) of compound 33 (MP: 110° C. (gum, Kofler)).

Example B32

Preparation of Compound 34 and Compound 35

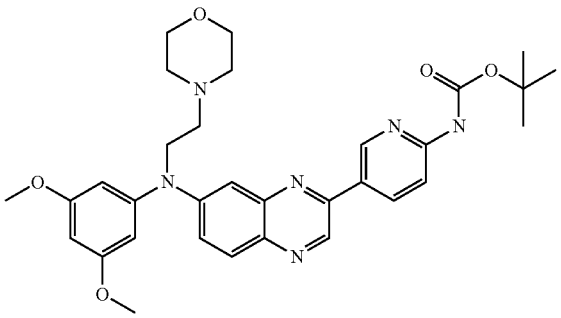

Compound 34

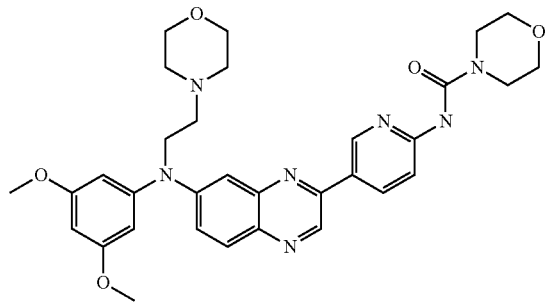

Compound 35

A mixture of intermediate 20 (792 mg; 1.33 mmol) and morpholine (585 μL; 6.65 mmol) in 1-methyl-2-pyrrolidinone (8 mL) was heated at 120° C. for 1 h. The r.m. was poured onto iced water. The precipitate was filtered, washed several times with water and dissolved in DCM. The organic layer was dried over MgSO$_4$, filtered and evaporated to dryness. The residue was purified by chromatography over silica gel (Spherical Silica 5 μm 150×30.0 mm; mobile phase: gradient from 0% NH$_4$OH, 100% DCM, 0% MeOH to 0.6% NH$_4$OH, 94% DCM, 6% MeOH). The pure fractions were collected and evaporated to dryness yielding 205 mg (26%) of compound 34 and 360 mg (45%) of compound 35 which was crystallized from ACN/DIPE. The precipitate was filtered and dried yielding 291 mg (36%) of compound 35 (MP: 153° C. (DSC)).

Example B33

Preparation of Compound 36

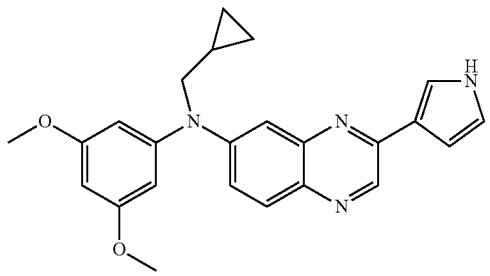 [SMILES: COc1cc(OC)cc(N(CC2CC2)c2ccc3ncc(-c4cc[nH]c4)nc3c2)c1]

A mixture of intermediate 21 (537 mg; 1.45 mmol), 1-(triisopropylsilyl)pyrrole-3-boronic acid (504 mg; 1.89 mmol) and Na$_2$CO$_3$ 1M in water (2.9 ml; 2.9 mmol) in DME (18 mL) were degassed with N2 for 10 min. Pd(PPh$_3$)$_4$ (198 mg; 0.145 mmol) was added and the r.m. was heated at 100° C. for 4 h. The mixture was cooled down to r.t. and TBAF (1M in THF) (2.9 ml; 2.9 mmol) was added. The mixture was stirred at r.t. for 1 h and partitioned between water and EtOAc. The organic layer was collected, dried over MgSO$_4$, filtered and concentrated. The residue was purified by chromatography over silica gel (Irregular SiOH 15-40 μm 300 g; mobile phase: 40% heptane, 60% EtOAc). The pure fractions were mixed and concentrated to give 380 mg (65%; orange solid) of compound 36 (MP: gum at 66° C. Kofler).

Example B34

Preparation of Compound 37

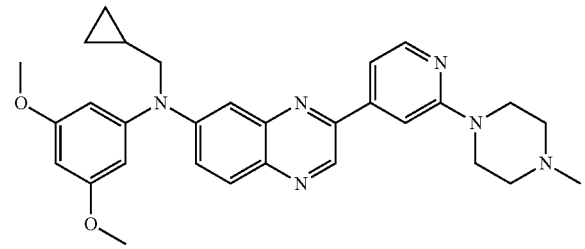 [SMILES: COc1cc(OC)cc(N(CC2CC2)c2ccc3ncc(-c4ccnc(N5CCN(C)CC5)c4)nc3c2)c1]

A mixture of intermediate 21 (313.5 mg; 0.85 mmol), 2-(4-methylpiperazin-1-yl)-pyridin-4-ylboronic acid (244 mg; 1.1 mmol) and a 2M aq. solution of Na$_2$CO$_3$ (0.85 mL; 1.7 mmol) in DME (9 mL) was degassed with N2 for 10 min. Then, Pd(PPh$_3$)$_4$ (98 mg; 0.085 mmol) was added and the r.m. was heated at 135° C. for 40 min under microwave irradiation, poured onto aq. K$_2$CO$_3$ and extracted with EtOAc. The organic layer was dried over MgSO$_4$, filtered and evaporated to dryness. The residue was purified by chromatography over silica gel (Irregular SiOH 15-40 μm 30 g; mobile phase: gradient from 100% DCM, 0% MeOH, 0% NH$_4$OH to 90% DCM, 10% MeOH, 0.1% NH$_4$OH). The pure fractions were mixed and evaporated to dryness yielding 240 mg (55%) of an intermediate fraction which was crystallized from a DIPE/pentane mixture. The precipitate was filtered to give 135 mg (31%) of compound 37 (MP: 125° C. (DSC)).

Example B35

Preparation of Compound 38

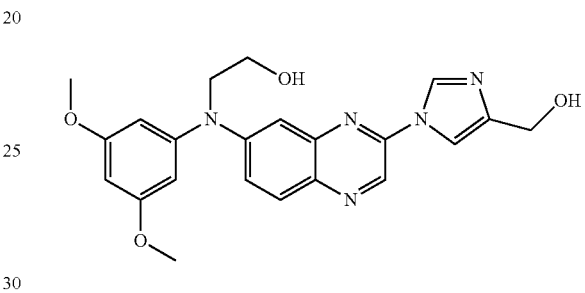

p-Toluenesulfonic acid (191 mg; 1.11 mmol) was added to a mixture of intermediate 28 (280 mg; 0.55 mmol) in MeOH (10 mL) and the r.m. was stirred for 2 h at r.t. The r.m. was poured onto ice, basified with saturated solution of NaHCO$_3$ and extracted with DCM. The organic layer was dried over MgSO$_4$, filtered and evaporated to dryness. The residue was purified by chromatography over silica gel (Spherical SiOH 10 μm 60 g; mobile phase: 0.5% NH$_4$OH, 92% DCM, 8% MeOH). The pure fractions were evaporated to dryness. The residue was crystallized from Et$_2$O and dried yielding 158 mg (68%) of compound 38 (MP: 215° C. (Kofler)).

Example B36

Preparation of Compound 39

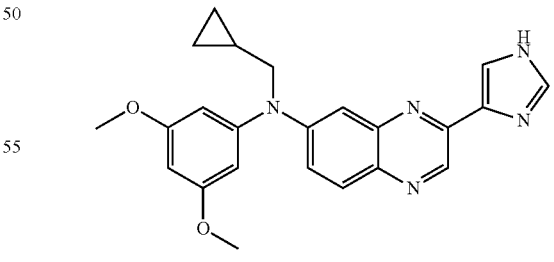

At r.t., concentrated HCl (0.6 mL) was added to a solution of intermediate 30 (0.188 g; 0.29 mmol) in MeOH (10 mL). The mixture was then heated at 50° C. for 3 h. The r.m. was poured onto water, basified with 10% aq. K$_2$CO$_3$ and extracted with DCM. The organic layer was dried over MgSO$_4$, filtered and concentrated until dryness. The residue was purified by chromatography over silica gel (Irregular SiOH 15-40 μm 30 g; mobile phase: 98% DCM, 2% MeOH). The pure fractions were collected and the solvent was evaporated to give 55 mg (46%) of an intermediate fraction which was crystallized from Et₂O/pentane (90/10). The precipitate was filtered, dried under vacuum to afford 42 mg (35%) of compound 39 (MP: 166° C. (DSC)).

Example B37

Preparation of Compound 40

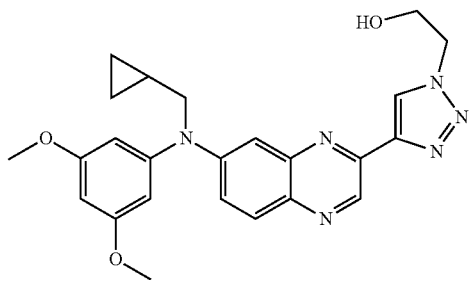 [SMILES: COc1cc(OC)cc(N(CC2CC2)c2ccc3ncc(-c4cn(CCO)nn4)nc3c2)c1]

Diisobutylaluminum hydride 1M in hexane (1.53 mL; 1.53 mmol) was added dropwise at 5° C. to a solution of intermediate 55 (250 mg; 0.51 mmol) in THF (5 mL). The r.m. was stirred at this temperature for 30 min, then allowed to warm to r.t. and stirred for 18 h. The r.m. was cooled again at 5° C. and additional diisobutylaluminum hydride 1M in hexane (1.53 mL; 1.53 mmol) was added to complete the reaction. The r.m. was stirred for 18 more h, quenched with water and extracted with EtOAc. The organic layer was decanted, dried over MgSO₄, filtered and evaporated to dryness. The residue was purified by chromatography over silica gel (Spherical Silica 5 μm 150×30.0 mm; mobile phase: gradient from 0.2% NH₄OH, 98% DCM, 2% MeOH to 0.9% NH₄OH, 91% DCM, 9% MeOH). The pure fractions were collected and evaporated to dryness. The residue was crystallized from Et₂O/DIPE. The precipitate was filtered and dried yielding 61 mg (26%) compound 40 (MP: 177° C. (DSC)).

Example B38

Preparation of Compound 41

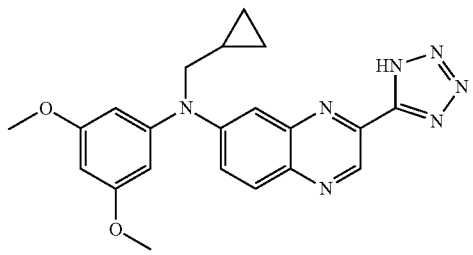 [SMILES: COc1cc(OC)cc(N(CC2CC2)c2ccc3ncc(-c4nnn[nH]4)nc3c2)c1]

A mixture of intermediate 29 (0.5 g; 1.39 mmol), sodium azide (0.27 g; 4.16 mmol) and ammonium chloride (0.3 g; 5.55 mmol) in DMF (7 mL) was heated for at 125° C. for 90 min. The r.m. was poured onto ice and extracted with EtOAc (by saturating the aq. layer with NaCl). The organic layer was dried over MgSO₄, filtered and evaporated till dryness. The residue was crystallized from Et₂O and dried to give 0.5 g (89%) of crude compound 41 (impure).

A part of crude compound 41 (200 mg) was purified by chromatography over silica gel (Irregular SiOH 15-40 μm 30 g; mobile phase: 1% NH₄OH, 89% DCM, 10% MeOH). The fractions containing the product were evaporated until dryness to give 114 mg of a fraction A which is crude compound 41 (not the required purity). This fraction and the mother liquors were mixed together, taken up by EtOAc and acidified with 3N HCl. The organic layer was extracted, dried over MgSO₄, filtered and evaporated till dryness. The residue was taken up by pentane and dried to give 220 mg of fraction B (still impure compound 41).

Fraction B was purified by chromatography over silica gel (Irregular SiOH 15-40 μm 30 g; mobile phase: gradient from 93% DCM, 7% MeOH to 80% DCM, 20% MeOH). The pure fractions were evaporated until dryness to give 180 mg of fraction C which was taken up by EtOAc, acidified with 1 equivalent of 5-6N HCl (in IprOH). The organic layer was washed with water, separated, dried with MgSO₄, filtered and evaporated until dryness. The resulting residue was taken up by pentane, filtered, washed with Et₂O and dried to give 139 mg of compound 41 (MP: 216° C. Kofler).

Example B39

Preparation of Compound 42

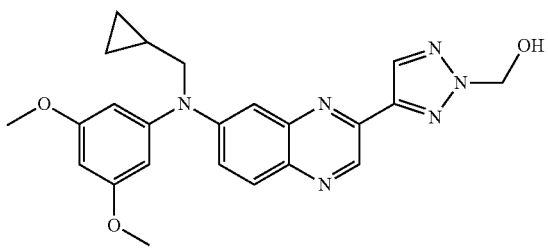 [SMILES: COc1cc(OC)cc(N(CC2CC2)c2ccc3ncc(-c4cnn(CO)n4)nc3c2)c1]

Sodium azide (257.7 mg; 3.96 mmol) was added at 5° C. to a solution of formaldehyde (1.98 mL; 26.4 mmol) and HOAc (227 μL; 3.96 mmol) in dioxane ((5 ml). The r.m. was stirred for 15 min and a solution of intermediate 23 (950 mg; 2.64 mmol) in dioxane (5 mL) was added. The r.m. was stirred at 5° C. for 10 min then, sodium L-ascorbate (105 mg; 0.529 mmol) was added followed by a 0.081 M aq. solution of copper sulfate (1.63 mL; 0.13 mmol). The r.m. was allowed to warm to r.t. and stirred for 3 h. Water was added and the r.m. was stirred at r.t. for 2 h. The precipitate was filtered off, washed successively with water (3×50 mL), ACN then Et₂O and dried yielding 970 mg (84%) of compound 42.

Example B40

Preparation of Compound 43

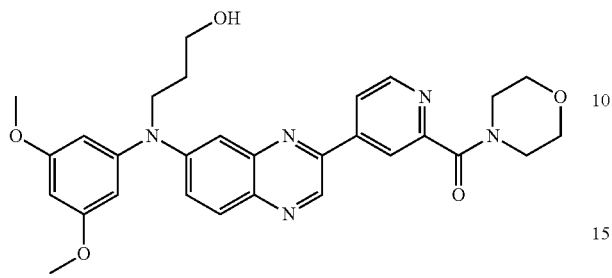

NaH 60% in oil (31.4 mg; 0.78 mmol) was added portion wise at 5° C. under N2 flow to a solution of intermediate 35 (184 mg; 0.26 mmol) in DMF (15 mL). The r.m. was allowed to warm to r.t. and stirred for 1 h, poured onto iced water and extracted with EtOAc. The organic layer was decanted, washed with brine, dried over MgSO$_4$, filtered and evaporated to dryness. The residue was purified by chromatography over silica gel (Spherical Silica 5 µm 150×30.0 mm; mobile phase: gradient from 98% DCM, 2% MeOH, 0.2% NH$_4$OH to 91% DCM, 9% MeOH, 0.9% NH$_4$OH). The pure fractions were collected and evaporated to dryness to give 105 mg of an oily residue which was crystallized from ACN. The precipitate was filtered and dried yielding 89 mg (64%) of compound 43 (MP:190° C. DSC).

Example B41 Preparation of Compound 44

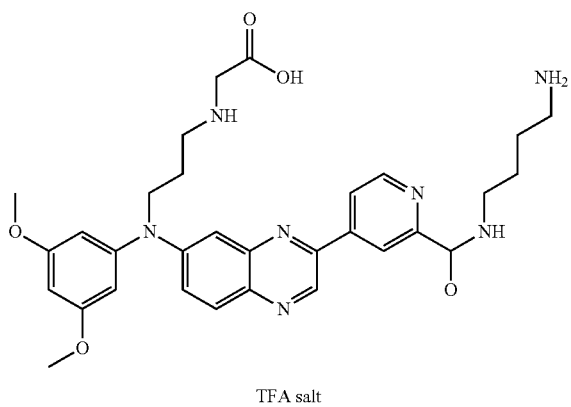 [SMILES: COc1cc(OC)cc(N(CCCNCC(=O)O)c2ccc3ncc(-c4ccnc(C(O)NCCCCN)c4)nc3c2)c1]

TFA salt

TFA (0.1 mL) was added at 0° C. to a solution of intermediate 41 (53 mg; 0.071 mmol) in DCM (1 mL). The r.m. was stirred at r.t. overnight. TFA (0.1 mL) was added 2 more times to complete the conversion. After 48 h, the r.m. was evaporated to dryness and the residue was purified by reverse phase chromatography (X-Bridge-C18 5 µm 30*150 mm; mobile phase: gradient from 80% TFA 10 mM in water, 20% ACN to 0% TFA 10 mM in water, 100% ACN). The pure fractions were collected and evaporated to dryness yielding 30 mg (60%) of compound 44 (.CF$_3$COOH; MP: 64° C. (gum, Kofler)).

Example B42

Preparation of Compound 46 and Compound 47 compound 46 (R or S)
compound 47 (S or R)

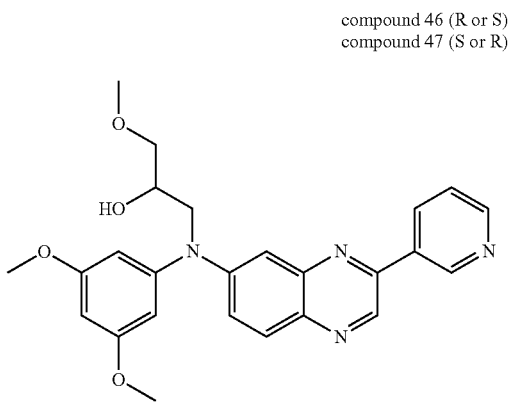 [SMILES: COCC(O)CN(c1cc(OC)cc(OC)c1)c1ccc2ncc(-c3cccnc3)nc2c1]

NaH 60% in oil (357 mg; 9 mmol) was added portion wise at 5° C. under N2 flow to a solution of intermediate 3 (1.6 g; 4.7 mmol) in DMF (20 mL). The r.m. was stirred at 5° C. for 1 h, then glycidyl methyl ether (0.6 mL; 6.7 mmol) was added dropwise. The r.m. was allowed to warm to r.t. and heated at 70° C. for 4 h. The r.m. was poured onto brine and extracted with EtOAc. The organic layer was washed with water, then brine, dried over MgSO$_4$, filtered and evaporated to dryness. The resulting residue was purified chromatography over silica gel (irregular SiOH 15-40 µm 90 g; mobile phase: 98% DCM, 2% MeOH, 0.1% NH$_4$OH). The residue was purified by achiral supercritical fluid chromatography (2-ethylpyridine 6 µm 150×21.2 mm; mobile phase: 85% CO$_2$, 15% MeOH, 0.3% isopropylamine). The resulting residue was purified by chiral supercritical fluid chromatography (CHIRALPAK AD-H 5 µm 250×20 mm; mobile phase: 55% CO$_2$, 45% iPrOH, 0.3% isopropylamine). The pure fractions were collected and the two enantiomers were evaporated to dryness.

The residue containing compound 46 (R or S) was taken up with Et$_2$O. The precipitate was filtered and dried yielding 343 mg (17%) of compound 46 (MP: 154° C. (DSC); [α]$_D$: +115.9° (c: 0.25 w/v %, DMF, 20° C.)).

The residue containing compound 47 (S or R) was taken up with Et$_2$O. The precipitate was filtered and dried yielding 338 mg (17%) of compound 47 (MP: 153° C. (DSC); [α]$_D$: −117.6° (c: 0.26 w/v %, DMF, 20° C.)).

Example B43

Preparation of Compound 48

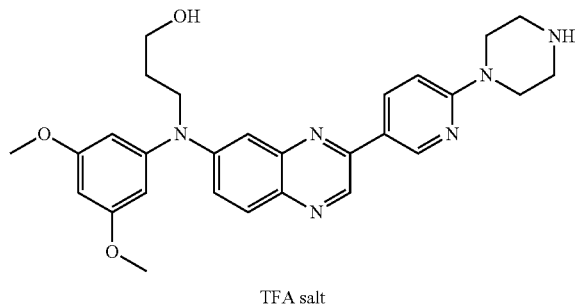 [SMILES: COc1cc(OC)cc(N(CCCO)c2ccc3ncc(-c4ccc(N5CCNCC5)nc4)nc3c2)c1]

TFA salt

TFA (1 mL) was added to a solution of intermediate 42 (300 mg; 0.42 mmol) in DCM (20 mL). The resulting solution was stirred for 3 days. The solution was basified with ammonia in MeOH and the solvent was evaporated under reduced pressure. The residue was purified by reversed phase chromatography (Hyperprep C18 HS BDS 100A 8 mu (Shandon); mobile phase: gradient from 75% water+0.2% TFA and 25% MeOH+0.2% TFA to 100% MeOH+0.2% TFA in 45 min). The fractions containing the product were collected and concentrated. The water-layer was again purified by reverse phase chromatography (Hyperprep C18 HS BDS 100A 8 mu (Shandon); mobile phase: 20 min 100% water and then a gradient to 100% MeOH in 30 min). The pure fractions were collected and concentrated to afford 0.14 g (66%) of compound 48 (0.5 CF$_3$COOH).

Example B44 a) Preparation of Compound 49 and Compound 49a

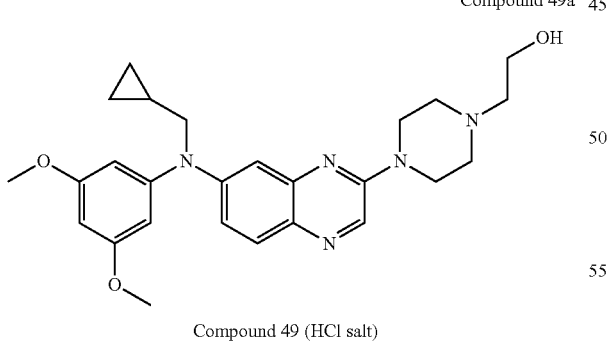

Compound 49a

Compound 49 (HCl salt)

A mixture of intermediate 21 (0.3 g; 0.81 mmol), 1-(2-hydroxyethyl)-piperazine (149 μL; 1.22 mmol) and Et$_3$N (169 μL; 1.22 mmol) in 1-butanol (5 mL) was heated at 100° C. overnight. The mixture was poured onto water and extracted with DCM. The organic layer was washed with brine, dried over MgSO$_4$, filtered and the solvent was evaporated. The residue was purified by chromatography over silica gel (SiOH 15-40 μm 30 g; mobile phase: 95% DCM, 5% MeOH). The pure fractions were collected and the solvent was evaporated. The residue (free base compound 49a) was dissolved in EtOH and 200 μL of a 5N solution of HCl in iPrOH was added dropwise at 5° C. The hydrochloride salt was filtered, washed with DIPE and dried under vacuum at 60° C. to give 127 mg of compound 49 (1.65 HCl 0.72 H$_2$O) (MP: gum at 208° C. (Kofler)).

b) Compound 63

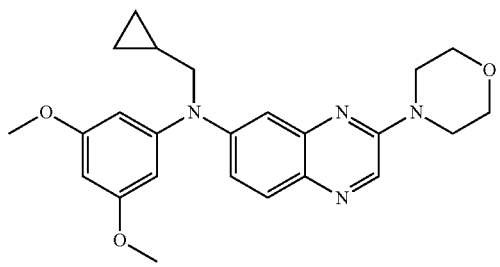 [SMILES: COc1cc(OC)cc(N(CC2CC2)c2ccc3ncc(N4CCOCC4)nc3c2)c1]

was prepared according to an analogous protocol: A mixture of intermediate 21 (300 mg; 0.81 mmol) and morpholine (714 μL; 8.11 mmol) in THF (7 mL) was heated at 60° C. overnight. The mixture was poured onto water. DCM was added and the organic layer was washed (brine), dried (MgSO$_4$), filtered and evaporated to dryness. The residue was purified by chromatography over silica gel (Irregular SiOH 15-40 μm; mobile phase: 98% DCM, 2% MeOH). The pure fractions were collected and evaporated to dryness. The residue (150 mg) was crystallized from DIPE/pentane (50/50). The precipitate was filtered, dried under vacuum, yielding 83 mg (24%) of compound 63 (MP: 114° C. (Kofler)).

c) Compound 64

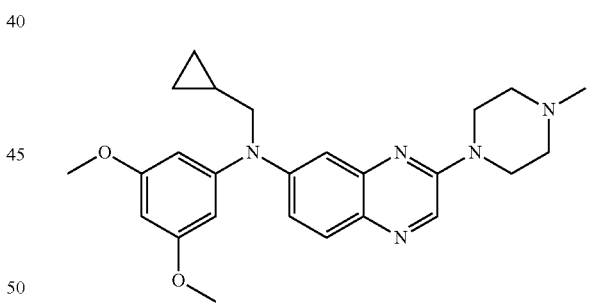

was prepared according to an analogous protocol: A mixture of intermediate 21 (300 mg; 0.811 mmol), 1-methylpiperazine (135 μL; 1.217 mmol) and Et$_3$N (169 μL; 1.22 mmol) in 1-butanol (6 mL) was heated at 100° C. overnight. The mixture was poured onto water and extracted with DCM. The organic layer was washed with brine, dried over MgSO$_4$, filtered and evaporated to dryness. The residue was purified by chromatography over silica gel (Irregular SiOH 15-40 μm; mobile phase: 95% DCM, 5% MeOH). The pure fractions were collected and evaporated to dryness. The resulting residue (200 mg) was crystallized from DIPE. The precipitate was filtered, dried under vacuum yielding 105 mg (30%) of compound 64 (MP: 92° C. (Kofler)).

d) Compound 65

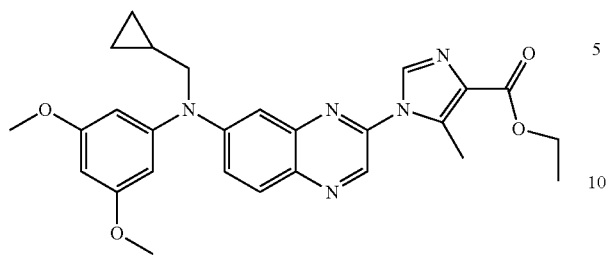

was prepared according to an analogous protocol: NaH (44 mg; 1.08 mmol) was added at 0° C. to a solution of ethyl 4-methyl-5-imidazoecarboxylate (167 mg; 1.08 mmol) in DMF (2 mL). The r.m. was stirred for 30 min at 0° C. and a solution of intermediate 21 (200 mg; 0.54 mmol) in DMF (1 mL) was added. The r.m. was heated at 65° C. overnight and partitioned between water and EtOAc. The organic layer was washed twice with brine, dried over MgSO$_4$, filtered and concentrated. The residue (0.48 g, orange oil) was purified by chromatography over silica gel (Spherical Silica 5 μm 150×30.0 mm; mobile phase: gradient from 0% NH$_4$OH, 100% DCM, 0% MeOH to 0.4% NH$_4$OH, 96% DCM, 4% MeOH). The pure fractions were mixed and concentrated. The resulting residue (0.187 g, yellow oil, 71%) was precipitated from a 1/1 mixture of Et$_2$O/ACN to afford 0.152 g (yellow solid, 58%) of compound 65 (MP: 138° C. (kofler)).

Example B45

Preparation of Compound 50

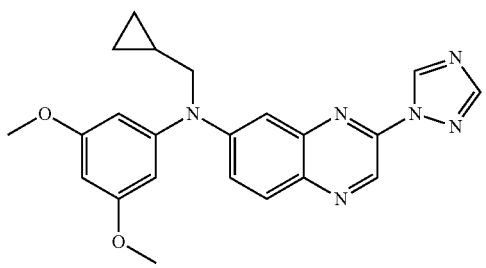 [SMILES: COc1cc(OC)cc(N(CC2CC2)c2ccc3ncc(-n4cncn4)nc3c2)c1]

A mixture of intermediate 21 (200 mg; 0.54 mmol), 1,2,4-triazole (56 mg; 0.81 mmol), 1,2,4-triazole sodium derivative (74 mg; 0.81 mmol) and Et$_3$N (113 μL; 0.81 mmol) in 1-butanol (5 mL) was heated at 100° C. overnight. The r.m. was poured onto water and extracted with DCM. The organic layer was washed with brine, dried over MgSO$_4$, filtered and the solvent was evaporated. The residue was purified by chromatography over silica gel (Spherical SiOH 10 μm 60 g; mobile phase: gradient from 0% MeOH, 95% DCM, 5% EtOAc to 2% MeOH, 98% DCM, 0% EtOAc). The pure fractions were evaporated until dryness to give 79 mg (36%) of compound 50 (MP: 168° C. (Kofler)).

Example B46

Preparation of Compound 51a and Compound 51

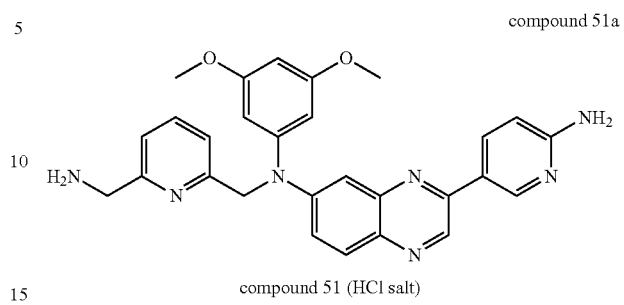

compound 51a compound 51 (HCl salt)

A mixture of intermediate 45 (220 mg; 0.35 mmol) and hydrazine monohydrate (77 μL; 2.47 mmol) in EtOH (4 mL) was refluxed overnight. The r.m. was cooled down to r.t., poured onto water and extracted with EtOAc. The organic layer was decanted, washed with brine, dried over MgSO$_4$, filtered and evaporated to dryness.

The residue was purified by chromatography over silica gel (Spherical Silica 5 μm 150×30.0 mm; mobile phase: gradient from 0.2% NH$_4$OH, 98% DCM, 2% MeOH to 1.2% NH$_4$OH, 88% DCM, 12% MeOH). The fractions containing the product were concentrated and the residue was crystallized from ACN and Et$_2$O to give after drying 84 mg of a fraction A which was not pure enough. This fraction was purified again by chromatography over silica gel (Spherical Silica 5 μm 150×30.0 mm; mobile phase: gradient from 0.2% NH$_4$OH, 98% DCM, 2% MeOH to 1.2% NH$_4$OH, 88% DCM, 12% MeOH). The fractions containing the product were concentrated. The resulting residue was crystallized from ACN and Et$_2$O to give after drying 83 mg of fraction B which again was not pure enough.

This last fraction was purified again by chromatography over silica gel (Spherical Silica 5 μm 150×30.0 mm; mobile phase: gradient from 0.2% NH$_4$OH, 98% DCM, 2% MeOH to 1.3% NH$_4$OH, 87% DCM, 13% MeOH). The pure fractions were concentrated to give an intermediate residue (0.05 g compound 51a, free base) which was dissolved in DCM; HCl 4N in 1,4-dioxane was added. The resulting solution was concentrated. The hydrochloride salt was taken up by Et$_2$O, filtered and dried to give 20 mg (10%) of compound 51 (1.84 HCl; MP: 170° C. (gum, Kofler)).

Example B47

Preparation of Compound 53 and Compound 54

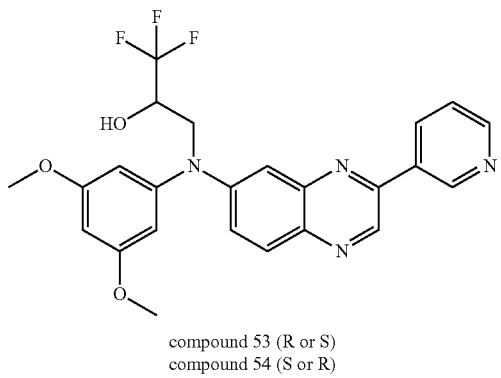 [SMILES: COc1cc(OC)cc(N(CC(O)C(F)(F)F)c2ccc3ncc(-c4cccnc4)nc3c2)c1]

compound 53 (R or S)
compound 54 (S or R)

This reaction was performed on 2 g of intermediate 3 but in 2 times respectively on a 1 g scale of intermediate 3. The r.m. were combined for the work-up.

NaH 60% in oil (223 mg; 5.58 mmol) was added portionwise at 5° C. under N2 flow to a solution of intermediate 3 (1 g; 2.79 mmol) in DMF (30 mL). The r.m. was stirred at 5° C. for 1 h, then 1.2-epoxy-3.3.3-trifluoropropane (0.36 mL) was added drop wise. The r.m. was heated at 70° C. for 4 h. The r.m. were combined and the resulting mixture was poured onto water and extracted with EtOAc and filtered through a pad of Celite®. The organic layer was washed twice with water, dried over MgSO₄, filtered and evaporated to dryness. The residue was purified by chromatography over silica gel (Irregular SiOH 20-45 µm 450 g; mobile phase: 97% DCM, 3% MeOH, 0.5% NH₄OH) yielding 1.2 g (46%). The residue was purified by achiral supercritical fluid chromatography (amino 6 µm 150×21.2 mm; mobile phase: 85% CO₂, 15% MeOH) yielding 1.06 g (40%) of residue. This residue was purified by chiral supercritical fluid chromatography (Chiralpak® AD-H 5 µm 250×20 mm; mobile phase: 60% CO₂, 40% MeOH, 0.3% isopropylamine). The pure fractions were collected and the two enantiomers were evaporated to dryness. The residue containing compound 53 was taken up with Et₂O. The precipitate was filtered and dried yielding 473 mg (19%) of compound 53 (R or S; MP: 211° C. (DSC); [α]$_D$: +196.3° (c: 0.27 w/v %, DMF, 20° C.)). The residue containing compound 54 was taken up with Et₂O. The precipitate was filtered and dried yielding 471 mg (18%) of compound 54 (S or R; MP: 210° C. (DSC); [α]$_D$:−195.8° (c: 0.28 w/v %, DMF, 20° C.)).

Example B48

Preparation of Compound 55

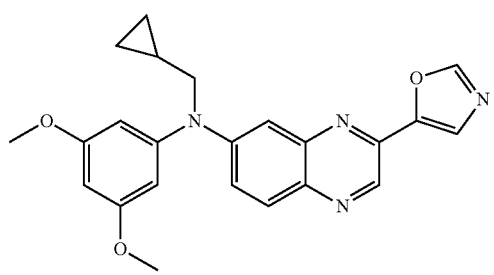 [SMILES: COc1cc(OC)cc(N(CC2CC2)c2ccc3ncc(-c4cnco4)nc3c2)c1]

A mixture of intermediate 53 (240 mg; 0.66 mmol), tosylmethyl isocyanide (142 mg; 0.73 mmol) and K₂CO₃ (110 mg; 0.79 mmol) in MeOH (7 mL) was refluxed for 3 h. The r.m. was cooled to r.t., poured onto water and extracted with DCM. The organic layer was decanted, dried over MgSO₄, filtered and evaporated to dryness. The residue was purified by chromatography over silica gel (Spherical SiOH 10 µm 60 g; mobile phase: 0.1% NH₄OH, 99% DCM, 1% MeOH). The pure fractions were collected and evaporated to dryness. The residue was crystallized from Et₂O/DIPE. The precipitate was filtered and dried yielding 139 mg (52%) of compound 55 (MP: 152° C. (DSC)).

Example B49

Preparation of Compound 56

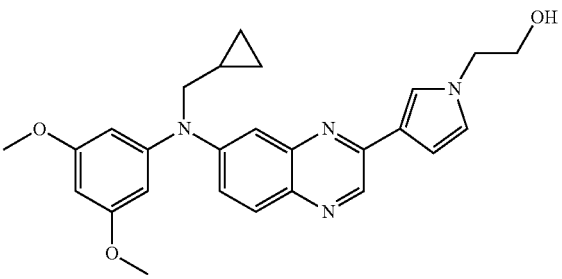 [SMILES: COc1cc(OC)cc(N(CC2CC2)c2ccc3ncc(-c4ccn(CCO)c4)nc3c2)c1]

TBAF (1M in THF) (1.12 mL; 1.12 mmol) was added dropwise to a solution of intermediate 54 (570 mg; 1.02 mmol) in THF (11 mL) at r.t. The r.m. was stirred for 2 h, poured onto aq. K₂CO₃ and extracted with EtOAc. The organic layer was dried over MgSO₄, filtered and evaporated to dryness. The residue was purified by chromatography over silica gel (Spherical Silica 5 µm 150×30.0 mm; mobile phase: gradient from 0% NH₄OH, 100% DCM, 0% MeOH to 0.5% NH₄OH, 95% DCM, 5% MeOH). The pure fractions were evaporated until dryness to give, after crystallization from Et₂O and drying, 199 mg (44%) of compound 56 (MP: 143° C. (Kofler)).

Example B50

Preparation of Compound 57

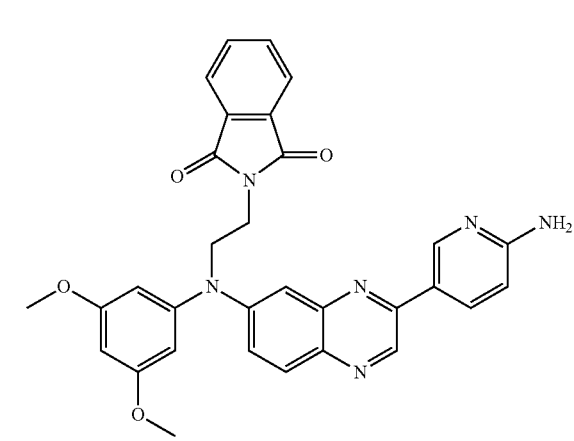 [SMILES: COc1cc(OC)cc(N(CCN2C(=O)c3ccccc3C2=O)c2ccc3ncc(-c4ccc(N)nc4)nc3c2)c1]

A mixture of intermediate 20 (420 mg; 0.705 mmol), phthalimide (207 mg; 1.41 mmol) and Na₂CO₃ (187 mg; 1.76 mmol) in NMP (3.5 mL) was heated at 130° C. for 24 h. The r.m. was cooled down to r.t., poured onto water and extracted with DCM. The organic layer was dried over MgSO₄, filtered and evaporated to dryness. The residue was taken up with DCM. The precipitate was filtered and dried yielding 240 mg (62%) of compound 57 (MP: 222° C. (Kofler)).

Compound 78

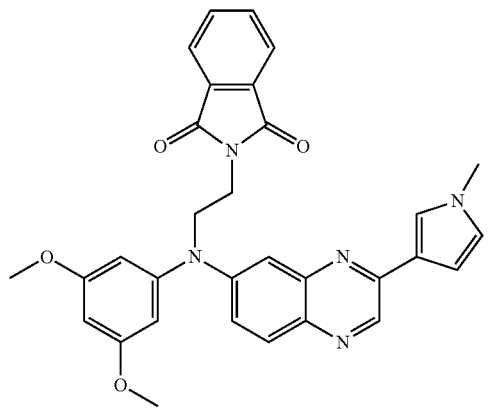 [SMILES: COc1cc(OC)cc(N(CCN2C(=O)c3ccccc3C2=O)c2ccc3ncc(-c4ccn(C)c4)nc3c2)c1]

was prepared by using an analogous reaction protocol as described for compound 57 (starting from intermediate 11).

Example B51

Preparation of Compound 85

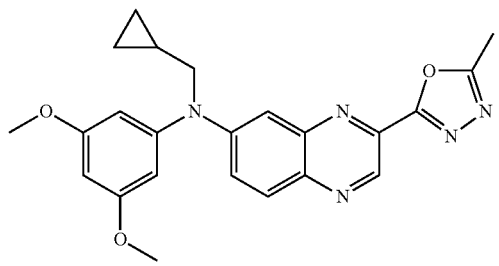

A mixture of intermediate 47 (300 mg; 0.76 mmol), triethylorthoacetate (2.8 mL; 15.25 mmol) and concentrated $H_2SO_4$ (20 μL) was heated at 80° C. for 5 h. The r.m. was cooled to r.t. and the precipitate was filtered. The filtrate was evaporated to dryness. The residue was partitioned between EtOAc and water. The resulting mixture was basified with a 10% aq. solution of $K_2CO_3$. The organic layer was separated, washed with brine, dried over $MgSO_4$, filtered and evaporated to dryness. The residue was purified by chromatography over silica gel (Irregular SiOH 15-40 μm 30 g; mobile phase: gradient from 100% DCM, 0% MeOH to 97% DCM, 3% MeOH). The pure fractions were collected and the solvent was evaporated to give 80 mg (25%) of an intermediate fraction which was crystallized from $Et_2O$. The precipitate was filtered, dried under vacuum to afford 32 mg (10%) of compound 85 (MP: 134° C. (Kofler)).

Example B52

Preparation of Compound 80 and Compound 81

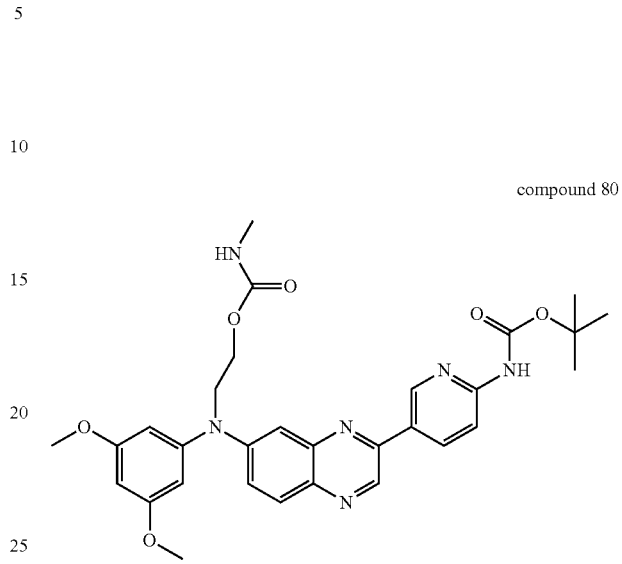

compound 80

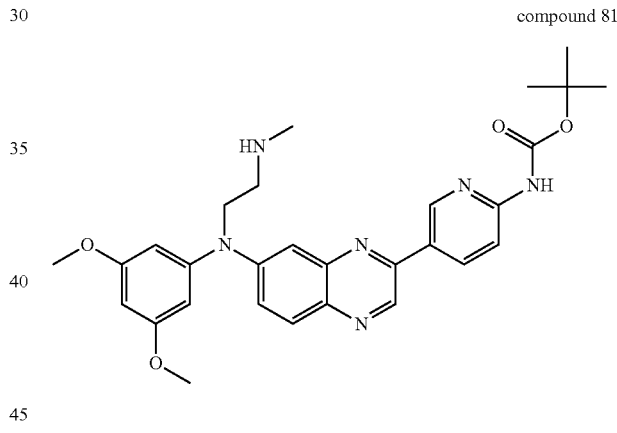

compound 81

In a pressure vessel, intermediate 20 (0.8 g; 1.34 mmol), methyl amine 33% weight solution in absolute EtOH (6.7 ml; 13.43 mmol), $K_2CO_3$ (930 mg; 6.7 mmol) were mixed in ACN (11 mL). The r.m. was heated at 80° C. overnight.

The r.m. was partitioned between DCM/MeOH (90/10) and water. The organic layer was separated, dried over $MgSO_4$, filtered and concentrated. The residue was purified by chromatography over silica gel (mobile phase: 95% DCM, 5% MeOH, 0.5% $NH_4OH$) to give 300 mg (42%, yellow solid) of compound 81 (MP: 194° C., Kofler) and 150 mg of fraction A (not pure enough). Fraction A was purified by chromatography over silica gel (Spherical SiOH 10 μm 60 g; mobile phase: 70% DCM, 30% EtOAc). The pure fractions were mixed and concentrated to give 130 mg of a residue which was taken up with $Et_2O$. The resulting precipitate was filtered, dried to give 123 mg (16%; yellow solid) of compound 80 (MP: 214° C. Kofler).

Example B53

Preparation of Compound 84 and Intermediate 75

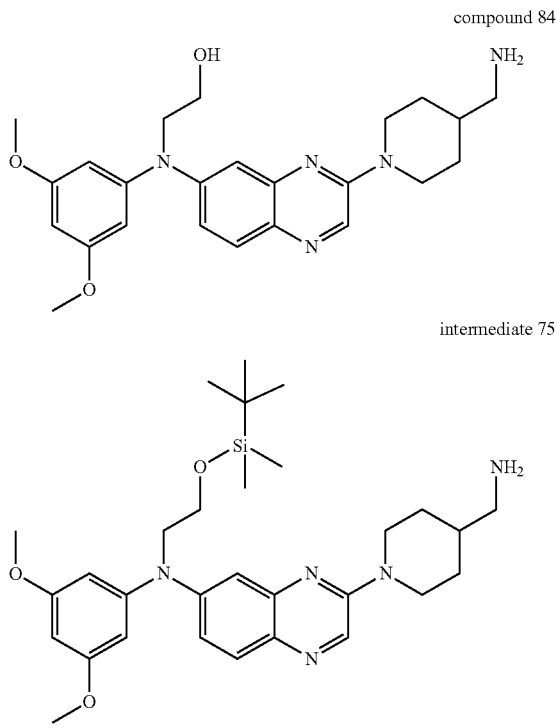 [SMILES: COc1cc(OC)cc(N(CCO)c2ccc3ncc(N4CCC(CN)CC4)nc3c2)c1 ; COc1cc(OC)cc(N(CCO[Si](C)(C)C(C)(C)C)c2ccc3ncc(N4CCC(CN)CC4)nc3c2)c1]

compound 84 intermediate 75

A mixture of intermediate 5b (700 mg; 1.48 mmol), 4-(aminomethyl)piperidine (337 mg; 2.95 mmol) and Cs$_2$CO$_3$ (962 mg; 2.95 mmol) in DMF (28 mL) was heated at 100° C. for 3 h. The r.m. was cooled to r.t., poured onto iced water and extracted with EtOAc. The organic layer was washed with brine, dried over MgSO$_4$, filtered and evaporated to dryness. The crude residue was purified by chromatography over silica gel (Irregular SiOH 15-40 µm 300 g; mobile phase: gradient from 1% NH$_4$OH, 90% DCM, 10% MeOH to 1.5% NH$_4$OH, 85% DCM, 15% MeOH). The pure fractions were collected and evaporated to dryness to give respectively 365 mg (48%) of intermediate 75 and 200 mg (31%) of an oily residue which was crystallized from ACN. The precipitate was filtered off and dried, yielding 160 mg (25%) of compound 84 (MP: 159° C. DSC).

Example B54

Preparation of Compound 186

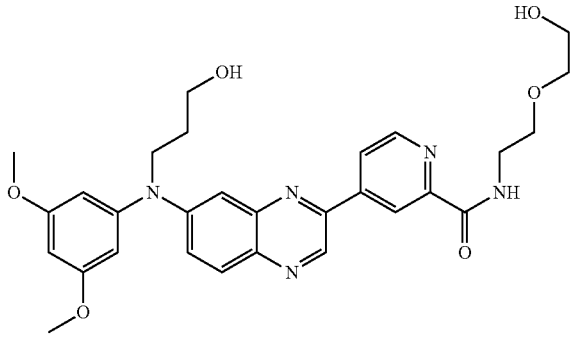 [SMILES: COc1cc(OC)cc(N(CCCO)c2ccc3ncc(-c4ccnc(C(=O)NCCOCCO)c4)nc3c2)c1]

TBAF 1M in THF (0.118 mL; 0.118 mmol) was added drop wise to a solution of intermediate 33 (60 mg; 0.091 mmol) in THF (1.325 mL) at room temperature and the reaction mixture was stirred at this temperature for 1 hour. The reaction mixture was quenched with water and extracted with DCM. The organic layer was decanted, dried over MgSO$_4$, filtered and evaporated to dryness.

The crude residue (77 g) was purified by chromatography over silica gel (Stability Silica 5 µm 150×30.0 mm, Mobile phase: Gradient from 0% NH$_4$OH, 100% DCM, 0% MeOH to 0.7% NH$_4$OH, 93% DCM, 7% MeOH). The product fractions were collected and evaporated to dryness yielding 24 mg of compound 186 (48%).

C. Conversion Reactions

Conversion C1

Preparation of Compound 2

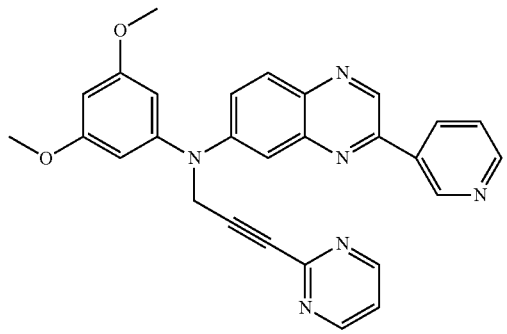 [SMILES: COc1cc(OC)cc(N(CC#Cc2ncccn2)c2ccc3ncc(-c4cccnc4)nc3c2)c1]

A suspension of compound 1 (0.4 g; 1.01 mmol), 2-bromopyrimidine (0.1 g; 0.63 mmol) and Et$_3$N (1.4 mL; 10.09 mmol) in DMSO (5 mL) was degassed under N2. PdCl$_2$(PPh$_3$)$_2$ (0.089 g; mg; 0.126 mmol) and CuI (0.012 g; 0.063 mmol) were added and the r.m. was stirred for 30 min at 90° C. Subsequently, the mixture was poured into water and extracted with EtOAc. The resulting mixture was filtered through a pad of Celite® (diatomaceous earth), and was then washed with brine and water (twice). The organic layer was dried (MgSO$_4$), filtered and the solvent was evaporated. The residue (380 mg) was purified by silica gel chromatography on (Spherical Silica 5 µM, 150×30.0 mm; mobile phase gradient from 0% NH$_4$OH, 100% DCM, 0% MeOH to 0.7% NH$_4$OH, 93% DCM, 7% MeOH). The desired fractions were collected and the solvent was evaporated. The residue (0.138 g) was crystallized from Et$_2$O to yield 0.109 g (36%) of compound 2 (MP: 184° C. (DSC)).

Conversion C2

Preparation of Compound 17

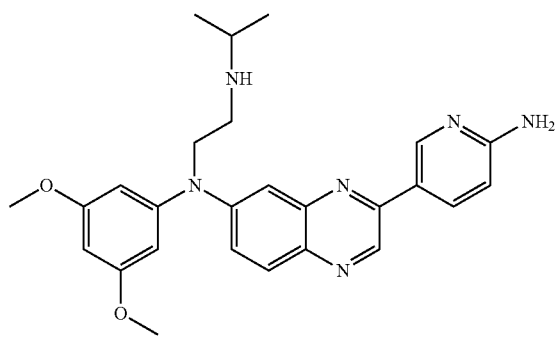 [SMILES: COc1cc(OC)cc(N(CCNC(C)C)c2ccc3ncc(-c4ccc(N)nc4)nc3c2)c1]

A mixture of compound 16 (1.6 g; 2.9 mmol) in HCl 3N (15 mL) and MeOH (30 mL) was refluxed for 5 h. The r.m. was cooled to 0° C., neutralized with a saturated solution of NaHCO$_3$. The aq. layer was extracted 3× with DCM. The combined organic layer were dried over MgSO$_4$, filtered and evaporated to dryness. The residue was purified by chromatography over silica gel (Irregular SiOH 20-45 μm 450 g; mobile phase: 0.5% NH$_4$OH, 92% DCM, 8% MeOH). The pure fractions were collected and evaporated to dryness and the residue (1.08 g) was crystallized from ACN/DIPE. The precipitate was filtered and dried yielding 0.88 g (67%) of compound 17 (MP: 144° C. (DSC)).

Conversion C3

Preparation of Compound 66

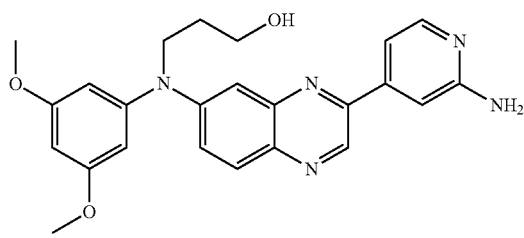 [SMILES: COc1cc(OC)cc(N(CCCO)c2ccc3ncc(-c4ccnc(N)c4)nc3c2)c1]

Compound 128 (0.08 g; 0.15 mmol) was treated with a pre-cooled solution of TFA (1 ml) in DCM (3 ml). The reaction mixture was stirred for 30 min at r.t. Subsequently, the mixture was diluted with DCM, cooled in an ice-bath and quenched with 10% aq. K$_2$CO$_3$. The reaction mixture was stirred for 15 minutes. The organic layer was decanted, dried (MgSO$_4$), filtered and evaporated to dryness. Yield: 0.07 g of compound 66. Alternatively, compound 66 may be prepared by analogy to the protocol described in Example B31.

Conversion C4

Preparation of Compound 67a and Compound 67

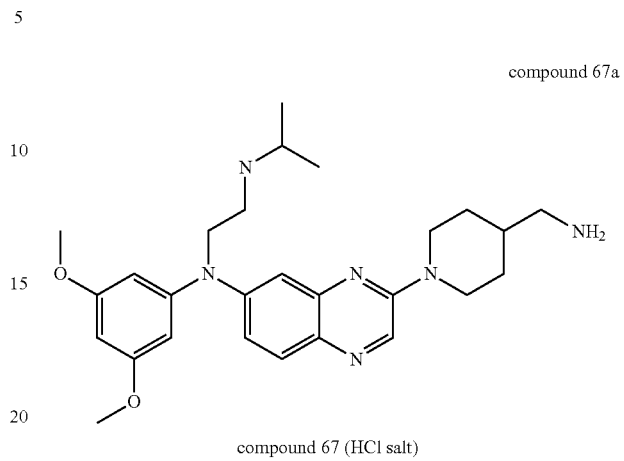

compound 67a compound 67 (HCl salt)

TFA (2 mL) was added to a pre-cooled (5° C.) solution of compound 147 (149 mg; 0.26 mmol) in DCM (3 mL). The r.m. was allowed to warm to r.t. and stirred for 18 h. The r.m. was diluted with DCM and basified with a 10% solution of K$_2$CO$_3$ aq. The organic layer was decanted, dried over MgSO$_4$, filtered and evaporated to dryness. The residue was purified by chromatography over silica gel (Spherical Silica 5 μm 150×30.0 mm; mobile phase: gradient from 0.5% NH$_4$OH, 95% DCM, 5% MeOH to 2% NH$_4$OH, 80% DCM, 20% MeOH). The pure fractions were collected and evaporated to dryness. The oily residue (compound 67a as free base; 80 mg; 65%) was dissolved in EtOH. The solution was cooled in an ice bath and an excess of HCl 4N in 1,4-dioxane was added followed by DIPE. The hydrochloride salt was filtered, washed with DiPE and dried at 50° C. under vacuum overnight yielding 76 mg (49%) of compound 67 (0.3.1 HCl 0.78 H$_2$O; MP: 193° C. (gum, Kofler)).

Conversion C5

Preparation of Compound 58a and Compound 58

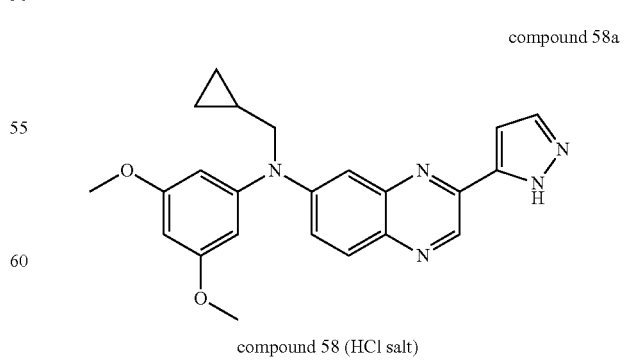

compound 58a compound 58 (HCl salt)

A solution of HCl 4M in 1,4-dioxane (0.6 mL; 2.4 mmol) was added to a solution of compound 100 (233 mg; 0.48 mmol) in 1,4-dioxane (8.5 mL) at r.t. The r.m. was stirred for 15 h, poured onto H₂O, basified with K₂CO₃ and extracted with EtOAc. The organic layer was dried over MgSO₄, filtered and evaporated to dryness. The residue was purified by chromatography over silica gel (Irregular SiOH 15-40 μm 30 g; mobile phase: gradient from 100% DCM 0% MeOH 0% NH₄OH to 95% DCM 5% MeOH 0.1% NH₄OH). The pure fractions were mixed and concentrated to afford 250 mg of a fraction A not pure enough.

Fraction A was purified by chromatography over silica gel (Irregular SiOH 15-40 μm 30 g; mobile phase: gradient from 100% DCM, 0% MeOH, 0% NH₄OH to 95% DCM, 5% MeOH, 0.1% NH₄OH). The pure fractions were mixed and concentrated to afford 199 mg of a fraction B (compound 58a; free base) which was dissolved in iPrOH and HCl (6N to 8N in iPrOH) was added. The mixture was stirred for 30 min and evaporated to dryness. The resulting salt was crystallized from Et₂O, filtered and dried to give 113 mg (50%) of compound 58 (1.25 HCl 0.36 iPrOH; MP: degradation at 99° C. (Kofler)).

Conversion C6 a) Preparation of Compound 59

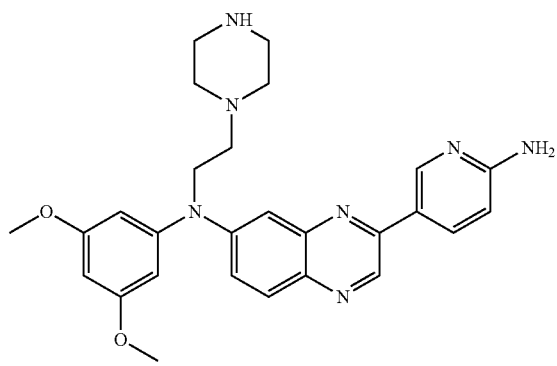 [SMILES: COc1cc(OC)cc(N(CCN2CCNCC2)c2ccc3ncc(-c4ccc(N)nc4)nc3c2)c1]

A mixture of compound 157 (770 mg; 1.23 mmol), in HCl 12N (2 mL) and MeOH (25 mL) was refluxed for 5 h. The r.m. was cooled in an ice bath and basified with a 10% solution of K₂CO₃ aq. The aq. layer was extracted 3 times with DCM. The organic layer was dried over MgSO₄, filtered and evaporated to dryness. The residue was purified by chromatography over silica gel (Spherical Silica 5 μm 150×30.0 mm; mobile phase: gradient from 0.3% NH₄OH, 97% DCM, 3% MeOH to 1.4% NH₄OH, 86% DCM, 14% MeOH). The pure fractions were collected and evaporated to dryness. The oily residue (318 mg; 53%) was crystallized from ACN/DIPE. The precipitate was filtered off and dried yielding 284 mg (47%) of compound 59 (MP: 111° C. (Kofler)).

b) Preparation of Compound 68

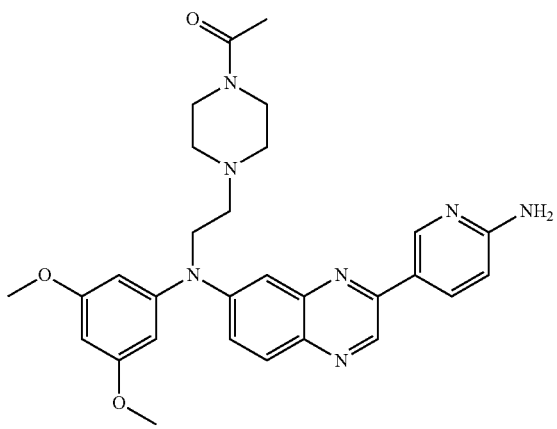 [SMILES: COc1cc(OC)cc(N(CCN2CCN(C(C)=O)CC2)c2ccc3ncc(-c4ccc(N)nc4)nc3c2)c1]

Acetyl chloride (35.6 μL; 0.50 mmol) was added dropwise at r.t. to a mixture of compound 59 (231 mg; 0.47 mmol), DMAP (11 mg; 0.0951 mmol) and Et₃N (99 μL; 0.714 mmol) in DCM (8 mL). The r.m. was stirred at r.t. for 1 h, poured onto water and extracted with DCM. The organic layer was decanted, dried over MgSO₄, filtered and evaporated to dryness. The residue was purified by chromatography over silica gel (Stability Silica 5 μm 150×30.0 mm; mobile phase: gradient from 98% DCM, 2% MeOH to 88% DCM, 12% MeOH). The pure fractions were collected and evaporated to dryness. The oily residue (150 mg; 60%) was crystallized from ACN/DIPE. The precipitate was filtered off and dried yielding 130 mg (52%) of compound 68 (MP: 167° C. (DSC)).

Conversion C7 a) Preparation of Compound 69

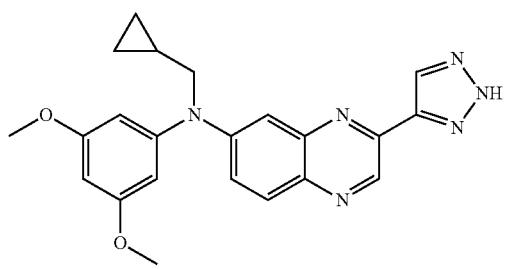 [SMILES: COc1cc(OC)cc(N(CC2CC2)c2ccc3ncc(-c4cn[nH]n4)nc3c2)c1]

A mixture of compound 42 (965 mg; 2.23 mmol) in NaOH 3M (4 mL) and THF (3 mL) was stirred at r.t. for 18 h. The r.m. was poured onto a 10% aq. NH₄Cl and extracted with EtOAc. The organic layer was decanted, dried over MgSO₄, filtered and evaporated to dryness. The residue was taken up with ACN. The precipitate was filtered, washed with ACN, then Et₂O and dried yielding 780 mg (87%) compound 69 (MP: 172° C. DSC).

b) Preparation of Compound 70, Compound 71 and Compound 72

Conversion C8

Preparation of Compound 73

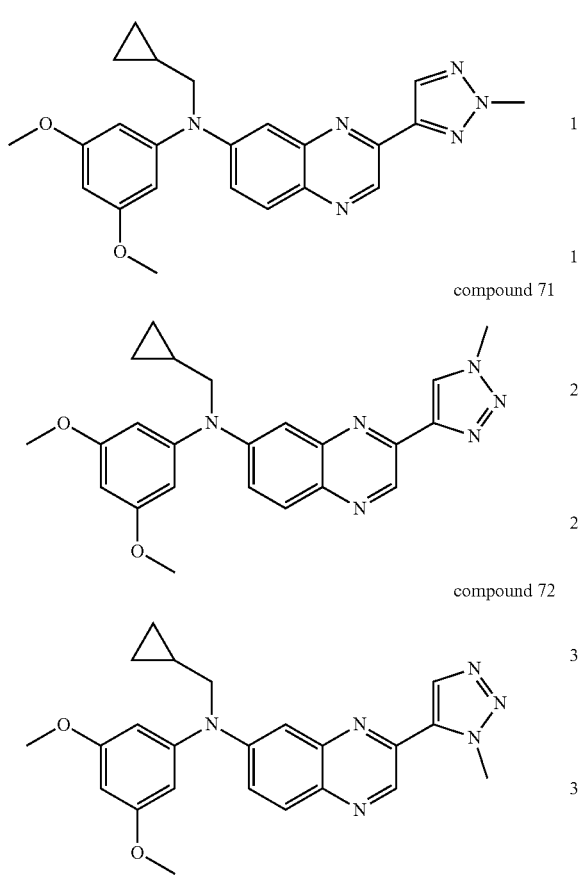

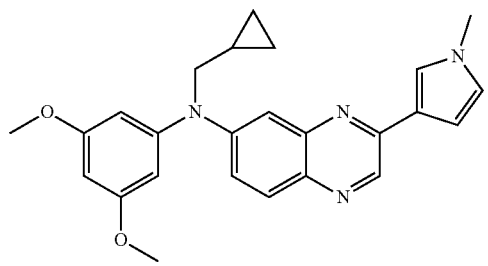 [SMILES: COc1cc(OC)cc(N(CC2CC2)c2ccc3ncc(-c4ccn(C)c4)nc3c2)c1]

Potassium tert-butoxide (71 mg; 0.63 mmol) and 18-crown-6 (15 mg; 0.6 mmol) were added at r.t. to a mixture of compound 36 (200 mg; 0.5 mmol) in a mixture of cyclohexane (3.6 mL) and DMSO (1.8 mL). Iodomethane (91 µL; 1.47 mmol) was added dropwise and the r.m. was stirred at r.t. for 1 h. The mixture was poured onto ice and extracted with EtOAc. The organic layer was dried over MgSO$_4$, filtered and evaporated until dryness. The residue (200 mg) was purified by chromatography over silica gel (Spherical SiOH 10 µm 60 g; mobile phase: 98% DCM, 2% MeOH). The pure fractions were mixed and evaporated until dryness. The residue was crystallized from Et$_2$O and dried to give 133 mg (65%) of compound 73 (MP: 110° C. (Kofler)).

Conversion C9

Preparation of Compound 74

A mixture of compound 69 (675 mg; 1.67 mmol), iodomethane (115 µL; 1.84 mmol) and K$_2$CO$_3$ (464 mg; 1.84 mmol in ACN (20 mL) was heated at 85° C. for 2 h. The r.m. was cooled to r.t., diluted with DCM and poured onto water. The organic layer was decanted, dried over MgSO$_4$, filtered and evaporated to dryness. The residue was purified by chromatography over silica gel on (Spherical Silica 5 µm 150×30.0 mm; mobile phase: gradient from 0% NH$_4$OH, 100% DCM, 0% MeOH to 0.3% NH$_4$OH, 97% DCM, 3% MeOH). The pure fractions were collected and evaporated to dryness yielding fractions A, B, C:
- 285 mg (40%, oily residue) of fraction A which was crystallized from Et$_2$O. The precipitate was filtered and dried yielding 175 mg (25%) of compound 70 (MP: 129° C., DSC).
- 140 mg (20%, oily residue) of fraction B which was crystallized from Et$_2$O. The precipitate was filtered and dried yielding 115 mg (16%) of compound 71 (MP: 140° C., DSC).
- 60 mg of an impure fraction C. This residue was purified by achiral Super critical fluid chromatography (2-ethylpyridine 6 µm 150×21.2 mm; mobile phase 0.3% isopropylamine, 88% CO$_2$, 12% MeOH). The pure fractions were collected and evaporated to dryness. The resulting residue was crystallized from Et$_2$O. The precipitate was filtered and dried yielding 32 mg (4.5%) of compound 72 (MP: 169° C., DSC).

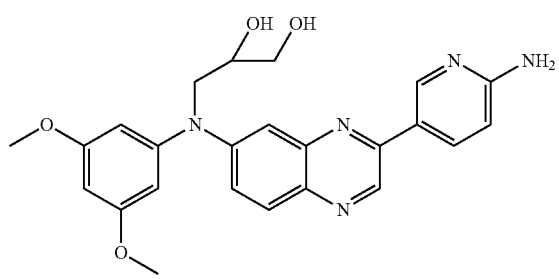 [SMILES: COc1cc(OC)cc(N(CC(O)CO)c2ccc3ncc(-c4ccc(N)nc4)nc3c2)c1]

Compound 110 (188 mg; 0.43 mmol) was diluted in 1,4-dioxane (7.5 mL) and water (1.7 mL). Then, TFA (0.1 mL) was added and the mixture was refluxed for 2 h. The r.m. was poured onto ice-saturated aq. NaHCO$_3$. The aq. layer was extracted twice with EtOAc. The organic layer was dried over MgSO$_4$, filtered and concentrated. The residue (orange oil, 210 mg) was purified by chromatography over silica gel (Spherical Silica 5 µm 150×30.0 mm; mobile phase: gradient from 0.2% NH$_4$OH, 98% DCM, 2% MeOH to 1.4% NH$_4$OH, 86% DCM, 14% MeOH). The pure fractions were mixed and concentrated to give an intermediate residue (118 mg, orange oil) which was taken up with ACN. Filtration and drying of the precipitate gave 89 mg (45%; yellow solid) of compound 74 (MP: 210° C. (Kofler)).

Conversion C10

Preparation of Compound 75

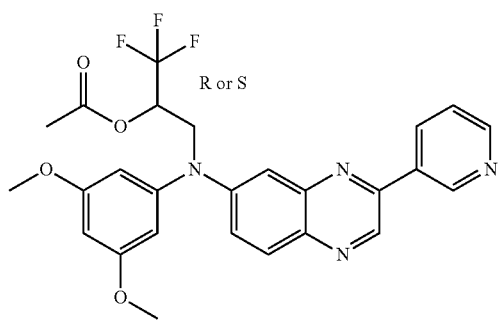 [SMILES: COc1cc(OC)cc(N(CC(OC(C)=O)C(F)(F)F)c2ccc3ncc(-c4cccnc4)nc3c2)c1]

NaH 60% in oil (114 mg; 2.84 mmol) was added at 0° C. under N2 flow to a solution of compound 53 (267 mg; 0.57 mmol) in THF (8 mL). The r.m. was stirred at 0° C. for 1 h, then acetyl chloride (0.4 mL; 5.68 mmol) was added. The r.m. was heated at 50° C. overnight. The solution was poured into water and extracted with EtOAc. The organic layer was washed with brine, dried over MgSO$_4$, filtered and evaporated to dryness. The residue was crystallized from Et$_2$O. The precipitate was filtered and dried yielding 283 mg (97%) of compound 75 (R or S; MP: 180° C. DSC; [α]$_D$: +79.4° (c: 0.33 w/v %, DMF, 20° C.).

Conversion C11

Preparation of Compound 76a and Compound 76

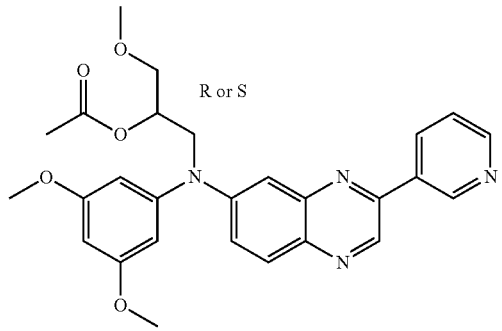

compound 76 (HCl salt)

NaH 60% in oil (32 mg; 0.806 mmol) was added at 0° C. under N2 flow to a solution of compound 46 (90 mg; 0.202 mmol) in THF (4 mL). The r.m. was stirred at 0° C. for 30 min and acetic anhydride (76 μL; 0.81 mmol) was added. The r.m. was refluxed for 4 h. Then acetyl chloride (72 μL; 1 mmol) was added. The r.m. was stirred at r.t. for 2 days. The solution was poured into water and EtOAc. The organic layer was washed with brine, dried over MgSO$_4$, filtered and evaporated to dryness. The residue was purified by chromatography over silica gel (Spherical silica 5 μm 150×30.0 mm; mobile phase: gradient from 71% heptane, 28% EtOAc, 1% MeOH to 0% heptane, 80% EtOAc, 20% MeOH).

The pure fractions were collected and evaporated to dryness. The residue (compound 76a; free base) (63 mg; 64%) was dissolved in Et$_2$O and the solution was cooled at 0° C. A solution of HCl in 1,4-dioxane (2 eq, 4M) was added dropwise and the r.m. was stirred at 0° C. overnight. The precipitate was filtered and dried yielding 45 mg (39%) of compound 76 (1.44 HCl 0.8 H$_2$O 0.24 C4H$_8$O$_2$) (MP: 80° C. gum Kofler) ([α]$_D$: +44.2° (c: 0.19 w/v %, DMF, 20° C.)).

Conversion C12

Preparation of Compound 77

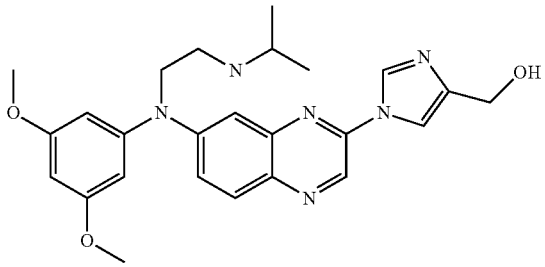

compound 77a compound 77 (HCl salt)

A solution of K$_2$CO$_3$ (148 mg; 1.07 mmol) in water (0.56 mL) was added to a solution of compound 167 (270 mg; 0.53 mmol) in MeOH (2.1 mL). The r.m. was stirred for 3 h at r.t., poured onto water and extracted with DCM. The organic layer was dried over MgSO$_4$, filtered and evaporated till dryness. The residue was purified by chromatography over silica gel (Stability Silica 5 μm 150×30.0 mm; mobile phase: gradient from 0.2% NH$_4$OH, 98% DCM, 2% MeOH to 0.8% NH$_4$OH, 92% DCM, 8% MeOH). The pure fractions were evaporated till dryness. The residue (compound 77a; free base) (150 mg; 61%) was dissolved in DCM and a solution of HCl 5-6N in isopropanol was added. The resulting hydrochloride salt was crystallized from Et$_2$O, filtered and dried yielding 126 mg (42%) of compound 77 (0.2.06 HCl 0.3 H$_2$O 0.24 C3H$_{80}$; MP: 150° C. gum, Kofler).

Conversion C13

Preparation of Compound 79

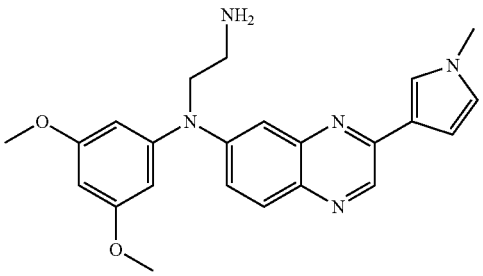 [SMILES: COc1cc(OC)cc(N(CCN)c2ccc3ncc(-c4ccn(C)c4)nc3c2)c1]

Hydrazine monohydrate (640 μL; 10.49 mmol) was added to a solution of compound 78 (800 mg; 1.5 mmol) in EtOH (40 mL). The mixture was heated to reflux overnight, cooled to r.t., poured into H$_2$O and extracted with EtOAc. The organic layer was dried over MgSO₄, filtered and evaporated to dryness. The residue was purified by chromatography over silica gel (Spherical SiOH 10 μm 60 g; mobile phase: 0.4% NH₄OH, 96% DCM, 4% MeOH). The pure fractions were collected and evaporated to dryness. The residue (285 mg; 47%) was crystallized from ACN/Et₂O. The precipitate was filtered and dried yielding 210 mg (35%) of compound 79 (MP: 106° C. DSC).

Conversion C14

Preparation of Compound 82 and Compound 83

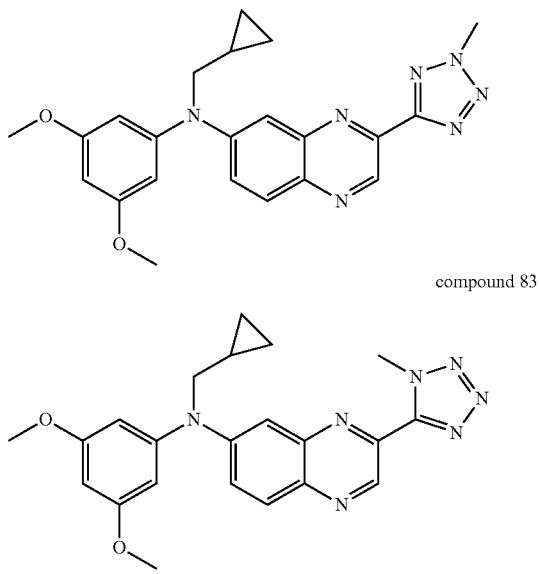

compound 82 compound 83

NaH (24 mg; 0.6 mmol) was added portionwise at 0° C. to compound 41 (220 mg; 0.54 mmol) and iodometane (37 μL; 0.6 mmol) in THF (5 mL). The mixture was refluxed overnight in a sealed tube, poured into ice and extracted with EtOAc. The organic layer was dried over MgSO₄, filtered and evaporated until dryness. The residue was purified by chromatography over silica gel (Spherical SiOH 10 μm 60 g; mobile phase: 98% DCM, 2% EtOAc). The pure fractions were evaporated until dryness to give 163 mg (72%) of compound 82 (MP: 143° C., Kofler) and 36 mg (16%) of compound 83 (MP: 168° C., Kofler).

Conversion C15

Preparation of compound 189

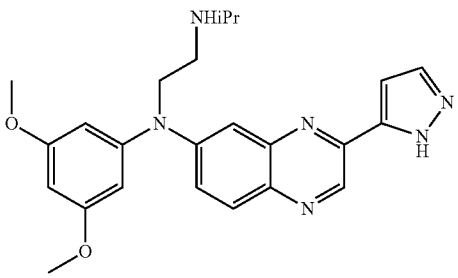

1.75 HCl HCl 4N in dioxane (0.484 mL; 1.94 mmol) was added to a solution of compound 188 (200 mg; 0.387 mmol) in dioxane (6.86 ml) and water (1 mL) at room temperature. The mixture was stirred for 2 hours at 100° C. then, at room temperature for 24 h. The mixture was poured into ice, basified with solid K₂CO₃ and extracted with DCM. The organic layer was washed with brine, dried over MgSO₄, filtered off and the solvent was evaporated. The residue (0.34 g) was purified by chromatography over silica gel (Irregular SiOH, 15-40 μm 30 g; mobile phase: 0.5% NH₄OH, 95% DCM, 5% MeOH). The product fractions were mixed and the solvent was evaporated to give: 0.165 g of an intermediate fraction. 4N HCl in dioxane was added to this fraction and the hydrochloride salt was crystallized from acetone and Et₂O, then filtered and dried to afford 0.151 g of compound 189 (74%). MP: 145° C. (gum, kofler).

The following compounds were prepared according to reaction protocols of one of the above Examples using alternative starting materials as appropriate.

In the table CoX (or BX) indicates that the preparation of this compound is described in Conversion X (or Method BX) or that this compound is prepared according to Conversion X (or Method BX).

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

TABLE A1

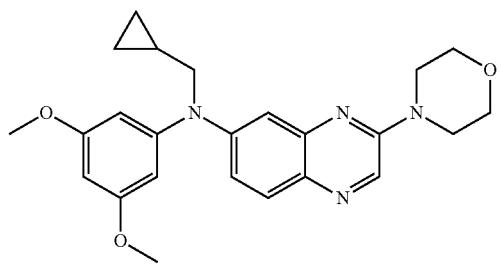 [SMILES: COc1cc(OC)cc(N(CC2CC2)c2ccc3ncc(N4CCOCC4)nc3c2)c1]

Co. 63; B44.b

TABLE A1-continued
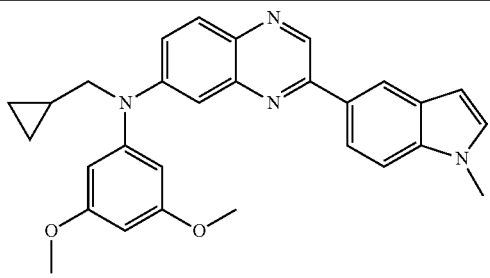
as a free base and as HCl salt
Co. 20 (•1.19HCl•0.68H₂O) and
Co. 20a freebase; B16
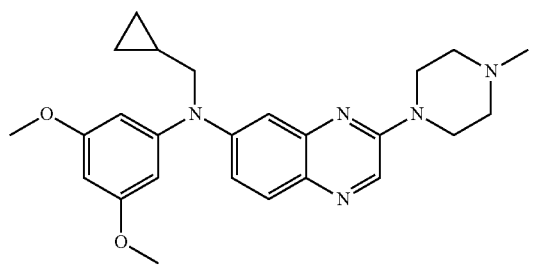
Co. 64; B44.c
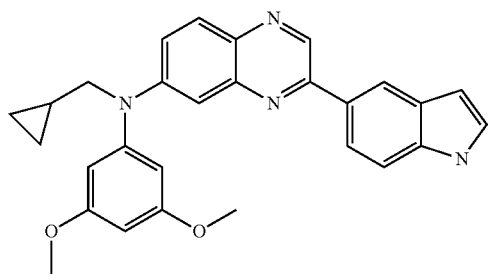 [SMILES: COc1cc(OC)cc(N(CC2CC2)c2ccc3ncc(-c4ccc5[nH]ccc5c4)nc3c2)c1]
Co. 86; B34
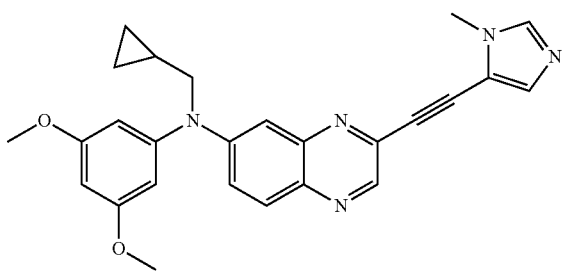 [SMILES: COc1cc(OC)cc(N(CC2CC2)c2ccc3ncc(C#Cc4cncn4C)nc3c2)c1]
Co. 22; B20
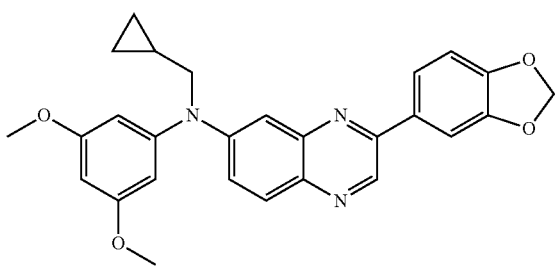 [SMILES: COc1cc(OC)cc(N(CC2CC2)c2ccc3ncc(-c4ccc5c(c4)OCO5)nc3c2)c1]
Co. 87; B15

TABLE A1-continued
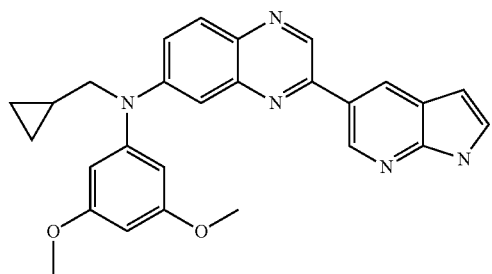 [SMILES: COc1cc(OC)cc(N(CC2CC2)c2ccc3ncc(-c4cnc5[nH]ccc5c4)nc3c2)c1]
Co. 88; B14
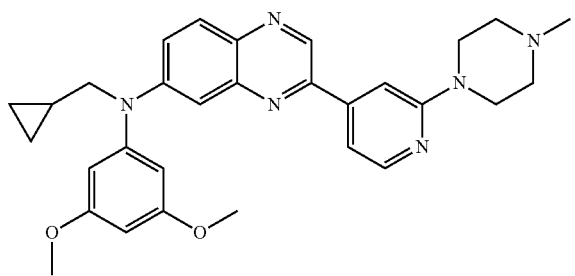 [SMILES: COc1cc(OC)cc(N(CC2CC2)c2ccc3ncc(-c4ccnc(N5CCN(C)CC5)c4)nc3c2)c1]
Co. 37; B34
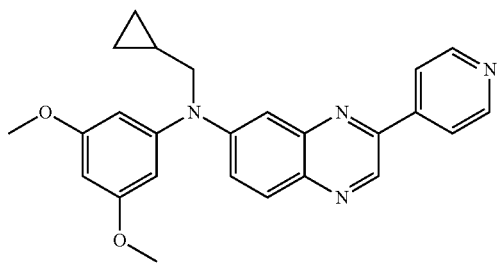 [SMILES: COc1cc(OC)cc(N(CC2CC2)c2ccc3ncc(-c4ccncc4)nc3c2)c1]
Co. 89; B15
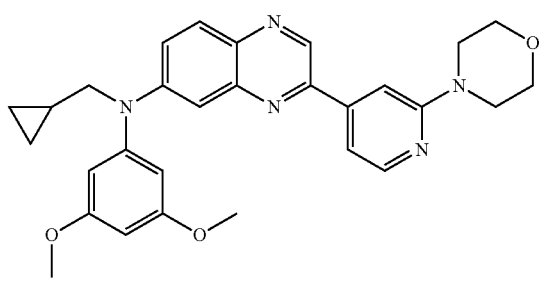 [SMILES: COc1cc(OC)cc(N(CC2CC2)c2ccc3ncc(-c4ccnc(N5CCOCC5)c4)nc3c2)c1]
Co. 90; B14
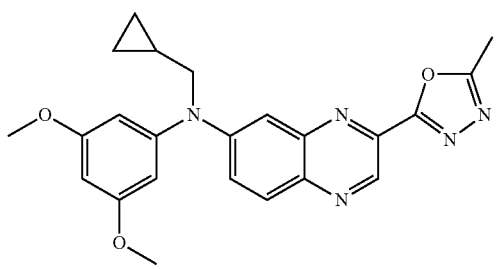
Co. 85; B51

TABLE A1-continued
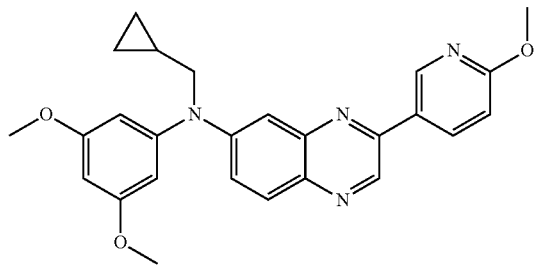
Co. 91; B15
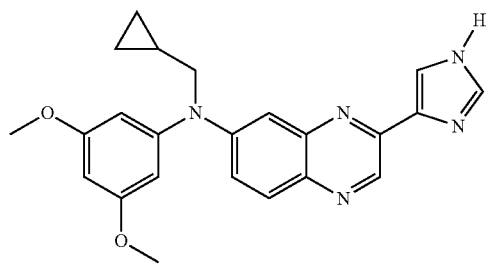 [SMILES: COc1cc(OC)cc(N(CC2CC2)c2ccc3ncc(-c4c[nH]cn4)nc3c2)c1]
Co. 39; B36
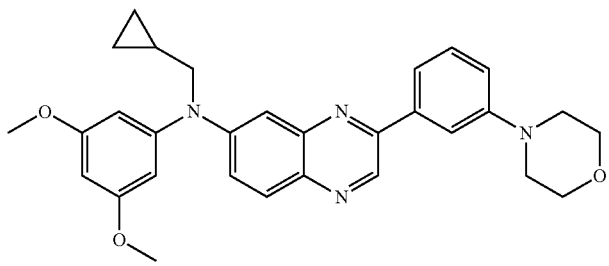 [SMILES: COc1cc(OC)cc(N(CC2CC2)c2ccc3ncc(-c4cccc(N5CCOCC5)c4)nc3c2)c1]
Co. 92; B15
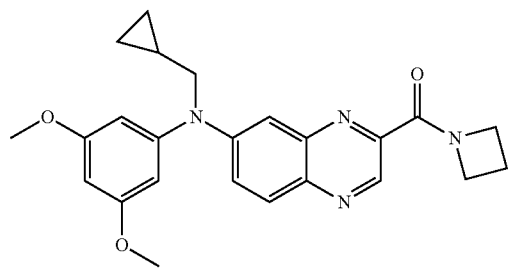 [SMILES: COc1cc(OC)cc(N(CC2CC2)c2ccc3ncc(C(=O)N4CCC4)nc3c2)c1]
Co. 93; B25
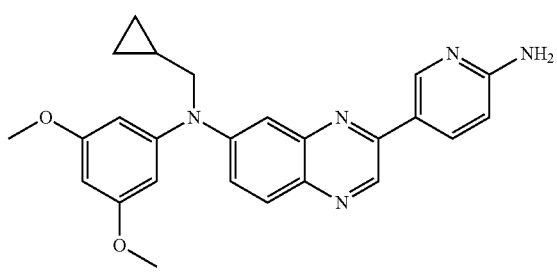 [SMILES: COc1cc(OC)cc(N(CC2CC2)c2ccc3ncc(-c4ccc(N)nc4)nc3c2)c1]
Co. 94; B15

TABLE A1-continued
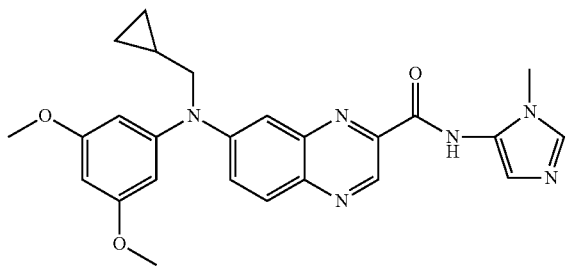 [SMILES: COc1cc(OC)cc(N(CC2CC2)c2ccc3ncc(C(=O)Nc4cncn4C)nc3c2)c1]
Co. 27; B25
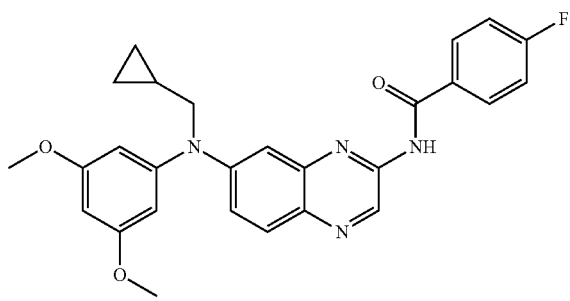 [SMILES: COc1cc(OC)cc(N(CC2CC2)c2ccc3ncc(NC(=O)c4ccc(F)cc4)nc3c2)c1]
Co. 28; B26
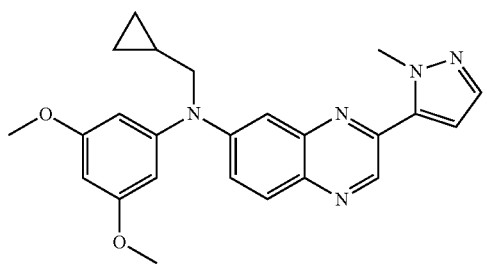 [SMILES: COc1cc(OC)cc(N(CC2CC2)c2ccc3ncc(-c4ccnn4C)nc3c2)c1]
Co. 18; B14
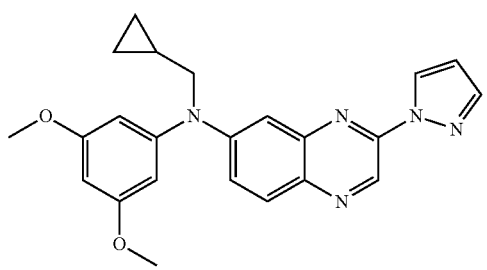 [SMILES: COc1cc(OC)cc(N(CC2CC2)c2ccc3ncc(-n4cccn4)nc3c2)c1]
Co. 95; B34
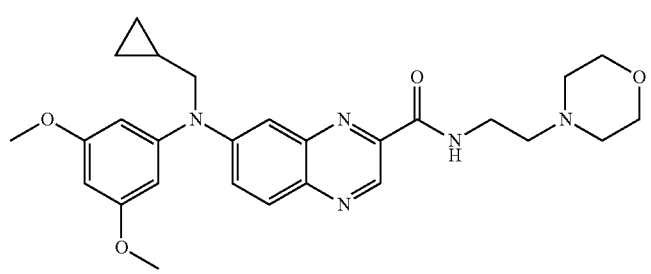 [SMILES: COc1cc(OC)cc(N(CC2CC2)c2ccc3ncc(C(=O)NCCN4CCOCC4)nc3c2)c1]
Co. 96; B25

TABLE A1-continued
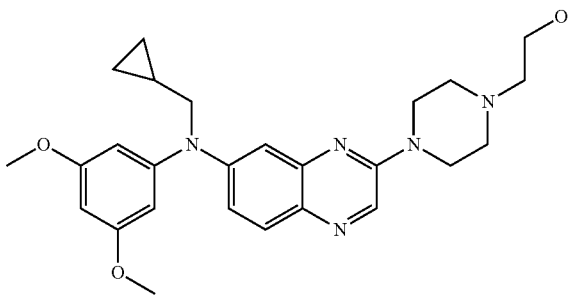 [SMILES: COc1cc(OC)cc(N(CC2CC2)c2ccc3ncc(N4CCN(CCO)CC4)nc3c2)c1]
as a free base and as HCl salt
Co. 49 (•1.65HCl•0.72H₂O) and
Co. 49a freebase; B44.a
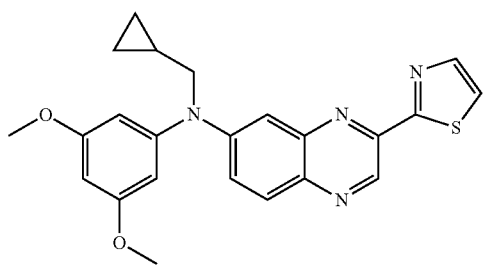 [SMILES: COc1cc(OC)cc(N(CC2CC2)c2ccc3ncc(-c4nccs4)nc3c2)c1]
Co. 97; B17
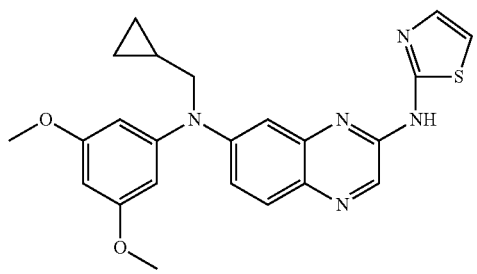 [SMILES: COc1cc(OC)cc(N(CC2CC2)c2ccc3ncc(Nc4nccs4)nc3c2)c1]
Co. 98; B18
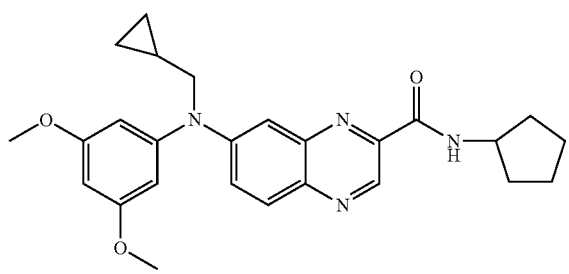 [SMILES: COc1cc(OC)cc(N(CC2CC2)c2ccc3ncc(C(=O)NC4CCCC4)nc3c2)c1]
Co. 99; B25
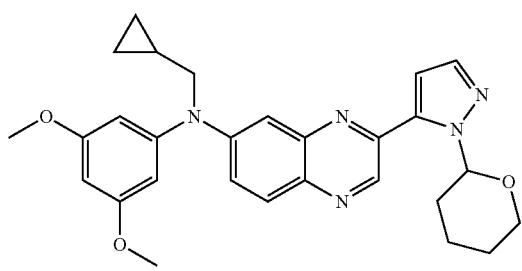 [SMILES: COc1cc(OC)cc(N(CC2CC2)c2ccc3ncc(-c4ccnn4C4CCCCO4)nc3c2)c1]
Co. 100; B14

TABLE A1-continued
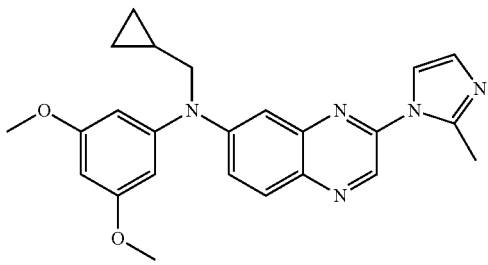 [SMILES: COc1cc(OC)cc(N(CC2CC2)c2ccc3ncc(-n4ccnc4C)nc3c2)c1]
as a free base and as HCl salt
Co. 32 (•0.99HCl) and Co. 32a;
freebase B30
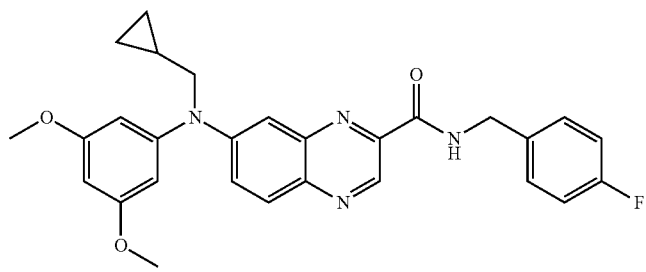 [SMILES: COc1cc(OC)cc(N(CC2CC2)c2ccc3ncc(C(=O)NCc4ccc(F)cc4)nc3c2)c1]
Co. 101; B25
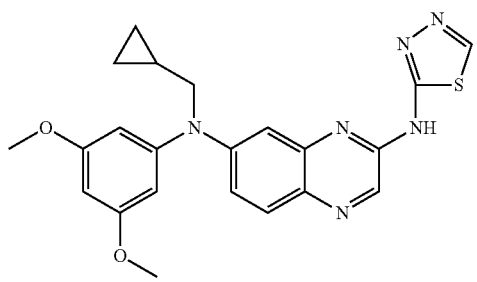 [SMILES: COc1cc(OC)cc(N(CC2CC2)c2ccc3ncc(Nc4nncs4)nc3c2)c1]
Co. 102; B18
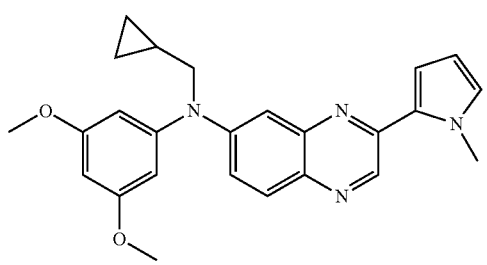 [SMILES: COc1cc(OC)cc(N(CC2CC2)c2ccc3ncc(-c4cccn4C)nc3c2)c1]
Co. 103; B17
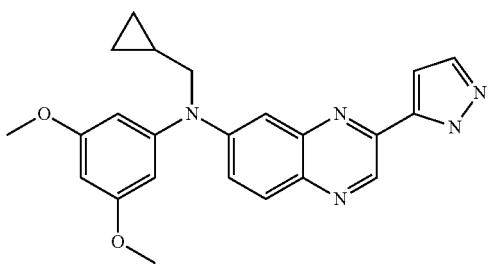 [SMILES: COc1cc(OC)cc(N(CC2CC2)c2ccc3ncc(-c4ccn[nH]4)nc3c2)c1]
Co. 58 (1.25HCl•0.36$C_3H_8O$) and
Co. 58a freebase; C5

TABLE A1-continued
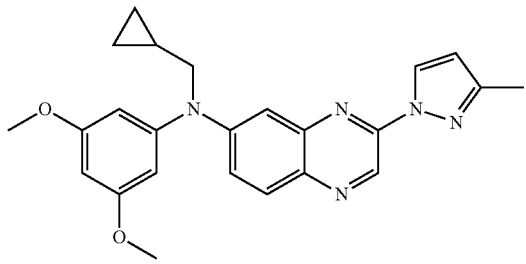
Co. 31; B29
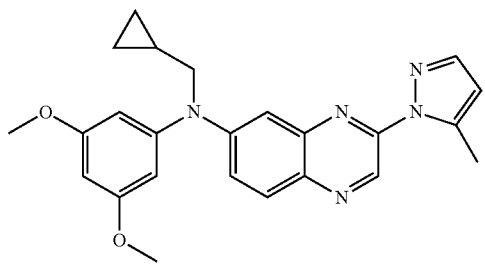 [SMILES: COc1cc(OC)cc(N(CC2CC2)c2ccc3ncc(-n4nccc4C)nc3c2)c1]
Co. 62; B29
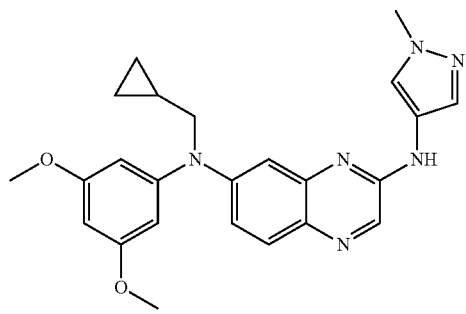 [SMILES: COc1cc(OC)cc(N(CC2CC2)c2ccc3ncc(Nc4cnn(C)c4)nc3c2)c1]
Co. 61; B18
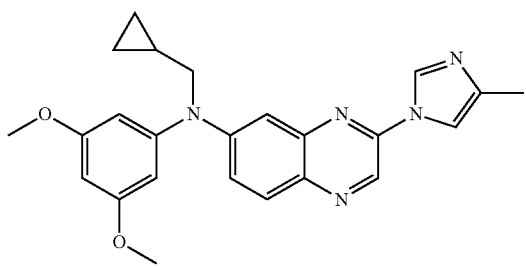
Co. 30; B28
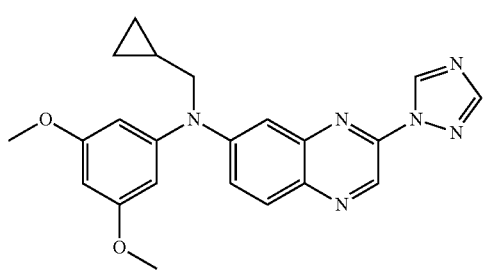 [SMILES: COc1cc(OC)cc(N(CC2CC2)c2ccc3ncc(-n4cncn4)nc3c2)c1]
Co. 50; B45

TABLE A1-continued
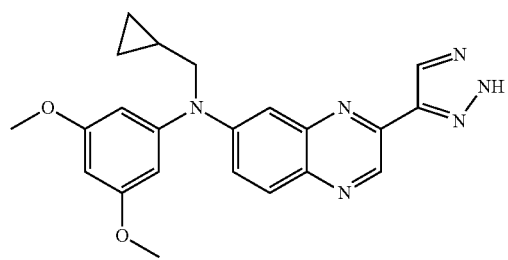 [SMILES: COc1cc(OC)cc(N(CC2CC2)c2ccc3ncc(/C(C=N)=N/N)nc3c2)c1]
Co. 69; C7.a
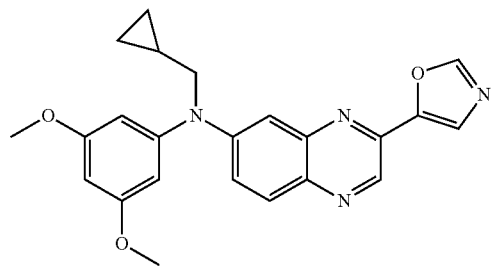
Co. 55; B48
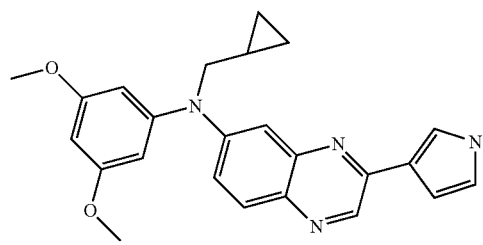 [SMILES: COc1cc(OC)cc(N(CC2CC2)c2ccc3ncc(-c4cc[nH]c4)nc3c2)c1]
Co. 36; B33
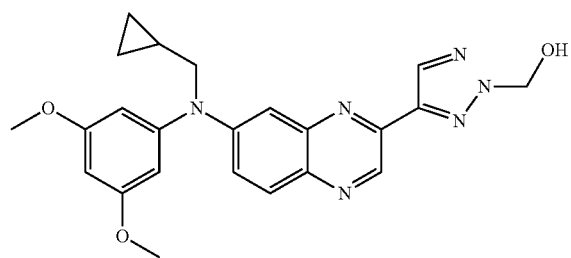 [SMILES: COc1cc(OC)cc(N(CC2CC2)c2ccc3ncc(/C(C=N)=N/NCO)nc3c2)c1]
Co. 42; B39
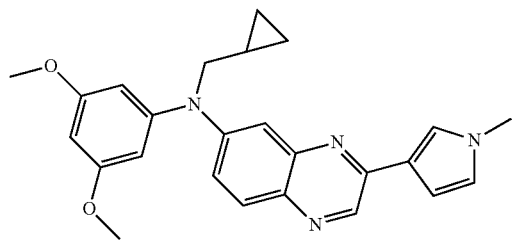
Co. 73; C8

TABLE A1-continued
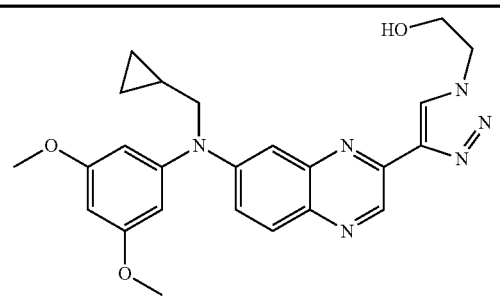
Co. 40; B37
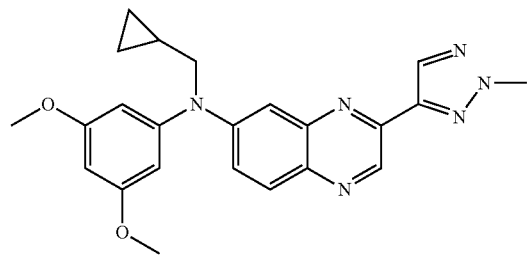
Co. 70; C7.b
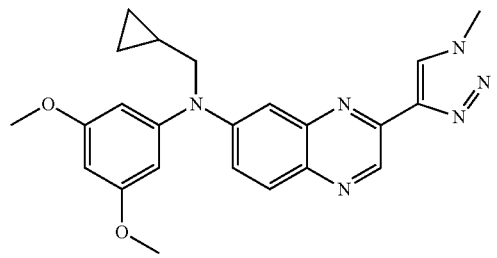 [SMILES: CN/C=C(\N=N)c1cnc2ccc(N(CC3CC3)c3cc(OC)cc(OC)c3)cc2n1]
Co. 71; C7.b
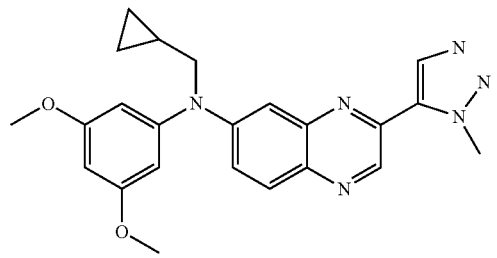 [SMILES: COc1cc(OC)cc(N(CC2CC2)c2ccc3ncc(/C(=C/N)N(C)N)nc3c2)c1]
Co. 72; C7.b
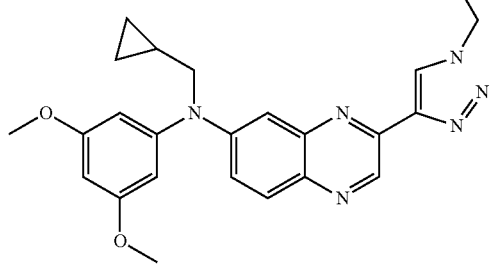
Co. 24; B22

TABLE A1-continued
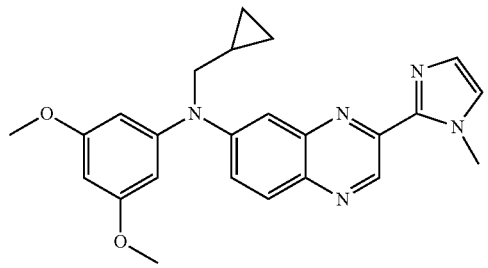 [SMILES: COc1cc(OC)cc(N(CC2CC2)c2ccc3ncc(-c4nccn4C)nc3c2)c1]
Co. 60; B17
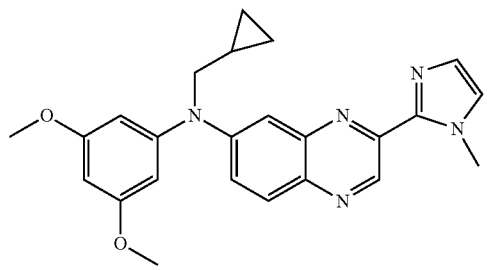 [SMILES: COc1cc(OC)cc(N(CC2CC2)c2ccc3ncc(-c4nccn4C)nc3c2)c1]
Co. 56; B49
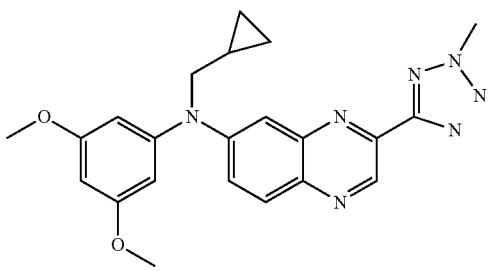 [SMILES: COc1cc(OC)cc(N(CC2CC2)c2ccc3ncc(/C(N)=N/N(C)N)nc3c2)c1]
Co. 82; C14
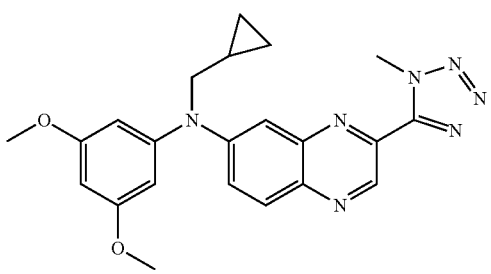 [SMILES: COc1cc(OC)cc(N(CC2CC2)c2ccc3ncc(C(=N)N(C)N=N)nc3c2)c1]
Co. 83; C14
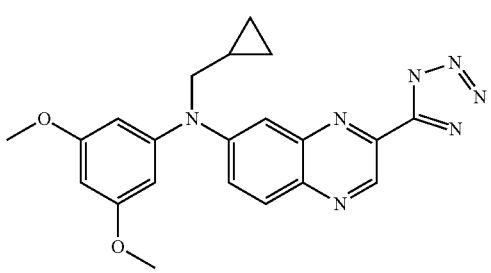 [SMILES: COc1cc(OC)cc(N(CC2CC2)c2ccc3ncc(C(=N)NN=N)nc3c2)c1]
Co. 41; B38

TABLE A1-continued
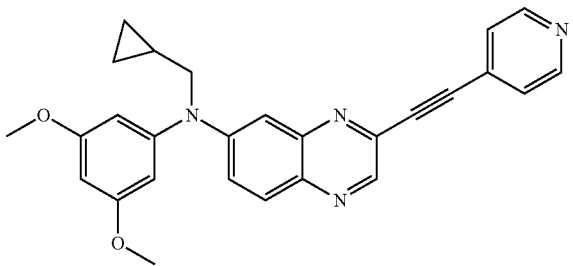 [SMILES: COc1cc(OC)cc(N(CC2CC2)c2ccc3ncc(C#Cc4ccncc4)nc3c2)c1]
Co. 23; B21
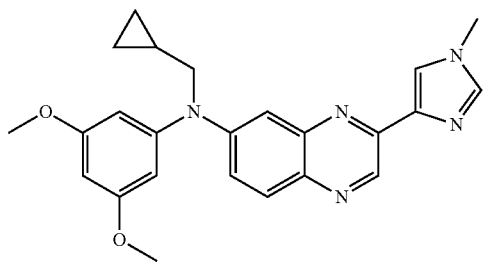 [SMILES: COc1cc(OC)cc(N(CC2CC2)c2ccc3ncc(-c4cn(C)cn4)nc3c2)c1]
Co. 21; B19
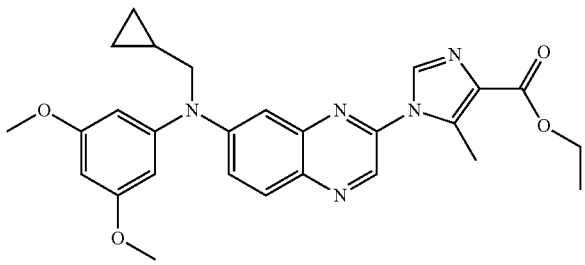 [SMILES: CCOC(=O)c1ncn(-c2cnc3ccc(N(CC4CC4)c4cc(OC)cc(OC)c4)cc3n2)c1C]
Co. 65; B44.d
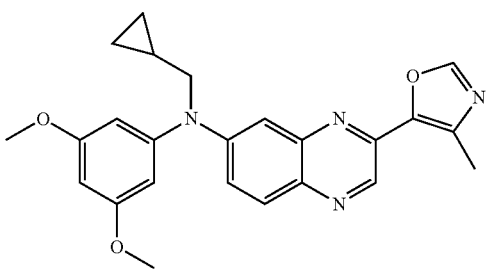 [SMILES: COc1cc(OC)cc(N(CC2CC2)c2ccc3ncc(-c4ocnc4C)nc3c2)c1]
Co. 104; B48
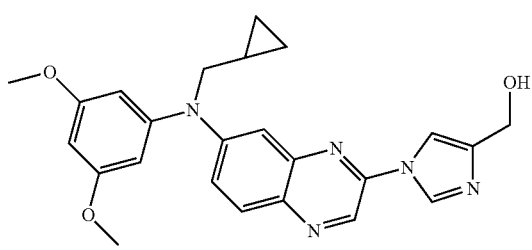 [SMILES: COc1cc(OC)cc(N(CC2CC2)c2ccc3ncc(-n4cnc(CO)c4)nc3c2)c1]
Co. 105; B49

TABLE A1-continued
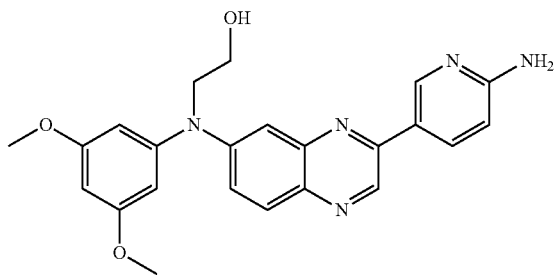 [SMILES: COc1cc(OC)cc(N(CCO)c2ccc3ncc(-c4ccc(N)nc4)nc3c2)c1]
Co. 106; B6/B8/B10/B12
alternative C3
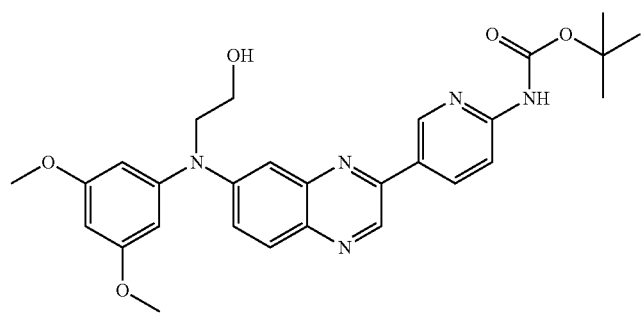 [SMILES: COc1cc(OC)cc(N(CCO)c2ccc3ncc(-c4ccc(NC(=O)OC(C)(C)C)nc4)nc3c2)c1]
Co. 15; B12
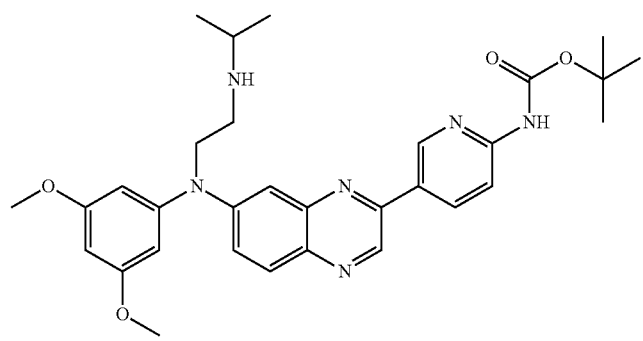 [SMILES: COc1cc(OC)cc(N(CCNC(C)C)c2ccc3ncc(-c4ccc(NC(=O)OC(C)(C)C)nc4)nc3c2)c1]
Co. 16; B13 (example)
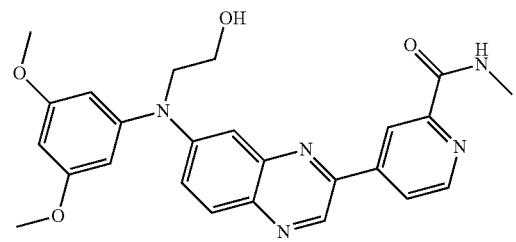
Co. 13; B10 (example)

TABLE A1-continued
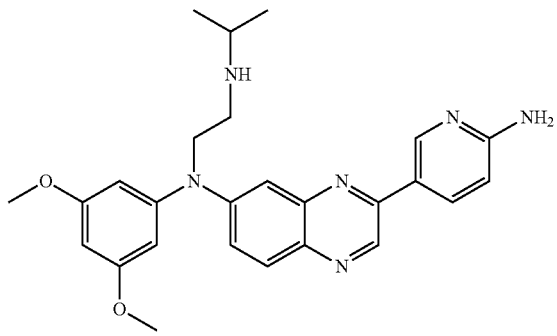 [SMILES: COc1cc(OC)cc(N(CCNC(C)C)c2ccc3ncc(-c4ccc(N)nc4)nc3c2)c1]
Co. 17; C2
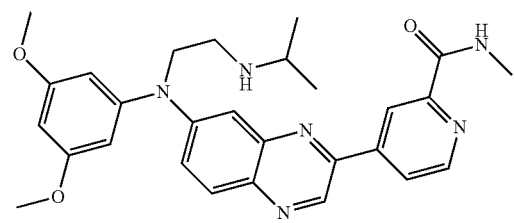
Co. 14; B11
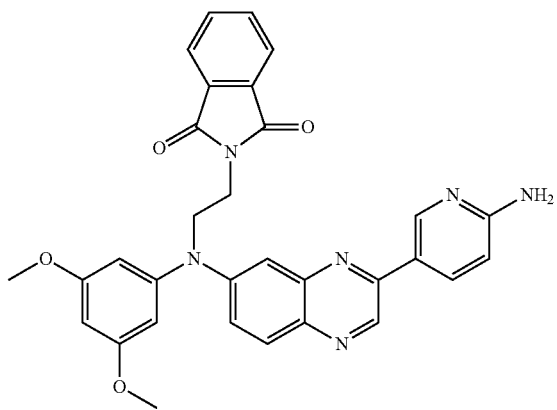 [SMILES: COc1cc(OC)cc(N(CCN2C(=O)c3ccccc3C2=O)c2ccc3ncc(-c4ccc(N)nc4)nc3c2)c1]
Co. 57; B50
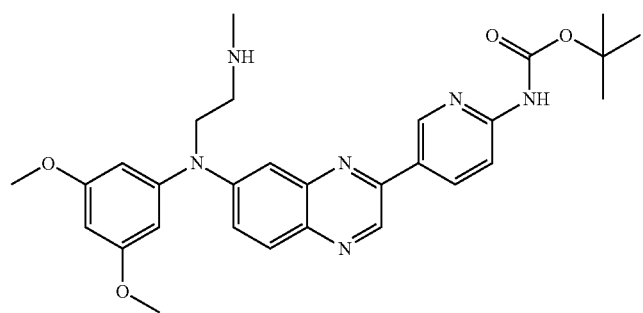
Co. 81; B52

TABLE A1-continued
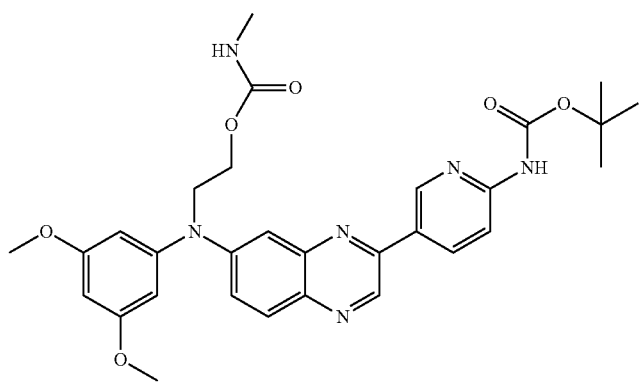 [SMILES: CNC(=O)OCCN(c1cc(OC)cc(OC)c1)c1ccc2ncc(-c3ccc(NC(=O)OC(C)(C)C)nc3)nc2c1]
Co. 80; B52
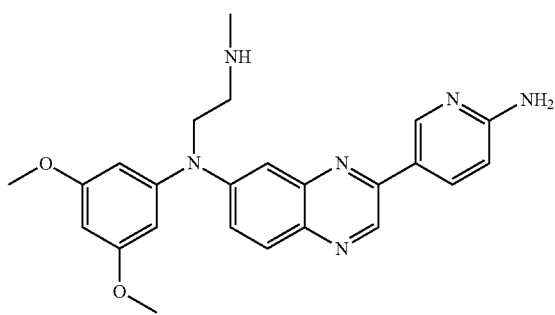 [SMILES: CNCCN(c1cc(OC)cc(OC)c1)c1ccc2ncc(-c3ccc(N)nc3)nc2c1]
as HCl salt
Co. 107 (2.22HCl·1.47H₂O); C2
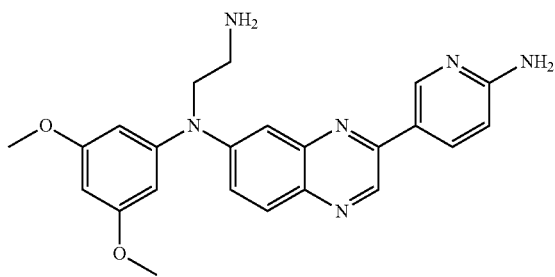 [SMILES: COc1cc(OC)cc(N(CCN)c2ccc3ncc(-c4ccc(N)nc4)nc3c2)c1]
Co. 108; C13
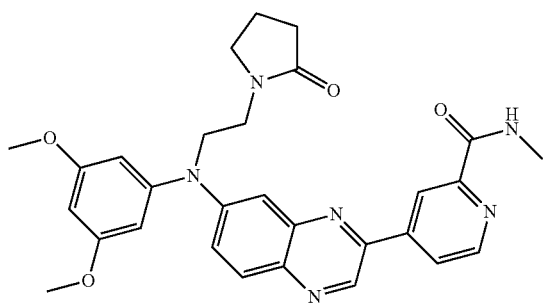
Co. 25; B23

TABLE A1-continued
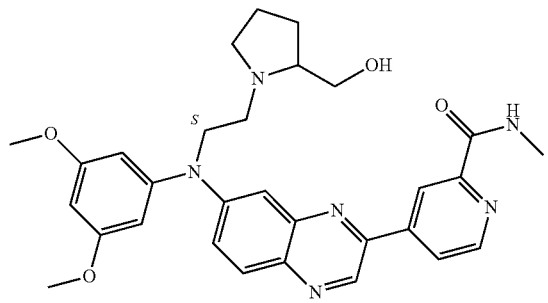
Co. 109 (S); B11
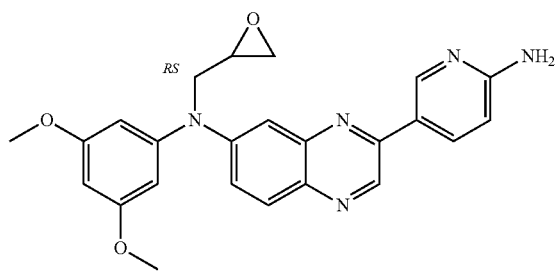 [SMILES: COc1cc(OC)cc(N(CC2CO2)c2ccc3ncc(-c4ccc(N)nc4)nc3c2)c1]
Co. 110 (RS); B15
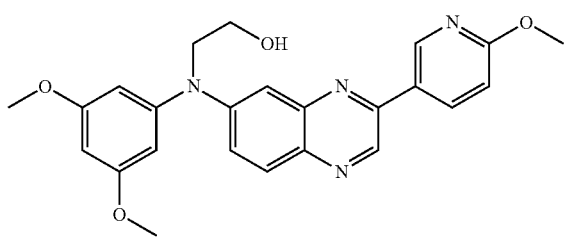
Co. 111; B6/B8/B10/B12
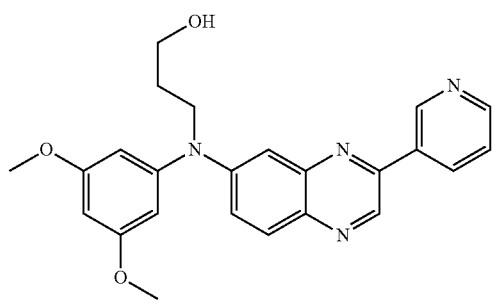 [SMILES: COc1cc(OC)cc(N(CCCO)c2ccc3ncc(-c4cccnc4)nc3c2)c1]
Co. 112; B6/B8/B10/B12
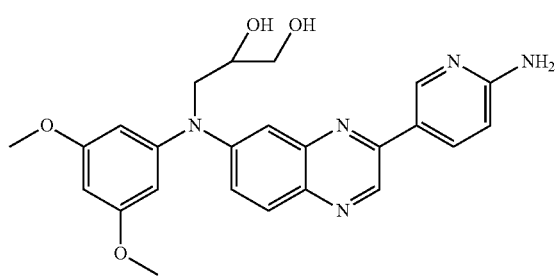 [SMILES: COc1cc(OC)cc(N(CC(O)CO)c2ccc3ncc(-c4ccc(N)nc4)nc3c2)c1]
Co. 74; C9

TABLE A1-continued
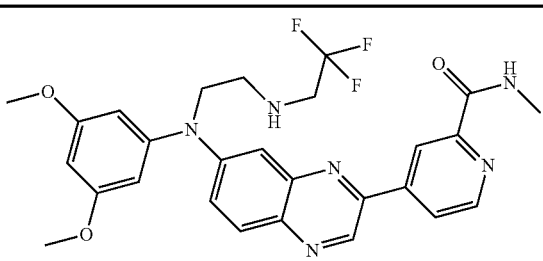
Co. 113; B9
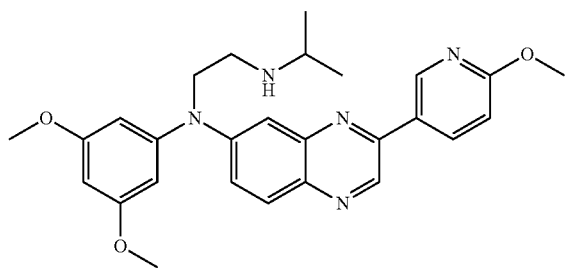
Co. 114; B11
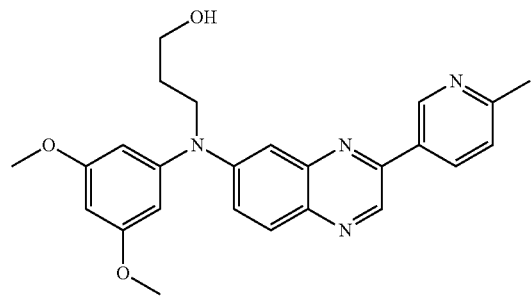
Co. 115; B6/B8/B10/B12
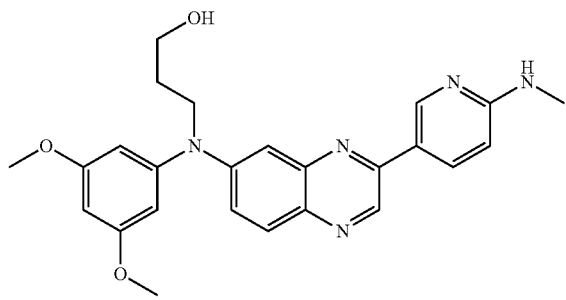
Co. 116; B6/B8/B10/B12
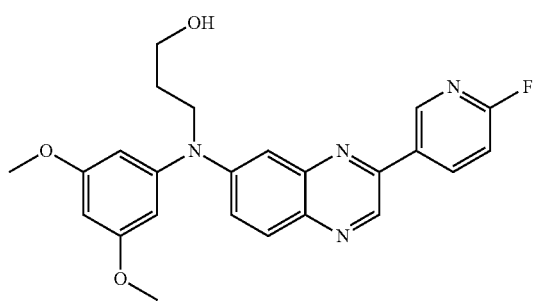 [SMILES: COc1cc(OC)cc(N(CCCO)c2ccc3ncc(-c4ccc(F)nc4)nc3c2)c1]
Co. 117; B6/B8/B10/B12

TABLE A1-continued
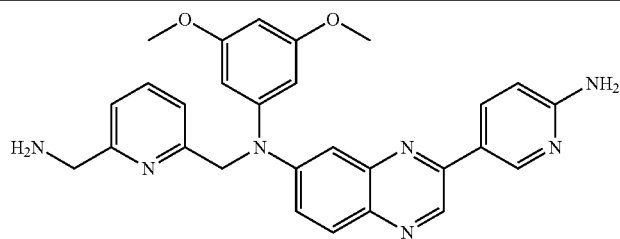
as a free base and as HCl salt
Co. 51 (•1.84HCl) and Co. 51a;
freebase; B46
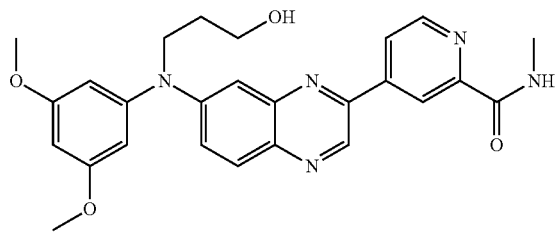 [SMILES: CNC(=O)c1cc(-c2cnc3ccc(N(CCCO)c4cc(OC)cc(OC)c4)cc3n2)ccn1]
Co. 118; B6/B8/B10/B12
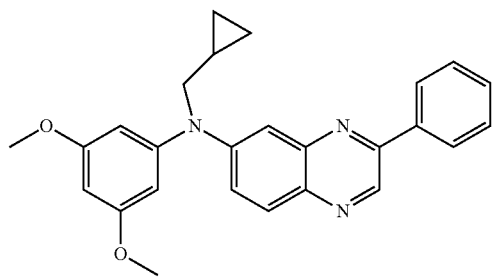 [SMILES: COc1cc(OC)cc(N(CC2CC2)c2ccc3ncc(-c4ccccc4)nc3c2)c1]
Co. 119; B34
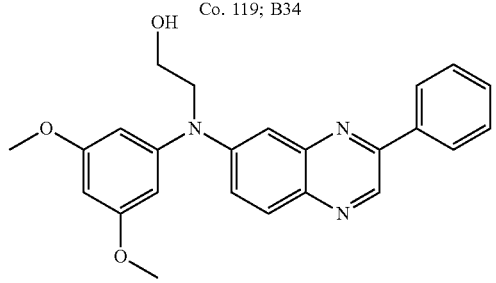
Co. 120; B6/B8/B10/B12
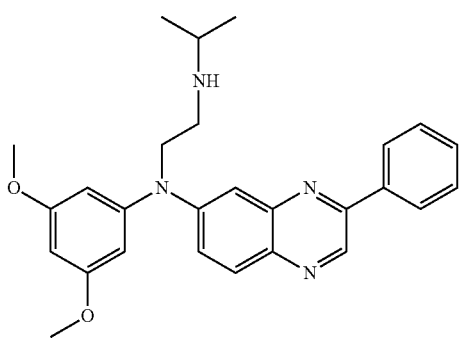 [SMILES: COc1cc(OC)cc(N(CCNC(C)C)c2ccc3ncc(-c4ccccc4)nc3c2)c1]
as a free base and as HCl salt
Co. 121 (•1.46HCl•0.79H$_2$O) and
Co. 121a; free baseB7

TABLE A1-continued
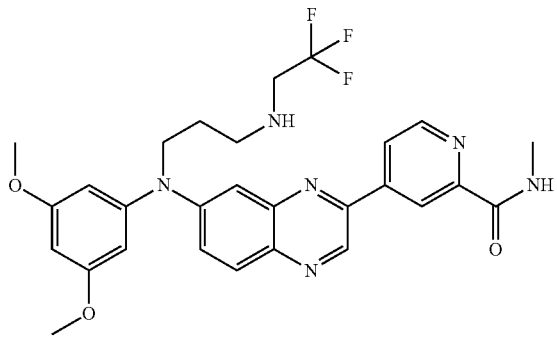 [SMILES: CNC(=O)c1cc(-c2cnc3ccc(N(CCCNCC(F)(F)F)c4cc(OC)cc(OC)c4)cc3n2)ccn1]
Co. 122; B13
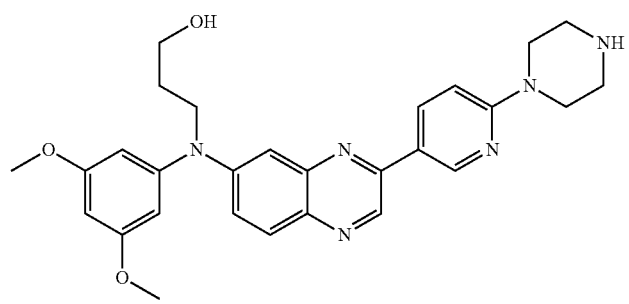 [SMILES: COc1cc(OC)cc(N(CCCO)c2ccc3ncc(-c4ccc(N5CCNCC5)nc4)nc3c2)c1]
as a trifluoroacetic acid salt
Co. 48 (•0.5 CF$_3$COOH); B43
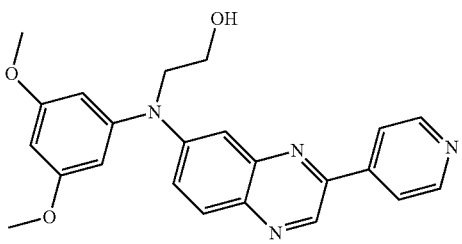 [SMILES: COc1cc(OC)cc(N(CCO)c2ccc3ncc(-c4ccncc4)nc3c2)c1]
Co. 11, B8
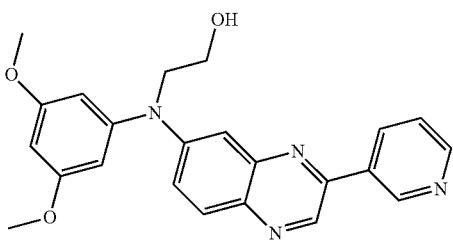 [SMILES: COc1cc(OC)cc(N(CCO)c2ccc3ncc(-c4cccnc4)nc3c2)c1]
Co. 9; B6
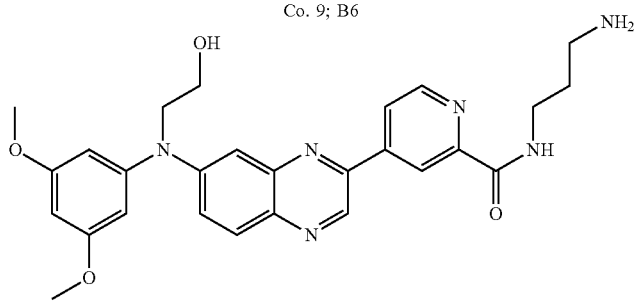
Co. 123; B31

TABLE A1-continued
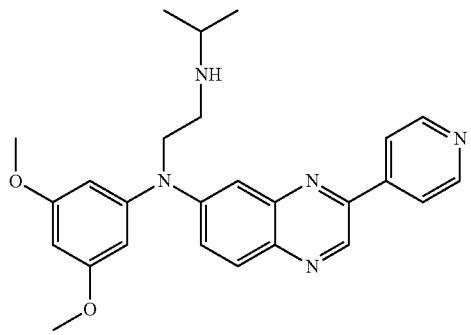 [SMILES: COc1cc(OC)cc(N(CCNC(C)C)c2ccc3ncc(-c4ccncc4)nc3c2)c1]
Co. 12; B9
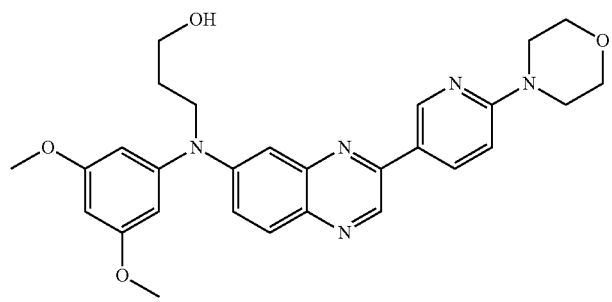 [SMILES: COc1cc(OC)cc(N(CCCO)c2ccc3ncc(-c4ccc(N5CCOCC5)nc4)nc3c2)c1]
Co. 124; B6/B8/B10/B12
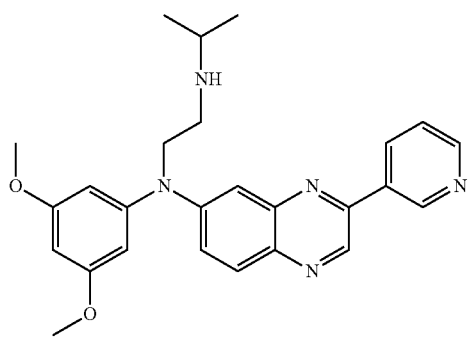 [SMILES: COc1cc(OC)cc(N(CCNC(C)C)c2ccc3ncc(-c4cccnc4)nc3c2)c1]
a free base and as HCl salt
Co. 10 (•2.14HCl•H₂O) and Co. 10a;
free baseB7
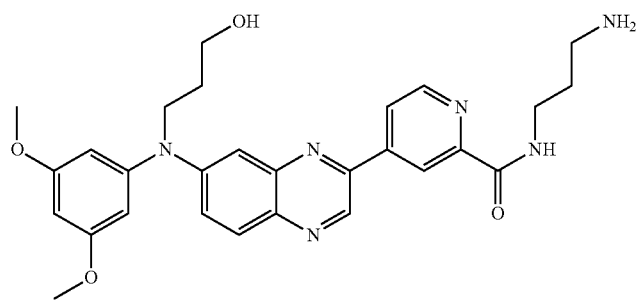 [SMILES: COc1cc(OC)cc(N(CCCO)c2ccc3ncc(-c4ccnc(C(=O)NCCCN)c4)nc3c2)c1]
Co. 33; B31

TABLE A1-continued
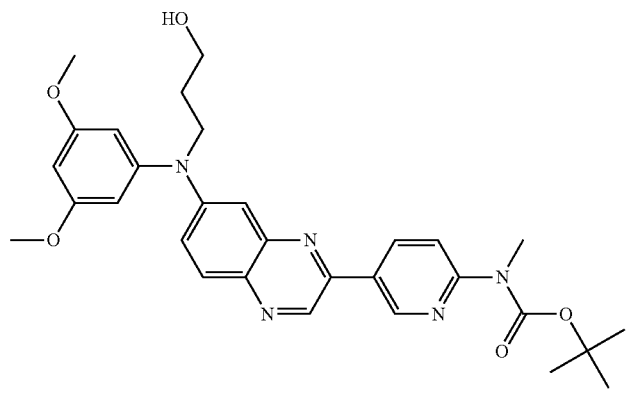 [SMILES: COc1cc(OC)cc(N(CCCO)c2ccc3ncc(-c4ccc(N(C)C(=O)OC(C)(C)C)nc4)nc3c2)c1]
Co. 125; B6/B8/B10/B12
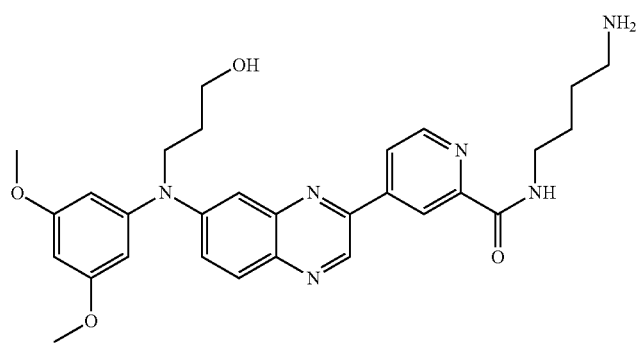 [SMILES: COc1cc(OC)cc(N(CCCO)c2ccc3ncc(-c4ccnc(C(=O)NCCCCN)c4)nc3c2)c1]
Co. 126; B31
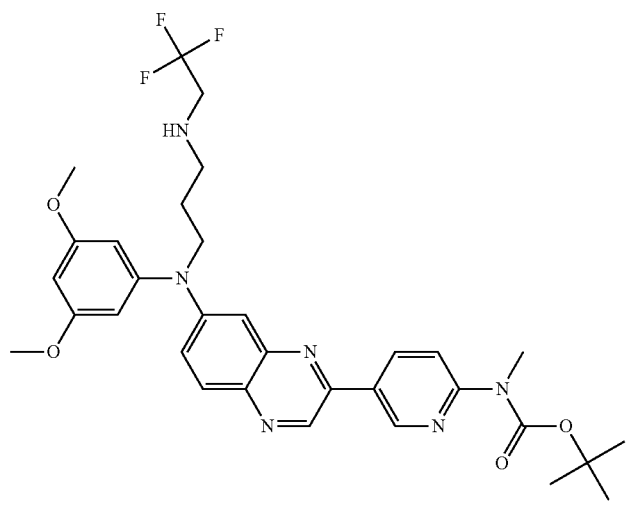 [SMILES: COc1cc(OC)cc(N(CCCNCC(F)(F)F)c2ccc3ncc(-c4ccc(N(C)C(=O)OC(C)(C)C)nc4)nc3c2)c1]
Co. 127; B7

TABLE A1-continued
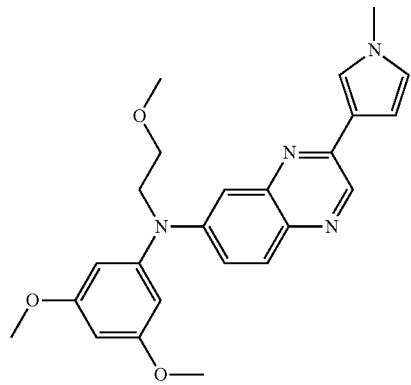 [SMILES: COCCN(c1cc(OC)cc(OC)c1)c1ccc2ncc(-c3ccn(C)c3)nc2c1]
Co. 6; B4
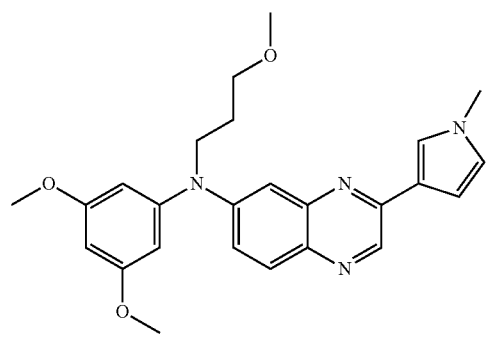 [SMILES: COCCCN(c1cc(OC)cc(OC)c1)c1ccc2ncc(-c3ccn(C)c3)nc2c1]
as a free base and as HCl salt
Co. 3 (•1.06HCl) and Co. 3a;
free baseB2
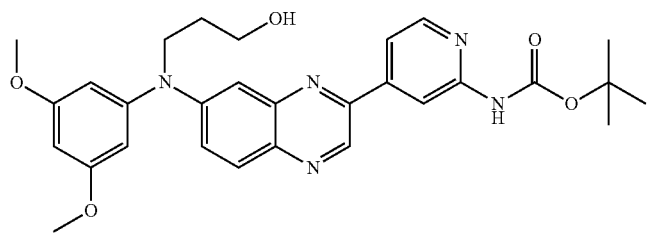 [SMILES: COc1cc(OC)cc(N(CCCO)c2ccc3ncc(-c4ccnc(NC(=O)OC(C)(C)C)c4)nc3c2)c1]
Co. 128; B6/B8/B10/B12
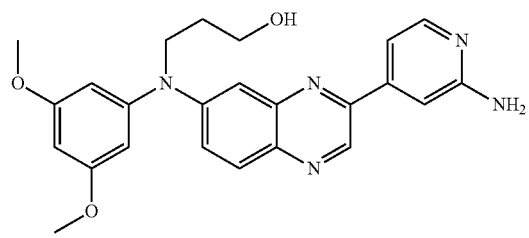 [SMILES: COc1cc(OC)cc(N(CCCO)c2ccc3ncc(-c4ccnc(N)c4)nc3c2)c1]
Co. 66; C3 or alternative B31

TABLE A1-continued
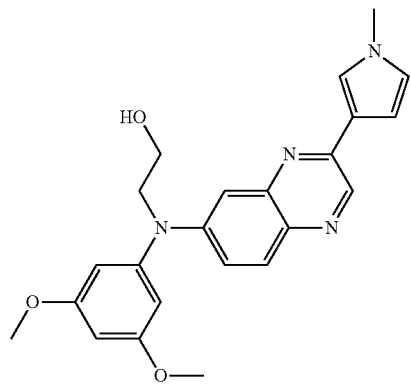 [SMILES: COc1cc(OC)cc(N(CCO)c2ccc3ncc(-c4ccn(C)c4)nc3c2)c1]
Co. 7; B4 (example)
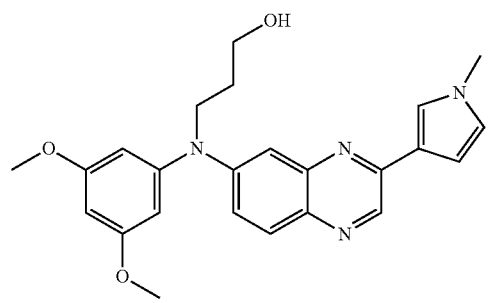 [SMILES: COc1cc(OC)cc(N(CCCO)c2ccc3ncc(-c4ccn(C)c4)nc3c2)c1]
Co. 4; B2 (example)
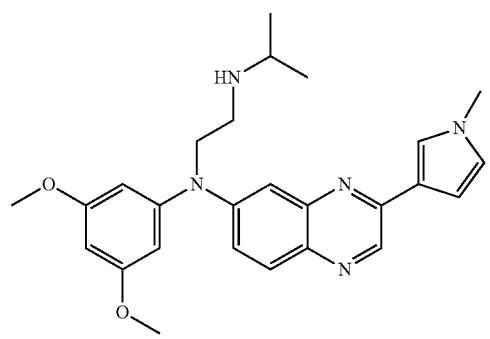 [SMILES: COc1cc(OC)cc(N(CCNC(C)C)c2ccc3ncc(-c4ccn(C)c4)nc3c2)c1]
as a free base and as HCl salt
Co. 8 (•1.79HCl) and Co. 8a;
free base B5
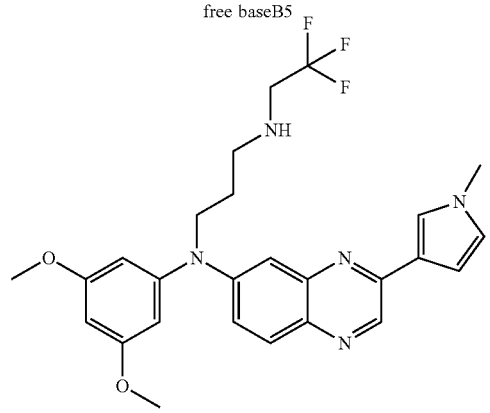
as a free base and as HCl salt
Co. 5 (•1.81HCl) and Co. 5a;
free base B3

TABLE A1-continued
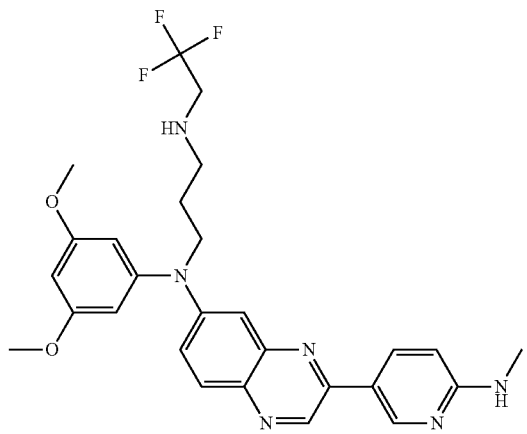
Co. 129; C3
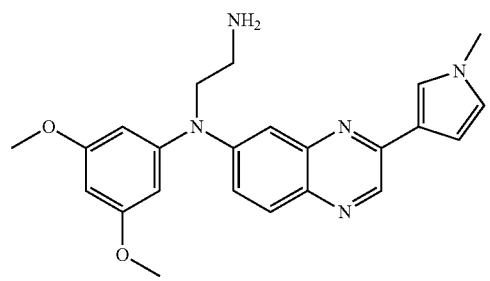 [SMILES: COc1cc(OC)cc(N(CCN)c2ccc3ncc(-c4ccn(C)c4)nc3c2)c1]
Co. 79; C13
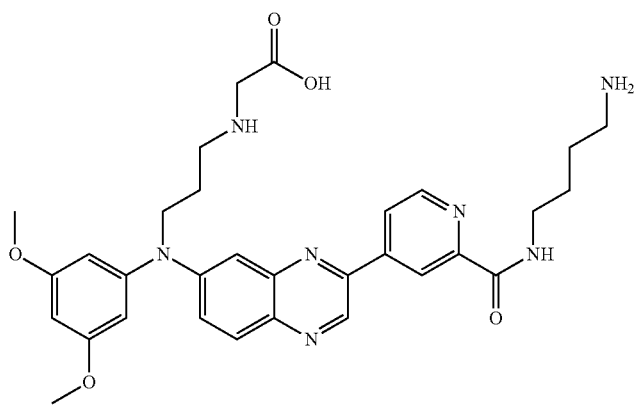 [SMILES: COc1cc(OC)cc(N(CCCNCC(=O)O)c2ccc3ncc(-c4ccnc(C(=O)NCCCCN)c4)nc3c2)c1]
as a trifluoroacetic acid salt
Co. 44 (•CF₃COOH); B41
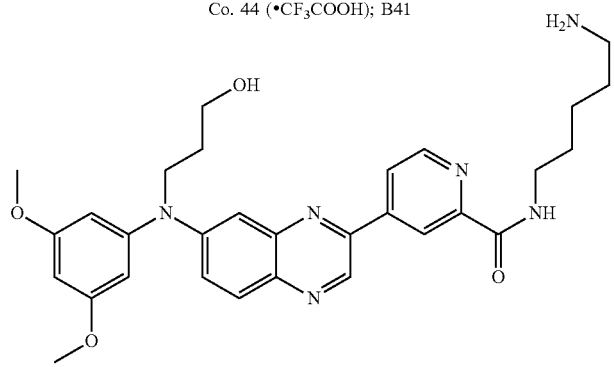
Co. 130; B31

TABLE A1-continued
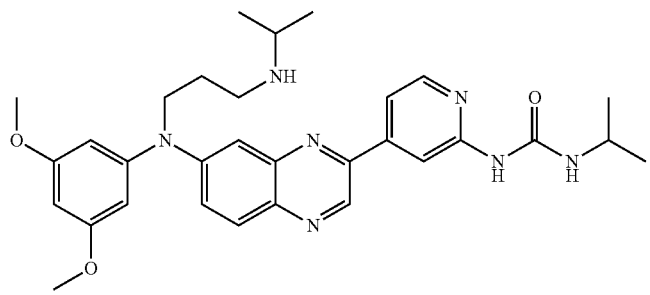 [SMILES: COc1cc(OC)cc(N(CCCNC(C)C)c2ccc3ncc(-c4ccnc(NC(=O)NC(C)C)c4)nc3c2)c1]
Co. 131; B11
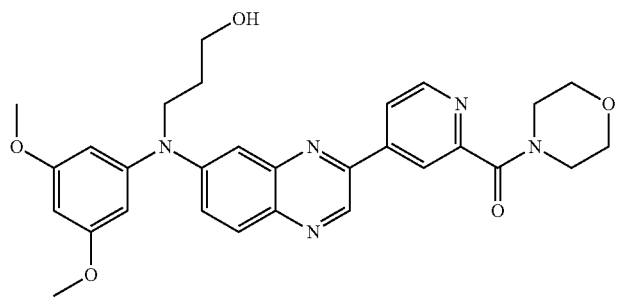 [SMILES: COc1cc(OC)cc(N(CCCO)c2ccc3ncc(-c4ccnc(C(=O)N5CCOCC5)c4)nc3c2)c1]
Co. 43; B40
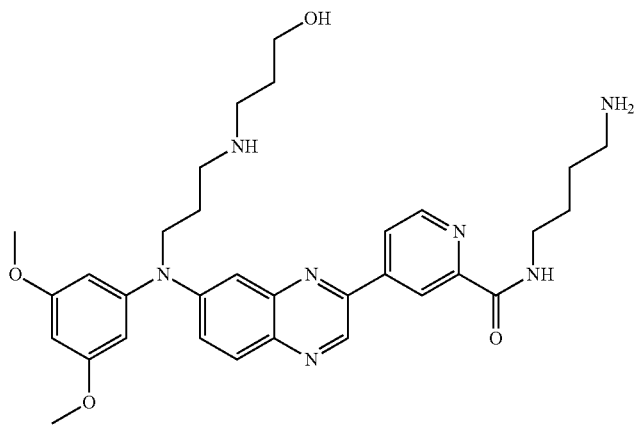 [SMILES: COc1cc(OC)cc(N(CCCNCCCO)c2ccc3ncc(-c4ccnc(C(=O)NCCCCN)c4)nc3c2)c1]
Co. 132; B31
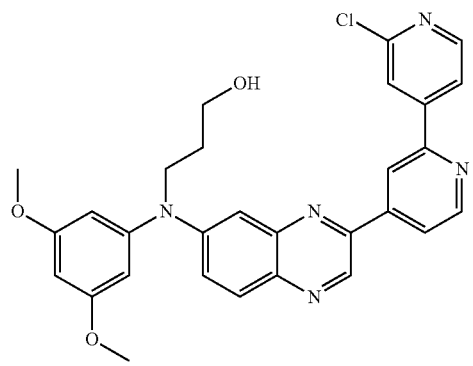 [SMILES: COc1cc(OC)cc(N(CCCO)c2ccc3ncc(-c4ccnc(-c5ccnc(Cl)c5)c4)nc3c2)c1]
Co. 133; B6/B8/B10/B12

TABLE A1-continued
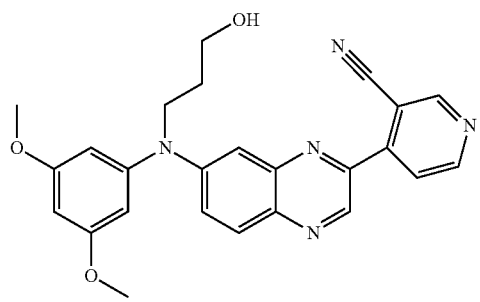 [SMILES: COc1cc(OC)cc(N(CCCO)c2ccc3ncc(-c4ccncc4C#N)nc3c2)c1]
Co. 134; B6/B8/B10/B12
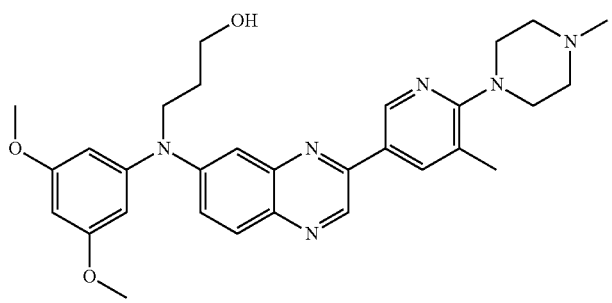 [SMILES: COc1cc(OC)cc(N(CCCO)c2ccc3ncc(-c4cnc(N5CCN(C)CC5)c(C)c4)nc3c2)c1]
Co. 135; B6/B8/B10/B12
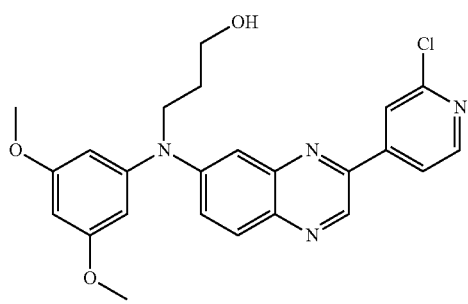
Co. 136; B6/B8/B10/B12
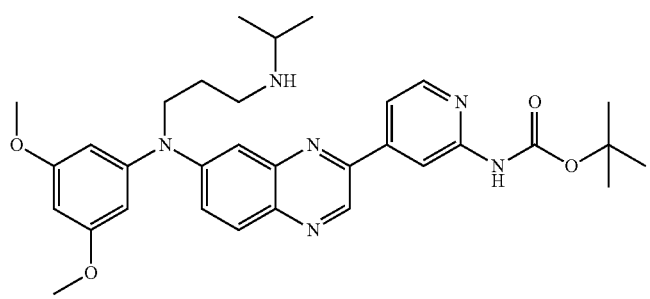 [SMILES: COc1cc(OC)cc(N(CCCNC(C)C)c2ccc3ncc(-c4ccnc(NC(=O)OC(C)(C)C)c4)nc3c2)c1]
Co. 137; B13

TABLE A1-continued
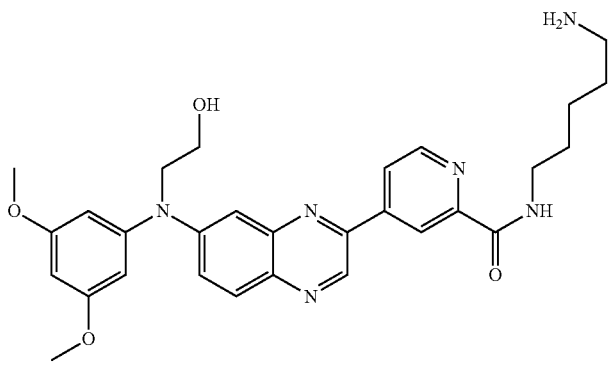 [SMILES: COc1cc(OC)cc(N(CCO)c2ccc3ncc(-c4ccnc(C(=O)NCCCCCN)c4)nc3c2)c1]
Co. 138; B31
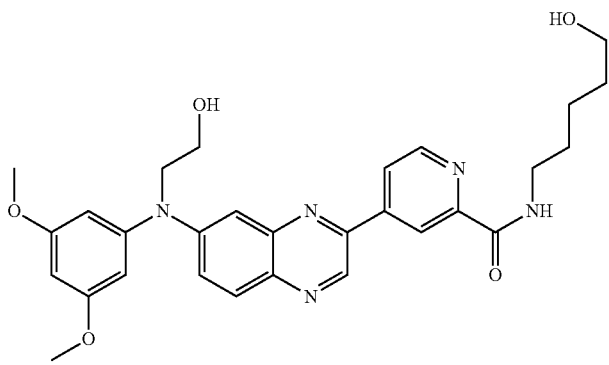 [SMILES: COc1cc(OC)cc(N(CCO)c2ccc3ncc(-c4ccnc(C(=O)NCCCCCO)c4)nc3c2)c1]
Co. 139; B6/B8/B10/B12
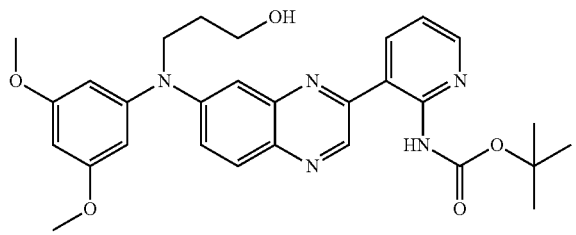 [SMILES: COc1cc(OC)cc(N(CCCO)c2ccc3ncc(-c4cccnc4NC(=O)OC(C)(C)C)nc3c2)c1]
Co. 140; B6/B8/B10/B12
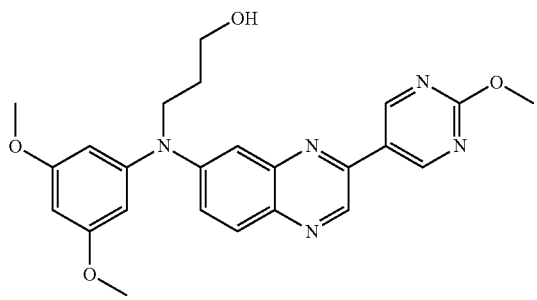 [SMILES: COc1cc(OC)cc(N(CCCO)c2ccc3ncc(-c4cnc(OC)nc4)nc3c2)c1]
Co. 141; B6/B8/B10/B12

TABLE A1-continued
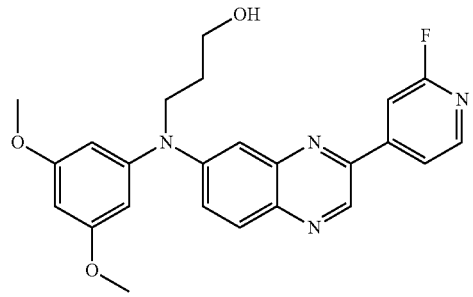
Co. 142; B6/B8/B10/B12
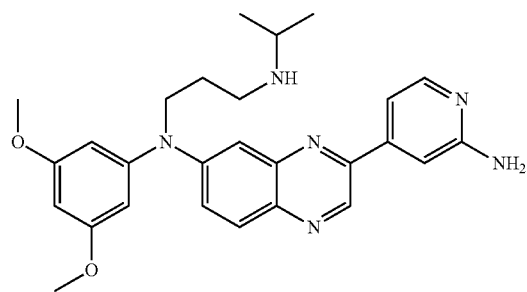 [SMILES: COc1cc(OC)cc(N(CCCNC(C)C)c2ccc3ncc(-c4ccnc(N)c4)nc3c2)c1]
Co. 143; C3
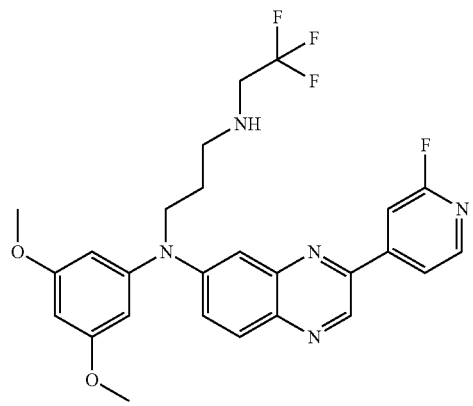 [SMILES: COc1cc(OC)cc(N(CCCNCC(F)(F)F)c2ccc3ncc(-c4ccnc(F)c4)nc3c2)c1]
Co. 144; B24
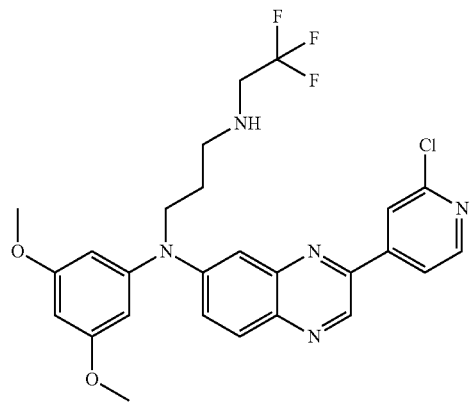 [SMILES: COc1cc(OC)cc(N(CCCNCC(F)(F)F)c2ccc3ncc(-c4ccnc(Cl)c4)nc3c2)c1]
Co. 145; B24

TABLE A1-continued
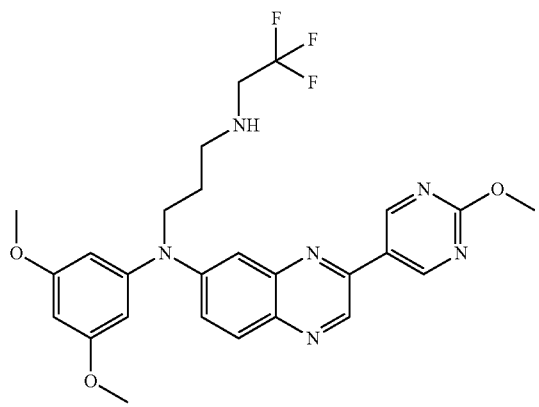 [SMILES: COc1cc(OC)cc(N(CCCNCC(F)(F)F)c2ccc3ncc(-c4cnc(OC)nc4)nc3c2)c1]
Co. 26; B24
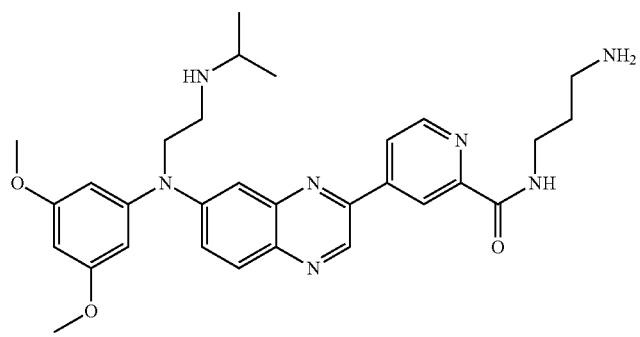 [SMILES: COc1cc(OC)cc(N(CCNC(C)C)c2ccc3ncc(-c4ccnc(C(=O)NCCCN)c4)nc3c2)c1]
as a free base and as HCl salt
Co. 146 (•3.59HCl•0.6H₂O) and
Co. 146a; free baseC4
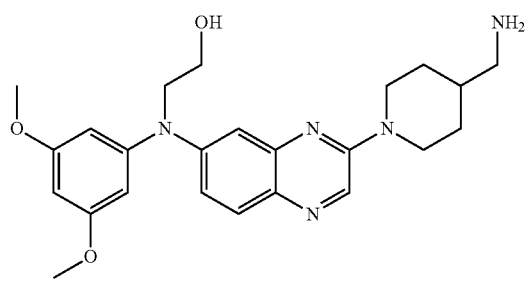 [SMILES: COc1cc(OC)cc(N(CCO)c2ccc3ncc(N4CCC(CN)CC4)nc3c2)c1]
Co. 84; B53
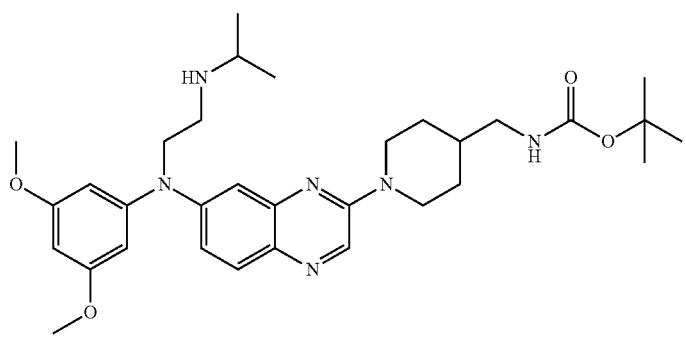 [SMILES: COc1cc(OC)cc(N(CCNC(C)C)c2ccc3ncc(N4CCC(CNC(=O)OC(C)(C)C)CC4)nc3c2)c1]
Co. 147; B9

TABLE A1-continued
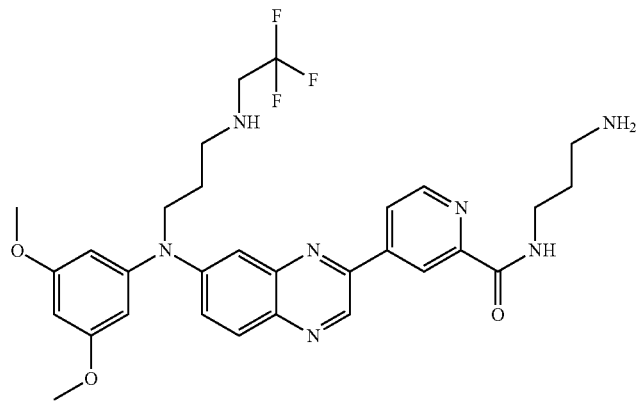 [SMILES: COc1cc(OC)cc(N(CCCNCC(F)(F)F)c2ccc3ncc(-c4ccnc(C(=O)NCCCN)c4)nc3c2)c1]
Co. 148; C3
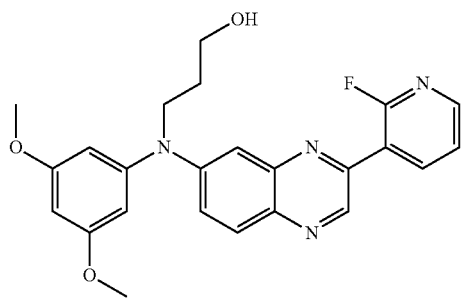 [SMILES: COc1cc(OC)cc(N(CCCO)c2ccc3ncc(-c4cccnc4F)nc3c2)c1]
Co. 149; B6/B8/B10/B12
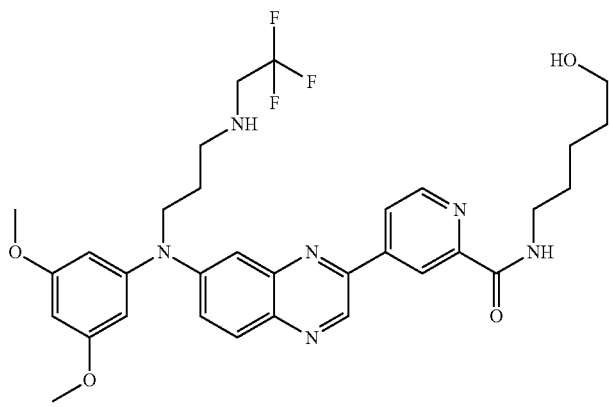 [SMILES: COc1cc(OC)cc(N(CCCNCC(F)(F)F)c2ccc3ncc(-c4ccnc(C(=O)NCCCCCO)c4)nc3c2)c1]
Co. 150; B9
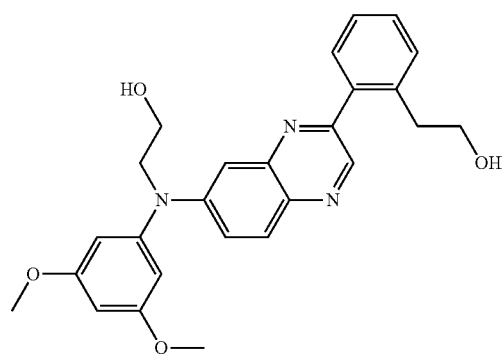 [SMILES: COc1cc(OC)cc(N(CCO)c2ccc3ncc(-c4ccccc4CCO)nc3c2)c1]
Co. 151; B6/B8/B10/B12

TABLE A1-continued
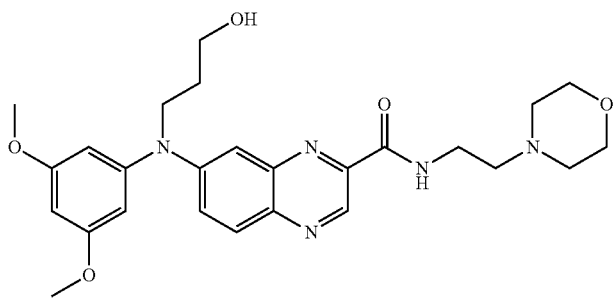 [SMILES: COc1cc(OC)cc(N(CCCO)c2ccc3ncc(C(=O)NCCN4CCOCC4)nc3c2)c1]
Co. 152; B6/B8/B10/B12
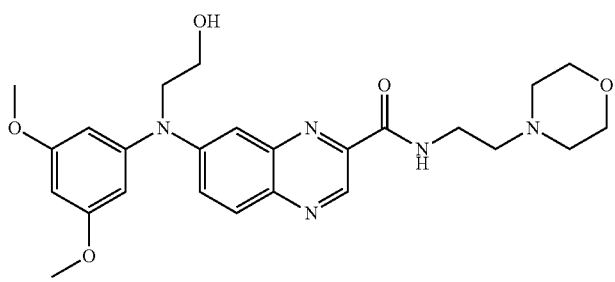 [SMILES: COc1cc(OC)cc(N(CCO)c2ccc3ncc(C(=O)NCCN4CCOCC4)nc3c2)c1]
Co. 153; B6/B8/B10/B12
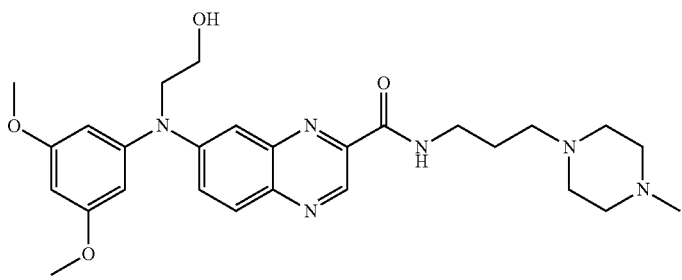 [SMILES: COc1cc(OC)cc(N(CCO)c2ccc3ncc(C(=O)NCCCN4CCN(C)CC4)nc3c2)c1]
Co. 154; B6/B8/B10/B12
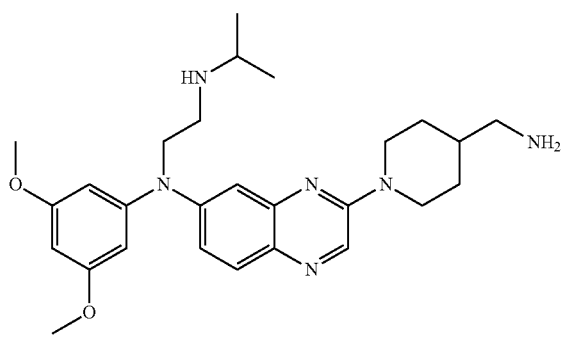 [SMILES: COc1cc(OC)cc(N(CCNC(C)C)c2ccc3ncc(N4CCC(CN)CC4)nc3c2)c1]
as a free base and as HCl salt
Co. 67 (•3.11HCl•0.78H$_2$O) and
Co. 67a; free baseC4

TABLE A1-continued
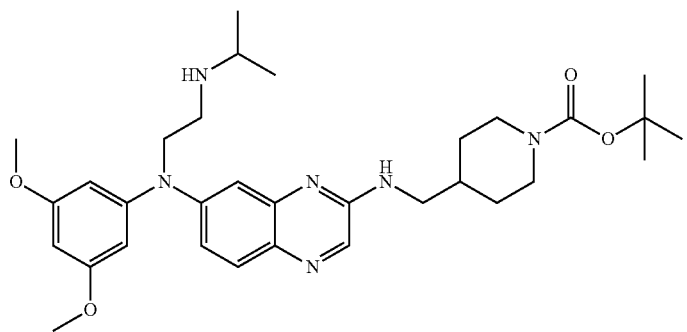 [SMILES: COc1cc(OC)cc(N(CCNC(C)C)c2ccc3ncc(NCC4CCN(C(=O)OC(C)(C)C)CC4)nc3c2)c1]
Co. 155; B9
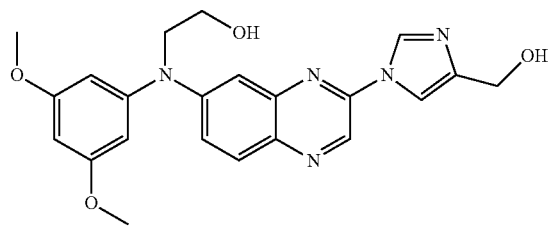 [SMILES: COc1cc(OC)cc(N(CCO)c2ccc3ncc(-n4cnc(CO)c4)nc3c2)c1]
Co. 38; B35 (example)
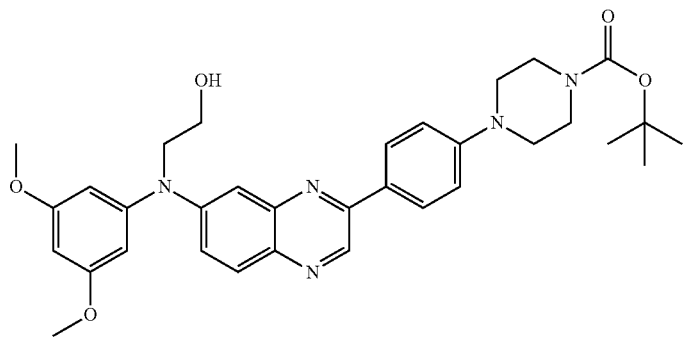 [SMILES: COc1cc(OC)cc(N(CCO)c2ccc3ncc(-c4ccc(N5CCN(C(=O)OC(C)(C)C)CC5)cc4)nc3c2)c1]
Co. 156; B15
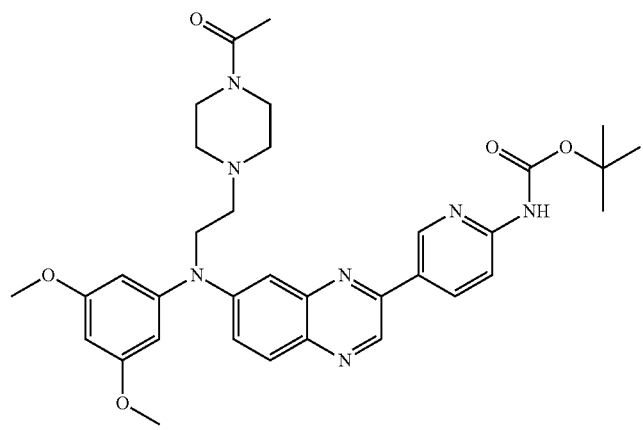 [SMILES: COc1cc(OC)cc(N(CCN2CCN(C(C)=O)CC2)c2ccc3ncc(-c4ccc(NC(=O)OC(C)(C)C)nc4)nc3c2)c1]
Co. 157; B13

TABLE A1-continued
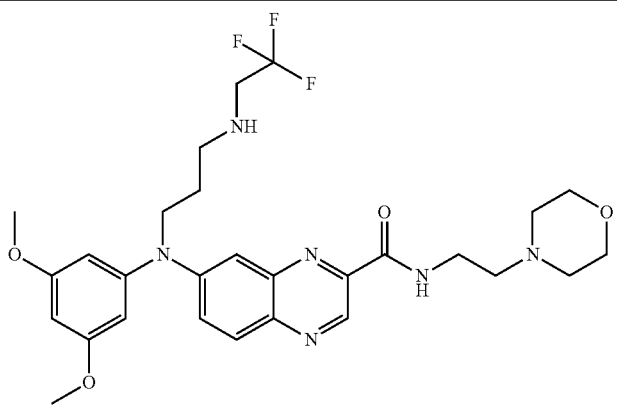
as a free base and as HCl salt
Co. 158 (•1.97HCl•1.84H₂O) and
Co. 158a; free baseB7
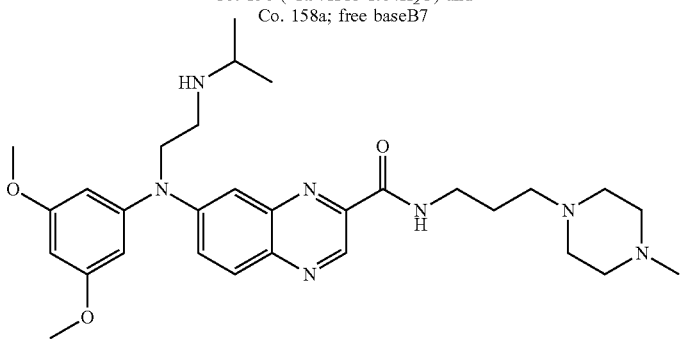
as a free base and as HCl salt
Co. 159 (•2.99HCl•2.14H₂O) and
Co. 159a; free baseB7
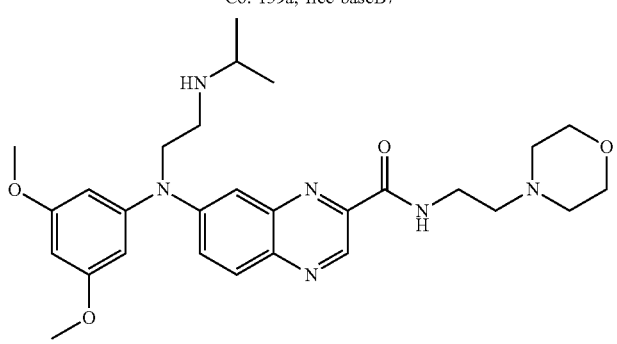
as a free base and as HCl salt
Co. 160 (•2.22HCl•1.27H₂O) and
Co. 160a; free baseB7
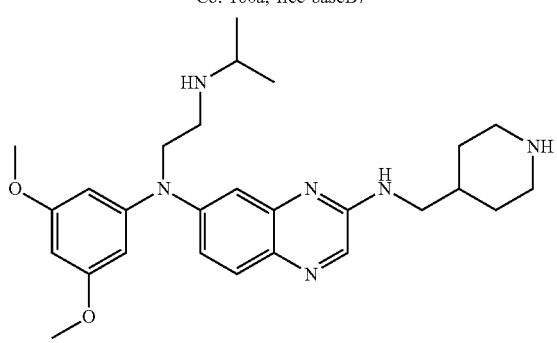
as a free base and as HCl salt
Co. 161 (•2.82HCl•1.45H₂O) and
Co. 161a; free baseC4

TABLE A1-continued
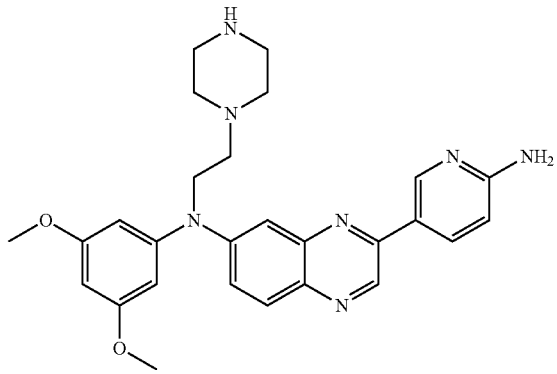 [SMILES: COc1cc(OC)cc(N(CCN2CCNCC2)c2ccc3ncc(-c4ccc(N)nc4)nc3c2)c1]
Co. 59; C6.a
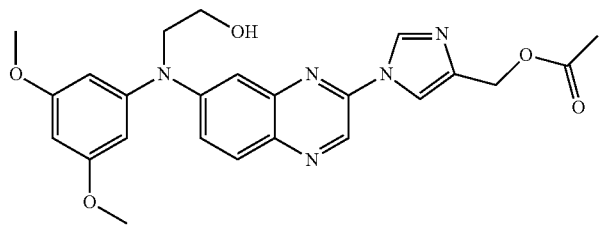 [SMILES: COc1cc(OC)cc(N(CCO)c2ccc3ncc(-n4cnc(COC(C)=O)c4)nc3c2)c1]
Co. 162; B6/B8/B10/B12
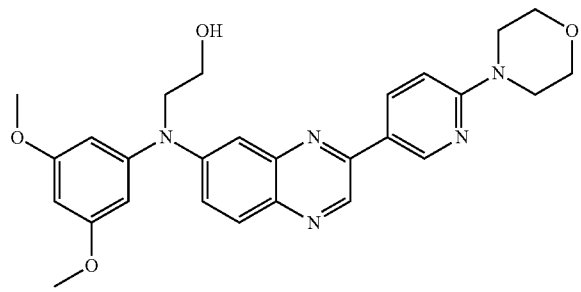 [SMILES: COc1cc(OC)cc(N(CCO)c2ccc3ncc(-c4ccc(N5CCOCC5)nc4)nc3c2)c1]
Co. 19; B15
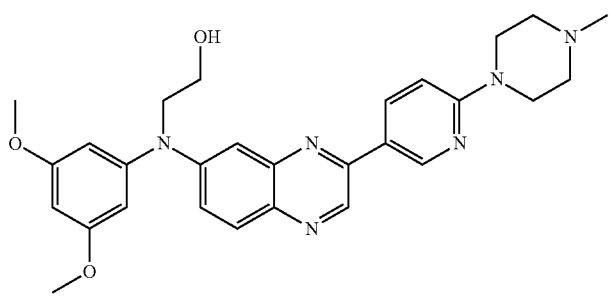 [SMILES: COc1cc(OC)cc(N(CCO)c2ccc3ncc(-c4ccc(N5CCN(C)CC5)nc4)nc3c2)c1]
Co. 163; B15

TABLE A1-continued
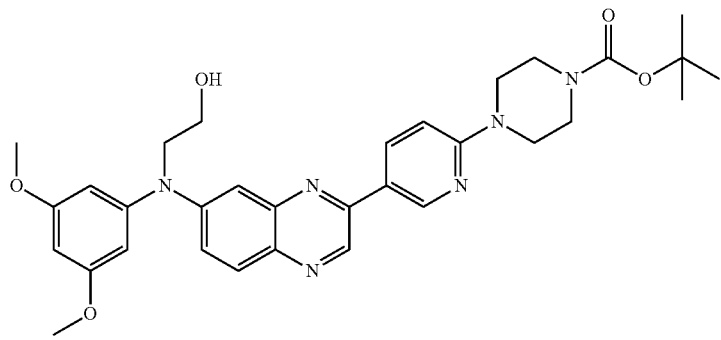 [SMILES: COc1cc(OC)cc(N(CCO)c2ccc3ncc(-c4ccc(N5CCN(C(=O)OC(C)(C)C)CC5)nc4)nc3c2)c1]
Co. 164; B15
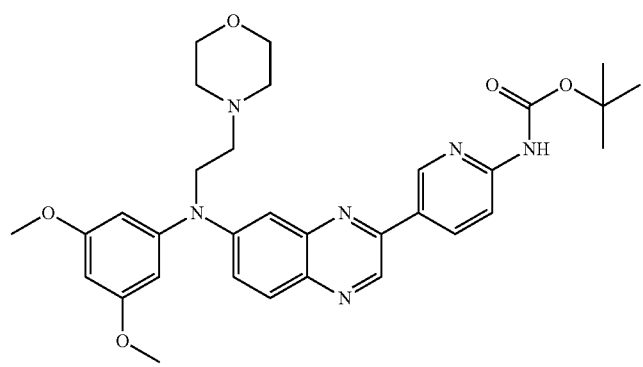 [SMILES: COc1cc(OC)cc(N(CCN2CCOCC2)c2ccc3ncc(-c4ccc(NC(=O)OC(C)(C)C)nc4)nc3c2)c1]
Co. 34; B32
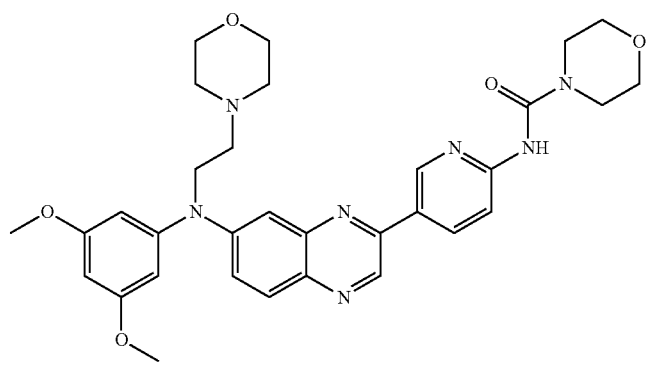 [SMILES: COc1cc(OC)cc(N(CCN2CCOCC2)c2ccc3ncc(-c4ccc(NC(=O)N5CCOCC5)nc4)nc3c2)c1]
Co. 35; B32
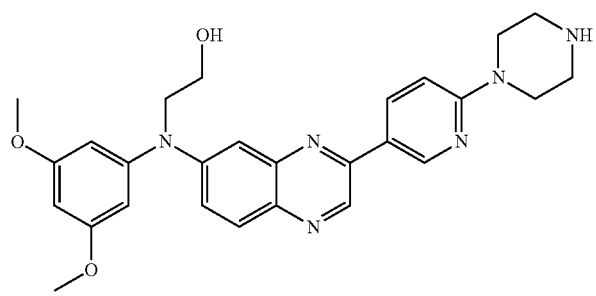 [SMILES: COc1cc(OC)cc(N(CCO)c2ccc3ncc(-c4ccc(N5CCNCC5)nc4)nc3c2)c1]
Co. 165; C2

TABLE A1-continued
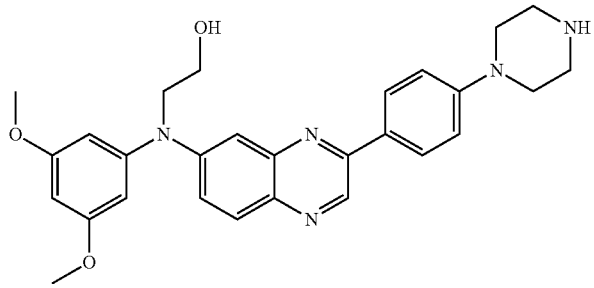 [SMILES: COc1cc(OC)cc(N(CCO)c2ccc3ncc(-c4ccc(N5CCNCC5)cc4)nc3c2)c1]
Co. 166; C3
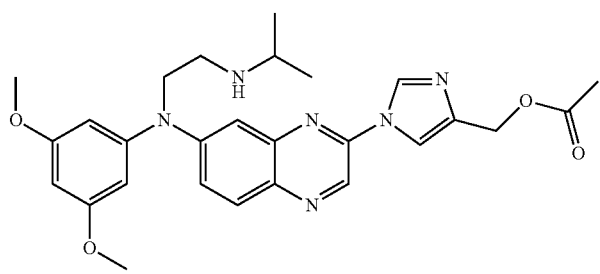 [SMILES: COc1cc(OC)cc(N(CCNC(C)C)c2ccc3ncc(-n4cnc(COC(C)=O)c4)nc3c2)c1]
Co. 167; B11
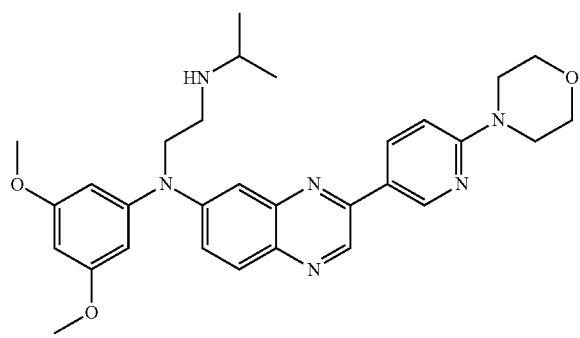 [SMILES: COc1cc(OC)cc(N(CCNC(C)C)c2ccc3ncc(-c4ccc(N5CCOCC5)nc4)nc3c2)c1]
Co. 168; B9
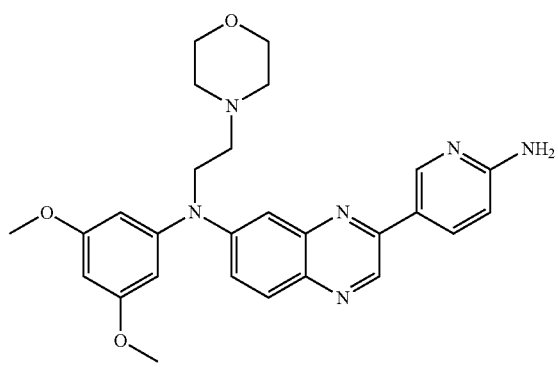 [SMILES: COc1cc(OC)cc(N(CCN2CCOCC2)c2ccc3ncc(-c4ccc(N)nc4)nc3c2)c1]
Co. 169; C2

TABLE A1-continued
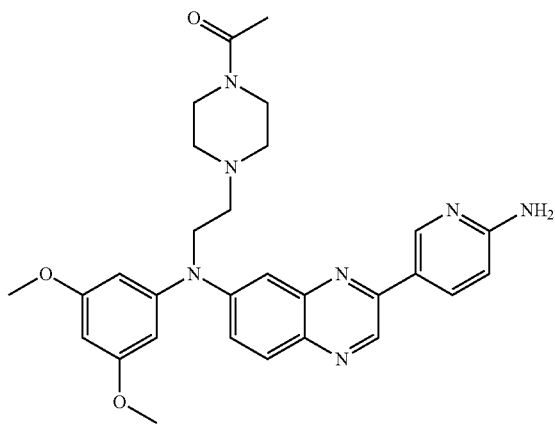 [SMILES: COc1cc(OC)cc(N(CCN2CCN(C(C)=O)CC2)c2ccc3ncc(-c4ccc(N)nc4)nc3c2)c1]
Co. 68; C6.b
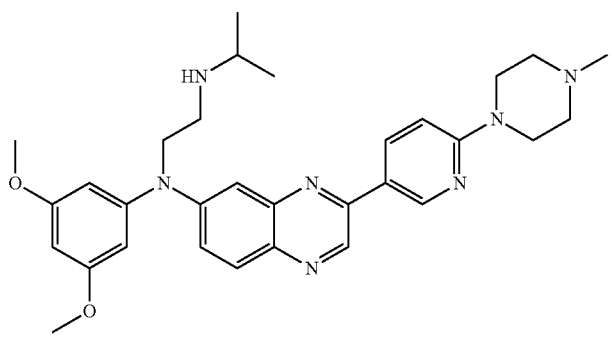 [SMILES: COc1cc(OC)cc(N(CCNC(C)C)c2ccc3ncc(-c4ccc(N5CCN(C)CC5)nc4)nc3c2)c1]
as a free base and as HCl salt
Co. 170 (•2.94 HCl•0.64 H$_2$O•0.4C$_6$H$_{14}$O) and
Co. 170a; free baseB7
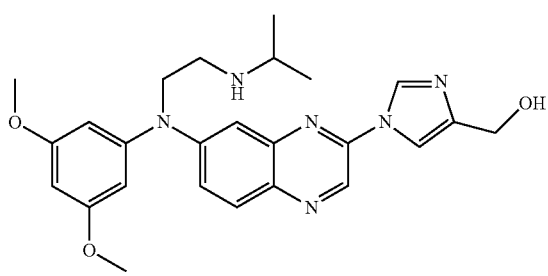 [SMILES: COc1cc(OC)cc(N(CCNC(C)C)c2ccc3ncc(-n4cnc(CO)c4)nc3c2)c1]
as a free base and as HCl salt
Co. 77 (•2.06 HCl•0.3 H$_2$O•0.24 C$_3$H$_8$O) and
Co. 77a; C12
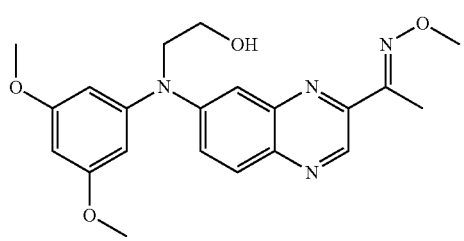 [SMILES: CO/N=C(\C)c1cnc2ccc(N(CCO)c3cc(OC)cc(OC)c3)cc2n1]
Co. 29; B27

TABLE A1-continued
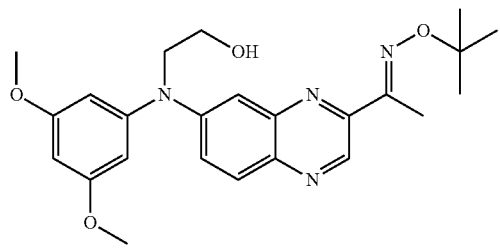 [SMILES: COc1cc(OC)cc(N(CCO)c2ccc3ncc(/C(C)=N/OC(C)(C)C)nc3c2)c1]
Co. 171; B27
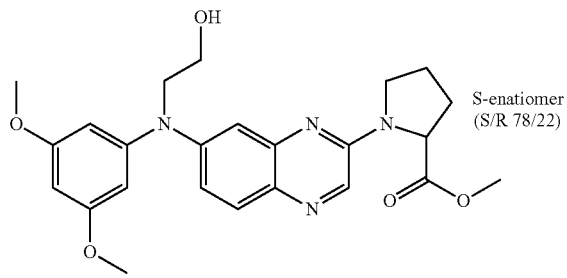 [SMILES: COC(=O)C1CCCN1c1cnc2ccc(N(CCO)c3cc(OC)cc(OC)c3)cc2n1]
as a free base and as HCl salt
Co. 172 (S enantiomer (S/R 78/22))
(•0.81 HCl•0.32 H₂O) and
Co. 172a (S enantiomer);
free baseB6/B8/B10/B12
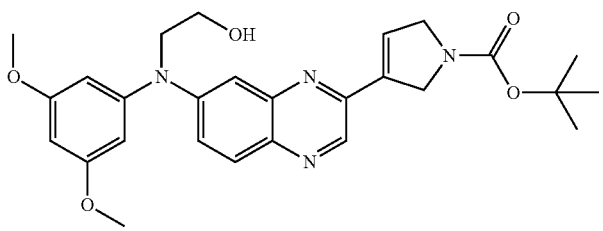 [SMILES: COc1cc(OC)cc(N(CCO)c2ccc3ncc(C4=CCN(C(=O)OC(C)(C)C)C4)nc3c2)c1]
Co. 173; B6/B8/B10/B12
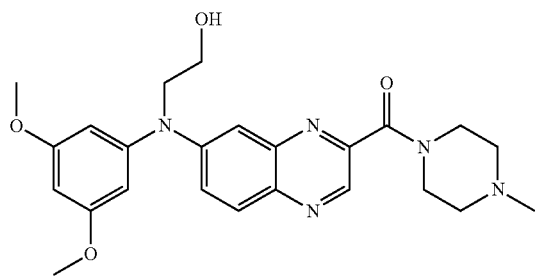 [SMILES: COc1cc(OC)cc(N(CCO)c2ccc3ncc(C(=O)N4CCN(C)CC4)nc3c2)c1]
Co. 174; B6/B8/B10/B12
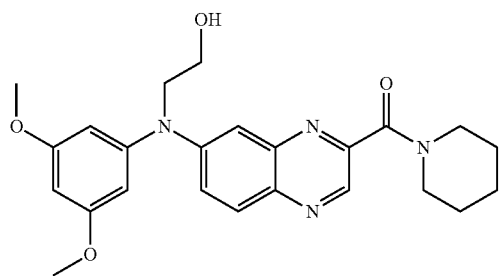 [SMILES: COc1cc(OC)cc(N(CCO)c2ccc3ncc(C(=O)N4CCCCC4)nc3c2)c1]
Co. 175; B6/B8/B10/B12

TABLE A1-continued
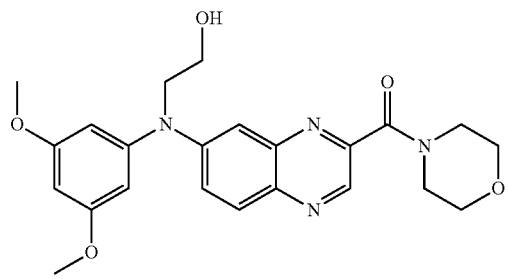 [SMILES: COc1cc(OC)cc(N(CCO)c2ccc3ncc(C(=O)N4CCOCC4)nc3c2)c1]
Co. 176; B6/B8/B10/B12
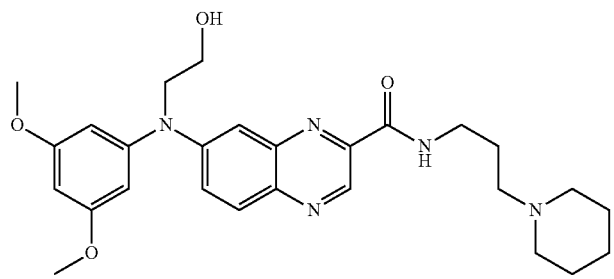 [SMILES: COc1cc(OC)cc(N(CCO)c2ccc3ncc(C(=O)NCCCN4CCCCC4)nc3c2)c1]
Co. 177; B6/B8/B10/B12
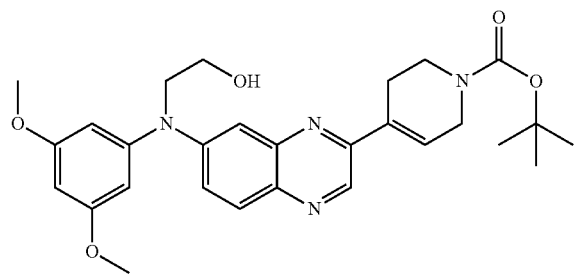 [SMILES: COc1cc(OC)cc(N(CCO)c2ccc3ncc(C4=CCN(C(=O)OC(C)(C)C)CC4)nc3c2)c1]
Co. 178; B6/B8/B10/B12
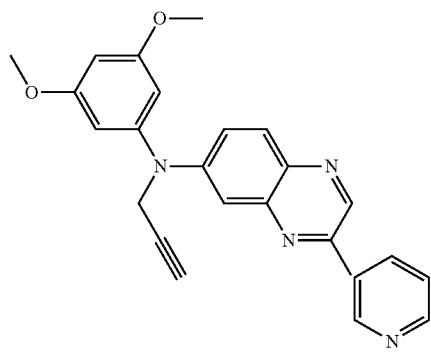
Co. 1; B1

TABLE A1-continued
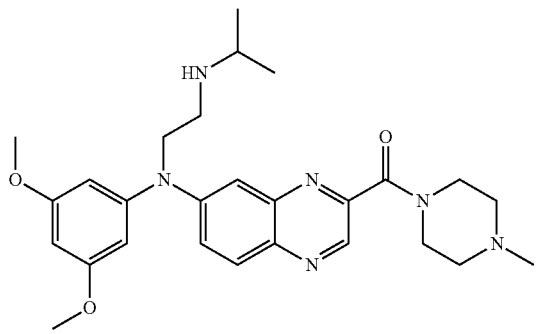 [SMILES: COc1cc(OC)cc(N(CCNC(C)C)c2ccc3ncc(C(=O)N4CCN(C)CC4)nc3c2)c1]
as a free base and as HCl salt
Co. 179 (•1.96 HCl•0.8 H$_2$O) and
Co. 179a; free baseB7
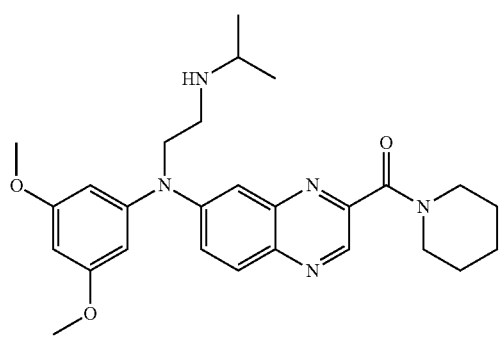 [SMILES: COc1cc(OC)cc(N(CCNC(C)C)c2ccc3ncc(C(=O)N4CCCCC4)nc3c2)c1]
as a free base and as HCl salt
Co. 180 (•1.04 HCl•0.26 H$_2$O) and
Co. 180a; free baseB7
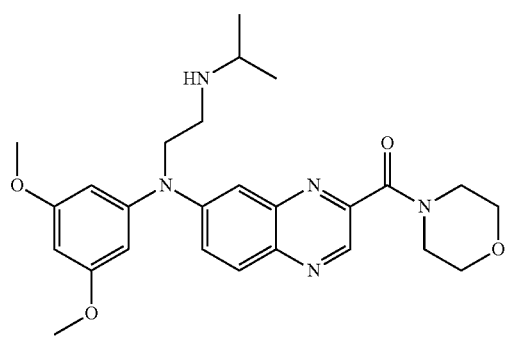 [SMILES: COc1cc(OC)cc(N(CCNC(C)C)c2ccc3ncc(C(=O)N4CCOCC4)nc3c2)c1]
as a free base and as HCl salt
Co. 181 (•0.98 HCl•0.33 H$_2$O) and
Co. 181a; free baseB7
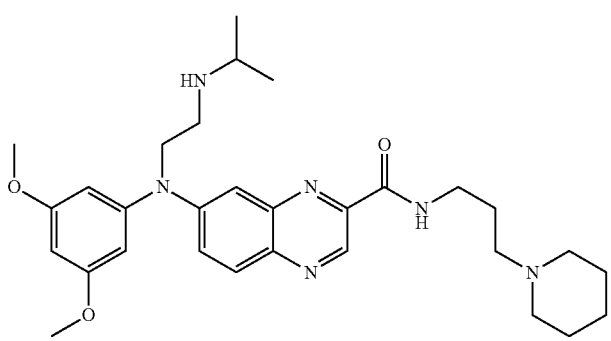 [SMILES: COc1cc(OC)cc(N(CCNC(C)C)c2ccc3ncc(C(=O)NCCCN4CCCCC4)nc3c2)c1]
Co. 182; B9

TABLE A1-continued
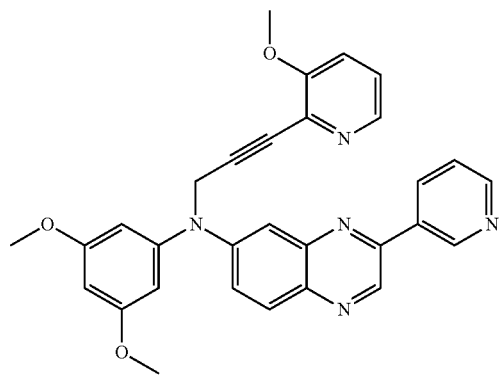 [SMILES: COc1cc(OC)cc(N(CC#Cc2ncccc2OC)c2ccc3ncc(-c4cccnc4)nc3c2)c1]
Co. 183; C1
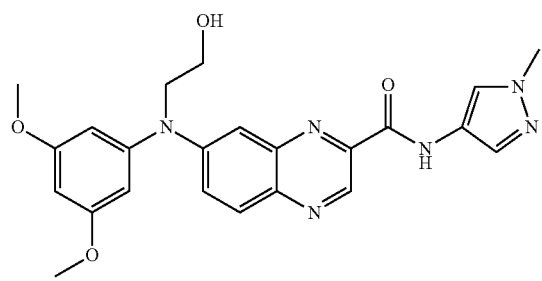 [SMILES: COc1cc(OC)cc(N(CCO)c2ccc3ncc(C(=O)Nc4cnn(C)c4)nc3c2)c1]
Co. 184; B6/B8/B10/B12
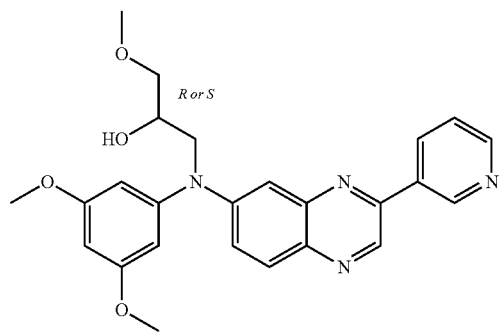 [SMILES: COCC(O)CN(c1cc(OC)cc(OC)c1)c1ccc2ncc(-c3cccnc3)nc2c1]
Co. 46 (R or S); B42
[α]$_D$: −115.9° (c: 0.25 w/v %, DMF, 20° C.)
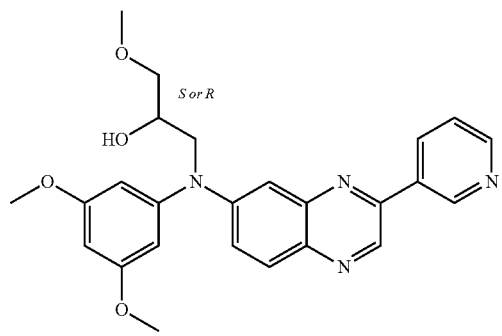 [SMILES: COCC(O)CN(c1cc(OC)cc(OC)c1)c1ccc2ncc(-c3cccnc3)nc2c1]
Co. 47 (S or R); B42
[α]$_D$: −117.6° (c: 0.26 w/v %, DMF, 20° C.)

TABLE A1-continued
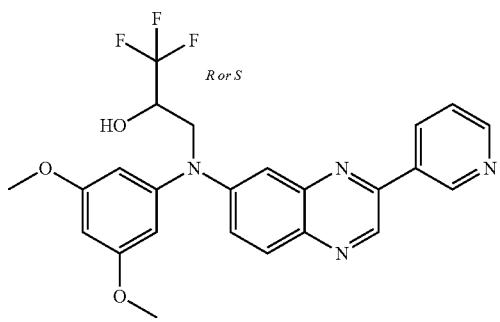 [SMILES: COc1cc(OC)cc(N(CC(O)C(F)(F)F)c2ccc3ncc(-c4cccnc4)nc3c2)c1]
Co. 53 (R or S); B47
α]_D: +196.3° (c: 0.27 w/v %, DMF, 20° C.)
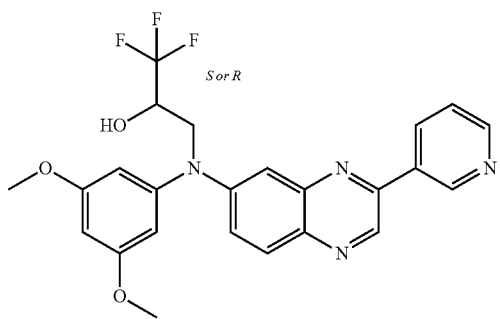 [SMILES: COc1cc(OC)cc(N(CC(O)C(F)(F)F)c2ccc3ncc(-c4cccnc4)nc3c2)c1]
Co. 54 (S or R); B47
[α]_D: −195.8° (c: 0.28 w/v %, DMF, 20° C.)
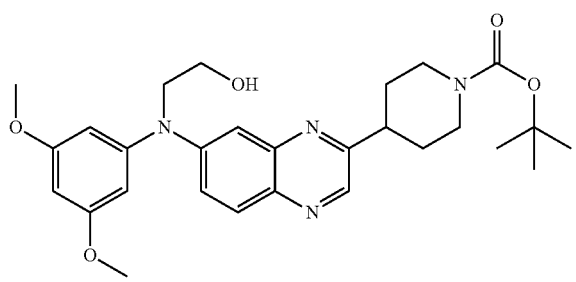 [SMILES: COc1cc(OC)cc(N(CCO)c2ccc3ncc(C4CCN(C(=O)OC(C)(C)C)CC4)nc3c2)c1]
Co. 185; B6/B8/B10/B12
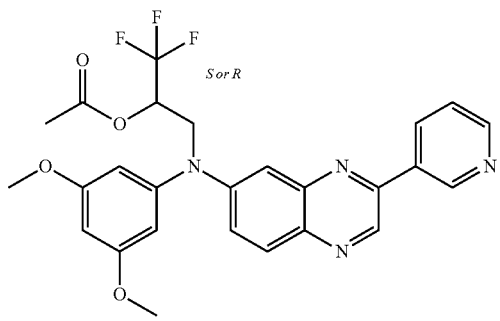 [SMILES: COc1cc(OC)cc(N(CC(OC(C)=O)C(F)(F)F)c2ccc3ncc(-c4cccnc4)nc3c2)c1]
Co. 45 (S or R); C10

TABLE A1-continued
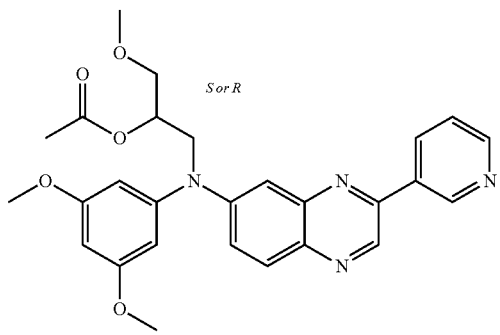 [SMILES: COCC(CN(c1cc(OC)cc(OC)c1)c1ccc2ncc(-c3cccnc3)nc2c1)OC(C)=O]
as a free base and as HCl salt
52 (S or R) (•1.39 HCl•1.11 H₂O); and
and Co. 52a; freebase; C11
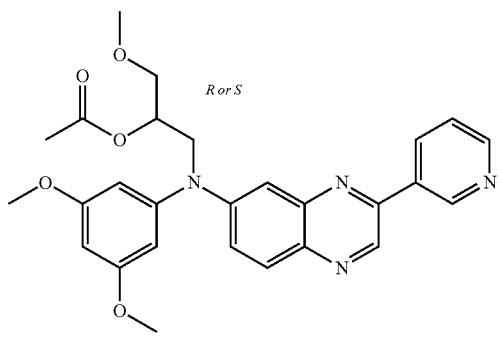 [SMILES: COCC(CN(c1cc(OC)cc(OC)c1)c1ccc2ncc(-c3cccnc3)nc2c1)OC(C)=O]
as a free base and as HCl salt
Co. 76 (R or S) (•1.44 HCl•0.8 H₂O•0.24 C₄H₈O₂)
([α]$_D$: +44.2° (c: 0.19 w/v %, DMF, 20° C.); and
Co. 76a; freebase; C11
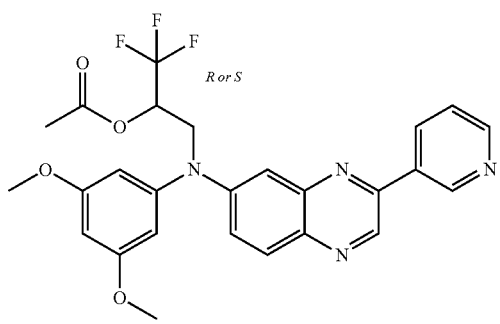 [SMILES: COc1cc(OC)cc(N(CC(OC(C)=O)C(F)(F)F)c2ccc3ncc(-c4cccnc4)nc3c2)c1]
Co. 75 (R or S); C10
[α]$_D$: +79.4° (c: 0.33 w/v %, DMF,
20° C.)
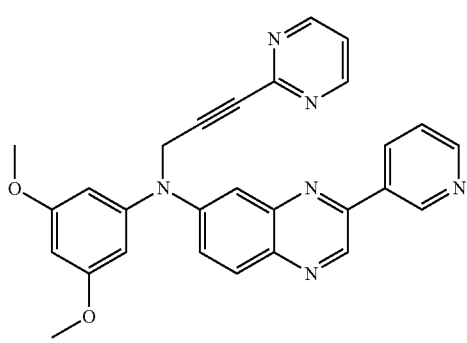 [SMILES: COc1cc(OC)cc(N(CC#Cc2ncccn2)c2ccc3ncc(-c4cccnc4)nc3c2)c1]
Co. 2; C1

TABLE A1-continued
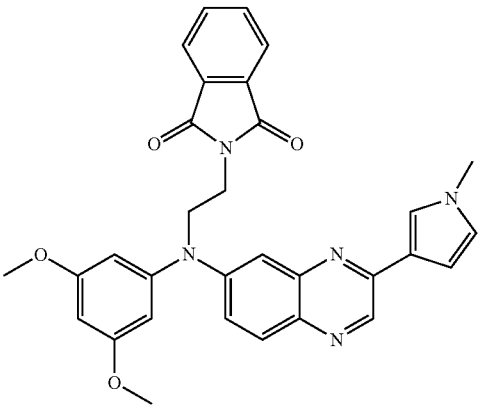 [SMILES: COc1cc(OC)cc(N(CCN2C(=O)c3ccccc3C2=O)c2ccc3ncc(-c4ccn(C)c4)nc3c2)c1]
Co. 78; B50
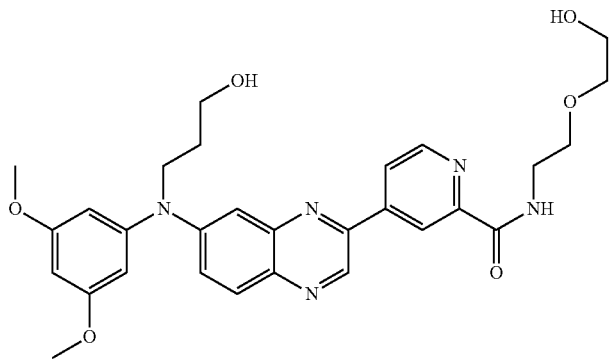 [SMILES: COc1cc(OC)cc(N(CCCO)c2ccc3ncc(-c4ccnc(C(=O)NCCOCCO)c4)nc3c2)c1]
Co. 186; B54
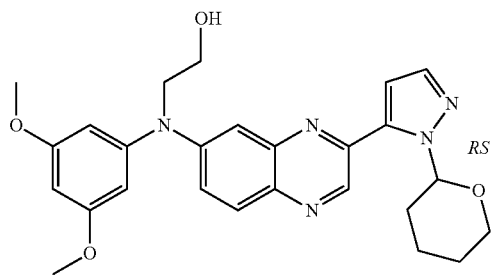 [SMILES: COc1cc(OC)cc(N(CCO)c2ccc3ncc(-c4ccnn4C4CCCCO4)nc3c2)c1]
Co. 187; B10
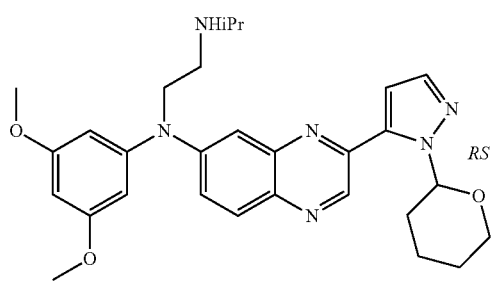
Co. 188; B11

TABLE A1-continued

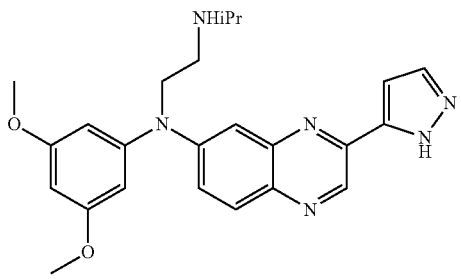

as a HCl salt
Co. 189; •1.75 HCl; C15

Analytical Part
LC/GC/NMR
General Procedure A

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

Method 1

In addition to general procedure A: Reversed phase UPLC was carried out on a Waters Acquity BEH (bridged ethylsiloxane/silica hybrid) C18 column (1.7 µm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 µl was used. Cone voltage was 20 V for positive and negative ionization mode. Mass spectra were acquired by scanning from 100 to 1000 in 0.2 seconds using an interscan delay of 0.1 seconds.

Method 2

In addition to general procedure A: Reversed phase UPLC was carried out on a Waters Acquity BEH (bridged ethylsiloxane/silica hybrid) C18 column (1.7 µm, 2.1×100 mm) with a flow rate of 0.343 ml/min. Two mobile phases (mobile phase A: 95% 7 mM ammonium acetate/5% acetonitrile; mobile phase B: 100% acetonitrile) were employed to run a gradient condition from 84.2% A and 15.8% B (hold for 0.49 minutes) to 10.5% A and 89.5% B in 2.18 minutes, hold for 1.94 min and back to the initial conditions in 0.73 min, hold for 0.73 minutes. An injection volume of 2 µl was used. Cone voltage was 20V for positive and negative ionization mode. Mass spectra were acquired by scanning from 100 to 1000 in 0.2 seconds using an interscan delay of 0.1 seconds.

General Procedure B

The LC measurement was performed using an Acquity UPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

Method 3

In addition to the general procedure B: Reversed phase UPLC (Ultra Performance Liquid Chromatography) was carried out on a bridged ethylsiloxane/silica hybrid (BEH) C18 column (1.7 µm, 2.1×50 mm; Waters Acquity) with a flow rate of 0.8 ml/min. Two mobile phases (25 mM ammonium acetate in $H_2O$/acetonitrile 95/5; mobile phase B: acetonitrile) were used to run a gradient condition from 95% A and 5% B to 5% A and 95% B in 1.3 minutes and hold for 0.3 minutes. An injection volume of 0.5 µl was used. Cone voltage was 30 V for positive ionization mode and 30 V for negative ionization mode.

General Procedure C

The HPLC measurement was performed using an Alliance HT 2795 (Waters) system comprising a quaternary pump with degasser, an autosampler, a diode-array detector (DAD) and a column as specified in the respective methods below, the column is hold at a temperature of 30° C. Flow from the column was split to a MS spectrometer. The MS detector was configured with an electrospray ionization source. The capillary needle voltage was 3 kV and the source temperature was maintained at 100° C. on the LCT (Time of Flight Zspray mass spectrometer from Waters). Nitrogen was used as the nebulizer gas. Data acquisition was performed with a Waters-Micromass MassLynx-Openlynx data system.

Method 4

In addition to the general procedure C: Reversed phase HPLC was carried out on a Supelco Ascentis Express C18 column (2.7 µm, 3.0×50 mm) with a flow rate of 0.7 ml/min. Two mobile phases (mobile phase A: 100% 7 mM ammonium acetate; mobile phase B: 100% acetonitrile) were employed to run a gradient condition from 80% A and 20% B (hold for 0.5 minute) to 5% A and 95% B in 2.5 minutes, hold for 4.5 minutes and back to the initial conditions in 1.5 minutes and hold for 1 min. An injection volume of 5 □l was used. Cone voltage was 20 V for positive and negative ionization mode. Mass spectra were acquired by scanning from 100 to 1000 in 0.4 seconds using an interscan delay of 0.3 seconds.

DSC:

The melting points (MP) were taken with a kofler hot bar. For a number of compounds, melting points (m.p.) were determined with a DSC1 Star$^e$ System (Mettler-Toledo). Melting points were measured with a temperature gradient of 10° C./minute. Maximum temperature was 350° C. Values are peak values."

OR:

Optical Rotation was measured with a polarimeter 341 Perkin Elmer. The polarized light was passed through a sample with a path length of 1 decimeter and a sample concentration of 0.250 to 0.500 gram per 100 milliliters.

$[\alpha]_d^T$: (red rotation×100)/(1.000 dm×concentration).

$^d$ is sodium D line (589 nanometer).

T is the temperature (° C.)

TABLE A2 physic-chemical data

| Comp. No. | Melting Point (° C.) | (Kofler(K) or DSC) | HPLC Rt (min) | MS M + (H$^+$) | LC/GC/MS method |
|---|---|---|---|---|---|
| 63 | 114 | K | 4.35 | 421 | 1 |
| 20 | 105 | K | 4.89 | 465 | 1 |
| 64 | 92 | K | 4.15 | 434 | 1 |
| 86 | 181 | DSC | 4.57 | 451 | 1 |
| 22 | 166 | K | 4.15 | 440 | 1 |
| 87 | 144 | K | 4.83 | 456 | 1 |
| 88 | 234 | DSC | 4.33 | 452 | 1 |
| 37 | 125 | DSC | 4.48 | 511 | 1 |
| 89 | 105 | DSC | 4.38 | 413 | 1 |
| 90 | 162 | DSC | 4.6 | 498 | 1 |
| 58 | 134 | K | 4.16 | 418 | 1 |
| 91 | 116 | K | 4.82 | 443 | 1 |
| 39 | 166 | DSC | 3.6 | 402 | 1 |
| 92 | 155 | K | 4.8 | 497 | 1 |
| 93 | 176 | K | 4.18 | 419 | 1 |
| 94 | 185 | DSC | 4.0 | 428 | 1 |
| 28 | 135 | DSC | 4.5 | 473 | 1 |
| 18 | 132 | DSC | 4.4 | 416 | 1 |
| 95 | 160 | DSC | 4.8 | 402 | 1 |
| 96 | 112 | K | 3.94 | 492 | 1 |
| 49 | Gum at 208 | K | 3.8 | 464 | 1 |
| 97 | 148 | DSC | 4.8 | 419 | 1 |
| 98 | 213 | DSC | 4.3 | 434 | 1 |
| 99 | 155 | K | 4.72 | 477 | 1 |
| 32a | 223 | DSC | 4.1 | 416 | 1 |
| 32 | 223 | DSC | 4.13 | 416 | 1 |
| 101 | 140 | K | 4.59 | 487 | 1 |
| 102 | 260 | K | 3.97 | 435 | 1 |
| 103 | 141 | DSC | 4.8 | 415 | 1 |
| 58 | Degradation at 99 | K | 4.03 | 402 | 1 |
| 31 | 107 | DSC | 4.91 | 416 | 1 |
| 62 | 139 | K | 4.82 | 416 | 1 |
| 61 | 160 | K | 3.91 | 431 | 1 |
| 30 | 113 | K | 4.26 | 416 | 1 |
| 50 | 168 | K | 4.32 | 403 | 1 |
| 69 | 173 | DSC | 3.85 | 403 | 1 |
| 55 | 152 | DSC | 4.2 | 403 | 1 |
| 36 | Gum at 66 | K | 4.14 | 401 | 1 |
| 73 | 110 | K | 4.4é | 415 | 1 |
| Int. 55 | Gum at 98 | K | 4.23 | 489 | 1 |
| 40 | 178 | DSC | 3.71 | 447 | 1 |
| 70 | 129 | DSC | 4.45 | 417 | 1 |
| 71 | 141 | DSC | 4.02 | 417 | 1 |
| 72 | 169 | DSC | 4.19 | 417 | 1 |
| 24 | 128 | DSC | 4.01 | 516 | 1 |
| 60 | 175 | DSC | 4.23 | 416 | 1 |
| 56 | 143 | K | 3.96 | 445 | 1 |
| 82 | 143 | K | 4.21 | 418 | 1 |
| 83 | 168 | K | 4.32 | 417 | 1 |
| 41 | 216 | K | 2.94 | 404 | 1 |
| 23 | 60 | K | 4.55 | 437 | 1 |
| 21 | 136 | DSC | 4.08 | 416 | 1 |
| 65 | 125 | DSC | 4.35 | 488 | 1 |
| 104 | 141 | DSC | 4.51 | 417 | 1 |
| 105 | 154 | K | 3.71 | 432 | 1 |
| 106 | 160 | DSC | 3.07 | 418 | 1 |
| 17 | 144 | DSC | 2.9 | 459 | 1 |
| 14 | 68 | K | 3.15 | 501 | 1 |
| 81 | 182 | K | 3.72 | 531 | 1 |
| 80 | 214 | K | 4.22 | 575 | 1 |
| 25 | 176 | DSC | 3.41 | 527 | 1 |
| 109 | 172 | DSC | 3.38 | 543 | 1 |
| 110 | 169 | K | 3.44 | 430 | 1 |
| 111 | 195 | DSC | 3.77 | 433 | 1 |
| 112 | 150 | DSC | 0.91 | 417 | 3 |
| 74 | 210 | K | 2.83 | 448 | 1 |
| 113 | 98 | K | 3.99 | 540 | 1 |
| 114 | 127 | K | 3.57 | 4745 | 1 |
| 115 | 166 | DSC | 1.05 | 431 | 3 |
| 116 | 188 | K | 1.02 | 446 | 3 |
| 117 | nd | nd | nd | nd | nd |
| 51 | 170 | K | 2.91 | 494 | 1 |
| 119 | 84 | DSC | 4.98 | 412 | 1 |
| 120 | 124 | DSC | 3.69 | 402 | 4 |
| 121 | 149 | DSC | 3.73 | 442 | 1 |
| 122 | Gum at 67 | K | 4.06 | 555 | 1 |
| 48 | 184 | K | 0.8 | 501 | 3 |
| 11 | 158 | K | 3.21 | 403 | 1 |
| 9 | 151 | DSC | 3.2 | 403 | 1 |
| 123 | 103 | K | 2.72 | 503 | 1 |
| 12 | 118 | DSC | 2.99 | 444 | 1 |
| 124 | — | | 1.02 | 502 | 3 |
| 10 | 174 | K | 2.99 | 444 | 1 |
| 33 | 110 | K | 2.82 | 517 | 1 |
| 125 | 143 | K | 4.41 | 546 | 1 |
| 126 | 130 | DSC | 2.85 | 531 | 1 |
| 127 | — | — | 5.02 | 627 | 1 |
| 6 | 135 | DSC | 4 | 419 | 1 |
| 3 | 145 | K | 4.15 | 433 | 1 |
| 128 | 213 | K | 4.09 | 532 | 1 |
| 66 | 137 | K | 3.12 | 432 | 1 |
| 8 | 200 | K | 3.24 | 446 | 1 |
| 5 | 186 | DSC | 4.19 | 500 | 1 |
| 129 | 165 | K | 4.02 | 527 | 1 |
| 79 | 106 | DSC | 2.92 | 404 | 1 |
| 44 | Gum at 64 | K | 2.36 | 588 | 1 |
| 130 | 161 | DSC | 2.95 | 545 | 1 |
| 131 | 155 | K | 3.38 | 558.6 | 1 |
| 43 | 190 | DSC | 3.15 | 530 | 1 |
| 132 | Gum at 50 | K | 2.39 | 588 | 1 |
| 133 | 172 | K | 4.12 | 528 | 1 |
| 134 | 158 | K | 3.36 | 432 | 1 |
| 135 | 179 | DSC | 3.45 | 529 | 1 |
| 136 | 175 | K | 3.88 | 451 | 1 |
| 137 | 172 | K | 3.76 | 573 | 1 |
| 138 | — | | 2.86 | 531 | 1 |
| 139 | — | | 3.22 | 532 | 1 |
| 141 | 182 | K | 3.41 | 448 | 1 |
| 142 | 155 | K | 3.71 | 435 | 1 |
| 143 | Gum at 84 | K | 2.83 | 473 | 1 |
| 144 | 128 | K | 4.42 | 516 | 1 |
| 145 | 130 | K | 4.58 | 532 | 1 |
| 26 | 96 | K | 4.15 | 529 | 1 |
| 146 | 188 | K | 2.54 | 544 | 1 |
| 84 | 159 | DSC | 2.61 | 438 | 1 |
| 148 | 87 | K | 3.42 | 598 | 1 |
| 149 | 115 | K | 3.64 | 435 | 1 |
| 150 | 95 | K | 3.94 | 627 | 1 |
| 151 | 133 | DSC | 3.51 | 446 | 1 |
| 67 | 193 | K | 2.39 | 479 | 1 |
| 38 | 215 | K | 2.76 | 422 | 1 |
| 156 | 80 | K | 3.43 | 586 | 2 |
| 158 | 138 | K | 3.72 | 577 | 1 |
| 159 | 176 | K | 2.48 | 550 | 1 |
| 160 | 149 | K | 2.74 | 523 | 1 |
| 161 | 185 | K | 2.35 | 479 | 1 |
| 59 | 111 | K | 2.66 | 486 | 1 |

TABLE A2-continued physic-chemical data

| Comp. No. | Melting Point (° C.) | (Kofler(K) or DSC) | HPLC Rt (min) | MS M + (H+) | LC/GC/MS method |
|---|---|---|---|---|---|
| 19 | 193 | K | 2.81 | 488 | 2 |
| 163 | 160 | K | 2.61 | 501 | 2 |
| 35 | 153 | DSC | 2.74 | 600 | 2 |
| 165 | 171 | DSC | 2.27 | 487 | 2 |
| 166 | 194 | K | 2.9 | 486 | 2 |
| 167 | 56 | K | 2.41 | 505 | 2 |
| 168 | 135 | DSC | 2.68 | 529 | 2 |
| 169 | 164 | DSC | 2.63 | 487 | 2 |
| 68 | 167 | DSC | 3.02 | 528 | 1 |
| 170 | Gum at 242 | K | 2.52 | 542 | 2 |
| 77 | 150 | K | 2.13 | 463 | 2 |
| 29 | 149 | K | 3.15 | 397 | 2 |
| 171 | 147 | K | 3.5 | 439 | 2 |
| 172 | Gum at 126 | K | 2.75 | 453 | 2 |
| 173 | 142 | K | 3.16 | 493 | 2 |
| 178 | 150 | K | 3.23 | 507 | 2 |
| 179 | 250 | K | 2.15 | 493 | 2 |
| 180 | 236 | K | 2.54 | 478 | 2 |
| 181 | 255 | K | 2.23 | 480 | 2 |
| 182 | 121 | K | 2.17 | 535 | 2 |
| 183 | 141 | DSC | 2.97 | 504 | 2 |
| 184 | 227 | K | 2.47 | 449 | 2 |
| 46 | 154 | DSC | 2.67 | 447 | 2 |
| 47 | 153 | DSC | 2.67 | 447 | 2 |
| 53 | 211 | dsc | 2.98 | 471 | 2 |
| 54 | 210 | DSC | 2.98 | 471 | 2 |
| 185 | Gum at 65 | K | 3.17 | 509 | 2 |
| 45 | 180 | DSC | 3.26 | 513 | 2 |
| 52 | Gum at 80 | K | 2.99 | 489 | 2 |
| 76 | Gum at 80 | K | 2.99 | 489 | 2 |
| 75 | 180 | DSC | 3.26 | 513 | 2 |
| 2 | 184 | DSC | 2.86 | 475 | 2 |
| 189 | 145 (gum) | K | 2.31 | 433 | 2 |
| 188 | 122 | K | 2.76 | 517 | 2 |
| 186 | — | K | 3.08 | 548 | 1 |

OR:

Compound 109: $[\alpha]_d$: −30.0° (c: 0.28 w/v %, DMF, 20° C.)

Compound 52: $[\alpha]_d$: −41.6° (c: 0.20 w/v %, DMF, 20° C.)

Compound 76: $[\alpha]_d$: +44.21° (c: 0.19 w/v %, DMF, 20° C.)

Compound 75: $[\alpha]_d$: +79.4° (c: 0.33 w/v %, DMF, 20° C.)

Compound 46: $[\alpha]_d$: +115.9° (c: 0.25 w/v %, DMF, 20° C.)

Compound 47: $[\alpha]_d$: −117.6° (c: 0.26 w/v %, DMF, 20° C.)

Compound 53: $[\alpha]_d$: +196.2° (c: 0.27 w/v %, DMF, 20° C.)

Compound 54: $[\alpha]_d$: −195.8° (c: 0.28 w/v %, DMF, 20° C.)

Compound 45: $[\alpha]_d$: −79.5° (c: 0.44 w/v %, DMF, 20° C.)

The below NMR experiments were carried out using a Bruker Avance 500 and a Bruker Avance DRX 400 spectrometers at ambient temperature, using internal deuterium lock and equipped with reverse triple-resonance ($^1$H, $^{13}$C, $^{15}$N TXI) probe head for the 500 MHz and with reverse double-resonance ($^1$H, $^{13}$C, SEI) probe head for the 400 MHz. Chemical shifts (δ) are reported in parts per million (ppm).

Compound 8
$^1$H NMR (500 MHz, DMSO-d$_6$) δ (ppm) 9.08 (m, 3H), 7.95 (br. s., 1H), 7.84 (d, J=9.1 Hz, 1H), 7.40 (d, J=9.1 Hz, 1H), 7.34 (br. s., 1H), 6.95 (m, 2H), 6.54 (s, 2H), 6.48 (s, 1H), 4.20 (t, J=7.3 Hz, 2H), 3.76 (s, 6H), 3.73 (s, 3H), 3.31-3.40 (m, 1H), 3.16 (m, 2H), 1.25 (d, J=6.3 Hz, 6H)

Compound 10
$^1$H NMR (500 MHz, DMSO-d$_6$) δ (ppm) 9.57 (s, 1H), 9.41 (s, 1H), 9.05 (br.s, 2H), 8.98 (d, J=7.6 Hz, 1H), 8.90 (d, J=5.0 Hz, 1H), 7.88-7.97 (m, 2H), 7.48 (dd, J=9.5, 2.5 Hz, 1H), 7.42 (d, J=2.5 Hz, 1H), 6.56 (d, J=1.9 Hz, 2H), 6.50 (d, J=1.9 Hz, 1H), 4.23 (t, J=7.7 Hz, 2H), 3.77 (s, 6H), 3.36 (spt, J=6.6 Hz 1H), 3.17 (m, 2H), 1.25 (d, J=6.6 Hz, 6H)

Compound 2
$^1$H NMR (DMSO-d$_6$, 500 MHz): δ (ppm) 9.46 (s, 1H), 9.38 (s, 1H), 8.71-8.77 (m, 3H), 8.64 (d, J=7.9 Hz, 1H), 7.95 (d, J=9.5 Hz, 1H), 7.60 (dd, J=7.9, 4.7 Hz, 1H), 7.54 (d, J=2.2 Hz, 1H), 7.43-7.48 (m, 2H), 6.55 (d, J=1.9 Hz, 2H), 6.48 (s, 1H), 5.03 (s, 2H), 3.76 (s, 6H).

Compound 17
$^1$H NMR (500 MHz, DMSO-d$_6$) δ (ppm) 9.12 (s, 1H), 8.86 (d, J=2.2 Hz, 1H), 8.26 (dd, J=8.8, 2.2 Hz, 1H), 7.77 (d, J=9.1 Hz, 1H), 7.27 (dd, J=9.1, 2.5 Hz, 1H), 7.20 (d, J=2.5 Hz, 1H), 6.58 (d, J=8.8 Hz, 1H), 6.52 (s, 2H), 6.46 (d, J=1.9 Hz, 2H), 6.40 (s, 1H), 3.88 (t, J=6.9 Hz, 2H), 3.74 (s, 6H), 2.79 (t, J=6.9 Hz, 2H), 2.70 (spt, J=6.6 Hz, 1H), 1.71 (br. s., 1H), 0.95 (d, J=6.6 Hz, 6H)

Compound 14
$^1$H NMR (500 MHz, DMSO-d$_6$) δ (ppm) 9.36 (s, 1H), 8.90 (qt, J=4.7 Hz, 1H), 8.84 (s, 1H), 8.82 (d, J=3.8 Hz, 1H), 8.43 (d, J=3.8 Hz, 1H), 7.88 (d, J=9.1 Hz, 1H), 7.40 (dd, J=9.1, 2.4 Hz, 1H), 7.36 (d, J=2.4 Hz, 1H), 6.51 (d, J=1.9 Hz, 2H), 6.45 (s, 1H), 3.87-3.96 (t, J=6.8 Hz, 2H), 3.75 (s, 6H), 2.87 (d, J=4.7 Hz, 3H), 2.81 (t, J=6.8 Hz, 2H), 2.71 (spt, J=6.3 Hz, 1H), 1.78 (br. s., 1H), 0.96 (d, J=6.3 Hz, 6H)

Compound 12
$^1$H NMR (500 MHz, DMSO-d$_6$) δ (ppm) 9.31 (s, 1H), 8.78 (d, J=5.7 Hz, 2H), 8.23 (d, J=5.7 Hz, 2H), 7.88 (d, J=9.1 Hz, 1H), 7.41 (dd, J=9.1, 2.2 Hz, 1H), 7.29 (d, J=2.2 Hz, 1H), 6.51 (d, J=1.9 Hz, 2H), 6.44 (s, 1H), 3.91 (t, J=6.9 Hz, 2H), 3.75 (s, 6H), 2.81 (t, J=6.9 Hz, 2H), 2.70 (spt, J=6.0 Hz, 1H), 1.75 (br. s., 1H), 0.95 (d, J=6.0 Hz, 6H)

Compound 5
$^1$H NMR (500 MHz, DMSO-d$_6$) δ (ppm) 9.04 (br. s., 1H), 7.93 (br. s., 1H), 7.80 (d, J=9.5 Hz, 2H), 7.33 (br. s., 1H), 7.25 (dd, J=9.5, 2.2 Hz, 2H), 6.94 (m, 3H), 6.42-6.49 (m, 3H), 4.11 (m, 2H), 3.93 (t, J=7.4 Hz, 2H), 3.75 (s, 6H), 3.72 (s, 3H) 3.14-3.21 (m, 2H), 2.06-2.15 (m, 2H)

Compound 9
$^1$H NMR (500 MHz, DMSO-d$_6$) δ (ppm) 9.43 (d, J=1.6 Hz, 1H), 9.29 (s, 1H), 8.72 (d, J=4.7 Hz, 1H), 8.62 (d, J=7.9 Hz, 1H), 7.86 (d, J=9.5 Hz, 1H), 7.60 (dd, J=7.9, 4.7 Hz, 1H), 7.41 (dd, J=9.5, 2.5 Hz, 1H), 7.34 (d, J=2.5 Hz, 1H), 6.50 (d, J=1.9 Hz, 2H), 6.42 (s, 1H), 4.95 (t, J=5.7 Hz, 1H), 3.95 (t, J=5.7 Hz, 2H), 3.74 (s, 6H), 3.68 (q, J=5.7 Hz, 2H)

Pharmacological Part

Biological Assays A

FGFR1 (Enzymatic Assay)

In a final reaction volume of 30 μL, FGFR1 (h) (25 ng/ml) was incubated with 50 mM HEPES pH 7.5, 6 mM MnCl$_2$, 1 mM DTT, 0.1 mM Na$_3$VO$_4$, 0.01% Triton-X-100, 500 nM Btn-Flt3 and 5 μM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 μM to 0.1 nM) was determined and used to calculate an IC$_{50}$ (M) and pIC$_{50}$ (−log IC$_{50}$) value.

FGFR2 (Enzymatic Assay)

In a final reaction volume of 30 μL, FGFR2 (h) (150 ng/ml) was incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 0.4 μM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in (Relative Fluorescence Units). In this assay, the inhibitory effect of different compound concentrations (range 10 μM to 0.1 nM) was determined and used to calculate an $IC_{50}$ (M) and $pIC_{50}$ ($-\log IC_{50}$) value.

FGFR3 (Enzymatic Assay)

In a final reaction volume of 30 μL, FGFR3 (h) (40 ng/ml) was incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 25 μM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 μM to 0.1 nM) was determined and used to calculate an $IC_{50}$ (M) and $pIC_{50}$ ($-\log IC_{50}$) value.

FGFR4 (Enzymatic Assay)

In a final reaction volume of 30 μL, FGFR4 (h) (60 ng/ml) was incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 5 μM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 μM to 0.1 nM) was determined and used to calculate an $IC_{50}$ (M) and $pIC_{50}$ ($-\log IC_{50}$) value.

KDR (VEGFR2) (Enzymatic Assay)

In a final reaction volume of 30 μL, KDR (h) (150 ng/ml) was incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 3 μM ATP in the presence of compound (1% DMSO final). After incubation for 120 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 μM to 0.1 nM) was determined and used to calculate an $IC_{50}$ (M) and $pIC_{50}$ ($-\log IC_{50}$) value.

Ba/F3-FGFR1 (Minus IL3 or Plus IL3) (Cellular Proliferation Assay)

In a 384 Well Plate

In a 384 well plate, 100 nl of compound dilution in DMSO was sprayed before adding 50 μl cell culture medium (phenol red free RPMI-1640, 10% FBS, 2 mM L-Glutamine and 50 μg/ml Gentamycin) containing 20000 cells per well of Ba/F3-FGFR1-transfected cells. Cells were put in an incubator at 37° C. and 5% $CO_2$. After 24 hours, 10 μl of Alamar Blue solution (0.5 mM $K_3Fe(CN)_6$, 0.5 mM $KaFe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a flurorescence plate reader.

In this assay, the inhibitory effect of different compound concentrations (range 10 μM to 0.1 nM) was determined and used to calculate an $IC_{50}$ (M) and $pIC_{50}$ ($-\log IC_{50}$) value. As a counterscreen the same experiment was performed in the presence of 10 ng/ml murine IL3.

In a 96 Well Plate

In a 96 well plate, 180 μl cell culture medium (phenol red free RPMI-1640, 10% FBS, 2 mM L-Glutamine and 50 μg/ml Gentamycin) containing 10000 cells per well of Ba/F3-FGFR1-transfected cells were pipette and 20 μl of compound dilution in DMSO was added. Cells were put in an incubator at 37° C. and 5% $CO_2$. After 24 hours, 40 μl of Alamar Blue solution (0.5 mM $K_3Fe(CN)_6$, 0.5 mM $KaFe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a flurorescence plate reader.

In this assay, the inhibitory effect of different compound concentrations (range 10 μM to 0.1 nM) was determined and used to calculate an $IC_{50}$ (M) and $pIC_{50}$ ($-\log IC_{50}$) value. As a counterscreen the same experiment was performed in the presence of 10 ng/ml murine IL3.

Ba/F3-FGFR3 (Minus IL3 or Plus IL3) (Cellular Proliferation Assay)

In a 384 Well Plate

In a 384 well plate, 100 nl of compound dilution in DMSO was sprayed before adding 50 μl cell culture medium (phenol red free RPMI-1640, 10% FBS, 2 mM L-Glutamine and 50 μg/ml Gentamycin) containing 20000 cells per well of Ba/F3-FGFR3-transfected cells. Cells were put in an incubator at 37° C. and 5% $CO_2$. After 24 hours, 10 μl of Alamar Blue solution (0.5 mM $K_3Fe(CN)_6$, 0.5 mM $KaFe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a flurorescence plate reader.

In this assay, the inhibitory effect of different compound concentrations (range 10 μM to 0.1 nM) was determined and used to calculate an $IC_{50}$ (M) and $pIC_{50}$ ($-\log IC_{50}$) value. As a counterscreen the same experiment was performed in the presence of 10 ng/ml murine IL3.

In a 96 Well Plate

In a 96 well plate, 180 μl cell culture medium (phenol red free RPMI-1640, 10% FBS, 2 mM L-Glutamine and 50 μg/ml Gentamycin) containing 10000 cells per well of Ba/F3-FGFR3-transfected cells were pipette and 20 μl of compound dilution in DMSO was added. Cells were put in an incubator at 37° C. and 5% $CO_2$. After 24 hours, 40 μl of Alamar Blue solution (0.5 mM $K_3Fe(CN)_6$, 0.5 mM $KaFe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a flurorescence plate reader.

In this assay, the inhibitory effect of different compound concentrations (range 10 μM to 0.1 nM) was determined and used to calculate an $IC_{50}$ (M) and $pIC_{50}$ ($-\log IC_{50}$) value. As a counterscreen the same experiment was performed in the presence of 10 ng/ml murine IL3.

Ba/F3-KDR (Minus IL3 or Plus IL3) (Cellular Proliferation Assay)

In a 384 Well Plate

In a 384 well plate, 100 nl of compound dilution in DMSO was sprayed before adding 50 μl cell culture medium (phenol red free RPMI-1640, 10% FBS, 2 mM L-Glutamine and 50 μg/ml Gentamycin) containing 20000 cells per well of Ba/F3-KDR-transfected cells. Cells were put in an incubator at 37° C. and 5% $CO_2$. After 24 hours, 10 μl of Alamar Blue solution (0.5 mM $K_3Fe(CN)_6$, 0.5 mM $KaFe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluorescence plate reader.

In this assay, the inhibitory effect of different compound concentrations (range 10 μM to 0.1 nM) was determined and used to calculate an $IC_{50}$ (M) and $pIC_{50}$ ($-\log IC_{50}$) value. As a counterscreen the same experiment was performed in the presence of 10 ng/ml murine IL3.

In a 96 Well Plate

In a 96 well plate, 180 μl cell culture medium (phenol red free RPMI-1640, 10% FBS, 2 mM L-Glutamine and 50 μg/ml Gentamycin) containing 10000 cells per well of Ba/F3-KDR-transfected cells were pipette and 20 μl of compound dilution in DMSO was added. Cells were put in an incubator at 37° C. and 5% $CO_2$. After 24 hours, 40 μl of Alamar Blue solution (0.5 mM $K_3Fe(CN)_6$, 0.5 mM $KaFe(CN)_6$, 0.15 mM Resazurin and 100 mM Phosphate Buffer) was added to the wells, incubated for 4 hours at 37° C. and 5% $CO_2$ RFU's (Relative Fluorescence Units) (ex. 540 nm., em. 590 nm.) were measured in a fluorescence plate reader.

In this assay, the inhibitory effect of different compound concentrations (range 10 μM to 0.1 nM) was determined and used to calculate an $IC_{50}$ (M) and $pIC_{50}$ ($-\log IC_{50}$) value. As a counterscreen the same experiment was performed in the presence of 10 ng/ml murine IL3.

Ba/F3-Flt3 (Minus IL3 or Plus IL3) (Cellular Proliferation Assay)

In a 384 Well Plate

In a 384 well plate, 100 nl of compound dilution in DMSO was sprayed before adding 50 μl cell culture medium (phenol red free RPMI-1640, 10% FBS, 2 mM L-Glutamine and 50 μg/ml Gentamycin) containing 20000 cells per well of Ba/F3-Flt3-transfected cells. Cells were put in an incubator at 37° C. and 5% $CO_2$. After 24 hours, 10 μl of Alamar Blue solution (0.5 mM $K_3Fe(CN)_6$, 0.5 mM $KaFe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluorescence plate reader.

In this assay, the inhibitory effect of different compound concentrations (range 10 μM to 0.1 nM) was determined and used to calculate an $IC_{50}$ (M) and $pIC_{50}$ ($-\log IC_{50}$) value. As a counterscreen the same experiment was performed in the presence of 10 ng/ml murine IL3.

In a 96 Well Plate

In a 96 well plate, 180 μl cell culture medium (phenol red free RPMI-1640, 10% FBS, 2 mM L-Glutamine and 50 μg/ml Gentamycin) containing 10000 cells per well of Ba/F3-Flt3-transfected cells were pipette and 20 μl of compound dilution in DMSO was added. Cells were put in an incubator at 37° C. and 5% $CO_2$. After 24 hours, 40 μl of Alamar Blue solution (0.5 mM $K_3Fe(CN)_6$, 0.5 mM $KaFe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluorescence plate reader.

In this assay, the inhibitory effect of different compound concentrations (range 10 μM to 0.1 nM) was determined and used to calculate an $IC_{50}$ (M) and $pIC_{50}$ ($-\log IC_{50}$) value. As a counterscreen the same experiment was performed in the presence of 10 ng/ml murine IL3.

Ba/F3-FGFR4 (Cellular Proliferation Assay)

In a 384 well plate, 100 nl of compound dilution in DMSO was sprayed before adding 50 μl cell culture medium (phenol red free RPMI-1640, 10% FBS, 2 mM L-Glutamine and 50 μg/ml Gentamycin) containing 20000 cells per well of Ba/F3-FGFR4-transfected cells. Cells were put in an incubator at 37° C. and 5% $CO_2$. After 24 hours, 10 μl of Alamar Blue solution (0.5 mM $K_3Fe(CN)_6$, 0.5 mM $KaFe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a flurorescence plate reader.

In this assay, the inhibitory effect of different compound concentrations (range 10 μM to 0.1 nM) was determined and used to calculate an $IC_{50}$ (M) and $pIC_{50}$ ($-\log IC_{50}$) value.

Data for the compounds of the invention in the above assays are provided in Table A3.

TABLE A3

(If data were generated multiple times for a compound or different batches were tested, average values are reported)

| Co No | FGFR 1 pIC50 | FGFR 2 pIC50 | FGFR 3 pIC50 | FGFR 4 pIC50 | KDR | BAF3-FGFR 1 (MIN IL3) 96 well $pIC_{50}$ | BAF3-FGFR 1 (PLUS IL3) 96 well $pIC_{50}$ | BAF3-FGFR 1 (MIN IL3) 384 well $pIC_{50}$ | BAF3-FGFR 1 (PLUS IL3) 384 well $pIC_{50}$ | BAF3-FGFR 3 (MIN IL3) 96 well $pIC_{50}$ | BAF3-FGFR 3 (PLUS IL3) 96 well $pIC_{50}$ | BAF3-FGFR 3 (MIN IL3) 384 well $pIC_{50}$ |
|---|---|---|---|---|---|---|---|---|---|---|---|---|
| 63 | 6.27 | 6.13 | 6.86 | 5.64 | 5.18 | | | <5 | <5 | <5 | <5 | <5 |
| 20 | 6.09 | 5.89 | 6.58 | 5.22 | <5 | | | <5 | <5 | 5.05 | <5 | <5 |
| 64 | 6.36 | 6.48 | 6.72 | 5.54 | 5.26 | | | <5 | <5 | 5.02 | <5 | <5 |
| 86 | 6.29 | 5.74 | 6.38 | 5.4 | <5 | | | <5 | <5 | 5.4 | <5 | <5 |
| 22 | 7.55 | 7.02 | 7.46 | 6.56 | 5.78 | | | <5 | <5 | 5.04 | <5 | <5.52 |
| 87 | 6.21 | 6.02 | 6.68 | 5.45 | <5 | | | <5.4 | <5.4 | | | <5.4 |
| 88 | 6.24 | 5.94 | 6.42 | <5 | <5 | | | <5 | <5 | <5 | <5 | <5 |
| 37 | 7.52 | 7.02 | 7.44 | 6.52 | 5.86 | 5.4 | 5.12 | 5.16 | <5 | 5.77 | ~5.27 | ~5.26 |

TABLE A3-continued (If data were generated multiple times for a compound or different batches were tested, average values are reported)

| | | | | | | | | | | | | | |
|---|---|---|---|---|---|---|---|---|---|---|---|---|---|
| 89 | 7.28 | 7 | 7.38 | 6.63 | 5.72 | | | 5.13 | <5 | 5.49 | <5 | ~5.16 |
| 90 | 6.23 | 6.17 | 6.55 | <5 | <5 | 5.06 | <5 | | | 5.09 | <5 | |
| 58 | 6.52 | 6.42 | 6.72 | 5.83 | 5.08 | | | <5 | <5 | 5.06 | <5 | <5 |
| 91 | 6.36 | 6.17 | 6.54 | 5.59 | <5 | | | <5 | <5 | 5.02 | <5 | <5 |
| 39 | 7.5 | 7.09 | 7.53 | 6.84 | 5.53 | | | <5 | <5 | 5.51 | <5 | 5.08 |
| 92 | 6.44 | 6.18 | 6.58 | 5.62 | 5.71 | <5 | | <5 | <5 | <5 | <5 | <5 |
| 93 | <5 | <5 | 5.63 | <5 | <5 | <5 | <5 | <5 | <5 | <5 | <5 | <5 |
| 94 | 7.27 | 7.03 | 7.64 | 6.48 | 5.67 | 5.48 | <5 | <5 | <5 | 5.8 | <5 | <5 |
| 27 | 6.57 | ~5.38 | 5.58 | <5 | <5 | <5 | <5 | <5 | <5 | <5 | <5 | <5 |
| 28 | 5.62 | 5.21 | 5.92 | <5 | <5 | | <5 | <5 | <5 | <5 | <5 | <5 |
| 18 | 6.52 | 6.33 | 6.6 | 5.64 | <5 | | <5 | <5 | <5 | 5.18 | <5 | <5 |
| 95 | 5.88 | <5 | 5.84 | <5 | <5 | | | <5 | <5 | <5 | <5 | <5 |
| 96 | ~6.44 | ~6.04 | 6.26 | <6 | <6 | | | <5 | <5 | 5.18 | <5 | <5 |
| 97 | 6.24 | 5.7 | 6.17 | 5.98 | <5 | | | <5 | <5 | <5 | <5 | <5 |
| 98 | 6.36 | 6.17 | 6.72 | <6 | <6 | | | <5 | <5 | <5 | <5 | <5 |
| 99 | <6 | <6 | <6 | <6 | <6 | | | <5 | <5 | <5 | <5 | <5 |
| 32 | 6.38 | 6.24 | 6.32 | <6 | <6 | <5 | <5 | <5 | <5 | <5 | <5 | <5 |
| 101 | <6 | <6 | <6 | <6 | <6 | <5 | <5 | <5 | <5 | <5 | <5 | <5 |
| 102 | <6 | <6 | <6 | <6 | <6 | <5 | <5 | <5 | <5 | <5 | <5 | <5 |
| 103 | <6 | <6 | ~6 | <6 | <6 | <5 | <5 | <5 | <5 | <5 | <5 | <5 |
| 58 | 6.87 | 6.27 | 7.09 | 6.26 | <6 | <5 | <5 | <5 | <5 | 5.56 | <5 | <5 |
| 31 | 6.03 | <6 | 6.47 | 6.11 | <6 | <5 | <5 | <5 | <5 | <5 | <5 | <5 |
| 62 | <6 | <6 | <6 | <6 | <6 | <5 | <5 | <5 | <5 | <5 | <5 | <5 |
| 61 | 6.27 | <6 | 6.39 | <6 | <6 | 5.13 | 5.16 | <5 | <5 | 5.42 | 5.4 | <5 |
| 30 | 7.29 | 7.17 | 7.57 | 6.67 | 6.3 | 5.03 | <5 | 5.32 | <5 | 5.94 | <5 | 5.51 |
| 50 | 6.12 | ~6.15 | 6.35 | <6 | <6 | <5 | <5 | <5 | <5 | <5 | <5 | <5 |
| 69 | 7.1 | 6.78 | 7.21 | 6.6 | <6 | 5.22 | <5 | 5.01 | <5 | <5 | <5 | <5 |
| 55 | 7.43 | 7.32 | 7.51 | 6.56 | 6.04 | 5.37 | <5 | <5 | <5 | 5.65 | <5 | ~5.25 |
| 36 | 7.31 | 7.13 | 7.66 | 6.39 | 6.17 | 5.47 | <5 | 5.39 | <5 | 5.71 | <5 | 5.39 |
| 73 | 7.41 | 7.16 | 7.75 | 6.75 | 6.53 | 6.17 | <5 | 5.53 | <5 | 5.15 | <5 | 5.38 |
| 40 | 7.11 | 7.05 | 7.31 | 6.52 | 6.4 | 5.4 | <5 | 5.24 | <5 | 5.04 | <5 | ~5.15 |
| 70 | 6.49 | 6.33 | 6.66 | ~6.03 | <6 | <5 | <5 | <5 | <5 | <5 | <5 | <5 |
| 71 | 6.99 | 7.14 | 7.42 | 6.53 | 6.09 | 5.28 | <5 | 5.1 | <5 | ~5 | <5 | ~5.12 |
| 72 | 6.27 | 6.32 | 6.41 | <6 | <6 | 5.23 | 5.1 | 5.18 | <5 | <5 | <5 | <5 |
| 24 | 7.69 | 7.6 | 8.02 | 6.72 | 6.08 | 5.42 | <5 | 5.39 | <5 | 5.59 | <5 | ~5.7 |
| 60 | 6.24 | 5.85 | 6.02 | 5.95 | <5 | <5 | <5 | <5 | <5 | <5 | <5 | <5 |
| 56 | 7.91 | 7.92 | 8.29 | 7.1 | 6.82 | 6.1 | <5 | 5.76 | <5 | 5.53 | <5 | 6.01 |
| 82 | 6.51 | 6.64 | 6.83 | <6 | <6 | 5.03 | <5 | <5 | <5 | 5.18 | <5 | <5 |
| 83 | <6 | <6 | <6 | <6 | <6 | <5 | <5 | <5 | <5 | <5 | <5 | <5 |
| 41 | 7.24 | 6.75 | 7.19 | 7.1 | 5.48 | <5 | <5 | <5 | <5 | <5 | <5 | <5 |
| 23 | 6.3 | 6.37 | 6.67 | <6 | <6 | 5.41 | 5.23 | 5.09 | <5 | 5.66 | 5.33 | 5.1 |
| 21 | 7.33 | 7.12 | 7.3 | 6.2 | 6.15 | 5.38 | <5 | <5 | <5 | 5.95 | <5 | ~5.24 |
| 65 | <6 | <6 | <6 | <6 | <6 | <5 | <5 | <5 | <5 | 5.08 | <5 | <5 |
| 104 | 6.41 | ~6.38 | 6.93 | 6.24 | <6 | | | <5 | <5 | | | <5 |
| 105 | 7.55 | 7.39 | 7.86 | 6.88 | 6.13 | | | 5.32 | <5 | | | 5.53 |
| 106 | 8.265 | 8.235 | 8.52 | 7.71 | 6.75 | | | 6.455 | <5 | | | ~6.54 |
| 17 | 8.91 | 8.675 | 8.495 | 8.095 | 7.025 | | | 6.975 | ~5.11 | | | ~7.09 |
| 14 | 8.21 | 8.25 | 8.02 | 7.38 | 6.31 | | | 6.61 | ~5.15 | | | 7.03 |
| 81 | 7.99 | 8.26 | 8 | 7.2 | 6.68 | | | 5.66 | ~5.55 | | | 5.91 |
| 80 | 6.4 | 6.04 | ~6.46 | <6 | <6 | | | 5.08 | <5 | | | 5.09 |
| 25 | 6.33 | 6.6 | 6.55 | <6 | <6 | | | 5.05 | <5 | | | 5.13 |
| 109 | 7.79 | 8.2 | 7.93 | 6.6 | 6.7 | | | 6.63 | <5 | | | ~6.77 |
| 110 | 7.56 | 7.76 | 7.67 | 6.84 | 6.56 | | | 6.25 | <5 | | | 6.81 |
| 111 | 7.58 | 7.63 | 8.01 | 7.15 | 6.13 | | | 5.65 | <5 | | | ~6.17 |
| 112 | 7.73 | 7.68 | 8.13 | 7.23 | 6.33 | | | 6.11 | <5 | | | ~6.39 |
| 74 | 8.14 | 7.94 | 8.36 | 7.57 | 6.51 | | | 6.62 | <5 | | | 6.69 |
| 113 | 7.07 | 7.34 | 7.47 | 6.77 | <6 | | | 5.44 | <5 | | | ~5.63 |
| 114 | 8.48 | 8.42 | 8.25 | 7.87 | 6.55 | | | 6.49 | <5 | | | 6.73 |
| 115 | 7.8 | 7.87 | 8.32 | 7.42 | 6.51 | | | 5.93 | <5 | | | 6.29 |
| 116 | 8.14 | 7.97 | 8.49 | 7.75 | 6.87 | | | 5.9 | <5 | | | 6.59 |
| 117 | 7.69 | 7.65 | 7.93 | 7.06 | 6.04 | | | 6.67 | <5 | | | 6.25 |
| 51 | 8.43 | 8.05 | 7.96 | 7.16 | 6.51 | | | 5.88 | <5 | | | ~5.77 |
| 119 | 6.29 | <6 | 6.43 | <6 | <6 | | | <5 | <5 | | | <5 |
| 120 | 8.05 | 7.82 | 8.4 | 7.7 | 6.58 | | | 5.71 | <5 | | | ~6.09 |
| 121 | 8.93 | 8.43 | 8.23 | 8.1 | 7.31 | | | 6.45 | 5.07 | | | 6.42 |
| 122 | 7.08 | 7.33 | 7.43 | 6.5 | <6 | | | 5.29 | <5 | | | 5.49 |
| 48 | 8.61 | 8.39 | 8.48 | 7.81 | 6.96 | | | 6.92 | ~5.28 | | | 6.87 |
| 11 | 8.09 | 7.85 | 8.35 | 7.38 | 6.57 | | | 6.01 | <5 | | | 6.65 |
| 9 | 8 | 7.77 | 8.33 | 7.28 | 6.53 | | | 6.25 | <5 | | | 6.59 |
| 123 | 7.73 | 7.59 | 7.84 | 6.61 | 6.24 | | | 5.22 | <5 | | | 5.57 |
| 12 | 8.67 | 8.61 | 8.35 | 7.69 | 7.02 | | | 7.27 | <5 | | | ~7.03 |
| 124 | 8.16 | 7.84 | 8.47 | 7.48 | 6.99 | | | 6.24 | <5 | | | ~6.64 |
| 10 | 8.56 | 8.23 | 7.99 | 7.63 | 6.53 | | | 7.55 | <5 | | | 7.53 |
| 33 | 7.9 | 7.64 | 7.72 | 6.94 | 6.24 | | | 5.1 | <5 | | | 5.51 |
| 125 | 7.46 | 6.51 | 7.09 | 6.76 | <6 | | | 5.37 | <5 | | | ~6.04 |
| 126 | 7.71 | 7.48 | 7.75 | 6.93 | 6.18 | | | 5.31 | <5 | | | 5.51 |
| 127 | 6.59 | 6.44 | 6.48 | 6.04 | <6 | | | <5 | <5 | | | <5 |
| 6 | 8.36 | 7.92 | 8.16 | 7.61 | 6.97 | | | 5.84 | <5 | | | ~6.27 |

TABLE A3-continued (If data were generated multiple times for a compound or different batches were tested, average values are reported)

| | | | | | | | | | | | | |
|---|---|---|---|---|---|---|---|---|---|---|---|---|
| 3 | 8.11 | 7.71 | 8 | 7.41 | 6.9 | | | 5.91 | <5 | | | 6.62 |
| 128 | 6.74 | 6.87 | 7.47 | <6 | <6 | | | <5 | <5 | | | <5 |
| 66 | 8.51 | 8.39 | 8.68 | 7.88 | 7.12 | | | 7.16 | <5 | | | ~7.05 |
| 8 | 9.34 | 8.58 | 8.63 | 8.46 | 7.7 | | | 8.13 | <5 | | | ~7.69 |
| 5 | 8.16 | 7.82 | 8.02 | 7.57 | 6.9 | | | 5.99 | <5 | | | 6.57 |
| 129 | 7.71 | 7.43 | 7.28 | 7.06 | 6.44 | | | 5.62 | <5 | | | 5.89 |
| 79 | 8.92 | 8.58 | 8.73 | 8.07 | 7.65 | | | 6.9 | <5 | | | ~6.64 |
| 44 | 7.76 | 7.96 | 7.95 | 7.29 | 6.52 | | | <5 | <5 | | | <5 |
| 130 | 7.76 | 8.08 | 7.95 | 6.82 | 6.26 | | | 5.1 | <5 | | | 5.2 |
| 131 | 8.68 | 8.33 | 8.23 | 7.67 | 6.7 | | | 6.44 | 5.4 | | | 6.08 |
| 43 | 7.8 | 7.88 | 8.42 | 7.34 | 6.61 | | | 6.28 | <5 | | | 6.25 |
| 132 | 8.36 | 8.06 | 7.73 | 6.93 | 6.51 | | | 5.8 | <5 | | | 5.57 |
| 133 | 6.96 | 6.94 | 7.3 | <6 | <6 | | | <5 | <5 | | | <5 |
| 134 | 7.55 | 7.34 | 7.68 | 7.21 | 6.19 | | | 6.06 | <5 | | | 5.66 |
| 135 | 8.7 | 8.21 | 8.61 | 7.54 | 6.77 | | | 6.42 | 5.28 | | | 6.3 |
| 136 | 7.62 | 7.59 | 7.99 | 7.01 | 6.11 | | | 5.63 | <5 | | | 5.71 |
| 137 | 8.43 | 8.08 | 8.07 | 7.37 | 6.56 | | | 5.75 | 5.58 | | | ~5.83 |
| 138 | 7.64 | ~7.5 | 7.79 | 6.75 | 6.12 | | | <5 | <5 | | | 5.04 |
| 139 | 7.5 | 7.4 | 7.94 | 7.01 | 6.16 | | | 5.35 | <5 | | | 5.72 |
| 141 | 7.32 | 7.3 | 7.71 | 6.74 | <6 | | | 5.4 | <5 | | | ~5.36 |
| 142 | 7.9 | 7.6 | 8.13 | 7.19 | 6.46 | | | 5.64 | <5 | | | 5.85 |
| 143 | 8.98 | 8.47 | 8.6 | 8.02 | 7.28 | | | 6.56 | 5.25 | | | 6.4 |
| 144 | 7.13 | ~7.07 | 7.25 | 6.33 | <6 | | | <5 | <5 | | | 5.1 |
| 145 | 6.94 | 6.78 | 7.01 | 6.06 | <6 | | | <5 | <5 | | | <5 |
| 26 | 6.95 | 6.86 | 7 | 6.32 | <6 | | | 5.13 | <5 | | | <5 |
| 146 | 8.7 | 8.09 | 7.91 | 7.31 | 6.57 | | | 6.46 | <5 | | | 6.41 |
| 84 | 7.35 | 7.04 | 7.39 | 6.21 | <6 | | | 5.05 | <5 | | | <5 |
| 148 | 7.44 | 7.23 | 7.21 | 6.22 | <6 | | | <5 | <5 | | | <5 |
| 149 | 7.22 | 6.99 | 7.45 | 6.78 | <6 | | | 5.32 | <5 | | | 5.32 |
| 150 | 7.04 | 7.15 | 7.31 | 6.65 | 6.15 | | | 5.16 | <5 | | | 5.11 |
| 151 | 6.55 | 6.29 | 6.7 | 6.05 | <6 | | | 5.52 | <5 | | | 5.11 |
| 67 | 8.48 | 8.2 | 7.78 | 6.7 | 6.35 | | | 6.23 | 5.07 | | | 5.83 |
| 38 | 7.82 | 7.59 | 7.98 | 7.03 | 6.15 | | | 6.31 | <5 | | | 6.23 |
| 156 | 7.34 | 7.02 | 7.62 | 7.02 | 6.39 | | | 5.7 | 5.05 | | | 5.79 |
| 158 | 6.4 | 6.18 | 6.27 | <6 | <6 | | | <5 | <5 | | | <5 |
| 159 | 7.5 | 7.18 | 6.81 | 6.31 | <6 | | | 5.74 | <5 | | | 5.82 |
| 160 | 7.37 | 7.24 | 7.04 | 6.51 | <6 | | | 5.86 | <5 | | | 6.1 |
| 161 | 8.23 | 7.85 | 7.35 | 6.48 | 6.21 | | | 5.42 | <5 | | | 5.38 |
| 59 | 8.44 | 8.39 | 8.04 | 7.19 | 7.34 | | | 6.22 | <5 | | | 5.9 |
| 19 | 8.41 | 7.97 | 8.71 | 7.75 | 6.77 | | | 6.41 | <5 | | | 6.17 |
| 163 | 8.13 | 7.8 | 8.1 | 6.92 | 6.45 | | | 6.15 | ~5 | | | ~6.14 |
| 35 | 7.92 | 7.58 | 8 | 7.17 | 6.64 | | | 6.36 | <5 | | | 6.19 |
| 165 | 8.41 | 7.9 | 8.31 | 7.54 | 6.89 | | | 6.56 | 5.18 | | | 6.12 |
| 166 | 9.29 | 8.44 | 9.08 | 8.14 | 7.63 | | | 6.7 | 5.32 | | | ~6.1 |
| 167 | 8.78 | 8.11 | 7.96 | 7.5 | 6.6 | | | 7.13 | <5 | | | 7.09 |
| 168 | 9.02 | 8.43 | 8.49 | 8.08 | 7.2 | | | 7.04 | 5.11 | | | ~7.15 |
| 169 | 8.06 | 7.8 | 8.19 | 7.27 | 6.9 | | | 6.37 | <5 | | | 6.19 |
| 68 | 7.59 | 7.47 | 7.47 | 6.55 | 6.64 | | | 6.13 | <5 | | | ~6.15 |
| 170 | 9.09 | 8.4 | 8.21 | 7.54 | 6.87 | | | 6.04 | 5.45 | | | 6.16 |
| 77 | 8.65 | 8.04 | 7.92 | 7.28 | 6.29 | | | 7.12 | <5 | | | 7.12 |
| 29 | 7.26 | 6.94 | 7.41 | 6.63 | <6 | | | 6.41 | <5 | | | 5.5 |
| 171 | 6.22 | 6.14 | 6.3 | 6.06 | <6 | | | <5 | <5 | | | <5 |
| 172 | 6.97 | 6.84 | 7.06 | 6.38 | <6 | | | 6.6 | <5 | | | 5.36 |
| 173 | 7.53 | 7.49 | 7.99 | 7 | 6.32 | | | 5.68 | <5 | | | 6.08 |
| 178 | 8.29 | 7.91 | 8.54 | 7.25 | <6 | | | 6.07 | <5 | | | 6.29 |
| 179 | 6.69 | 6.37 | 6.42 | <6 | 7.11 | | | 5.62 | <5 | | | 5.19 |
| 180 | 6.64 | 6.52 | 6.58 | 6.01 | 6.72 | | | 5.51 | <5 | | | 5.28 |
| 181 | 6.53 | 6.31 | 6.3 | <6 | <6 | | | 5.44 | <5 | | | 5.16 |
| 182 | 7.71 | 7.58 | 6.9 | 6.22 | 6.95 | | | 5.89 | <5 | | | 5.64 |
| 183 | 6.81 | 7.09 | 6.79 | 6.37 | <6 | | | 6.76 | <5 | | | 7.1 |
| 184 | 6.85 | 6.81 | 6.96 | 6.51 | <6 | | | 5.28 | <5 | | | 5.27 |
| 46 | 7.9 | 7.92 | 8.14 | 7.32 | 6.53 | | | 6.49 | <5 | | | 6.65 |
| 47 | 7.67 | 7.76 | 7.65 | 6.94 | 6.47 | | | 6.29 | <5 | | | 6.3 |
| 53 | 8.48 | 8.11 | 9.11 | 7.75 | 6.44 | | | 6.76 | <5 | | | 6.82 |
| 54 | 7.9 | 7.7 | 8.15 | 7.14 | 6.1 | | | 6.22 | <5 | | | ~6.18 |
| 185 | 6.5 | 6.67 | 6.96 | <6 | <6 | | | <5 | <5 | | | 5.01 |
| 45 | 6.45 | 6.21 | 6.38 | <6 | <6 | | | 5.65 | <5 | | | 5.69 |
| 52 | 7.06 | 7.04 | 7.54 | 6.39 | <6 | | | 5.96 | <5 | | | ~6.17 |
| 76 | 7.93 | 7.7 | 8.24 | 6.97 | 6.41 | | | 6.3 | <5 | | | 6.59 |
| 75 | 6.96 | 6.8 | 6.85 | 6.02 | <6 | | | 6.43 | <5 | | | 6.5 |
| 2 | 7.08 | 7.46 | 7.25 | 6.71 | <6 | | | 6.8 | 5.13 | | | 7.13 |
| 49 | 6.5 | 6.4 | 6.9 | 5.8 | 5.4 | | | <5 | <5 | 5.5 | <5 | <5 |
| 189 | 8.55 | 8.64 | 8.21 | 8.14 | 6.9 | — | — | 7.29 | <5 | — | — | ~7.1 |
| 188 | 8.00 | 8.13 | 7.75 | 7.15 | 6.6 | — | — | 6.46 | <5 | — | — | 6.17 |
| 186 | 7.35 | 7.44 | 7.79 | 6.9 | 6.06 | — | — | 5.98 | <5 | — | — | 5.8 |

TABLE A3-continued (If data were generated multiple times for a compound or different batches were tested, average values are reported)

| Co No | BAF3-FGFR 3 (PLUS IL3) 384 well $pIC_{50}$ | BAF3-KDR (MIN IL3) 384 well $pIC_{50}$ | BAF3-KDR (PLUS IL3) 284 well $pIC_{50}$ | BAF3-KDR (MIN IL3) 96 well $pIC_{50}$ | BAF3-KDR (PLUS IL3) 96 well $pIC_{50}$ | BAF3-FLT3 (MIN IL3) 96 well $pIC_{50}$ | BAF3-FLT3 (PLUS IL3) 96 well $pIC_{50}$ | BAF3-FLT3 (MIN IL3) 384 well $pIC_{50}$ | BAF3-FLT3 (PLUS IL3) 384 well $pIC_{50}$ | BAF3-FGFR 4 $pIC_{50}$ |
|---|---|---|---|---|---|---|---|---|---|---|
| 63 | <5 | <5 | <5 | | | <5 | <5 | <5 | <5 | <5 |
| 20 | <5 | <5 | <5 | | | <5 | <5 | <5 | <5 | <5 |
| 64 | <5 | <5 | <5 | | | ~5.12 | <5 | <5 | <5 | <5 |
| 86 | <5 | <5 | <5 | | | <5 | <5 | <5 | <5 | <5 |
| 22 | <5 | <5 | <5 | | | <5 | <5 | <5 | <5 | <5 |
| 87 | <5.4 | <5.4 | <5.4 | | | | | <5.4 | <5.4 | <5 |
| 88 | <5 | <5 | <5 | | | <5 | <5 | <5 | <5 | <5 |
| 37 | ~5.27 | <5 | 5.02 | | | 5.59 | ~5.33 | 5.05 | 5.1 | 5.3 |
| 89 | <5 | <5 | <5 | | | <5 | <5 | <5 | <5 | <5 |
| 90 | | | | | | <5 | <5 | | | |
| 58 | <5 | <5 | <5 | | | <5 | <5 | <5 | <5 | <5 |
| 91 | <5 | <5 | <5 | | | <5 | <5 | <5 | <5 | <5 |
| 39 | <5 | <5 | <5 | | | <5 | <5 | <5 | <5 | <5 |
| 92 | <5 | <5 | <5 | | | <5 | <5 | <5 | <5 | <5 |
| 93 | <5 | <5 | <5 | | | <5 | <5 | <5 | <5 | <5 |
| 94 | <5 | <5 | <5 | <5 | <5 | <5 | <5 | <5 | <5 | <5 |
| 27 | <5 | <5 | <5 | | | <5 | <5 | <5 | <5 | <5 |
| 28 | <5 | <5 | <5 | | | <5 | <5 | <5 | <5 | <5 |
| 18 | <5 | <5 | <5 | | | <5 | <5 | <5 | <5 | <5 |
| 95 | <5 | <5 | <5 | | | <5 | <5 | <5 | <5 | <5 |
| 96 | <5 | <5 | <5 | | | <5 | <5 | <5 | <5 | <5 |
| 97 | <5 | <5 | <5 | | | <5 | <5 | <5 | <5 | <5 |
| 98 | <5 | <5 | <5 | | | <5 | <5 | <5 | <5 | <5 |
| 99 | <5 | <5 | <5 | | | <5 | <5 | <5 | <5 | <5 |
| 32 | <5 | <5 | <5 | | | <5 | <5 | <5 | <5 | <5 |
| 101 | <5 | <5 | <5 | | | <5 | <5 | <5 | <5 | <5 |
| 102 | <5 | <5 | <5 | | | ~5 | <5 | <5 | <5 | <5 |
| 103 | <5 | <5 | <5 | | | 5.17 | <5 | <5 | <5 | <5 |
| 58 | <5 | <5 | <5 | | | <5 | <5 | <5 | 5.08 | <5 |
| 31 | <5 | <5 | <5 | | | <5 | <5 | <5 | <5 | <5 |
| 62 | <5 | <5 | <5 | | | <5 | <5 | <5 | <5 | <5 |
| 61 | <5 | <5 | <5 | | | 5.25 | 5.17 | <5 | <5 | <5 |
| 30 | <5 | 5.07 | <5 | 5.11 | <5 | 5.06 | <5 | <5 | <5 | <5.35 |
| 50 | <5 | <5 | <5 | <5 | <5 | <5 | <5 | <5 | <5 | <5 |
| 69 | <5 | <5 | <5 | <5 | <5 | <5 | <5 | <5 | <5 | <5 |
| 55 | <5 | <5 | <5 | <5 | ~5 | <5 | <5 | <5 | <5 | <5 |
| 36 | <5 | <5 | <5 | <5 | <5 | <5 | <5 | <5 | <5 | ~5.2 |
| 73 | <5 | 5.07 | <5 | <5 | 5.23 | 5.31 | <5 | 5.03 | <5 | <5 |
| 40 | <5 | <5 | <5 | <5 | <5 | <5 | <5 | <5 | <5 | ~5.0 |
| 70 | <5 | <5 | <5 | <5 | <5 | <5 | <5 | <5 | <5 | <5 |
| 71 | <5 | <5 | <5 | <5 | <5 | <5 | <5 | <5 | <5 | <5 |
| 72 | <5 | 5.03 | <5 | 5.47 | 5.26 | <5 | <5 | 5.09 | <5 | <5 |
| 24 | <5 | <5 | <5 | <5 | <5 | <5 | <5 | <5 | <5 | ~5.1 |
| 60 | <5 | <5 | <5 | | | <5 | <5 | <5 | <5 | <5 |
| 56 | <5 | ~5 | <5 | 5.29 | <5 | <5 | <5 | <5 | <5 | 5.5 |
| 82 | <5 | <5 | <5 | <5 | <5 | <5 | <5 | <5 | <5 | <5 |
| 83 | <5 | <5 | <5 | <5 | <5 | <5 | <5 | <5 | <5 | <5 |
| 41 | <5 | <5 | <5 | | <5 | <5 | <5 | <5 | <5 | <5 |
| 23 | <5 | <5 | <5 | 5.36 | 5.22 | 5.31 | 5.25 | <5 | <5 | <5 |
| 21 | <5 | <5 | <5 | <5 | <5 | <5 | <5 | <5 | <5 | <5 |
| 65 | <5 | <5 | <5 | <5 | <5 | <5 | <5 | <5 | <5 | <5 |
| 104 | <5 | <5 | <5 | | | | | <5 | <5 | <5 |
| 105 | <5 | <5 | <5 | | | | | <5 | <5 | 5.53 |
| 106 | <5 | 5.335 | <5 | | | | | <5.025 | <5 | 6.3 |
| 17 | ~5.07 | 5.82 | 5.035 | | | | | 5.17 | <5.02 | ~7.11 |
| 14 | ~5.22 | 5.35 | <5 | | | | | 5.02 | <5 | 6.8 |
| 81 | ~5.83 | 5.62 | 5.58 | | | | | 5.76 | 5.73 | 5.9 |
| 80 | <5 | <5 | <5 | | | | | <5 | <5 | <5 |
| 25 | <5 | <5 | <5 | | | | | <5 | <5 | <5 |
| 109 | <5 | 5.24 | <5 | | | | | <5 | <5 | 6.2 |
| 110 | <5 | 5.45 | <5 | | | | | 5.04 | <5 | 6.2 |
| 111 | <5 | <5 | <5 | | | | | <5 | <5 | 5.9 |
| 112 | <5 | <5 | <5 | | | | | 5.07 | <5 | 5.8 |
| 74 | <5 | <5 | <5 | | | | | <5 | <5 | 6.1 |
| 113 | <5 | <5 | <5 | | | | | <5 | <5 | 5.5 |
| 114 | <5 | 5.26 | 5.05 | | | | | 5.04 | <5 | 6.5 |
| 115 | <5 | 5.06 | <5 | | | | | 4.99 | <5 | 5.7 |
| 116 | <5 | 5.19 | <5 | | | | | <5 | <5 | 6.4 |
| 117 | <5 | <5 | <5 | | | | | <5 | <5 | 5.5 |
| 51 | ~5.09 | 5.04 | <5 | | | | | 5.27 | ~5.15 | 5.7 |
| 119 | <5 | <5 | <5 | | | | | <5 | <5 | <5 |
| 120 | <5 | <5 | <5 | | | | | <5 | <5 | 6.0 |

TABLE A3-continued (If data were generated multiple times for a compound or different batches were tested, average values are reported)

| | | | | | | |
|---|---|---|---|---|---|---|
| 121 | ~5.19 | ~5.3 | 5.25 | ~5.34 | 5.36 | 6.4 |
| 122 | <5 | <5 | <5 | <5 | <5 | ~5.1 |
| 48 | 5.26 | 5.39 | 5.28 | 5.44 | 5.38 | 6.5 |
| 11 | <5 | 5.1 | <5 | <5 | <5 | 5.9 |
| 9 | <5 | 5.12 | <5 | <5 | <5 | 5.8 |
| 123 | <5 | <5 | <5 | <5 | <5 | 5.2 |
| 12 | <5 | 5.53 | <5 | 5.14 | <5 | 6.8 |
| 124 | <5 | 5.11 | <5 | <5 | <5 | 6.1 |
| 10 | <5 | 5.56 | <5 | ~5.01 | 5.03 | 6.6 |
| 33 | <5 | <5 | <5 | <5 | <5 | 5.2 |
| 125 | <5 | <5 | <5 | <5 | <5 | <5 |
| 126 | <5 | <5 | <5 | <5 | <5 | 5.1 |
| 127 | <5 | <5 | <5 | <5 | <5 | <5 |
| 6 | <5 | 5.18 | <5 | <5 | <5 | 5.6 |
| 3 | <5 | 5.07 | <5 | 5.07 | <5 | 6.4 |
| 128 | <5 | <5 | <5 | <5 | <5 | <5 |
| 66 | <5 | 5.52 | <5 | 5.06 | <5 | 6.3 |
| 8 | <5 | 6.19 | <5 | 5.2 | <5 | 7.2 |
| 5 | <5 | 5.07 | <5 | <5 | <5 | 5.7 |
| 129 | <5 | <5 | <5 | <5 | <5 | 5.4 |
| 79 | <5 | 5.45 | <5 | 5.04 | <5 | 6.7 |
| 44 | <5 | <5 | <5 | <5 | <5 | <5.35 |
| 130 | <5 | <5 | <5 | <5 | <5 | 5.0 |
| 131 | ~5.34 | 5.37 | ~5.28 | 5.5 | 5.44 | 6.0 |
| 43 | <5 | 5.07 | <5 | <5 | <5 | 6.0 |
| 132 | ~5.13 | 5.04 | <5 | 5.31 | ~5.26 | 5.6 |
| 133 | <5 | <5 | <5 | <5 | <5 | <5 |
| 134 | <5 | <5 | <5 | <5 | <5 | 5.8 |
| 135 | ~5.49 | 5.33 | 5.24 | 5.43 | 5.35 | 6.1 |
| 136 | <5 | <5 | <5 | <5 | <5 | <5 |
| 137 | ~5.96 | 5.67 | 5.71 | 5.91 | 5.87 | 6.1 |
| 138 | <5 | <5 | <5 | <5 | <5 | 5.1 |
| 139 | <5 | <5 | <5 | <5 | <5 | <5 |
| 141 | <5 | <5 | <5 | <5 | <5 | 5.2 |
| 142 | <5 | <5 | <5 | <5 | <5 | 5.6 |
| 143 | ~5.22 | 5.33 | 5.11 | ~5.25 | 5.18 | 6.9 |
| 144 | <5 | <5 | <5 | <5 | <5 | <5 |
| 145 | <5 | <5 | <5 | <5 | <5 | <5.35 |
| 26 | <5 | <5 | <5 | <5 | <5 | ~5.1 |
| 146 | 5.25 | <5 | <5 | <5 | <5 | 6.3 |
| 84 | <5 | <5 | <5 | <5 | <5 | <5 |
| 148 | <5 | <5 | <5 | <5 | <5 | <5 |
| 149 | <5 | <5 | <5 | <5 | <5 | 5.6 |
| 150 | <5 | <5 | <5 | <5 | <5 | ~5.0 |
| 151 | <5 | <5 | <5 | <5 | <5 | <5 |
| 67 | <5 | 5 | <5 | 5 | <5 | 6.2 |
| 38 | <5 | <5 | <5 | <5 | <5 | 5.8 |
| 156 | <5 | <5 | <5 | <5 | <5 | 5.4 |
| 158 | <5 | <5 | <5 | <5 | <5 | 5.1 |
| 159 | <5 | <5 | <5 | <5 | <5 | ~5.5 |
| 160 | <5 | <5 | <5 | <5 | <5 | 5.8 |
| 161 | <5 | <5 | <5 | <5 | <5 | <5 |
| 59 | ~5.19 | 5.66 | <5 | 5.28 | <5 | 6.1 |
| 19 | <5 | <5 | <5 | <5 | <5 | 6.1 |
| 163 | <5 | 5.3 | 5.12 | 5.32 | <5 | <5 |
| 35 | <5 | 5.11 | <5 | <5 | <5 | 6.0 |
| 165 | <5 | 5.36 | <5 | 5.38 | ~5.24 | 6.6 |
| 166 | ~5.22 | 5.55 | 5.22 | 5.46 | ~5.25 | 6.7 |
| 167 | <5 | <5 | <5 | <5 | <5 | 6.4 |
| 168 | ~5.03 | 5.75 | 5.15 | 5.13 | ~5.08 | 6.9 |
| 169 | <5 | 5.1 | <5 | <5 | <5 | 6.0 |
| 68 | <5 | <5 | <5 | <5 | <5 | 5.7 |
| 170 | 5.01 | <5 | <5 | 5.47 | 5.3 | 6.2 |
| 77 | <5 | 5.29 | <5 | <5 | <5 | 6.9 |
| 29 | <5 | <5 | <5 | <5 | <5 | <5 |
| 171 | <5 | <5 | <5 | <5 | <5 | <5 |
| 172 | <5 | <5 | <5 | 5.19 | <5 | 5.1 |
| 173 | <5 | <5 | <5 | <5 | <5 | 5.6 |
| 178 | <5 | <5 | <5 | <5 | <5 | 5.9 |
| 179 | <5 | <5 | <5 | <5 | <5 | <5 |
| 180 | <5 | <5 | <5 | <5 | <5 | 5.2 |
| 181 | <5 | <5 | <5 | <5 | <5 | <5 |
| 182 | ~5.16 | <5 | <5 | <5 | <5 | 5.7 |
| 183 | <5 | <5 | <5 | 5.04 | <5 | ~6.5 |
| 184 | <5 | <5 | <5 | <5 | <5 | 5.1 |
| 46 | <5 | <5 | <5 | <5 | <5 | 5.8 |
| 47 | <5 | <5 | <5 | <5 | <5 | 5.5 |
| 53 | <5 | <5 | <5 | <5 | <5 | 6.2 |

TABLE A3-continued (If data were generated multiple times for a compound or different batches were tested, average values are reported)

| | | | | | | | | | |
|---|---|---|---|---|---|---|---|---|---|
| 54 | <5 | <5 | <5 | | | | <5 | <5 | 5.7 |
| 185 | <5 | <5 | <5 | | | | <5 | <5 | <5 |
| 45 | <5 | <5 | <5 | | | | <5 | <5 | <5 |
| 52 | <5 | <5 | <5 | | | | <5 | <5 | 5.2 |
| 76 | <5 | <5 | <5 | | | | <5 | <5 | 5.6 |
| 75 | <5 | <5 | <5 | | | | <5 | <5 | 5.6 |
| 2 | <5 | <5 | 5.02 | | | | <5 | <5 | 6.9 |
| 49 | <5 | <5 | <5 | | 5.2 | <5 | <5 | <5 | <5 |
| 189 | <5 | 5.14 | <5 | — | — | — | — | — | 6.23 |
| 188 | <5 | 5.14 | <5 | — | — | — | — | — | 6.05 |
| 186 | <5 | <5 | <5 | — | — | — | <5 | <5 | 5.57 |

Biological Assays B

FGFR3, VEGFR2 and PDGFR In Vitro Kinase Inhibitory Activity Assays

Enzymes (from Upstate), prepared at 2× final concentration, were incubated with test compounds, biotinylated Flt3 substrate (biotin-VASSDNEYFYVDF) (Cell Signalling Technology Inc.) and ATP in the appropriate assay buffer (Table 1). The reaction was allowed to proceed for 3 hours (FGFR3), 1 hour (VEGFR2, PDGFR-beta) at room temperature on a plate shaker at 700 rpm before being stopped with 35 mM EDTA, pH 8 (FGFR3, VEGFR2) or 55 mM EDTA, pH 8 (PDGFR-beta). 5× detection mix (50 mM HEPES pH 7.5, 0.1% BSA, 11.34 nM Eu-anti-pY (PY20) (PerkinElmer) 74 nM SA-XL665 (Cisbio) for FGFR3, 50 mM HEPES, pH 7.5, 0.1% BSA, 11.34 nM Eu-anti-pY (PY20), 187.5 nM SA-XL665 for VEGFR2 and 50 mM HEPES, pH 7.5, 0.1% BSA, 11.34 nM Eu-anti-pY (PT66) (PerkinElmer), 375 nM SA-XL665 (Cisbio) for PDGFR-beta) was then added to each well and the plate sealed and incubated at room temperature for one hour on a plate shaker at 700 rpm. The plate was then read on a Packard Fusion plate reader or a BMG Pherastar both in TRF mode.

TABLE 1

Final assay conditions for FGFR3, VEGFR2 and PDGFR-beta assays

| Enzyme | 1 × Assay Buffer | Flt3 substrate concentration | ATP concentration |
|---|---|---|---|
| FGFR3 | A | 0.125 μM | 8 μM |
| VEGFR2 | B | 0.5 μM | 0.5 μM |
| PDGFR-beta | C | 1 μM | 70 μM |

Kinase Assay buffers were:

A: 50 mM HEPES pH 7.5, 6 mM MnCl$_2$, 1 mM DTT, 0.01% TritonX-100

B: 50 mM HEPES pH 7.5, 6 mM MnCl$_2$, 1 mM DTT, 0.01% TritonX-100, 0.1 mM Sodium orthovanadate C: 20 mM HEPES pH 7.5, 10 mM MnCl$_2$, 0.01% Triton X-100, 1 mM DTT, 0.1 mM Sodium orthovanadate FGFR3 and VEGFR2 Data for the compounds of the invention in the above assays are provided in Table A3.

Ba/F3-TEL-FGFR3 & Ba/F3 (WT) Cell Proliferation Assays

Stably transfected Ba/F3-TEL-FGFR3 cells were plated out into black 96-well tissue culture plates with clear bottoms in RPMI medium containing 10% FBS and 0.25 mg/ml G418 at a density of 5×10$^3$ cells/well (200 μl per well). The parental wild-type Ba/F3 cells (DSMZ no.: ACC 300) were plated out into black 96-well tissue culture plates with clear bottoms in RPMI medium containing 10% FBS and 2 ng/ml mouse IL-3 (R&D Systems) at a density of 2.5×10$^3$ cells/well (200 μl per well). Plates were placed in an incubator overnight before adding the compounds the following day. Dilutions of compounds were made in DMSO starting at 10 mM and were diluted into the wells to give a final DMSO concentration of 0.1% in assay. Compounds were left on the cells for 72 hours before the plates were removed from the incubator and 20 μl of Alamar Blue™ (Biosource) was added to each well. Plates were placed in the incubator for 4-6 hours before reading plates at 535 nm (excitation)/590 nm (emission) on a Fusion plate reader (Packard). Where inhibition is high an IC$_{50}$ can be determined.

The invention claimed is:

1. A method for inhibiting fibroblast growth factor receptor kinase activity in a subject suffering from, or being at risk of suffering from a disease state or condition mediated by a fibroblast growth factor receptor kinase, said method comprising administering to the subject a compound selected from the group consisting of a compound of formula (I):

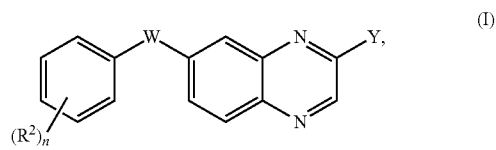

a tautomeric form, and stereochemically isomeric form thereof, wherein

W represents —N(R$^3$)— or —C(R$^{3a}$R$^{3b}$)—;

each R$^2$ independently represents hydroxyl, halogen, cyano, C$_{1-4}$ alkyl, C$_{2-4}$alkenyl, C$_{2-4}$alkynyl, C$_{1-4}$alkoxy, hydroxyC$_{1-4}$hydroxyC$_{1-4}$alkoxy, haloC$_{1-4}$alkyl, haloC$_{1-4}$alkoxy, hydroxyhaloC$_{1-4}$alkyl, hydroxyhaloC$_{1-4}$alkoxy, C$_{1-4}$alkoxyC$_{1-4}$alkyl, haloC$_{1-4}$alkoxyC$_{1-4}$alkyl, C$_{1-4}$alkoxyC$_{1-4}$alkyl wherein each C$_{1-4}$alkyl may optionally be substituted with one or two hydroxyl groups, hydroxyhaloC$_{1-4}$alkoxy C$_{1-4}$alkyl, R$^{13}$, C$_{1-4}$alkyl substituted with R$^{13}$, C$_{1-4}$alkyl substituted with —C(=O)—R$^{13}$, C$_{1-4}$alkoxy substituted with R$^{13}$, C$_{1-4}$alkoxy substituted with —C(=O)—R$^{13}$, —C(=O)—R$^{13}$, C$_{1-4}$alkyl substituted with —NR$^7$R$^8$, C$_{1-4}$alkyl substituted with —C(=O)—NR$^7$R$^8$, C$_{1-4}$ alkoxy substituted with —NR$^7$R$^8$, C$_{1-4}$alkoxy substituted with —C(=O)—NR$^7$R$^8$, —NR$^7$R$^8$ or —C(=O)—NR$^7$R$^8$; or when two R$^2$ groups are attached to adjacent carbon atoms they may be taken together to form a radical of formula:

—O—(C(R$^{17}$)$_2$)$_p$—O—;

—X—CH=CH—; or

—X—CH=N—; wherein R$^{17}$ represents hydrogen or fluoro, p represents 1 or 2 and X represents O or S;

Y represents —CR$^{18}$=N—OR$^{19}$ or -E-D;

E represents a bond, —(CR$^{22}$R$^{23}$)$_n$—, C$_{2-4}$alkenediyl optionally substituted with R$^{22}$, C$_{2-4}$alkynediyl optionally substituted with R$^{22}$, —CO—(CR$^{22}$R$^{23}$)$_s$—, —(CR$^{22}$R$^{23}$)$_s$—CO—, —NR$^{22}$—(CR$^{22}$R$^{23}$)$_s$—, —(CR$^{22}$R$^{23}$)$_s$—NR$^{22}$—, —O—(CR$^{22}$R$^{23}$)$_s$—, —(CR$^{22}$R$^{23}$)$_s$—O—, —S(O)$_m$—(CR$^{22}$R$^{23}$)$_s$—, —(CR$^{22}$R$^{23}$)$_s$—S(O)$_m$—, —(CR$^{22}$R$^{23}$)$_s$—CO—NR$^{22}$—(CR$^{22}$R$^{23}$)$_s$— or —(CR$^{22}$R$^{23}$)$_s$—NR$^{22}$—CO—(CR$^{22}$R$^{23}$)$_s$—;

D represents a 3 to 12 ring membered monocyclic or bicyclic carbocyclyl or a 3 to 12 ring membered monocyclic or bicyclic heterocyclyl containing at least one heteroatom selected from N, O and S, wherein said carbocyclyl and heterocyclyl may each be optionally substituted by one or more R$^1$ groups;

provided that when Y represents -E-D, and E represents a bond, then D does not represent

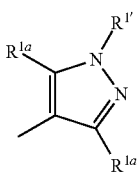

wherein R$^{1'}$ represents hydrogen, C$_{1-6}$alkyl, C$_{2-4}$ alkenyl, hydroxyC$_{1-6}$ alkyl, haloC$_{1-6}$alkyl, hydroxyhaloC$_{1-6}$alkyl, cyanoC$_{1-4}$alkyl, C$_{1-6}$alkoxyC$_{1-6}$alkyl wherein each C$_{1-6}$alkyl may optionally be substituted with one or two hydroxyl groups, C$_{1-6}$ alkyl substituted with —NR$^4$R$^5$, C$_{1-6}$ alkyl substituted with —C(=O)—NR$^4$R$^5$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$ alkyl, C$_{1-6}$alkyl substituted with —NR$^{12}$—S(=O)$_2$—NR$^{14}$R$^{15}$, R$^6$, C$_{1-6}$ alkyl substituted with R$^6$, C$_{1-6}$alkyl substituted with —C(=O)—R$^6$, hydroxyC$_{1-6}$alkyl substituted with R$^6$, C$_{1-6}$alkyl substituted with —Si(CH$_3$)$_3$, C$_{1-6}$ alkyl substituted with —P(=O)(OH)$_2$ or C$_{1-6}$ alkyl substituted with —P(=O)(OC$_{1-6}$alkyl)$_2$; and each R$^{1a}$ is independently selected from hydrogen, C$_{1-4}$alkyl, hydroxyC$_{1-4}$alkyl, C$_{1-4}$alkyl substituted with amino or mono- or di(C$_{1-4}$alkyl)amino or —NH(C$_{3-8}$ cycloalkyl), cyanoC$_{1-4}$ alkyl, C$_{1-4}$ alkoxyC$_{1-4}$ alkyl, and C$_{1-4}$ alkyl substituted with one or more fluoro atoms;

R$^1$ represents hydrogen, halo, cyano, C$_{1-6}$ alkyl, C$_{1-6}$ alkoxy, —C(=O)—O—C$_{1-6}$alkyl, C$_{2-4}$alkenyl, hydroxyC$_{1-6}$ alkyl, haloC$_{1-6}$ alkyl, hydroxyhaloC$_{1-6}$ alkyl, cyanoC$_{1-4}$ alkyl, C$_{1-6}$alkoxyC$_{1-6}$ alkyl wherein each C$_{1-6}$ alkyl may optionally be substituted with one or two hydroxyl groups, —NR$^4$R$^5$, C$_{1-6}$alkyl substituted with —O—C(=O)—C$_{1-6}$alkyl, C$_{1-6}$ alkyl substituted with —NR$^4$R$^5$, —C(=O)—NR$^4$R$^5$, —C(=O)—C$_{1-6}$alkyl-NR$^4$R$^5$, C$_{1-6}$alkyl substituted with —C(=O)—NR$^4$R$^5$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$ alkyl, C$_{1-6}$ alkyl substituted with —S(=O)$_2$—NR$^{14}$R$^{15}$, C$_{1-6}$alkyl substituted with —NH—S(=O)$_2$—C$_{1-6}$ alkyl, C$_{1-6}$alkyl substituted with —NH—S(=O)$_2$-haloC$_{1-6}$alkyl, C$_{1-6}$alkyl substituted with —NR$^{12}$—S(=O)$_2$—NR$^{14}$R$^{15}$, R$^6$, C$_{1-6}$alkyl substituted with R$^6$, —C(=O)—R$^6$, C$_{1-6}$alkyl substituted with —C(=O)—R$^6$, hydroxyC$_{1-6}$alkyl substituted with R$^6$, C$_{1-6}$ alkyl substituted with —Si(CH$_3$)$_3$, C$_{1-6}$ alkyl substituted with —P(=O)(OH)$_2$ or C$_{1-6}$ alkyl substituted with —P(=O)(OC$_{1-6}$alkyl)$_2$;

R$^{3a}$ represents —NR$^{10}$R$^{11}$, hydroxyl, C$_{1-6}$alkoxy, hydroxyC$_{1-6}$alkoxy, C$_{1-6}$ alkoxy substituted with —NR$^{10}$R$^{11}$, C$_{1-6}$alkyl, C$_{2-6}$alkenyl, C$_{2-6}$alkynyl, haloC$_{1-6}$alkyl optionally substituted with —O—C(=O)—C$_{1-6}$alkyl, hydroxyC$_{1-6}$alkyl optionally substituted with —O—C(=O)—C$_{1-6}$ alkyl, hydroxyC$_{2-6}$alkenyl, hydroxyC$_{2-6}$alkynyl, hydroxyhaloC$_{1-6}$alkyl, cyanoC$_{1-6}$ alkyl, C$_{1-6}$alkyl substituted with carboxyl, C$_{1-6}$alkyl substituted with —C(=O)—C$_{1-6}$alkyl, C$_{1-6}$alkyl substituted with —C(=O)—O—C$_{1-6}$alkyl, C$_{1-6}$alkyl substituted with C$_{1-6}$alkoxyC$_{1-6}$alkyl-O—C(=O)—, C$_{1-6}$alkyl substituted with C$_{1-6}$ alkoxyC$_{1-6}$alkyl-C(=O)—, C$_{1-6}$ alkyl substituted with —O—C(=O)—C$_{1-6}$ alkyl, C$_{1-6}$alkoxyC$_{1-6}$alkyl wherein each C$_{1-6}$alkyl may optionally be substituted with one or two hydroxyl groups or with —O—C(=O)—C$_{1-6}$ alkyl, C$_{2-6}$alkenyl substituted with C$_{1-6}$alkoxy, C$_{2-6}$ alkynyl substituted with C$_{1-6}$ alkoxy, C$_{1-6}$ alkyl substituted with R$^9$ and optionally substituted with —O—C(=O)—C$_{1-6}$alkyl, C$_{1-6}$alkyl substituted with —C(=O)—R$^9$, C$_{1-6}$alkyl substituted with hydroxyl and R$^9$, C$_{2-6}$ alkenyl substituted with R$^9$, C$_{2-6}$ alkynyl substituted with R$^9$, C$_{1-6}$ alkyl substituted with —NR$^{10}$R$^{11}$, C$_{2-6}$ alkenyl substituted with —NR$^{10}$R$^{11}$, C$_{2-6}$alkynyl substituted with —NR$^{10}$R$^{11}$, C$_{1-6}$alkyl substituted with hydroxyl and —NR$^{10}$R$^{11}$, C$_{1-6}$alkyl substituted with one or two halogens and —NR$^{10}$R$^{11}$, —C$_{1-6}$ alkyl-C(R$^{12}$)=N—O—R$^{12}$, C$_{1-6}$ alkyl substituted with —C(=O)—NR$^{10}$R$^{11}$, C$_{1-6}$ alkyl substituted with —O—C(=O)—NR$^{10}$R$^{11}$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$ alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$ alkyl substituted with —NR$^{12}$—S(=O)$_2$—C$_{1-6}$ alkyl, C$_{1-6}$alkyl substituted with —NH—S(=O)$_2$-haloC$_{1-6}$alkyl, C$_{1-6}$alkyl substituted with —NR$^{12}$—S(=O)$_2$—NR$^{14}$R$^{15}$, R$^{13}$, C$_{1-6}$alkyl substituted with —P(=O)(OH)$_2$ or C$_{1-6}$alkyl substituted with —P(=O)(OC$_{1-6}$alkyl)$_2$;

R$^{3b}$ represents hydrogen or hydroxyl; provided that if R$^{3a}$ represents —NR$^{10}$R$^{11}$, then R$^{3b}$ represents hydrogen; or R$^{3a}$ and R$^{3b}$ are taken together to form =O, to form =NR$^{10}$, to form cyclopropyl together with the carbon atom to which they are attached, to form =CH—C$_{0-4}$alkyl substituted with R$^{3c}$, or to form

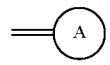

wherein ring A is a monocyclic 5 to 7 membered saturated heterocycle containing one heteroatom selected from N, O and S, said heteroatom not being positioned in alpha position of the double bond, wherein ring A is optionally being substituted with cyano, C$_{1-4}$alkyl, hydroxyC$_{1-4}$alkyl, H$_2$N—C$_{1-4}$alkyl, (C$_{1-4}$alkyl)NH—C$_{1-4}$alkyl, (C$_{1-4}$alkyl)$_2$N—C$_{1-4}$alkyl, haloC$_{1-4}$alkyl)NH—C$_{1-4}$alkyl, C$_{1-4}$alkoxyC$_{1-4}$alkyl, —C(=O)—NH$_2$, —C(=O)—NH(C$_{1-4}$ alkyl), —C(=O)—N(C$_{1-4}$alkyl)$_2$;

$R^{3c}$ represents hydrogen, hydroxyl, $C_{1-6}$alkoxy, $R^9$, —$NR^{10}R^{11}$, cyano, —C(=O)—$C_{1-6}$alkyl or —CH(OH)—$C_{1-6}$alkyl;

$R^3$ represents hydroxyl, $C_{1-6}$ alkoxy, hydroxy$C_{1-6}$ alkoxy, $C_{1-6}$ alkoxy substituted with —$NR^{10}R^{11}$, $C_{1-6}$alkyl, $C_{2-6}$alkenyl, $C_{2-6}$alkynyl, halo$C_{1-6}$alkyl optionally substituted with —O—C(=O)—$C_{1-6}$alkyl, hydroxy$C_{1-6}$alkyl optionally substituted with —O—C(=O)—$C_{1-6}$ alkyl, hydroxy$C_{2-6}$alkenyl, hydroxy$C_{2-6}$alkynyl, hydroxyhalo$C_{1-6}$alkyl, cyano$C_{1-6}$alkyl, $C_{1-6}$alkyl substituted with carboxyl, $C_{1-6}$alkyl substituted with —C(=O)—$C_{1-6}$alkyl, $C_{1-6}$alkyl substituted with —C(=O)—O—$C_{1-6}$alkyl, $C_{1-6}$alkyl substituted with $C_{1-6}$alkoxy$C_{1-6}$alkyl-O—C(=O)—, $C_{1-6}$alkyl substituted with $C_{1-6}$alkoxy$C_{1-6}$alkyl-C(=O)—, $C_{1-6}$ alkyl substituted with —O—C(=O)—$C_{1-6}$ alkyl, $C_{1-6}$alkoxy$C_{1-6}$alkyl wherein each $C_{1-6}$alkyl may optionally be substituted with one or two hydroxyl groups or with —O—C(=O)—$C_{1-6}$ alkyl, C2-6alkenyl substituted with $C_{1-6}$alkoxy, $C_{2-6}$alkynyl substituted with $C_{1-6}$alkoxy, $C_{1-6}$alkyl substituted with $R^9$ and optionally substituted with —O—C(=O)—$C_{1-6}$alkyl, $C_{1-6}$alkyl substituted with —C(=O)—$R^9$, $C_{1-6}$alkyl substituted with hydroxyl and $R^9$, $C_{2-6}$alkenyl substituted with $R^9$, $C_{2-6}$alkynyl substituted with $R^9$, $C_{1-6}$alkyl substituted with —$NR^{10}R^{11}$, $C_{2-6}$alkenyl substituted with —$NR^{10}R^{11}$, $C_{2-6}$alkynyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, —$C_{1-6}$alkyl-C($R^{12}$)=N—O—$R^{12}$, $C_{1-6}$ alkyl substituted with —C(=O)—$NR^{10}R^{11}$, $C_{1-6}$ alkyl substituted with —O—C(=O)—$NR^{10}R^{11}$, —S(=O)$_2$—$C_{1-6}$alkyl, —S(=O)$_2$-halo$C_{1-6}$alkyl, —S(=O)$_2$—$NR^{14}R^{15}$, $C_{1-6}$ alkyl substituted with —S(=O)$_2$—$C_{1-6}$ alkyl, $C_{1-6}$ alkyl substituted with —S(=O)$_2$-halo$C_{1-6}$ alkyl, $C_{1-6}$ alkyl substituted with —S(=O)$_2$—$NR^{14}R^{15}$, $C_{1-6}$ alkyl substituted with —$NR^{12}$—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^{13}$, $C_{1-6}$alkyl substituted with —P(=O)(OH)$_2$ or $C_{1-6}$alkyl substituted with —P(=O)(O$C_{1-6}$alkyl)$_2$;

$R^4$ and $R^5$ each independently represent hydrogen, $C_{1-6}$alkyl, $C_{1-6}$alkyl substituted with —$NR^{14}R^{15}$, hydroxy$C_{1-6}$ alkyl, halo$C_{1-6}$ alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, —S(=O)$_2$—$C_{1-6}$alkyl, —S(=O)$_2$-halo$C_{1-6}$alkyl, —S(=O)$_2$—$NR^{14}R^{15}$, —C(=O)—$NR^{14}R^{15}$, —C(=O)—O—$C_{1-6}$alkyl, —C(=O)—$R^{13}$, $C_{1-6}$alkyl substituted with —S(=O)$_2$—$C_{1-6}$alkyl, $C_{1-6}$alkyl substituted with —S(=O)$_2$-halo$C_{1-6}$ alkyl, $C_{1-6}$ alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NH—S(=O)$_2$—$NR^{14}R^{15}$, $R^{13}$ or $C_{1-6}$alkyl substituted with $R^{13}$;

$R^6$ represents $C_{3-8}$ cycloalkyl, $C_{3-8}$ cycloalkenyl, phenyl, 4 to 7-membered monocyclic heterocyclyl containing at least one heteroatom selected from N, O and S; said $C_{3-8}$cycloalkyl, $C_{3-8}$ cycloalkenyl, phenyl, 4 to 7-membered monocyclic heterocyclyl, optionally and each independently being substituted by 1, 2, 3, 4 or 5 substituents, each substituent independently being selected from cyano, $C_{1-6}$alkyl, cyano$C_{1-6}$alkyl, hydroxyl, carboxyl, hydroxy$C_{1-6}$alkyl, halogen, halo$C_{1-6}$alkyl, hydroxyhalo$C_{1-6}$alkyl, $C_{1-6}$alkoxy, $C_{1-6}$alkoxy$C_{1-6}$alkyl, $C_{1-6}$alkyl-O—C(=O)—, —$NR^{14}R^{15}$, —C(=O)—$NR^{14}R^{15}$, $C_{1-6}$ alkyl substituted with $C_{1-6}$alkyl substituted with —C(=O)—$NR^{14}R^{15}$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl or $C_{1-6}$alkyl substituted with —NH—S(=O)$_2$—$NR^{14}R^{15}$;

$R^7$ and $R^8$ each independently represent hydrogen, $C_{1-6}$alkyl, hydroxy$C_{1-6}$alkyl, halo$C_{1-6}$alkyl, hydroxyhalo$C_{1-6}$alkyl or $C_{1-6}$alkoxy$C_{1-6}$alkyl;

$R^9$ represents $C_{3-8}$ cycloalkyl, $C_{3-8}$ cycloalkenyl, phenyl, naphthyl, or 3 to 12 membered monocyclic or bicyclic heterocyclyl containing at least one heteroatom selected from N, O and S, said $C_{3-8}$ cycloalkyl, $C_{3-8}$ cycloalkenyl, phenyl, naphthyl, or 3 to 12 membered monocyclic or bicyclic heterocyclyl each optionally and each independently being substituted with 1, 2, 3, 4 or 5 substituents, each substituent independently being selected from =O, $C_{1-4}$alkyl, hydroxyl, carboxyl, hydroxy$C_{1-4}$alkyl, cyano, cyano$C_{1-4}$alkyl, $C_{1-4}$alkyl-O—C(=O)—, $C_{1-4}$alkyl substituted with $C_{1-4}$alkyl-O—C(=O)—, $C_{1-4}$alkyl-C(=O)—, $C_{1-4}$alkoxy$C_{1-4}$alkyl wherein each $C_{1-4}$alkyl may optionally be substituted with one or two hydroxyl groups, halogen, halo$C_{1-4}$alkyl, hydroxyhalo$C_{1-4}$alkyl, —$NR^{14}R^{15}$, —C(=O)—$NR^{14}R^{15}$, $C_{1-4}$alkyl substituted with —$NR^{14}R^{15}$, $C_{1-4}$alkyl substituted with —C(=O)—$NR^{14}R^{15}$, $C_{1-4}$ alkoxy, —S(=O)$_2$—$C_{1-4}$alkyl, —S(=O)$_2$-halo$C_{1-4}$alkyl, —S(=O)$_2$—$NR^{14}R^{15}$, $C_{1-4}$alkyl substituted with —S(=O)$_2$—$NR^{14}R^{15}$, $C_{1-4}$alkyl substituted with —NH—S(=O)$_2$—$C_{1-4}$alkyl, $C_{1-4}$alkyl substituted with —NH—S(=O)$_2$-halo$C_{1-4}$alkyl, $C_{1-4}$alkyl substituted with —NH—S(=O)$_2$—$NR^{14}R^{15}$, $R^{13}$, —C(=O)—$R^{13}$, $C_{1-4}$ alkyl substituted with $R^{13}$, phenyl optionally substituted with $R^{16}$, phenyl$C_{1-6}$alkyl wherein the phenyl is optionally substituted with $R^{16}$, a 5 or 6-membered aromatic monocyclic heterocyclyl containing at least one heteroatom selected from N, O and S wherein said heterocyclyl is optionally substituted with $R^{16}$;

or when two of the substituents of $R^9$ are attached to the same atom, they may be taken together to form a 4 to 7-membered saturated monocyclic heterocyclyl containing at least one heteroatom selected from N, O and S;

$R^{10}$ and $R^{11}$ each independently represent hydrogen, carboxyl, $C_{1-6}$alkyl, cyano$C_{1-6}$alkyl, $C_{1-6}$alkyl substituted with —$NR^{14}R^{15}$, $C_{1-6}$ alkyl substituted with —C(=O)—$NR^{14}R^{15}$, halo$C_{1-6}$alkyl, hydroxy$C_{1-6}$ alkyl, hydroxyhalo$C_{1-6}$ alkyl, $C_{1-6}$ alkoxy, $C_{1-6}$alkoxy$C_{1-6}$alkyl wherein each $C_{1-6}$ alkyl may optionally be substituted with one or two hydroxyl groups, $R^6$, $C_{1-6}$ alkyl substituted with $R^6$, —C(=O)—$R^6$, —C(=O)—$C_{1-6}$ alkyl, —C(=O)-hydroxy$C_{1-6}$ alkyl, —C(=O)-halo$C_{1-6}$alkyl, —C(=O)-hydroxyhalo$C_{1-6}$alkyl, $C_{1-6}$alkyl substituted with —Si(CH$_3$)$_3$, —S(=O)$_2$—$C_{1-6}$ alkyl, —S(=O)$_2$-halo$C_{1-6}$alkyl, —S(=O)$_2$—$NR^{14}R^{15}$, $C_{1-6}$ alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$ alkyl substituted with —NH—S(=O)$_2$-halo$C_{1-6}$alkyl, $C_{1-6}$alkyl substituted with carboxyl, or $C_{1-6}$alkyl substituted with —NH—S(=O)$_2$—NR$^{14}$R$^{15}$;

$R^{12}$ represents hydrogen or $C_{1-4}$alkyl optionally substituted with $C_{1-4}$alkoxy;

$R^{13}$ represents $C_{3-8}$cycloalkyl or a saturated 4 to 6-membered monocyclic heterocyclyl containing at least one heteroatom selected from N, O and S, wherein said $C_{3-8}$ cycloalkyl or monocyclic heterocyclyl is optionally substituted with 1, 2 or 3 substituents each independently selected from halogen, hydroxyl, $C_{1-6}$alkyl, halo$C_{1-6}$alkyl, =O, cyano, —C(=O)—$C_{1-6}$alkyl, $C_{1-6}$alkoxy, or —NR$^{14}$R$^{15}$;

$R^{14}$ and $R^{15}$ each independently represent hydrogen, or halo$C_{1-4}$alkyl, or $C_{1-4}$alkyl optionally substituted with a substituent selected from hydroxyl, $C_{1-4}$alkoxy, amino or mono- or di($C_{1-4}$alkyl)amino;

$R^{16}$ represents hydroxyl, halogen, cyano, $C_{1-4}$alkyl, $C_{1-4}$alkoxy, —NR$^{14}$R$^{15}$ or —C(=O)NR$^{14}$R$^{15}$;

$R^{18}$ represents hydrogen, $C_{1-6}$ alkyl, $C_{3-8}$ cycloalkyl, $C_{1-4}$alkyl substituted with $C_{3-8}$ cycloalkyl;

$R^{19}$ represents hydrogen; $C_{1-6}$ alkyl; $C_{3-8}$ cycloalkyl; $C_{1-6}$alkyl substituted with —O—R$^{20}$; —(CH$_2$)$_r$—CN; —(CH$_2$)$_r$—CONR$^{20}$R$^{21}$; —(CH$_2$)$_{r1}$—NR$^{20}$R$^{21}$; —(CH$_2$)$_{r1}$—NR$^{20}$COR$^{21}$; —(CH$_2$)$_{r1}$—NR$^{20}$; —(CH$_2$)$_s$—SO$_2$—R$^{21}$; —(CH$_2$)$_{r1}$—SO$_2$—NR$^{20}$R$^{21}$; —(CH$_2$)$_{r1}$—NR$^{20}$CO$_2$R$^{21}$; —(CH$_2$)$_r$—SO$_2$NR$^{20}$R$^{21}$; phenyl optionally substituted with 1, 2, 3, 4 or 5 substituents each independently selected from halogen, $C_{1-4}$alkyl, $C_{1-4}$alkyloxy, cyano and amino; a 5- or 6-membered aromatic monocyclic heterocycle containing at least one heteroatom selected from N, O and S, said heterocycle being optionally substituted with 1, 2, 3 or 4 substituents each independently selected from halogen, $C_{1-4}$ alkyl, $C_{1-4}$ alkyloxy, cyano or amino; wherein said $C_{1-6}$ alkyl and $C_{3-8}$ cycloalkyl, may be optionally substituted by one or more R$^{20}$ groups;

$R^{20}$ and $R^{21}$ independently represent hydrogen, C1-6 alkyl, hydroxy$C_{1-6}$ alkyl, —(CH$_2$)$_n$—O—$C_{1-6}$alkyl, or when attached to a nitrogen atom R$^{20}$ and R$^{21}$ can be taken together to form with the nitrogen atom to which they are attached a monocyclic saturated 4, 5 or 6-membered ring which optionally contains a further heteroatom selected from O, S and N;

$R^{22}$ and $R^{23}$ independently represent hydrogen, $C_{1-6}$ alkyl, or hydroxy$C_{1-6}$ alkyl;

m independently represents 0, 1 or 2;

n independently represents 0, 1, 2, 3 or 4;

s independently represents 0, 1, 2, 3 or 4;

r independently represents 1, 2, 3, or 4; and r1 independently represents 2, 3 or 4;

provided that when R$^{3a}$ and R$^{3b}$ are taken together to form =O, n represents 0, Y represents -E-D, and E represents a bond, then D does not represent unsubstituted phenyl;

or an N-oxide thereof, a pharmaceutically acceptable salt thereof or a solvate thereof.

2. The method according to claim 1 wherein the compound is selected from the group consisting of a compound of formula (I), a tautomeric form, and stereochemically isomeric form thereof, wherein Y represents —CR$^{18}$=N—OR$^{19}$, or an N-oxide thereof, a pharmaceutically acceptable salt thereof or a solvate thereof.

3. The method according to claim 1 wherein the compound is selected from the group consisting of a compound of formula (I), a tautomeric form, and stereochemically isomeric form thereof, wherein Y is -E-D, or an N-oxide thereof, a pharmaceutically acceptable salt thereof or a solvate thereof.

4. The method according to claim 3 wherein the compound is selected from the group consisting of a compound of formula (I), a tautomeric form, and stereochemically isomeric form thereof, wherein E represents (i) a bond, $C_{2-4}$alkenediyl, —CO—(CR$^{22}$R$^{23}$)$_s$—, —(CR$^{22}$R$^{23}$)$_s$—CO—, —NR$^{22}$—(CR$^{22}$R$^{23}$)$_s$—, —(CR$^{22}$R$^{23}$)$_s$—NR$^{22}$—, —(CR$^{22}$R$^{23}$)$_s$—CO—NR$^{22}$—(CR$^{22}$R$^{23}$)$_s$— or —(CR$^{22}$R$^{23}$)$_s$—NR$^{22}$—CO—(CR$^{22}$R$^{23}$)$_s$—; or (ii) a bond; or (iii) $C_{2-4}$alkenediyl, —CO—(CR$^{22}$R$^{23}$)$_s$—, —(CR$^{22}$R$^{23}$)$_s$—CO—, —NR$^{22}$—(CR$^{22}$R$^{23}$)$_s$—, —(CR$^{22}$R$^{23}$)$_s$—NR$^{22}$—, —(CR$^{22}$R$^{23}$)$_s$—CO—NR$^{22}$—(CR$^{22}$R$^{23}$)$_s$— or —(CR$^{22}$R$^{23}$)$_s$—NR$^{22}$—CO—(CR$^{22}$R$^{23}$)$_s$—, or an N-oxide thereof, a pharmaceutically acceptable salt thereof or a solvate thereof.

5. The method according to claim 3 wherein the compound is selected from the group consisting of a compound of formula (I), a tautomeric form, and stereochemically isomeric form thereof, wherein D represents optionally substituted pyrazolyl, or an N-oxide thereof, a pharmaceutically acceptable salt thereof or a solvate thereof.

6. The method according to claim 1 wherein the compound is selected from the group consisting of a compound of formula (I), a tautomeric form, and stereochemically isomeric form thereof, wherein D represents piperidinyl, pyridinyl, phenyl, pyrrolyl, imidazolyl, triazolyl, pyrrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrrolyl, pyrimidinyl, pyrrolidinyl, thiadiazolyl, or oxadiazolyl, said rings being optionally substituted, or an N-oxide thereof, a pharmaceutically acceptable salt thereof or a solvate thereof.

7. The method according to claim 1 wherein the compound is selected from the group consisting of a compound of formula (I), a tautomeric form, and stereochemically isomeric form thereof, wherein W represents —N(R$^3$)—, or an N-oxide thereof, a pharmaceutically acceptable salt thereof or a solvate thereof.

8. The method according to claim 1 wherein the compound is selected from the group consisting of a compound of formula (I), a tautomeric form, and stereochemically isomeric form thereof, wherein W represents —C(R$^{3a}$R$^{3b}$)—, or an N-oxide thereof, a pharmaceutically acceptable salt thereof or a solvate thereof.

9. The method according to claim 1 wherein the compound is selected from the group consisting of a compound of formula (I), a tautomeric form, and stereochemically isomeric form thereof, wherein each R$^2$ independently represents hydroxyl, halogen, cyano, $C_{1-4}$ alkyl, $C_{2-4}$ alkenyl, $C_{1-4}$ alkoxy, hydroxy$C_{1-4}$alkyl, hydroxy$C_{1-4}$alkoxy, halo $C_{1-4}$alkoxy, $C_{1-4}$ alkoxy$C_{1-4}$alkyl, R$^{13}$, $C_{1-4}$ alkoxy substituted with R$^{13}$, —C(=O)—R$^{13}$, $C_{1-4}$alkyl substituted with NR$^7$R$^8$, $C_{1-4}$ alkoxy substituted with NR$^7$R$^8$, —NR$^7$R$^8$ or —C(=O) NR$^7$R$^8$, or an N-oxide thereof, a pharmaceutically acceptable salt thereof or a solvate thereof.

10. The method according to claim 9 wherein the compound is selected from the group consisting of a compound of formula (I), a tautomeric form, and stereochemically isomeric form thereof, wherein R$^2$ represents $C_{1-4}$ alkoxy, or an N-oxide thereof, a pharmaceutically acceptable salt thereof or a solvate thereof.

11. The method according to claim 1 wherein the compound is selected from the group consisting of a compound of formula (I), a tautomeric form, and stereochemically isomeric form thereof, wherein $R^3$ represents:
- (i) $C_{1-6}$alkyl, hydroxy$C_{1-6}$alkyl, hydroxyhalo$C_{1-6}$alkyl, halo$C_{1-6}$ alkyl, $C_{1-6}$alkyl substituted with —C(=O)—$C_{1-6}$ alkyl, $C_{1-6}$alkoxy$C_{1-6}$alkyl wherein each $C_{1-6}$alkyl may optionally be substituted with one or two hydroxyl groups, $C_{1-6}$alkyl substituted with $R^9$, $C_{1-6}$ alkyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, $C_{1-6}$ alkyl substituted with —C(=O)—O—$C_{1-6}$ alkyl, $C_{1-6}$alkyl substituted with —O—C(=O)—$NR^{10}R^{11}$, $C_{1-6}$ alkyl substituted with carboxyl, $C_{1-6}$alkyl substituted with —$NR^{12}$—S(=O)$_2$—$C_{1-6}$alkyl, $C_{1-6}$alkyl substituted with —$NR^{12}$—S(=O)$_2$—$NR^{14}R^{15}$, $C_{1-6}$ alkyl substituted with hydroxyl and $R^9$, —$C_{1-6}$ alkyl-C($R^{12}$)=N—O—$R^{12}$, $C_{1-6}$alkyl substituted with —C(=O)—$NR^{10}R^{11}$, $C_{1-6}$ alkyl substituted with —C(=O)—$R^9$, $C_{2-6}$alkynyl substituted with $R^9$, hydroxy$C_{1-6}$alkoxy, $C_{2-6}$alkenyl, $C_{2-6}$alkynyl or $R^{13}$, or
- (ii) $C_{2-6}$alkynyl, halo$C_{1-6}$alkyl optionally substituted with —O—C(=O)—$C_{1-6}$ alkyl, hydroxy$C_{1-6}$alkyl optionally substituted with —O—C(=O)—$C_{1-6}$alkyl, hydroxyhalo$C_{1-6}$ alkyl, $C_{1-6}$alkoxy$C_{1-6}$alkyl wherein each $C_{1-6}$ alkyl may optionally be substituted with one or two hydroxyl groups or with —O—C(=O)—$C_{1-6}$alkyl, $C_{1-6}$alkyl substituted with $R^9$, $C_{2-6}$alkynyl substituted with $R^9$, $C_{1-6}$alkyl substituted with —$NR^{10}R^{11}$, $C_{1-6}$ alkyl substituted with —O—C(=O)—$NR^{10}R^{11}$, or an N-oxide thereof, a pharmaceutically acceptable salt thereof or a solvate thereof.

12. The method according to claim 1 wherein the compound is selected from the group consisting of a compound of formula (I), a tautomeric form, and stereochemically isomeric form thereof, wherein:

Y represents —$CR^{18}$=N—$OR^{19}$ or -E-D;
$R^{18}$ and $R^{19}$ represent $C_{1-6}$alkyl;
E represents a bond, $C_{2-4}$alkenediyl, —CO—($CR^{22}R^{23}$)$_s$—, —$NR^{22}$—($CR^{22}R^{23}$)$_s$—, —($CR^{22}R^{23}$)$_s$—$NR^{22}$—, —($CR^{22}R^{23}$)$_s$—CO—$NR^{22}$—($CR^{22}R^{23}$)$_s$— or —($CR^{22}R^{23}$)$_s$—$NR^{22}$—CO—($CR^{22}R^{23}$)$_s$—;
D represents piperidinyl, pyridinyl, phenyl, pyrrolyl, imidazolyl, triazolyl, pyrrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrrolyl, pyrimidinyl, pyrrolidinyl, thiadiazolyl, oxadiazolyl, or pyrazolyl, said rings being optionally substituted with halo, cyano, $C_{1-6}$alkyl, $C_{1-6}$alkoxy, —C(=O)—O—$C_{1-6}$alkyl, hydroxy$C_{1-6}$alkyl, —$NR^4R^5$, $C_{1-6}$alkyl substituted with —O—C(=O)—$C_{1-6}$alkyl, $C_{1-6}$alkyl substituted with —$NR^4R^5$, —C(=O)—$NR^4R^5$, —C(=O)—$C_{1-6}$alkyl-$NR^4R^5$, $R^6$, or $C_{1-6}$alkyl substituted with $R^6$;
W represents —N($R^3$)—;
$R^2$ represents $C_{1-4}$alkoxy;
n represents 2;
$R^3$ represents $C_{2-6}$alkynyl, halo$C_{1-6}$alkyl optionally substituted with —O—C(=O)—$C_{1-6}$alkyl, hydroxy $C_{1-6}$alkyl optionally substituted with —O—C(=O)—$C_{1-6}$ alkyl, hydroxyhalo$C_{1-6}$alkyl, $C_{1-6}$alkoxy$C_{1-6}$ alkyl wherein each $C_{1-6}$ alkyl may optionally be substituted with one or two hydroxyl groups or with —O—C(=O)—$C_{1-6}$ alkyl, $C_{1-6}$alkyl substituted with $R^9$, $C_{2-6}$alkynyl substituted with $R^9$, $C_{1-6}$alkyl substituted with —$NR^{10}R^{11}$, $C_{1-6}$alkyl substituted with —O—C(=O)—$NR^{10}R^{11}$;

$R^9$ represents $C_{3-6}$cycloalkyl, a 3 membered saturated heterocyclyl, an optionally substituted 5 membered saturated heterocycle, an optionally substituted 6 membered aromatic or saturated heterocycle, an optionally substituted bicyclic heterocycle;
$R^{10}$ and $R^{11}$ represents hydrogen, $C_{1-6}$alkyl, halo$C_{1-6}$alkyl, hydroxy$C_{1-6}$alkyl, $C_{1-6}$alkyl substituted with —$NR^{14}R^{15}$, $C_{1-6}$ alkyl substituted with carboxyl;
$R^6$ represents a 6-membered monocyclic saturated or aromatic heterocyclyl which is optionally substituted;
$R^{14}$ and $R^{15}$ each independently represent hydrogen or $C_{1-4}$ alkyl; and
$R^{22}$ and $R^{23}$ each independently represent hydrogen, or an N-oxide thereof, a pharmaceutically acceptable salt thereof or a solvate thereof.

13. The method according to claim 1 comprising administering to the subject a compound selected from the group consisting of a compound of formula (I), a tautomeric form, and stereochemically isomeric form thereof, or a pharmaceutically acceptable salt or solvate thereof.

14. The method according to claim 1, wherein the subject is a subject suffering from, or being at risk of suffering from cancero.

15. The method according to claim 14, wherein the cancer is selected from multiple myeloma, myeloproliferative disorders, endometrial cancer, prostate cancer, bladder cancer, lung cancer, ovarian cancer, breast cancer, gastric cancer, colorectal cancer, and oral squamous cell carcinoma.

16. The method according to claim 15, wherein the cancer is multiple myeloma.

17. The method according to claim 15, wherein the cancer is bladder cancer.

18. The method according to claim 14, wherein the cancer is selected from lung cancer, squamous cell carcinoma, liver cancer, kidney cancer, breast cancer, colon cancer, colorectal cancer, and prostate cancer.

19. The method according to claim 14, wherein the cancer is urothelial carcinoma.

20. The method according to claim 1, wherein the subject is a subject suffering from, or being at risk of suffering from a carcinoma, wherein the carcinoma is selected from a carcinoma of the bladder, breast, colon, kidney, epidermis, liver, lung, oesophagus, head and neck, gall bladder, ovary, pancreas, stomach, gastrointestinal (also known as gastric) cancer, cervix, endometrium, thyroid, prostate, or skin, a hematopoietic tumour of lymphoid lineage; a hematopoietic tumour of myeloid lineage; multiple myeloma; thyroid follicular cancer; a tumour of mesenchymal origin; a tumour of the central or peripheral nervous system; melanoma; seminoma; teratocarcinoma; osteosarcoma; xeroderma pigmentosum; keratoctanthoma; or Kaposi's sarcoma.

* * * * *

UNITED STATES PATENT AND TRADEMARK OFFICE
CERTIFICATE OF CORRECTION

PATENT NO.        : 10,052,320 B2
APPLICATION NO.   : 15/014156
DATED             : August 21, 2018
INVENTOR(S)       : Woodhead et al.

Page 1 of 1

It is certified that error appears in the above-identified patent and that said Letters Patent is hereby corrected as shown below:

In the Claims

Column 324, Line 47: Claim 1, Delete "$C_{1-4}$ alkyl" and insert -- $C_{1-4}$alkyl --

Column 324, Line 48: Claim 1, Delete "hydroxy$C_{1-4}$alkylhydroxy$C_{1-4}$alkoxy," and insert -- hydroxy$C_{1-4}$alkyl, hydroxy$C_{1-4}$alkoxy, --

Column 325, Line 7: Claim 1, Delete "-$(CR^{22}R^{23})_s$-," and insert -- -$(CR^{22}R^{23})_s$-O-, --

Column 328, Line 4: Claim 1, Delete "with $C_{1-6}$alkyl" and insert -- with -$NR^{14}R^{15}$, $C_{1-6}$alkyl --

Signed and Sealed this
Twenty-third Day of October, 2018

Andrei Iancu
*Director of the United States Patent and Trademark Office*